US012735434B2

(12) United States Patent
Lyssikatos et al.

(10) Patent No.: US 12,735,434 B2
(45) **Date of Patent: *Sep. 15, 2026**

(54) FUSED TETRACYCLIC QUINAZOLINE DERIVATIVES AS INHIBITORS OF ERBB2

(71) Applicant: Enliven Inc., Burlingame, CA (US)

(72) Inventors: Joseph P. Lyssikatos, Boulder, CO (US); Samuel Kintz, Boulder, CO (US); Li Ren, Superior, CO (US); Qiang Su, Beijing (CN)

(73) Assignee: Enliven Inc., Burlingame, CA (US)

( * ) Notice: Subject to any disclaimer, the term of this patent is extended or adjusted under 35 U.S.C. 154(b) by 405 days.

This patent is subject to a terminal disclaimer.

(21) Appl. No.: 18/197,663

(22) Filed: May 15, 2023

(65) Prior Publication Data

US 2023/0382923 A1 Nov. 30, 2023

Related U.S. Application Data

(63) Continuation of application No. 18/051,826, filed on Nov. 1, 2022, now Pat. No. 11,807,649.

(60) Provisional application No. 63/417,219, filed on Oct. 18, 2022.

(30) Foreign Application Priority Data

Nov. 2, 2021 (WO) ................ PCT/CN2021/128110

(51) Int. Cl.

*C07D 498/18* (2006.01)
*A61P 35/02* (2006.01)
*C07D 519/00* (2006.01)

(52) U.S. Cl.

CPC ............ *C07D 498/18* (2013.01); *A61P 35/02* (2018.01); *C07D 519/00* (2013.01); *C07B 2200/05* (2013.01)

(58) Field of Classification Search

CPC ... C07D 498/18; C07D 519/00; C07D 498/22
See application file for complete search history.

(56) References Cited

U.S. PATENT DOCUMENTS

| | | | |
|---|---|---|---|
| 6,127,374 | A | 10/2000 | Bridges |
| 7,750,007 | B2 | 7/2010 | Bearss et al. |
| 8,648,087 | B2 | 2/2014 | Lyssikatos et al. |
| 9,693,989 | B2 | 7/2017 | Lyssikatos et al. |
| 10,780,073 | B2 | 9/2020 | Lyssikatos et al. |
| 10,828,305 | B2 | 11/2020 | Xia |
| 11,806,649 | B2 | 11/2023 | Lyssikatos et al. |
| 2003/0186987 | A1 | 10/2003 | Bridges et al. |
| 2007/0032508 | A1 | 2/2007 | Bradbury et al. |
| 2008/0194596 | A1 | 8/2008 | Letrent |
| 2016/0168129 | A1 | 6/2016 | Wang et al. |
| 2019/0233440 | A1 | 8/2019 | Planken et al. |
| 2020/0190091 | A1 | 6/2020 | Xia et al. |
| 2021/0008023 | A1 | 1/2021 | Lyssikatos et al. |
| 2021/0040114 | A1 | 2/2021 | Zhang et al. |
| 2021/0332054 | A1 | 10/2021 | Wilding et al. |
| 2023/0159557 | A1 | 5/2023 | Lyssikatos et al. |
| 2023/0265098 | A1 | 8/2023 | Lyssikatos |
| 2023/0382923 | A1 | 11/2023 | Lyssikatos et al. |
| 2024/0116921 | A1 | 4/2024 | Lyssikatos |

FOREIGN PATENT DOCUMENTS

| | | | |
|---|---|---|---|
| EP | 3760633 | A1 | 1/2021 |
| JP | 2007502295 | A | 2/2007 |
| JP | 2007510708 | A | 4/2007 |
| JP | 2019507170 | A | 3/2019 |
| JP | 2023545219 | A | 10/2023 |
| JP | 2023546352 | A | 11/2023 |
| WO | 199843960 | A1 | 10/1998 |
| WO | 199935132 | A1 | 7/1999 |
| WO | 2005016346 | A1 | 2/2005 |
| WO | 2005044302 | A1 | 5/2005 |
| WO | 2007059257 | A2 | 5/2007 |
| WO | 2014117698 | A1 | 8/2014 |
| WO | 2015007219 | A1 | 1/2015 |
| WO | 2019042409 | A1 | 3/2019 |
| WO | 2019170088 | A1 | 9/2019 |
| WO | 2020068867 | A1 | 4/2020 |
| WO | 2020197991 | A1 | 10/2020 |
| WO | 2021156178 | A1 | 8/2021 |
| WO | 2021156180 | A1 | 8/2021 |
| WO | 2022006386 | A1 | 1/2022 |
| WO | 2022076973 | A1 | 4/2022 |
| WO | 2022076975 | A1 | 4/2022 |

(Continued)

OTHER PUBLICATIONS

Feldinger, K., "Profile of neratinib and its potential in the treatment of breast cancer." Breast Cancer: Targets and Therapy 7 (2015): 147-162.*

Bauer, R. A., "Covalent inhibitors in drug discovery: from accidental discoveries to avoided liabilities and designed therapies." Drug discovery today 20.9 (2015): 1061-1073.*

Anastassiadis, T. et al. (Nov. 2011, e-pub. Oct. 30, 2011). "Comprehensive Assay Of Kinase Catalytic Activity Reveals Features Of Kinase Inhibitor Selectivity," Nat Biotechnol. 29(11):1039-1045.

International Preliminary Report on Patentability issued on May 2, 2024, for PCT Application No. PCT/US2021/128110, filed on Nov. 2, 2021, 7 pages.

International Preliminary Report on Patentability issued on May 2, 2024, for PCT Application No. PCT/US2022/079038, filed on Nov. 1, 2022, 5 pages.

(Continued)

*Primary Examiner* — Susanna Moore
(74) *Attorney, Agent, or Firm* — Morrison & Foerster LLP

(57) ABSTRACT

The present disclosure relates generally to compounds and compositions thereof for inhibition of ErbB2, including mutant forms of ErbB2, particularly those harboring an Exon 20 mutation, methods of preparing said compounds and compositions, and their use in the treatment or prophylaxis of various cancers, such as lung, glioma, skin, head neck, salivary gland, breast, esophageal, liver, stomach (gastric), uterine, cervical, biliary tract, pancreatic, colorectal, renal, bladder or prostate cancer.

36 Claims, No Drawings

(56) References Cited

FOREIGN PATENT DOCUMENTS

| | | | |
|---|---|---|---|
| WO | 2022140769 | A1 | 6/2022 |
| WO | 2022221227 | A1 | 10/2022 |
| WO | 2022269531 | A1 | 12/2022 |
| WO | 2023077259 | A1 | 5/2023 |
| WO | 2023081637 | A1 | 5/2023 |
| WO | 2023154124 | A1 | 8/2023 |

OTHER PUBLICATIONS

PubChem. (Feb. 13, 2015). "PubChem SID 237890001," deposited on Feb. 13, 2015, 1-8.

Pubmed Compound Record for CID 18535775, 'N-14-(3-Chloro-4-pyridin-2-yloxyanilino)pyrido[3,4-d]pyrimidin-6-yl]-7-morpholin-4-ylhept-2-ynamidê', U.S. National Library of Medicine, Dec. 4, 2007, pp. 1-8.

Pubmed Compound Record for CID 18535833, 'N-[4-[3-Chloro-4-[hydroxy(pyridin-3-yl)rnethyl]anilinoquinazolin-6-yl]-7-morpholin-4-ylhept-2-ynamide', U.S. National Library of Medicine, Dec. 4, 2007, pp. 1-8.

Bauer, R.A. (Sep. 2015). "Covalent Inhibitors in Drug Discovery: from Accidental Discoveries to Avoided Liabilities and Designed Therapies," Drug Discovery Today 20(9):1061-1073.

Feldinger, K, et al. (2015). "Profile of Neratinib arid its Potential in the Treatment of Breast Cancer," Breast Cancer: Targets and Therapy 7:147-162.

GenBank Accession No. NM004448.3, last updated May 3, 2020, located at https://ww.ncbi.nlm.nih.gov/nuccore/NM_004448.3, last visited on Feb. 10, 2023, sixteen pages.

GenBank Accession No. NM005228.3, last updated Nov. 8, 2016, located at https://ww.ncbi.nlm.nih.gov/nuccore/NM_005228.3, last visited on Feb. 10, 2023, fourteen pages.

International Search Report and Written Opinion mailed on Aug. 1, 2022, for PCT Application No. PCT/CN2021/128110, filed on Nov. 2, 2021, 15 pages.

International Search Report and Written Opinion mailed on Feb. 7, 2023, for PCT Application No. PCT/US22/79038, filed on Oct. 31, 2022, 13 pages.

Li, D. et al. (Mar. 23, 2022). "Discovery of SPH5030, a Selective, Potent, and Irreversible Tyrosine Kinase Inhibitor for HER-2-Amplified and HER2-Mutnat Cancer Treatment," J. Med. Chem. 65:5334-5354.

Schroeder, R. L. et al. (Sep. 23, 2014). "Small Molecule Tyrosine Kinase Inhibitors of ErbB2/HER2/Neu in the Treatment of Aggressive Breast Cancer," Molecules 19:15196-15212.

U.S. Appl. No. 18/012,488, filed Dec. 22, 2022, for Lyssikatos (U.S. Patent Applicationis not submitted herewith pursuant to the waiver of 37 C.F.R. § 1.98(a)(2)(iii) issued by the Office on Sep. 21, 2004.).

Extended European Search Report mailed on Aug. 8, 2025, for European Patent Application No. 22890974.3, 7 pages.

Sun, M. et al. (2020). "Design and Synthesis of a Novel Class EGFR/HER2 Dual Inhibitors Containing Tricyclic Oxazine Fused Quinazolines Scaffold," Bioorganic & Medicinal Chemistry Letters 30:127045, 6 pages.

* cited by examiner

FUSED TETRACYCLIC QUINAZOLINE DERIVATIVES AS INHIBITORS OF ERBB2

CROSS-REFERENCE TO RELATED APPLICATIONS

This application is a continuation Application of U.S. application Ser. No. 18/051,826, filed Nov. 1, 2022, which claims priority to and the benefit of International Patent Application No. PCT/CN2021/128110, filed Nov. 2, 2021, and U.S. Provisional Patent Application No. 63/417,219, filed Oct. 18, 2022, the disclosures of each of which are incorporated herein by reference in their entireties.

FIELD OF THE INVENTION

The present disclosure relates generally to compounds and compositions thereof for inhibition of ErbB2, including mutant forms of ErbB2, particularly those harboring an Exon 20 mutation, methods of preparing said compounds and compositions, and their use in the treatment or prophylaxis of various cancers, such as lung, glioma, skin, head and neck, salivary gland, breast, esophageal, liver, stomach (gastric), uterine, cervical, biliary tract, pancreatic, colorectal, renal, bladder or prostate cancer.

BACKGROUND

ErbB2 (or HER2) is a member of the ErbB receptor tyrosine kinase family consisting of four related receptors, including ErbB1 (also known as epidermal growth factor receptor, or EGFR), ErbB3 and ErbB4. Although there are no known ligands that bind to monomeric ErbB2, it can dimerize with other ErbB receptors, particularly ErbB3, and regulate downstream signaling cascades including, but not limited to, the MAPK and PI3K pathways, that promote cell proliferation and survival. Aberrant overexpression of ErbB2 or certain genetic alterations (including point mutations that lead to certain amino acid substitutions or small in-frame insertions in Exon 20 that lead to the deletion and/or insertion of certain small stretches of amino acids) are known to confer elevated or constitutive tyrosine kinase activation to the receptor. Accordingly, the overexpression or mutation of ErbB2 is highly associated with aggressive forms of solid cancers, including breast, ovarian, stomach, and lung cancer (NSCLC).

Currently, there are few approved treatments for cancers associated with ErbB2 overexpression, including tyrosine kinase inhibitors (TKIs) such as tucatinib. Although these TKIs can be effective at ameliorating cancers associated with ErbB2 overexpression, their therapeutic utility is often limited by inadequate selectivity for ErbB2 over EGFR, and consequently are dose-limited by toxicity concerns related to EGFR inhibition (especially gastrointestinal and skin-related toxicities). These toxicities necessitate restrictive dosing regimens, leading to suboptimal target engagement and thus limited therapeutic benefit. Moreover, while current TKIs provide therapeutic benefit for cancers driven by ErbB2 overexpression, they may have limited efficacy in patients harboring specific genetic alterations, such as EGFR or ERBB2 exon 20 insertions, specific point mutations or genetic alterations associated with ErbB family ligands, such as NRG1 gene fusions.

For example, in a small proportion of lung cancer patients, certain especially pernicious mutations in EGFR and ErbB2 known as EGFR exon 20 insertions/ErbB2 insertions are markedly less sensitive to first and second generation reversible TKIs. An added challenge to the development of viable therapies for these specific ErbB Exon 20 mutants (20 ins or E20I) is the fact these alterations are heterogeneous, encompassing a diversity of amino acid insertions/deletions. In addition to E20I mutations, a number of other genetic alterations of the receptor, specifically point mutations leading to single amino acid substitutions, have been associated with the development of a variety of cancers, including lung cancer. Although the resistance mechanisms associated with each of these mutations are not fully understood, it is believed that the mutations may share a commonality in promoting ligand-independent activation of the kinases. Further investigation of the underlying mechanisms and development of TKIs tailored to these mutants are needed.

Other aggressive, refractory cancers exhibiting ErbB2 overexpression have been observed to harbor NRG1 gene re-arrangements resulting in novel fusion proteins. NRG1 gene fusions may induce overproduction of neuregulin-1, the cognate ligand for ErbB3. The simultaneous overexpression of ErbB2 and overproduction of neuregulin-1 may lead to excess activation of ErbB2-ErbB3 heterodimers and resultant hyperplasia.

Accordingly, there remains a need for new therapeutics for the treatment of cancers driven by dysregulated ErbB2 receptor kinase activity, not only with improved safety and selectivity for ErbB2 over EGFR, but also for addressing mutation-associated sub-variants of ErbB2 (e.g., E20I mutations and NRG1 gene fusions) with enhanced potency.

SUMMARY OF THE INVENTION

In one aspect provided is a compound of formula (I')

(I')

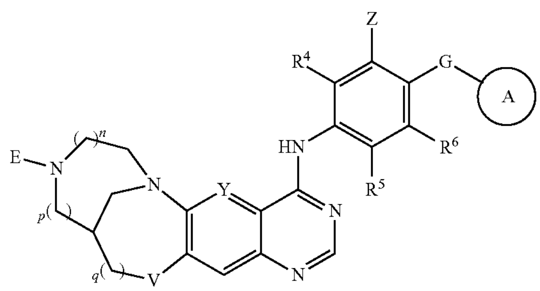

or a pharmaceutically acceptable salt, solvate, hydrate, or co-crystal thereof, or a mixture of any of the foregoing, wherein:

Ring A is

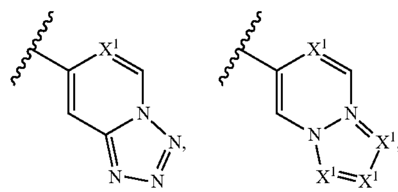

-continued

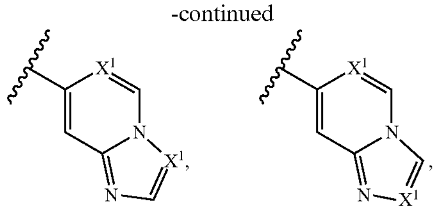

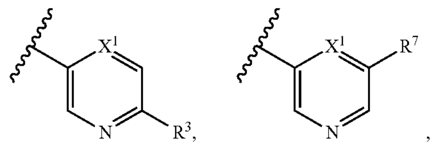

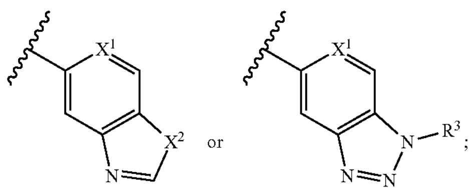

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$;

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen;

$R^6$ is —H or halogen;

$R^7$ is —H, halogen, $C_1$-$C_6$ alkyl, —$CD_3$ or $C_1$-$C_6$ cycloalkyl;

n is 1 or 2;

p is 0 or 1; and q is 1 or 2.

In one aspect, provided herein are compounds of formula (I)

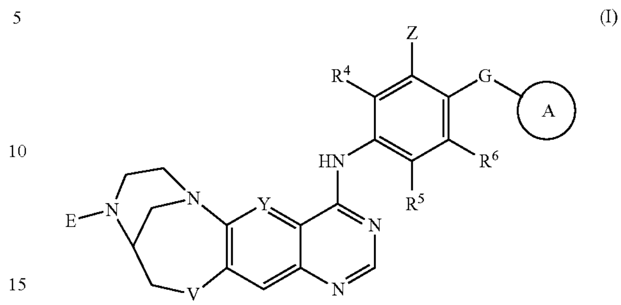

(I)

or a pharmaceutically acceptable salt, solvate, hydrate, or co-crystal thereof, or a mixture of any of the foregoing, wherein:

Ring A is N

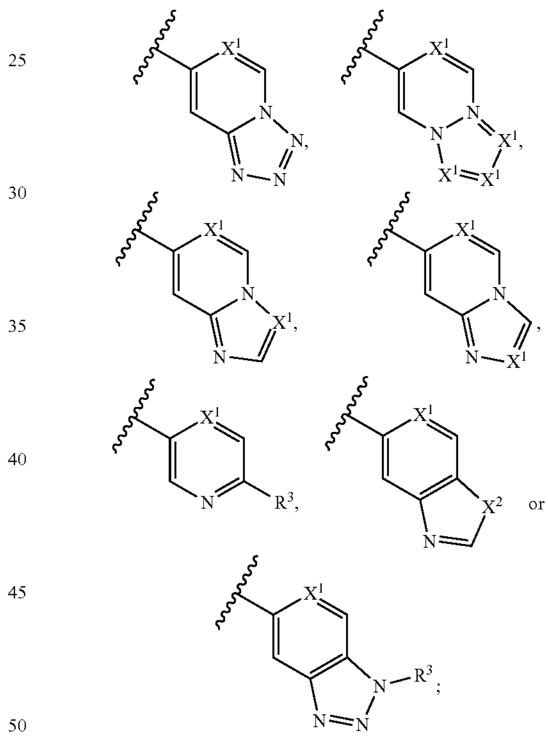

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen; and $R^6$ is —H or halogen.

In some embodiments of the present aspect, ring A is

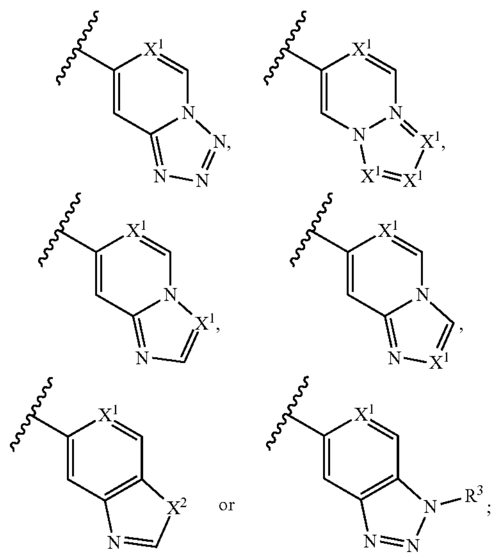

or

In certain embodiments, ring A is

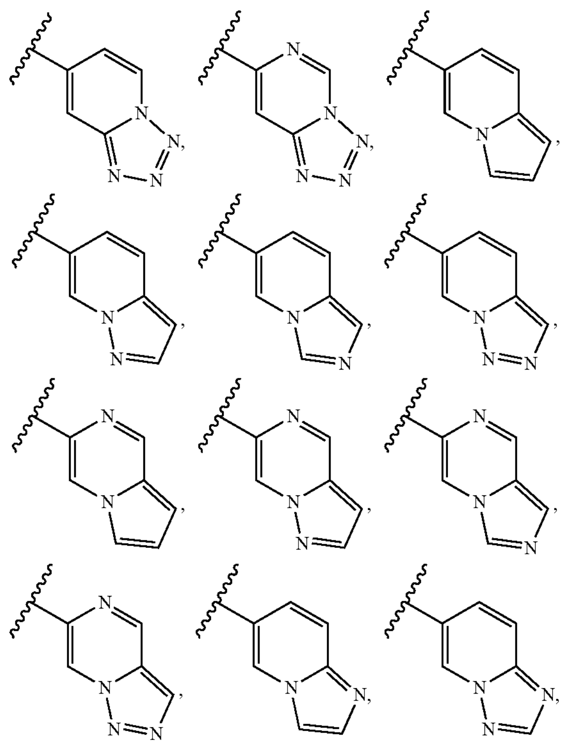

-continued

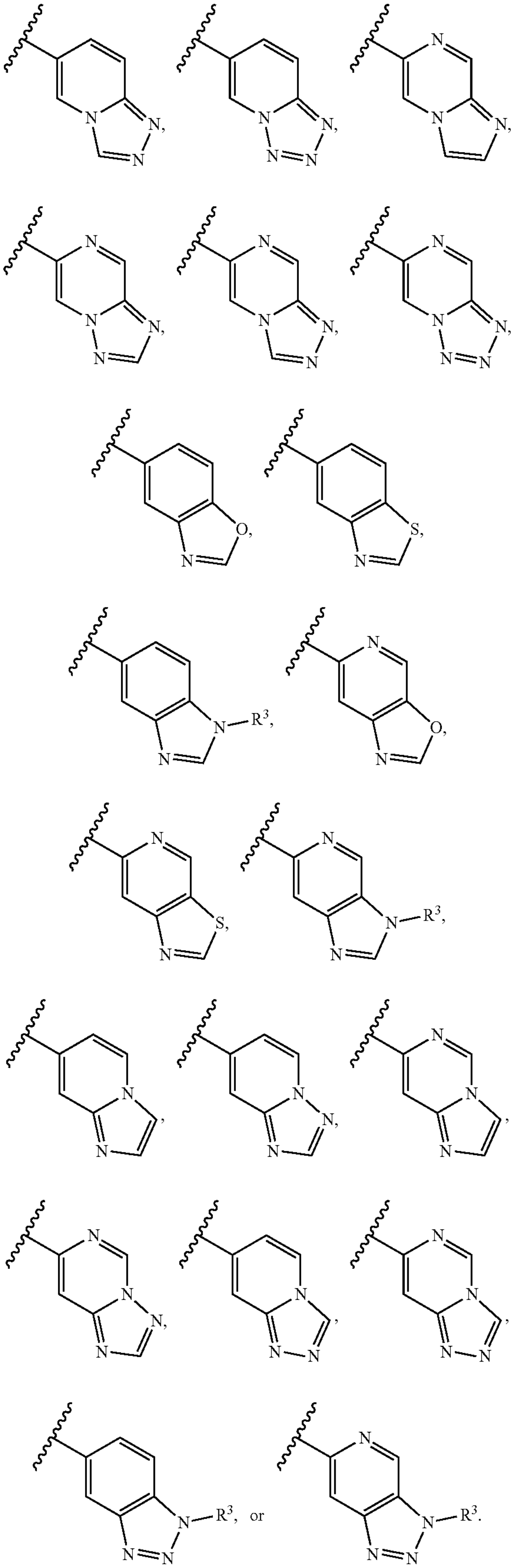

or

In some embodiments of the present aspect, ring A is

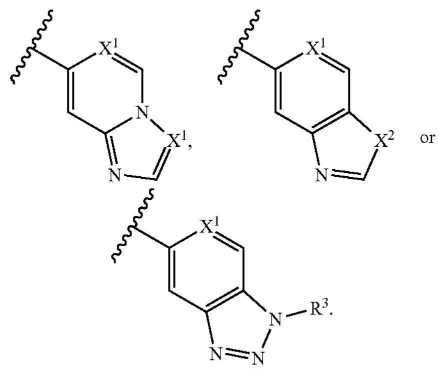

or

In some embodiments, ring A is

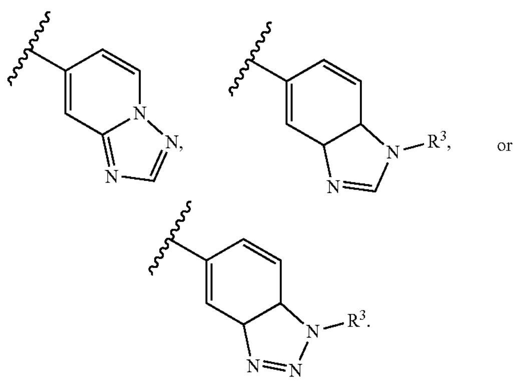

or

In other embodiments, ring A is

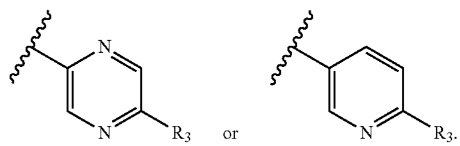

or

In other embodiments ring A is

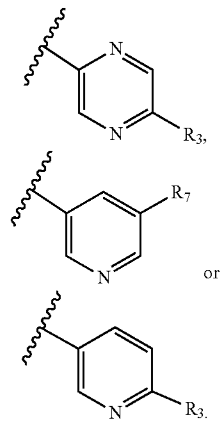

or

In some embodiments, which may be combined with any of the preceding embodiments, $R^3$ is —$CH_3$. In some embodiments, which may be combined with any of the preceding embodiments, Z is —H, —F, —Cl, —C≡CH, —$OCH_3$, or —$CH_3$. In certain embodiments, Z is —$CH_3$. In some embodiments, which may be combined with any of the preceding embodiments, $R^1$ is $C_2$-$C_4$ alkenyl, optionally substituted by —$NR^{1a}R^{1b}$. In certain embodiments, $R^1$ is —CH═$CH_2$. In certain other embodiments, $R^1$ is —CH═CH—$CH_2$—$N(CH_3)_2$. In yet other embodiments, which may be combined with any of the preceding embodiments, $R^1$ is $C_2$-$C_4$ alkynyl, optionally substituted by —$NR^{1a}R^{1b}$. In certain embodiments, $R^1$ is —C≡C≡$CH_3$.

In some embodiments, which may be combined with any of the preceding embodiments, $R^3$ is —$CH_3$. In some embodiments, which may be combined with any of the preceding embodiments, $R^7$ is —$CH_3$, —$CH_2CH_3$, or F. In some embodiments, which may be combined with any of the preceding embodiments, Z is —H, —F, —Cl, —C≡CH, —$OCH_3$, or —$CH_3$. In certain embodiments, Z is —$CH_3$. In some embodiments, which may be combined with any of the preceding embodiments, $R^1$ is $C_2$-$C_4$ alkenyl, optionally substituted by —$NR^{1a}R^{1b}$. In certain embodiments, $R^1$ is —CH═$CH_2$. In certain other embodiments, $R^1$ is —CH═CH—$CH_2$—$N(CH_3)_2$ or —CH═CH—$CH(CH_3)$—$N(CH_3)_2$. In yet other embodiments, which may be combined with any of the preceding embodiments, $R^1$ is $C_2$-$C_4$ alkynyl, optionally substituted by —$NR^{1a}R^{1b}$ In certain embodiments, $R^1$ is —C≡C—$CH_3$.

In some embodiments, Y is N. In other embodiments Y is C—$R^y$. In certain embodiments, Y is C—$R^y$, and $R^y$ is —H. In certain other embodiments, Y is C—$R^y$, and $R^y$ is —F. In some embodiments, V is 0. In other embodiments, V is S. In yet other embodiments, V is N—$R^2$. In some embodiments, G is —O—. In other embodiments, G is —C(═O)—. In yet other embodiments, G is —S—, —S(O)—, or —$S(O)_2$—. In still other embodiments, G is —$CH_2$—. In some embodiments, $R^4$ is —H. In other embodiments, $R^4$ is halogen. In some embodiments, $R^5$ is —H. In other embodiments, $R^5$ is halogen. In some embodiments, $R^6$ is —H. In other embodiments, $R^6$ is halogen.

In another aspect, provided herein are compounds as described herein in Table 1. In yet another aspect, provided herein are pharmaceutical compositions comprising a compound of formula (I'), formula (I) or of Table 1 as described herein, or a pharmaceutically acceptable salt, solvate, hydrate, or co-crystal thereof, or a mixture of any of the foregoing, and at least one pharmaceutically acceptable excipient.

In one aspect, provided herein is a method of inhibiting kinase activity of a human receptor tyrosine kinase ErbB2 or a mutant form of human ErbB2 comprising contacting the ErbB2 or the mutant form with a therapeutically effective amount of a compound of formula (I'), or a pharmaceutically acceptable salt thereof, as described herein, or a therapeutically effective amount of the pharmaceutical composition as described herein. In some embodiments of the present aspect, the mutant form of human ErbB2 comprises a mutation in Exon 20. In some embodiments of the present aspect, the mutant form of human ErbB2 comprises one or more mutations that introduce amino acid deletions and/or insertions selected from the group consisting of: A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775_G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777_G778insG, G778_S779insLPS, and G778_S779insAVG. In further embodiments of the present aspect, the mutant form of human ErbB2 comprises one or more mutations that introduce amino acid deletions and/or insertions selected from the group consisting of: A775_A776insYVMA, G778_P780insGSP, G776delinsVC, P780_Y781insGSP, M774delinsWLV, A775_G776insSVMA, A775_G776insI, G776delinsLC, G778_S779InsCPG, and V777_G778insGSP. In other embodiments of the present aspect, the mutant form of human ErbB2 comprises a disease-associated point mutation in ErbB2. In other embodiments of the present aspect, the mutant form of human ErbB2 comprises one or more point mutations in ErbB2 that introduce (a) amino acid substitutions selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In still further embodiments of the present aspect, the mutant form of human ErbB2 comprises one or more point mutations in ErbB2 that introduce amino acid substitutions selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In other embodiments, the mutant form of human ErbB2 comprises one or more point mutations in ErbB2 that introduce (a) an amino acid substitution selected from the group consisting of are P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232. In other embodiments, the mutant form of human ErbB2 comprises amino terminally truncated carboxyl-terminal fragments of HER2, collectively known as p95HER2.

In yet another aspect, provided herein is a method of treating a patient having a cancer, comprising administering to the patient a therapeutically effective amount of a compound of formula (I'), or a pharmaceutically acceptable salt, solvate, hydrate, or co-crystal thereof, or a mixture of any of the foregoing, as described herein, or a therapeutically effective amount of the pharmaceutical composition as described herein. In some embodiments of the present aspect, the cancer comprises cells or cell tissue having increased ErbB2 kinase activity. In some embodiments of the present aspect, the cancer comprises cells or cell tissue having increased ErbB2 kinase activity as compared to a control. In certain embodiments, the cancer comprises cells or cell tissue having increased ErbB2 kinase activity as compared to ErbB2 kinase activity in control cell or in control cell tissue. In further embodiments of the present aspect, the cancer comprises cells or cell tissue having one or more mutations in Exon 20 of the ErbB2. In certain variations, the one or more mutations in Exon 20 of the ErbB2 that introduce certain amino acid deletions and/or insertions selected from the group consisting of: A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775 G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777_G778insG, G778_S779insLPS, and G778_S779insAVG. In certain embodiments, the cancer comprises cells or cell tissue having one or more mutations in Exon 20 of the ErbB2 that introduce amino acid deletions and/or insertions selected from the group consisting of A775_A776insYVMA, G778_P780insGSP, G776delinsVC, P780_Y781insGSP, M774delinsWLV, A775_G776insSVMA, A775_G776insI, G776delinsLC, G778_S779InsCPG, and V777_G778insGSP. In certain embodiments, the cancer comprises cells or cell tissue having one or more point mutations that introduce (a) an amino acid substitution selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In other embodiments, the cancer comprises cells or cell tissue having one or more disease-associated point mutations in ErbB2. In certain other embodiments, the cancer comprises cells or cell tissue having one or more point mutations that introduce amino acid substitutions selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In certain embodiments, the cancer comprises cells or cell tissue having one or more point mutations that introduce (a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232.

In some embodiments of the present aspect, which may be combined with any of the preceding embodiments, the cancer is lung, glioma, skin, head and neck, salivary gland, breast, esophageal, liver, stomach (gastric), uterine, cervical, biliary tract, pancreatic, colorectal, renal, bladder or prostate cancer. In certain embodiments, the cancer is non-small cell lung cancer. In still other embodiments, which may be combined with any of the preceding embodiments, the patient has received at least one, at least two, or at least three prior therapies for the cancer. In certain embodiments, one or more of the prior therapies selected from the group consisting of lapatinib, neratinib, afatinib, pyrotinib, poziotinib, TAK-788, and tucatinib. In some embodiments, the method further comprises administering one or more additional anti-cancer agents. In some embodiments, the method further comprises administering an anti-HER2 antibody or an anti-HER2 drug conjugate. In certain embodiments, the method further comprises administering KADCYLA® (ado-trastuzumab emtansine), ENHERTU® (fam-trastuzumab deruxtecan-nxki), or any biosimilar thereof.

DETAILED DESCRIPTION

The following description sets forth exemplary methods, parameters and the like. It should be recognized, however, that such description is not intended as a limitation on the scope of the present disclosure but is instead provided as a description of exemplary embodiments.

I. Definitions

As used herein, the following definitions shall apply unless otherwise indicated. Further, if any term or symbol used herein is not defined as set forth below, it shall have its ordinary meaning in the art.

The term "excipient" as used herein means an inert or inactive substance that may be used in the production of a drug or pharmaceutical, such as a tablet containing a compound of the present disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The terms "individual", "subject" and "patient" refer to mammals and includes humans and non-human mammals. Examples of patients include, but are not limited to, mice, rats, hamsters, guinea pigs, pigs, rabbits, cats, dogs, goats, sheep, cows, and humans. In some embodiments, patient refers to a human.

As used herein, the term "mammal" includes, but is not limited to, humans, mice, rats, guinea pigs, monkeys, dogs, cats, horses, cows, pigs, and sheep.

"Pharmaceutically acceptable" refers to safe and non-toxic, and suitable for in vivo or for human administration.

As used herein, the term "alkyl", by itself or as part of another substituent, means, unless otherwise stated, a straight or branched chain hydrocarbon radical, having the number of carbon atoms designated (i.e., $C_1$-$C_6$ means one to six carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. In some embodiments, the term "alkyl" may encompass $C_1$-$C_6$ alkyl, $C_2$-$C_6$ alkyl, $C_3$-$C_6$ alkyl, $C_4$-$C_6$ alkyl, $C_5$-$C_6$ alkyl, $C_1$-$C_5$ alkyl, $C_2$-$C_5$ alkyl, $C_3$-$C_5$ alkyl, $C_4$-$C_5$ alkyl, $C_1$-$C_4$ alkyl, $C_2$-$C_4$ alkyl, $C_3$-$C_4$ alkyl, $C_1$-$C_3$ alkyl, $C_2$-$C_3$ alkyl, or $C_1$-$C_2$ alkyl.

As used herein, the term "alkenyl" refers to an unsaturated branched or straight-chain alkyl group having the indicated number of carbon atoms (e.g., 2 to 8, or 2 to 6 carbon atoms) and at least one carbon-carbon double bond. The group may be in either the cis or trans configuration (Z or E configuration) about the double bond(s). Alkenyl groups include, but are not limited to, ethenyl, propenyl (e.g., prop-1-en-1-yl, prop-1-en-2-yl, prop-2-en-1-yl (allyl), prop-2-en-2-yl), and butenyl (e.g., but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl). In some embodiments, the alkenyl group may be attached to the rest of the molecule by a carbon atom in the carbon-carbon double bond. In other embodiments, the "alkenyl" may be attached to the rest of the molecule by a saturated carbon atom, and the carbon-carbon double bond is located elsewhere along the branched or straight-chain alkyl group.

As used herein, the term "alkynyl" refers to an unsaturated branched or straight-chain alkyl group having the indicated number of carbon atoms (e.g., 2 to 8 or 2 to 6 carbon atoms) and at least one carbon-carbon triple bond. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). In some embodiments, the alkynyl group may be attached to the rest of the molecule by a carbon atom in the carbon-carbon triple bond. In other embodiments, the "alkynyl" may be attached to the rest of the molecule by a saturated carbon atom, and the carbon-carbon triple bond is located elsewhere along the branched or straight-chain alkyl group.

The term "cycloalkyl", "carbocyclic", or "carbocycle" refers to hydrocarbon rings having the indicated number of ring atoms (e.g., $C_3$-$C_6$ cycloalkyl means 3-6 carbons) and being fully saturated or having no more than one double bond between ring vertices. In some embodiments, "cycloalkyl" encompasses $C_3$-$C_7$ cycloalkyl, $C_4$-$C_7$ cycloalkyl, $C_5$-$C_7$ cycloalkyl, $C_5$-$C_7$ cycloalkyl, $C_3$-$C_6$ cycloalkyl, $C_4$-$C_6$ cycloalkyl, $C_5$-$C_6$ cycloalkyl, $C_3$-$C_5$ cycloalkyl, $C_4$-$C_5$ cycloalkyl, or $C_3$-$C_4$ cycloalkyl. In some embodiments, the term "cycloalkyl" may be further described as a "spirocycloalkyl" or a "fused cycloalkyl". The term "spirocycloalkyl" refers to hydrocarbon rings having the indicated number of ring atoms (e.g., $C_3$-$C_6$ cycloalkyl means 3-6 carbons) and being fully saturated or having no more than one double bond between ring vertices, wherein the hydrocarbon ring is attached to the rest of the molecule at a single ring vertex (e.g., ring carbon atom) by two covalent bonds. The term "fused "cycloalkyl" refers to hydrocarbon rings having the indicated number of ring atoms (e.g., $C_3$-$C_6$ cycloalkyl means 3-6 carbons) and being fully saturated or having no more than one double bond between ring vertices, wherein the hydrocarbon ring is attached to the rest of the molecule at two ring vertices (e.g. two carbon atoms) by two covalent bonds. In some embodiments, "cycloalkyl", "cycloalkyl", "carbocyclic", or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic $C_{5-12}$ alkane, etc. In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) 0, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include $-CH_2-CH_2-O-CH_3$, $-CH_2-CH_2-O-CF_3$, $-CH_2-CH_2-NH-CH_3$, $-CH_2-CH_2-N(CH_3)-CH_3$, $-CH_2-S-CH_2-CH_3$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH=N(CH_3)-CH_3$. Up to two heteroatoms can be consecutive, such as, for example, $-CH_2-NH-OCH_3$ and $-CH_2-O-Si(CH_3)_3$.

The term "heterocycloalkyl", "heterocyclic", "heterocyclyl", or "heterocycle" refers to a cycloalkyl radical group having the indicated number of ring atoms (e.g., 5-6 membered heterocycloalkyl) that contain from one to five heteroatoms selected from the group consisting of N, O, and S, wherein the nitrogen and sulfur atoms are optionally oxidized, nitrogen atom(s) are optionally quaternized, as ring atoms. In some embodiments, a "heterocycloalkyl," "heterocyclic," or "heterocycle" ring can be a monocyclic, a bicyclic, bridged or fused ring system, spirocyclic or a polycyclic ring system. Non-limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4 (1H,3H)-dione, 1,4-dioxane, morpholine, thiomorpholine, thiomorpholine-5-oxide, thiomorpholine-S,S-oxide, piperazine, pyran, pyridone, 3-pyrroline, thiopyran, pyrone, tetrahydrofuran, tetrhydrothiophene, quinuclidine, tropane and the like. A "heterocycloalkyl," "heterocyclic," or "heterocycle" group can be attached to the remainder of the molecule through one or more ring carbons or heteroatoms. In some embodiments, "heterocycloalkyl" encompasses 3- to 10-membered heterocycloalkyl, 4- to 10-membered heterocycloalkyl, 5- to 10-membered heterocycloalkyl, 6- to 10-membered heterocycloalkyl, 7- to 10-membered heterocycloalkyl, 8- to 10-membered heterocycloalkyl, 9- to 10-membered heterocycloalkyl, 3- to 9-membered heterocycloalkyl, 4- to 9-membered heterocycloalkyl, 5- to 9-membered heterocycloalkyl, 6- to 9-membered heterocycloalkyl, 7- to 9-membered heterocycloalkyl, 8- to 9-membered heterocycloalkyl, 3- to 8-membered heterocycloalkyl, 4- to 8-membered heterocycloalkyl, 5- to 8-membered heterocycloalkyl, 6- to 8-membered heterocycloalkyl, 7- to 8-membered heterocycloalkyl, 3- to 7-membered heterocycloalkyl, 4- to 7-membered heterocycloalkyl, 5- to 7-membered heterocycloalkyl, 6- to 7-membered heterocycloalkyl, 3- to 6-membered heterocycloalkyl, 4- to 6-membered heterocycloalkyl, 5- to 6-membered heterocycloalkyl, 3- to 10-membered heterocycloalkyl, 4- to 5-membered heterocycloalkyl, or 3- to 4-membered heterocycloalkyl. In other embodiments, "heterocycloalkyl" may be characterized by the number of carbon atoms in the ring, provided that the ring contains at least one heteroatom. For example, in some embodiments, "heterocycloalkyl" encompasses $C_3$-$C_9$ heterocycloalkyl, $C_3$-$C_8$ heterocycloalkyl, $C_3$-$C_7$ heterocycloalkyl, $C_3$-$C_6$ heterocycloalkyl, $C_3$-$C_5$ heterocycloalkyl, $C_3$-$C_4$ heterocycloalkyl, $C_4$-$C_9$ heterocycloalkyl, $C_4$-$C_8$ heterocycloalkyl, $C_4$-$C_7$ heterocycloalkyl, $C_4$-$C_6$ heterocycloalkyl, $C_4$-$C_5$ heterocycloalkyl, $C_5$-$C_9$ heterocycloalkyl, $C_5$-$C_5$ heterocycloalkyl, $C_5$-$C_7$ heterocycloalkyl, $C_5$-$C_6$ heterocycloalkyl, $C_6$-$C_9$ heterocycloalkyl, $C_6$-$C_8$ heterocycloalkyl, $C_6$-$C_7$ heterocycloalkyl, $C_7$-$C_9$ heterocycloalkyl, $C_7$-$C_8$ heterocycloalkyl, or $C_5$-$C_9$ heterocycloalkyl. It should be recognized that "heterocycloalkyl" as described by the number of ring atoms may also be described by number of carbon atoms in the ring. For example, a piperazinyl ring may be described as a $C_4$ heterocycloalkyl ring or a 6-membered heterocycloalkyl ring; an azetidinyl or oxetanyl ring may each be described as a $C_3$ heterocycloalkyl ring or a 4-membered heterocycloalkyl ring.

The term "alkylene" by itself or as part of another substituent means a divalent radical derived from an alkane, as exemplified by $-CH_2CH_2CH_2CH_2-$. Typically, an alkyl (or alkylene) group will have from 1 to 24 carbon atoms. In some embodiments, an alkyl (or alkylene) group will have 10 or fewer carbon atoms.

The term "heteroalkylene" by itself or as part of another substituent means a divalent radical, saturated or unsaturated or polyunsaturated, derived from heteroalkyl, as exemplified by $-CH_2-CH_2-S-CH_2CH_2-$, $-CH_2-S-CH_2-CH_2-NH-CH_2-$, $-O-CH_2-CH=CH-$, $-CH_2-CH=C(H)CH_2-O-CH_2-$ and $-S-CH_2-C\equiv C-$. For heteroalkylene groups, heteroatoms can also occupy either or both of the chain termini (e.g., alkyleneoxy, alkylenedioxy, alkyleneamino, alkylenediamino, and the like).

The term "heterocycloalkylene" by itself or as part of another substituent means a divalent radical, saturated or unsaturated or polyunsaturated, derived from heterocycloalkyl. For heterocycloalkylene groups, heteroatoms can also occupy either or both of the chain termini.

The terms "alkoxy" and "alkylamino" are used in their conventional sense, and refer to those alkyl groups attached to the remainder of the molecule via an oxygen atom or an amino group, respectively.

The term "heterocycloalkoxy" refers to a heterocycloalkyl-O— group in which the heterocycloalkyl group is as previously described herein.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "$C_1$-$C_4$ haloalkyl" is mean to include trifluoromethyl, 2,2,2-trifluoroethyl, 4-chlorobutyl, 3-bromopropyl, difluoromethyl, and the like.

The term "haloalkyl-OH" refers to a haloalkyl group as described above which is also substituted by one or more hydroxyl groups. The term "haloalkyl-OH" is meant to include haloalkyl substituted by one hydroxyl group, as well as haloalkyl substituted by multiple hydroxyl groups. For example, the term "haloalkyl-OH" includes $-CH(F)OH$, $-CH_2CFHCH_2OH$, $-CH(OH)CF_3$, and the like.

The term "alkyl-OH" refers to an alkyl substituted by one or more hydroxyl groups. The term "alkyl-OH" is meant to include alkyl substituted by one hydroxyl group, as well as alkyl substituted by multiple hydroxyl groups. For example, the term "alkyl-OH" includes $-CH_2OH$, $-CH(OH)CH_3$, $-CH_2CH_2OH$, and the like.

The term "aryl" means, unless otherwise stated, a polyunsaturated, typically aromatic, hydrocarbon group, which can be a single ring or multiple rings (up to three rings) which are fused together. In some embodiments, "aryl" encompasses $C_6$-$C_{14}$ aryl, $C_5$-$C_{14}$ aryl, $C_{10}$-$C_{14}$ aryl, $C_{12}$-$C_{14}$ aryl, $C_6$-$C_{12}$ aryl, $C_5$-$C_{12}$ aryl, $C_{10}$-$C_{12}$ aryl, $C_6$-$C_{10}$ aryl, $C_5$-$C_{10}$ aryl, or $C_6$-$C_8$ aryl. In some instances, both rings of a polycyclic aryl group are aromatic (e.g., naphthyl). In other instances, polycyclic aryl groups may include a non-aromatic ring fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl," as defined herein, regardless of the point of attachment (e.g., both quinolin-5-yl and quinolin-2-yl are heteroaryl groups). In some instances, aryl is phenyl or naphthyl. In certain instances, aryl is phenyl.

The term "heteroaryl" refers to aryl groups (or rings) that contain from one to five heteroatoms selected from the group consisting of N, O, and S, wherein the nitrogen and sulfur atoms are optionally oxidized, and the nitrogen atom(s) are optionally quaternized. A heteroaryl group can be attached to the remainder of the molecule through a heteroatom as valency permits. In some instances, both rings of a polycyclic heteroaryl group are aromatic. In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. In some embodiments, the term "heteroaryl" encompasses 5- to 10-membered heteroaryl, 6- to 10-membered heteroaryl, 7- to 10-membered heteroaryl, 8- to 10-membered heteroaryl, 9- to 10-membered heteroaryl, 5- to 9-membered heteroaryl, 6- to 9-membered heteroaryl, 7- to 9-membered heteroaryl, 8- to 9-membered heteroaryl, 5- to 8-membered heteroaryl, 6- to 8-membered heteroaryl, 7- to 8-membered heteroaryl, 5- to 7-membered heteroaryl, 6- to 7-membered heteroaryl, or 5- to 6-membered heteroaryl.

The above terms (e.g., "alkyl," "aryl" and "heteroaryl"), in some embodiments, will include both substituted and unsubstituted forms of the indicated radical. The term "substituted" means that the specified group or moiety bears one or more substituents including, but not limited to, substituents such as alkoxy, acyl, acyloxy, alkoxycarbonyl, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, alkyl, alkenyl, alkynyl, heterocycloalkyl, heterocycloalkenyl, aralkyl, aminosulfonyl, sulfonylamino, sulfonyl, oxo and the like. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

As used herein, the term "heteroatom" is meant to include oxygen (O), nitrogen (N), sulfur (S), boron (B), and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein, a wavy line "" that intersects a bond in a chemical structure indicates the point of attachment of the atom to which the wavy bond is connected in the chemical structure to the remainder of a molecule, or to the remainder of a fragment of a molecule.

As used herein, the representation of a group (e.g., $X^a$) in parenthesis followed by a subscript integer range (e.g., $(X^a)_{0-1}$) means that the group can have the number of occurrences as designated by the integer range. For example, $(X^a)_{0-1}$ means the group $X^a$ can be absent or can occur one time.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the present disclosure can contain asymmetric or chiral centers, and therefore exist in different stereoisomeric forms. It is intended that all stereoisomeric forms of the compounds of the present disclosure, including but not limited to, diastereomers, enantiomers and atropisomers, as well as mixtures thereof such as racemic mixtures, form part of the present disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the present disclosure. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water. Certain compounds of the present disclosure can exist in unsolvated forms as well as solvated forms, including hydrated forms. In general, the solvated forms are equivalent to unsolvated forms and are intended to be encompassed within the scope of the present disclosure.

The term "co-crystal" as used herein refers to a solid that is a crystalline single phase material composed of two or more different molecular or ionic compounds generally in a stoichiometric ratio which are neither solvates nor simple salts. A co-crystal consists of two or more components that form a unique crystalline structure having unique properties. Co-crystals are typically characterized by a crystalline structure, which is generally held together by freely reversible, non-covalent interactions. As used herein, a co-crystal refers to a compound of the present disclosure and at least one other component in a defined stoichiometric ratio that form a crystalline structure.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure.

The compounds of the present disclosure can also contain unnatural proportions of atomic isotopes at one or more of the atoms that constitute such compounds. For example, the present disclosure also embraces isotopically-labeled variants of the present disclosure which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the present disclosure and include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present disclosure (e.g., those labeled with $^{3}H$ or 14C) are useful in compound and/or substrate tissue distribution assays. Tritiated ($^{3}H$) and carbon-14 ($^{14}C$) isotopes are useful for their ease of preparation and detectability. Further substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$ $^{11}C$, and $^{18}F$ are useful for positron emission tomography (PET) studies to examine substrate receptor occupancy. Isotopically labeled compounds of the present disclosure can generally be prepared by following procedures analogous to those disclosed in the Schemes and/or in the Examples herein below, by substituting an isotopically labeled reagent for a non-isotopically labeled reagent.

"Treating" or "treatment" of a disease in a patient refers to inhibiting the disease or arresting its development; or ameliorating or causing regression of the disease. As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the present disclosure contemplate any one or more of these aspects of treatment.

"Preventing", "prevention", or "prophylaxis" of a disease in a patient refers to preventing the disease from occurring in a patient that is predisposed or does not yet display symptoms of the disease.

The phrase "therapeutically effective amount" means an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "cancer" and "cancerous" refer to or describe the physiological condition in mammals that is typically characterized by unregulated cell growth.

It is appreciated that certain features of the present disclosure, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

II. Compounds

In one aspect, provided herein is a compound of formula (I')

(I')

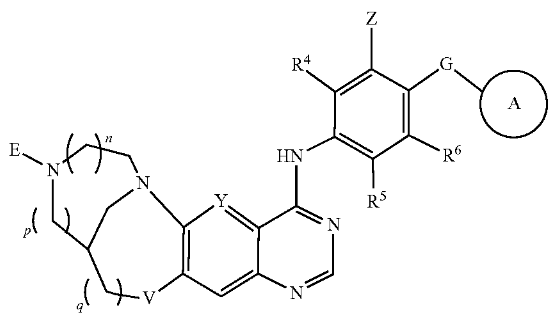

or a pharmaceutically acceptable salt, solvate, hydrate, or co-crystal thereof, or a mixture of any of the foregoing, wherein:

Ring A is

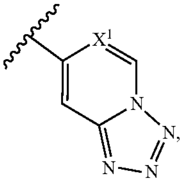

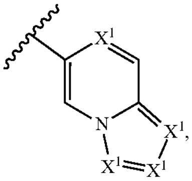

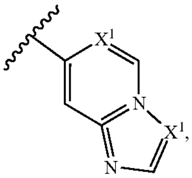

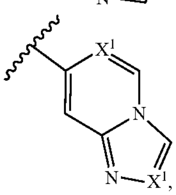

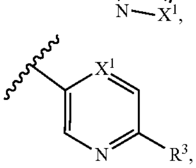

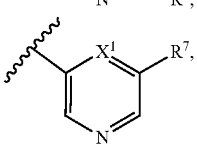

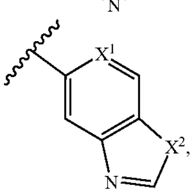

or

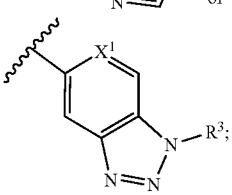

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen;

$R^6$ is —H or halogen;

$R^7$ is —H, halogen, $C_1$-$C_6$ alkyl, —$CD_3$ or $C_1$-$C_6$ cycloalkyl;

n is 1 or 2;

p is 0 or 1; and q is 1 or 2.

In some embodiments, n is 1 or 2. In some embodiments, n is 1. In other embodiments, n is 2. In some embodiments, p is 0 or 1. In some embodiments, p is 0. In other embodiments, p is 1. In some embodiments, q is 1 or 2. In some embodiments, q is 1. In other embodiments, q is 2. In some embodiments, n is 1, p is 0, and q is 1. In some embodiments, n is 1, p is 0, and q is 2. In some embodiments, n is 1, p is 1, and q is 1. In some embodiments, n is 1, p is 1, and q is 2. In some embodiments, n is 2, p is 0, and q is 1. In some embodiments, n is 2, p is 0, and q is 2. In some embodiments, n is 2, p is 1, and q is 1. In some embodiments, n is 2, p is 1, and q is 2.

In some embodiments, the compound of formula (I') is a compound of formula (I), or a pharmaceutically acceptable salt, solvate, hydrate, or co-crystal thereof, or a mixture of any of the foregoing. In one aspect, provided herein is a compound of formula (I)

(I)

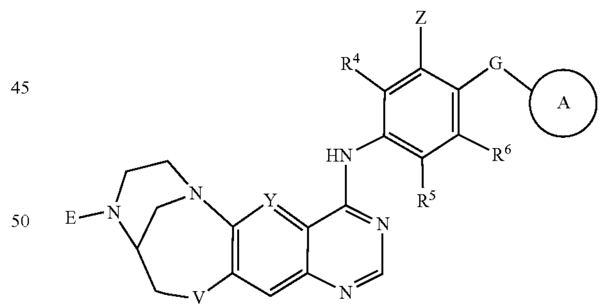

or a pharmaceutically acceptable salt solvate, hydrate, or co-crystal thereof, or a mixture of any of the foregoing, wherein:

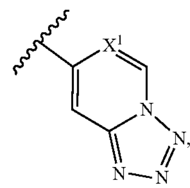

-continued

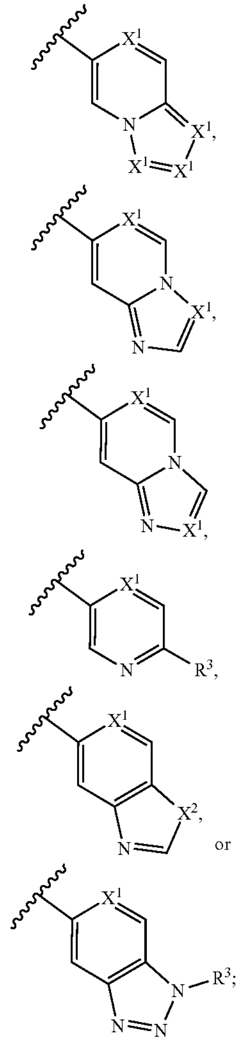

or

Ring A is

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$;

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen; and $R^6$ is —H or halogen.

In some embodiments, ring A is

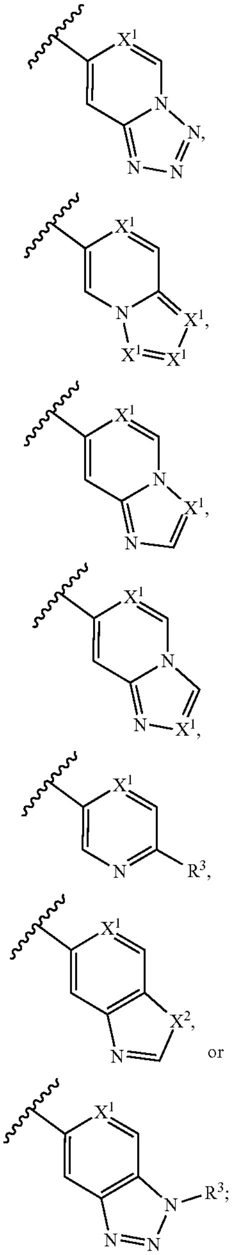

or

In some embodiments, ring A is

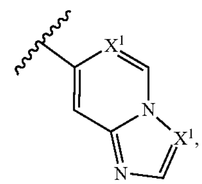

-continued
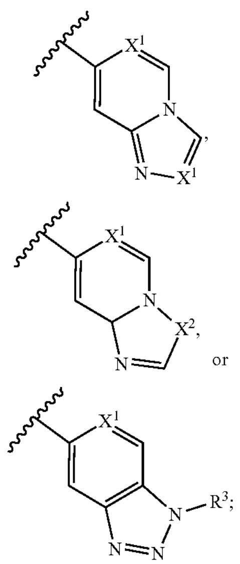
or
In some embodiments, ring A is
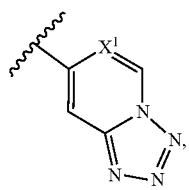
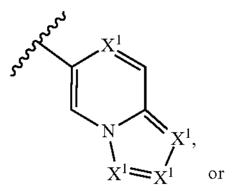
or
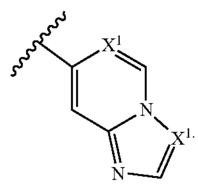
In some embodiments, ring A is
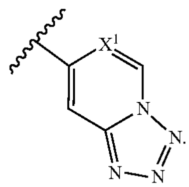
In some embodiments, ring A is
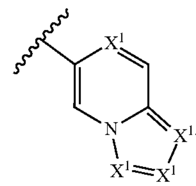
In some embodiments, ring A is
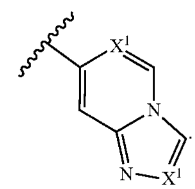
In some embodiments, ring A is
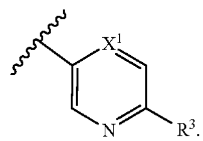
In some embodiments, ring A is
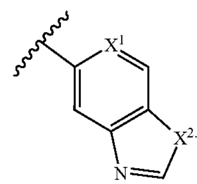
In some embodiments, ring A is
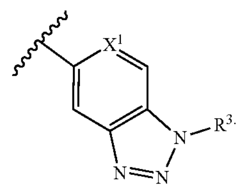
In some embodiments, ring A is
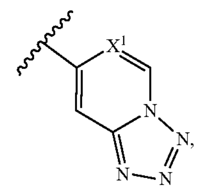

-continued
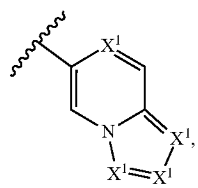
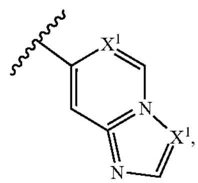
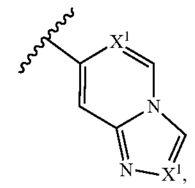
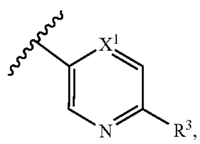
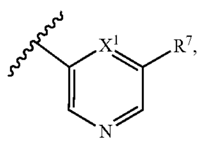
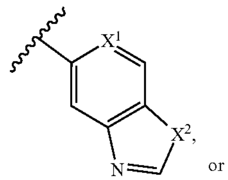
or
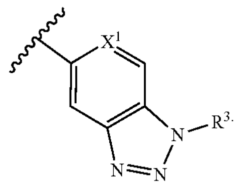
In some embodiments, ring A is
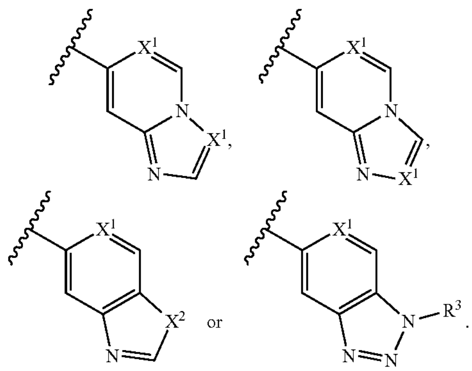
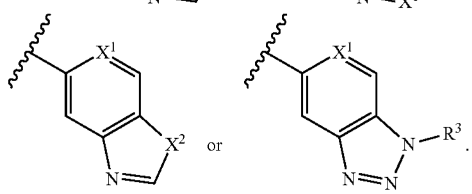
In some embodiments, ring A is
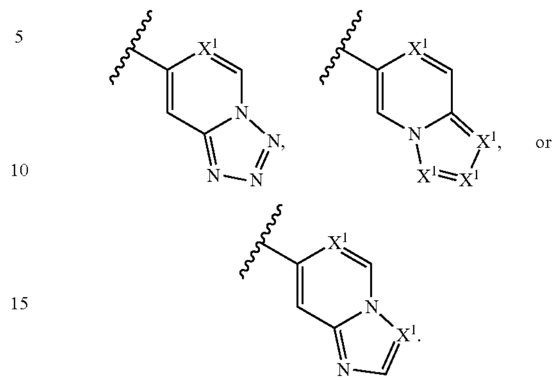
In some embodiments, ring A is
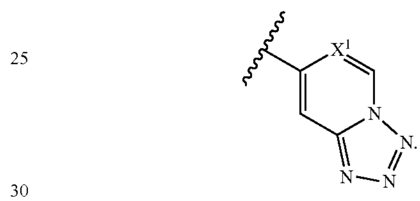
In some embodiments, ring A is
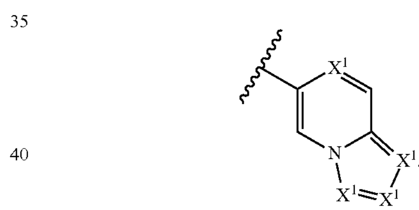
In some embodiments, ring A is
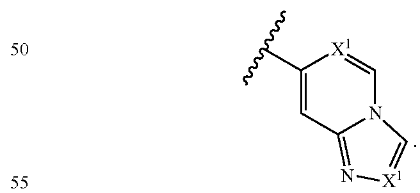
In some embodiments, ring A is
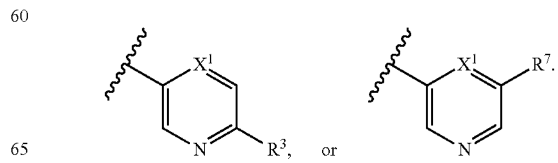

In some embodiments, ring A is
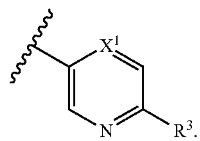
In some embodiments, ring A is
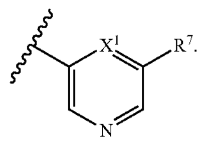
In some embodiments, ring A is
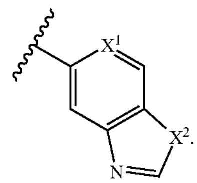
In some embodiments, ring A is
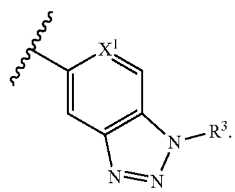
In some embodiments, ring A is
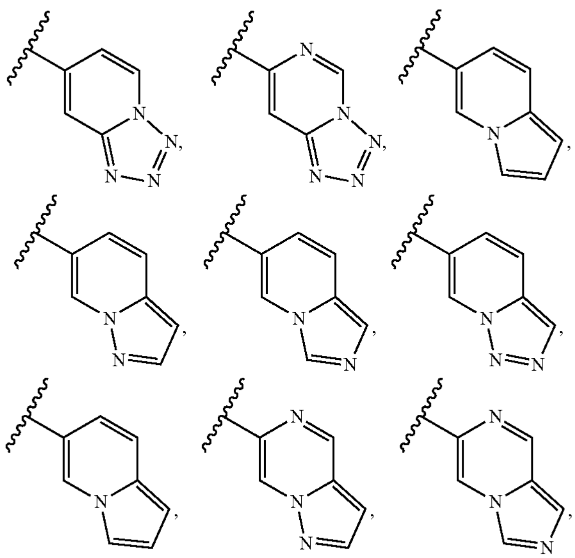
-continued
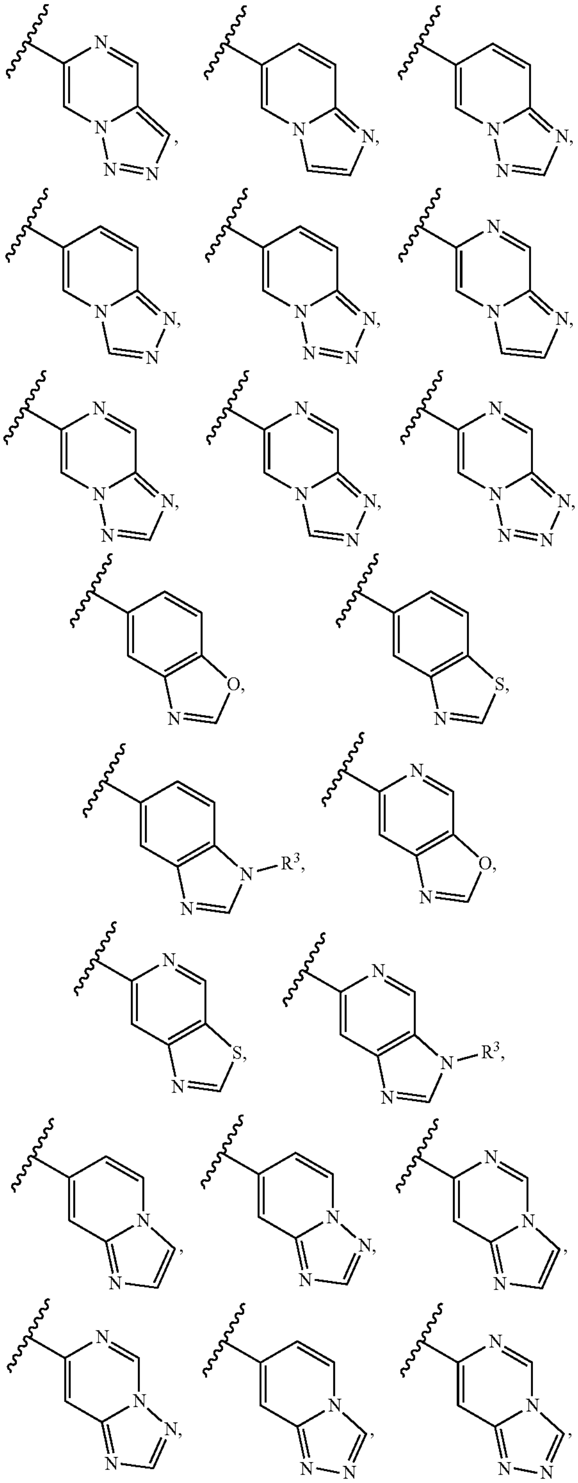
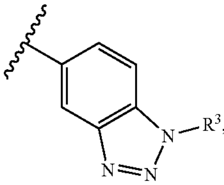
or
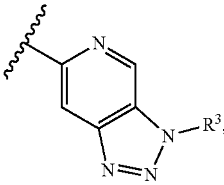
and $R^3$ is —H, $C_1$-$C_6$ alkyl, —$CD_3$ or $C_1$-$C_6$ cycloalkyl. In some embodiments, ring A is

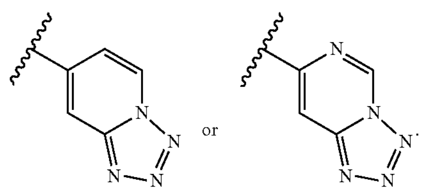 [SMILES: *c1ccn2nnnc2c1 ; *c1cc2nnnn2cn1]
or
In some embodiments, ring A is
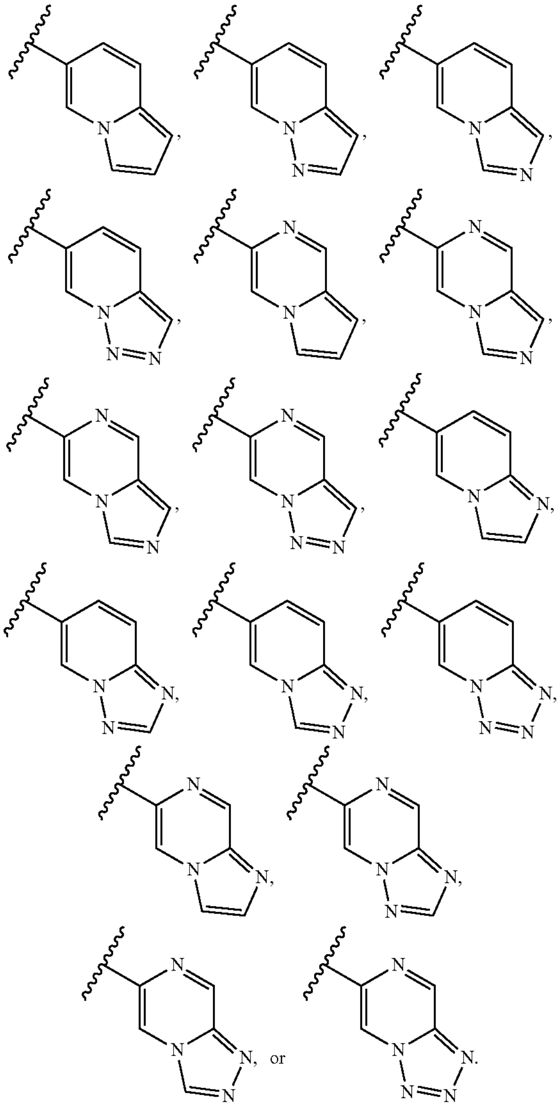
or
In some embodiments, ring A is
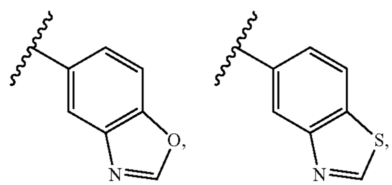
-continued
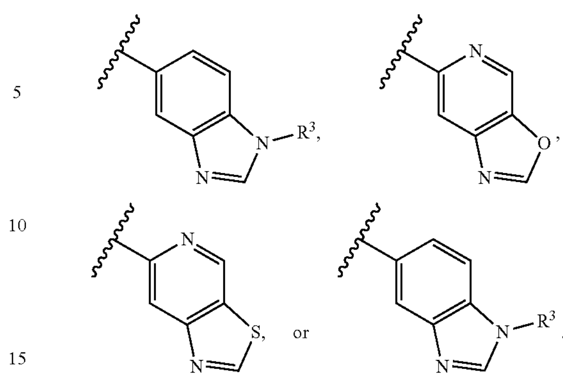
or
In some embodiments, ring A is
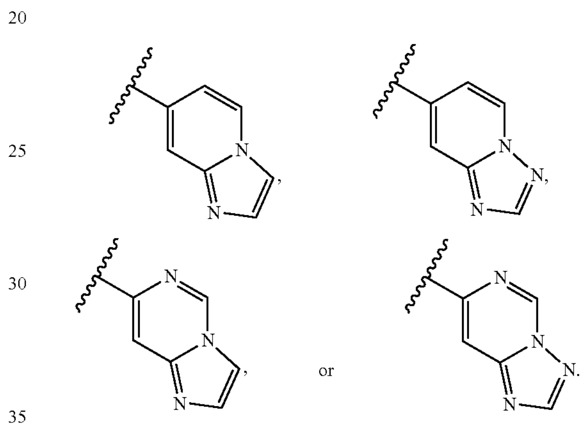
or
In some embodiments, ring A is
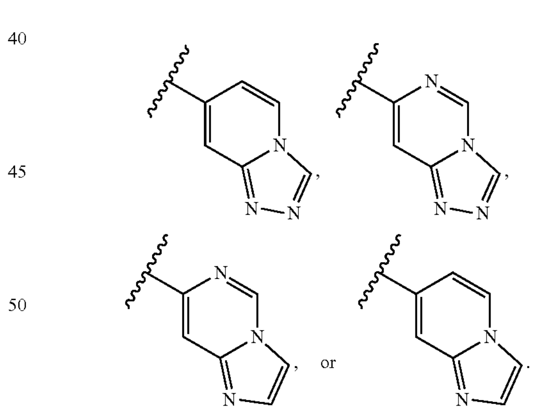
or
In some embodiments, ring A is
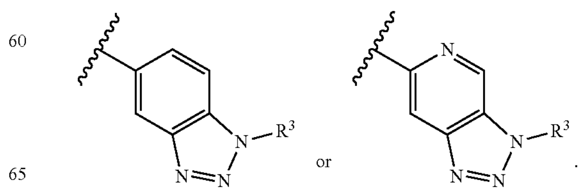
or In some embodiments, ring A is
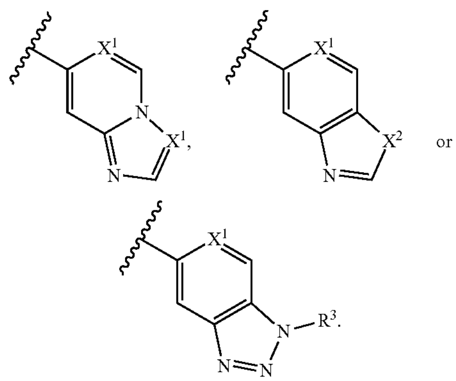
In some embodiments, ring A is
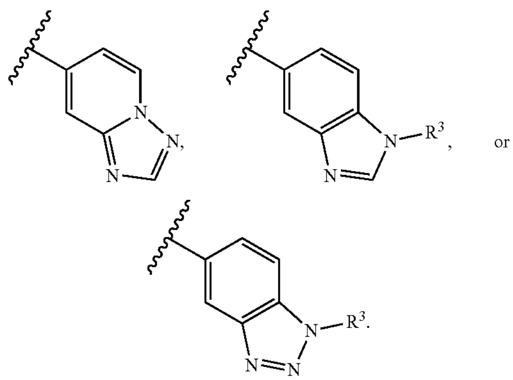
In some embodiments, ring A is
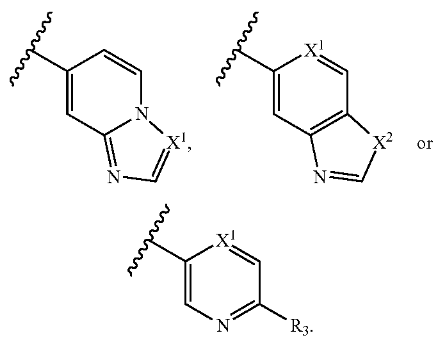
In some embodiments, ring A is
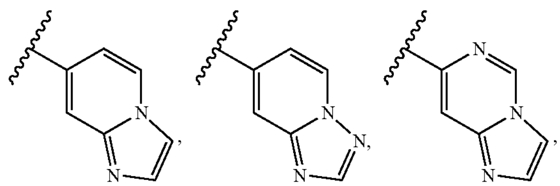
-continued
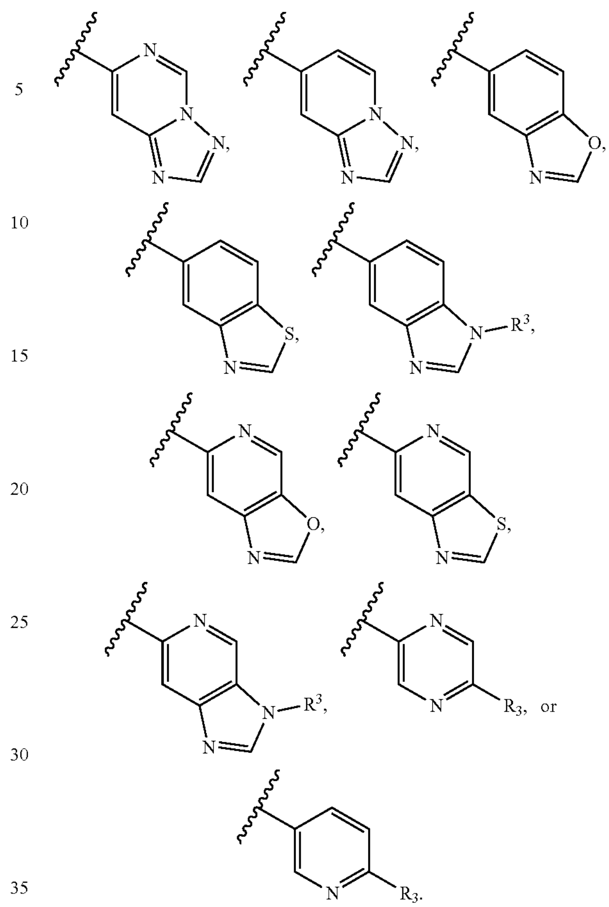
In some embodiments, ring A is
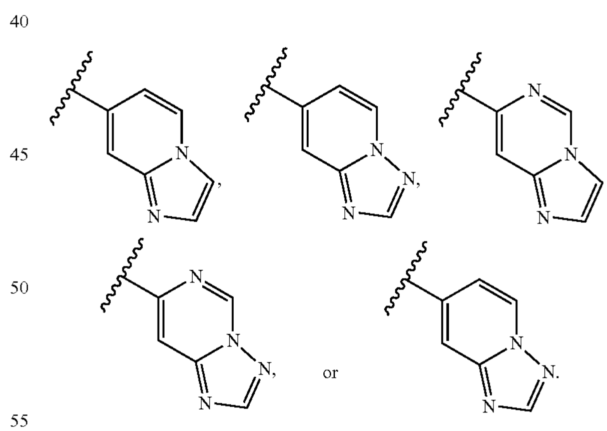
In some embodiments, ring A is
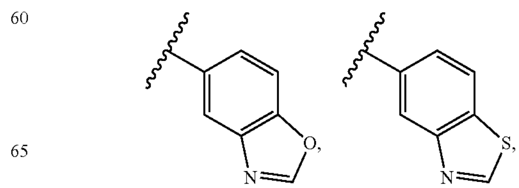

-continued
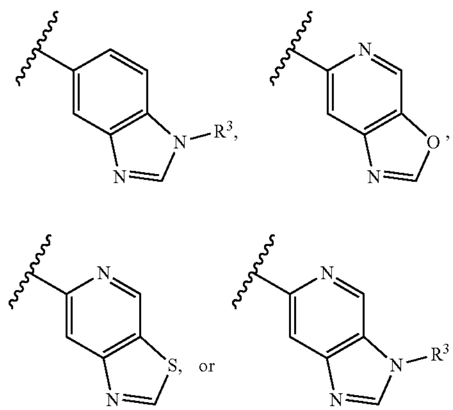
In some embodiments, ring A is
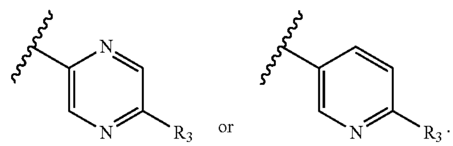
In some embodiments, ring A is
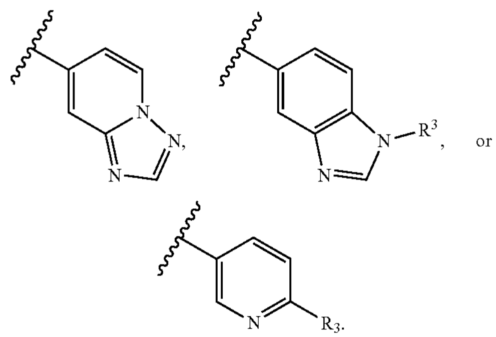
In some embodiments, ring A is
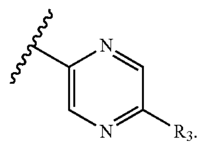
In some embodiments, ring A is
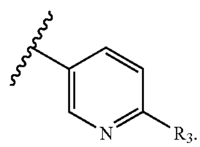
In some embodiments, ring A is
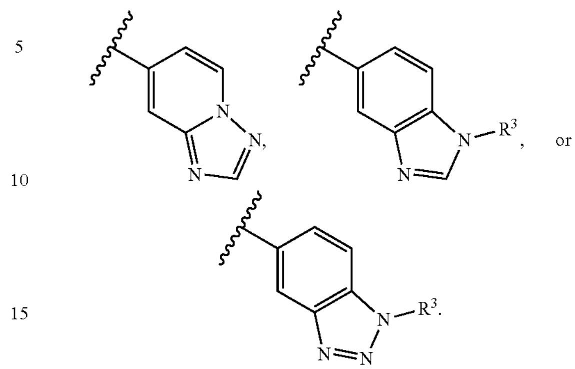
In some embodiments, ring A is
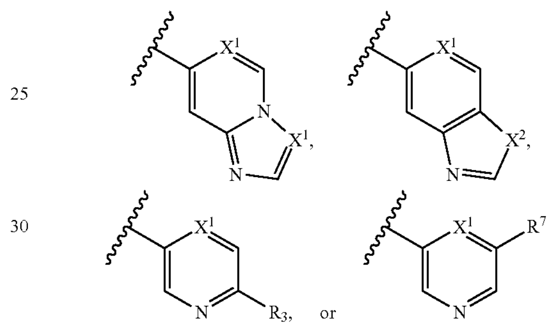
In some embodiments, In some embodiments, ring A is
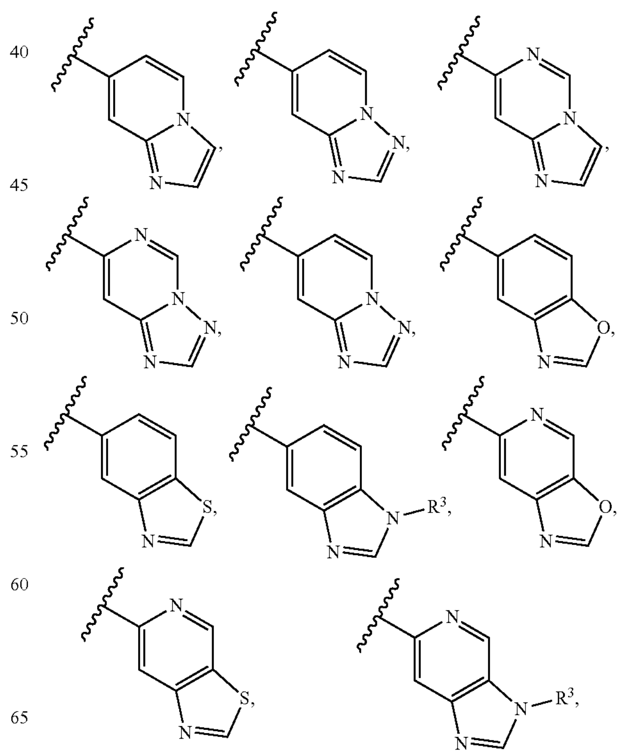

-continued

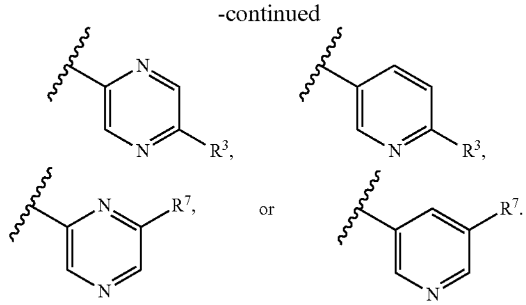

In some embodiments, ring A is

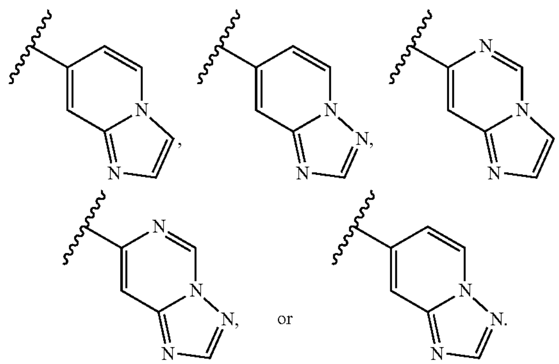

In some embodiments, ring A is

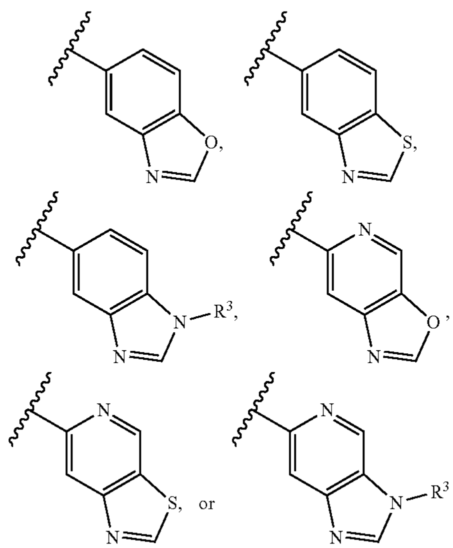

In some embodiments, ring A is

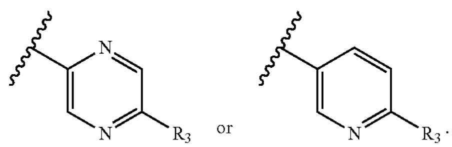

In some embodiments, ring A is

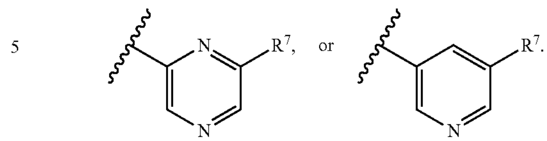

In some embodiments, ring A is

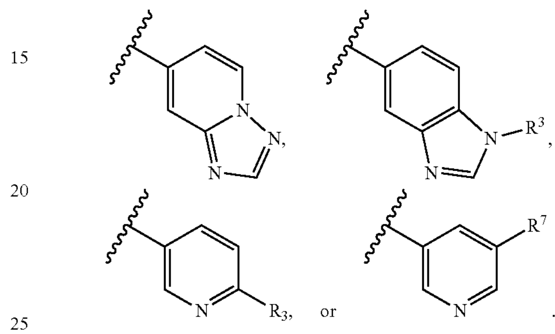

In some embodiments, ring A is

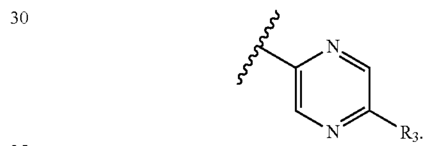

In some embodiments, ring A is

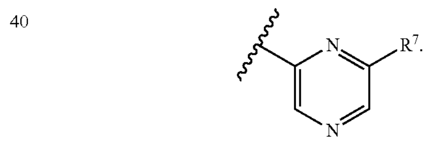

In some embodiments, ring A is

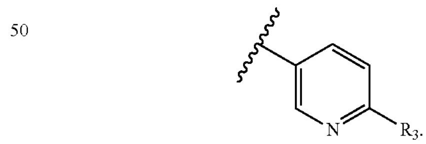

In some embodiments, ring A is

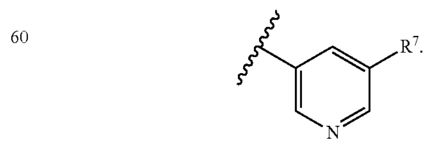

In some embodiments, $R^3$ is —H, $C_1$-$C_6$ alkyl, —$CD_3$ or $C_1$-$C_6$ cycloalkyl. In some embodiments, $R^3$ is —H. In some embodiments, $R^3$ is $C_1$-$C_6$ alkyl. In some embodiments, $R^3$ is methyl, ethyl, n-propyl, isopropyl, n-butyl, sec-butyl, isobutyl, tert-butyl,

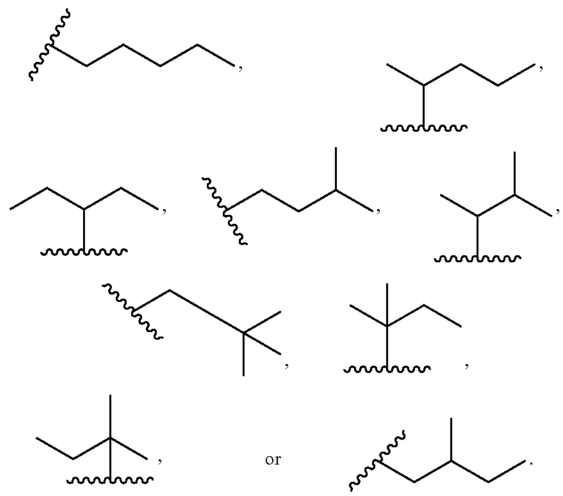

In some embodiments, $R^3$ is —H or —$CH_3$. In some embodiments, $R^3$ is —H. In some embodiments, $R^3$ is —$CH_3$. In some embodiments, $R^3$ is —$CD_3$.

In some embodiments, $R^7$ is —H, halogen, $C_1$-$C_6$ alkyl, —$CD_3$ or $C_1$-$C_6$ cycloalkyl. In some embodiments, $R^7$ is —H. In some embodiments, $R^7$ is halogen. In some embodiments, $R^7$ is F, Cl, or I. In some embodiments, $R^7$ is F. In some embodiments, $R^7$ is $C_1$. In some embodiments, $R^7$ is $C_1$-$C_6$ alkyl. In some embodiments, $R^7$ is methyl, ethyl, n-propyl, isopropyl, n-butyl, sec-butyl, isobutyl, tert-butyl,

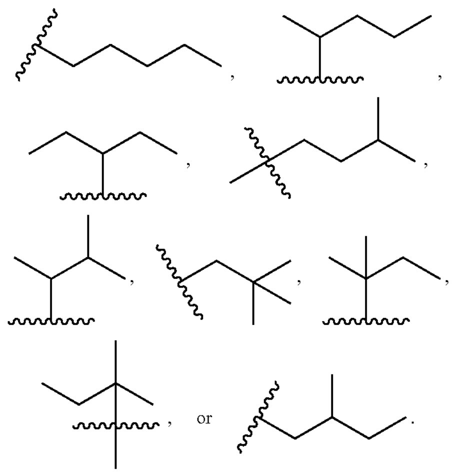

In some embodiments, $R^7$ is —H, F, —$CH_3$, or —$CH_2CH_3$. In some embodiments, $R^7$ is —H. In some embodiments, $R^7$ is F. In some embodiments, $R^7$ is —$CH_3$. In some embodiments, $R^7$ is —$CH_2CH_3$. In some embodiments, $R^7$ is —$CD_3$.

In some embodiments, $R^3$ is $C_1$-$C_6$ cycloalkyl. In some embodiments, $R^3$ is cyclopropyl, cyclobutyl, cyclopentyl, or cyclohexyl.

In some embodiments, ring A is

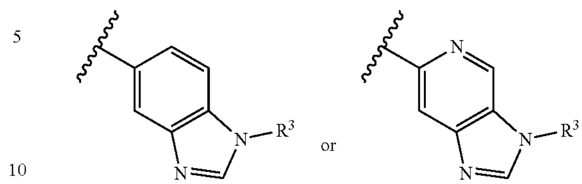

and $R^3$ is —H, $C_1$-$C_6$ alkyl, —$CD_3$ or $C_1$-$C_6$ cycloalkyl. In some embodiments, ring A is

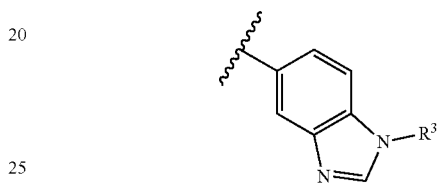

and $R^3$ is —H, $C_1$-$C_6$ alkyl, —$CD_3$ or $C_1$-$C_6$ cycloalkyl. In some embodiments, ring A is

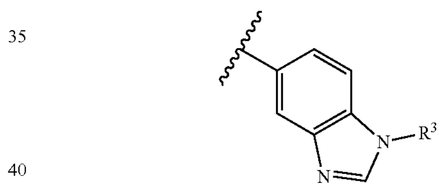

and $R^3$ is —H or $C_1$-$C_6$ alkyl. In some embodiments, ring A is

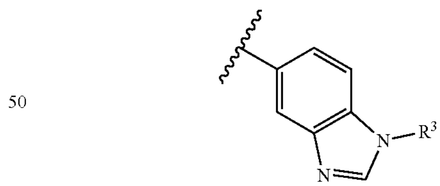

and $R^3$ is $C_1$-$C_6$ alkyl or $C_1$-$C_6$ cycloalkyl. In some embodiments, ring A is

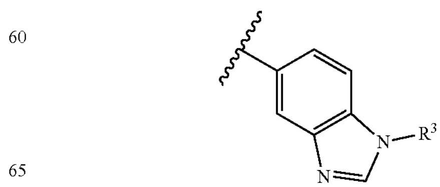

and $R^3$ is —H or $C_1$-$C_6$ cycloalkyl. In some embodiments, ring A is

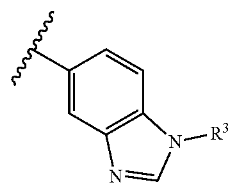

and $R^3$ is —$CD_3$. In some embodiments, ring A is

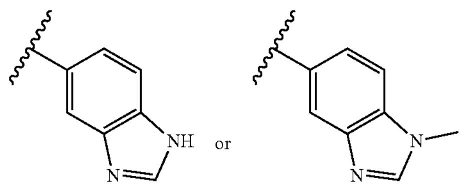

In some embodiments, ring A is

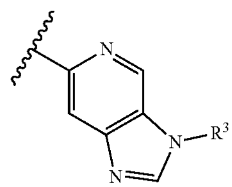

and $R^3$ is —H, $C_1$-$C_6$ alkyl, —$CD_3$ or $C_1$-$C_6$ cycloalkyl. In some embodiments, ring A is

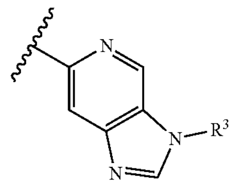

and $R^3$ is —H or $C_1$-$C_6$ alkyl. In some embodiments, ring A is

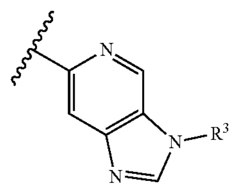

and $R^3$ is $C_1$-$C_6$ alkyl or $C_1$-$C_6$ cycloalkyl. In some embodiments, ring A is

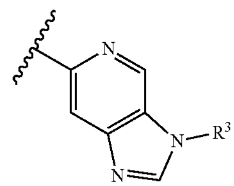

and $R^3$ is —H or $C_1$-$C_6$ cycloalkyl. In some embodiments, ring A is

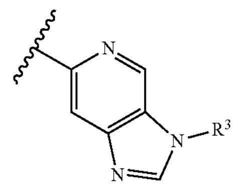

and $R^3$ is —$CD_3$. In some embodiments, ring A is

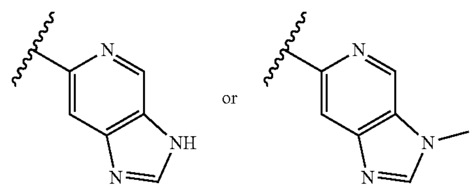

In some embodiments, ring A is

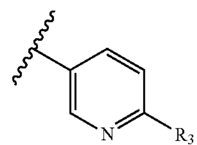

and $R^3$ is —H, $C_1$-$C_6$ alkyl, —$CD_3$ or $C_1$-$C_6$ cycloalkyl. In some embodiments, ring A is

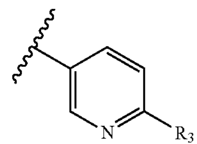

and $R^3$ is —H or $C_1$-$C_6$ alkyl. In some embodiments, ring A is

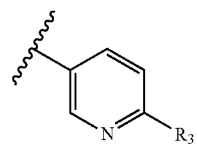

and $R^3$ is —H or $C_1$-$C_6$ cycloalkyl. In some embodiments, ring A is

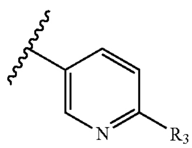

and $R^3$ is $C_1$-$C_6$ alkyl or $C_1$-$C_6$ cycloalkyl. In some embodiments, ring A is

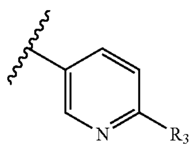

and $R^3$ is $C_1$-$C_6$ alkyl. In some embodiments, ring A is

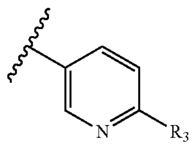

and $R^3$ is —$CD_3$. In some embodiments, ring A is

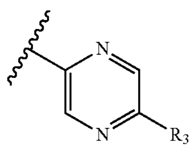

and $R^3$ is —H, $C_1$-$C_6$ alkyl, —$CD_3$ or $C_1$-$C_6$ cycloalkyl. In some embodiments, ring A is

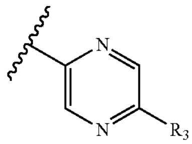

and $R^3$ is —H or $C_1$-$C_6$ alkyl. In some embodiments, ring A is

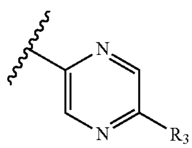

and $R^3$ is —H or $C_1$-$C_6$ cycloalkyl. In some embodiments, ring A is

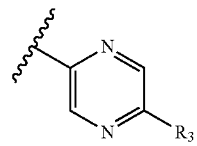

and $R^3$ is $C_1$-$C_6$ alkyl or $C_1$-$C_6$ cycloalkyl. In some embodiments, ring A is

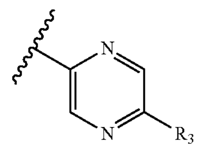

and $R^3$ is $C_1$-$C_6$ alkyl. In some embodiments, ring A is

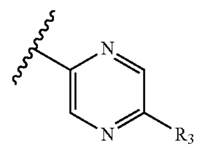

and $R^3$ is —$CD_3$. In some embodiments, ring A is

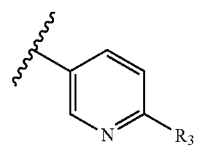

and $R^3$ is $C_1$-$C_6$ cycloalkyl. In some embodiments, ring A is

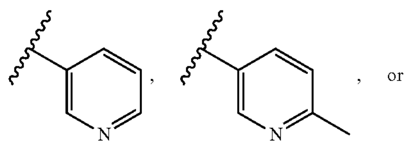

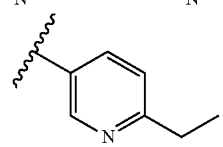

In some embodiments, ring A is

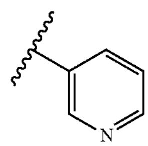

In some embodiments, ring A is

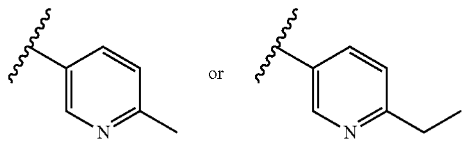

In some embodiments, ring A is

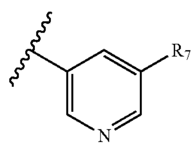

and $R^7$ is —H, halogen, $C_1$-$C_6$ alkyl, —$CD_3$ or $C_1$-$C_6$ cycloalkyl. In some embodiments, ring A is

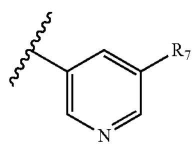

and $R^7$ is —H, or halogen. In some embodiments, ring A is

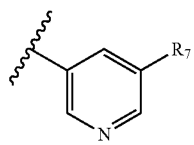

and $R^7$ is —H, or $C_1$-$C_6$ alkyl. In some embodiments, ring A is

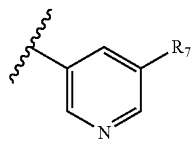

and $R^7$ is —H or $C_1$-$C_6$ cycloalkyl. In some embodiments, ring A is

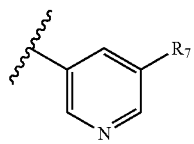

and $R^7$ is $C_1$-$C_6$ alkyl or $C_1$-$C_6$ cycloalkyl. In some embodiments, ring A is

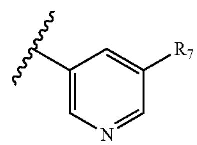

and $R^7$ is halogen or $C_1$-$C_6$ alkyl. In some embodiments, ring A is

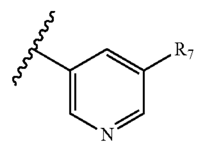

and $R^7$ is halogen. In some embodiments, ring A is

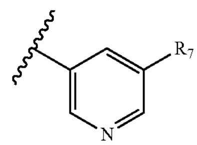

and $R^7$ is $C_1$-$C_6$ alkyl. In some embodiments, ring A is

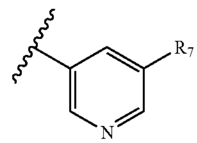

and $R^7$ is —$CD_3$. In some embodiments, ring A is

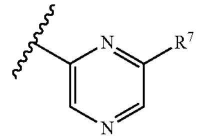

and $R^7$ is —H, halogen, $C_1$-$C_6$ alkyl, —$CD_3$ or $C_1$-$C_6$ cycloalkyl. In some embodiments, ring A is

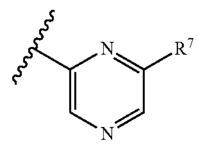

and $R^7$ is —H, or halogen. In some embodiments, ring A is

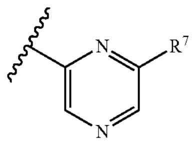

and $R^7$ is —H, or $C_1$-$C_6$ alkyl. In some embodiments, ring A is

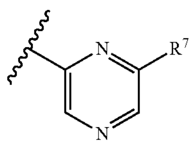

and $R^7$ is —H or $C_1$-$C_6$ cycloalkyl. In some embodiments, ring A is

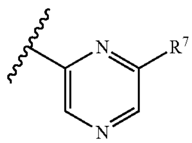

and $R^7$ is halogen, or $C_1$-$C_6$ alkyl. In some embodiments, ring A is

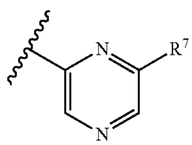

and $R^7$ is $C_1$-$C_6$ alkyl or $C_1$-$C_6$ cycloalkyl. In some embodiments, ring A is

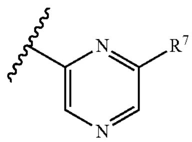

and $R^7$ is $C_1$-$C_6$ alkyl. In some embodiments, ring A is

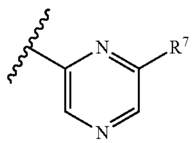

and $R^7$ is —$CD_3$. In some embodiments, ring A is

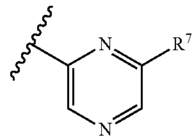

and $R^7$ is $C_1$-$C_6$alkyl. In some embodiments, ring A is

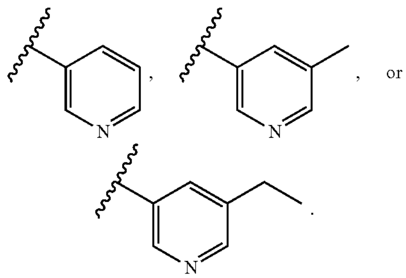

In some embodiments, ring A is

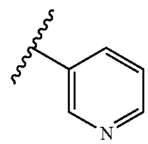

In some embodiments, ring A is

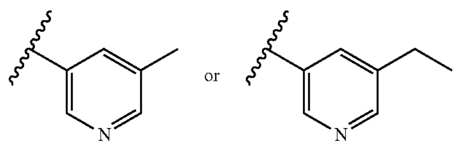

In some embodiments, ring A is

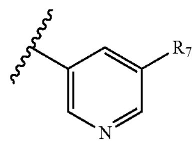

and $R^7$ is halogen. In some embodiments, ring A is

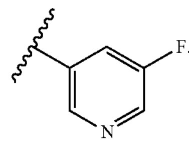 [SMILES: *c1cncc(F)c1]

In some embodiments, Z is —H, halogen, —C≡CH, —$OCH_3$, or $C_1$-$C_2$ alkyl. In some embodiments, Z is —H, —F —Cl, —Br, —I, —C≡CH, —$OCH_3$, —$CH_3$, or —$CH_2CH_3$. In some embodiments, Z is —H, —F, —Cl, —C≡CH, —$OCH_3$, or —$CH_3$. In some embodiments, Z is —H, —F, —Cl, or —$CH_3$. In some embodiments, Z is —H, —F, —Cl, —$CH_3$ or —$CH_2CH_3$. In some embodiments, Z is —$CH_3$. In some embodiments, Z is —H, —F, —Cl, or —$CH_3$. In some embodiments, Z is —F, —Cl, —$CH_3$ or —$CH_2CH_3$. In some embodiments, Z is —H, —F, or —Cl. In some embodiments, Z is —F or —Cl. In some embodiments, Z is —H or —F. In some embodiments, Z is —H or —Cl. In some embodiments, Z is —H, —$CH_3$ or —$CH_2CH_3$. In some embodiments, Z is —H or —$CH_3$. In some embodiments, Z is —$CH_3$ or —$CH_2CH_3$. In some embodiments, Z is —H. In some embodiments, Z is halogen. In some embodiments, Z is —F. In some embodiments, Z is —Cl. In some embodiments, Z is —C≡CH. In some embodiments, Z is —$OCH_3$. In some embodiments, Z is —$CH_3$. In some embodiments, Z is —$CH_2CH_3$.

In some embodiments, $R^1$ is $C_2$-$C_4$ alkenyl, optionally substituted by 1-4 substituents selected from the group consisting of halogen or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl. In some embodiments, $R^1$ is unsubstituted $C_2$-$C_4$ alkenyl. In some embodiments, $R^1$ is —CH═$CH_2$, —CH═CH—$CH_3$, or —C($CH_3$)═$CH_2$. In some embodiments, $R^1$ is —CH═$CH_2$, —CH═CH—$CH_3$, —CH═CH—$CH_2$—$CH_3$ or —C($CH_3$)═$CH_2$.

In some embodiments, $R^1$ is $C_2$-$C_4$ alkenyl, optionally substituted by 1-4 substituents selected from the group consisting of halogen. In some embodiments, $R^1$ is $C_2$-$C_4$ alkenyl, optionally substituted by 1-4 substituents selected from the group consisting of —F, —Cl, —Br, and —I. In some embodiments, $R^1$ is —CH═$CH_2$, —CH═CH—$CH_3$, or —C($CH_3$)═$CH_2$, each of which is independently optionally substituted by 1-4 substituents selected from the group consisting of —F, —Cl, —Br, and —I. In some embodiments, $R^1$ is —CH═$CH_2$ or —CH═CH—$CH_3$, optionally substituted by 1-4 substituents selected from the group consisting of —F, —Cl, —Br, and —I. In certain embodiments, $R^1$ is —CF═$CH_2$.

In some embodiments, $R^1$ is $C_2$-$C_4$ alkenyl, optionally substituted by 1-4 substituents selected from the group consisting of $C_1$-$C_3$ alkyl. In some embodiments, $R^1$ is $C_2$-$C_4$ alkenyl, optionally substituted by 1-4 substituents selected from the group consisting of $C_1$-$C_3$ alkyl. In some embodiments, $R^1$ is —CH═$CH_2$, —CH═CH—$CH_3$, or —C($CH_3$)═$CH_2$, each of which is independently optionally substituted by 1-4 substituents selected from the group consisting of $C_1$-$C_3$ alkyl. In some embodiments, $R^1$ is —CH═$CH_2$ or —CH═CH—$CH_3$, optionally substituted by 1-4 substituents selected from the group consisting of $C_1$-$C_3$ alkyl.

In some embodiments, $R^1$ is $C_2$-$C_4$ alkenyl, optionally substituted by 1-4 substituents selected from the group consisting of 3- to 7-membered carbon-linked N-heterocycloalkyl. In some embodiments, $R^1$ is $C_2$-$C_4$ alkenyl, optionally substituted by 1-4 substituents selected from the group consisting of 3- to 7-membered carbon-linked N-heterocycloalkyl, wherein each heterocyclic nitrogen atom, if present, is independently optionally substituted with $C_1$-$C_3$ alkyl. In some embodiments, $R^1$ is —CH═$CH_2$, —CH═CH—$CH_3$, or —C($CH_3$)═$CH_2$, each of which is independently optionally substituted by 1-4 substituents selected from the group consisting of 3- to 7-membered carbon-linked N-heterocycloalkyl, wherein each heterocyclic nitrogen atom, if present, is independently optionally substituted with $C_1$-$C_3$ alkyl. In some embodiments, $R^1$ is —CH═$CH_2$ or —CH═CH—$CH_3$, optionally substituted by 1-4 substituents selected from the group consisting of 3- to 7-membered carbon-linked N-heterocycloalkyl, wherein each heterocyclic nitrogen atom, if present, is independently optionally substituted with $C_1$-$C_3$ alkyl. In some embodiments, $R^1$ is CH═$CH_2$ or —CH═CH—$CH_3$, each of which is independently optionally substituted by 1-4 substituents selected from the group consisting of

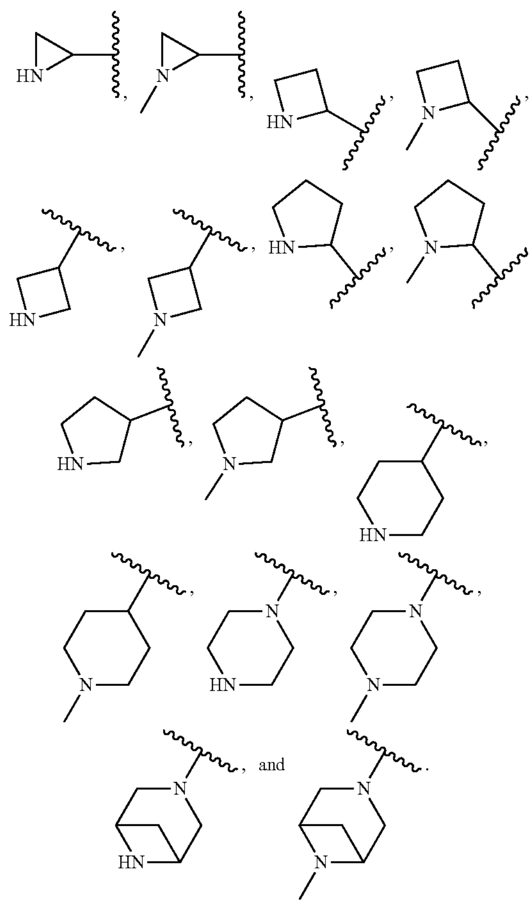

In other embodiments, $R^1$ is $C_2$-$C_4$ alkenyl, optionally substituted by 1-4 substituents selected from the group consisting of —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, wherein each heterocyclic nitrogen atom, if present, is independently optionally substituted with $C_1$-$C_3$ alkyl. In other embodiments, $R^1$ is $C_2$-$C_4$ alkenyl, optionally substituted by 1-4 substituents selected from the group consisting of —$NR^{1a}R^{1b}$, wherein each $R^{1a}$ and $R^{1b}$ are independently —H, $C_1$-$C_3$ alkyl, or —$CD_3$. In other embodiments, $R^1$ is $C_2$-$C_4$ alkenyl, optionally substituted by 1-4 substituents selected from the group consisting of —$NR^{1a}R^{1b}$ wherein each pair of geminal $R^{1a}$ and $R^{1b}$ may be taken together with the nitrogen atom to which they are attached to form a 3- to 6-membered N-heterocyclyl, wherein each heterocyclic nitrogen atom, if present, is independently optionally substituted with $C_1$-$C_3$ alkyl. In some embodiments, $R^1$ is —CH═$CH_2$, —CH═CH—$CH_3$, or —$C(CH_3)$=$CH_2$, each of which is independently optionally substituted by 1-4 substituents selected from the group consisting of —$NH_2$, —NH(methyl), —NH(ethyl), —NH(n-propyl), —NH(isopropyl), —N(methyl)(methyl), —N(methyl)(ethyl), —N(methyl)(n-propyl), —N(methyl)(isopropyl), —N(ethyl)(ethyl), —N(ethyl)(n-propyl), —N(ethyl)(isopropyl), —N(n-propyl)(n-propyl), —N(n-propyl)(isopropyl), —N(isopropyl)(isopropyl),

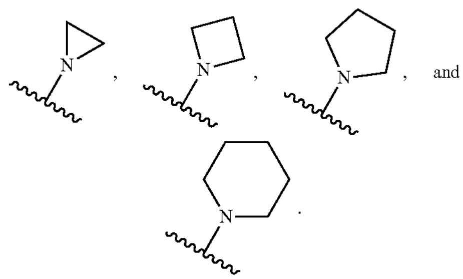

, , , and .

In some embodiments, $R^1$ is —CH=$CH_2$. In other embodiments, $R^1$ is —CH=CH—$CH_2$—$N(CH_3)_2$.

In some embodiments, $R^1$ is $C_2$-$C_4$ alkynyl, optionally substituted by 1-4 substituents selected from the group consisting of halogen or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$may be taken together with the nitrogen atom to which they are attached to form a 3- to 6-membered N-heterocyclyl. In some embodiments, $R^1$ is unsubstituted $C_2$-$C_4$ alkynyl. In some embodiments, $R^1$ is —C≡CH, —C≡C—$CH_3$, or —$CH_2$—C≡CH. In some embodiments, $R^1$ is —C≡C—$CH_3$.

In some embodiments, $R^1$ is $C_2$-$C_4$ alkynyl, optionally substituted by 1-4 substituents selected from the group consisting of halogen. In some embodiments, $R^1$ is $C_2$-$C_4$ alkynyl, optionally substituted by 1-4 substituents selected from the group consisting of —F, —Cl, —Br, and —I. In some embodiments, $R^1$ is —C≡CH, —C≡C—$CH_3$, or —$CH_2$—C≡CH, each of which is independently optionally substituted by 1-4 substituents selected from the group consisting of —F, —Cl, —Br, and —I. In some embodiments, $R^1$ is —C≡CH or —C≡C—$CH_3$, optionally substituted by 1-4 substituents selected from the group consisting of —F, —Cl, —Br, and —I.

In some embodiments, $R^1$ is $C_2$-$C_4$ alkynyl, optionally substituted by 1-4 substituents selected from the group consisting of $C_1$-$C_3$ alkyl. In some embodiments, $R^1$ is —C≡CH, —C≡C—$CH_3$, or —$CH_2$—C≡CH, each of which is independently optionally substituted by 1-4 substituents selected from the group consisting of $C_1$-$C_3$ alkyl. In some embodiments, $R^1$ is —C≡CH or —C≡C—$CH_3$, optionally substituted by 1-4 substituents selected from the group consisting of $C_1$-$C_3$ alkyl.

In some embodiments, $R^1$ is $C_2$-$C_4$ alkynyl, optionally substituted by 1-4 substituents selected from the group consisting of 3- to 7-membered carbon-linked N-heterocycloalkyl, wherein each heterocyclic nitrogen atom, if present, is independently optionally substituted with $C_1$-$C_3$ alkyl. In some embodiments, $R^1$ is —C≡CH, —C≡C—$CH_3$, or —$CH_2$—C≡CH, each of which is independently optionally substituted by 1-4 substituents selected from the group consisting of 3- to 7-membered carbon-linked N-heterocycloalkyl, wherein each heterocyclic nitrogen atom, if present, is independently optionally substituted with $C_1$-$C_3$ alkyl. In some embodiments, $R^1$ is —C≡CH or —C≡C—$CH_3$, optionally substituted by 1-4 substituents selected from the group consisting of 3- to 7-membered carbon-linked N-heterocycloalkyl, wherein each heterocyclic nitrogen atom, if present, is independently optionally substituted with $C_1$-$C_3$ alkyl. In some embodiments, $R^1$ is —C≡CH or —C≡C—$CH_3$, each of which is independently optionally substituted by 1-4 substituents selected from the group consisting of

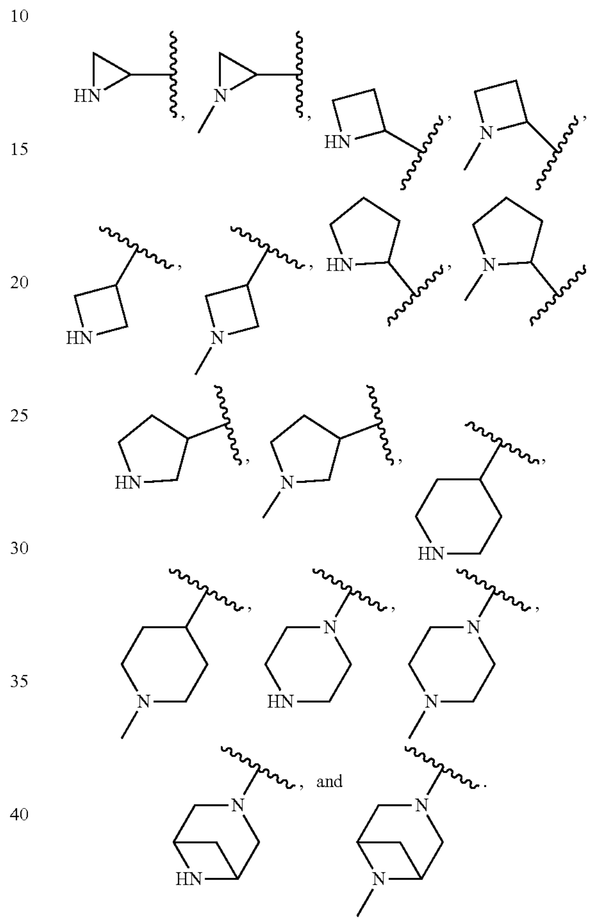

, , , , , , , , , , , , , , and .

In some embodiments, $R^1$ is $C_2$-$C_4$ alkynyl, optionally substituted by 1-4 substituents selected from the group consisting of —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, wherein each heterocyclic nitrogen atom, if present, is independently optionally substituted with $C_1$-$C_3$ alkyl. In some embodiments, $R^1$ is $C_2$-$C_4$ alkynyl, optionally substituted by 1-4 substituents selected from the group consisting of halogen or —$NR^{1a}R^{1b}$ wherein each $R^{1a}$ and $R^{1b}$ are independently —H, $C_1$-$C_3$ alkyl, or —$CD_3$. In some embodiments, $R^1$ is $C_2$-$C_4$ alkynyl, optionally substituted by 1-4 substituents selected from the group consisting of halogen or —$NR^{1a}R^{1b}$, wherein each pair of geminal $R^{1a}$ and $R^{1b}$ may be taken together with the nitrogen atom to which they are attached to form a 3- to 6-membered N-heterocyclyl, wherein each heterocyclic nitrogen atom, if present, is independently optionally substituted with $C_1$-$C_3$ alkyl. In some embodiments, $R^1$ is —C≡CH, —C≡C≡$CH_3$, or —$CH_2$—C≡CH, each of which is independently optionally substituted by 1-4 substituents selected from the group consisting of —$NH_2$, —NH(methyl), —NH(ethyl), —NH(n-propyl), —NH(isopropyl), —N(methyl)(methyl), —N(methyl)(ethyl), —N(methyl)(n-propyl), —N(methyl)(isopropyl), —N(ethyl)(ethyl), —N(ethyl)(n-propyl), —N(ethyl)(isopropyl), —N(n-propyl)(n-propyl), —N(n-propyl)(isopropyl), —N(isopropyl)(isopropyl),

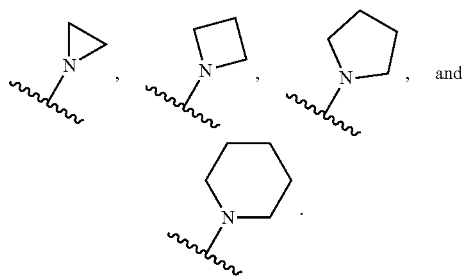

In some embodiments, the double bond of the $C_2$-$C_4$ alkenyl or the triple bond of the $C_2$-$C_4$ alkynyl of $R^1$ is conjugated to the carbonyl to which $R^1$ is attached.

In some embodiments, Y is N. In other embodiments, Y is C—$R^y$, wherein $R^y$ is —H or —F. In some embodiments, Y is C—$R^y$, wherein $R^y$ is —H. In other embodiments, Y is C—$R^y$, wherein $R^y$ is —F. In some embodiments, Y is N or C—$R^y$, wherein $R^y$ is —H. In some embodiments, Y is N or C—$R^y$, wherein $R^y$ is —F.

In some embodiments, V is O or S. In some embodiments, V is O or N—$R^2$. In some embodiments, V is S or N—$R^2$. In some embodiments V is O. In other embodiments, V is S. In other embodiments, V is N—$R^2$.

In some embodiments, V is N—$R^2$ and $R^2$ is $C_1$-$C_6$ alkyl optionally substituted by 1-4 fluorines. In some embodiments, V is methyl, ethyl, n-propyl, isopropyl, n-butyl, sec-butyl, isobutyl, tert-butyl,

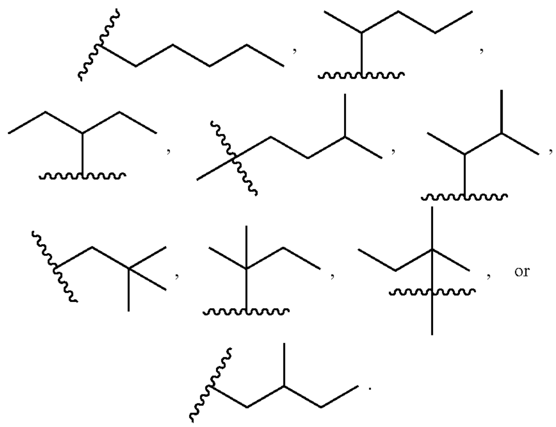

In some embodiments, V is N—$R^2$ and $R^2$ is $C_1$-$C_6$ cycloalkyl optionally substituted by 1-4 fluorines. In some embodiments, V is N—$R^2$ and $R^2$ is cyclopropyl, cyclobutyl, cyclopentyl, or cyclohexyl.

In some embodiments, Y is N and V is O or S. In some embodiments, Y is N and V is O or N—$R^2$. In some embodiments, Y is N and V is S or N—$R^2$. In some embodiments, Y is C—$R^y$ and V is O or N—$R^2$. In some embodiments, Y is C—$R^y$ and V is S or N—$R^2$. In some embodiments, Y is N or C—$R^y$ and V is O. In some embodiments, Y is N or C—$R^y$ and V is S. In some embodiments, Y is N or C—$R^y$ and V is N—$R^2$.

In some embodiments, Y is N and V is O. In some embodiments, Y is N and V is S. In some embodiments, Y is N and V is N—$R^2$. In some embodiments, Y is C—$R^y$ and V is O or S. In some embodiments, Y is C—$R^y$ and V is O. In some embodiments, Y is C—$R^y$ and V is S. In some embodiments, Y is C—$R^y$ and V is N—$R^2$.

In some embodiments, G is —O—, —C(=O)—, —S—, —S(O)—, —$S(O)_2$—, or —$CH_2$—. In some embodiments, G is —O—, —S—, or —$CH_2$—. In some embodiments, G is —C(=O)—, —S(O)—, or —$S(O)_2$—. In some embodiments, G is —O—, —C(=O)—, or —$CH_2$—. In some embodiments, G is —O— or —S—. In some embodiments, G is —O— or —$CH_2$—. In some embodiments, G is —C(=O) or —S(O)—. In some embodiments, G is —O—. In other embodiments, G is —C(=O)—. In other embodiments, G is —S—, —S(O)—, or —$S(O)_2$—. In other embodiments, G is —$CH_2$—.

In some embodiments, $R^4$ is —H. In other embodiments, $R^4$ is halogen. In some embodiments, $R^4$ is —F, —Cl, —Br, or —I. In other embodiments, $R^4$ is —F. In some embodiments, $R^5$ is —H. In other embodiments, $R^5$ is halogen. In some embodiments, $R^5$ is —F, —Cl, —Br, or —I. In some embodiments, $R^5$ is —F. In some embodiments, $R^4$ is —H and $R^5$ is —H. In some embodiments, $R^4$ is —H and $R^5$ is —F. In some embodiments, $R^4$ is —F and $R^5$ is —H. In some embodiments, $R^4$ is —F and $R^5$ is —F.

In some embodiments, $R^6$ is —H. In other embodiments, $R^6$ is halogen. In some embodiments $R^6$ is —F, —Cl, —Br, or —I. In some embodiments, $R^6$ is —H, —F or —Cl. In some embodiments, $R^6$ is —F. In other embodiments, $R^6$ is —Cl.

In some embodiments, the compound of formula (I) is a compound of formula (I-a-1), (I-a-2), or (I-a-3):

(I-a-1)

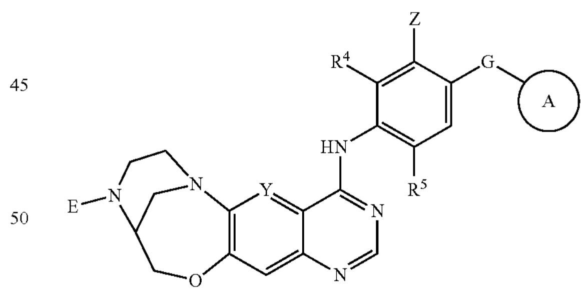

, (I-a-2)

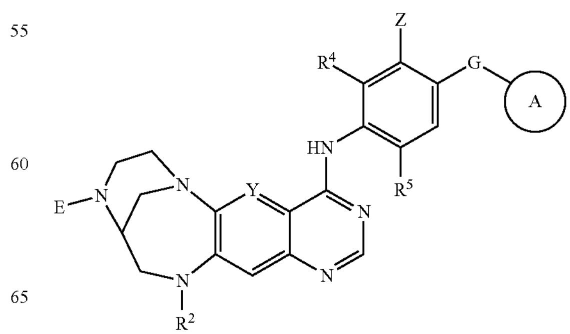

or

-continued (I-a-3)

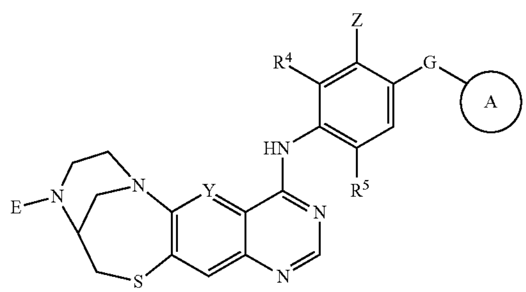

wherein $R^4$, $R^5$, E, Y, Z, G, and ring A are as defined for formula (I). In some embodiments, the compound is a compound of formula (I-a-1). In some embodiments, the compound is a compound of formula (I-a-2). In some embodiments, the compound is a compound of formula (I-a-3). In any variation of formula (I-a-1), (I-a-2), or (I-a-3), Z is —H, —F, —Cl, —Br, —I, —C≡CH, —$OCH_3$, —$CH_3$, or —$CH_2CH_3$; Y is N, C—H, or C—F; G is —O—, —C(=O)—, —S—, —S(O)—, —$S(O)_2$—, or —$CH_2$—; and ring A is

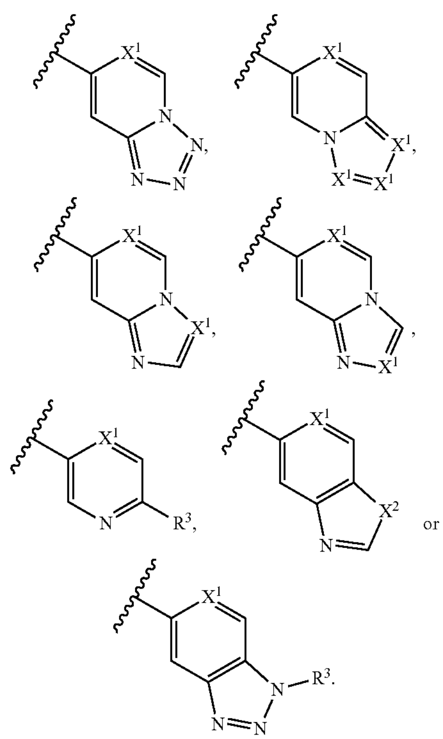

or

In some embodiments, ring A is

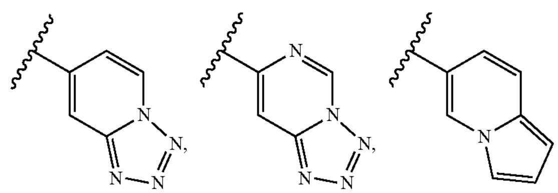

-continued

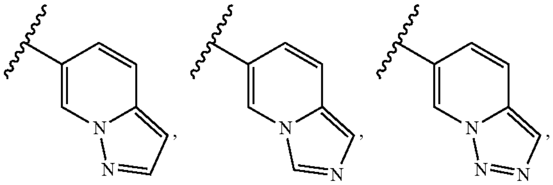

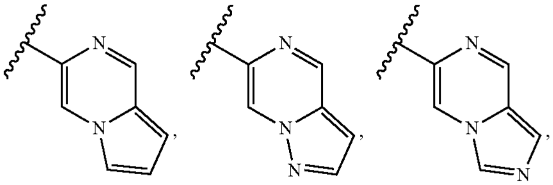

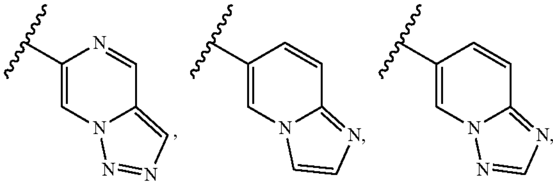

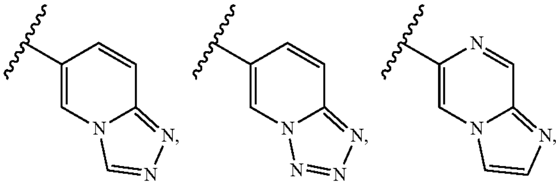

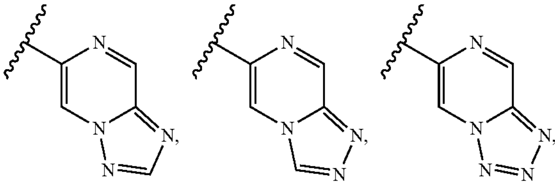

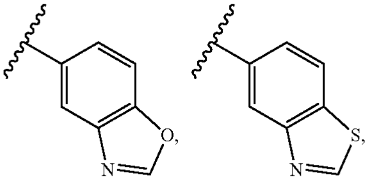

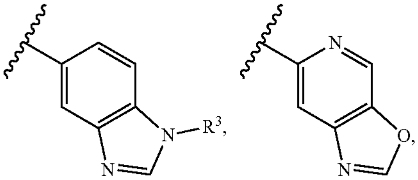

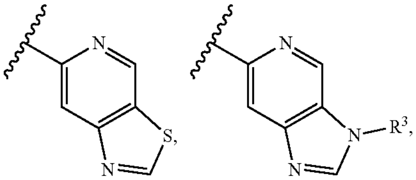

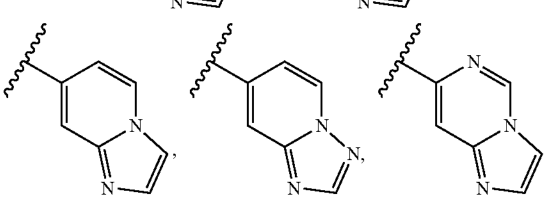

-continued

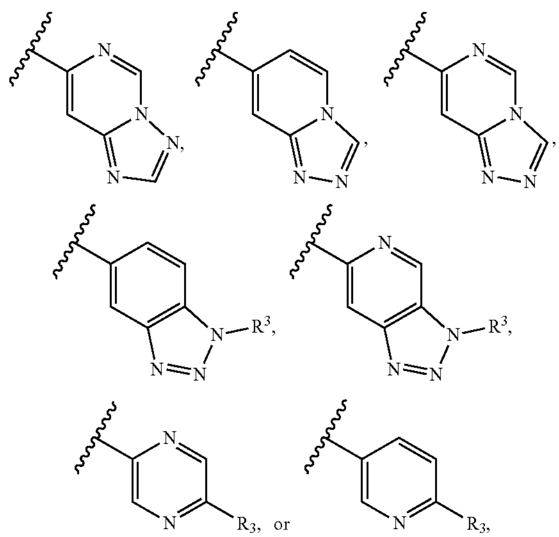

and $R^3$ is is —H, $C_1$-$C_6$ alkyl, —$CD_3$ or $C_1$-$C_6$ cycloalkyl. In some variations, $R^4$, $R^5$, E, Y, Z, G, and ring A of formula (I-a-1), (I-a-2), or (I-a-3) are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-a-1), (I'-a-2), or (I-a-3):

(I'-a-1)

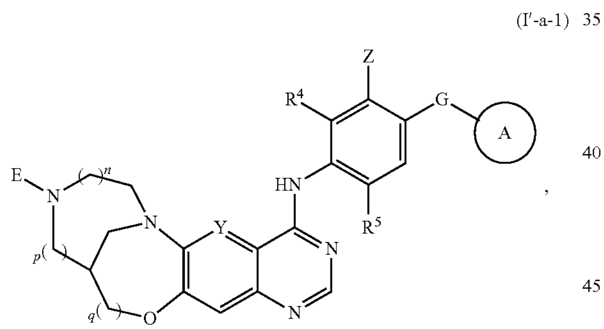

(I'-a-2)

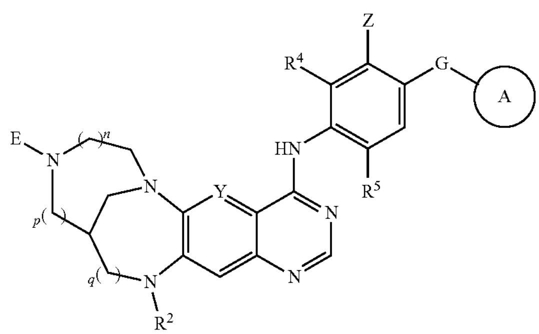

or,

-continued (I'-a-3)

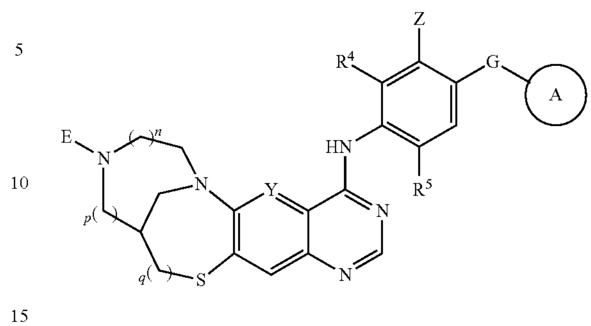

wherein $R^4$, $R^5$, $R^7$, E, Y, Z, G, ring A, n, p, and q, are as defined for formula (I'). In some embodiments, the compound is a compound of formula (I'-a-1). In some embodiments, the compound is a compound of formula (I'-a-2). In some embodiments, the compound is a compound of formula (I'-a-3). In any variation of formula (I'-a-1), (I'-a-2), or (I'-a-3), Z is —H, —F, —Cl, —Br, —I, —C≡CH, —$OCH_3$, —$CH_3$, or —$CH_2CH_3$; Y is N, C—H, or C—F; G is —O—, —C(═O)—, —S—, —S(O)—, —$S(O)_2$—, or —$CH_2$—; and ring A is

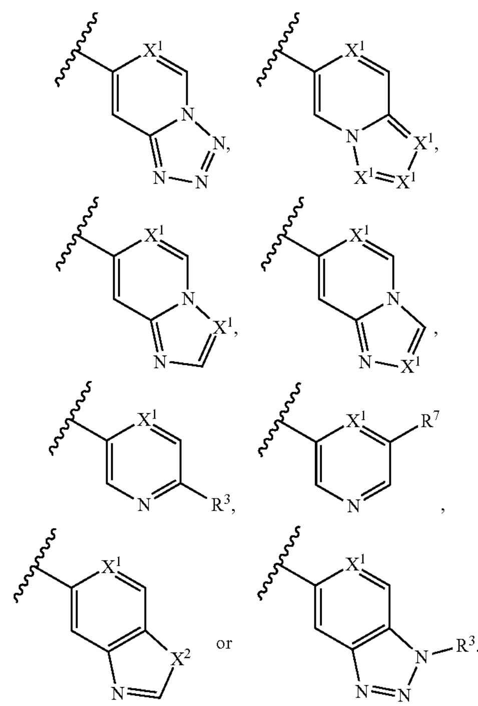

In some embodiments, ring A is NKR

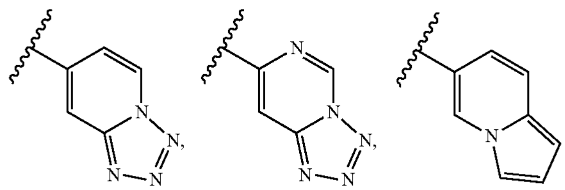

-continued

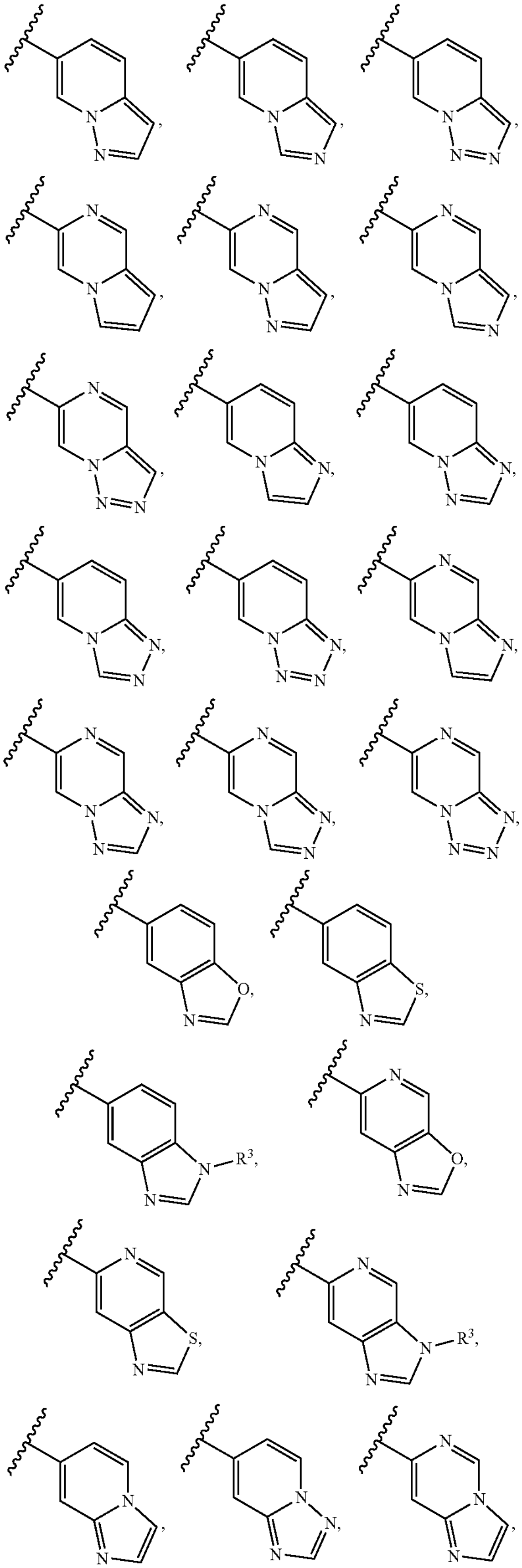

-continued

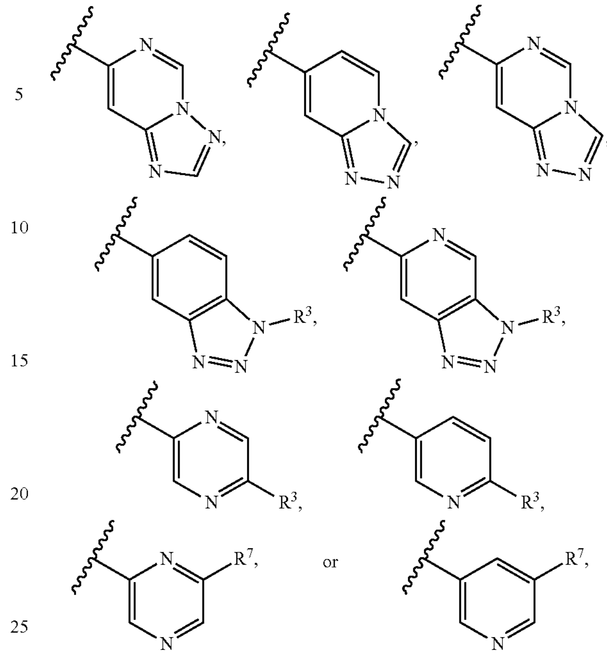

wherein $R^3$ is —H, $C_1$-$C_6$ alkyl, —$CD_3$ or $C_1$-$C_6$ cycloalkyl, and $R^7$ is —H, halogen, $C_1$-$C_6$ alkyl, —$CD_3$ or $C_1$-$C_6$ cycloalkyl.

In some embodiments, the compound of formula (I) is a compound of formula (I-b-1) or (I-b-2):

(I-b-1)

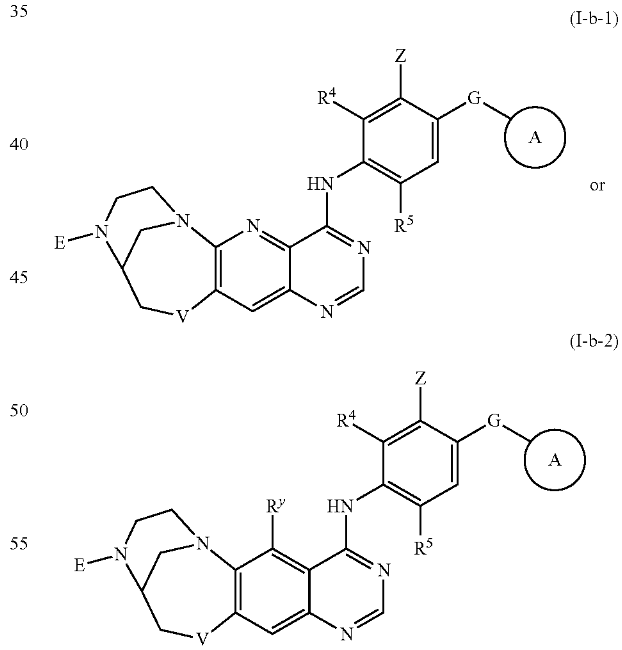

or (I-b-2)

wherein $R^4$, $R^5$, E, V, $R^y$, Z, G, and ring A are as defined for formula (I). In some embodiments, the compound is a compound of formula (I-b-1). In some embodiments, the compound is a compound of formula (I-b-2). In any variation of formula (I-b-1) or (I-b-2), Z is —H, —F —Cl, —Br, —I, —C≡CH, —$OCH_3$, —$CH_3$, or —$CH_2CH_3$; V is O, S, or $NR^2$, wherein $R^2$ is $C_1$-$C_6$ alkyl or $C_1$-$C_6$ cycloalkyl, each of which is independently optionally substituted by 1-4 fluorines; G is —O—, —C(═O)—, —S—, —S(O)—, —$S(O)_2$—, or —$CH_2$—; and ring A is
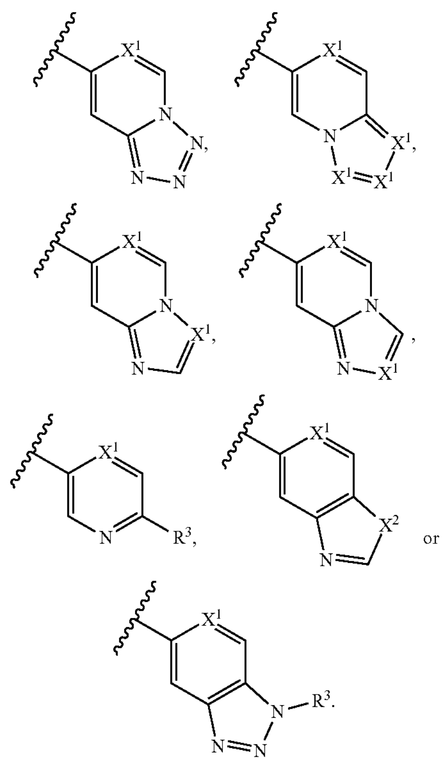
or
In some embodiments, ring A is
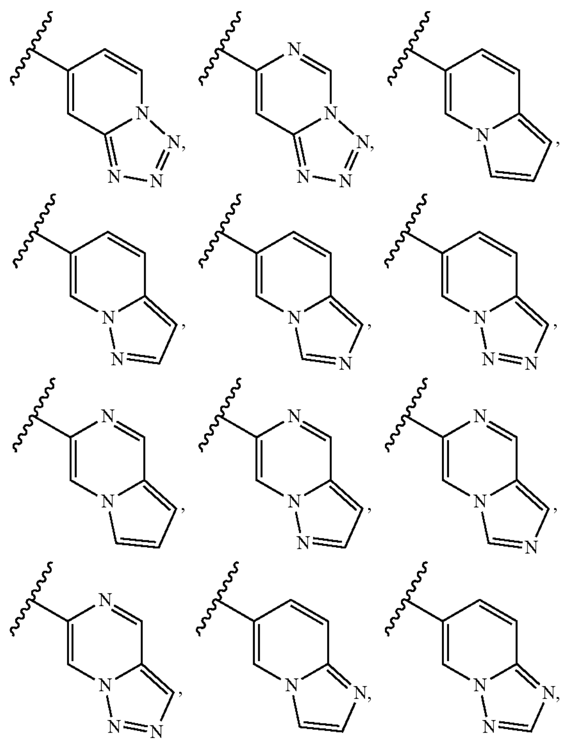
-continued
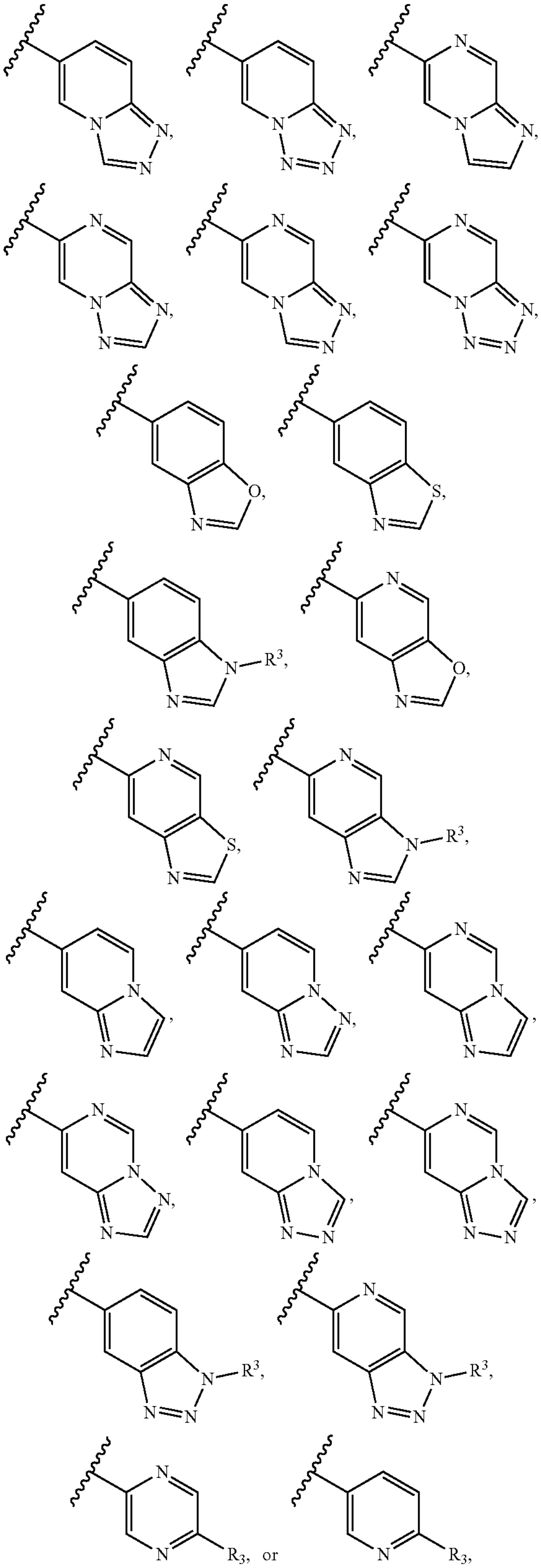
or
and $R^3$ is —H, $C_1$-$C_6$ alkyl, —$CD_3$ or $C_1$-$C_6$ cycloalkyl. In some variations, $R^4$, $R^5$, E, V, $R^y$, Z, G, and ring A of formula (I-b-1) or (1-b-2) are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-b-1) or (I'-b-2):

(I'-b-1)

or (I'-b-2)

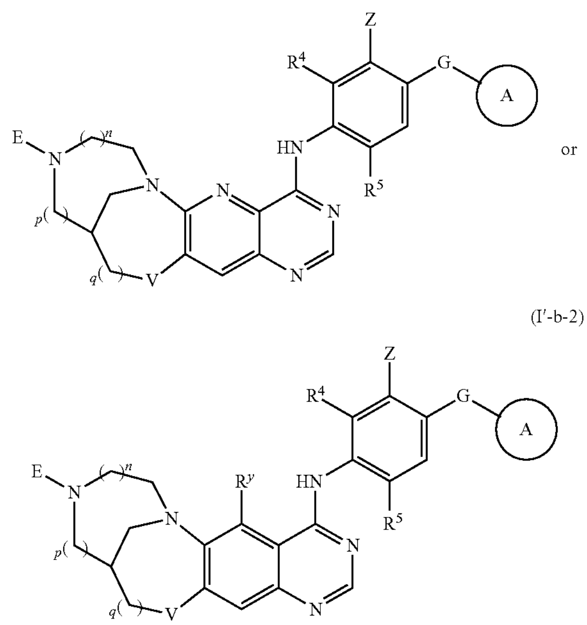

wherein $R^4$, $R^5$, $R^7$, E, V, $R^y$, Z, G, ring A, n, p, and q, are as defined for formula (I'). In some embodiments, the compound is a compound of formula (I'-b-1). In some embodiments, the compound is a compound of formula (I'-b-2). In any variation of formula (I'-b-1) or (I'-b-2), Z is —H, —F —Cl, —Br, —I, —C≡CH, —$OCH_3$, —$CH_3$, or —$CH_2CH_3$; V is O, S, or $NR^2$, wherein $R^2$ is $C_1$-$C_6$ alkyl or $C_1$-$C_6$ cycloalkyl, each of which is independently optionally substituted by 1-4 fluorines; G is —O—, —C(═O)—, —S—, —S(O)—, —S(O)$_2$—, or —$CH_2$—; and ring A is

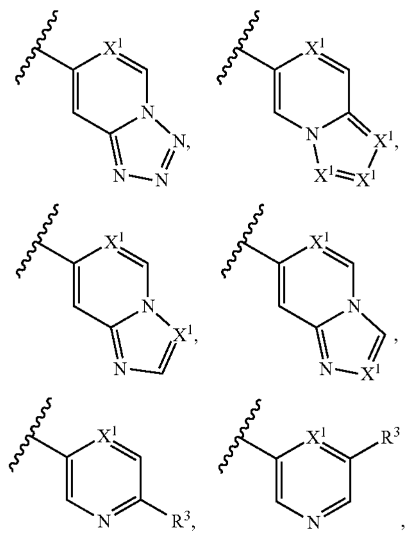

-continued

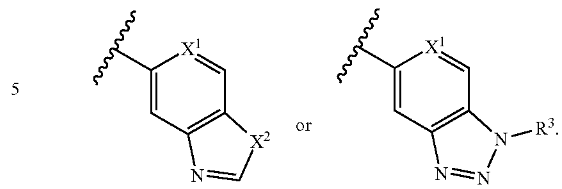

or

In some embodiments, ring A is

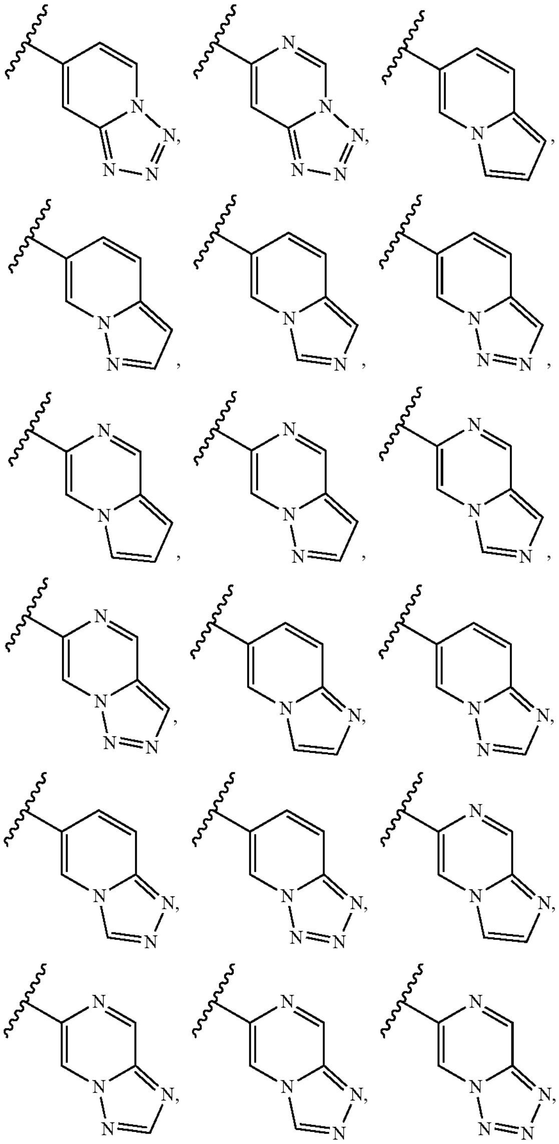

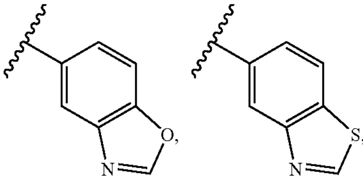

-continued
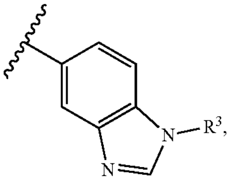,
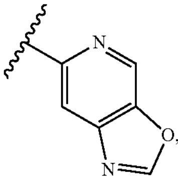,
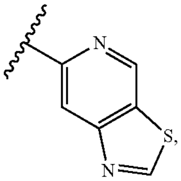,
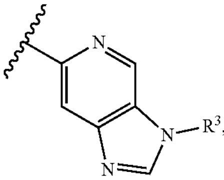,
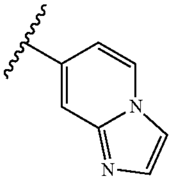,
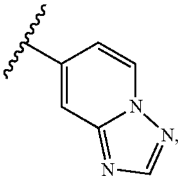,
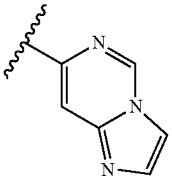,
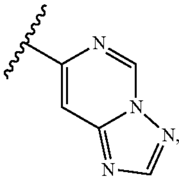,
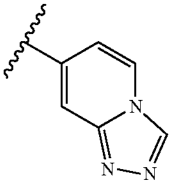,
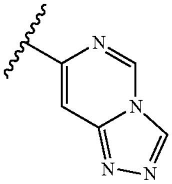,
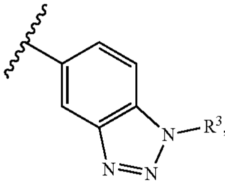,
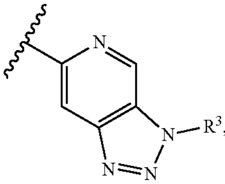,
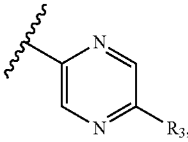,
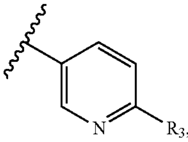,
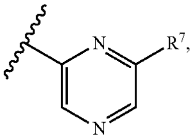, or
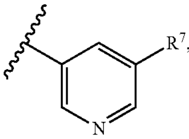,
or wherein $R^3$ is —H, $C_1$-$C_6$ alkyl, —$CD_3$ or $C_1$-$C_6$ cycloalkyl, and $R^7$ is —H, halogen, $C_1$-$C_6$ alkyl, —$CD_3$ or $C_1$-$C_6$ cycloalkyl.
In some embodiments, the compound of formula (I) is a compound of formula (I-c-1), (I-c-2), (I-c-3), (I-c-4), (I-c-5), or (I-c-6):
(I-c-1)
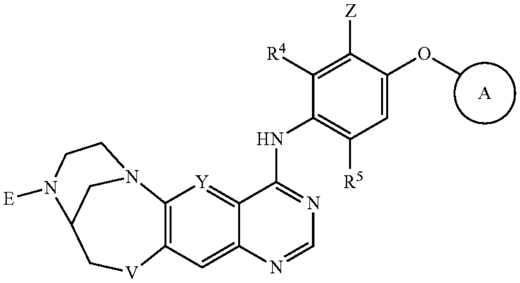,
(I-c-2)
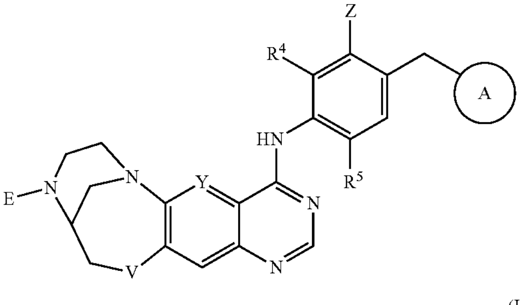,
(I-c-3)
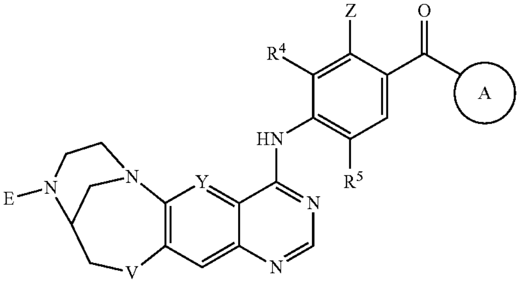,
(I-c-4)
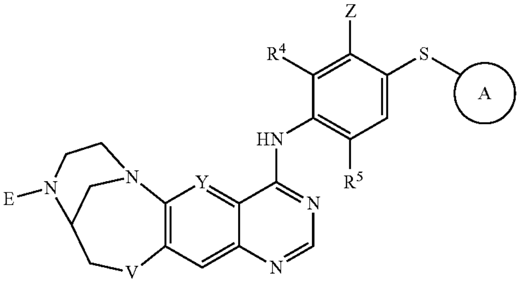,
(I-c-5)
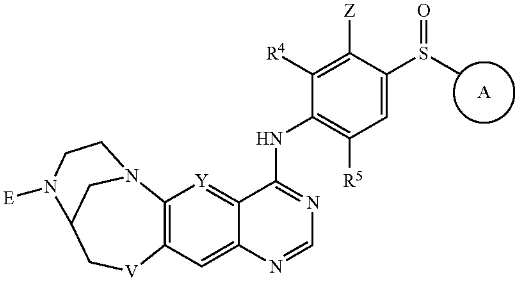 or -continued (I-c-6)

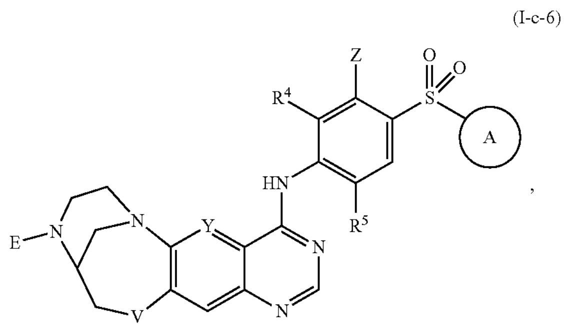

wherein $R^4$, $R^5$, E, V, Y, Z, and ring A are as defined for formula (I). In some embodiments, the compound is a compound of formula (I-c-1). In some embodiments, the compound is a compound of formula (I-c-2). In some embodiments, the compound is a compound of formula (I-c-3). In some embodiments, the compound is a compound of formula (I-c-4). In some embodiments, the compound is a compound of formula (I-c-5). In some embodiments, the compound is a compound of formula (I-c-6). In any variation of formula (I-c-1), (I-c-2), (I-c-3), (I-c-4), (I-c-5), or (I-c-6), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; and ring A is

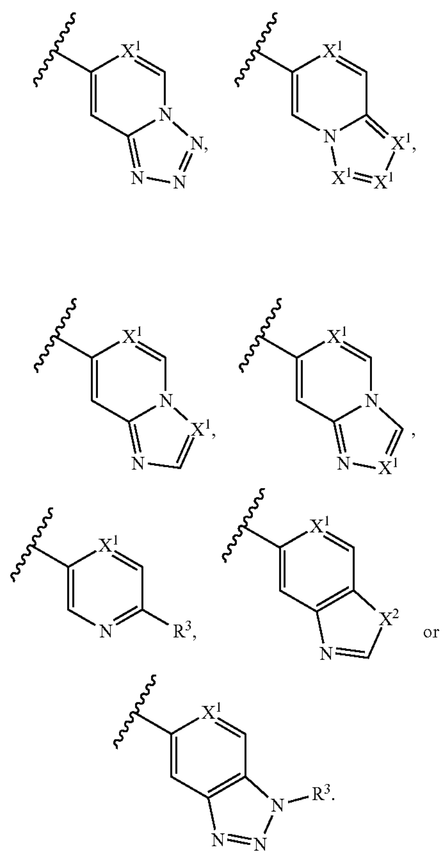

or

In some embodiments, ring A is

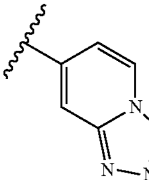
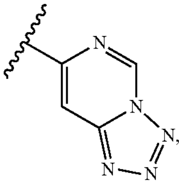
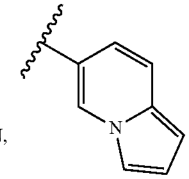
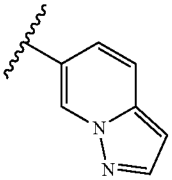
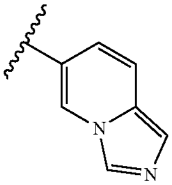
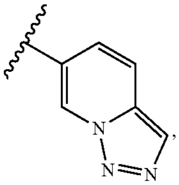
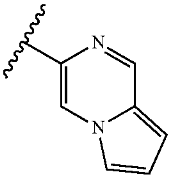
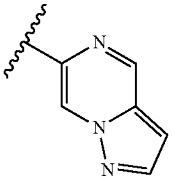
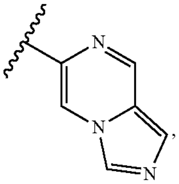
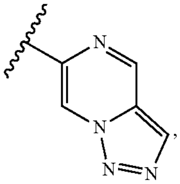
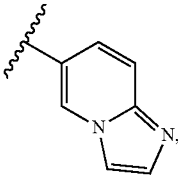
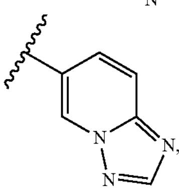
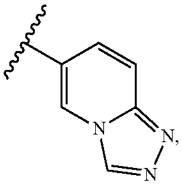
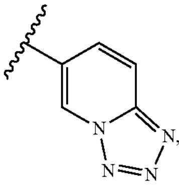
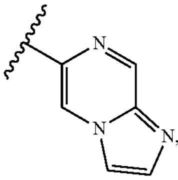
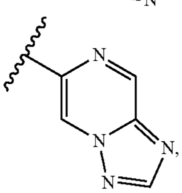
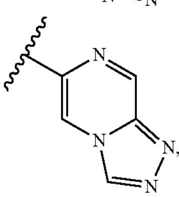
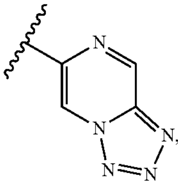
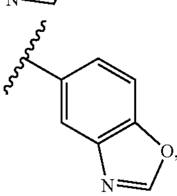
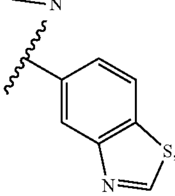
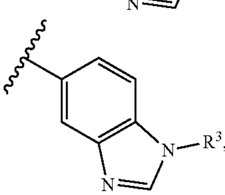
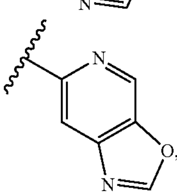
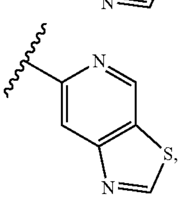
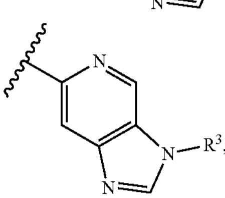

-continued

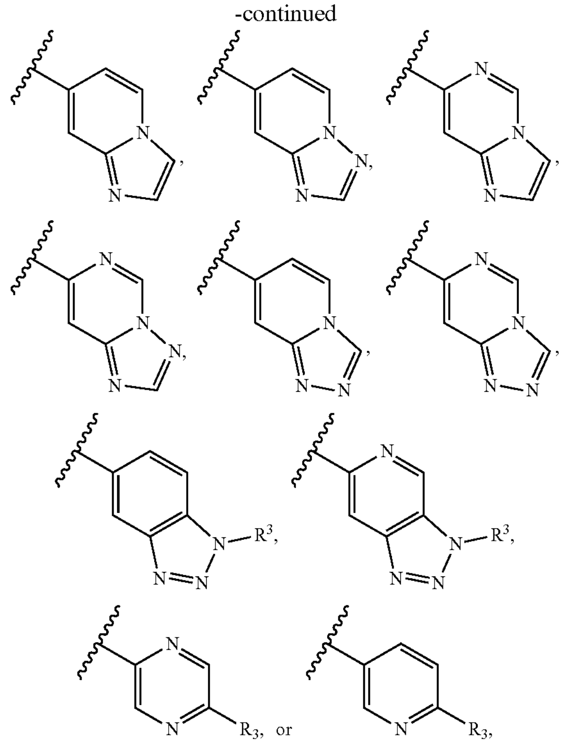

and $R^3$ is is —H, $C_1$-$C_6$ alkyl, —$CD_3$ or $C_1$-$C_6$ cycloalkyl. In some variations, $R^4$, $R^5$, E, V, Y, Z, and ring A of formula (I-c-1), (I-c-2), (I-c-3), (I-c-4), (I-c-5), or (I-c-6) are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-c-1), (I'-c-2), (I'-c-3), (I'-c-4), (I'-c-5), or (I'-c-6):

(I'-c-1)

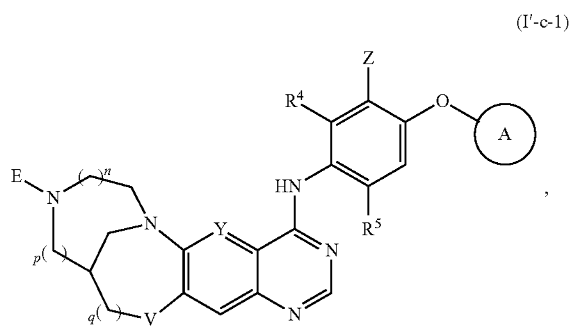

(I'-c-2)

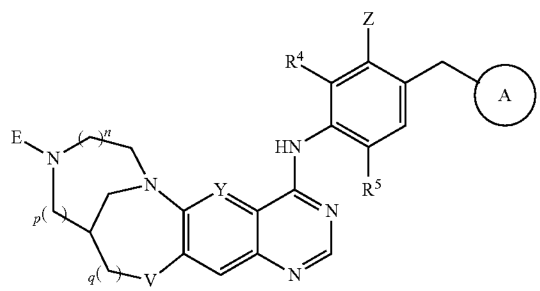

-continued (I'-c-3)

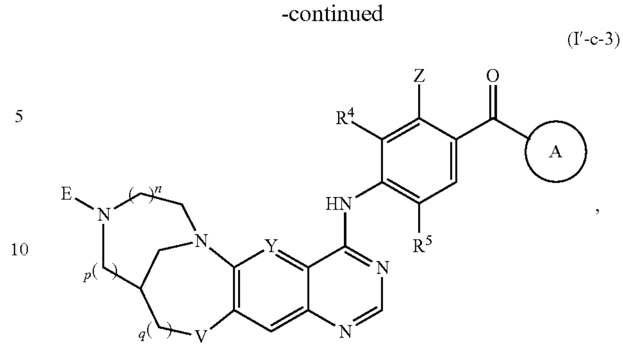

(I'-c-4)

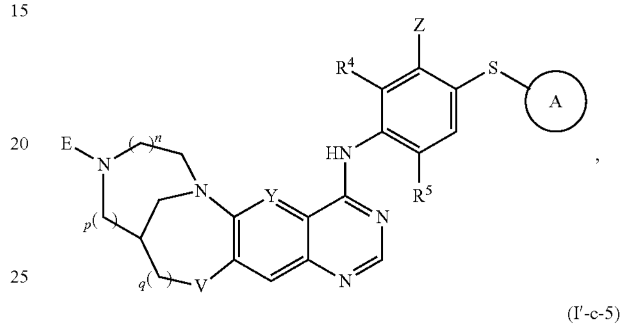

(I'-c-5)

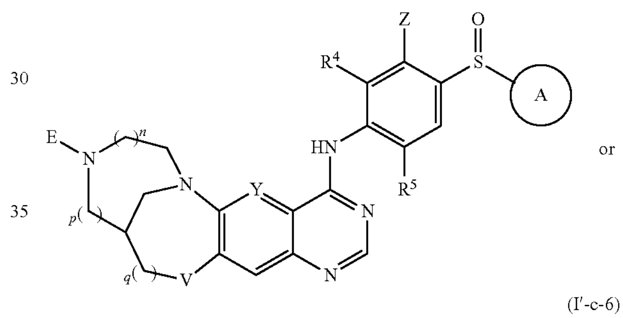

or (I'-c-6)

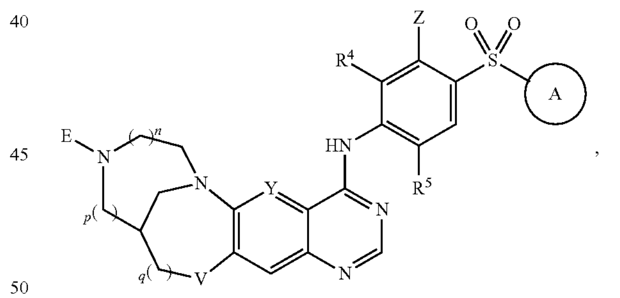

wherein $R^4$, $R^5$, $R^7$, E, V, Y, Z, ring A, n, p, and q, are as defined for formula (I'). In some embodiments, the compound is a compound of formula (I'-c-1). In some embodiments, the compound is a compound of formula (I'-c-2). In some embodiments, the compound is a compound of formula (I'-c-3). In some embodiments, the compound is a compound of formula (I'-c-4). In some embodiments, the compound is a compound of formula (I'-c-5). In some embodiments, the compound is a compound of formula (I'-c-6). In any variation of formula (I'-c-1), (I'-c-2), (I'-c-3), (I'-c-4), (I'-c-5), or (I'-c-6), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; and ring A is

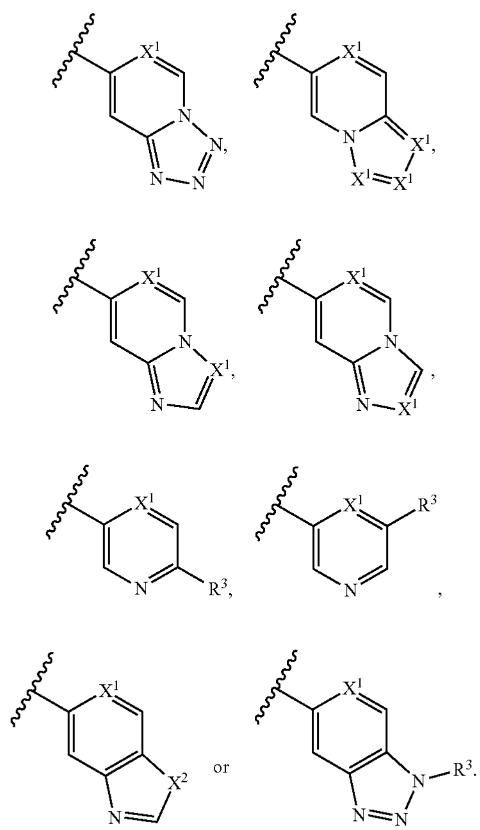
or
In some embodiments, ring A is
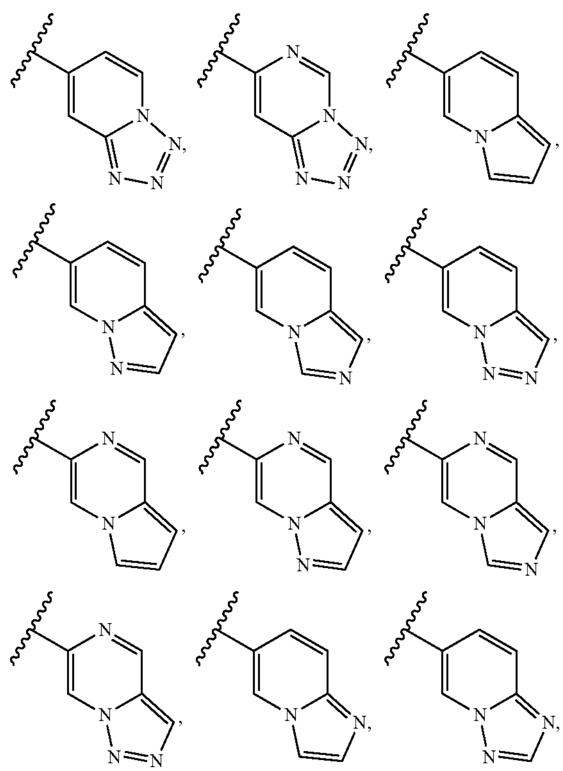
-continued
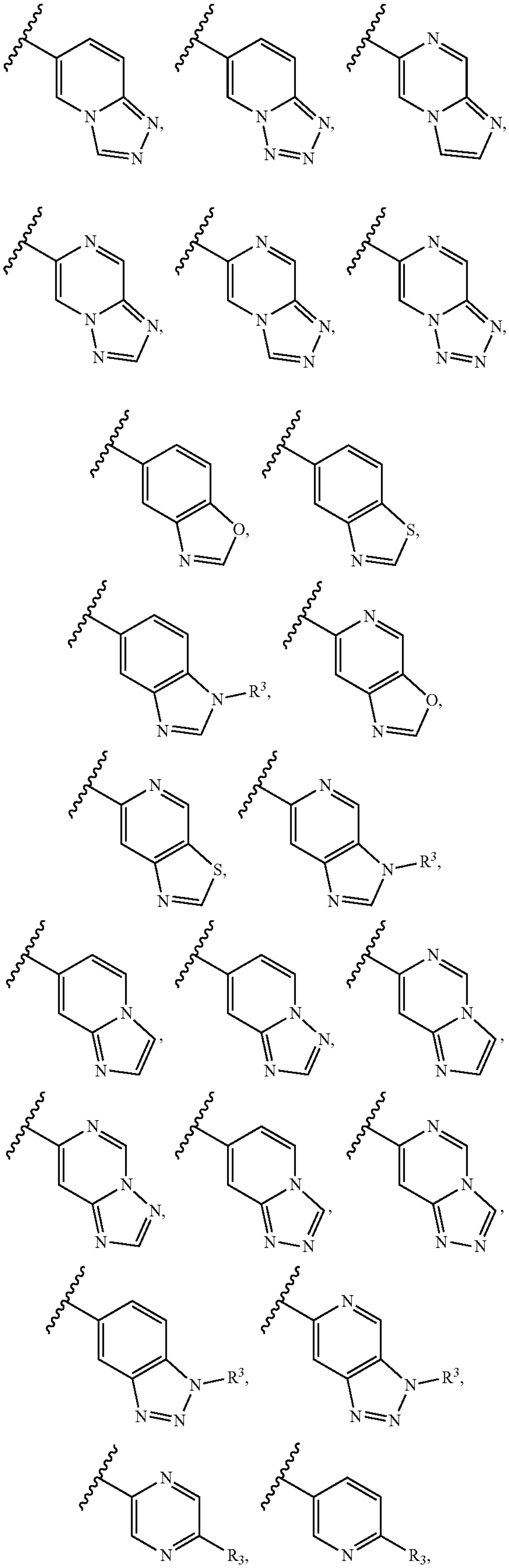

-continued

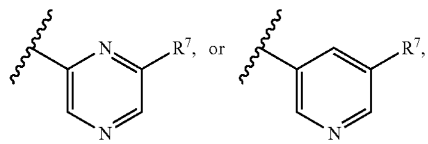

wherein $R^3$ is —H, $C_1$-$C_6$ alkyl, —$CD_3$ or $C_1$-$C_6$ cycloalkyl, and $R^7$ is —H, halogen, $C_1$-$C_6$ alkyl, —$CD_3$ or $C_1$-$C_6$ cycloalkyl.

In some embodiments, the compound of formula (I) is a compound of formula (I-d-1), (I-d-2), (i-d-3), (i-d-4), (i-d-5), (i-d-6), or (I-d-7):

(I-d-1)

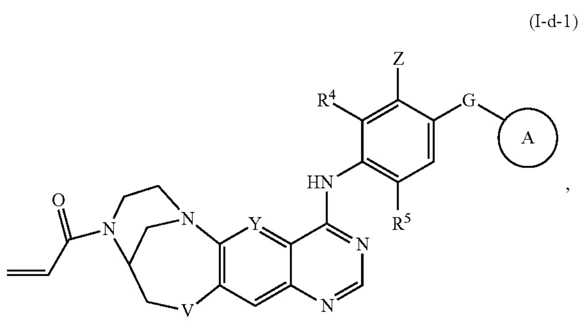

, (I-d-2)

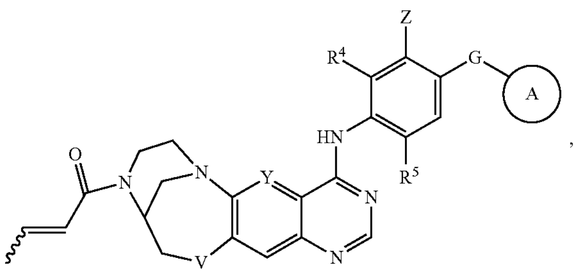

, (I-d-3)

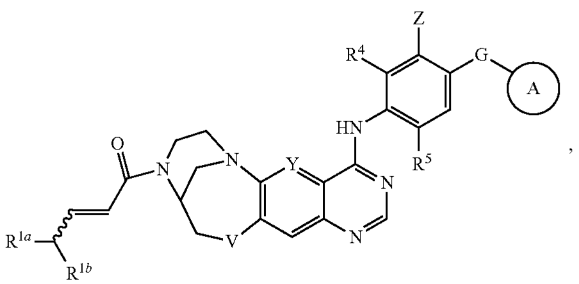

, (I-d-4)

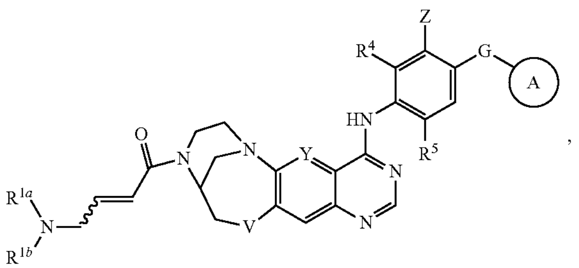

,

-continued (I-d-5)

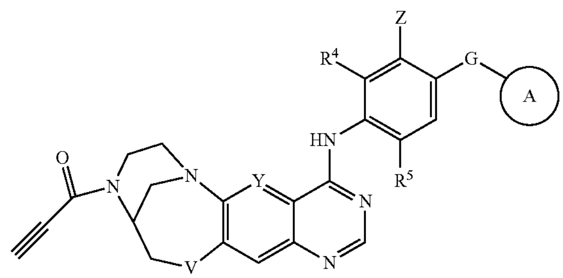

, (I-d-6)

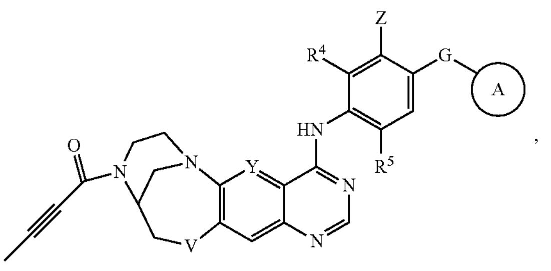

, or (I-d-7)

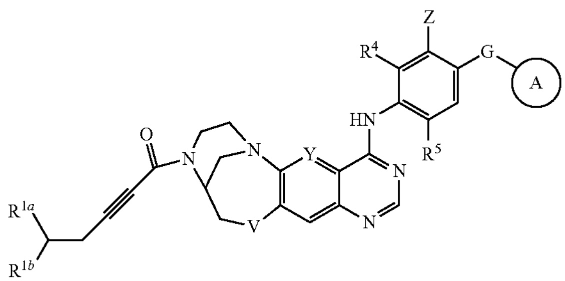

, wherein Ria, $R^{1b}$, $R^4$, $R^5$, V, Y, Z, G, and ring A are as defined for formula (I). In some embodiments, the compound is a compound of formula (I-d-1). In some embodiments, the compound is a compound of formula (I-d-2). In some embodiments, the compound is a compound of formula (I-d-3). In some embodiments, the compound is a compound of formula (I-d-4). In some embodiments, the compound is a compound of formula (I-d-5). In some embodiments, the compound is a compound of formula (I-d-6). In some embodiments, the compound is a compound of formula (I-d-7). In any variation of formula (I-d-1), (I-d-2), (I-d-3), (I-d-4), (I-d-5), (I-d-6), or (I-d-7), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; G is —O—, —C(═O)—, —S—, —S(O)—, —$S(O)_2$—, or —$CH_2$—; and ring A is

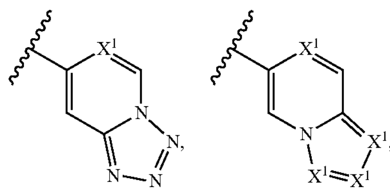

-continued

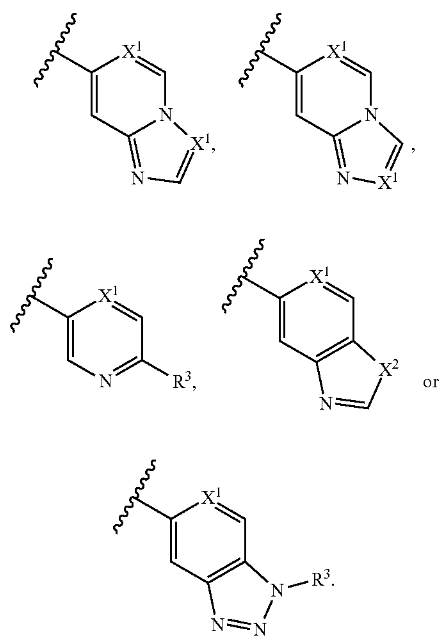

or

In some embodiments, ring A is

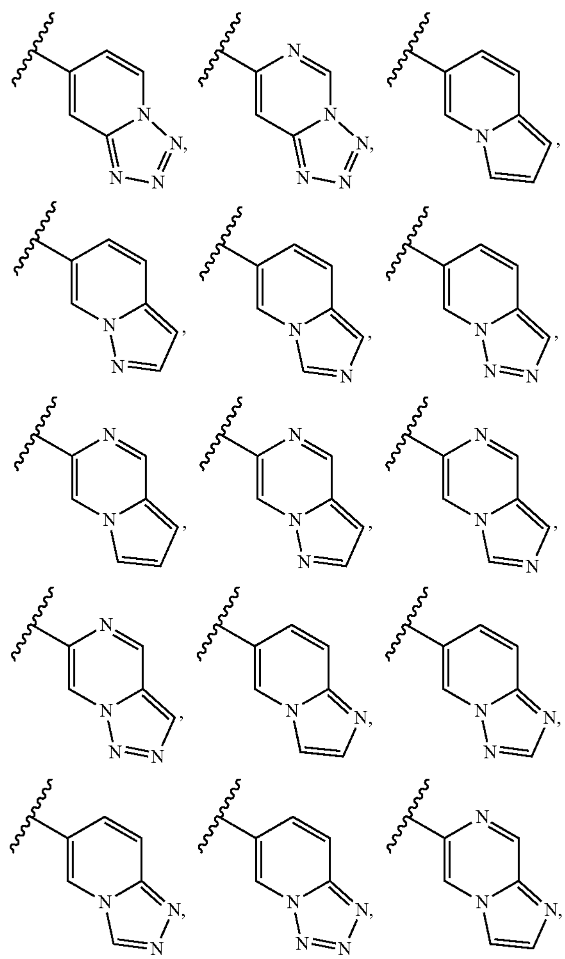

-continued

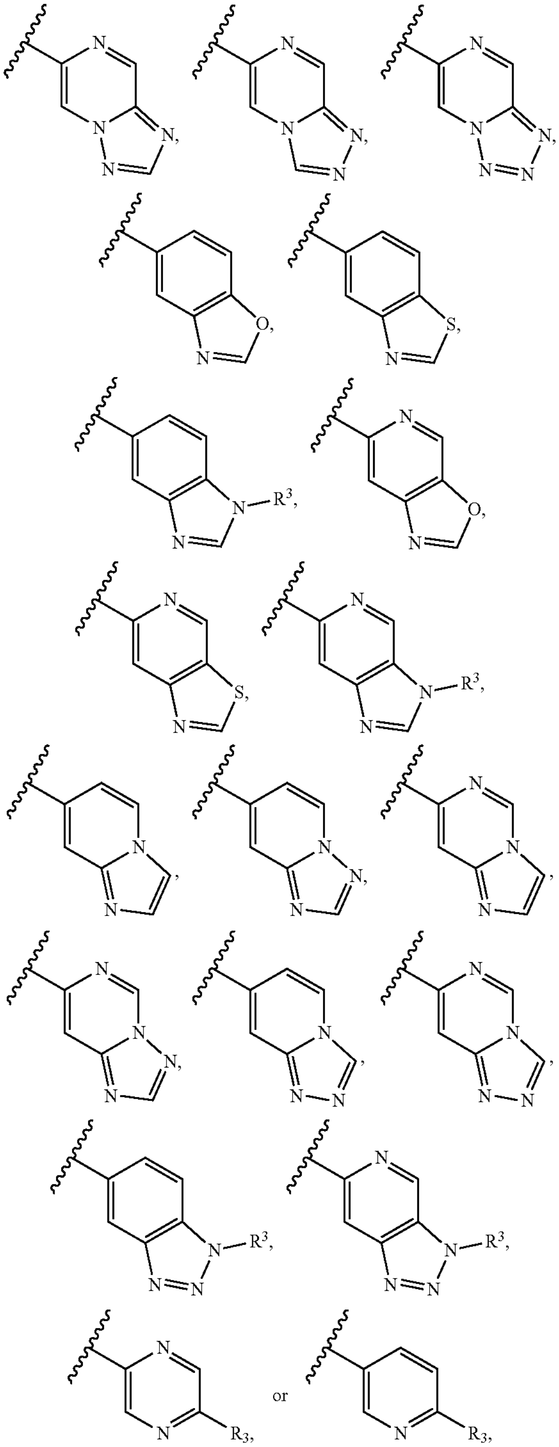

or and $R^3$ is is —H, $C_1$-$C_6$ alkyl, —$CD_3$ or $C_1$-$C_6$ cycloalkyl. In some variations, Ria, $R^{1b}$, $R^4$, $R^5$, V, Y, Z, G, and ring A of formula (I-d-1), (I-d-2), (I-d-3), (I-d-4), (I-d-5), (I-d-6), or (I-d-7), are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-d-1), (I'-d-2), (I'-d-3), (I'-d-4), (I'-d-5), (I'-d-6), or (I'-d-7):

(I'-d-1)

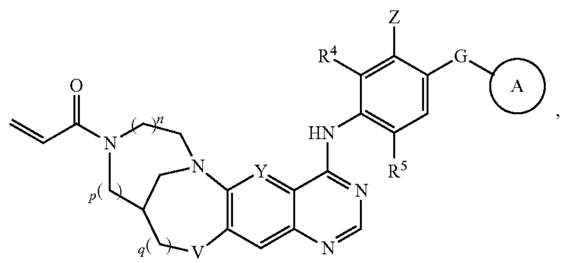

, (I'-d-2)

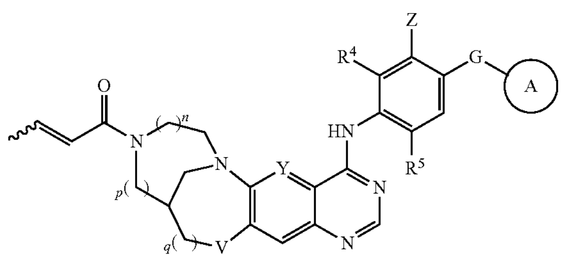

, (I'-d-3)

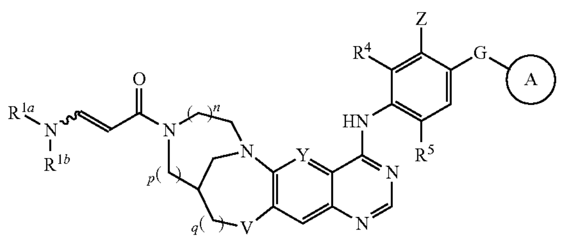

, (I'-d-4)

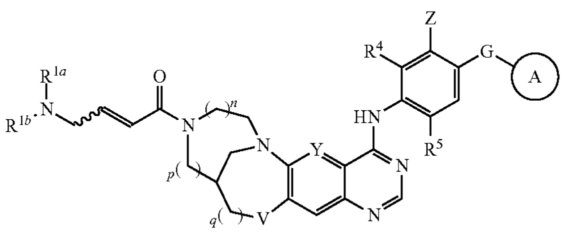

, (I'-d-5)

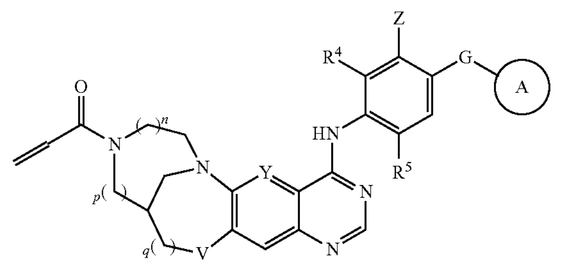

, (I'-d-6)

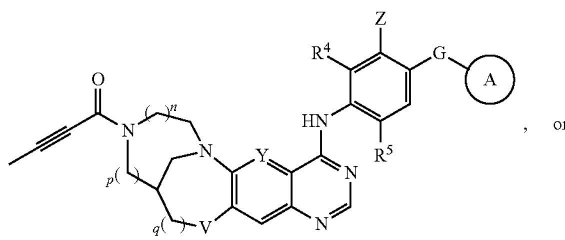

, or

-continued (I'-d-7)

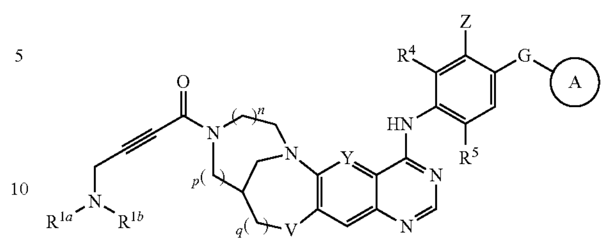

, wherein Ria, $R^{1b}$, $R^4$, $R^5$, $R^7$, V, Y, Z, G, ring A, n, p, and q, are as defined for formula (I'). In some embodiments, the compound is a compound of formula (I'-d-1). In some embodiments, the compound is a compound of formula (I'-d-2). In some embodiments, the compound is a compound of formula (I'-d-3). In some embodiments, the compound is a compound of formula (I'-d-4). In some embodiments, the compound is a compound of formula (I'-d-5). In some embodiments, the compound is a compound of formula (I'-d-6). In some embodiments, the compound is a compound of formula (I'-d-7). In any variation of formula (I'-d-1), (I'-d-2), (I'-d-3), (I'-d-4), (I'-d-5), (I'-d-6), or (I'-d-7), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; G is —O—, —C(═O)—, —S—, —S(O)—, —$S(O)_2$—, or —$CH_2$—; and ring A is

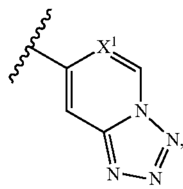

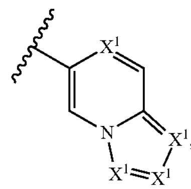

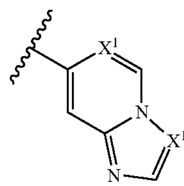

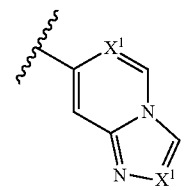

,

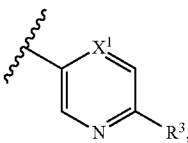

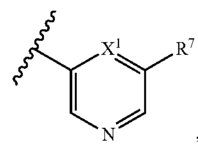

,

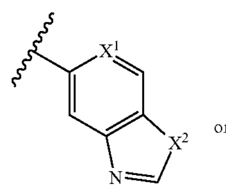

or

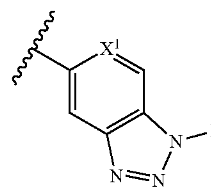

In some embodiments, ring A is
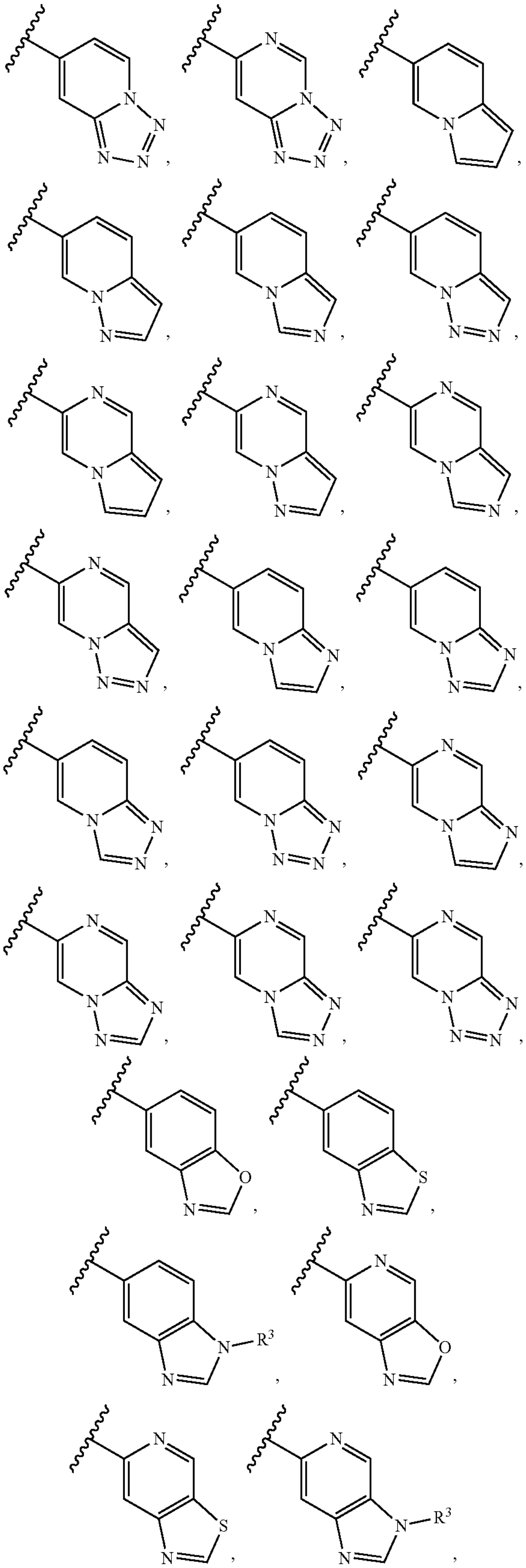
-continued
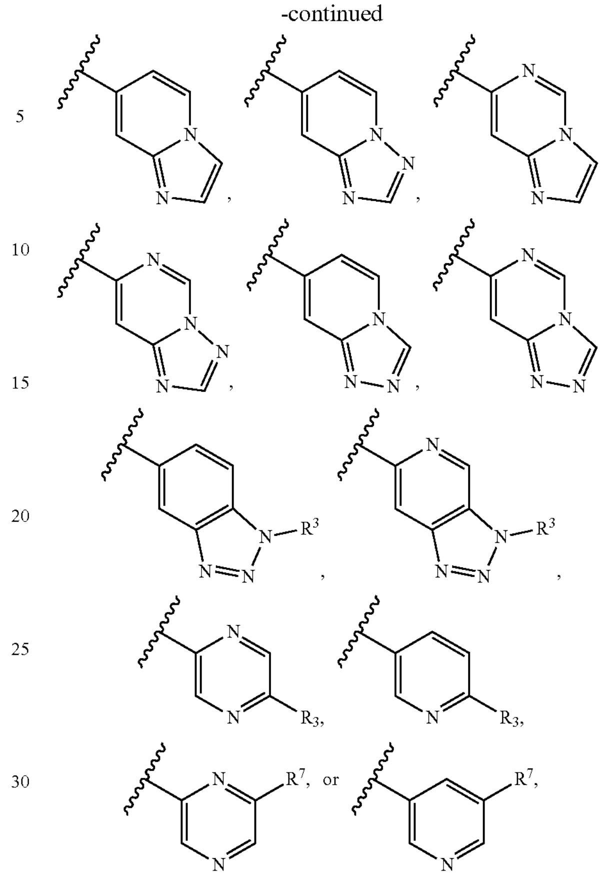
and $R^3$ is —H, $C_1$-$C_6$ alkyl, —$CD_3$ or $C_1$-$C_6$ cycloalkyl, and $R^7$ is —H, halogen, $C_1$-$C_6$ alkyl, —$CD_3$ or $C_1$-$C_6$ cycloalkyl.
In some embodiments, the compound of formula (I) is a compound of formula (I-e-1), (I-e-2), (I-e-3), (I-e-4), (I-e-5), (I-e-6), or (I-e-7):
(I-e-1)
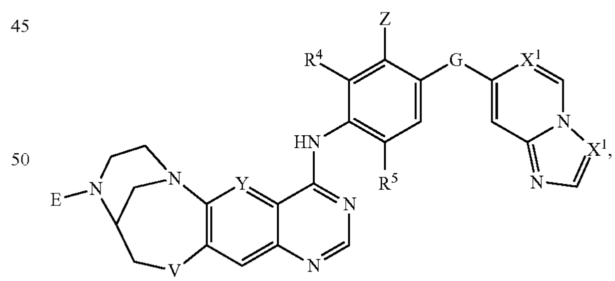
(I-e-2)
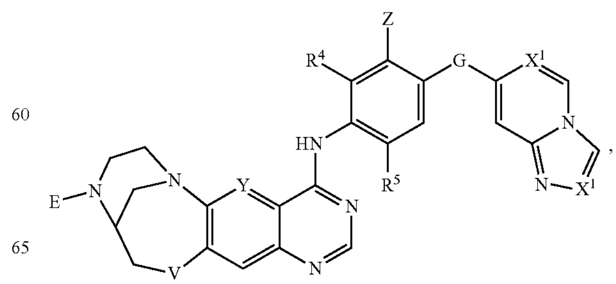

-continued (I-e-3)

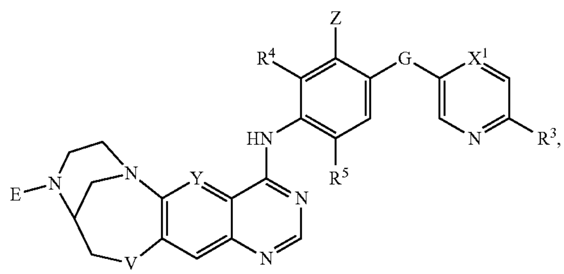

(I-e-4)

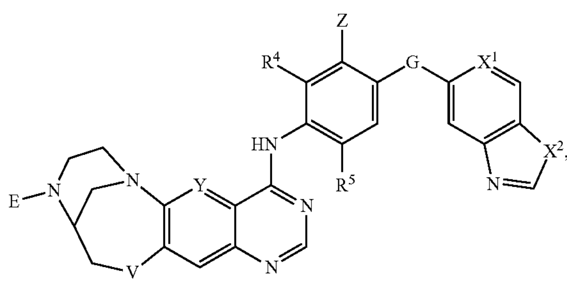

(I-e-5)

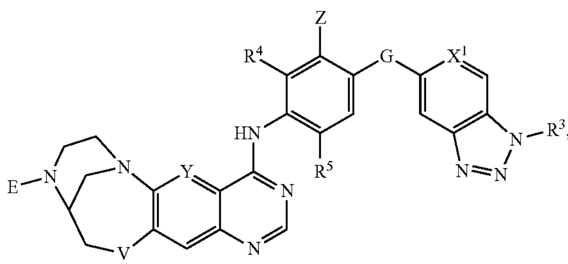

(I-e-6)

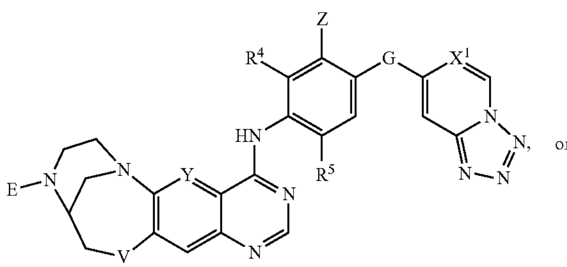

or (I-e-7)

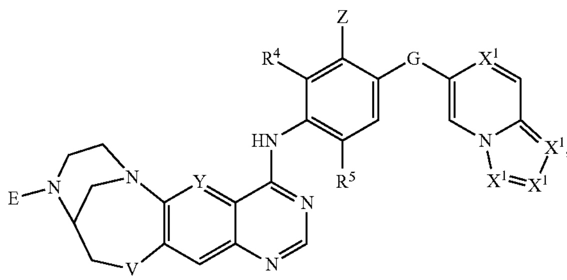

wherein E, $R^3$, $R^4$, $R^5$, V, Y, Z, G, $X^1$, and $X^2$ are as defined for formula (I). In some embodiments, the compound is a compound of formula (I-e-1). In some embodiments, the compound is a compound of formula (I-e-2). In some embodiments, the compound is a compound of formula (I-e-3). In some embodiments, the compound is a compound of formula (I-e-4). In some embodiments, the compound is a compound of formula (I-e-5). In some embodiments, the compound is a compound of formula (I-e-6). In some embodiments, the compound is a compound of formula (I-e-7). In any variation of formula (I-e-1), (I-e-2), (I-e-3), (I-e-4), (I-e-5), (I-e-6), or (I-e-7), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; and G is —O—, —C(═O)—, —S—, —S(O)—, —$S(O)_2$—, or —$CH_2$—. In some variations, E, $R^3$, $R^4$, $R^5$, V, Y, Z, G, $X^1$, and $X^2$ of formula (I-e-1), (I-e-2), (I-e-3), (I-e-4), (I-e-5), (I-e-6), or (I-e-7) are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-e-1), (I'-e-2), (I'-e-3), (I'-e-4), (I'-e-5), (I'-e-6), (I'-e-7), or (I'-e-8):

(I'-e-1)

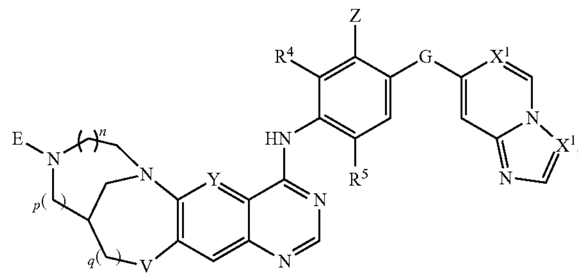

(I'-e-2)

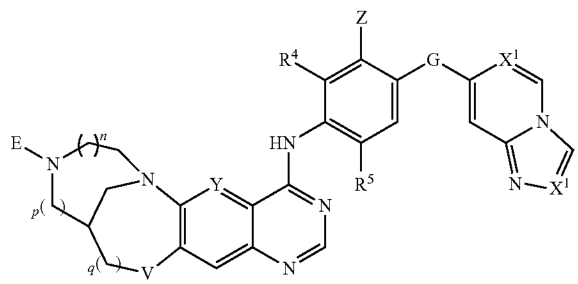

, (I'-e-3)

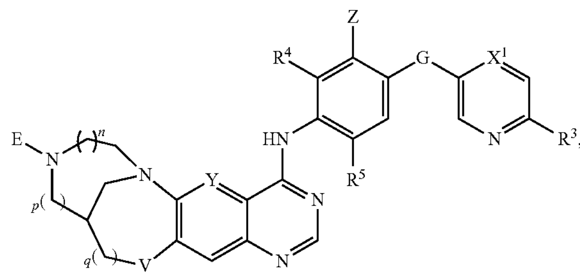

-continued (I'-e-4)

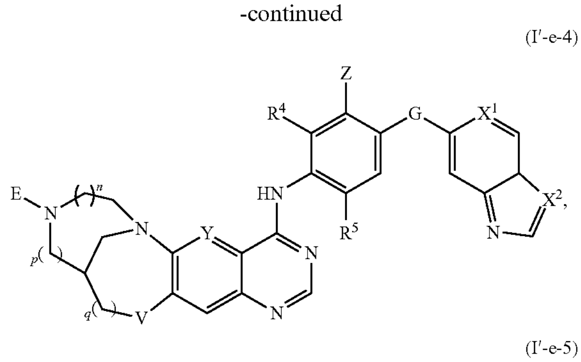

(I'-e-5)

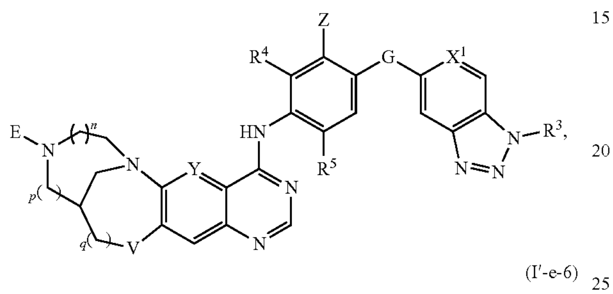

(I'-e-6)

(I'-e-7)

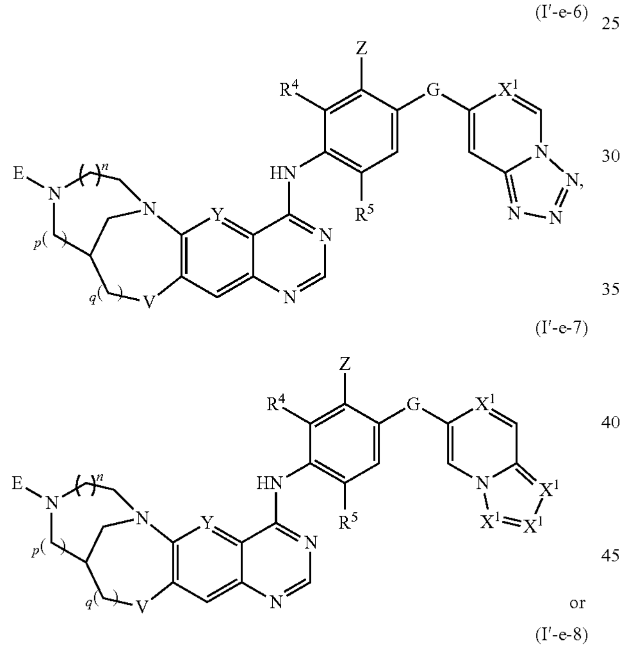

or (I'-e-8)

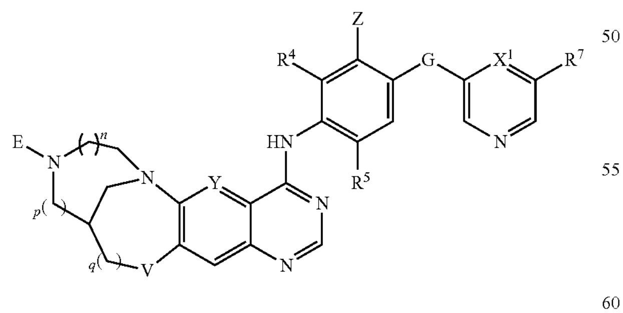

wherein E, $R^3$, $R^4$, $R^5$, $R^7$, V, Y, Z, G, $X^1$, $X^2$, n, p, and q, are as defined for formula (I'). In some embodiments, the compound is a compound of formula (I'-e-1). In some embodiments, the compound is a compound of formula (I'-e-2). In some embodiments, the compound is a compound of formula (I'-e-3). In some embodiments, the compound is a compound of formula (I'-e-4). In some embodiments, the compound is a compound of formula (I'-e-5). In some embodiments, the compound is a compound of formula (I'-e-6). In some embodiments, the compound is a compound of formula (I'-e-7). In some embodiments, the compound is a compound of formula (I'-e-8). In any variation of formula (I'-e-1), (I'-e-2), (I'-e-3), (I'-e-4), (I'-e-5), (I'-e-6), (I'-e-7), or (I'-e-8), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; and G is —O—, —C(═O)—, —S—, —S(O)—, —$S(O)_2$—, or —$CH_2$—.

In some embodiments, the compound of formula (I) is a compound of formula (I-f-1), (I-f-2), (I-f-3), (I-f-4), (I-f-5), or (I-f-6):

(I-f-1)

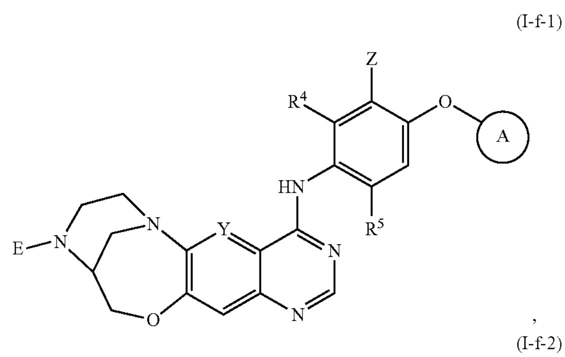

, (I-f-2)

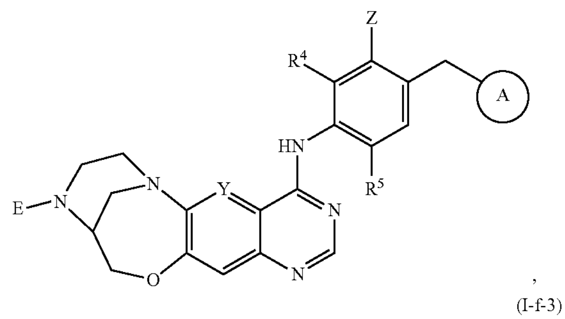

, (I-f-3)

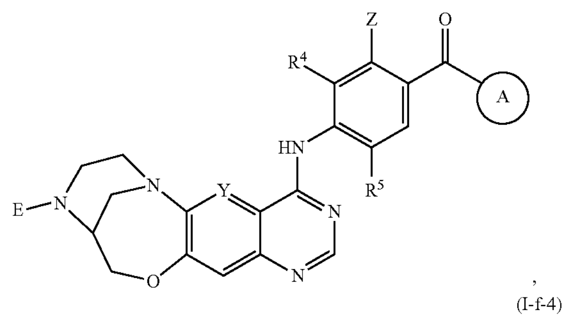

, (I-f-4)

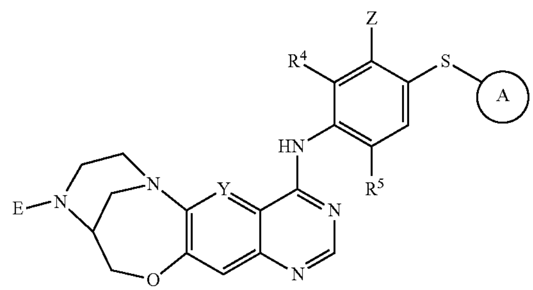

,

-continued (I-f-5)

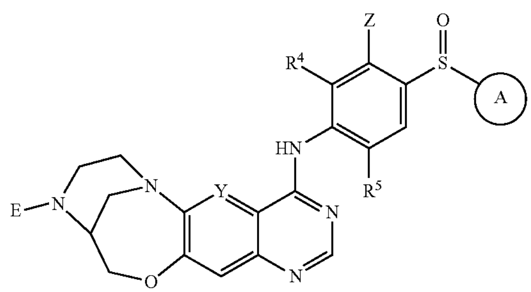

or (I-f-6)

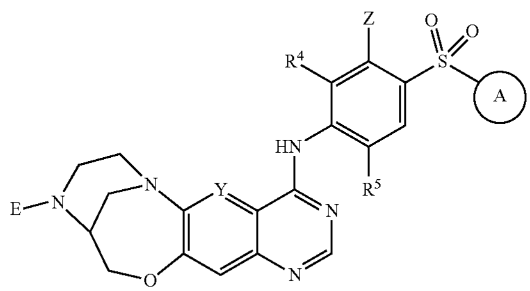

, wherein E, $R^4$, $R^5$, Y, Z, $X^1$ and $X^2$ are as defined for formula (I). In some embodiments, the compound is a compound of formula (I-f-1). In some embodiments, the compound is a compound of formula (I-f-2). In some embodiments, the compound is a compound of formula (I-f-3). In some embodiments, the compound is a compound of formula (I-f-4). In some embodiments, the compound is a compound of formula (I-f-5). In some embodiments, the compound is a compound of formula (I-f-6). In any variation of formula (I-f-1), (I-f-2), (I-f-3), (I-f-4), (I-f-5), or (I-f-6); ring A is

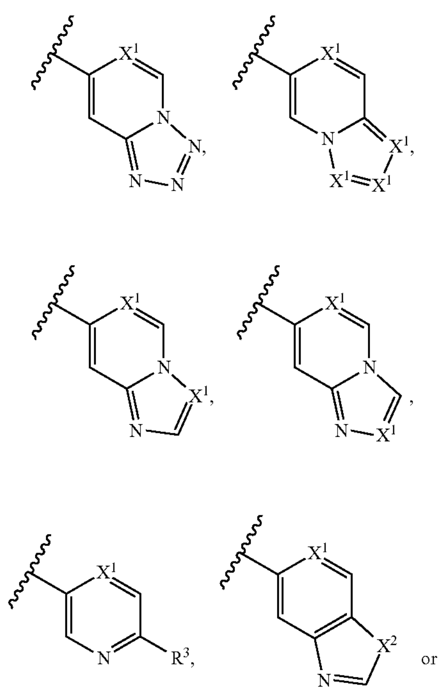

-continued

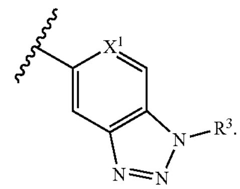

In some embodiments, ring A is

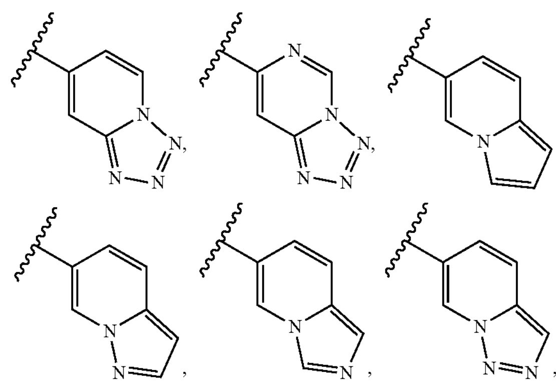

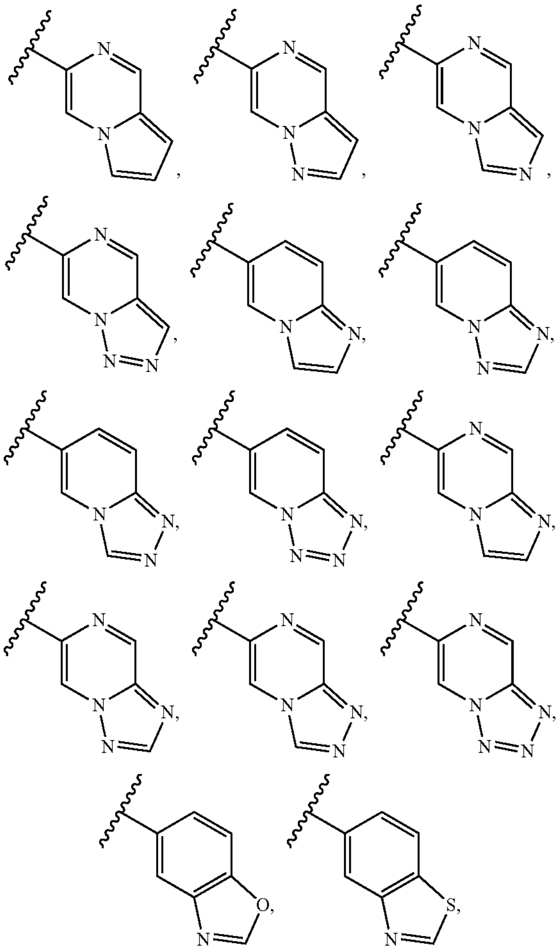

-continued

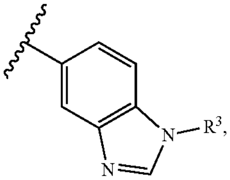

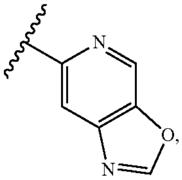

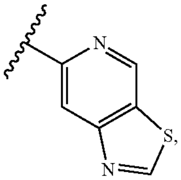

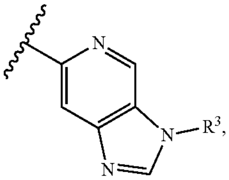

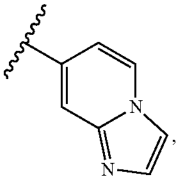

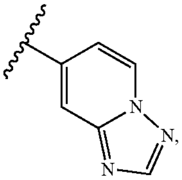

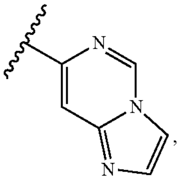

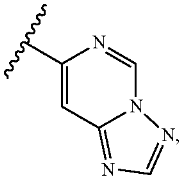

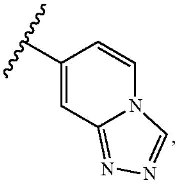

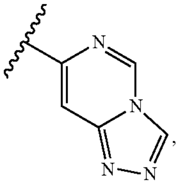

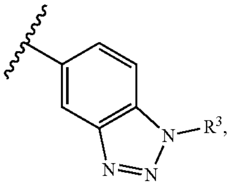

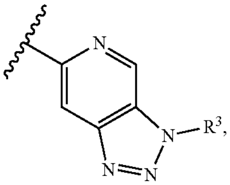

or

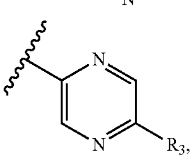

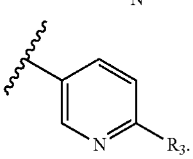

In some embodiments, Y is N or CH. In some embodiments, Z is —H, —F —Cl, —Br, —I, —C≡CH, —$OCH_3$, —$CH_3$, or —$CH_2CH_3$; $R^4$ is —H or —F; and $R^5$ is —H or —F. In some variations, E, $R^4$, $R^5$, Y, Z, $X^1$ and $X^2$ of formula (I-f-1), (I-f-2), (I-f-3), (I-f-4), (I-f-5), or (I-f-6), are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-f-1), (I'-f-2), (I'-f-3), (I'-f-4), (I'-f-5), or (I'-f-6):

(I'-f-1)

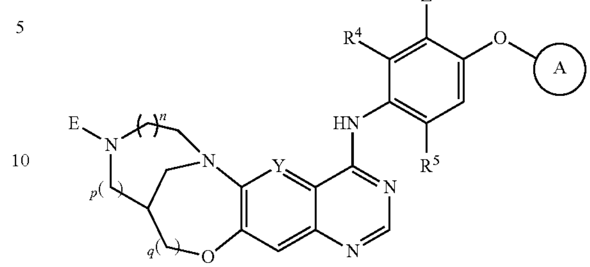

, (I'-f-2)

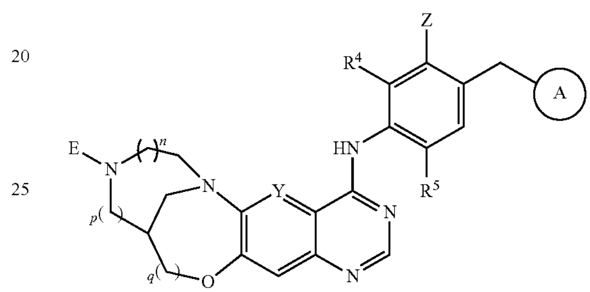

, (I'-f-3)

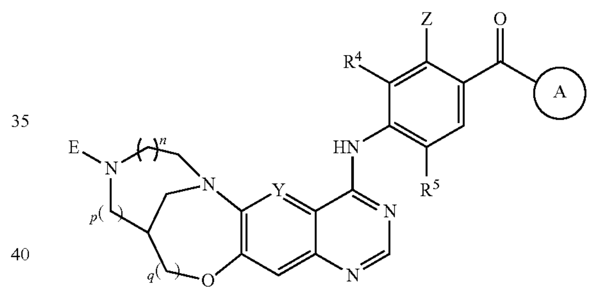

, (I'-f-4)

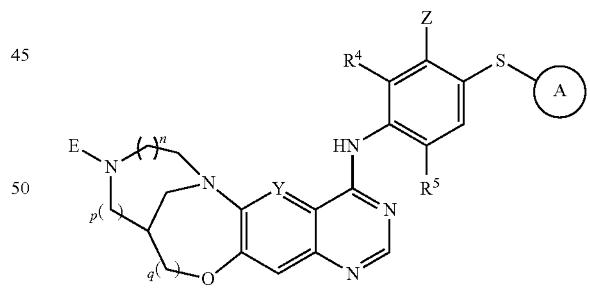

, (I'-f-5)

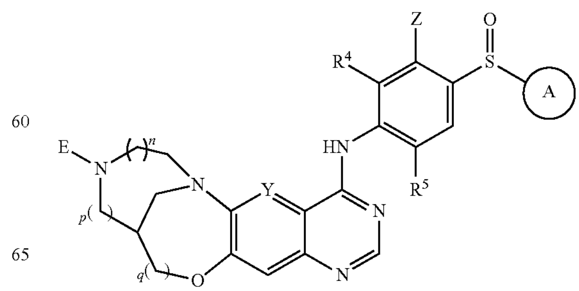

or

-continued (I'-f-6)

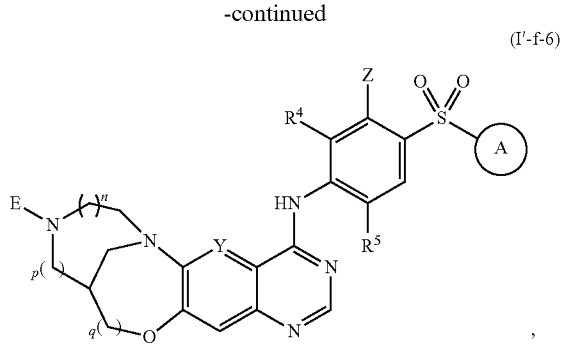

wherein E, $R^4$, $R^5$, Y, Z, $X^1$, $X^2$, n, p, and q, are as defined for formula (I'). In some embodiments, the compound is a compound of formula (I'-f-1). In some embodiments, the compound is a compound of formula (I'-f-2). In some embodiments, the compound is a compound of formula (I'-f-3). In some embodiments, the compound is a compound of formula (I'-f-4). In some embodiments, the compound is a compound of formula (I'-f-5). In some embodiments, the compound is a compound of formula (I'-f-6). In any variation of formula (I'-f-1), (I'-f-2), (I'-f-3), (I'-f-4), (I'-f-5), or (I'-f-6); ring A is

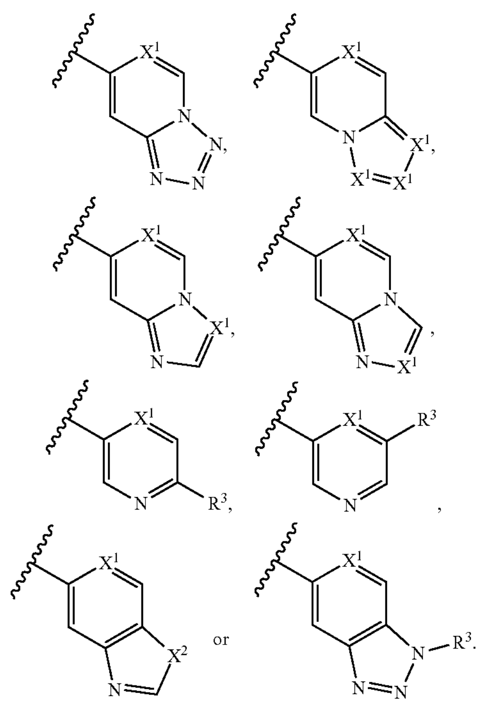

In some embodiments, ring A is

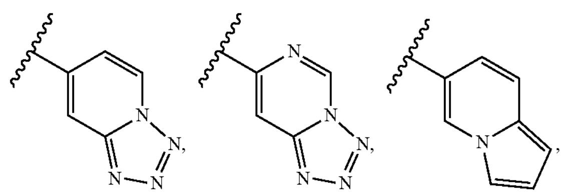

-continued

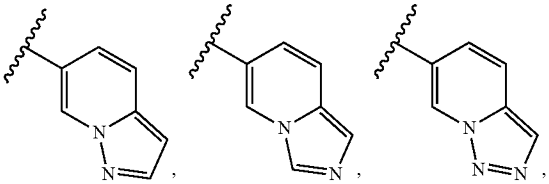

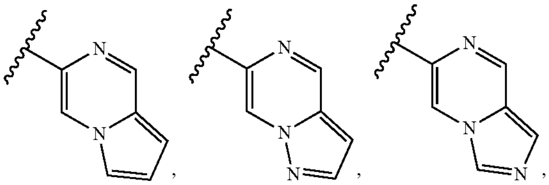

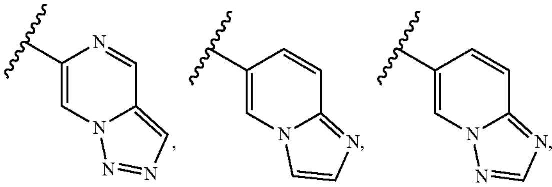

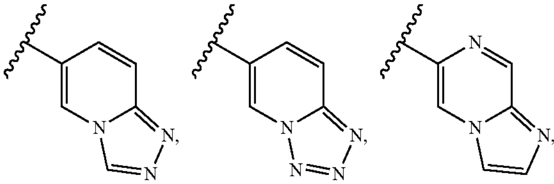

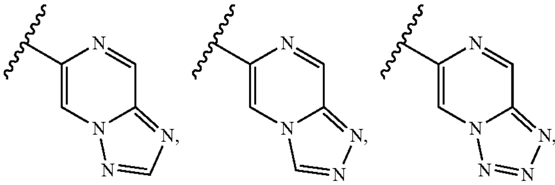

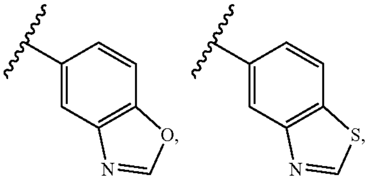

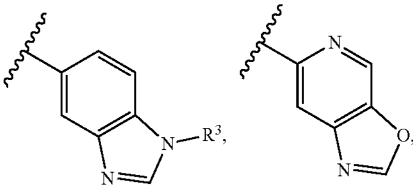

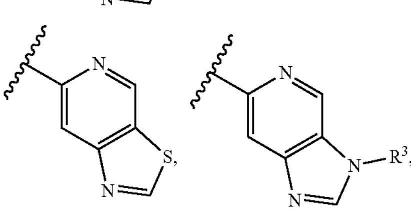

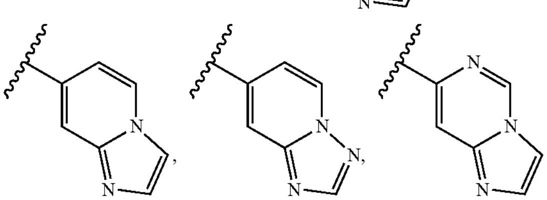

-continued

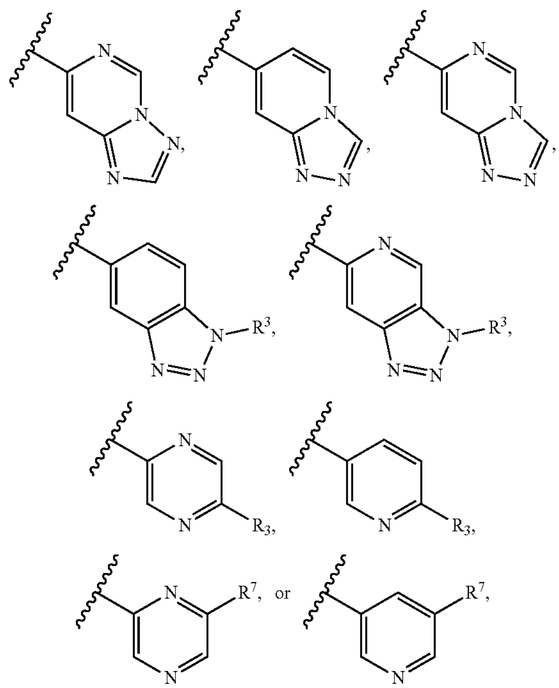

In some embodiments, Y is N or CH. In some embodiments, Z is —H, —F —Cl, —Br, —I, —C≡CH, —$OCH_3$, —$CH_3$, or —$CH_2CH_3$; $R^4$ is —H or —F; and $R^5$ is —H or —F.

In some embodiments, the compound of formula (I) is a compound of formula (I-g-1), (I-g-2), (I-g-3), (I-g-4), (I-g-5), (I-g-6), or (I-g-7):

(I-g-1)

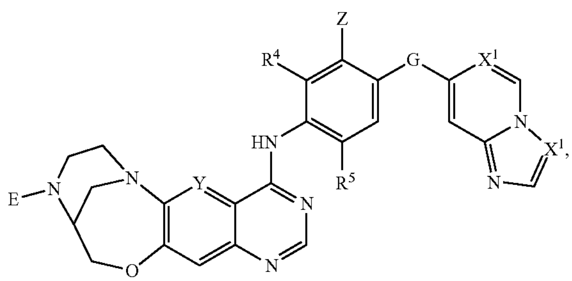

(I-g-2)

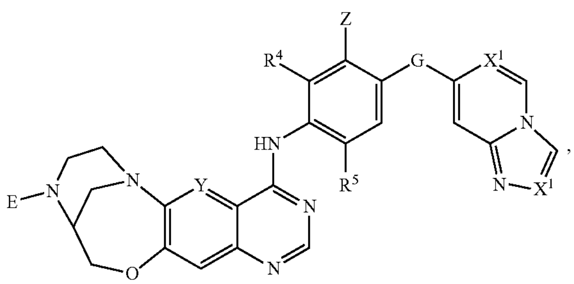

-continued (I-g-3)

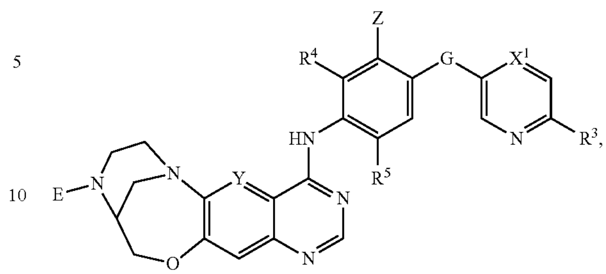

(I-g-4)

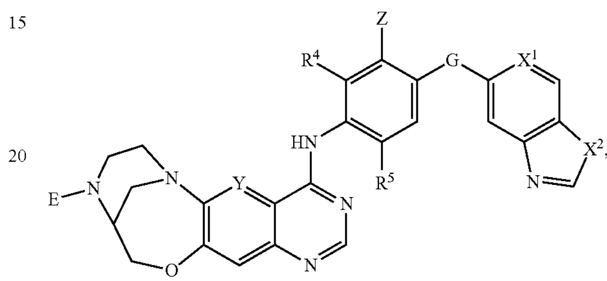

(I-g-5)

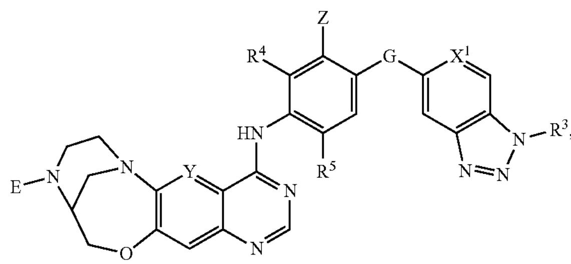

(I-g-6)

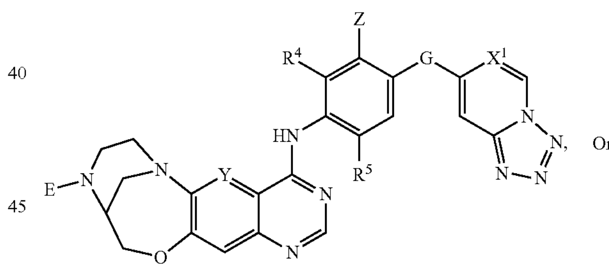

Or (I-g-7)

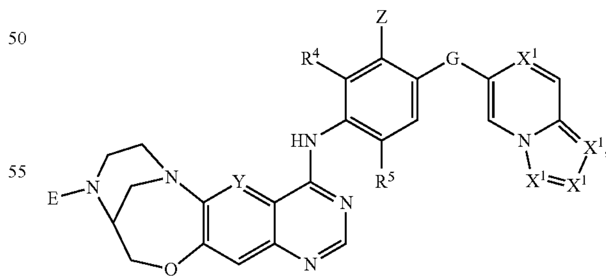

wherein E, $R^3$, $R^4$, $R^5$, V, Y, Z, G, $X^1$, and $X^2$ are as defined for formula (I). In some embodiments, the compound is a compound of formula (I-g-1). In some embodiments, the compound is a compound of formula (I-g-2). In some embodiments, the compound is a compound of formula (I-g-3). In some embodiments, the compound is a compound of formula (I-g-4). In some embodiments, the compound is a compound of formula (I-g-5). In some embodiments, the compound is a compound of formula (I-g-6). In some embodiments, the compound is a compound of formula (I-g-7). In any variation of formula (I-g-1), (I-g-2), (I-g-3), (I-g-4), (I-g-5), (I-g-6), or (I-g-7), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; and G is —O—, —C(═O)—, —S—, —S(O)—, —$S(O)_2$—, or —$CH_2$—. In some variations, E, $R^3$, $R^4$, $R^5$, V, Y, Z, G, $X^1$, and $X^2$ of formula (I-g-1), (I-g-2), (I-g-3), (I-g-4), (I-g-5), (I-g-6), or (I-g-7), are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-g-1), (I'-g-2), (I'-g-3), (I'-g-4), (I'-g-5), (I'-g-6), (I'-g-7), or (I'-g-8):

(I'-g-1)

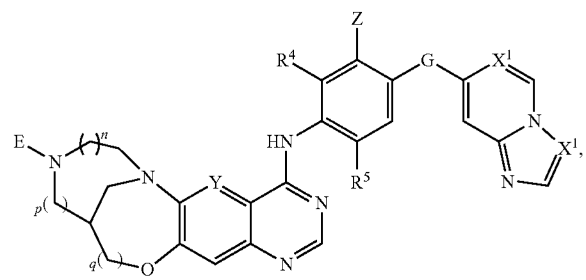

(I'-g-2)

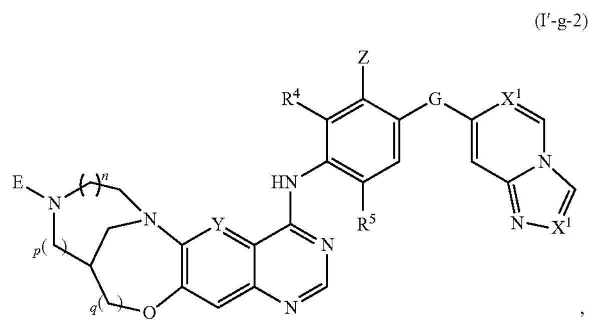

, (I'-g-3)

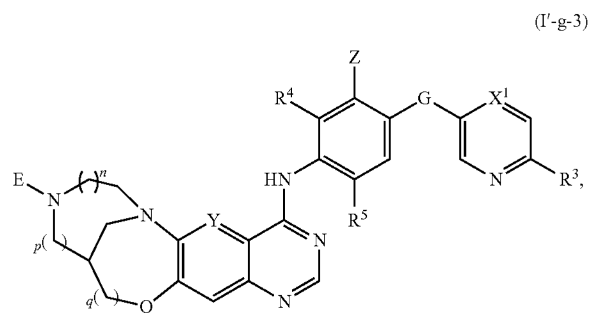

-continued (I'-g-4)

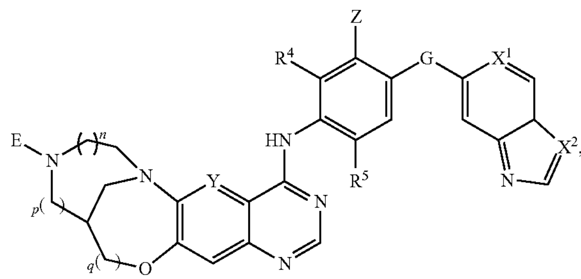

(I'-g-5)

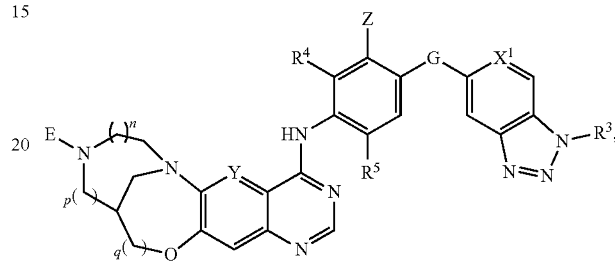

(I'-g-6)

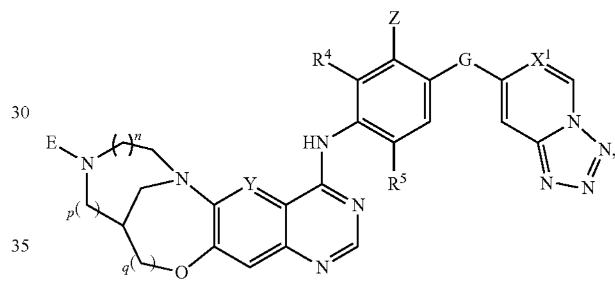

(I'-g-7)

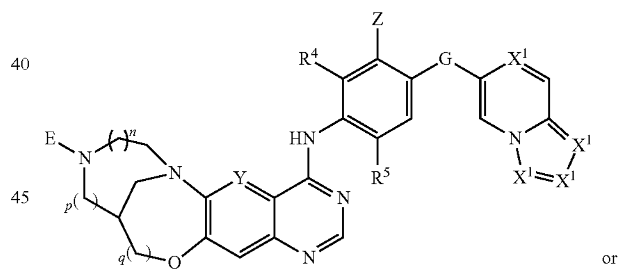

or (I'-g-8)

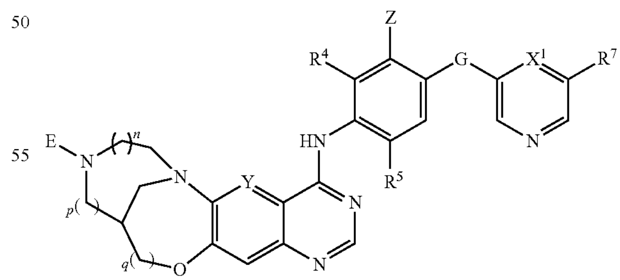

wherein E, $R^3$, $R^4$, $R^5$, $R^7$, V, Y, Z, G, $X^1$, $X^2$, n, p, and q, are as defined for formula (I'). In some embodiments, the compound is a compound of formula (I'-g-1). In some embodiments, the compound is a compound of formula (I'-g-2). In some embodiments, the compound is a compound of formula (I'-g-3). In some embodiments, the compound is a compound of formula (I'-g-4). In some embodiments, the compound is a compound of formula (I'-g-5). In some embodiments, the compound is a compound of formula (I'-g-6). In some embodiments, the compound is a compound of formula (I'-g-7). In some embodiments, the compound is a compound of formula (I'-g-8). In any variation of formula (I'-g-1), (I'-g-2), (I'-g-3), (I'-g-4), (I'-g-5), (I'-g-6), or (I'-g-7), (I'-g-8), Z is —H, —F —Cl, —Br, —I, —C≡CH, —$OCH_3$, —$CH_3$, or —$CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; and G is —O—, —C(═O)—, —S—, —S(O)—, —$S(O)_2$—, or —$CH_2$—.

In some embodiments, the compound of formula (I) is a compound of formula (I-h-1), (I-h-2), (I-h-3), (I-h-4), (I-h-5), (I-h-6), or (I-h-7):

(I-h-1)

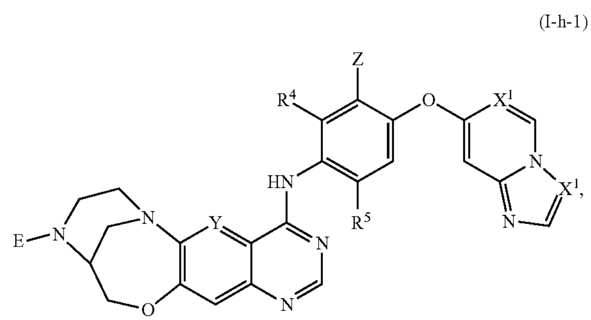

(I-h-2)

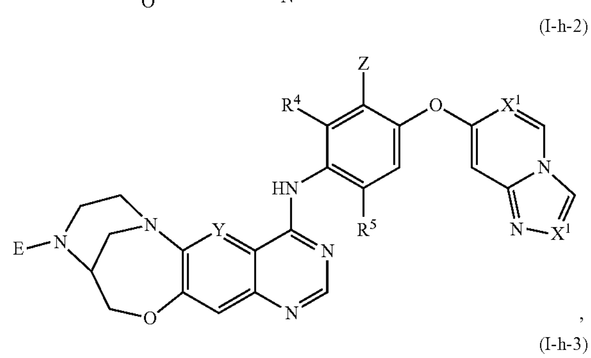

, (I-h-3)

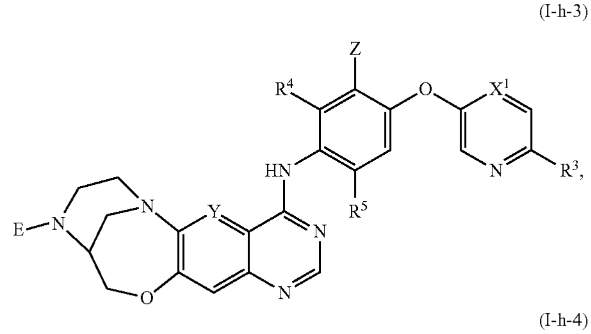

(I-h-4)

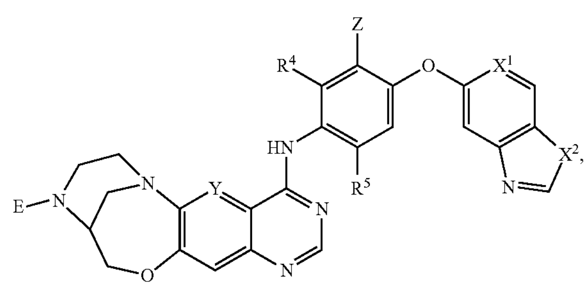

-continued (I-h-5)

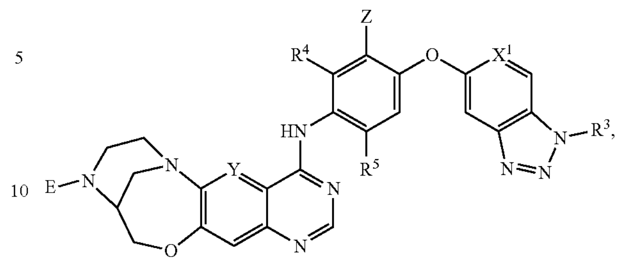

(I-h-6)

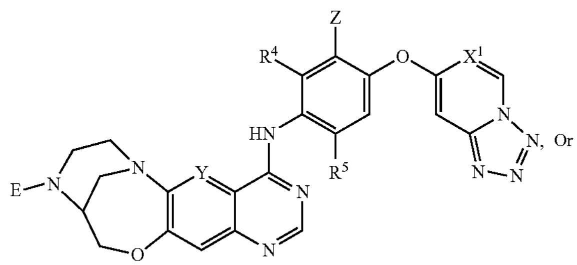

Or (I-h-7)

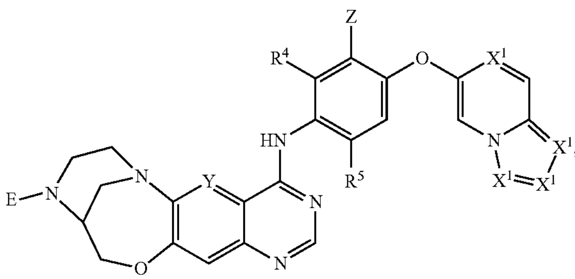

wherein E, $R^3$, $R^4$, $R^5$, Y, Z, $X^1$, and $X^2$ are as defined for formula (I). In some embodiments, the compound is a compound of formula (I-h-1). In some embodiments, the compound is a compound of formula (I-h-2). In some embodiments, the compound is a compound of formula (I-h-3). In some embodiments, the compound is a compound of formula (I-h-4). In some embodiments, the compound is a compound of formula (I-h-5). In some embodiments, the compound is a compound of formula (I-h-6). In some embodiments, the compound is a compound of formula (I-h-7). In any variation of formula (I-h-1), (I-h-2), (I-h-3), (I-h-4), (I-h-5), (I-h-6), or (I-h-7), Z is —H, —F —Cl, —Br, —I, —C≡CH, —$OCH_3$, —$CH_3$, or —$CH_2CH_3$; Y is N, C—H, or C—F; V is O, S, or $NR^2$, and $R^2$ is $C_1$-$C_6$ alkyl or $C_1$-$C_6$ cycloalkyl, each of which is independently optionally substituted by 1-4 fluorines. In some variations, E, $R^3$, $R^4$, $R^5$, Y, Z, $X^1$, and $X^2$ of formula (I-h-1), (I-h-2), (I-h-3), (I-h-4), (I-h-5), (I-h-6), or (I-h-7) are as defined for a compound of formula (I'), or a pharmaceutically acceptable salt, solvate, hydrate, or co-crystal thereof, or a mixture of any of the foregoing.

In some embodiments, the compound of formula (I') is a compound of formula (I'-h-1), (I'-h-2), (I'-h-3), (I'-h-4), (I'-h-5), (I'-h-6), (I'-h-7) or (I'-h-8):

(I'-h-1)

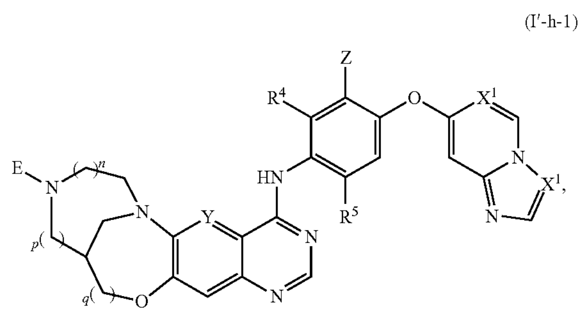

(I'-h-2)

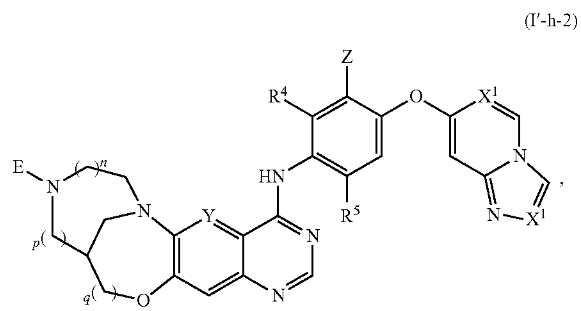

(I'-h-3)

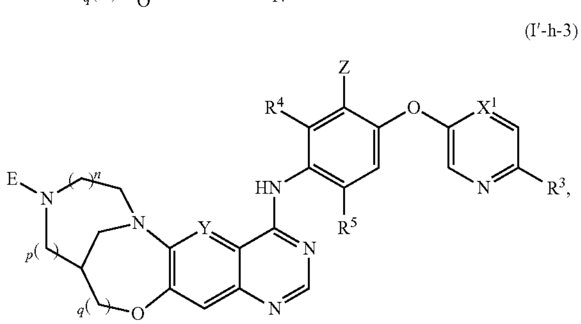

(I'-h-4)

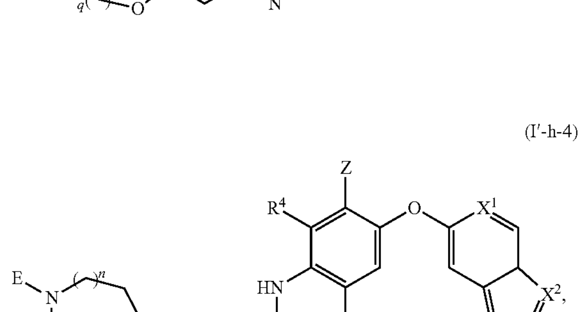

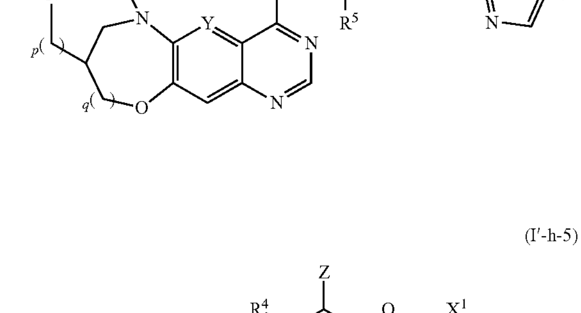

(I'-h-5)

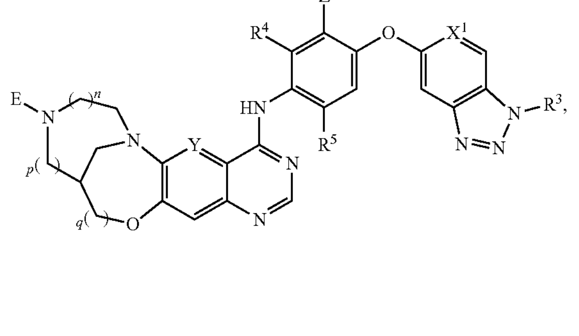

-continued (I'-h-6)

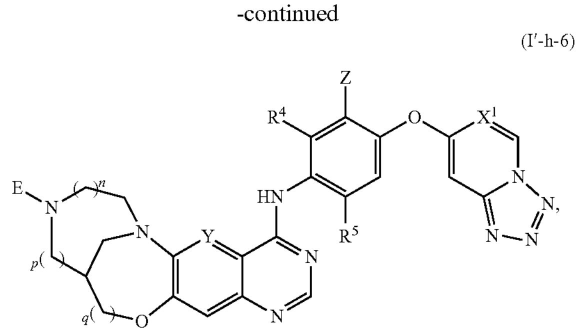

(I'-h-7)

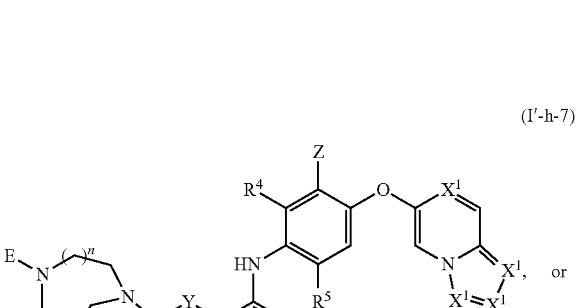

or

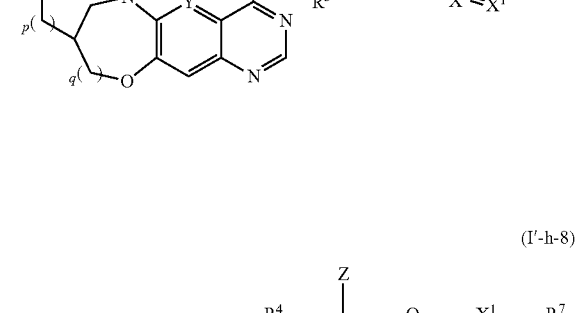

(I'-h-8)

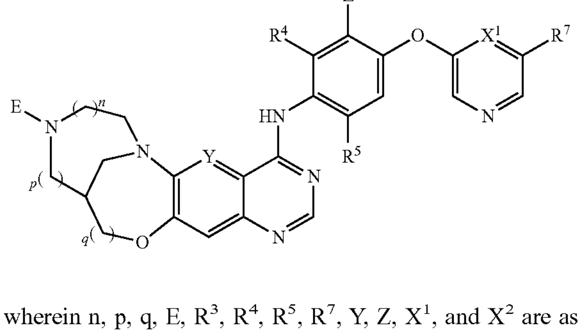

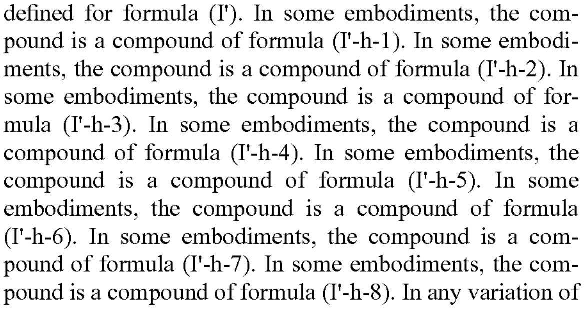

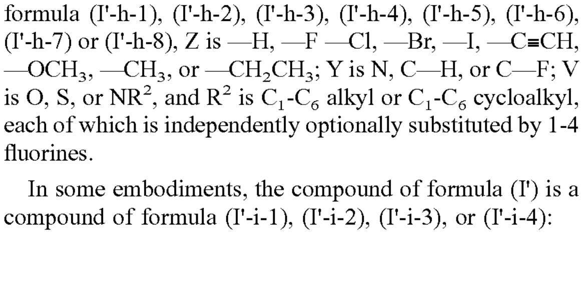

wherein n, p, q, E, $R^3$, $R^4$, $R^5$, $R^7$, Y, Z, $X^1$, and $X^2$ are as defined for formula (I'). In some embodiments, the compound is a compound of formula (I'-h-1). In some embodiments, the compound is a compound of formula (I'-h-2). In some embodiments, the compound is a compound of formula (I'-h-3). In some embodiments, the compound is a compound of formula (I'-h-4). In some embodiments, the compound is a compound of formula (I'-h-5). In some embodiments, the compound is a compound of formula (I'-h-6). In some embodiments, the compound is a compound of formula (I'-h-7). In some embodiments, the compound is a compound of formula (I'-h-8). In any variation of formula (I'-h-1), (I'-h-2), (I'-h-3), (I'-h-4), (I'-h-5), (I'-h-6), (I'-h-7) or (I'-h-8), Z is —H, —F —Cl, —Br, —I, —C≡CH, —$OCH_3$, —$CH_3$, or —$CH_2CH_3$; Y is N, C—H, or C—F; V is O, S, or $NR^2$, and $R^2$ is $C_1$-$C_6$ alkyl or $C_1$-$C_6$ cycloalkyl, each of which is independently optionally substituted by 1-4 fluorines.

In some embodiments, the compound of formula (I') is a compound of formula (I'-i-1), (I'-i-2), (I'-i-3), or (I'-i-4):

(I'-i-1)

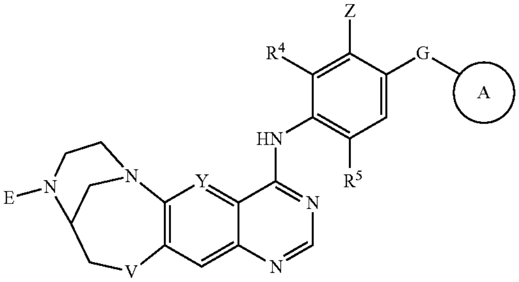

, (I'-i-2)

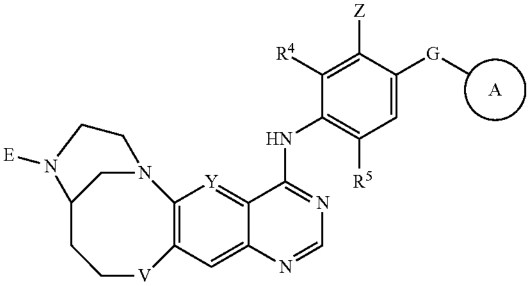

, (I'-i-3)

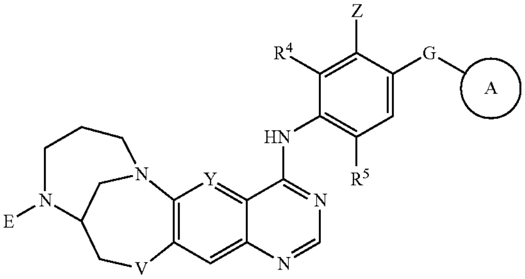

, or (I'-i-4)

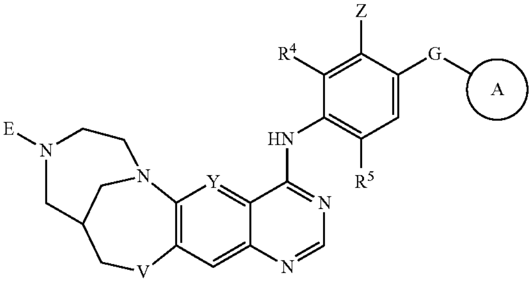

, wherein $R^4$, $R^5$, E, V, Z, G, Y, and ring A, are as defined for formula (I'). In some embodiments, the compound is a compound of formula (I'-i-1). In some embodiments, the compound is a compound of formula (I'-i-2). In some embodiments, the compound is a compound of formula (I'-i-3). In some embodiments, the compound is a compound of formula (I'-i-4). In any variation of formula (I'-i-1), (I'-i-2), (I'-i-3), or (I'-i-4), Z is —H, —F —Cl, —Br, —I, —C≡CH, $—OCH_3$, $—CH_3$, or $—CH_2CH_3$; Y is N, C—H, or C—F; V is O, S, or $NR^2$, wherein $R^2$ is $C_1$-$C_6$ alkyl or $C_1$-$C_6$ cycloalkyl, each of which is independently optionally substituted by 1-4 fluorines; G is —O—, —C(═O)—, —S—, —S(O)—, $—S(O)_2—$, or $—CH_2—$; and ring A is

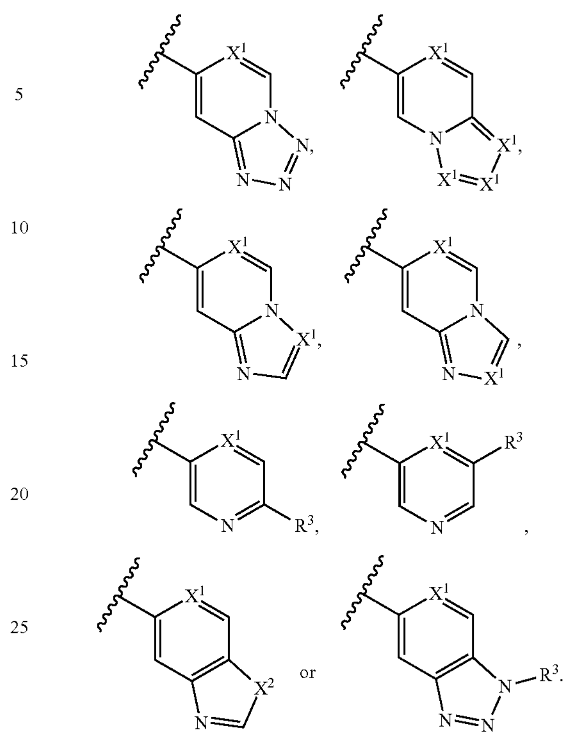

In some embodiments, ring A is

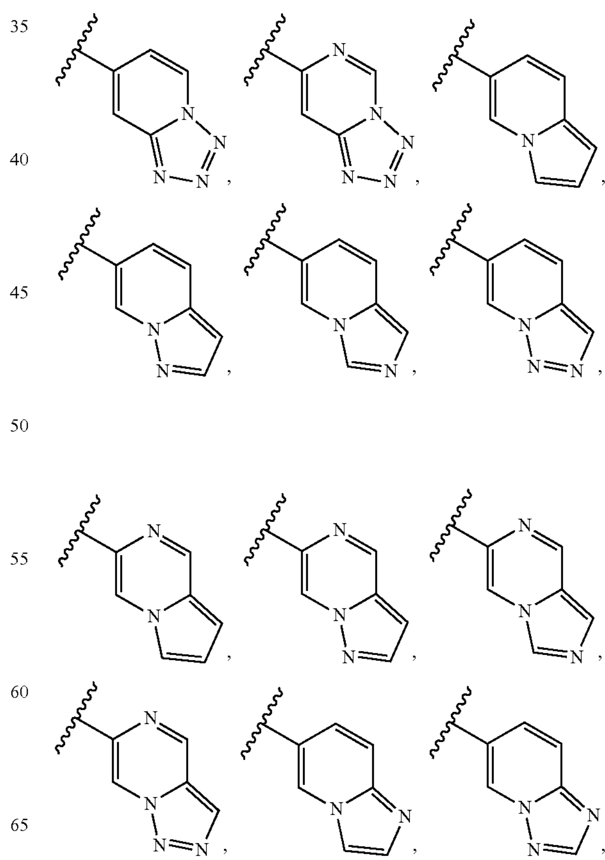

-continued
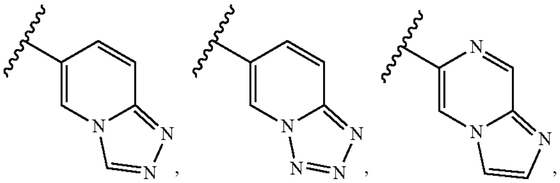
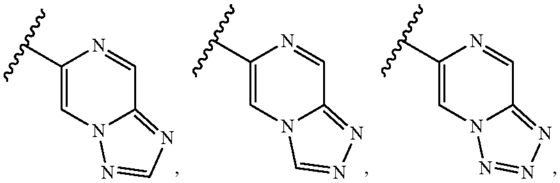
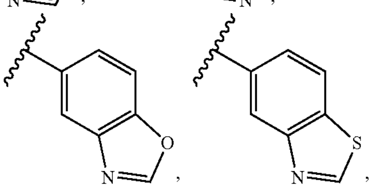
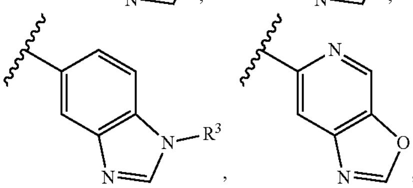
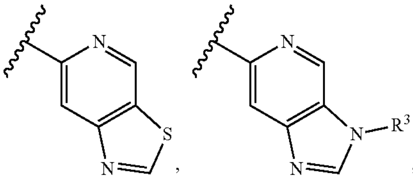
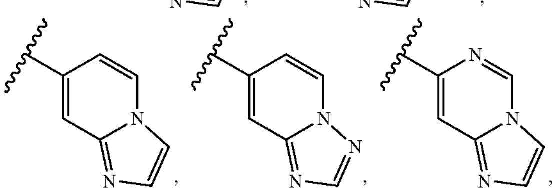
-continued
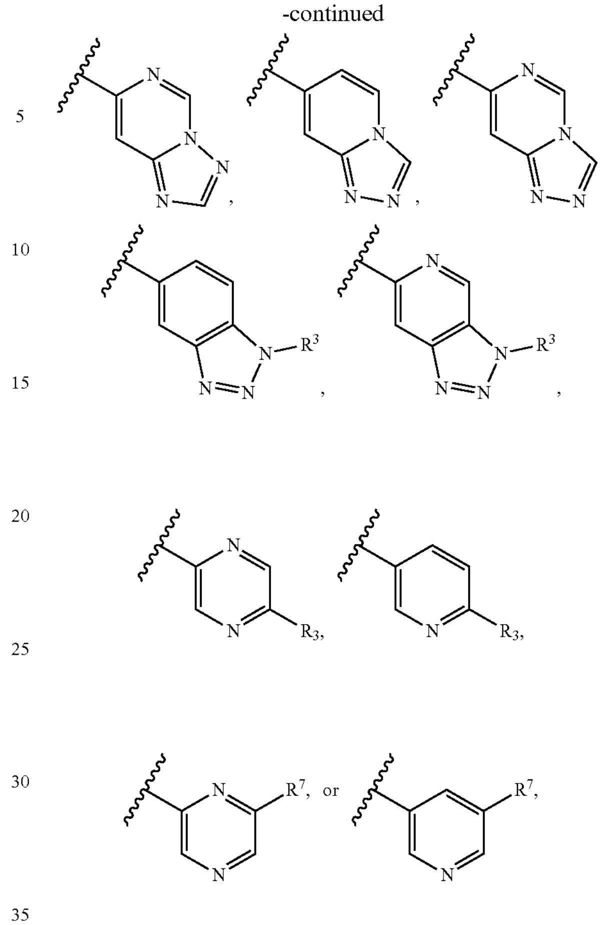
and $R^3$ is —H, $C_1$-$C_6$ alkyl, —$CD_3$ or $C_1$-$C_6$ cycloalkyl, and $R^7$ is —H, halogen, $C_1$-$C_6$ alkyl, —$CD_3$ or $C_1$-$C_6$ cycloalkyl.
In some embodiments, provided is a compound of formula (I') or formula (I) selected from the compounds in Table 1, or pharmaceutically acceptable salt, solvate, hydrate, or co-crystal thereof, or a mixture of any of the foregoing.

TABLE 1
| Cmpd No. | Structure | Cmpd No. | Structure |
| --- | --- | --- | --- |
| 1 | 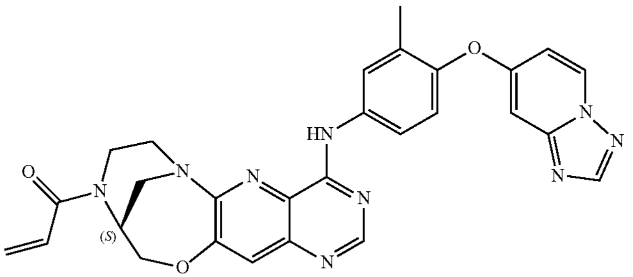 | 1-1 | 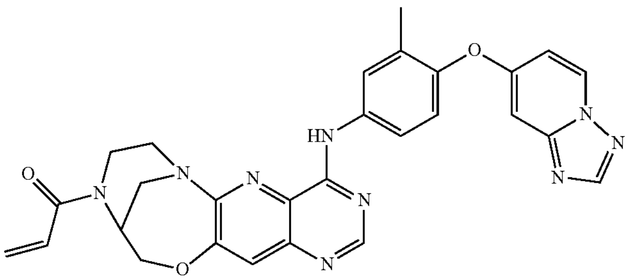 [SMILES: C=CC(=O)N1CCN2CC1COc1cc3ncnc(Nc4ccc(Oc5ccn6ncnc6c5)c(C)c4)c3nc12] |
| 2 | 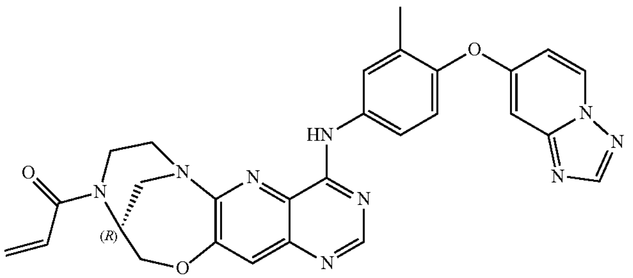 | 1-1 | 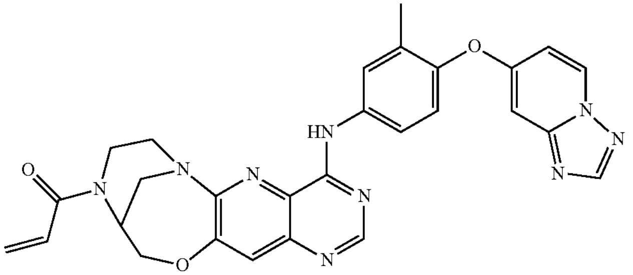 [SMILES: C=CC(=O)N1CCN2CC1COc1cc3ncnc(Nc4ccc(Oc5ccn6ncnc6c5)c(C)c4)c3nc12] |
| 3 | 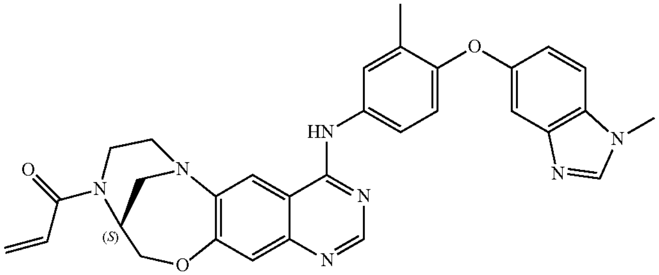 | 3-1 | 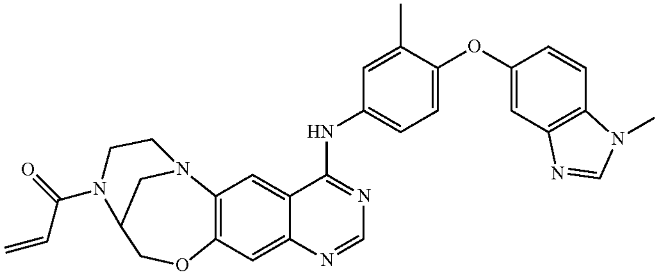 [SMILES: C=CC(=O)N1CCN2CC1COc1cc3ncnc(Nc4ccc(Oc5ccc6c(c5)ncn6C)c(C)c4)c3cc12] |

TABLE 1-continued
| Cmpd No. | Structure | Cmpd No. | Structure |
| --- | --- | --- | --- |
| 4 | 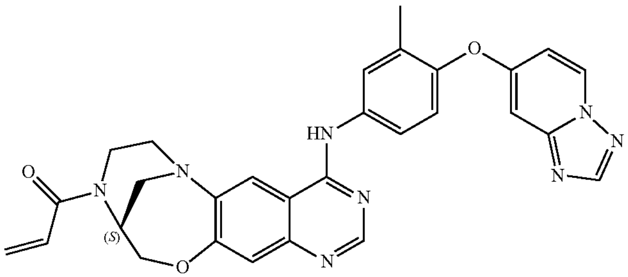 | 4-1 | 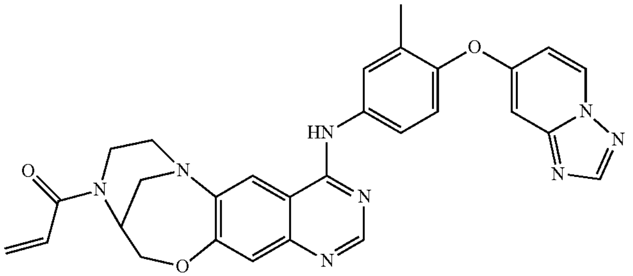 [SMILES: C=CC(=O)N1CCN2CC1COc1cc3ncnc(Nc4ccc(Oc5ccn6ncnc6c5)c(C)c4)c3cc12] |
| 5 | 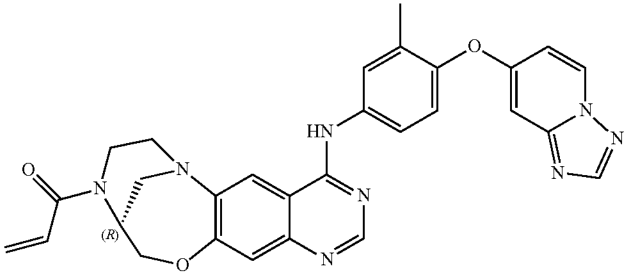 | 4-1 | 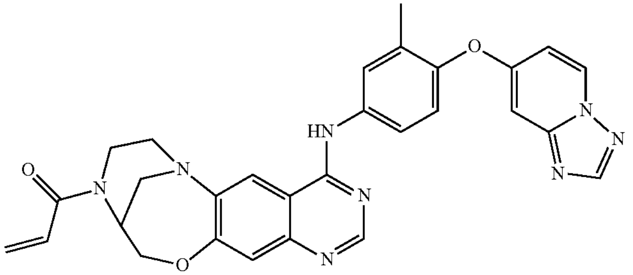 [SMILES: C=CC(=O)N1CCN2CC1COc1cc3ncnc(Nc4ccc(Oc5ccn6ncnc6c5)c(C)c4)c3cc12] |
| 6 | 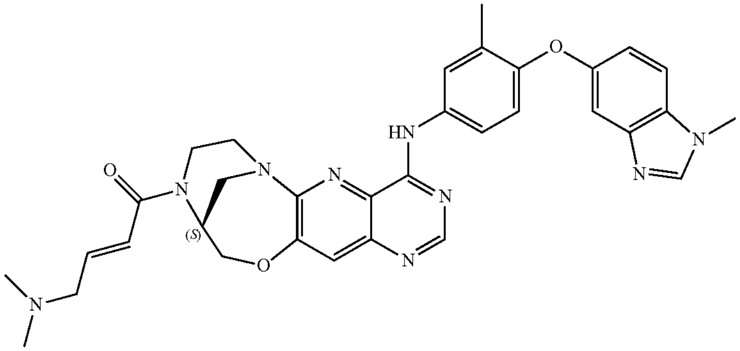 | 6-1 | 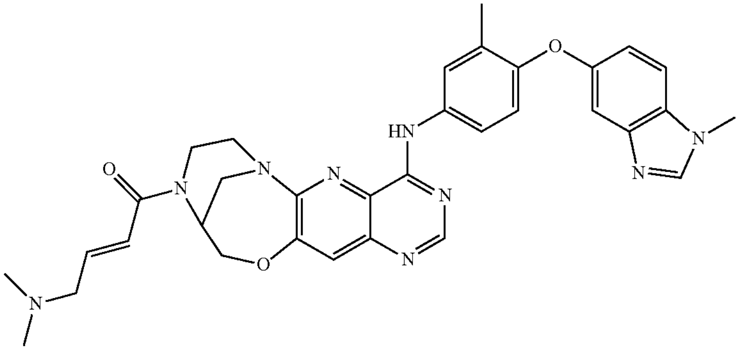 |

TABLE 1-continued
| Cmpd No. | Structure | Cmpd No. | Structure |
| --- | --- | --- | --- |
| 7 | 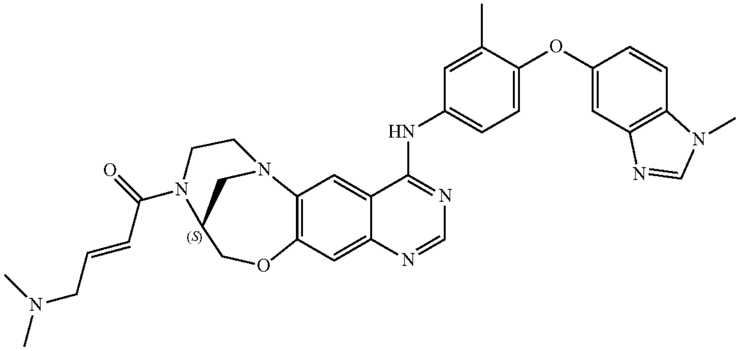 | 7-1 | 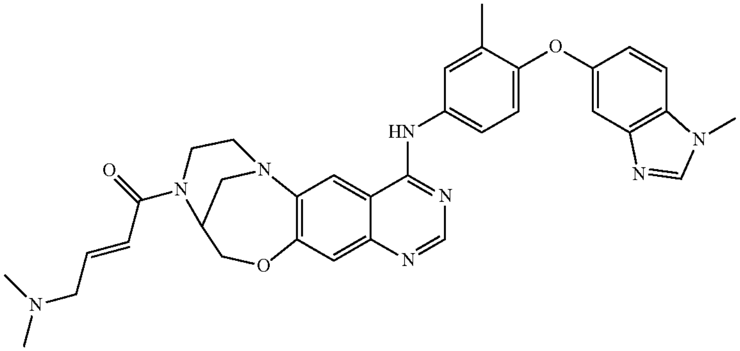 |
| 8 | 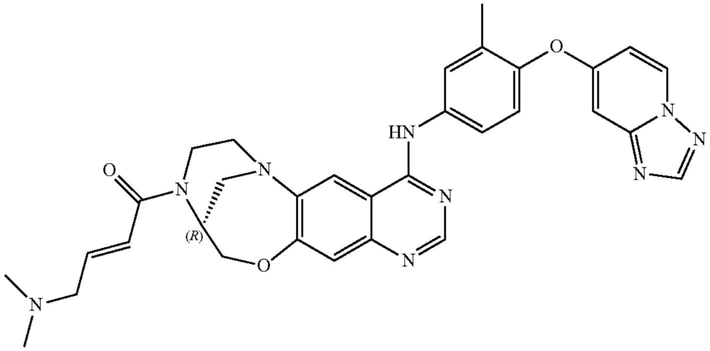 | 8-1 | 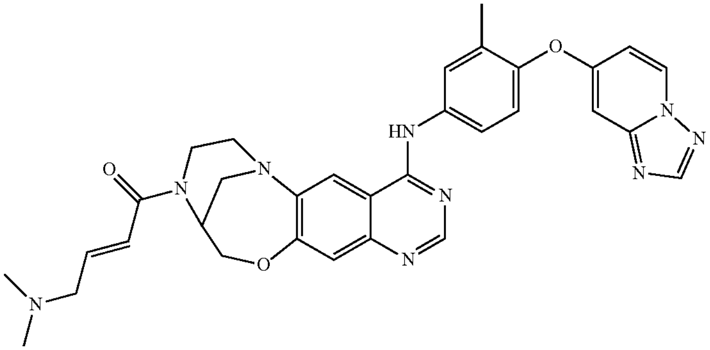 |

TABLE 1-continued
| Cmpd No. | Structure | Cmpd No. | Structure |
|---|---|---|---|
| 9 | 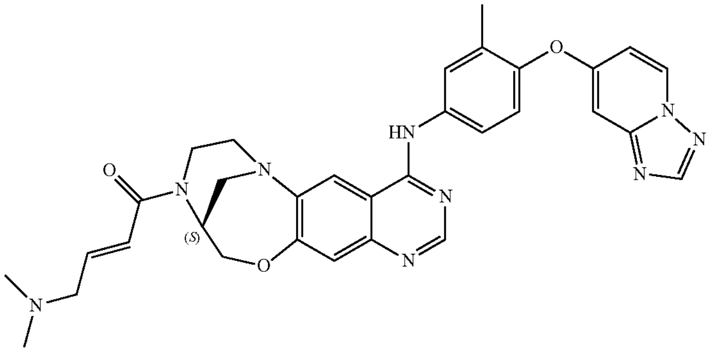 | 8-1 | 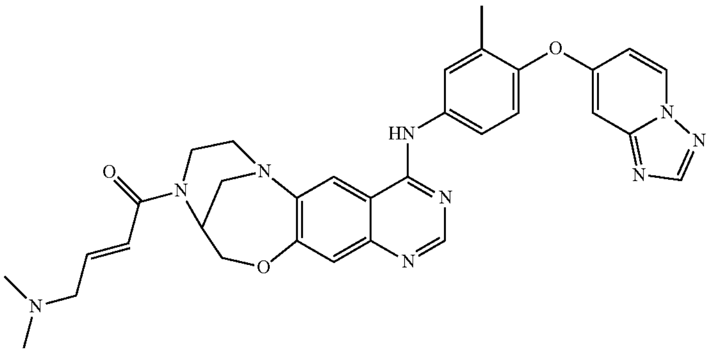 [SMILES: Cc1cc(Nc2ncnc3cc4c(cc23)N2CCN(C(=O)/C=C/CN(C)C)C(CO4)C2)ccc1Oc1ccn2ncnc2c1] |
| 10 | 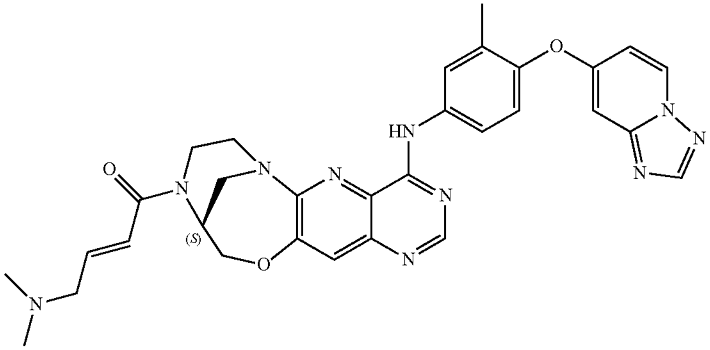 | 10-1 | 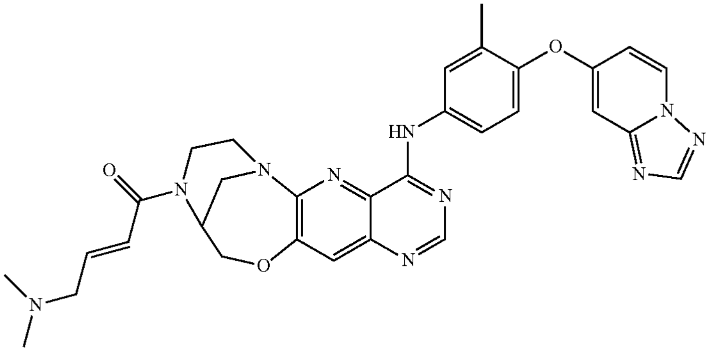 [SMILES: Cc1cc(Nc2ncnc3cc4c(nc23)N2CCN(C(=O)/C=C/CN(C)C)C(CO4)C2)ccc1Oc1ccn2ncnc2c1] |
| 11 | 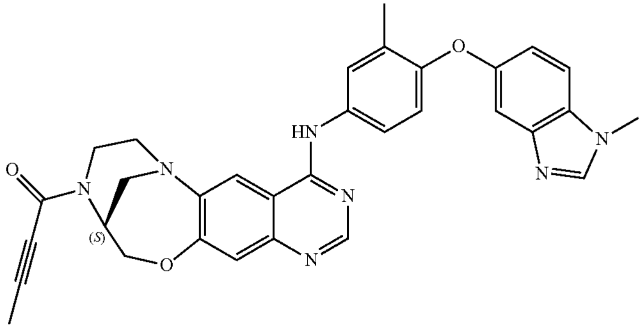 | 11-1 | 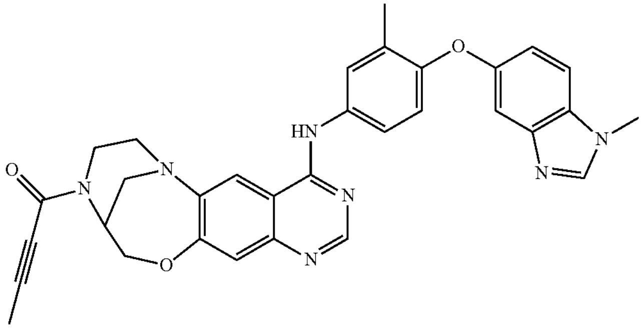 [SMILES: CC#CC(=O)N1CCN2CC1COc1cc3ncnc(Nc4ccc(Oc5ccc6c(c5)ncn6C)c(C)c4)c3cc12] |

TABLE 1-continued
| Cmpd No. | Structure | Cmpd No. | Structure |
|---|---|---|---|
| 12 | 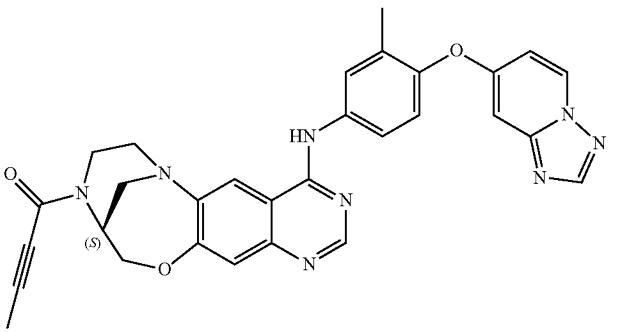 | 12-1 | 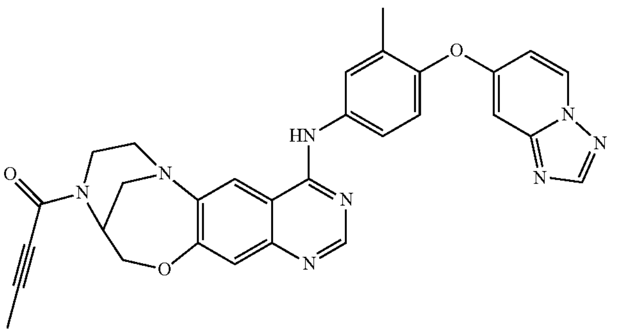 [SMILES: CC#CC(=O)N1CCN2CC1COc1cc3ncnc(Nc4ccc(Oc5ccn6ncnc6c5)c(C)c4)c3cc12] |
| 13 | 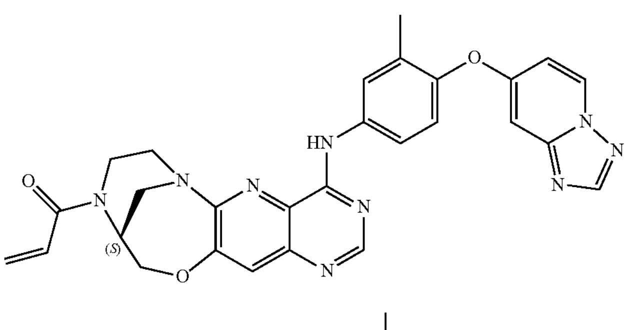 | 13-1 | 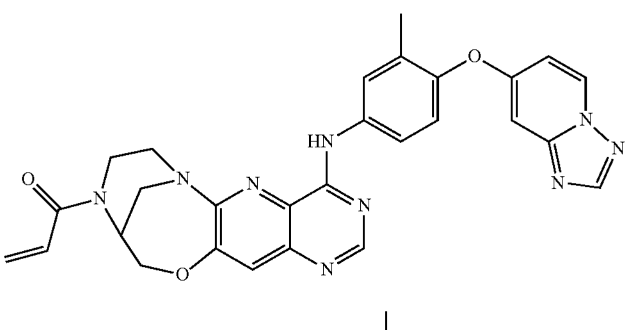 |
| 14 | 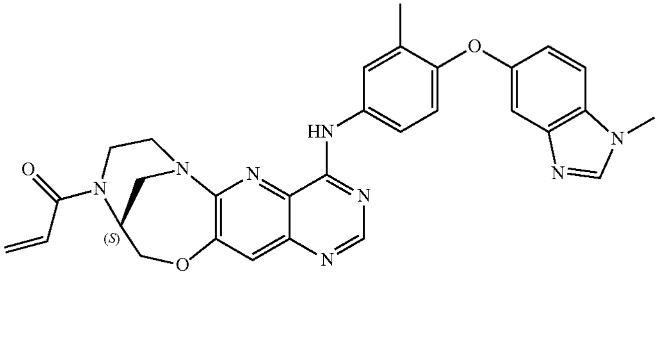 | 14-1 | 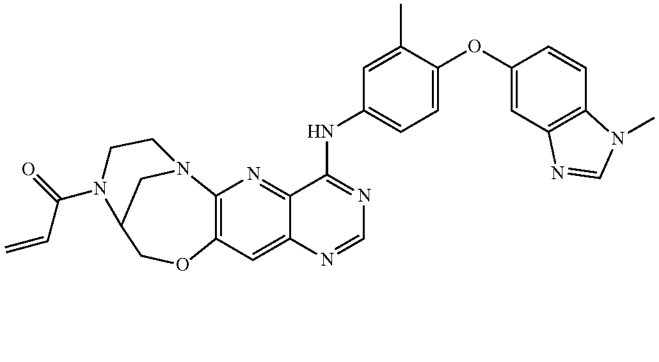 [SMILES: C=CC(=O)N1CCN2CC1COc1cc3ncnc(Nc4ccc(Oc5ccc6c(c5)ncn6C)c(C)c4)c3nc12] |

TABLE 1-continued
| Cmpd No. | Structure | Cmpd No. | Structure |
| --- | --- | --- | --- |
| 15 | 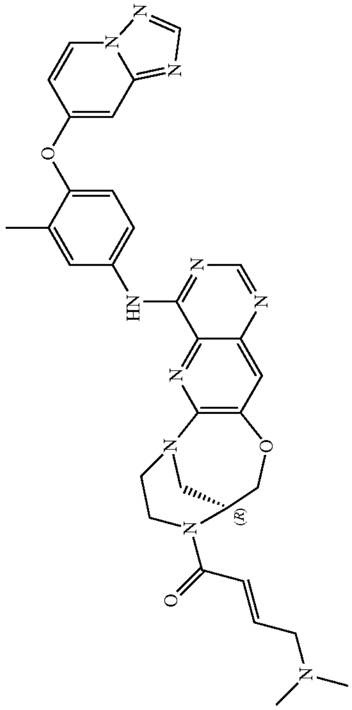 | 10-1 | 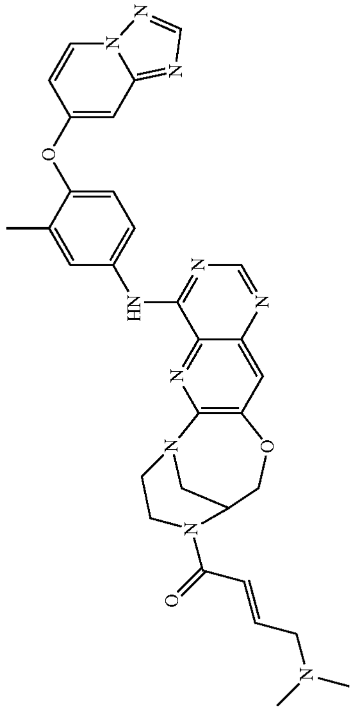 |
| 16 | 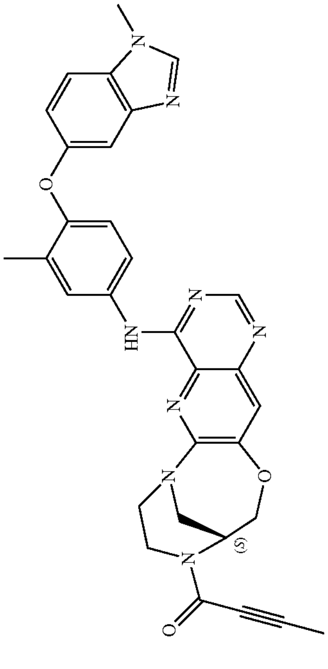 | 16-1 | 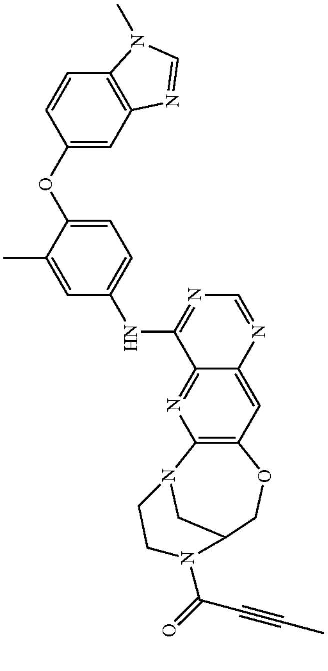 |
| 17 | 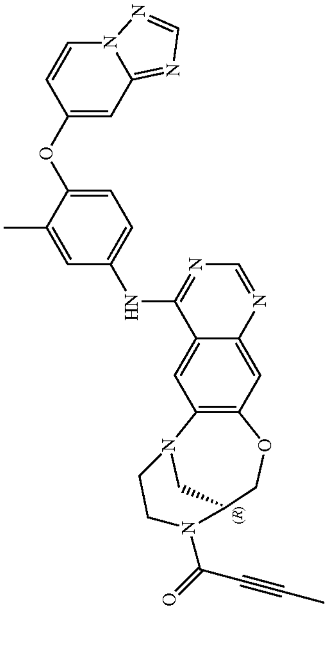 | 12-1 | 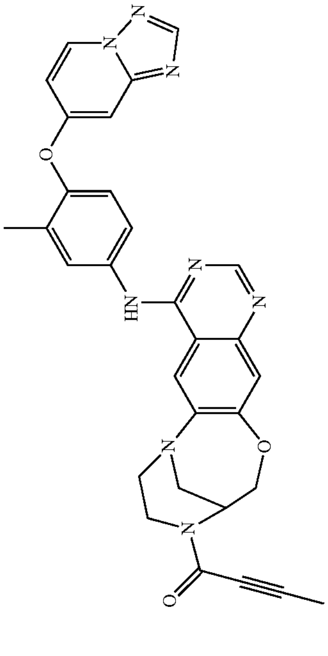 |

TABLE 1-continued
| Cmpd No. | Structure | Cmpd No. | Structure |
|---|---|---|---|
| 18 | 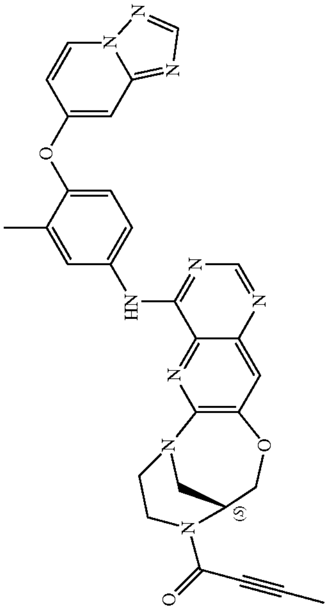 | 18-1 | 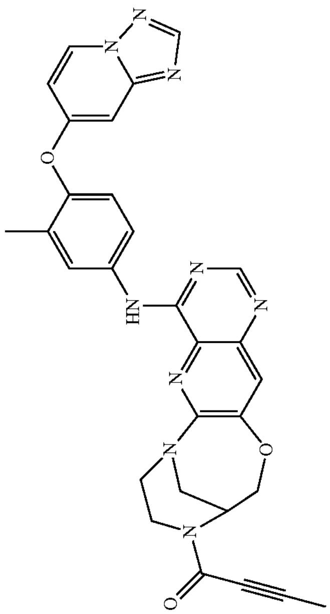 |
| 19 | 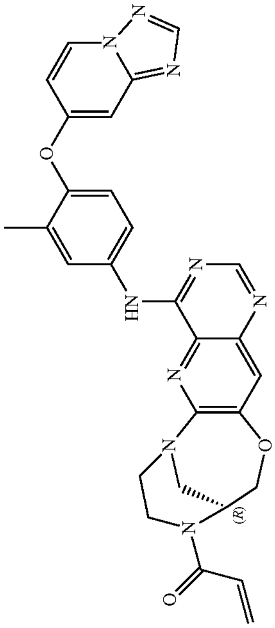 | 19-1 | 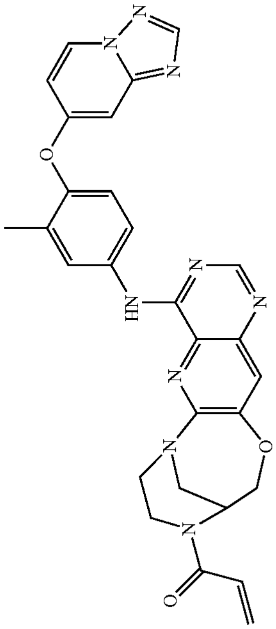 |
| 20 | 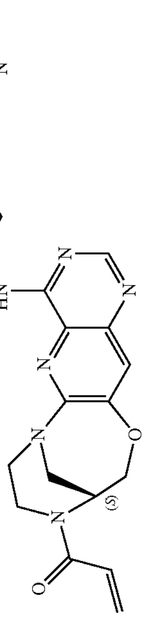 | 20-1 | 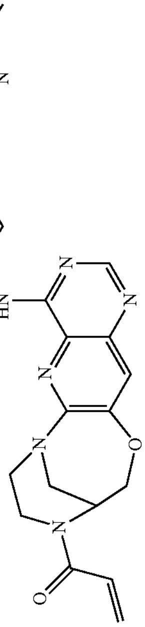 |

TABLE 1-continued
| Cmpd No. | Structure | Cmpd No. | Structure |
| --- | --- | --- | --- |
| 21 | 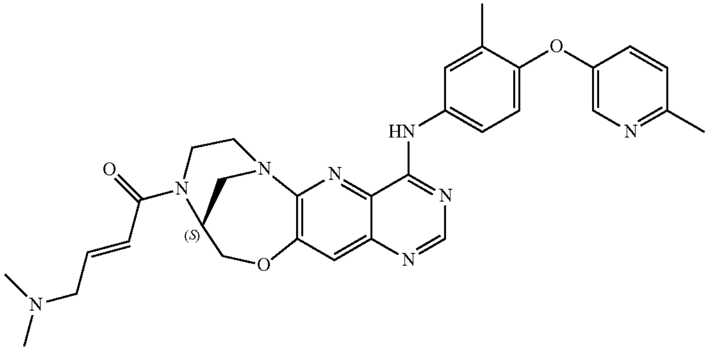 | 21-1 | 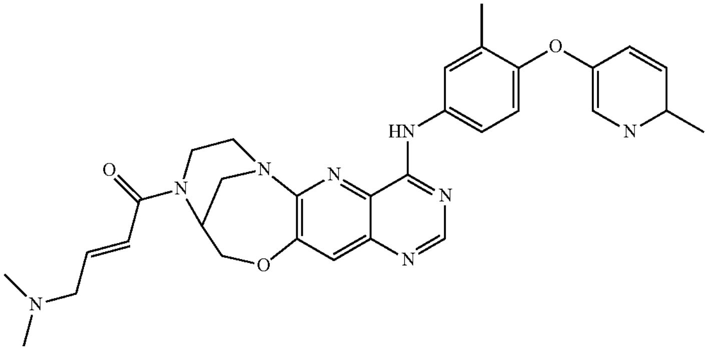 |
| 22 | 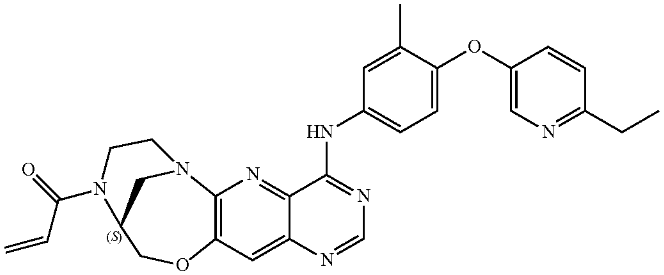 | 22-1 | 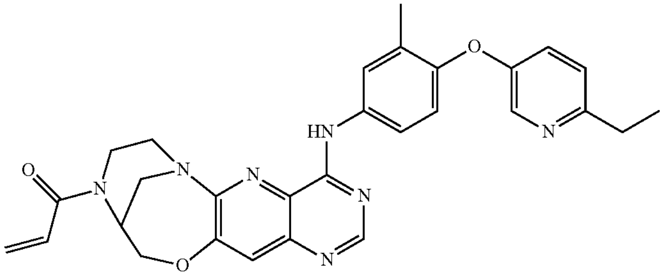 [SMILES: C=CC(=O)N1CCN2CC1COc1cc3ncnc(Nc4ccc(Oc5ccc(CC)nc5)c(C)c4)c3nc12] |
| 23 | 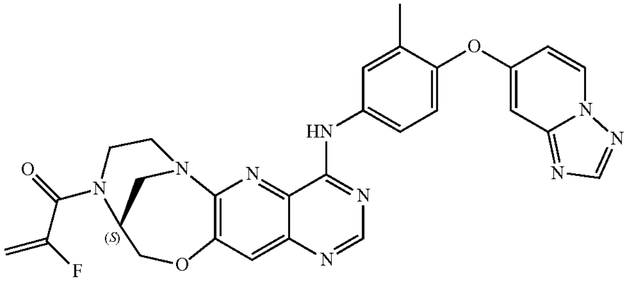 | 23-1 | 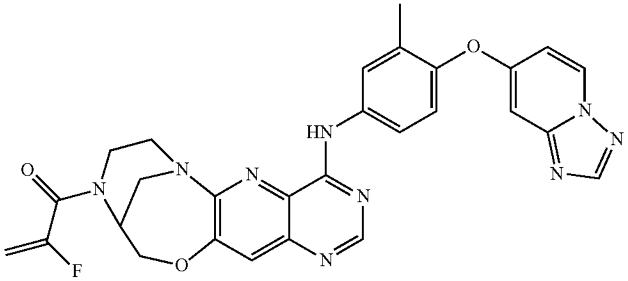 [SMILES: C=C(F)C(=O)N1CCN2CC1COc1cc3ncnc(Nc4ccc(Oc5ccn6ncnc6c5)c(C)c4)c3nc12] |

TABLE 1-continued
| Cmpd No. | Structure | Cmpd No. | Structure |
| --- | --- | --- | --- |
| 24 | 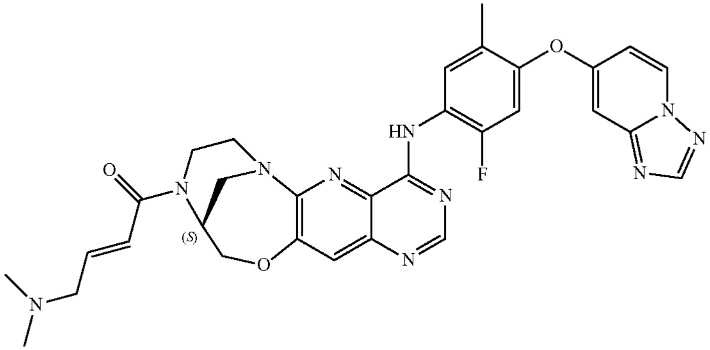 | 24-1 | 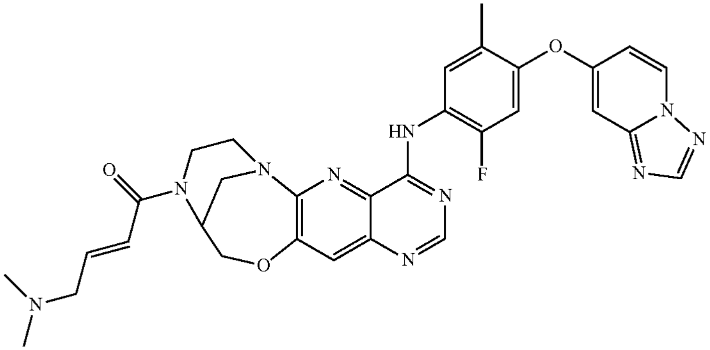 [SMILES: Cc1cc(Nc2ncnc3cc4c(nc23)N2CCN(C(=O)/C=C/CN(C)C)C(CO4)C2)c(F)cc1Oc1ccn2ncnc2c1] |
| 25 | 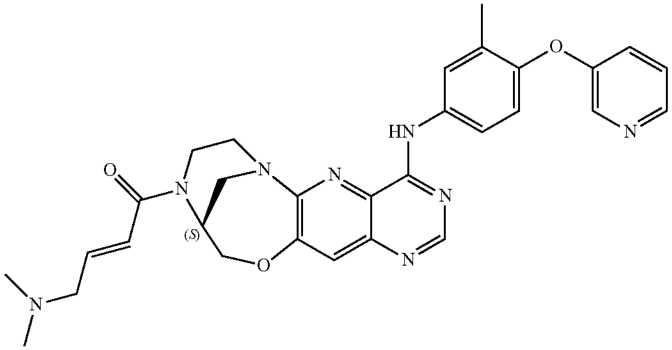 | 25-1 | 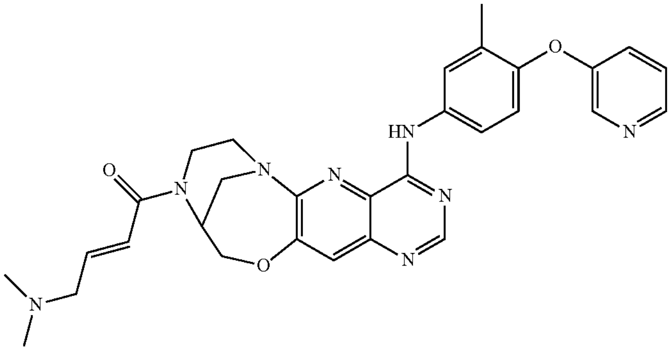 [SMILES: Cc1cc(Nc2ncnc3cc4c(nc23)N2CCN(C(=O)/C=C/CN(C)C)C(CO4)C2)ccc1Oc1cccnc1] |

TABLE 1-continued
| Cmpd No. | Structure | Cmpd No. | Structure |
|---|---|---|---|
| 26 | 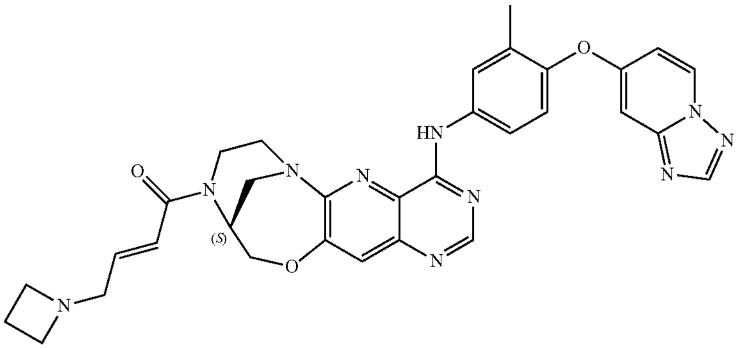 | 26-1 | 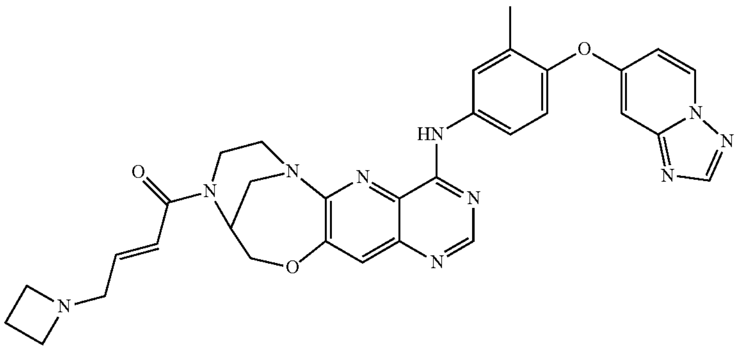 [SMILES: Cc1cc(Nc2ncnc3cc4c(nc23)N2CCN(C(=O)/C=C/CN3CCC3)C(CO4)C2)ccc1Oc1ccn2ncnc2c1] |
| 27 | 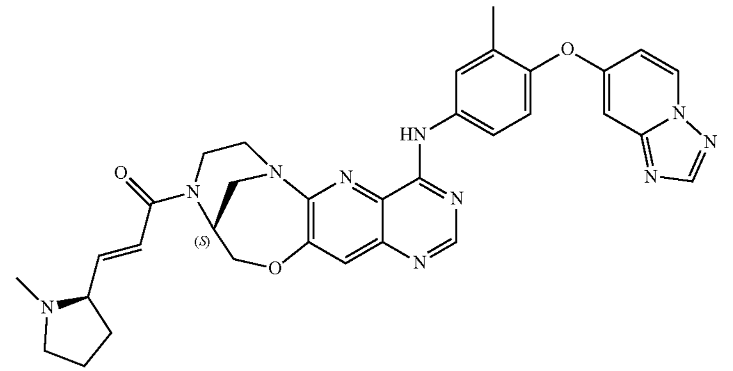 | 27-1 | 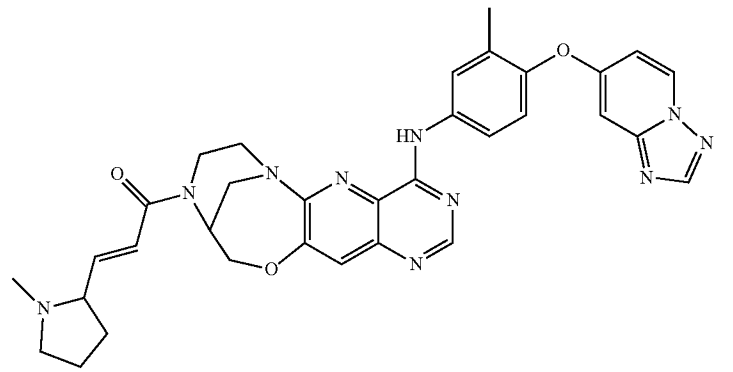 [SMILES: Cc1cc(Nc2ncnc3cc4c(nc23)N2CCN(C(=O)/C=C/C3CCCN3C)C(CO4)C2)ccc1Oc1ccn2ncnc2c1] |

TABLE 1-continued
| Cmpd No. | Structure | Cmpd No. | Structure |
|---|---|---|---|
| 28 | 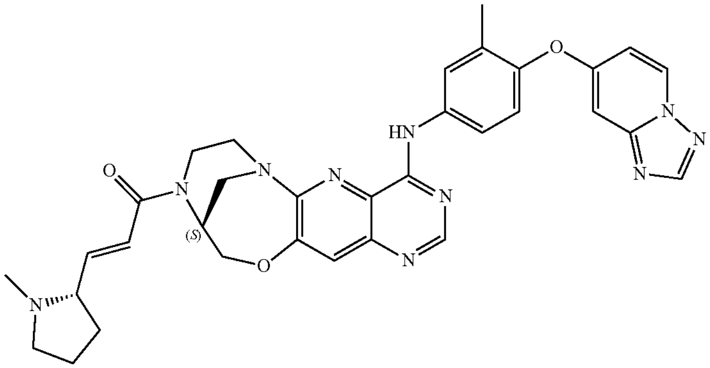 | 27-1 | 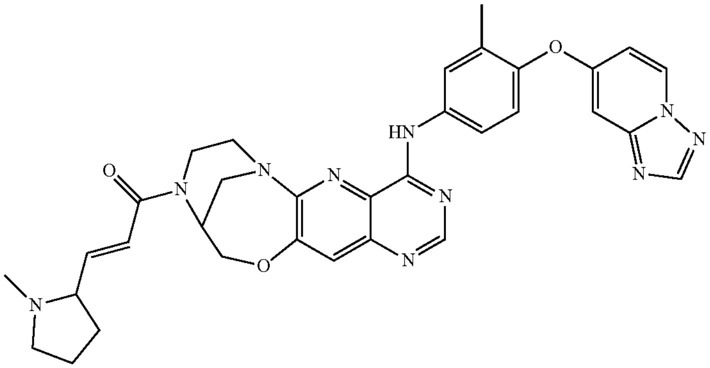 [SMILES: Cc1cc(Nc2ncnc3cc4c(nc23)N2CCN(C(=O)/C=C/C3CCCN3C)C(CO4)C2)ccc1Oc1ccn2ncnc2c1] |
| 29 | 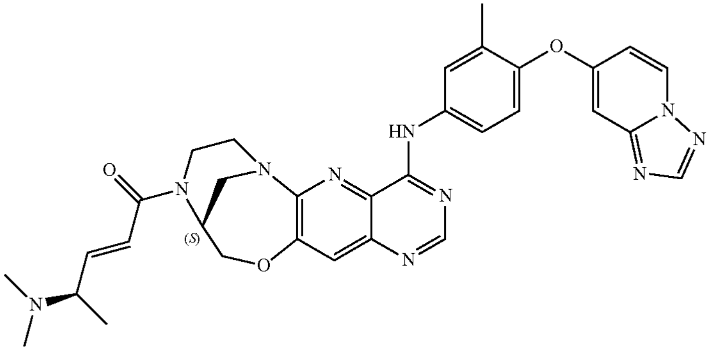 | 29-1 | 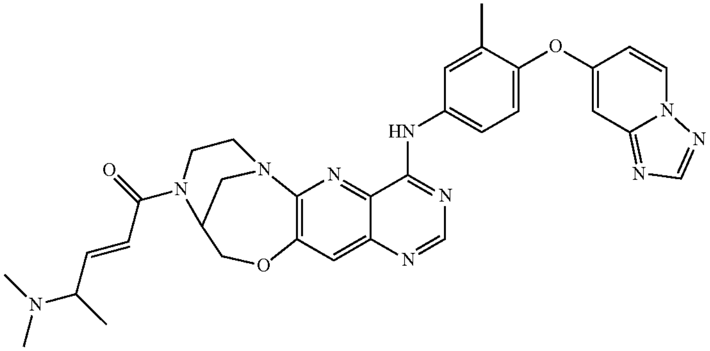 [SMILES: Cc1cc(Nc2ncnc3cc4c(nc23)N2CCN(C(=O)/C=C/C(C)N(C)C)C(CO4)C2)ccc1Oc1ccn2ncnc2c1] |

TABLE 1-continued
| Cmpd No. | Structure | Cmpd No. | Structure |
| --- | --- | --- | --- |
| 30 | 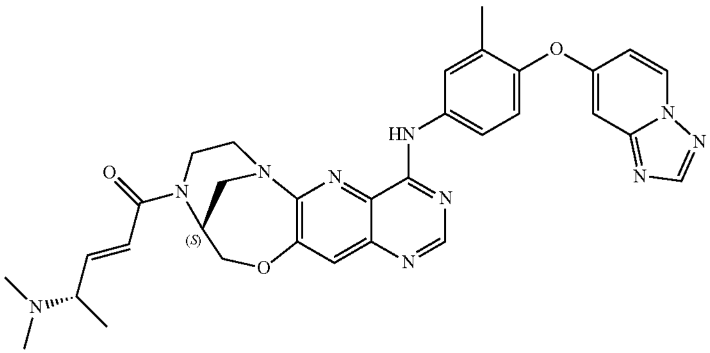 | 29-1 | 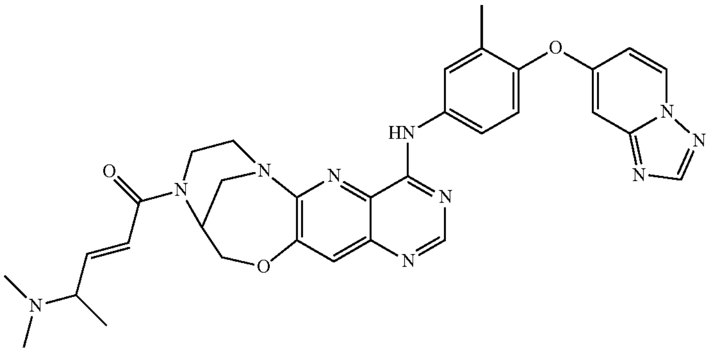 [SMILES: Cc1cc(Nc2ncnc3cc4c(nc23)N2CCN(C(=O)/C=C/C(C)N(C)C)C(CO4)C2)ccc1Oc1ccn2ncnc2c1] |
| 31 | 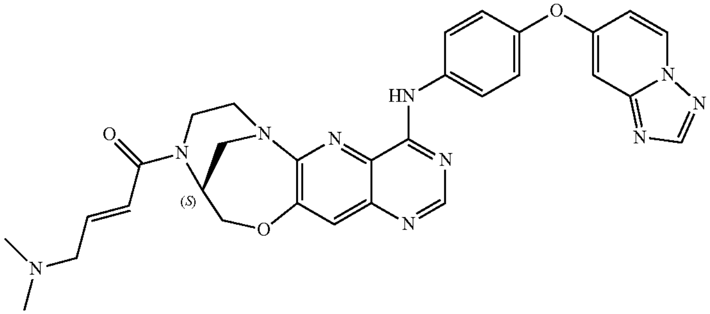 | 31-1 | 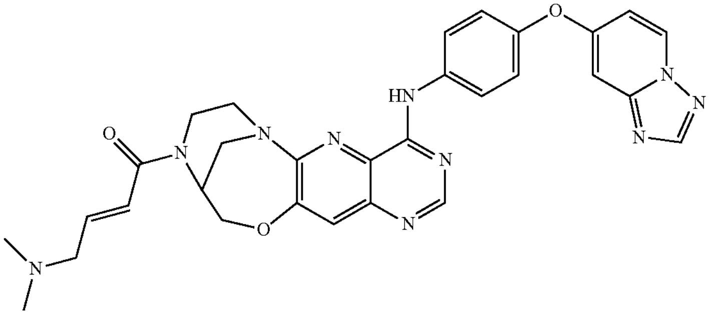 [SMILES: CN(C)C/C=C/C(=O)N1CCN2CC1COc1cc3ncnc(Nc4ccc(Oc5ccn6ncnc6c5)cc4)c3nc12] |
| 32 | 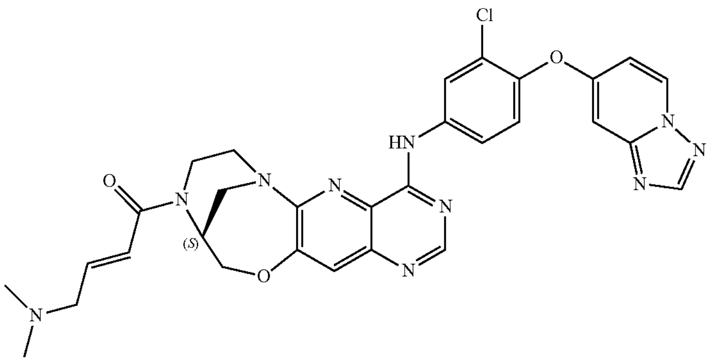 | 32-1 | 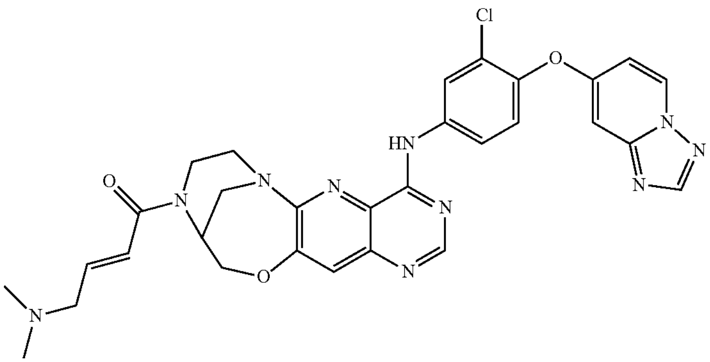 [SMILES: CN(C)C/C=C/C(=O)N1CCN2CC1COc1cc3ncnc(Nc4ccc(Oc5ccn6ncnc6c5)c(Cl)c4)c3nc12] |

TABLE 1-continued
| Cmpd No. | Structure | Cmpd No. | Structure |
|---|---|---|---|
| 33 | 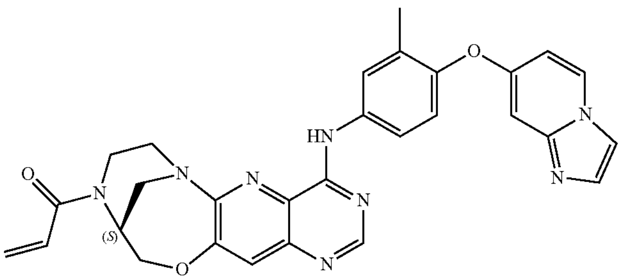 | 33-1 | 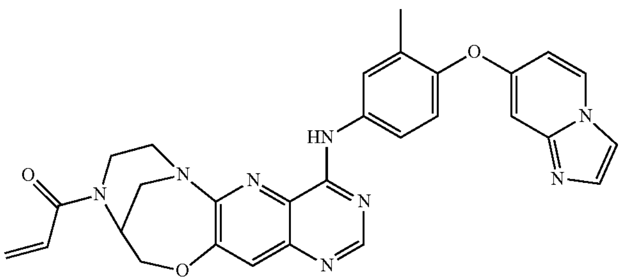 [SMILES: C=CC(=O)N1CCN2CC1COc1cc3ncnc(Nc4ccc(Oc5ccn6ccnc6c5)c(C)c4)c3nc12] |
| 34 | 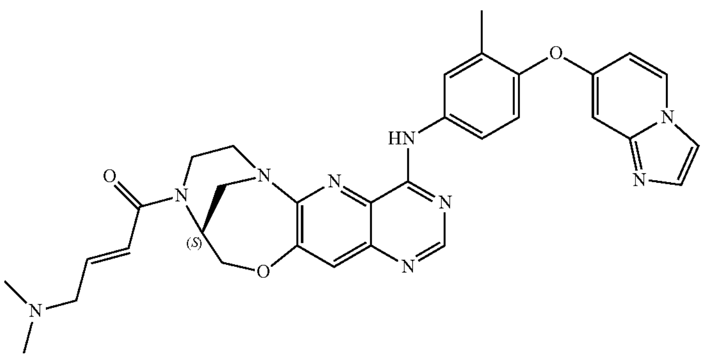 | 34-1 | 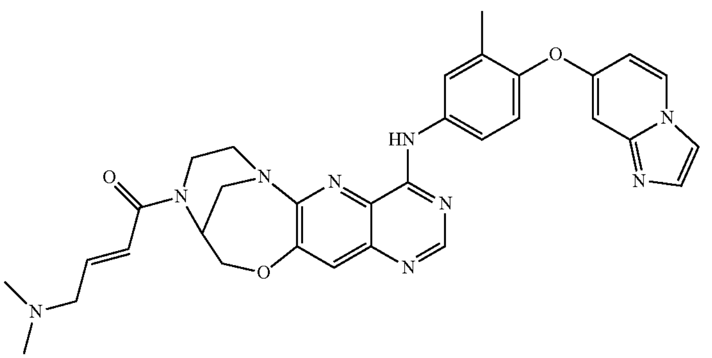 [SMILES: Cc1cc(Nc2ncnc3cc4c(nc23)N2CCN(C(=O)/C=C/CN(C)C)C(CO4)C2)ccc1Oc1ccn2ccnc2c1] |
| 35 | 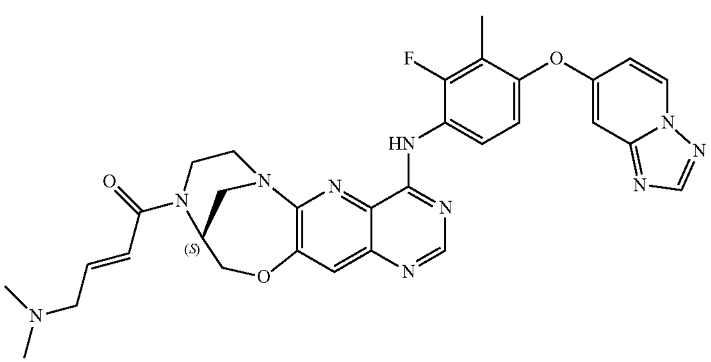 | 35-1 | 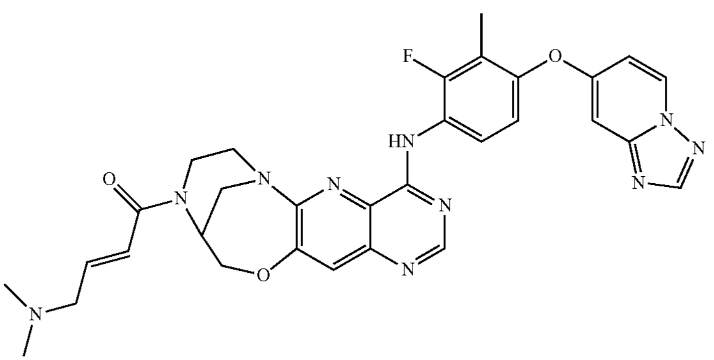 [SMILES: Cc1c(Oc2ccn3ncnc3c2)ccc(Nc2ncnc3cc4c(nc23)N2CCN(C(=O)/C=C/CN(C)C)C(CO4)C2)c1F] |

TABLE 1-continued
| Cmpd No. | Structure | Cmpd No. | Structure |
| --- | --- | --- | --- |
| 36 | 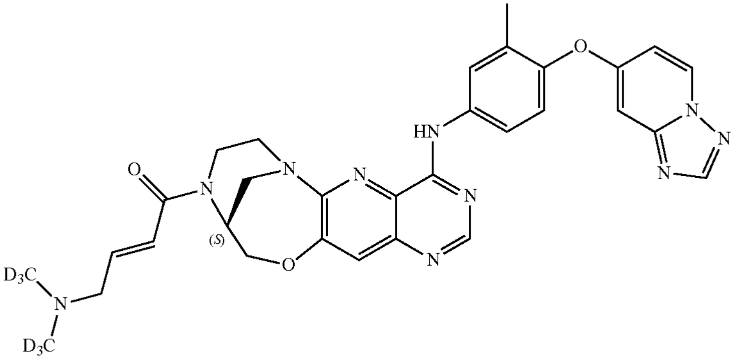 | 36-1 | 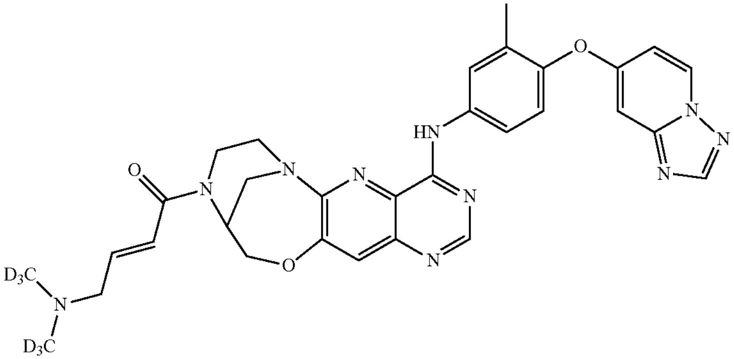 [SMILES: [2H]C([2H])([2H])N(C/C=C/C(=O)N1CCN2CC1COc1cc3ncnc(Nc4ccc(Oc5ccn6ncnc6c5)c(C)c4)c3nc12)C([2H])([2H])[2H]] |
| 37 | 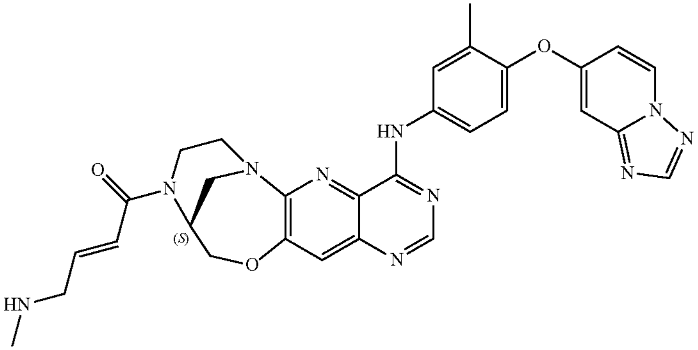 | 37-1 | 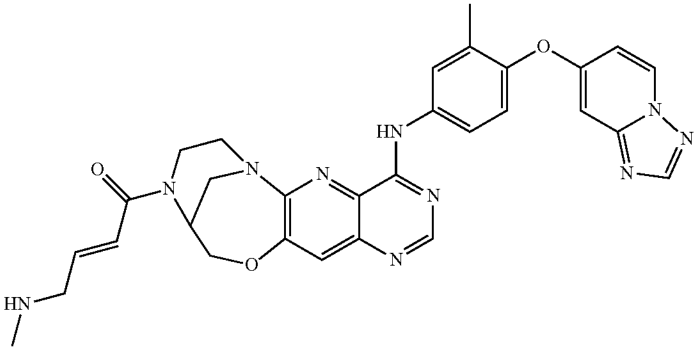 [SMILES: CNC/C=C/C(=O)N1CCN2CC1COc1cc3ncnc(Nc4ccc(Oc5ccn6ncnc6c5)c(C)c4)c3nc12] |

TABLE 1-continued
| Cmpd No. | Structure | Cmpd No. | Structure |
|---|---|---|---|
| 38 | 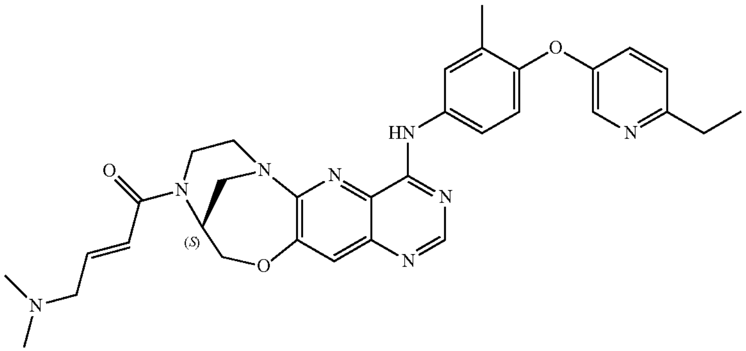 | 38-1 | 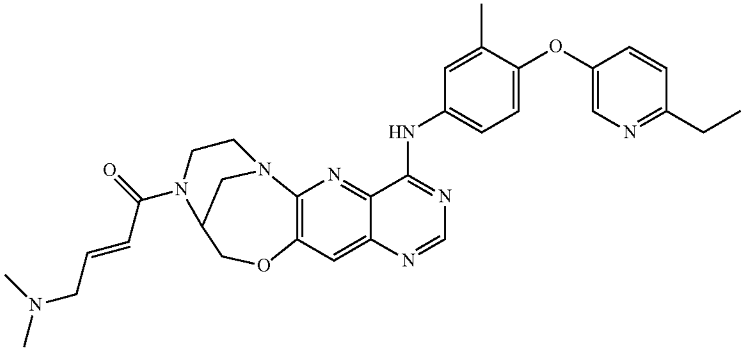 [SMILES: CCc1ccc(Oc2ccc(Nc3ncnc4cc5c(nc34)N3CCN(C(=O)/C=C/CN(C)C)C(CO5)C3)cc2C)cn1] |
| 39 | 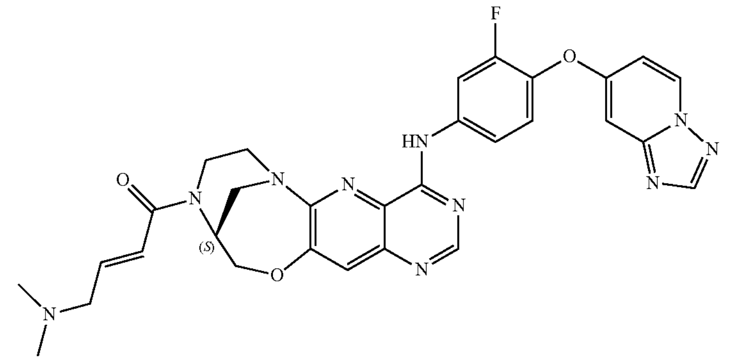 | 39-1 | 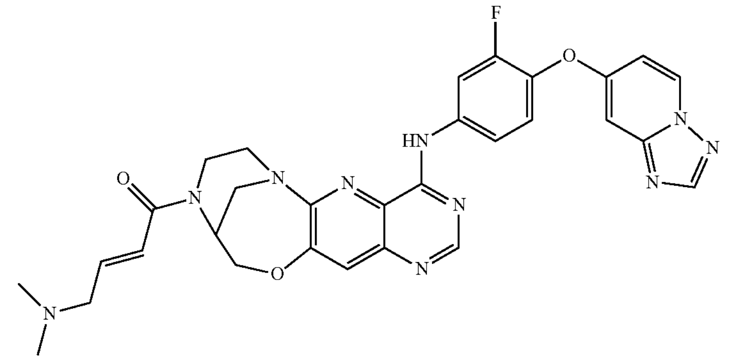 [SMILES: CN(C)C/C=C/C(=O)N1CCN2CC1COc1cc3ncnc(Nc4ccc(Oc5ccn6ncnc6c5)c(F)c4)c3nc12] |

TABLE 1-continued
| Cmpd No. | Structure | Cmpd No. | Structure |
| --- | --- | --- | --- |
| 40 | 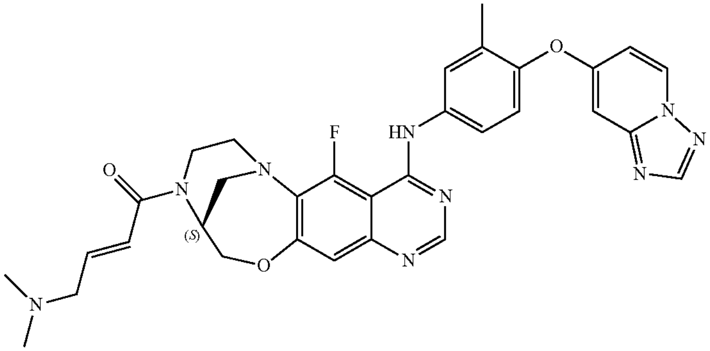 | 40-1 | 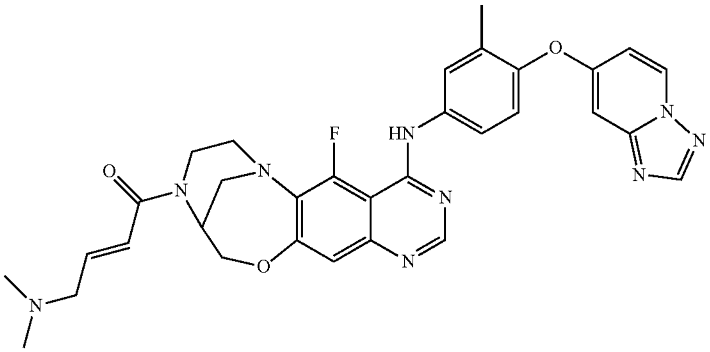 [SMILES: Cc1cc(Nc2ncnc3cc4c(c(F)c23)N2CCN(C(=O)/C=C/CN(C)C)C(CO4)C2)ccc1Oc1ccn2ncnc2c1] |
| 41 | 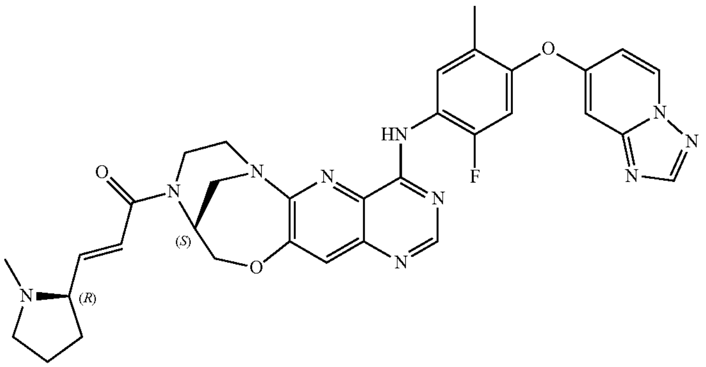 | 41-1 | 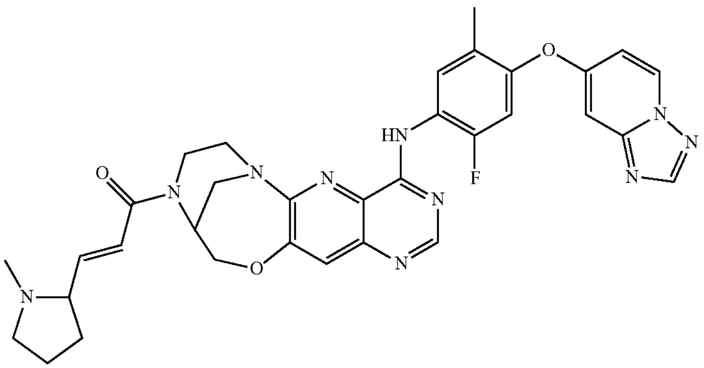 [SMILES: Cc1cc(Nc2ncnc3cc4c(nc23)N2CCN(C(=O)/C=C/C3CCCN3C)C(CO4)C2)c(F)cc1Oc1ccn2ncnc2c1] |
| 42 | 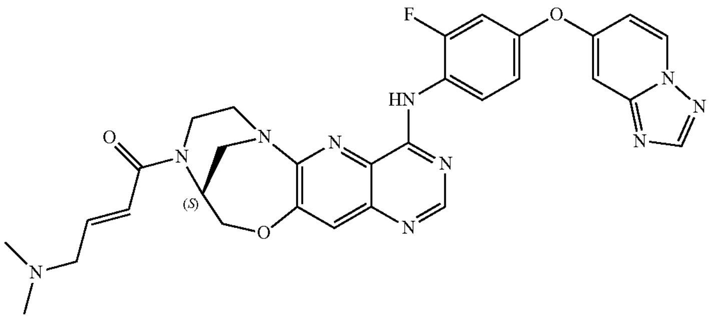 | 42-1 | 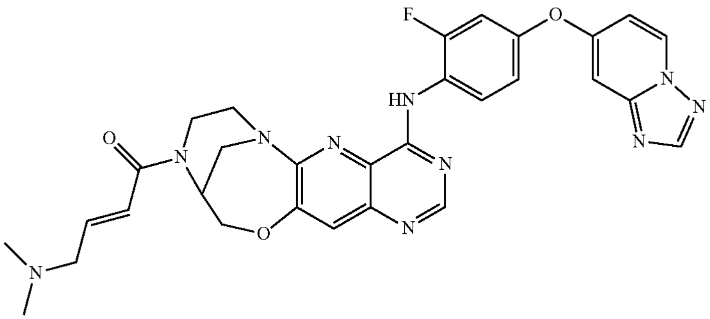 [SMILES: CN(C)C/C=C/C(=O)N1CCN2CC1COc1cc3ncnc(Nc4ccc(Oc5ccn6ncnc6c5)cc4F)c3nc12] |

TABLE 1-continued
| Cmpd No. | Structure | Cmpd No. | Structure |
|---|---|---|---|
| 43 | 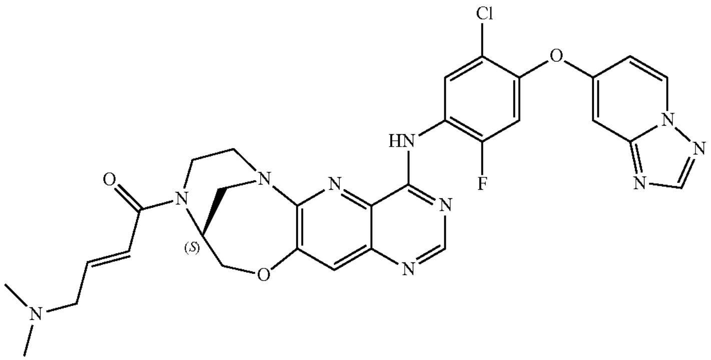 | 43-1 | 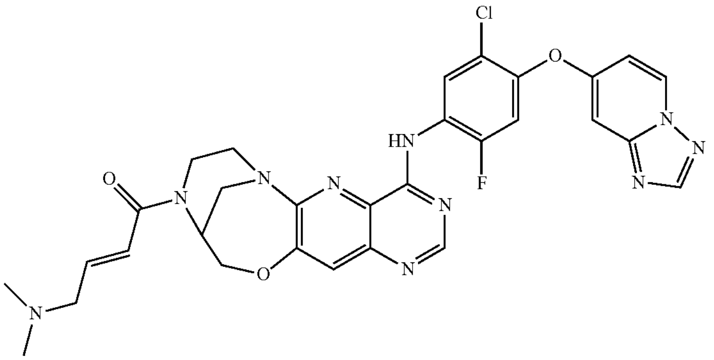 [SMILES: CN(C)C/C=C/C(=O)N1CCN2CC1COc1cc3ncnc(Nc4cc(Cl)c(Oc5ccn6ncnc6c5)cc4F)c3nc12] |
| 44 | 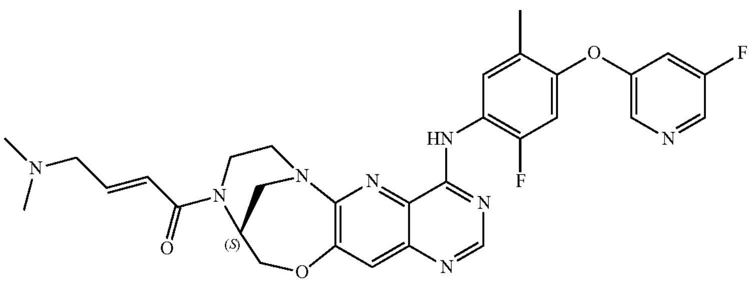 | 44-1 | 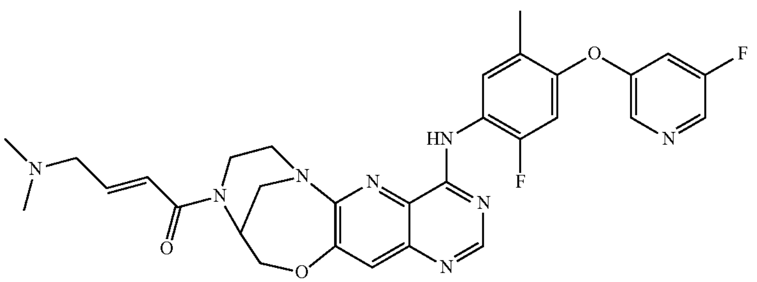 [SMILES: Cc1cc(Nc2ncnc3cc4c(nc23)N2CCN(C(=O)/C=C/CN(C)C)C(CO4)C2)c(F)cc1Oc1cncc(F)c1] |

TABLE 1-continued
| Cmpd No. | Structure | Cmpd No. | Structure |
|---|---|---|---|
| 45 | 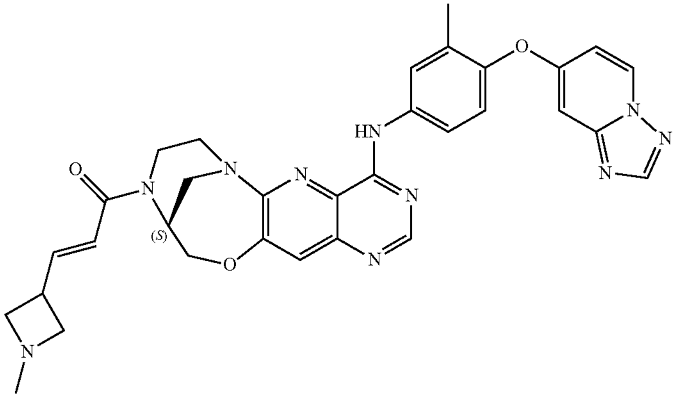 | 45-1 | 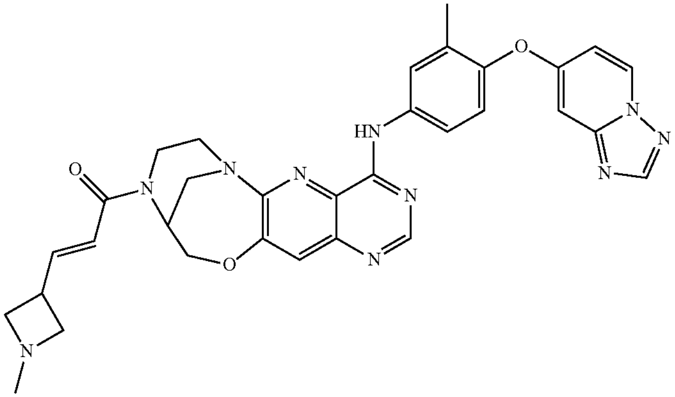 [SMILES: Cc1cc(Nc2ncnc3cc4c(nc23)N2CCN(C(=O)/C=C/C3CN(C)C3)C(CO4)C2)ccc1Oc1ccn2ncnc2c1] |
| 46 | 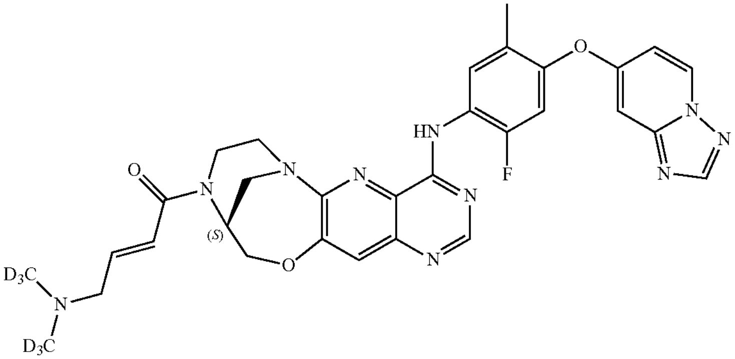 | 46-1 | 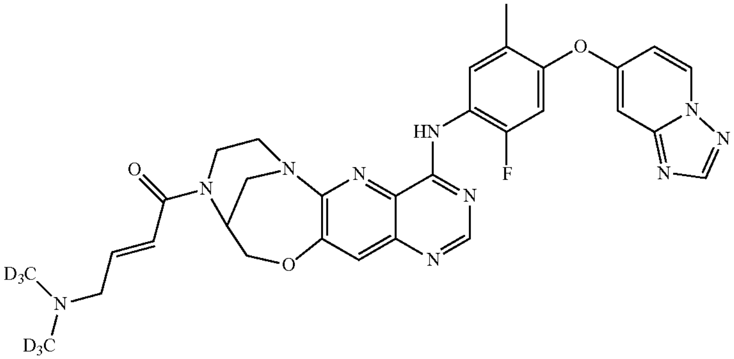 [SMILES: [2H]C([2H])([2H])N(C/C=C/C(=O)N1CCN2CC1COc1cc3ncnc(Nc4cc(C)c(Oc5ccn6ncnc6c5)cc4F)c3nc12)C([2H])([2H])[2H]] |

TABLE 1-continued
| Cmpd No. | Structure | Cmpd No. | Structure |
|---|---|---|---|
| 47 | 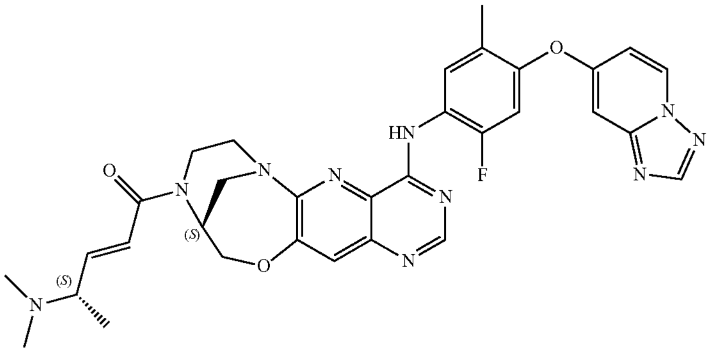 | 47-1 | 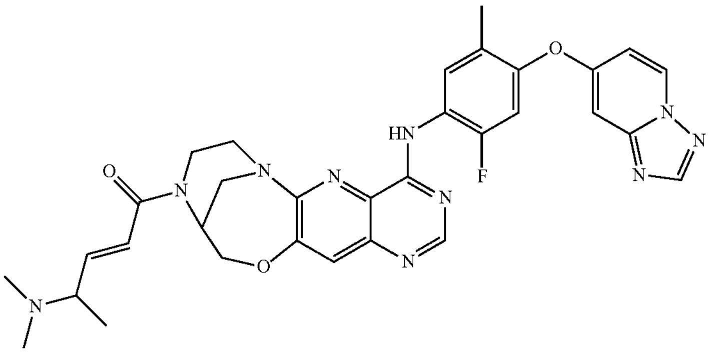 [SMILES: Cc1cc(Nc2ncnc3cc4c(nc23)N2CCN(C(=O)/C=C/C(C)N(C)C)C(CO4)C2)c(F)cc1Oc1ccn2ncnc2c1] |
| 48 | 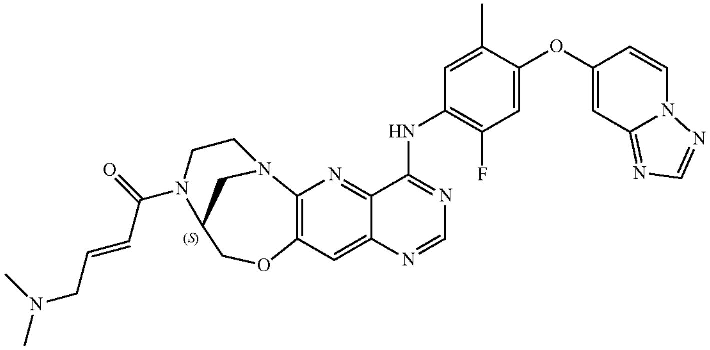 | 48-1 | 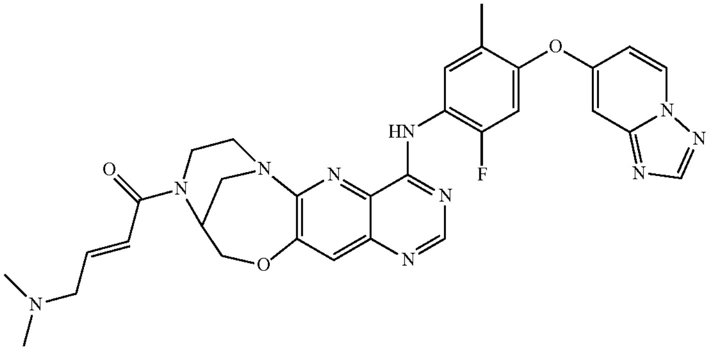 [SMILES: Cc1cc(Nc2ncnc3cc4c(nc23)N2CCN(C(=O)/C=C/CN(C)C)C(CO4)C2)c(F)cc1Oc1ccn2ncnc2c1] |

TABLE 1-continued
| Cmpd No. | Structure | Cmpd No. | Structure |
|---|---|---|---|
| 49 | 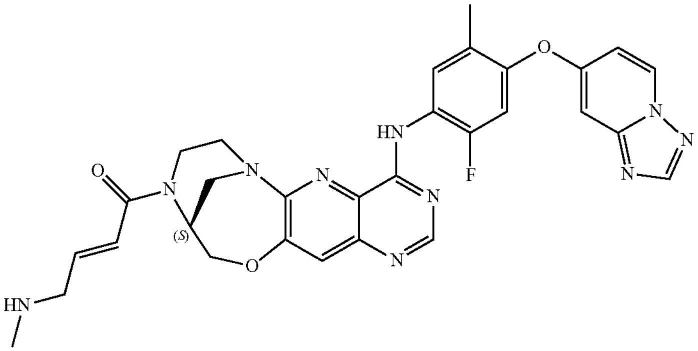 | 49-1 | 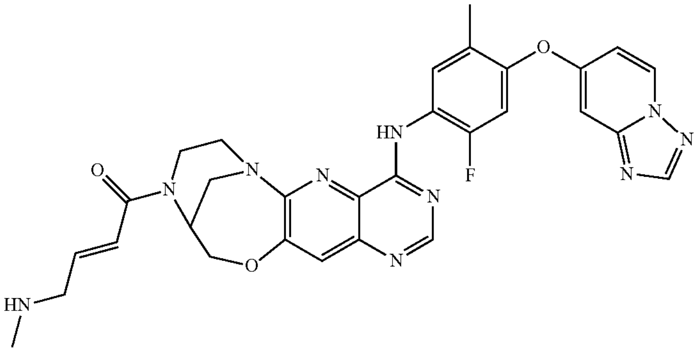 [SMILES: CNC/C=C/C(=O)N1CCN2CC1COc1cc3ncnc(Nc4cc(C)c(Oc5ccn6ncnc6c5)cc4F)c3nc12] |
| 50 | 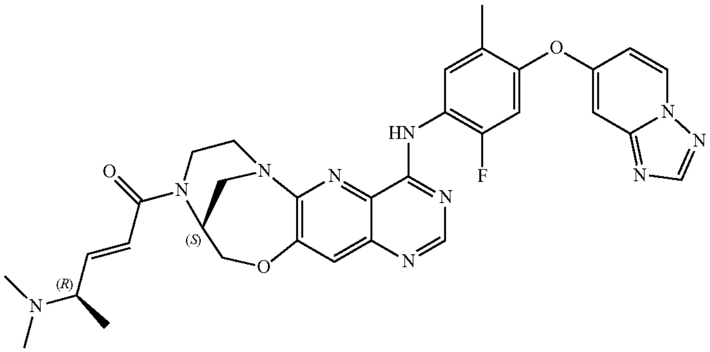 | 47-1 | 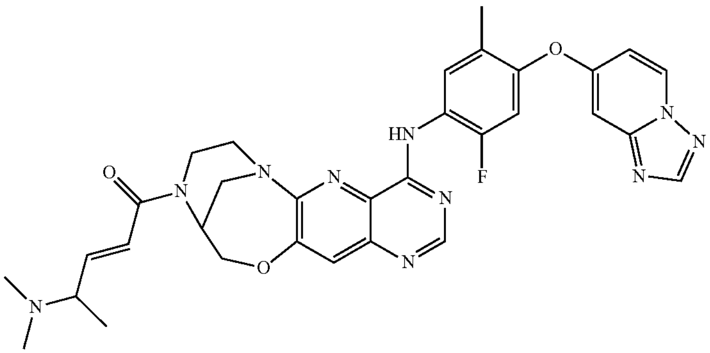 [SMILES: Cc1cc(Nc2ncnc3cc4c(nc23)N2CCN(C(=O)/C=C/C(C)N(C)C)C(CO4)C2)c(F)cc1Oc1ccn2ncnc2c1] |

TABLE 1-continued
| Cmpd No. | Structure | Cmpd No. | Structure |
|---|---|---|---|
| 51 | 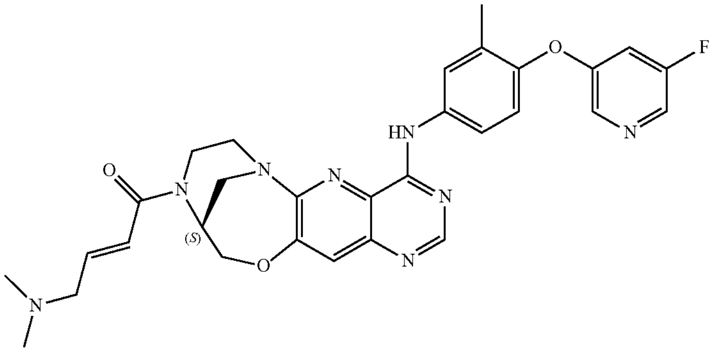 | 51-1 | 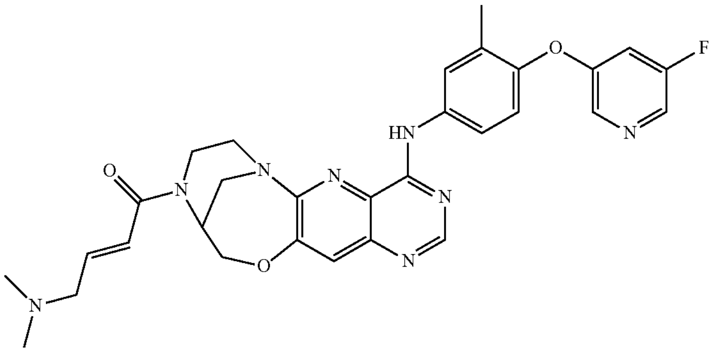 [SMILES: Cc1cc(Nc2ncnc3cc4c(nc23)N2CCN(C(=O)/C=C/CN(C)C)C(CO4)C2)ccc1Oc1cncc(F)c1] |
| 52 | 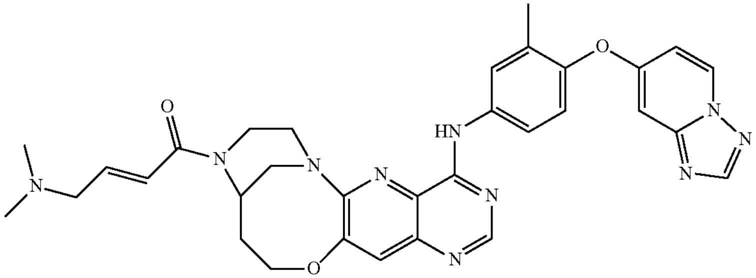 [SMILES: Cc1cc(Nc2ncnc3cc4c(nc23)N2CCN(C(=O)/C=C/CN(C)C)C(CCO4)C2)ccc1Oc1ccn2ncnc2c1] | | |
| 53 | 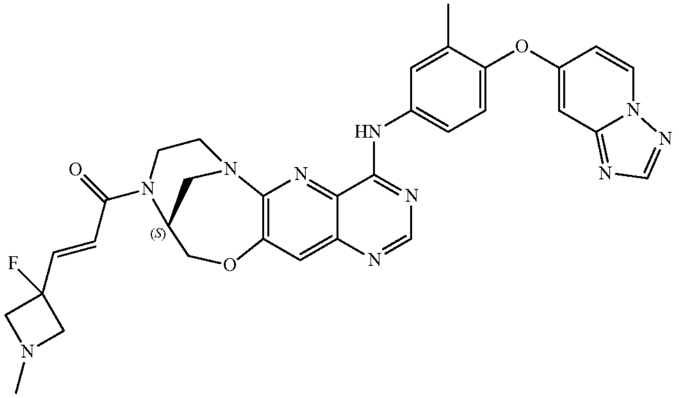 | 53-1 | 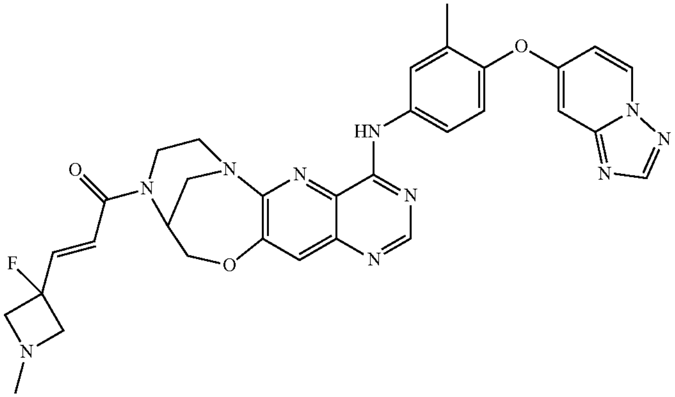 [SMILES: Cc1cc(Nc2ncnc3cc4c(nc23)N2CCN(C(=O)/C=C/C3(F)CN(C)C3)C(CO4)C2)ccc1Oc1ccn2ncnc2c1] |

TABLE 1-continued
| Cmpd No. | Structure | Cmpd No. | Structure |
| --- | --- | --- | --- |
| 54 | 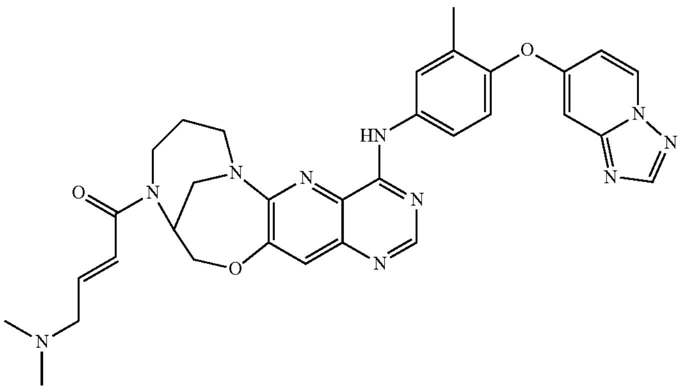 [SMILES: Cc1cc(Nc2ncnc3cc4c(nc23)N2CCCN(C(=O)/C=C/CN(C)C)C(CO4)C2)ccc1Oc1ccn2ncnc2c1] | | |
| 55 | 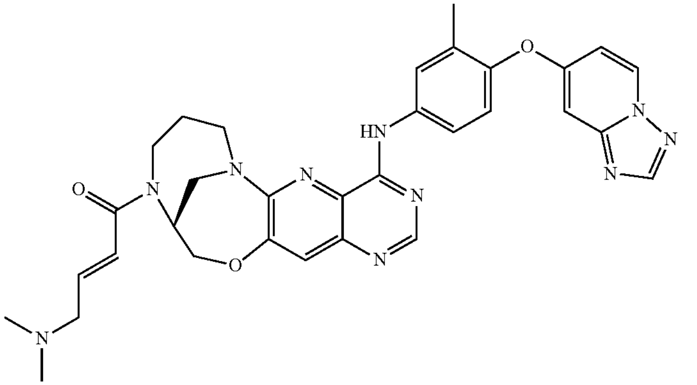 [SMILES: Cc1cc(Nc2ncnc3cc4c(nc23)N2CCCN(C(=O)/C=C/CN(C)C)[C@@H](CO4)C2)ccc1Oc1ccn2ncnc2c1] | 54-1 | 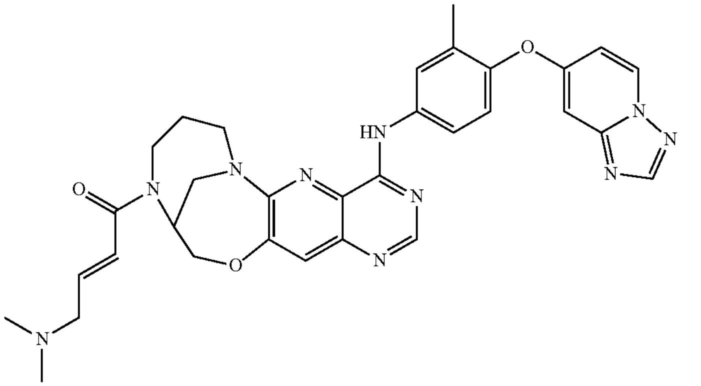 [SMILES: Cc1cc(Nc2ncnc3cc4c(nc23)N2CCCN(C(=O)/C=C/CN(C)C)C(CO4)C2)ccc1Oc1ccn2ncnc2c1] |

TABLE 1-continued
| Cmpd No. | Structure | Cmpd No. | Structure |
|---|---|---|---|
| 56 | 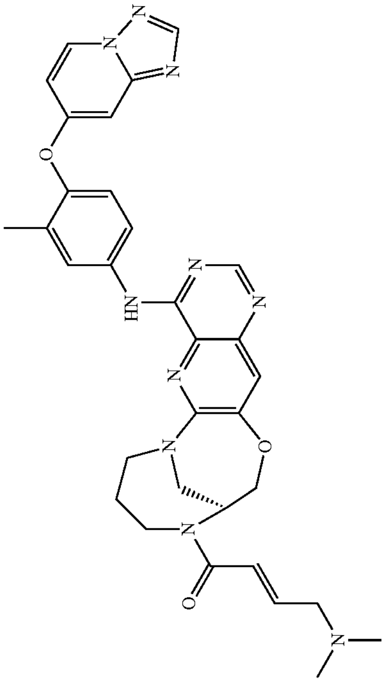 | 54-1 | 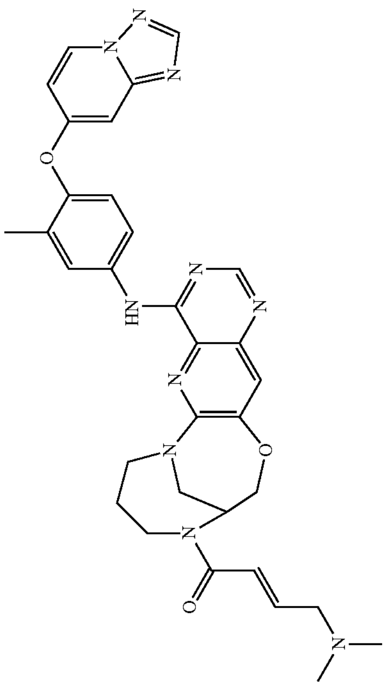 |
| 57 | 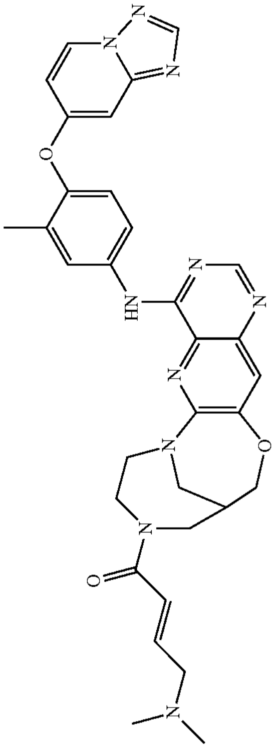 | | |
| 58 | 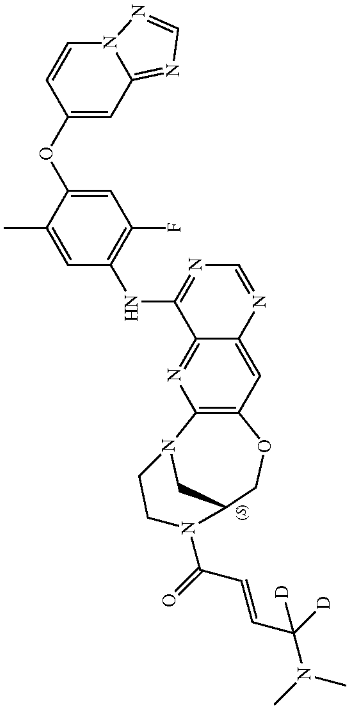 | 58-1 | 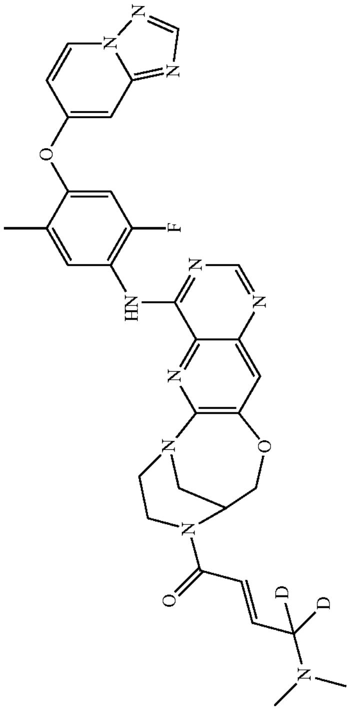 |

TABLE 1-continued
| Cmpd No. | Structure | Cmpd No. | Structure |
|---|---|---|---|
| 59 | 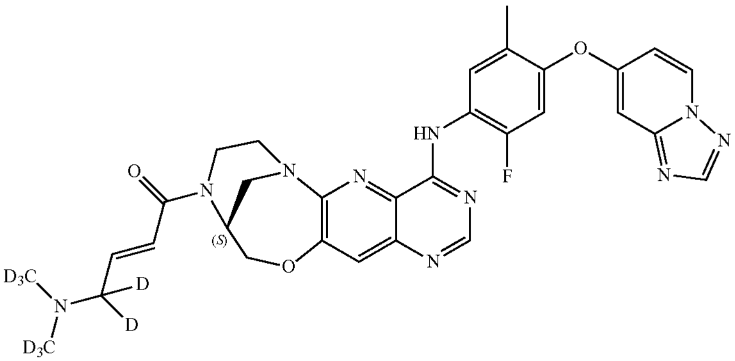 | 59-1 | 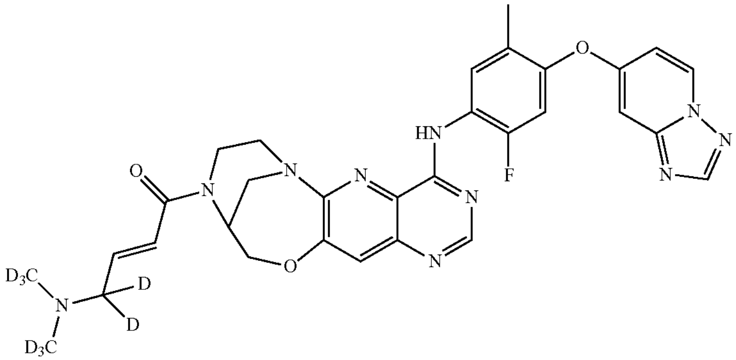 [SMILES: [2H]C([2H])([2H])N(C([2H])([2H])[2H])C([2H])([2H])/C=C/C(=O)N1CCN2CC1COc1cc3ncnc(Nc4cc(C)c(Oc5ccn6ncnc6c5)cc4F)c3nc12] |

Although certain compounds described in Table 1 are presented as specific stereoisomers and/or in a non-stereochemical form, it is understood that any or all non-stereochemical forms and any or all stereochemical forms, including any enantiomeric or diastereomeric forms, and any tautomers or other forms of any of the compounds of Table 1 are herein described. In some embodiments, the compound described herein is selected from Compound Nos. 1-59.

This disclosure also includes all salts, such as pharmaceutically acceptable salts, of compounds referred to herein. This disclosure also includes any or all of the stereochemical forms, including any enantiomeric or diastereomeric forms, and any tautomers or other forms, such as N-oxides, solvates, hydrates, or isotopomers, of the compounds described. The present disclosure also includes co-crystals of the compounds described herein. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

III. Pharmaceutical Compositions and Formulations

Any of the compounds described herein may be formulated as a pharmaceutically acceptable composition.

Pharmaceutical compositions of any of the compounds detailed herein are embraced by this disclosure. Thus, the present disclosure includes pharmaceutical compositions comprising a compound as detailed herein, or a pharmaceutically acceptable salt, solvate, hydrate, or co-crystal thereof, or a mixture of any of the foregoing, and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound, or a pharmaceutically acceptable salt, solvate, hydrate, or co-crystal thereof, or a mixture of any of the foregoing, as detailed herein are provided, such as compositions of substantially pure compounds. In some embodiments, a composition containing a compound, or a pharmaceutically acceptable salt, solvate, hydrate, or co-crystal thereof, or a mixture of any of the foregoing, as detailed herein is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 intends a composition that contains no more than 35% impurity, wherein the impurity denotes a compound other than the compound of Table 1. In one variation, a composition of substantially pure compound, or a pharmaceutically acceptable salt, solvate, hydrate, or co-crystal thereof, or a mixture of any of the foregoing, is provided wherein the composition contains no more than 25% impurity. In another variation, a composition of substantially pure compound, or a pharmaceutically acceptable salt, solvate, hydrate, or co-crystal thereof, or a mixture of any of the foregoing, is provided wherein the composition contains or no more than 20% impurity. In still another variation, a composition of substantially pure compound, or a pharmaceutically acceptable salt, solvate, hydrate, or co-crystal thereof, or a mixture of any of the foregoing, is provided wherein the composition contains or no more than 10% impurity. In a further variation, a composition of substantially pure compound, or a pharmaceutically acceptable salt, solvate, hydrate, or co-crystal thereof, or a mixture of any of the foregoing, is provided wherein the composition contains no more than 5% impurity. In another variation, a composition of substantially pure compound, or a pharmaceutically acceptable salt, solvate, hydrate, or co-crystal thereof, or a mixture of any of the foregoing, is provided wherein the composition contains no more than 3% impurity. In still another variation, a composition of substantially pure compound, or a pharmaceutically acceptable salt, solvate, hydrate, or co-crystal thereof, or a mixture of any of the foregoing, is provided wherein the composition contains no more than 1% impurity. In a further variation, a composition of substantially pure compound, or a pharmaceutically acceptable salt, solvate, hydrate, or co-crystal thereof, or a mixture of any of the foregoing, is provided wherein the composition contains no more than 0.5% impurity. In yet other variations, a composition of substantially pure compound means that the composition contains no more than 15%, no more than 10%, no more than 5%, no more than 3%, or no more than 1% impurity, which impurity may be the compound in a different stereochemical form. For instance, and without limitation, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein. In some embodiments, the compounds and compositions as provided herein are sterile. Methods for sterilization known in the art may be suitable for any compounds or form thereof and compositions thereof as detailed herein.

A compound detailed herein, or a pharmaceutically acceptable salt, solvate, hydrate, or co-crystal thereof, or a mixture of any of the foregoing, may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound, or a pharmaceutically acceptable salt, solvate, hydrate, or co-crystal thereof, or a mixture of any of the foregoing, may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound detailed herein, or a pharmaceutically acceptable salt, solvate, hydrate, or co-crystal thereof, or a mixture of any of the foregoing, can be used in the preparation of a formulation, such as a pharmaceutical formulation, by combining the compound or compounds, or a pharmaceutically acceptable salt, solvate, hydrate, or co-crystal thereof, or a mixture of any of the foregoing, with a pharmaceutically acceptable carrier. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington's The Science and Practice of Pharmacy, Academic Press, 23$^{rd}$ ed. (2020), which is incorporated herein by reference.

A compound detailed herein, or a pharmaceutically acceptable salt, solvate, hydrate, or co-crystal thereof, or a mixture of any of the foregoing, may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds, or a pharmaceutically acceptable salt, solvate, hydrate, or co-crystal thereof, or a mixture of any of the foregoing, described herein can be formulated in a tablet in any dosage form described, for example, a compound as described herein, or a pharmaceutically acceptable salt, solvate, hydrate, or co-crystal thereof, or a mixture of any of the foregoing, can be formulated as a 10 mg tablet.

Compositions comprising a compound, or a pharmaceutically acceptable salt, solvate, hydrate, or co-crystal thereof, or a mixture of any of the foregoing, provided herein are also described. In one variation, the composition comprises a compound, or a pharmaceutically acceptable salt, solvate, hydrate, or co-crystal thereof, or a mixture of any of the foregoing, and a pharmaceutically acceptable carrier or excipient. In another variation, a composition of substantially pure compound, or a pharmaceutically acceptable salt, solvate, hydrate, or co-crystal thereof, or a mixture of any of the foregoing, is provided. In some embodiments, the composition is for use as a human or veterinary medicament. In some embodiments, the composition is for use in a method described herein. In some embodiments, the composition is for use in the treatment of a disease or disorder described herein.

Compositions formulated for co-administration of a compound provided herein and one or more additional pharmaceutical agents are also described. The co-administration can be simultaneous or sequential in any order. A compound provided herein may be formulated for co-administration with the one or more additional pharmaceutical agents in the same dosage form (e.g., single tablet or single i.v.) or separate dosage forms (e.g., two separate tablets, two separate i.v., or one tablet and one i.v.). Furthermore, co-administration can be, for example, 1) concurrent delivery, through the same route of delivery (e.g., tablet or i.v.), 2) sequential delivery on the same day, through the same route or different routes of delivery, or 3) delivery on different days, through the same route or different routes of delivery.

IV. Methods of Use

Compounds and compositions detailed herein, such as a pharmaceutical composition containing a compound of formula (I') or formula (I) or any variations thereof provided herein, or a pharmaceutically acceptable salt, solvate, hydrate, or co-crystal thereof, or a mixture of any of the foregoing, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided herein is a method of inhibiting kinase activity of a human receptor tyrosine kinase ErbB2 or a mutant form of human ErbB2, comprising contacting the ErbB2 or the mutant form with a therapeutically effective amount of a compound or composition provided herein. In some embodiments, provided herein is a method of inhibiting kinase activity of a human receptor tyrosine kinase ErbB2 or a mutant form of human ErbB2 in a cell, comprising administering an effective amount of a compound or composition of the disclosure to the cell. In some embodiments, provided herein is a method of inhibiting kinase activity of a human receptor tyrosine kinase ErbB2 or a mutant form of human ErbB2 in an individual in need thereof, comprising administering an effective amount of a compound or composition of the disclosure to the individual.

In some embodiments of the present aspect, the mutant form of human ErbB2 comprises one or more mutations that introduce amino acid deletions and/or insertions selected from the group consisting of: A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775 G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777 G778insG, G778_S779insLPS, and G778_S779insAVG. In some embodiments, the mutant form of human ErbB2 comprises a mutation in Exon 20 that introduces certain amino acid deletions and/or insertions selected from the group consisting of:

A775_A776insYVMA, G778_P780insGSP, G776delinsVC, P780_Y781insGSP, M774delinsWLV, A775 G776insSVMA, A775_G776insI, G776delinsLC, G778_S779InsCPG, V777_G778insGSP. In other embodiments of the present aspect, the mutant form of human ErbB2 comprises one or more point mutations in ErbB2 that introduce (a) amino acid substitutions selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G, or (b) a frameshift at A1232. In other embodiments, the mutant form of human ErbB2 comprises one or more mutations that introduce certain amino acid substitutions selected from the group consisting of: P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In still further embodiments of the present aspect, the mutant form of human ErbB2 comprises one or more point mutations in ErbB2 that introduce (a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232. In other embodiments, the mutant form of human ErbB2 comprises amino terminally truncated carboxyl-terminal fragments of HER2, collectively known as p95HER2.

In some variations, the compounds provided herein are selective for inhibiting human receptor tyrosine kinase ErbB2. As such, in some embodiments, provided herein is a method of selectively inhibiting human receptor tyrosine kinase ErbB2, as compared to other receptor tyrosine kinases, including but not limited to ErbB1 (EGFR), ErbB3, or ErbB4.

The compounds and compositions described herein may be used in a method of treating a disease or disorder in an individual, wherein the individual has cells or cell tissue having increased ErbB2 kinase activity, for example, as compared to the ErbB2 kinase activity in a corresponding cell type or cell tissue from a healthy individual. In some embodiments, the compound or composition is administered according to a dosage described herein.

In some embodiments, provided herein is a method for treating a disease or disorder in an individual, wherein the individual has cells or cell tissue having increased ErbB2 kinase activity, comprising administering to an individual in need of treatment a therapeutically effective amount of a compound of formula (I') or formula (I) or any variations thereof, or a pharmaceutically acceptable salt, solvate, hydrate, or co-crystal thereof, or a mixture of any of the foregoing, or a therapeutically effective amount of a composition as described herein. In some embodiments, the disease or disorder is cancer. In some embodiments, the disease or disorder is lung cancer, glioma, head and/or neck cancer, salivary gland cancer, breast cancer, esophageal cancer, liver cancer, stomach (gastric) cancer, uterine cancer, cervical cancer, biliary tract cancer, pancreatic cancer, colorectal cancer, renal cancer, bladder cancer, or prostate cancer. In some embodiments, the cancer is non-small cell lung cancer. In some embodiments, the individual has received at least one, at least two or at least three prior therapies for the cancer. In certain embodiments, the one or more prior therapies are selected from the group consisting of lapatinib, neratinib, afatinib, pyrotinib, poziotinib, TAK-788 and tucatinib.

In some embodiments, the disease or disorder is refractory or resistant to first-line treatment, second-line treatment, and/or third-line treatment. In certain embodiments, the condition having increased activation of ErbB2 kinase activity is refractory or resistant to treatment with one or more tyrosine kinase inhibitors selected from the group consisting of lapatinib, neratinib, afatinib, pyrotinib, poziotinib, TAK-788, and tucatinib.

Resistant subtypes of tyrosine kinase-mediated diseases or disorders may be associated with any number of ErbB2 independent resistance mechanisms. In some embodiments wherein the disease or disorder in the individual having cells or cell tissue with increased ErbB2 kinase activity is refractory to treatment, the disease or disorder is characterized as being associated with one or more ErbB2 dependent resistance mechanisms. ErbB2-dependent resistance mechanisms include, but are not limited to, one or more mutations in Exon 20 of ErbB2 or other disease-associated point mutations. The one or more mutations of ErbB2 introduce certain amino acid deletions and/or insertions, for example, A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775_G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777_G778insG, G778_S779insLPS, and/or G778_S779insAVG. In other variations, the mutations introduce certain amino acid substitutions, for example, P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and/or A1232fs. In some variations, the mutations introduce certain (a) amino acid substitutions, for example, P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, and N1219S, G222C, A1057V, V842I, G776S/C/V/A, V773M, L869R,Y803F, H878Y, R896G, and E1195G, and/or (b) frameshifts, such as a frameshift at A1232. In other embodiments, ErbB2-dependent resistance mechanisms include expression or overexpression of amino terminally truncated carboxyl-terminal fragments of HER2, collectively known as p95HER2. In some variations, the refractory disease or disorder in an individual having increased activation of the ErbB2 kinase activity is associated with one or more mutations in Exon 20 of the ErbB2. In certain variations, the one or more mutations in Exon 20 of the ErbB2 that introduce certain amino acid deletions and/or insertions selected from the group consisting of: A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780 Y781insGSP, M774delinsWLV, A775 G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777 G778insQ, V777 G778insG, G778_S779insLPS, and G778_S779insAVG. In certain variations, the one or more mutations in Exon 20 of the ErbB2 that introduce certain amino acid deletions and/or insertions selected from the group consisting of: A775_A776insYVMA, G778_P780insGSP, G776delinsVC, P780 Y781insGSP, M774delinsWLV, A775 G776insSVMA, A775_G776insI, G776delinsLC, G778_S779InsCPG, and V777_G778insGSP. In other variations, the refractory disease or disorder in an individual having increased activation of the ErbB2 kinase activity is associated with one or more disease-associated point mutations. In certain variations, the one or more point mutations introduce (a) amino acid substitutions selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In certain variations, the one or more point mutations introduce certain amino acid substitutions selected from the group consisting of: P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In other embodiments, the one or more point mutations introduce (a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232. In other embodiments, the refractory disease or disorder in an individual having increased activation of the ErbB2 kinase activity is associated with expression or overexpression of amino terminally truncated carboxyl-terminal fragments of HER2, collectively known as p95HER2.

In some embodiments, provided is a method for treating cancer in an individual in need thereof, comprising administering to the individual a therapeutically effective amount of a compound of formula (I') or formula (I) or any variations thereof as described herein, or a therapeutically effective amount of a composition as described herein. In some embodiments, the cancer comprises cells or cell tissue having increased ErbB2 kinase activity, for example, as compared to the ErbB2 kinase activity in a corresponding cell type or cell tissue from a healthy individual. In some embodiments, the cancer comprises cells or cell tissue having one or more mutations in Exon 20 of the ErbB2. In certain embodiments, the one or more mutations in Exon 20 of the ErbB2 introduce certain amino acid deletions and/or insertions selected from the group consisting of A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780 Y781insGSP, M774delinsWLV, A775 G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777 G778insQ, V777 G778insG, G778_S779insLPS, and G778_S779insAVG. In certain embodiments, the one or more mutations in Exon 20 of the ErbB2 introduce certain amino acid deletions and/or insertions selected from the group consisting of A775_A776insYVMA, G778_P780insGSP, G776delinsVC, P780 Y781insGSP, M774delinsWLV, A775 G776insSVMA, A775_G776insI, G776delinsLC, G778_S779InsCPG, and V777_G778insGSP. In some embodiments, the cancer comprises cells or cell tissue comprising one or more disease-associated point mutations. In certain embodiments, the cancer comprises cells or cell tissue having one or more point mutations that introduce (a) an amino acid substitution selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In certain embodiments, the one or more point mutations introduce certain amino acid substitutions selected from the group consisting of: P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In certain other embodiments, the cancer comprises cells or cell tissue having one or more point mutations that introduce (a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232. In other embodiments, the cancer comprises cells or cell tissue have or are associated with expression or overexpression of amino terminally truncated carboxyl-terminal fragments of HER2, collectively known as p95HER2. In some embodiments, the disease or disorder is lung cancer, glioma, head and/or neck cancer, salivary gland cancer, breast cancer, esophageal cancer, liver cancer, stomach (gastric) cancer, uterine cancer, cervical cancer, biliary tract cancer, pancreatic cancer, colorectal cancer, renal cancer, bladder cancer, or prostate cancer. In some embodiments, the cancer is non-small cell lung cancer.

In one aspect, provided herein is a method of treating cancer in an individual in need thereof, wherein modulation of ErbB2 kinase activity inhibits or ameliorates the pathology and/or symptomology of the cancer, comprising administering to the individual a therapeutically effective amount of a compound or composition provided herein. In one embodiment, provided herein is a method of treating cancer, wherein modulation of ErbB2 kinase activity inhibits the pathology and/or symptomology of the cancer, in an individual, comprising administering to the individual a therapeutically effective amount of a compound or composition provided herein. In one embodiment, provided herein is a method of treating a cancer, wherein modulation of ErbB2 kinase activity ameliorates the pathology and/or symptomology of the cancer, in an individual, comprising administering to the individual a therapeutically effective amount of a compound or composition provided herein.

In another aspect, provided herein is a method of preventing cancer, wherein modulation of ErbB2 kinase activity prevents the pathology and/or symptomology of the cancer, in an individual, comprising administering to the individual a therapeutically effective amount of a compound or composition provided herein. In another aspect, provided herein is a method of delaying the onset and/or development of a cancer in an individual (such as a human) who is at risk for developing the cancer, e.g., an individual who has cells or cell tissue having increased ErbB2 kinase activity. It is appreciated that delayed development may encompass prevention in the event the individual does not develop the cancer.

In one aspect, provided herein is a method of delaying the onset and/or development of cancer in an individual having cells or cell tissue having increased ErbB2 kinase activity in need thereof, comprising administering to the individual a therapeutically effective amount of a compound or composition provided herein. In some embodiments, the cancer is lung cancer, glioma, head and/or neck cancer, salivary gland cancer, breast cancer, esophageal cancer, liver cancer, stomach (gastric) cancer, uterine cancer, cervical cancer, biliary tract cancer, pancreatic cancer, colorectal cancer, renal cancer, bladder cancer, or prostate cancer. In some embodiments, the cancer is non-small cell lung cancer.

In one aspect, provided herein is a compound of formula (I') or formula (I) or any variations thereof, or a pharmaceutically acceptable salt, solvate, hydrate, or co-crystal thereof, or a mixture of any of the foregoing, for use in therapy. In some embodiments, provided herein is a compound of formula (I') or formula (I) or any variations thereof, or a pharmaceutically acceptable salt, solvate, hydrate, or co-crystal thereof, or a mixture of any of the foregoing, or pharmaceutical composition comprising such compound, for use in the treatment of cancer. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer comprises cells or cell tissue having increased activation of ErbB2 kinase activity. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer comprises cells or cell tissue having one or more mutations in Exon 20 of the ErbB2. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer cells comprise one or more genetic alterations in Exon 20 of the ErbB2 that introduce certain amino acid deletions and/or insertions selected from the group consisting of A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775_G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777 G778insG, G778_S779insLPS, and G778_S779insAVG. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer cells comprise one or more genetic alterations in Exon 20 of the ErbB2 that introduce certain amino acid deletions and/or insertions selected from the group consisting of A775_A776insYVMA, G778_P780insGSP, G776delinsVC, P780 Y781insGSP, M774delinsWLV, A775_G776insSVMA, A775_G776insI, G776delinsLC, G778_S779InsCPG, and V777_G778insGSP. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer comprises cells or cell tissue having one or more disease-associated point mutations in ErbB2. In certain other embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer comprises cells or cell tissue having one or more point mutations that introduce (a) an amino acid substitution selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In certain embodiments, the cancer comprises cells or cell tissue having one or more point mutations that introduce certain amino acid substitutions selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In certain other embodiments, the cancer comprises cells or cell tissue having one or more point mutations that introduce (a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of cancer, wherein the cancer comprises cells or cell tissue expressing or overexpressing of amino terminally truncated carboxyl-terminal fragments of HER2, collectively known as p95HER2. In some embodiments, provided is a compound of formula (I') or formula (I) or any variations thereof, or a pharmaceutically acceptable salt, solvate, hydrate, or co-crystal thereof, or a mixture of any of the foregoing, or a pharmaceutical composition comprising such compound, for use in the treatment of lung cancer, glioma, head and/or neck cancer, salivary gland cancer, breast cancer, esophageal cancer, liver cancer, stomach (gastric) cancer, uterine cancer, cervical cancer, biliary tract cancer, pancreatic cancer, colorectal cancer, renal cancer, bladder cancer, or prostate cancer. In some embodiments, the lung cancer is non-small cell lung cancer.

In another embodiment, provided herein is a compound of formula (I') or formula (I) or any variations thereof, or a pharmaceutically acceptable salt, solvate, hydrate, or co-crystal thereof, or a mixture of any of the foregoing, for use in the manufacture of a medicament for the treatment of cancer. In another embodiment, provided herein is a compound of formula (I') or formula (I) or any variations thereof, or a pharmaceutically acceptable salt, solvate, hydrate, or co-crystal thereof, or a mixture of any of the foregoing, for use in the manufacture of a medicament for the treatment of cancer, wherein the cancer comprises cells or cell tissue having increased ErbB2 kinase activity. In another embodiment, provided herein is a compound of formula (I') or formula (I) or any variations thereof, or a pharmaceutically acceptable salt, solvate, hydrate, or co-crystal thereof, or a mixture of any of the foregoing, for use in the manufacture of a medicament for the treatment of cancer, wherein the cancer cells or cancer cell tissue comprise one or more mutations in Exon 20 of the ErbB2. In some embodiments, the medicament is for the treatment of cancer, wherein the cancer cells comprise one or more genetic alterations in Exon 20 of the ErbB2 that introduce certain amino acid deletions and/or insertions selected from the group consisting of A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775_G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777_G778insG, G778_S779insLPS, and G778_S779insAVG. In some embodiments, the medicament is for the treatment of cancer, wherein the cancer cells comprise one or more genetic alterations in Exon 20 of the ErbB2 that introduce certain amino acid deletions and/or insertions selected from the group consisting of A775_A776insYVMA, G778_P780insGSP, G776delinsVC, P780_Y781insGSP, M774delinsWLV, A775_G776insSVMA, A775_G776insI, G776delinsLC, G778_S779InsCPG, and V777_G778insGSP. In another embodiment, provided herein is a compound of formula (I') or formula (I) or any variations thereof, or a pharmaceutically acceptable salt, solvate, hydrate, or co-crystal thereof, or a mixture of any of the foregoing, for use in the manufacture of a medicament for the treatment of cancer, wherein the cancer cells or cancer cell tissue comprise one or more disease-associated point mutations in ErbB2. In some embodiments, the medicament is for the treatment of cancer, wherein the cancer cells comprise one or more point mutations that introduce (a) an amino acid substitution selected from the group consisting of: P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In some embodiments, the medicament is for the treatment of cancer, wherein the cancer cells comprise one or more point mutations that introduce certain amino acid substitutions selected from the group consisting of: P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In some embodiments, the medicament is for the treatment of cancer, wherein the cancer cells comprise one or more point mutations that introduce (a) an amino acid substitution selected from the group consisting of: P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S, or (b) a frameshift at A1232. In some embodiments, the medicament is for the treatment of cancer, wherein the cancer cells comprise, express or over-express amino terminally truncated carboxyl-terminal fragments of HER2, collectively known as p95HER2. In some embodiments, the medicament is for the treatment of lung cancer, glioma, head and/or neck cancer, salivary gland cancer, breast cancer, esophageal cancer, liver cancer, stomach (gastric) cancer, uterine cancer, cervical cancer, biliary tract cancer, pancreatic cancer, colorectal cancer, renal cancer, bladder cancer, or prostate cancer. In some embodiments, the medicament is for the treatment of non-small cell lung cancer.

In some embodiments, the individual is a mammal. In some embodiments, the individual is a primate, dog, cat, rabbit, or rodent. In some embodiments, the individual is a primate. In some embodiments, the individual is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old.

In some embodiments, the method further comprises administering one or more additional pharmaceutical agents. In some embodiments, the method further comprises administering one or more additional anti-cancer agents to the patient. In some embodiments, the method further comprises administering radiation. In some embodiments, the method further comprises administering one or more additional pharmaceutical agents and radiation.

In some embodiments, the method further comprises administering an anti-HER2 antibody or an anti-HER2 drug conjugate. In certain embodiments, the method further comprises administering KADCYLA® (ado-trastuzumab emtansine), ENHERTU® (fam-trastuzumab deruxtecan-nxki), or any biosimilar thereof.

V. Dosing and Method of Administration

The dose of a compound described herein, or a pharmaceutically acceptable salt, solvate, hydrate, or co-crystal thereof, or a mixture of any of the foregoing, administered to an individual (such as a human) may vary with the particular compound or salt thereof, the method of administration, and the particular cancer, such as type and stage of cancer, being treated. In some embodiments, the amount of the compound, or a pharmaceutically acceptable salt, solvate, hydrate, or co-crystal thereof, or a mixture of any of the foregoing, is a therapeutically effective amount.

The compounds provided herein, or a pharmaceutically acceptable salt, solvate, hydrate, or co-crystal thereof, or a mixture of any of the foregoing, may be administered to an individual via various routes, including, e.g., intravenous, intramuscular, subcutaneous, oral, and transdermal.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a pharmaceutically acceptable salt, solvate, hydrate, or co-crystal thereof, or a mixture of any of the foregoing, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

VI. Articles of Manufacture and Kits

The present disclosure further provides articles of manufacture comprising a compound described herein, or a pharmaceutically acceptable salt, solvate, hydrate, or co-crystal thereof, or a mixture of any of the foregoing, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein, or a pharmaceutically acceptable salt, solvate, hydrate, or co-crystal thereof, or a mixture of any of the foregoing, thereof. The kits may be used for any one or more of the uses described herein, and, accordingly, may contain instructions for the treatment of any disease or described herein, for example for the treatment of cancer, including lung, glioma, skin, head and neck, salivary gland, breast, esophageal, liver, stomach (gastric), uterine, cervical, biliary tract, pancreatic, colorectal, renal, bladder or prostate cancer. In some embodiments, the kit may contain instructions for the treatment of non-small cell lung cancer.

In certain embodiments of the foregoing, the cancer comprises cells or cell tissue having one or more mutations in Exon 20 of the ErbB2. In still further embodiments, the cancer cells or cancer cell tissue comprise one or more mutations in Exon 20 of the ErbB2 that introduce certain amino acid deletions and/or insertions selected from the group consisting of: A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780_Y781insGSP, M774delinsWLV, A775_G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777_G778insQ, V777_G778insG, G778_S779insLPS, and G778_S779insAVG. In still further embodiments, the cancer cells or cancer cell tissue comprise one or more mutations in Exon 20 of the ErbB2 that introduce certain amino acid deletions and/or insertions selected from the group consisting of A775_A776insYVMA, G778_P780insGSP, G776delinsVC, P780_Y781insGSP, M774delinsWLV, A775_G776insSVMA, A775_G776insI, G776delinsLC, G778_S779InsCPG, and V777_G778insGSP. In certain other embodiments of the cancer comprises cells or cell tissue having one or more disease-associated point mutations in ErbB2. In other embodiments, the cancer comprises cells or cell tissue having one or more point mutations that introduce (a) an amino acid substitution selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232. In still further embodiments, the cancer cells or cancer cell tissue comprise the one or more point mutations that introduce amino acid substitutions selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, N1219S, and A1232fs. In other embodiments, the cancer comprises cells or cell tissue having one or more point mutations that introduce (a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232. In still yet other embodiments, the cancer comprises cells or cell tissue having, expressing or over-expressing amino terminally truncated carboxyl-terminal fragments of HER2, collectively known as p95HER2.

The kits optionally further comprise a container comprising one or more additional pharmaceutical agents and which kits further comprise instructions on or in the package insert for treating the subject with an effective amount of the one or more additional pharmaceutical agents.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

VII. Enumerated Embodiments

The following enumerated embodiments are representative of some aspects of the invention.

Embodiment 1. A compound of formula (I)

(I)

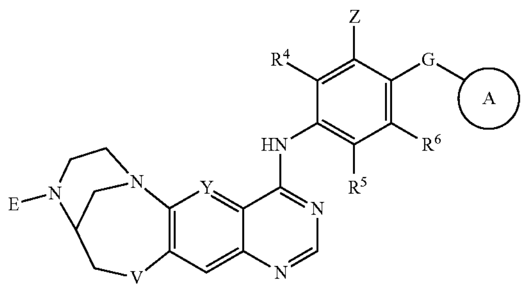

or a pharmaceutically acceptable salt, solvate, hydrate, or co-crystal thereof, or a mixture of any of the foregoing, wherein:

Ring A is

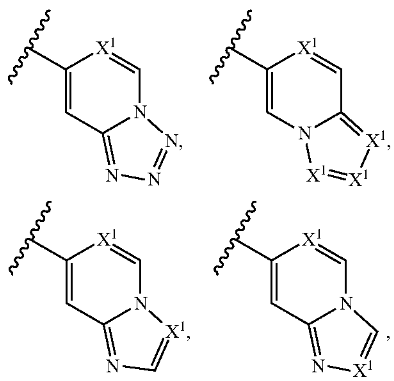

-continued

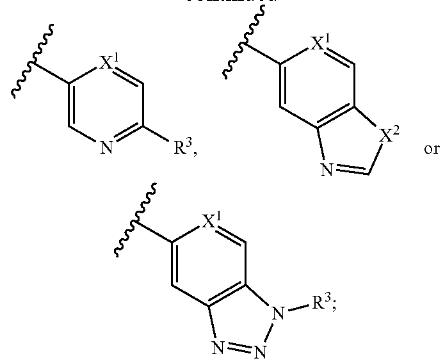

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$;

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen; and $R^6$ is —H or halogen.

Embodiment 2. The compound of embodiment 1, or a pharmaceutically acceptable salt, solvate, hydrate, or co-crystal thereof, or a mixture of any of the foregoing, wherein: ring A is

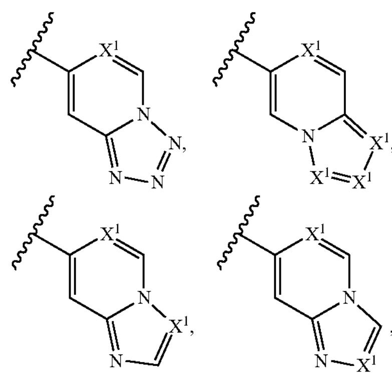

-continued

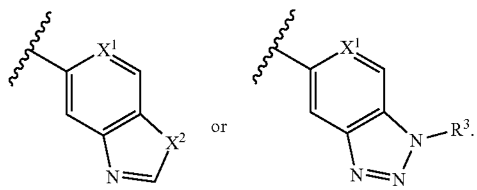

Embodiment 3. The compound of embodiment 1 or embodiment 2, or a pharmaceutically acceptable salt, solvate, hydrate, or co-crystal thereof, or a mixture of any of the foregoing, wherein:

ring A is

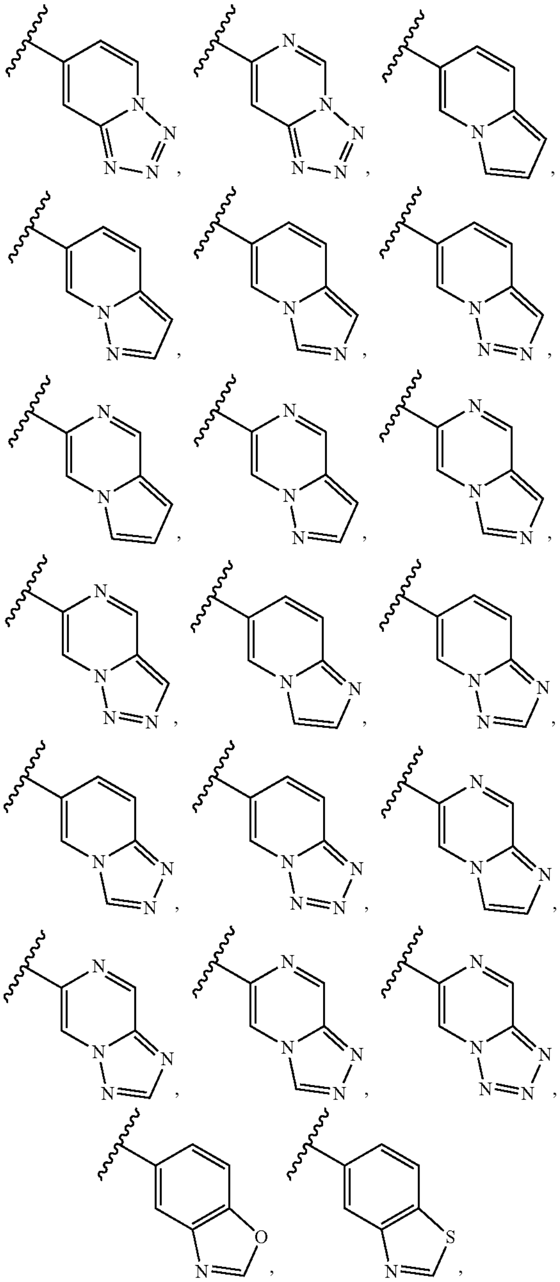

-continued

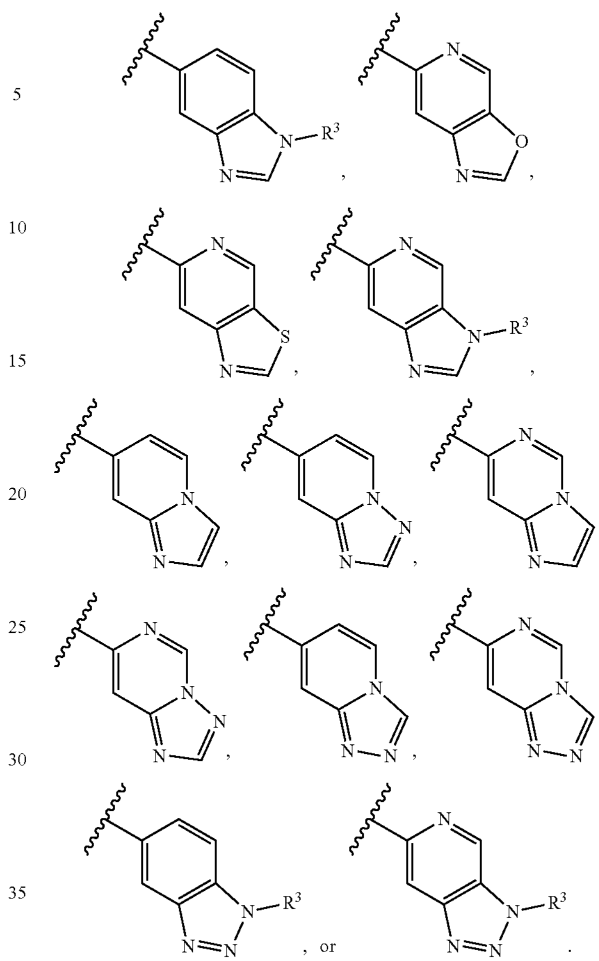

Embodiment 4. The compound of embodiment 1 or embodiment 2, or a pharmaceutically acceptable salt, solvate, hydrate, or co-crystal thereof, or a mixture of any of the foregoing, wherein:

ring A is

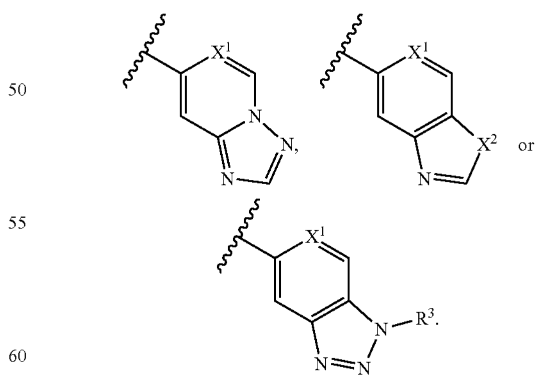

Embodiment 5. The compound of any one of embodiments 1 to 4, or a pharmaceutically acceptable salt, solvate, hydrate, or co-crystal thereof, or a mixture of any of the foregoing, wherein:

ring A is

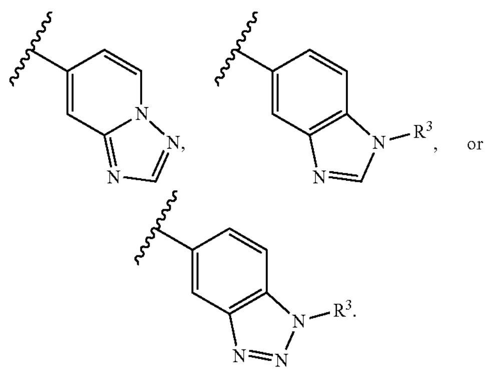

or

Embodiment 6. The compound of embodiment 1, or a pharmaceutically acceptable salt, solvate, hydrate, or co-crystal thereof, or a mixture of any of the foregoing, wherein:

ring A is

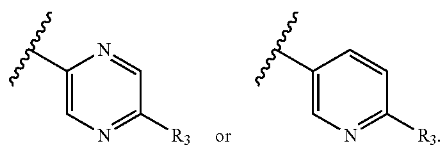

or

Embodiment 7. The compound of any one of embodiments 1 to 6, or a pharmaceutically acceptable salt, solvate, hydrate, or co-crystal thereof, or a mixture of any of the foregoing, wherein $R^3$ is —$CH_3$.

Embodiment 8. The compound of any one of embodiments 1 to 7, or a pharmaceutically acceptable salt, solvate, hydrate, or co-crystal thereof, or a mixture of any of the foregoing, wherein Z is —H, —F, —Cl, —C≡CH, —$OCH_3$, or —$CH_3$.

Embodiment 9. The compound of any one of embodiments 1 to 8, or a pharmaceutically acceptable salt, solvate, hydrate, or co-crystal thereof, or a mixture of any of the foregoing, wherein Z is —$CH_3$.

Embodiment 10. The compound of any one of embodiments 1 to 9, or a pharmaceutically acceptable salt, solvate, hydrate, or co-crystal thereof, or a mixture of any of the foregoing, wherein $R^1$ is $C_2$-$C_4$ alkenyl, optionally substituted by —$NR^{1a}R^{1b}$.

Embodiment 11. The compound of any one of embodiments 1 to 10, or a pharmaceutically acceptable salt, solvate, hydrate, or co-crystal thereof, or a mixture of any of the foregoing, wherein $R^1$ is —CH═$CH_2$.

Embodiment 12. The compound of any one of embodiments 1 to 10, or a pharmaceutically acceptable salt, solvate, hydrate, or co-crystal thereof, or a mixture of any of the foregoing, wherein $R^1$ is —CH═CH—$CH_2$—$N(CH_3)_2$.

Embodiment 13. The compound of any one of embodiments 1 to 9, or a pharmaceutically acceptable salt, solvate, hydrate, or co-crystal thereof, or a mixture of any of the foregoing, wherein $R^1$ is $C_2$-$C_4$ alkynyl, optionally substituted by —$NR^{1a}R^{1b}$.

Embodiment 14. The compound of any one of embodiments 1 to 9 and 13, or a pharmaceutically acceptable salt, solvate, hydrate, or co-crystal thereof, or a mixture of any of the foregoing, wherein $R^1$ is —C≡C—$CH_3$.

Embodiment 15. The compound of any one of embodiments 1 to 14, pharmaceutically acceptable salt, solvate, hydrate, or co-crystal thereof, or a mixture of any of the foregoing, wherein Y is N.

Embodiment 16. The compound of any one of embodiments 1 to 14, pharmaceutically acceptable salt, solvate, hydrate, or co-crystal thereof, or a mixture of any of the foregoing, wherein Y is C—$R^y$.

Embodiment 17. The compound of any one of embodiments 1 to 14 and 16, or a pharmaceutically acceptable salt, solvate, hydrate, or co-crystal thereof, or a mixture of any of the foregoing, wherein Y is C—$R^y$, and $R^y$ is —H.

Embodiment 18. The compound of any one of embodiments 1 to 14 and 16, or a pharmaceutically acceptable salt, solvate, hydrate, or co-crystal thereof, or a mixture of any of the foregoing, wherein Y is C—$R^y$, and $R^y$ is —F.

Embodiment 19. The compound of any one of embodiments 1 to 18, or a pharmaceutically acceptable salt, solvate, hydrate, or co-crystal thereof, or a mixture of any of the foregoing, wherein V is O.

Embodiment 20. The compound of any one of embodiments 1 to 18, or a pharmaceutically acceptable salt, solvate, hydrate, or co-crystal thereof, or a mixture of any of the foregoing, wherein V is S.

Embodiment 21. The compound of any one of embodiments 1 to 18, or a pharmaceutically acceptable salt, solvate, hydrate, or co-crystal thereof, or a mixture of any of the foregoing, wherein V is N—$R^2$.

Embodiment 22. The compound of any one of embodiments 1 to 21, or a pharmaceutically acceptable salt, solvate, hydrate, or co-crystal thereof, or a mixture of any of the foregoing, wherein G is —O—.

Embodiment 23. The compound of any one of embodiments 1 to 21, or a pharmaceutically acceptable salt, solvate, hydrate, or co-crystal thereof, or a mixture of any of the foregoing, wherein G is —C(═O)—.

Embodiment 24. The compound of any one of embodiments 1 to 21, or a pharmaceutically acceptable salt, solvate, hydrate, or co-crystal thereof, or a mixture of any of the foregoing, wherein G is —S—, —S(O)—, or —$S(O)_2$—.

Embodiment 25. The compound of any one of embodiments 1 to 21, or a pharmaceutically acceptable salt, solvate, hydrate, or co-crystal thereof, or a mixture of any of the foregoing, wherein G is —$CH_2$—.

Embodiment 26. The compound of any one of embodiments 1 to 25, or a pharmaceutically acceptable salt, solvate, hydrate, or co-crystal thereof, or a mixture of any of the foregoing, wherein $R^4$ is —H.

Embodiment 27. The compound of any one of embodiments 1 to 25, or a pharmaceutically acceptable salt, solvate, hydrate, or co-crystal thereof, or a mixture of any of the foregoing, wherein $R^4$ is halogen.

Embodiment 28. The compound of any one of embodiments 1 to 27, or a pharmaceutically acceptable salt, solvate, hydrate, or co-crystal thereof, or a mixture of any of the foregoing, wherein $R^5$ is —H.

Embodiment 29. The compound of any one of embodiments 1 to 27, or a pharmaceutically acceptable salt, solvate, hydrate, or co-crystal thereof, or a mixture of any of the foregoing, wherein $R^5$ is halogen.

Embodiment 30. The compound of any one of embodiments 1 to 29, or a pharmaceutically acceptable salt, solvate, hydrate, or co-crystal thereof, or a mixture of any of the foregoing, wherein $R^6$ is —H.

Embodiment 31. The compound of any one of embodiments 1 to 29, or a pharmaceutically acceptable salt, solvate, hydrate, or co-crystal thereof, or a mixture of any of the foregoing, wherein $R^6$ is halogen.
Embodiment 32. A compound selected from the group consisting of:
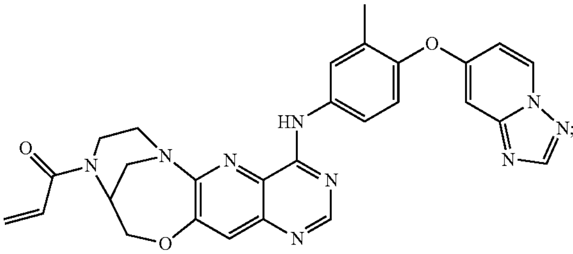
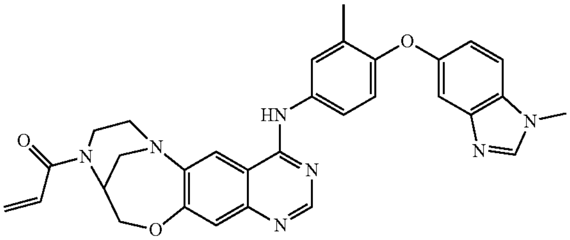
;
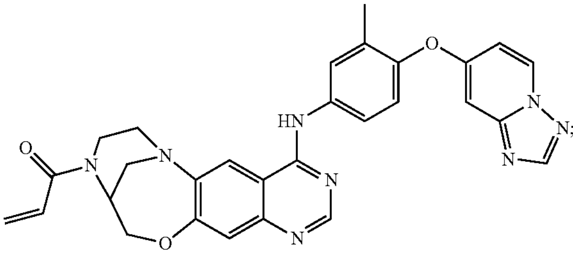
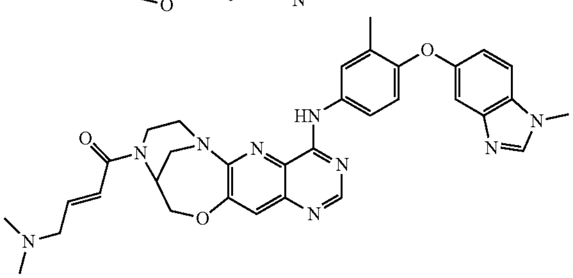
;
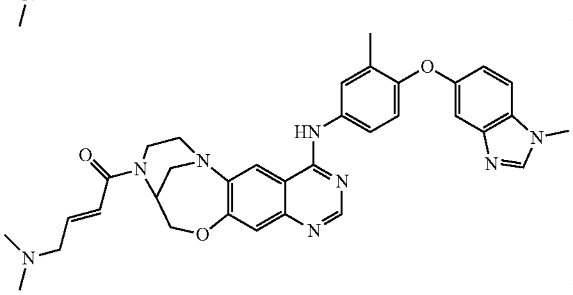
;
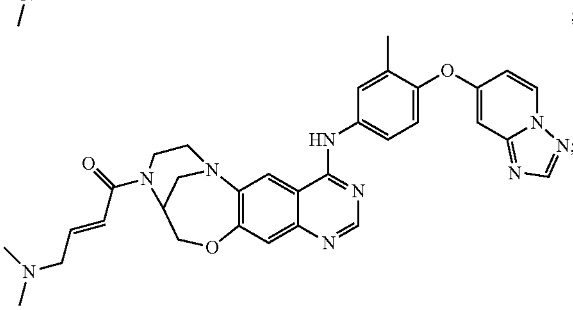
-continued
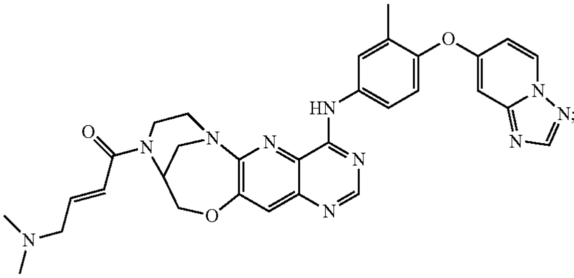
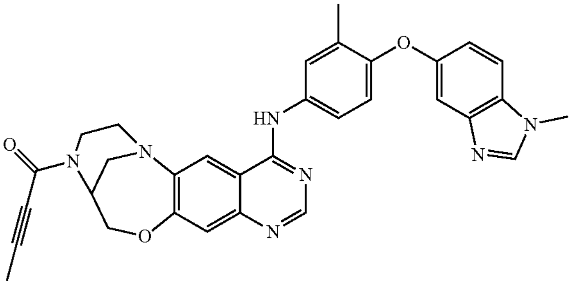
;
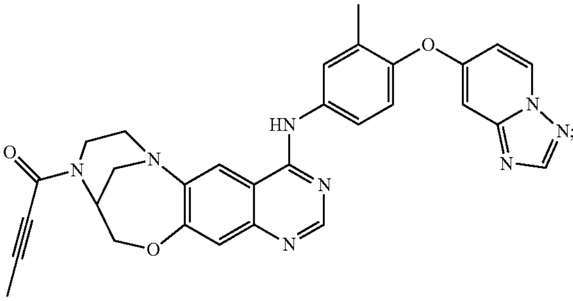
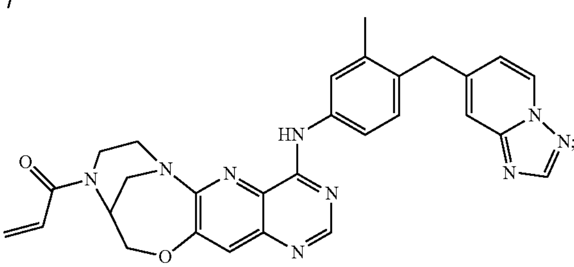
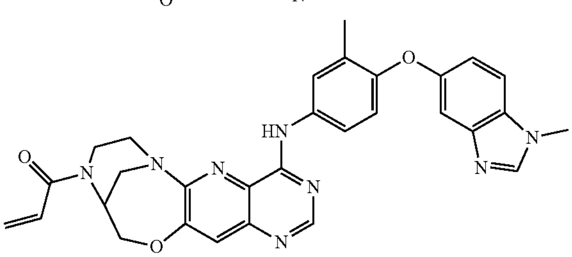
;
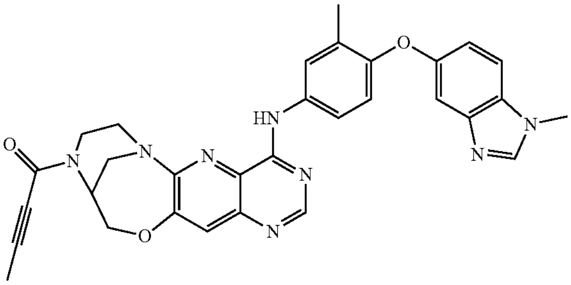
;

-continued
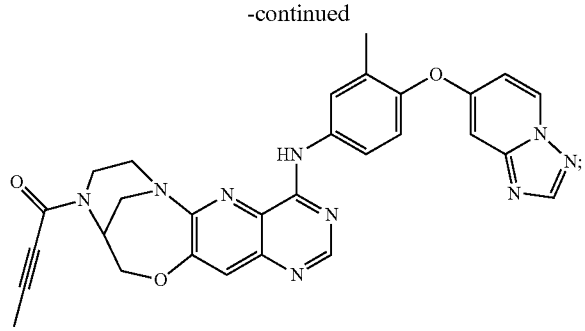
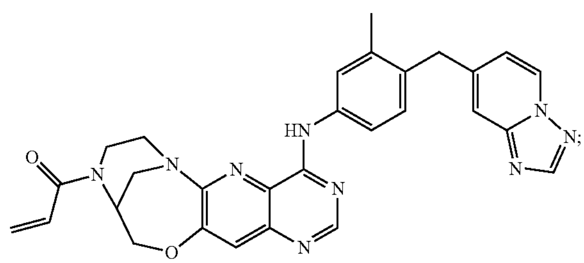
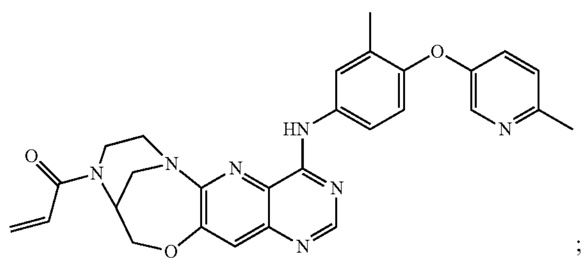
;
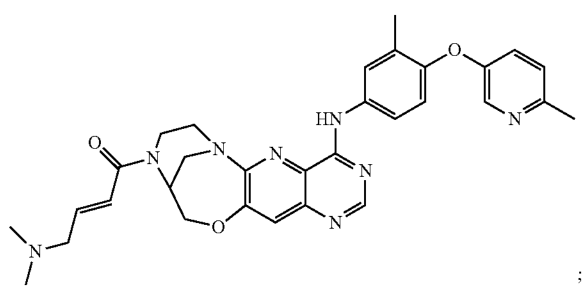
;
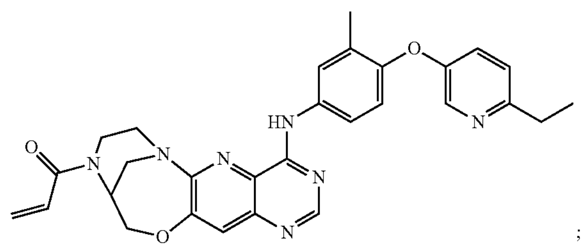
;
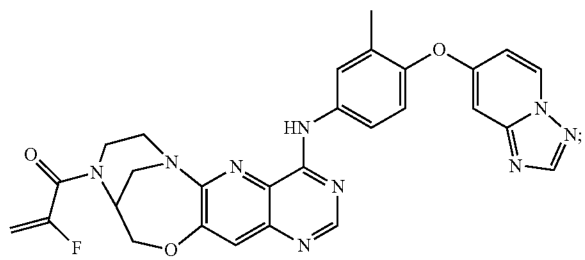
-continued
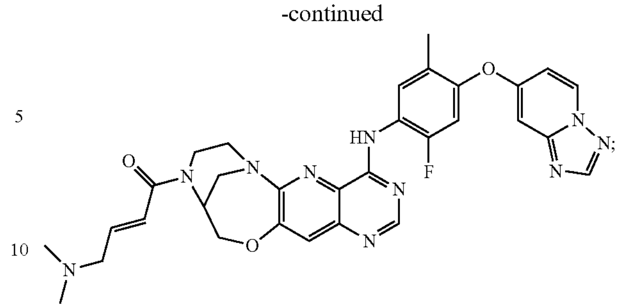
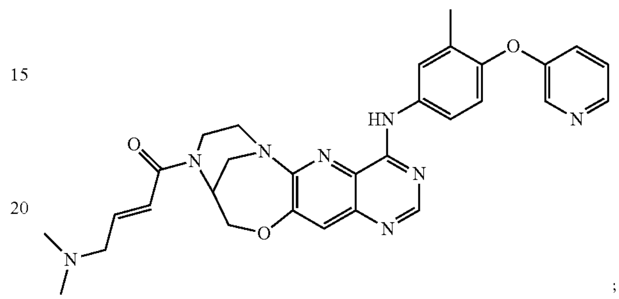
;
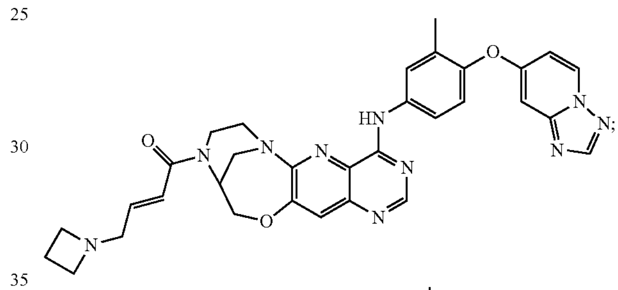
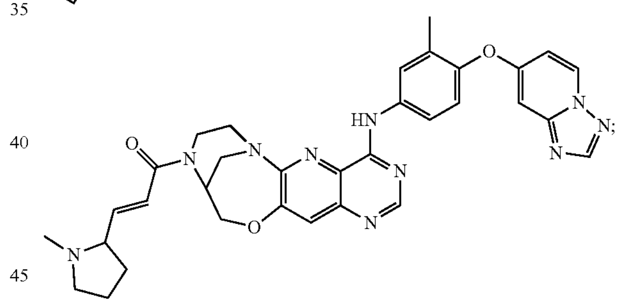
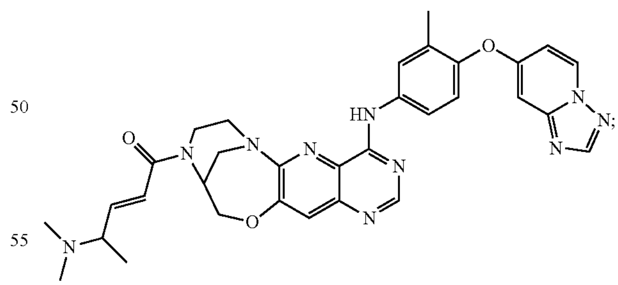
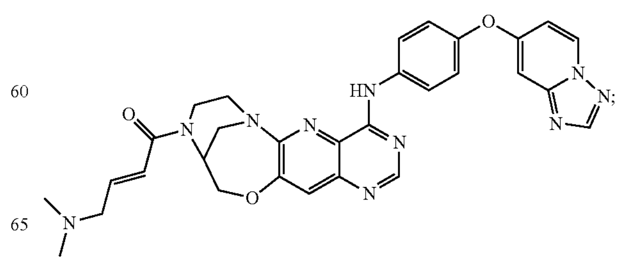

-continued
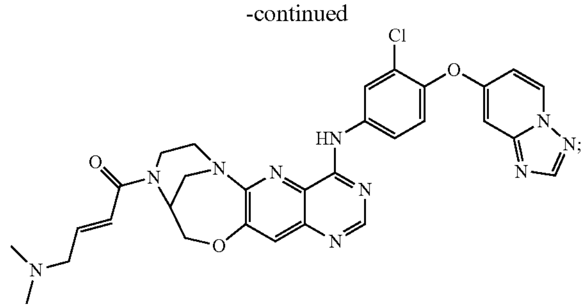
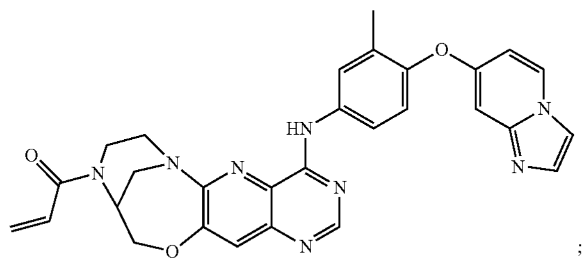
;
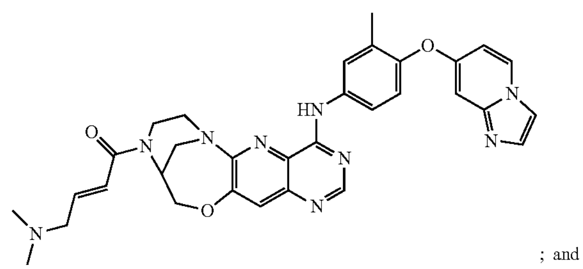
; and
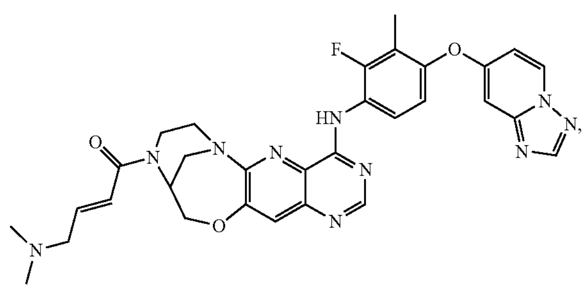
or a pharmaceutically acceptable salt, solvate, hydrate, or co-crystal thereof, or a mixture of any of the foregoing.
Embodiment 33. A compound selected from the group consisting of:
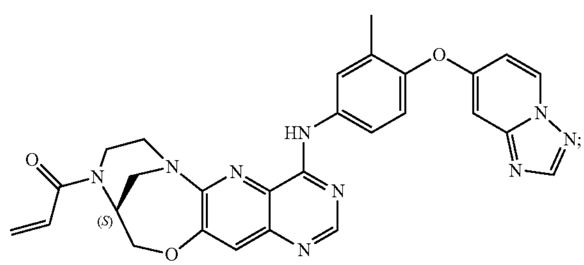
-continued
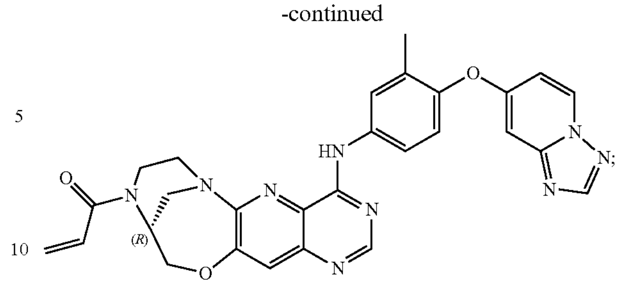
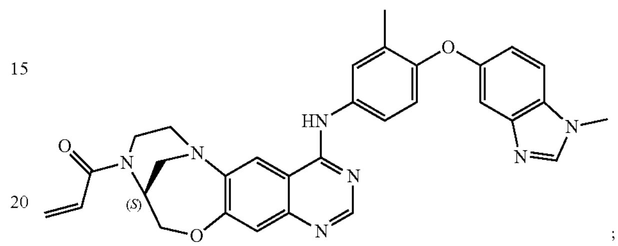
;
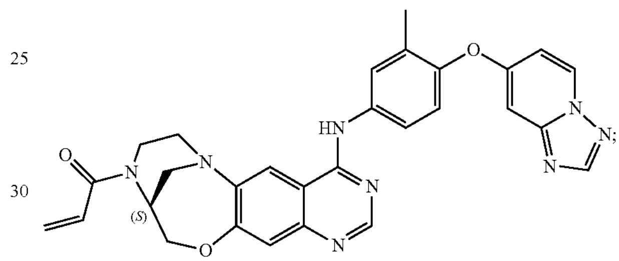
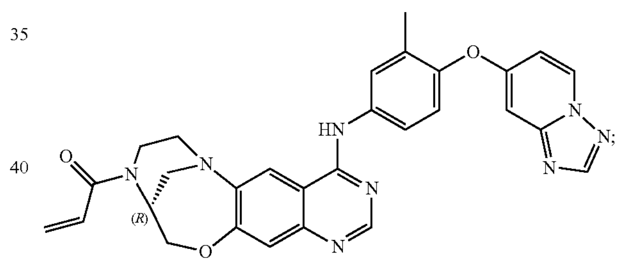
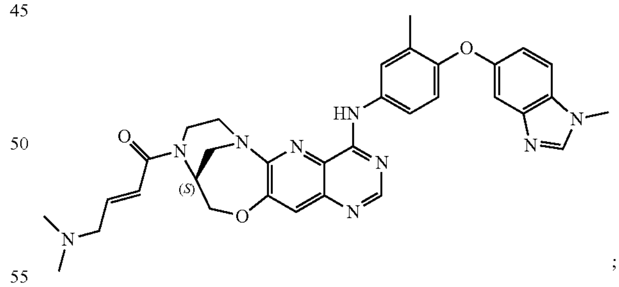
;
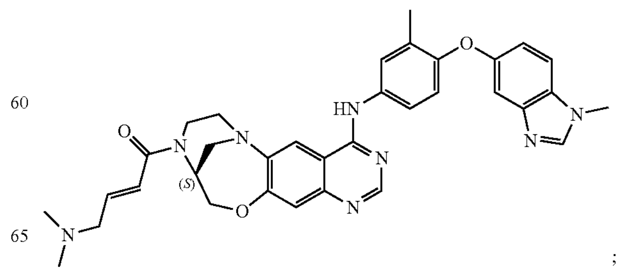
;

-continued
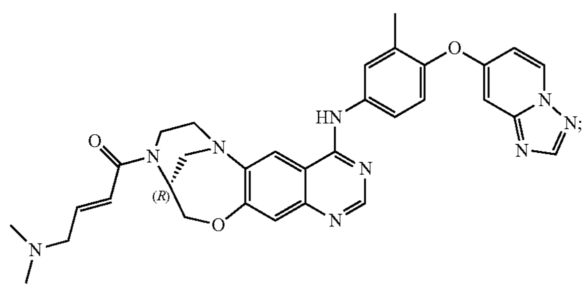
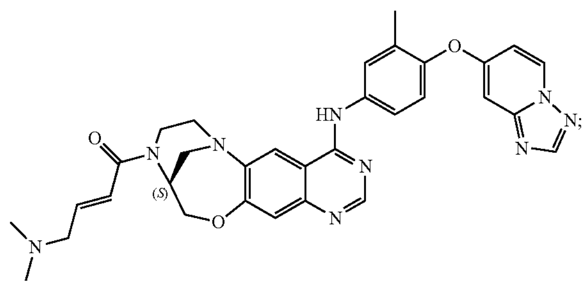
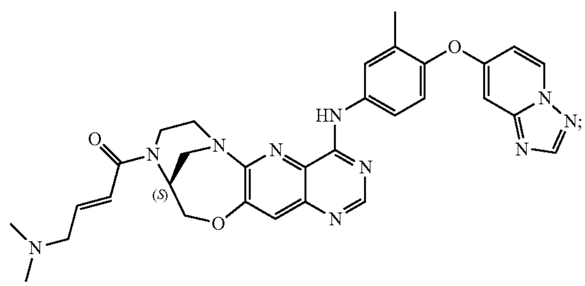
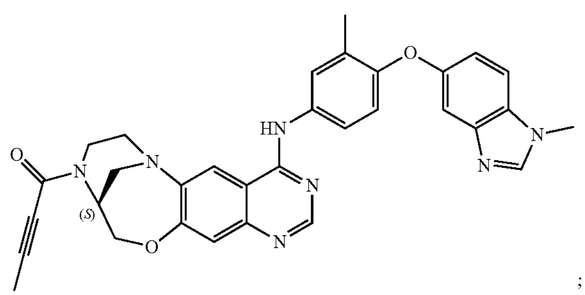
;
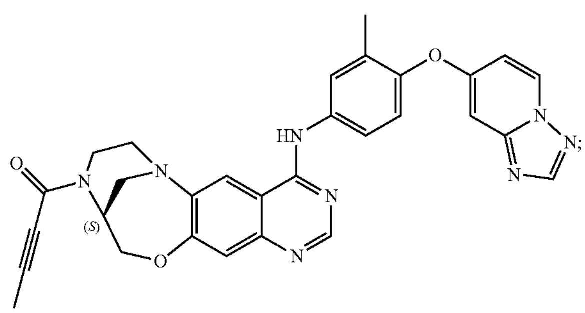
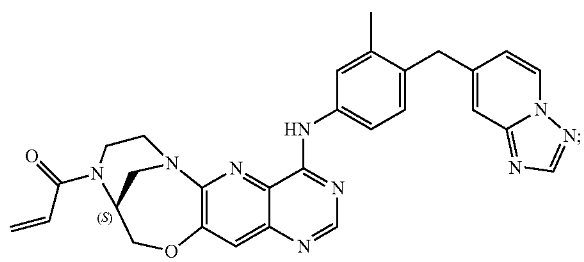
-continued
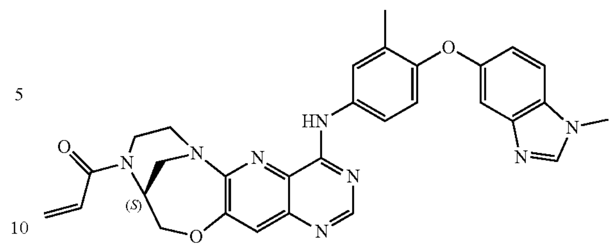
,
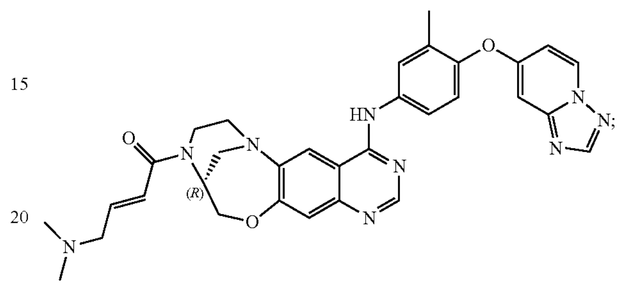
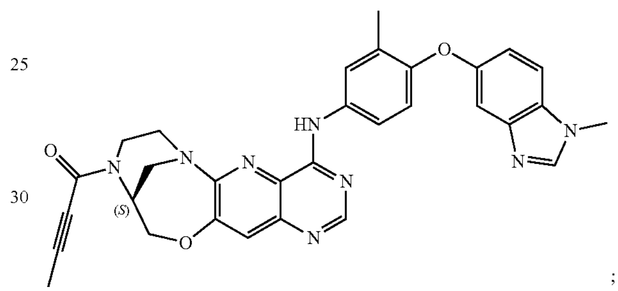
;
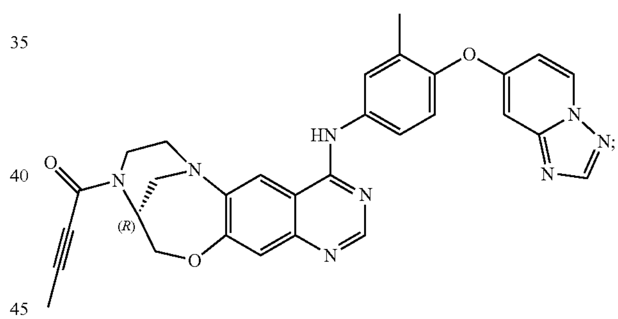
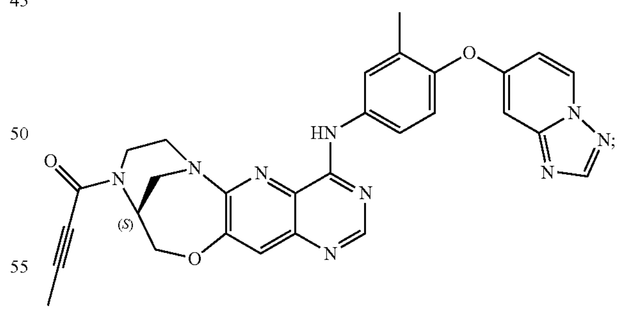
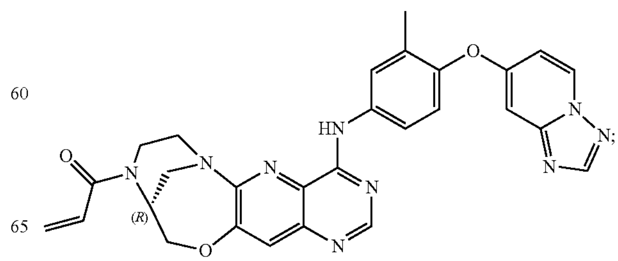

-continued
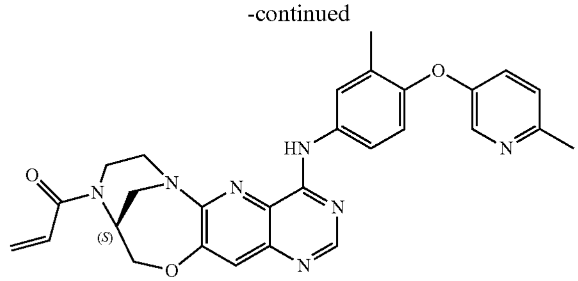
;
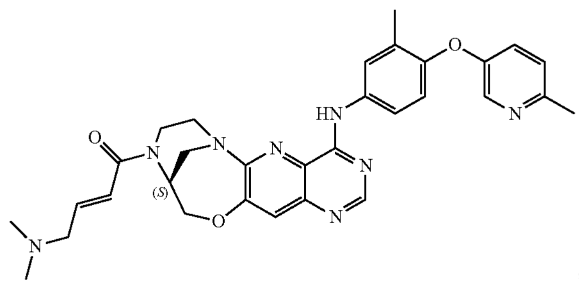
;
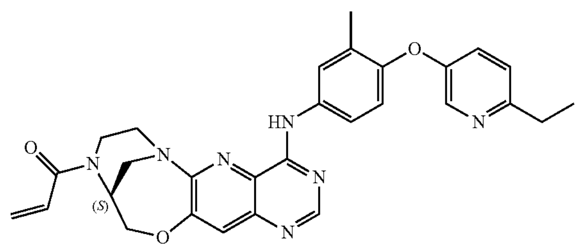
;
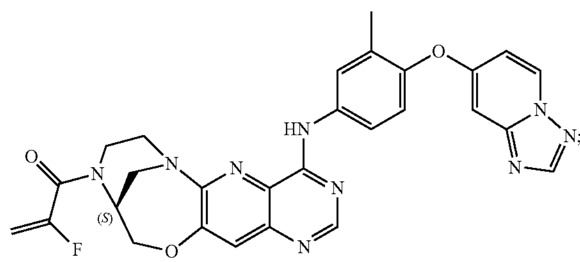
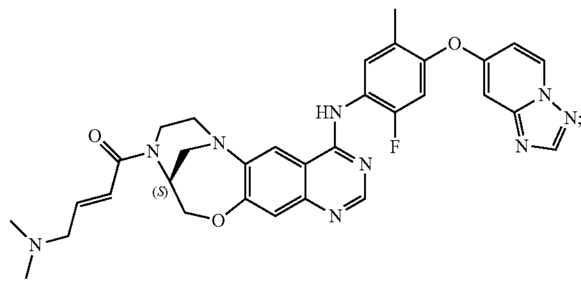
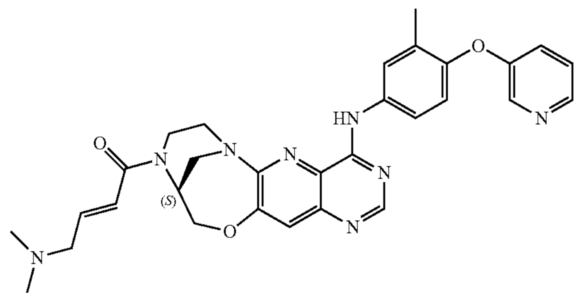
;
-continued
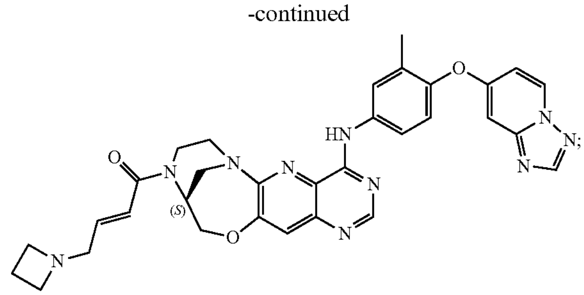
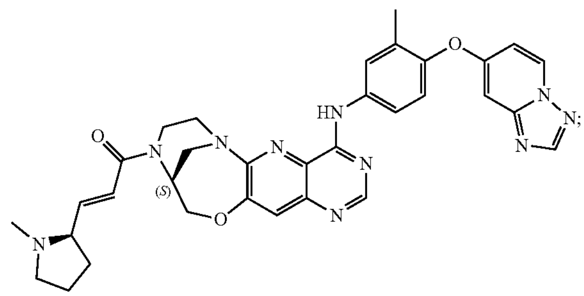
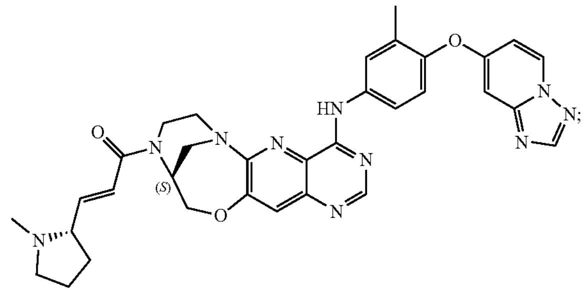
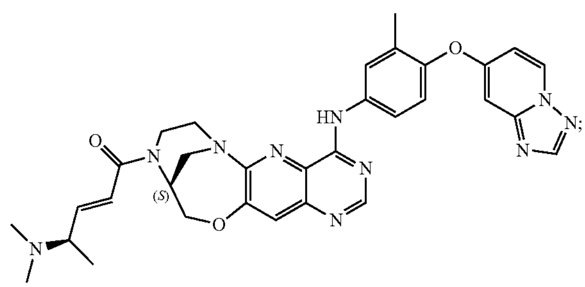
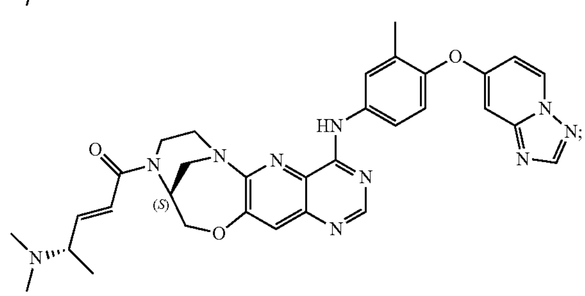
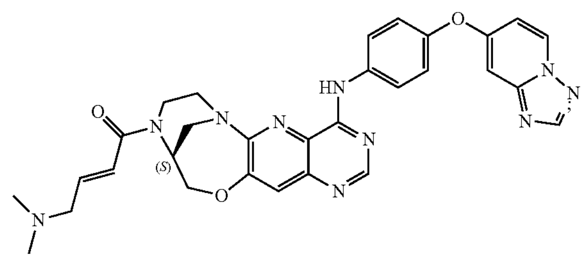

-continued

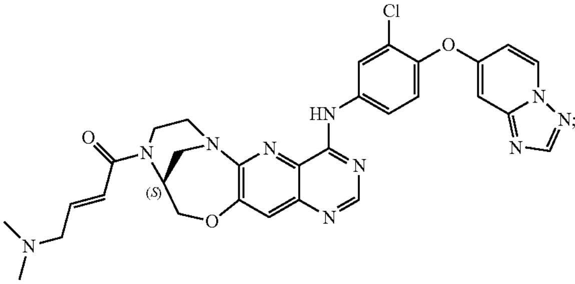

;

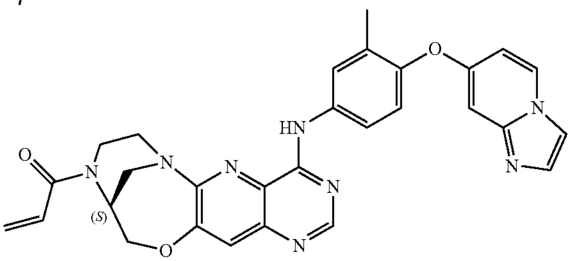

;

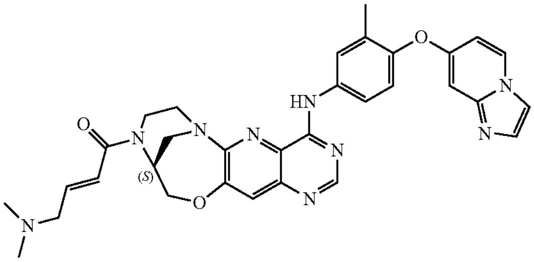

; and

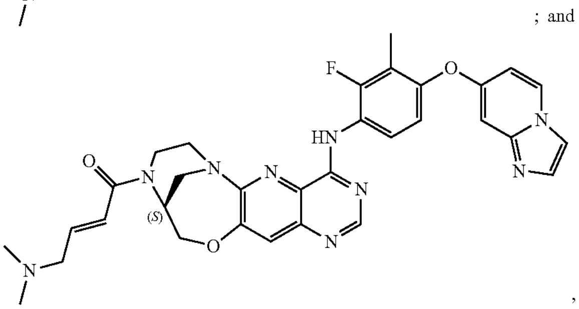

, or a pharmaceutically acceptable salt, solvate, hydrate, or co-crystal thereof, or a mixture of any of the foregoing.

Embodiment 34. A pharmaceutical composition comprising the compound of any one of embodiments 1 to 33, or a pharmaceutically acceptable salt, solvate, hydrate, or co-crystal thereof, or a mixture of any of the foregoing, and at least one pharmaceutically acceptable excipient.

Embodiment 35. A method of inhibiting kinase activity of a human receptor tyrosine kinase ErbB2 or a mutant form of human ErbB2 comprising contacting the ErbB2 or the mutant form with a therapeutically effective amount of the compound of any one of embodiments 1 to 33, or a pharmaceutically acceptable salt thereof, or a therapeutically effective amount of the pharmaceutical composition of embodiment 34.

Embodiment 36. The method of embodiment 35, wherein the mutant form of human ErbB2 comprises a mutation in Exon 20.

Embodiment 37. The method of embodiment 35 or embodiment 36, wherein the mutant form of human ErbB2 comprises one or more mutations that introduce amino acid deletions and/or insertions selected from the group consisting of: A775_A776insYVMA, G778_P780insGSP, G776delinsVC, P780_Y781insGSP, M774delinsWLV, A775 G776insSVMA, A775_G776insI, G776delinsLC, G778_S779InsCPG, and V777_G778insGSP.

Embodiment 38. The method of embodiment 35, wherein the mutant form of human ErbB2 comprises a disease-associated point mutation in ErbB2.

Embodiment 39. The method of embodiment 35 or 38, wherein the mutant form of human ErbB2 comprises one or more point mutations in ErbB2 that introduce:

(a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232.

Embodiment 40. A method of treating a patient having a cancer, comprising administering to the patient a therapeutically effective amount of the compound of any one of embodiments 1 to 33, or a pharmaceutically acceptable salt thereof, or a therapeutically effective amount of the pharmaceutical composition of embodiment 34.

Embodiment 41. The method of embodiment 40, wherein the cancer comprises cells or cell tissue having increased ErbB2 kinase activity as compared to a control.

Embodiment 42. The method of embodiment 40 or embodiment 41, wherein the cancer comprises cells or cell tissue having one or more mutations in Exon 20 of the ErbB2.

Embodiment 43. The method of any one of embodiments 40 to 42, wherein the cancer comprises cells or cell tissue having one or more mutations in Exon 20 of the ErbB2 that introduce amino acid deletions and/or insertions selected from the group consisting of A775_A776insYVMA, G778_P780insGSP, G776delinsVC, P780_Y781insGSP, M774delinsWLV, A775 G776insSVMA, A775_G776insI, G776delinsLC, G778_S779InsCPG, and V777_G778insGSP.

Embodiment 44. The method of embodiment 40 or embodiment 41, wherein the cancer comprises cells or cell tissue having one or more disease-associated point mutations in ErbB2.

Embodiment 45. The method of any one of embodiments 40 to 41 and 44, wherein the cancer comprises cells or cell tissue having one or more point mutations that introduce:

(a) an amino acid substitution selected from the group consisting of P122L, R217C, I263T, A293T, S305C, S310F/Y, H470Q, I655V, V659E, G660D, R678Q/C, L755R/S/P, I767M, D769H/N/Y, V777L/M, V842I, R868W, H878Y, E930K/D, E1021Q, F1030C, V1128I, and N1219S; or (b) a frameshift at A1232.

Embodiment 46. The method of any one of embodiments 40 to 45, wherein the cancer is lung, glioma, skin, head and neck, salivary gland, breast, esophageal, liver, stomach (gastric), uterine, cervical, biliary tract, pancreatic, colorectal, renal, bladder or prostate cancer.

Embodiment 47. The method of any one of embodiments 40 to 46, wherein the cancer is non-small cell lung cancer.

Embodiment 48. The method of any one of embodiments 40 to 47, wherein the patient has received at least one, at least two, or at least three prior therapies for the cancer.

Embodiment 49. The method of embodiment 48, wherein one or more of the prior therapies selected from the group consisting of lapatinib, neratinib, afatinib, pyrotinib, poziotinib, TAK-788, and tucatinib.

Embodiment 50. The method of any one of embodiments 40 to 49, wherein the method further comprises administering one or more additional anti-cancer agents.

Embodiment 51. A compound of formula (I')

(I')

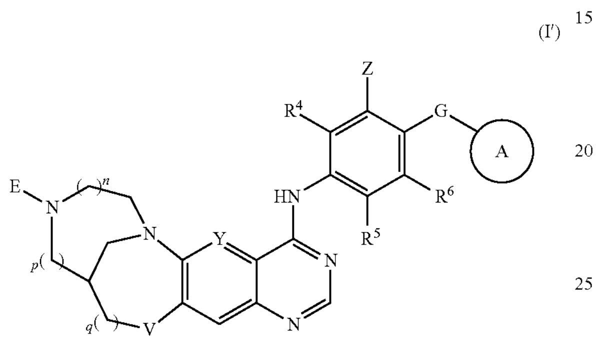

or a pharmaceutically acceptable salt, solvate, hydrate, or co-crystal thereof, or a mixture of any of the foregoing, wherein: Ring A is

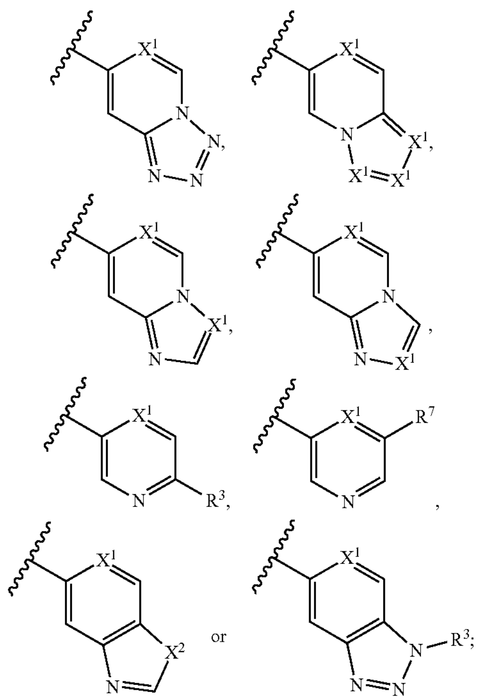

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen;

$R^6$ is —H or halogen;

$R^7$ is —H, halogen, $C_1$-$C_6$ alkyl, —$CD_3$ or $C_1$-$C_6$ cycloalkyl;

n is 1 or 2;

p is 0 or 1; and q is 1 or 2.

Embodiment 52. The compound of embodiment 51, or a pharmaceutically acceptable salt, solvate, hydrate, or co-crystal thereof, or a mixture of any of the foregoing, wherein Ring A is N

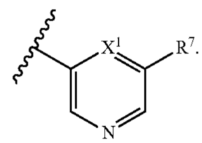

Embodiment 53. The compound of embodiment 51 or 52, or a pharmaceutically acceptable salt, solvate, hydrate, or co-crystal thereof, or a mixture of any of the foregoing, wherein Ring A is

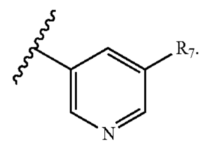

Embodiment 54. The compound of embodiment 52 or 53, or a pharmaceutically acceptable salt, solvate, hydrate, or co-crystal thereof, or a mixture of any of the foregoing, wherein $R^7$ is —F.

Embodiment 55. The compound of embodiment 51, or a pharmaceutically acceptable salt, solvate, hydrate, or co-crystal thereof, or a mixture of any of the foregoing, wherein the compound is a compound of formula (I)

(I)

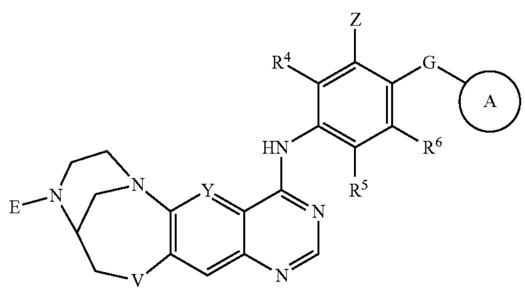

or a pharmaceutically acceptable salt, solvate, hydrate, or co-crystal thereof, or a mixture of any of the foregoing, wherein:

Ring A is

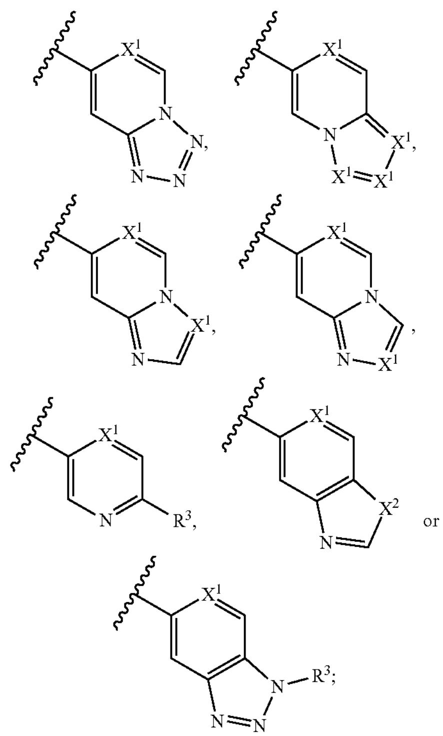

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen; and $R^6$ is —H or halogen.

Embodiment 56. The compound of embodiment 51 or 55, or a pharmaceutically acceptable salt, solvate, hydrate, or co-crystal thereof, or a mixture of any of the foregoing, wherein:

ring A is

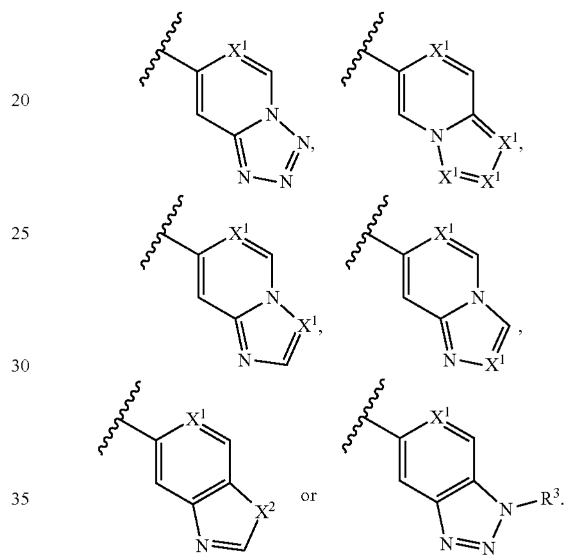

Embodiment 57. The compound of any one of embodiments 51, 55 and 56, or a pharmaceutically acceptable salt, solvate, hydrate, or co-crystal thereof, or a mixture of any of the foregoing, wherein:

ring A is

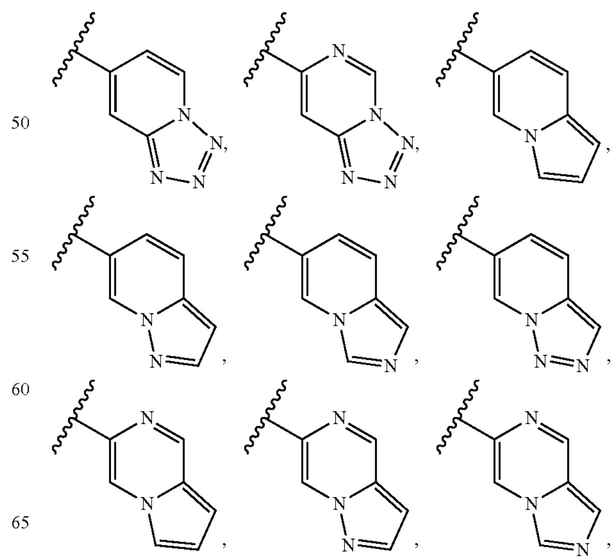

-continued

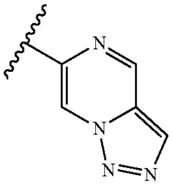, 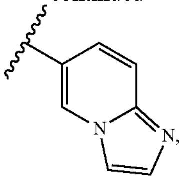, 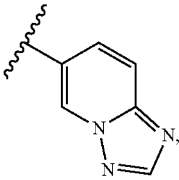, 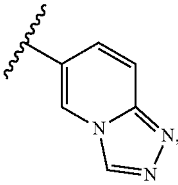, 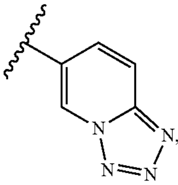, 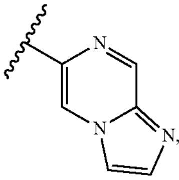, 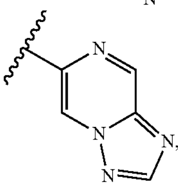, 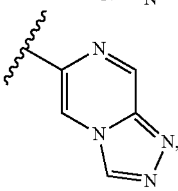, 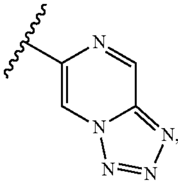, 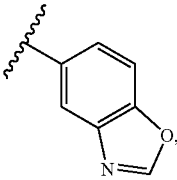, 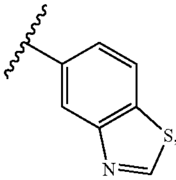, 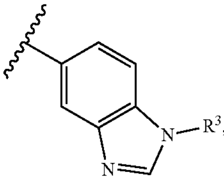, 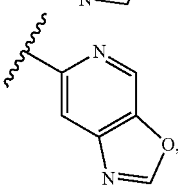, 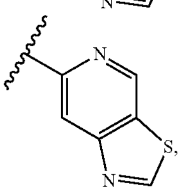, 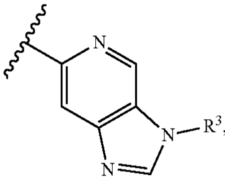, 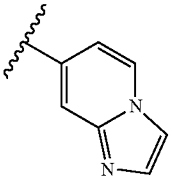, 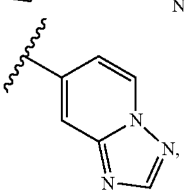, 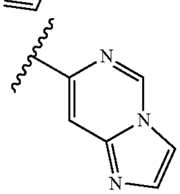, 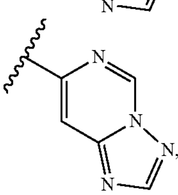, 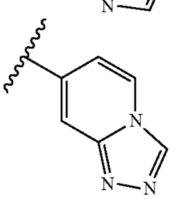, 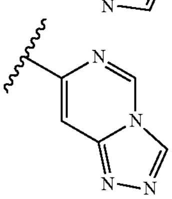, 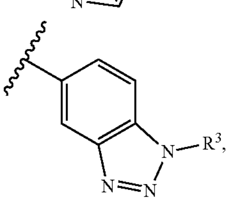, or 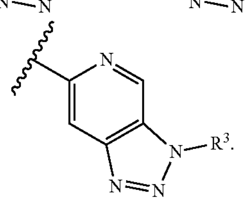.

Embodiment 58. The compound of any one of embodiments 51, 55 and 56, or a pharmaceutically acceptable salt, solvate, hydrate, or co-crystal thereof, or a mixture of any of the foregoing, wherein:

ring A is

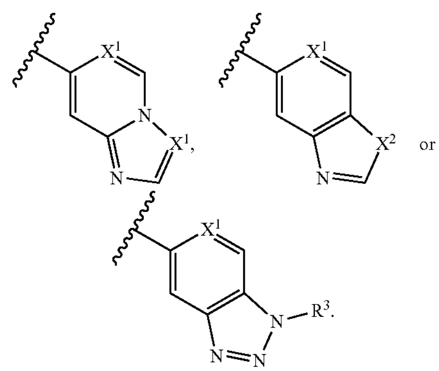

Embodiment 59. The compound of any one of embodiments 51 and 55 to 58, or a pharmaceutically acceptable salt, solvate, hydrate, or co-crystal thereof, or a mixture of any of the foregoing, wherein:

ring A is

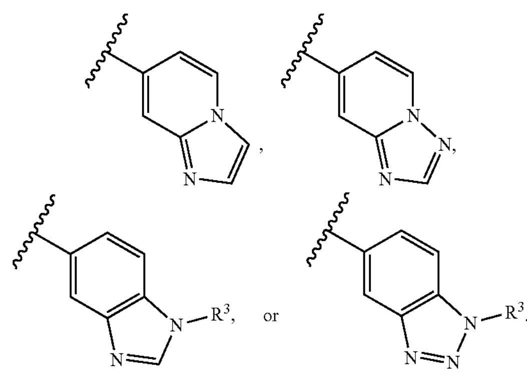

Embodiment 60. The compound of embodiment 51 or 55, or a pharmaceutically acceptable salt, solvate, hydrate, or co-crystal thereof, or a mixture of any of the foregoing, wherein:

ring A is

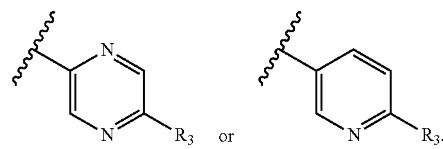

Embodiment 61. The compound of any one of embodiments 51 and 55 to 60, or a pharmaceutically acceptable salt, solvate, hydrate, or co-crystal thereof, or a mixture of any of the foregoing, wherein $R^3$ is $—CH_3$.

Embodiment 62. The compound of any one of embodiments 51 to 61, or a pharmaceutically acceptable salt, solvate, hydrate, or co-crystal thereof, or a mixture of any of the foregoing, wherein Z is —H, —F, —Cl, —C≡CH, $—OCH_3$, or $—CH_3$.

Embodiment 63. The compound of any one of embodiments 51 to 62, or a pharmaceutically acceptable salt, solvate, hydrate, or co-crystal thereof, or a mixture of any of the foregoing, wherein Z is —$CH_3$.

Embodiment 64. The compound of any one of embodiments 51 to 63, or a pharmaceutically acceptable salt, solvate, hydrate, or co-crystal thereof, or a mixture of any of the foregoing, wherein $R^1$ is $C_2$-$C_4$ alkenyl, optionally substituted by —$NR^{1a}R^{1b}$.

Embodiment 65. The compound of any one of embodiments 51 to 64, or a pharmaceutically acceptable salt, solvate, hydrate, or co-crystal thereof, or a mixture of any of the foregoing, wherein $R^1$ is —CH═$CH_2$.

Embodiment 66. The compound of any one of embodiments 51 to 64, or a pharmaceutically acceptable salt, solvate, hydrate, or co-crystal thereof, or a mixture of any of the foregoing, wherein $R^1$ is —CH═CH—$CH_2$—$N(CH_3)_2$ or —CH═CH—$CH(CH_3)$—$N(CH_3)_2$.

Embodiment 67. The compound of any one of embodiments 51 to 63, or a pharmaceutically acceptable salt, solvate, hydrate, or co-crystal thereof, or a mixture of any of the foregoing, wherein $R^1$ is $C_2$-$C_4$ alkynyl, optionally substituted by —$NR^{1a}R^{1b}$.

Embodiment 68. The compound of any one of embodiments 51 to 63 and 67, or a pharmaceutically acceptable salt, solvate, hydrate, or co-crystal thereof, or a mixture of any of the foregoing, wherein $R^1$ is —C≡C—$CH_3$.

Embodiment 69. The compound of any one of embodiments 51 to 68, pharmaceutically acceptable salt, solvate, hydrate, or co-crystal thereof, or a mixture of any of the foregoing, wherein Y is N.

Embodiment 70. The compound of any one of embodiments 51 to 68, pharmaceutically acceptable salt, solvate, hydrate, or co-crystal thereof, or a mixture of any of the foregoing, wherein Y is C—$R^y$.

Embodiment 71. The compound of any one of embodiments 51 to 68 and 70, or a pharmaceutically acceptable salt, solvate, hydrate, or co-crystal thereof, or a mixture of any of the foregoing, wherein Y is C—$R^y$, and $R^y$ is —H.

Embodiment 72. The compound of any one of embodiments 51 to 68 and 70, or a pharmaceutically acceptable salt, solvate, hydrate, or co-crystal thereof, or a mixture of any of the foregoing, wherein Y is C—$R^y$, and $R^y$ is —F.

Embodiment 73. The compound of any one of embodiments 51 to 72, or a pharmaceutically acceptable salt, solvate, hydrate, or co-crystal thereof, or a mixture of any of the foregoing, wherein V is O.

Embodiment 74. The compound of any one of embodiments 51 to 72, or a pharmaceutically acceptable salt, solvate, hydrate, or co-crystal thereof, or a mixture of any of the foregoing, wherein V is S.

Embodiment 75. The compound of any one of embodiments 51 to 72, or a pharmaceutically acceptable salt, solvate, hydrate, or co-crystal thereof, or a mixture of any of the foregoing, wherein V is N—$R^2$.

Embodiment 76. The compound of any one of embodiments 51 to 75, or a pharmaceutically acceptable salt, solvate, hydrate, or co-crystal thereof, or a mixture of any of the foregoing, wherein G is —O—.

Embodiment 77. The compound of any one of embodiments 51 to 75, or a pharmaceutically acceptable salt, solvate, hydrate, or co-crystal thereof, or a mixture of any of the foregoing, wherein G is —C(═O)—.

Embodiment 78. The compound of any one of embodiments 51 to 75, or a pharmaceutically acceptable salt, solvate, hydrate, or co-crystal thereof, or a mixture of any of the foregoing, wherein G is —S—, —S(O)—, or —$S(O)_2$—.

Embodiment 79. The compound of any one of embodiments 51 to 75, or a pharmaceutically acceptable salt, solvate, hydrate, or co-crystal thereof, or a mixture of any of the foregoing, wherein G is —$CH_2$—.

Embodiment 80. The compound of any one of embodiments 51 to 79, or a pharmaceutically acceptable salt, solvate, hydrate, or co-crystal thereof, or a mixture of any of the foregoing, wherein $R^4$ is —H.

Embodiment 81. The compound of any one of embodiments 51 to 79, or a pharmaceutically acceptable salt, solvate, hydrate, or co-crystal thereof, or a mixture of any of the foregoing, wherein $R^4$ is halogen.

Embodiment 82. The compound of any one of embodiments 51 to 81, or a pharmaceutically acceptable salt, solvate, hydrate, or co-crystal thereof, or a mixture of any of the foregoing, wherein $R^5$ is —H.

Embodiment 83. The compound of any one of embodiments 51 to 81, or a pharmaceutically acceptable salt, solvate, hydrate, or co-crystal thereof, or a mixture of any of the foregoing, wherein $R^5$ is halogen.

Embodiment 84. The compound of any one of embodiments 51 to 83, or a pharmaceutically acceptable salt, solvate, hydrate, or co-crystal thereof, or a mixture of any of the foregoing, wherein $R^6$ is —H.

Embodiment 85. The compound of any one of embodiments 51 to 83, or a pharmaceutically acceptable salt, solvate, hydrate, or co-crystal thereof, or a mixture of any of the foregoing, wherein $R^6$ is halogen.

Embodiment 86. A compound selected from the group consisting of:

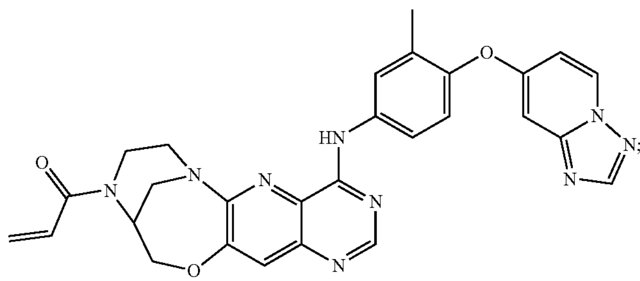;

-continued
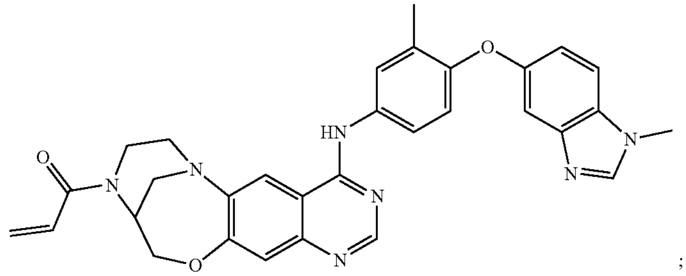
;
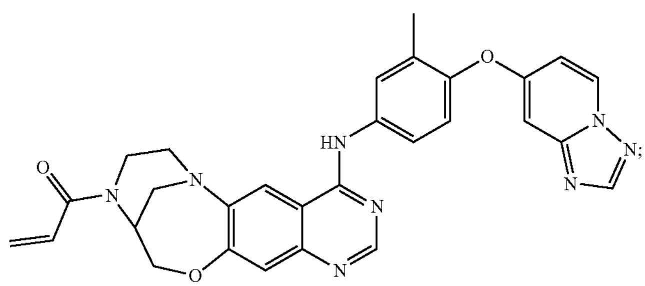
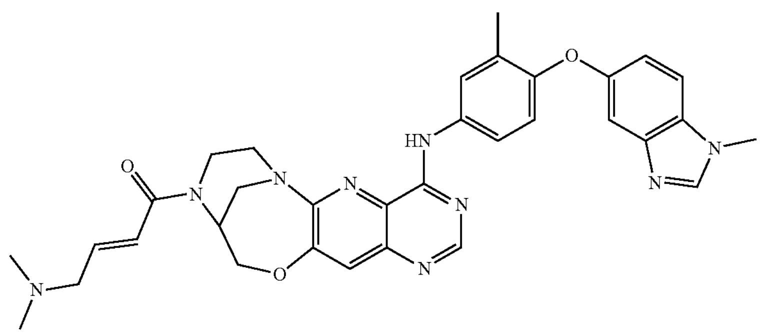
;
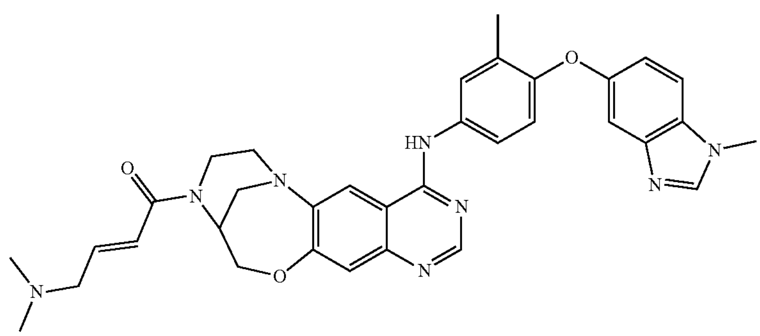
;
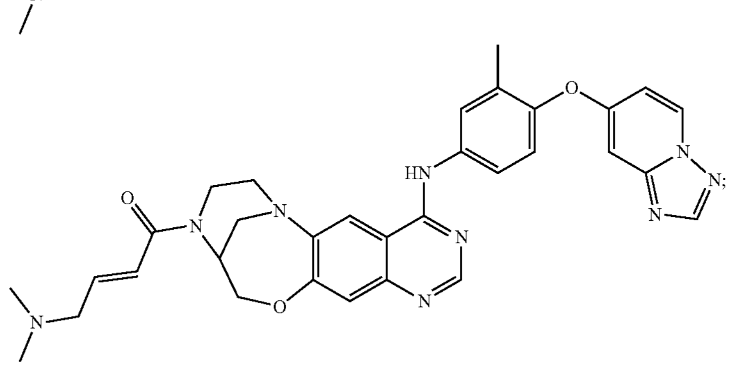

-continued
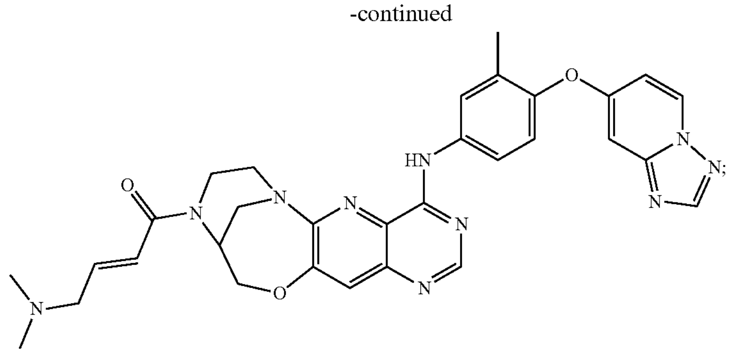
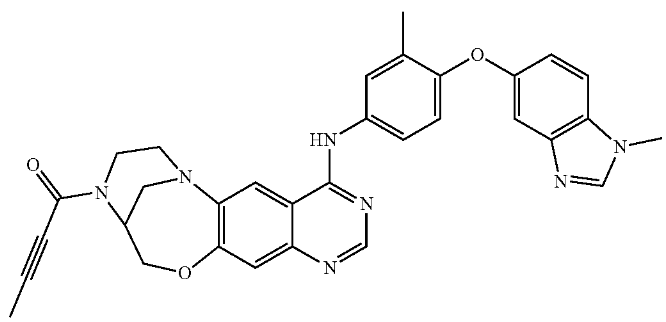
;
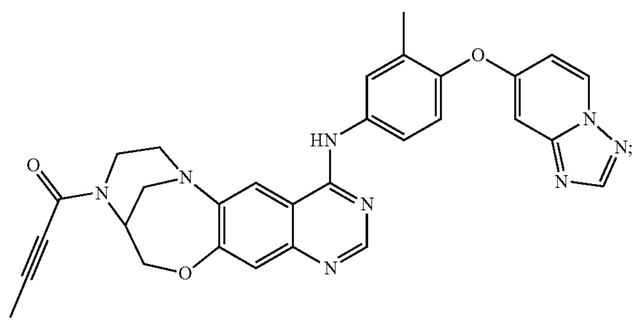
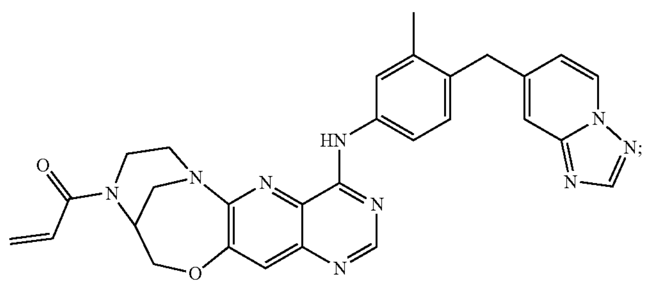
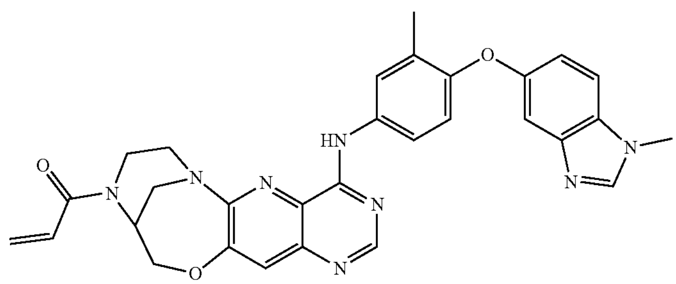
;

-continued
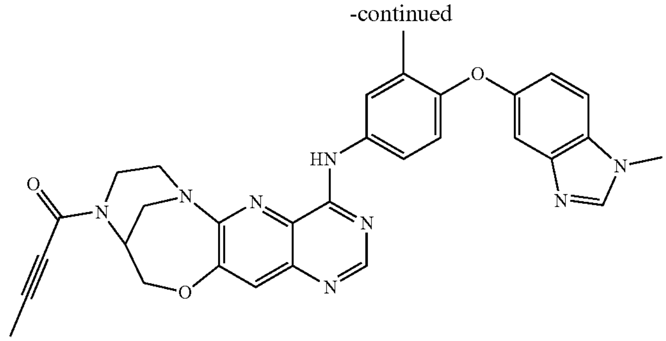
,
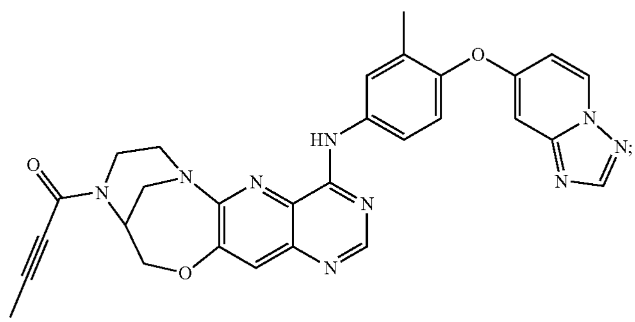
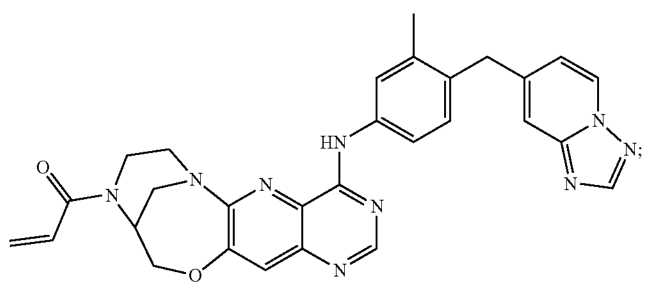
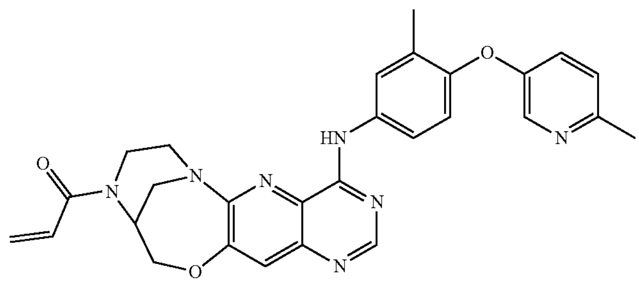
;
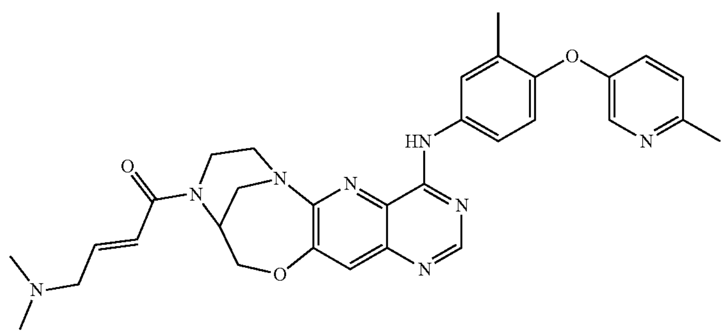
;

-continued
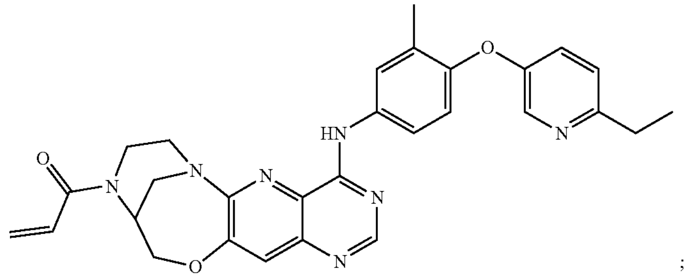
;
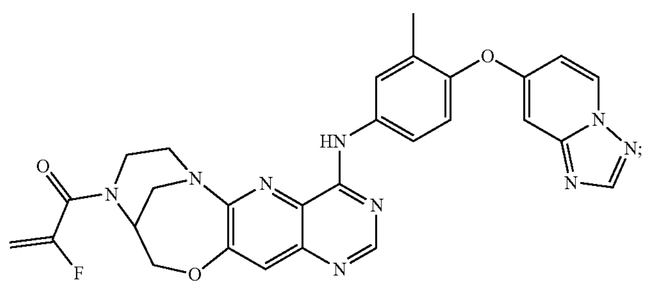
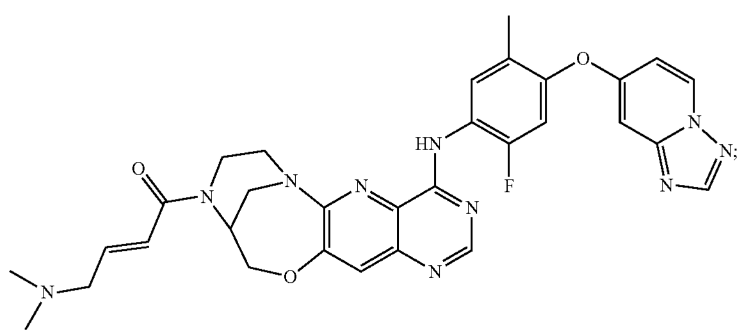
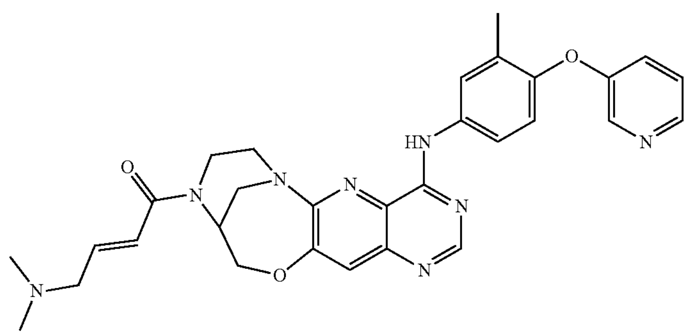
;
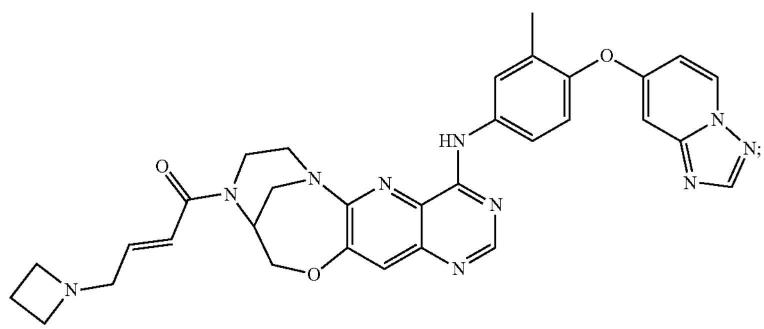

-continued
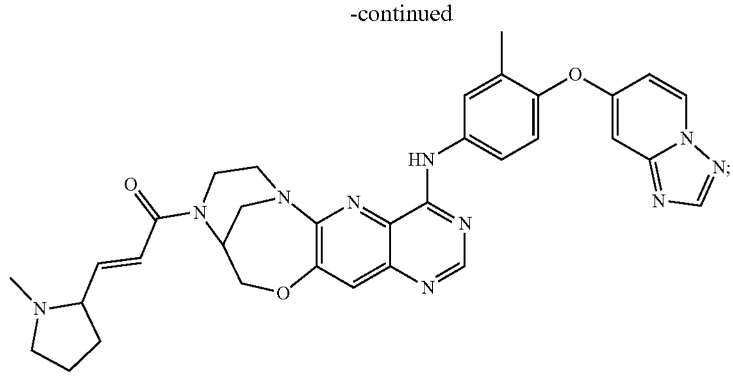
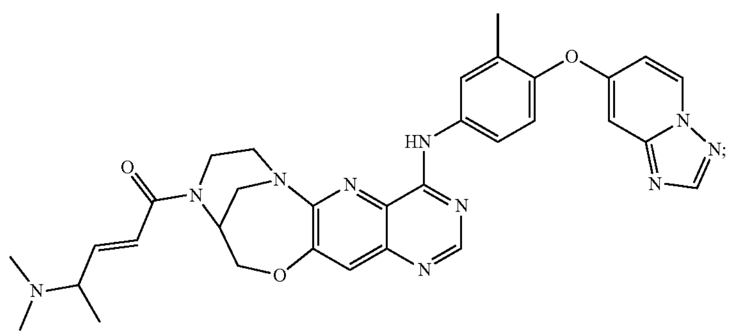
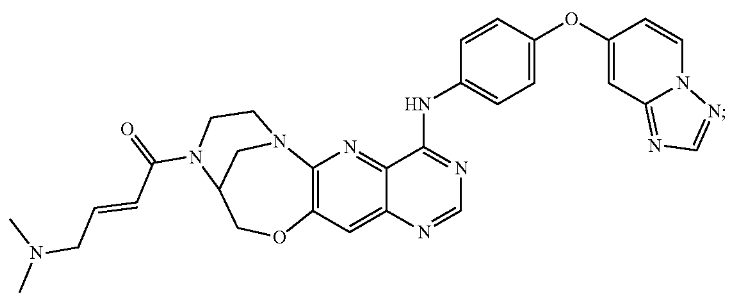
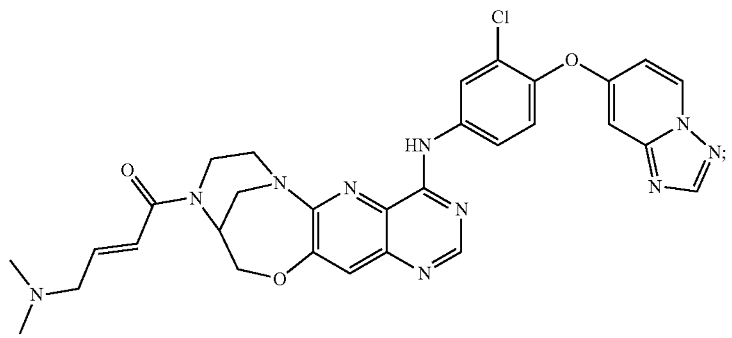
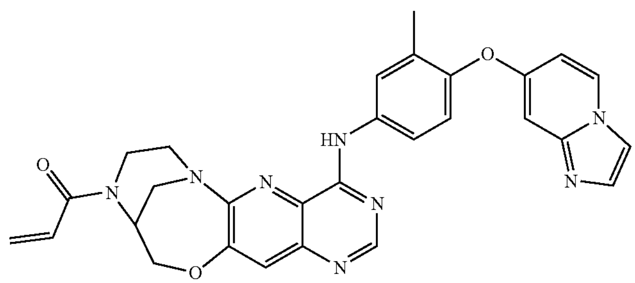
;

-continued
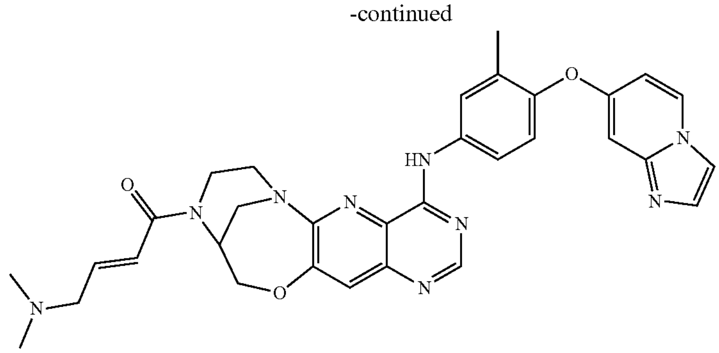
;
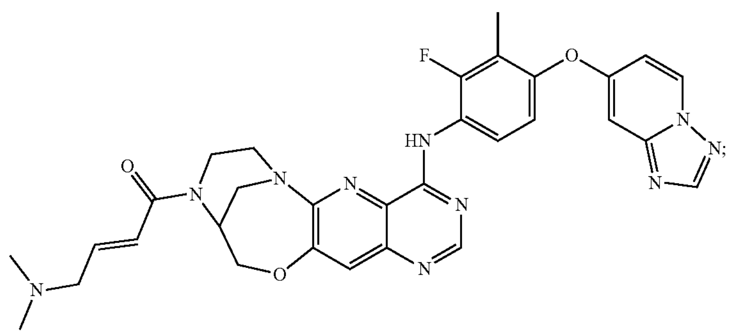
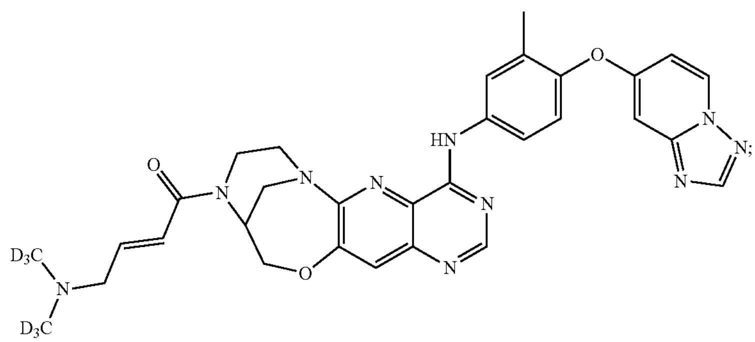
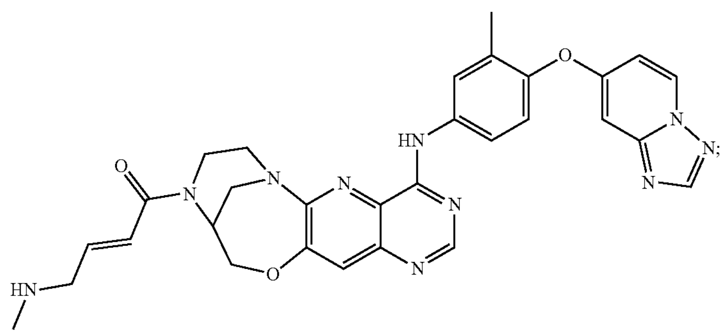
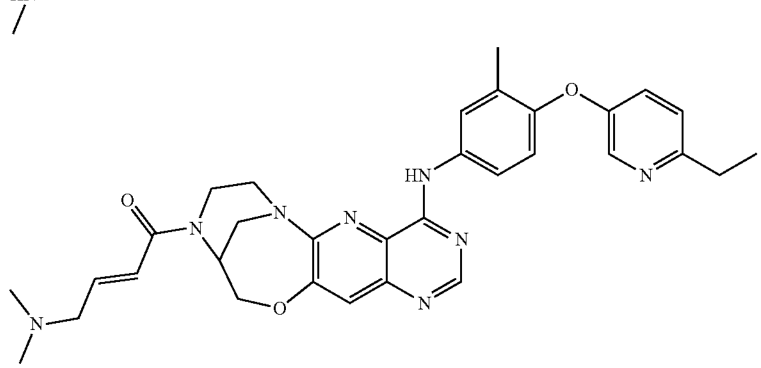
;

-continued
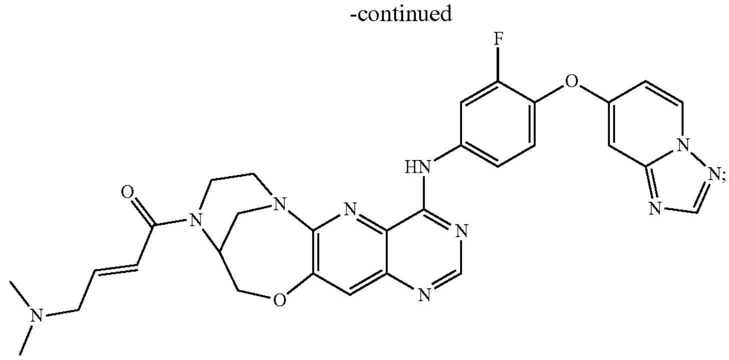
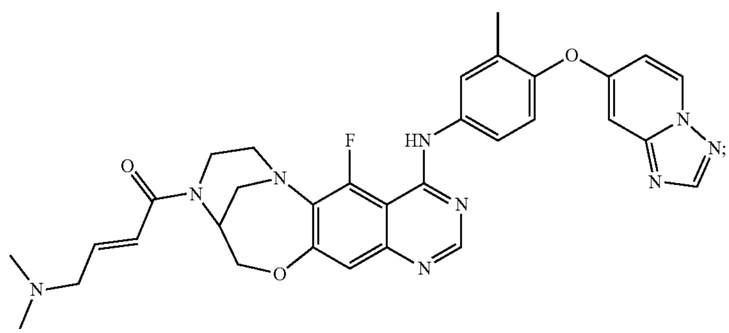
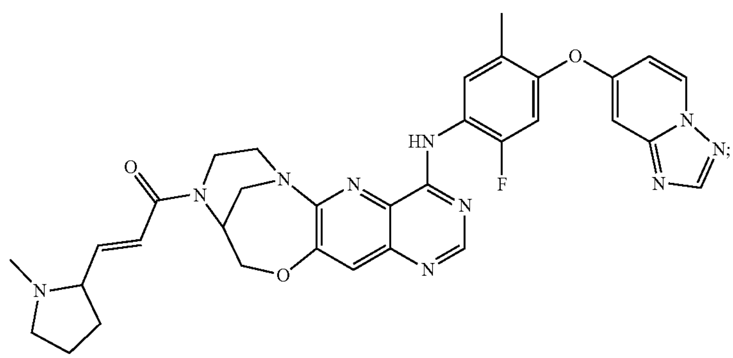
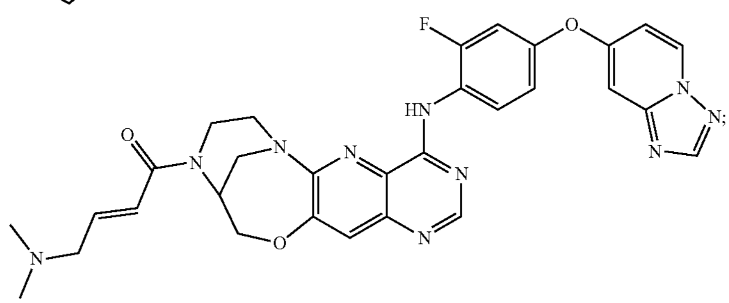
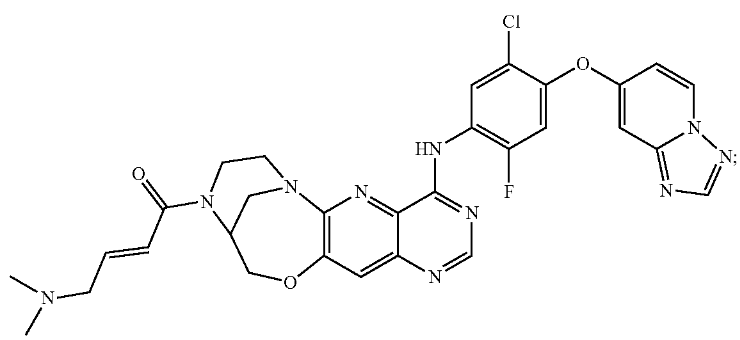

-continued
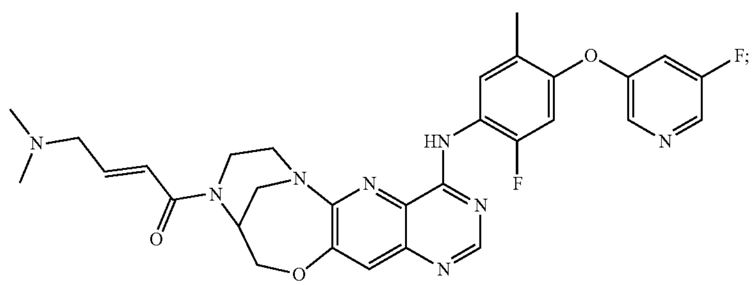
;
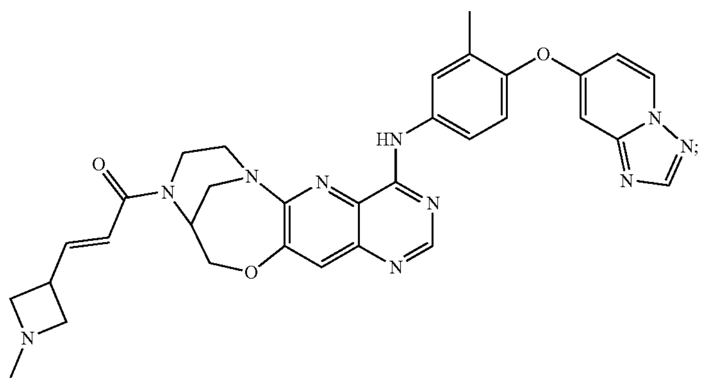
;
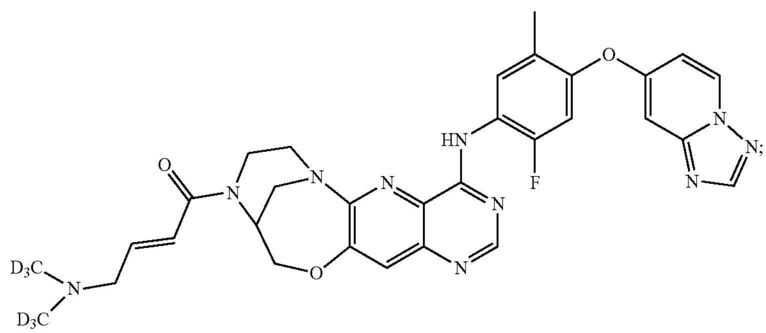
;
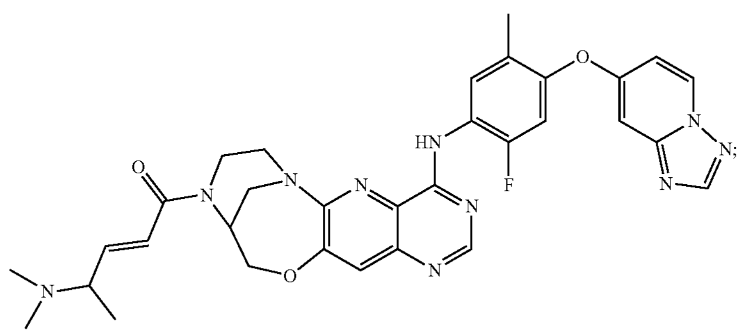
;
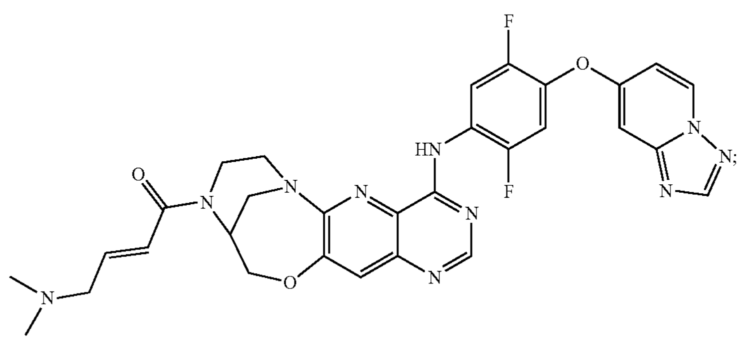
;

-continued
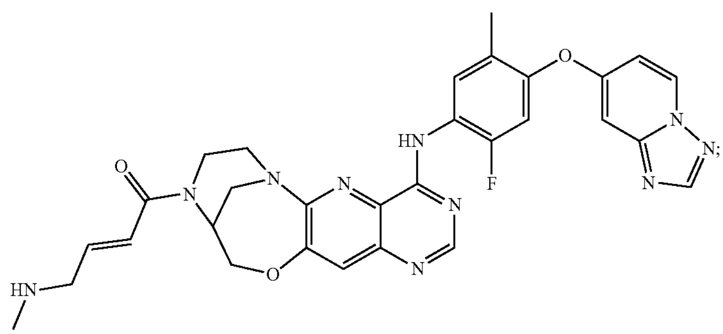
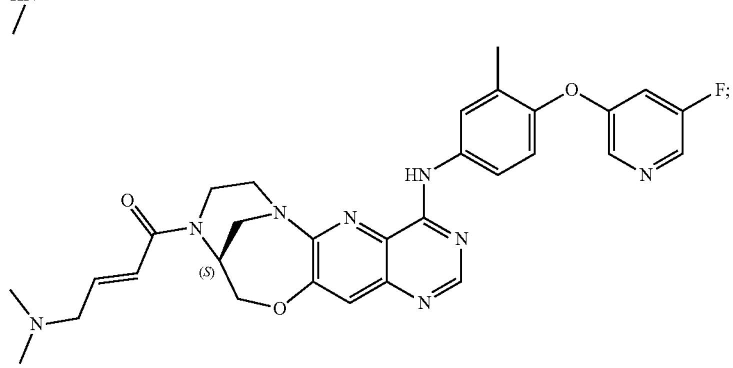
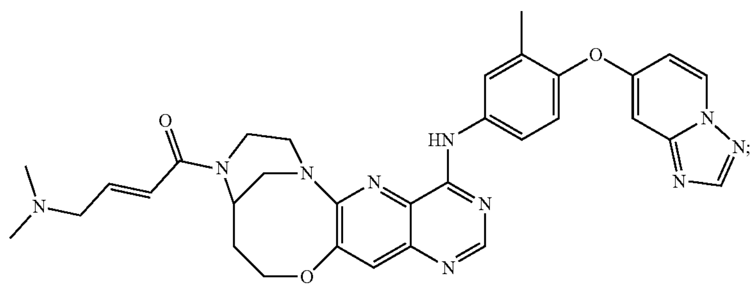
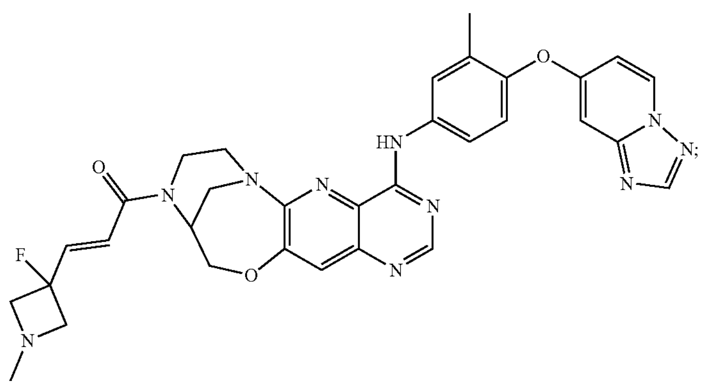
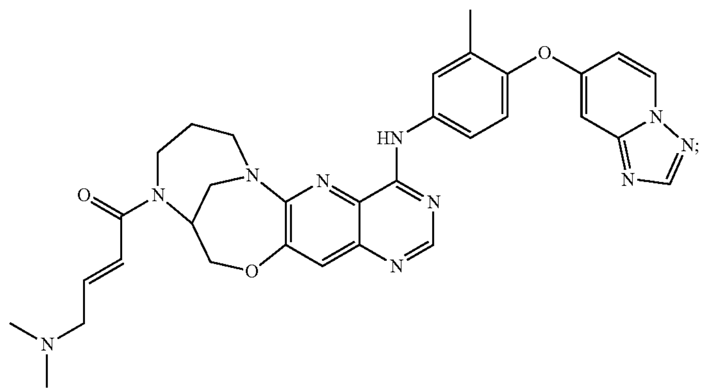

-continued
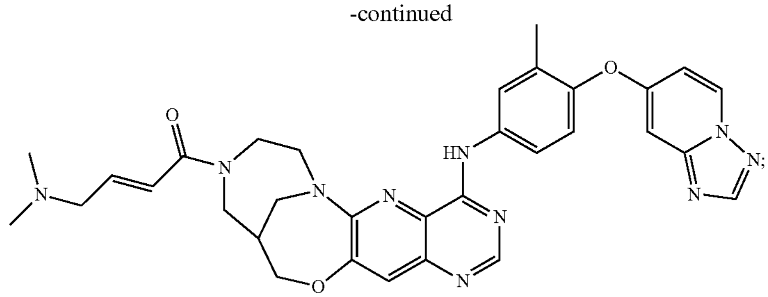
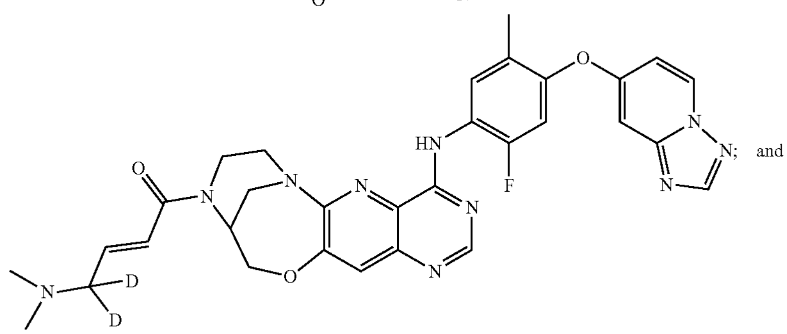
and
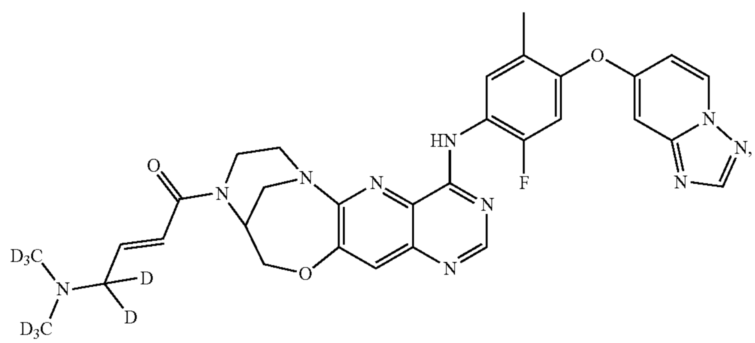
or a pharmaceutically acceptable salt, solvate, hydrate, or co-crystal thereof, or a mixture of any of the foregoing.
Embodiment 87. A compound selected from the group consisting of:
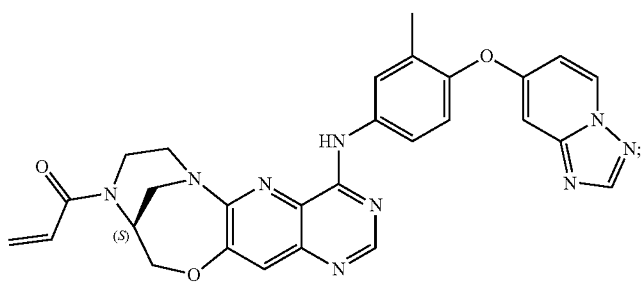
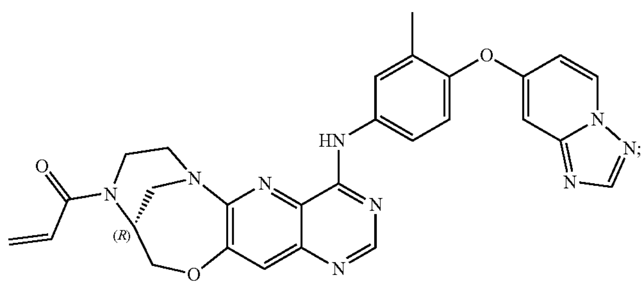

-continued
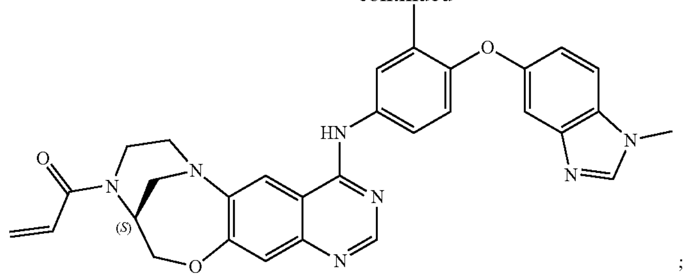
;
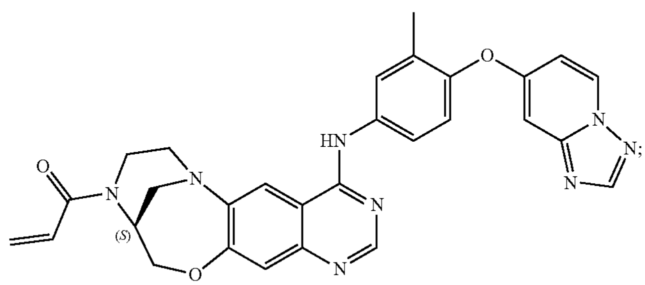
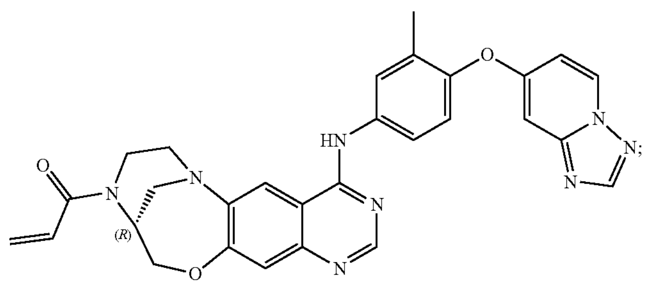
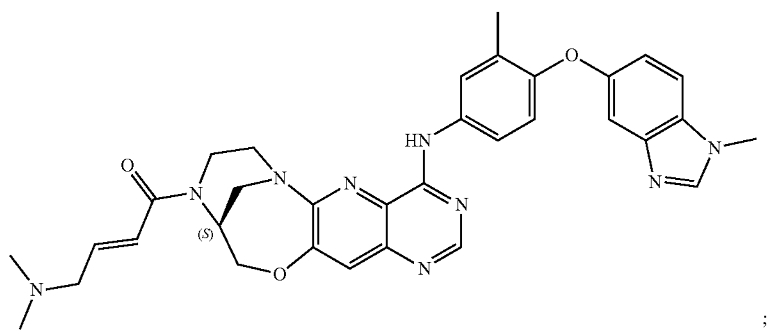
;
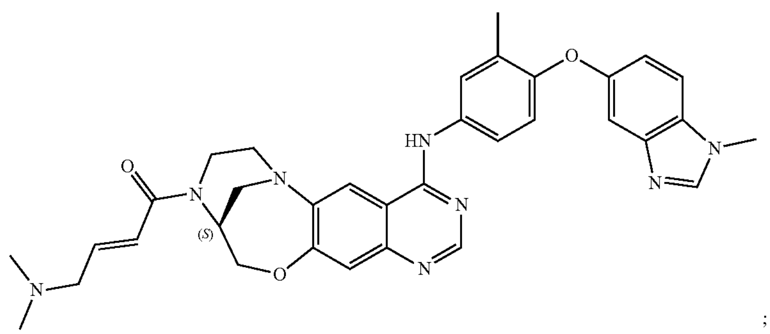
;

-continued
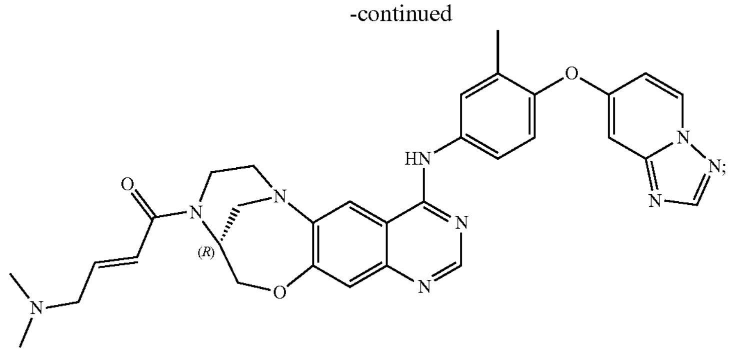
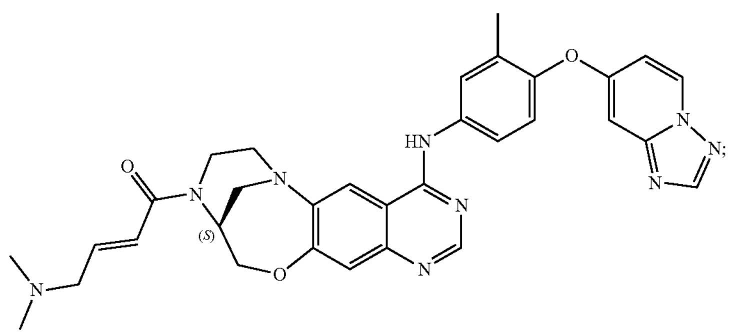
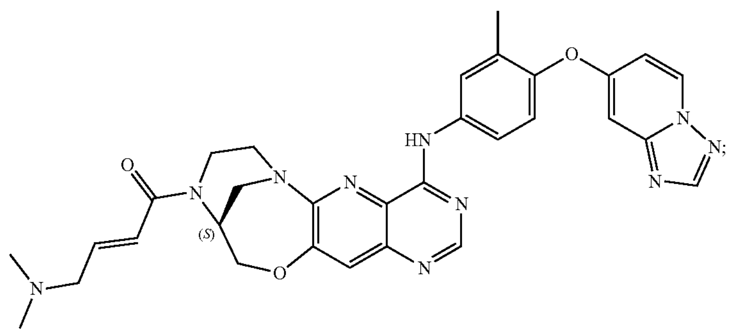
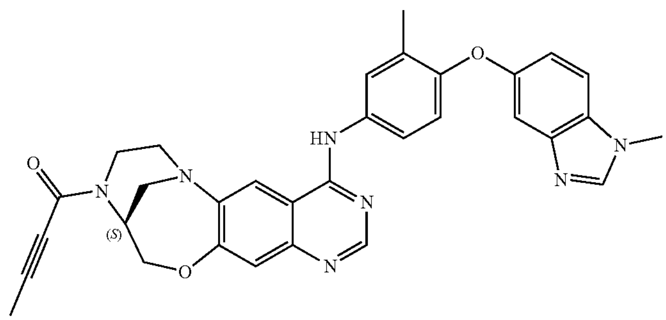
;
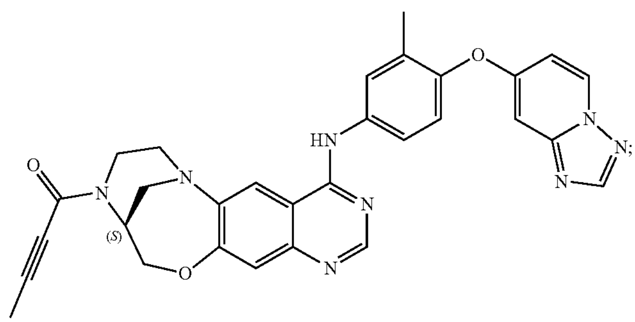

-continued
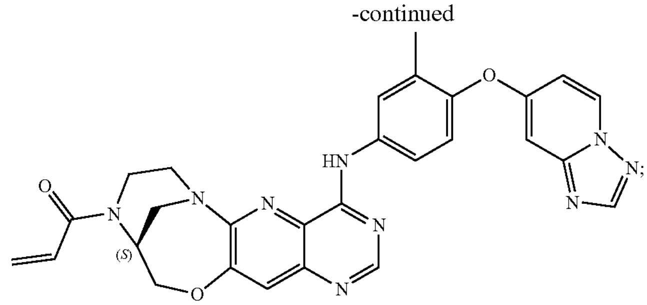
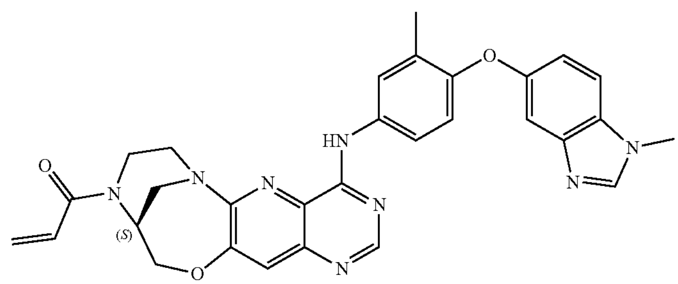
,
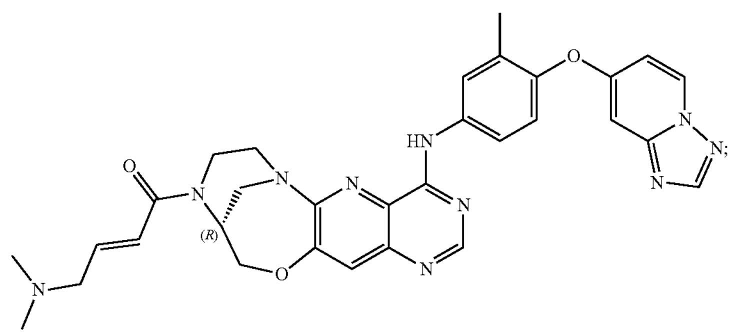
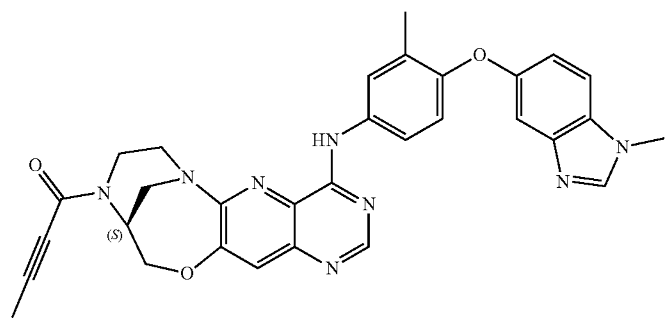
;
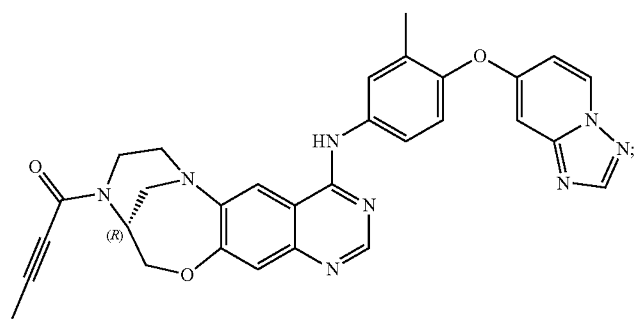

-continued
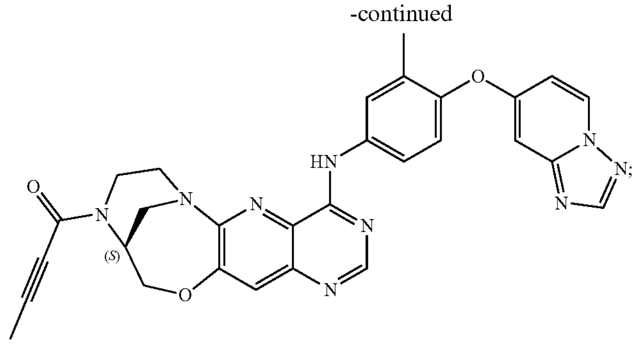
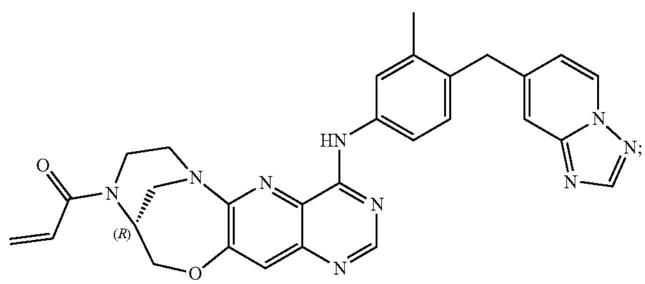
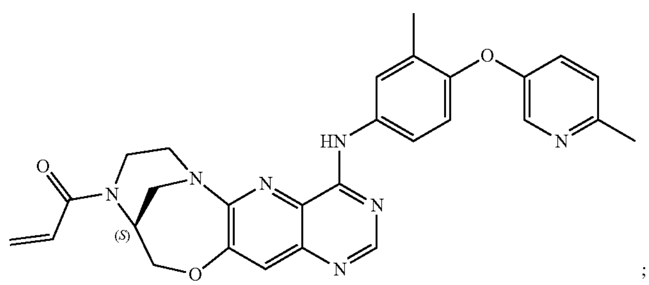
;
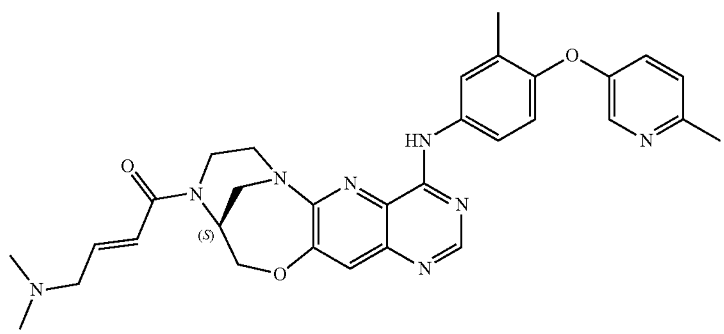
;
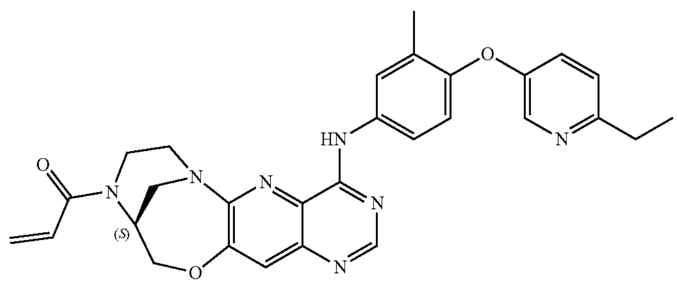
;

-continued
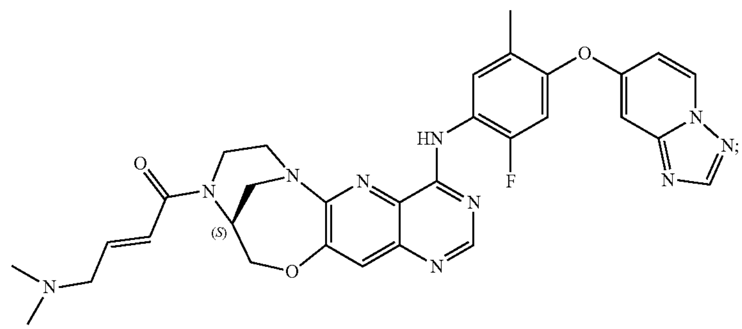
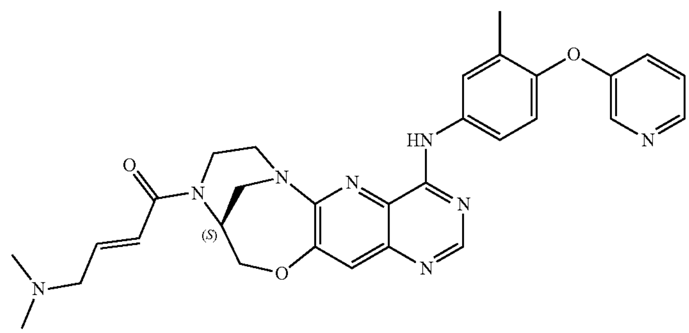
;
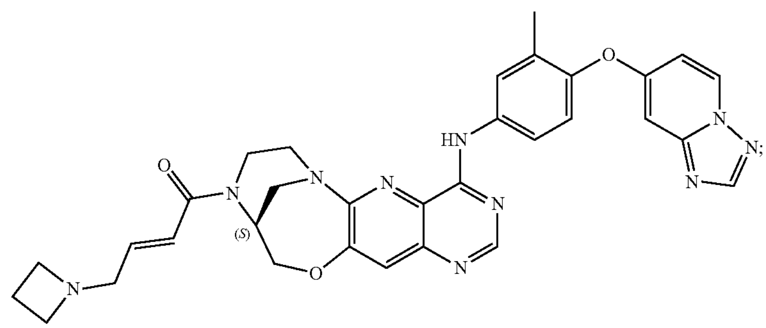
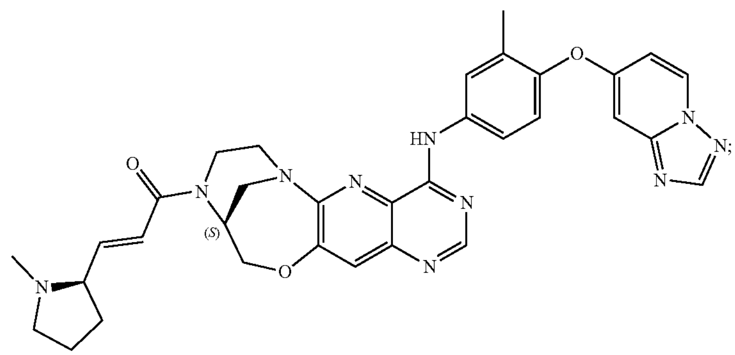

-continued
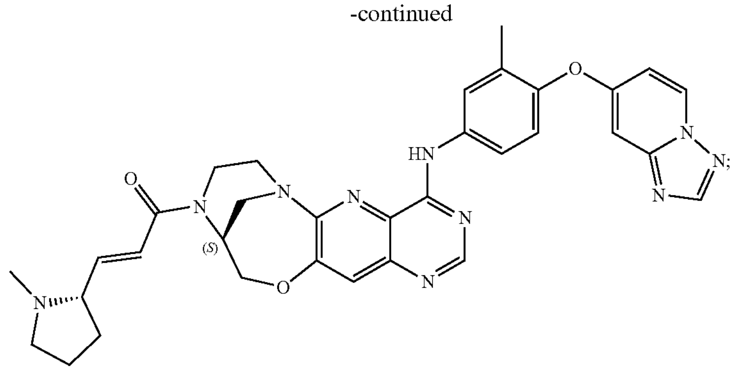
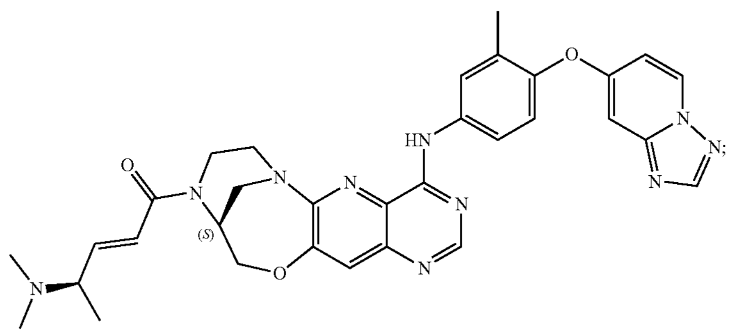
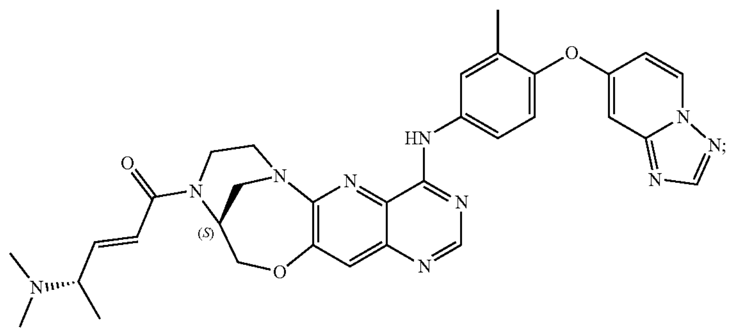
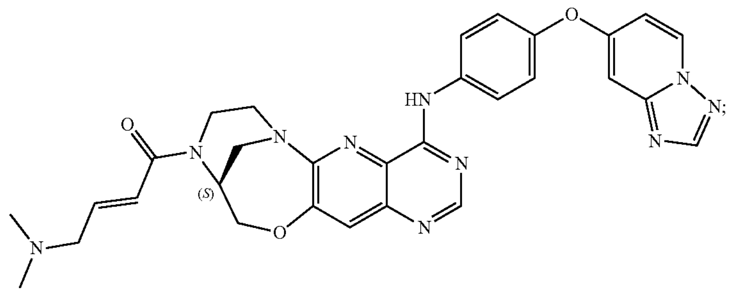
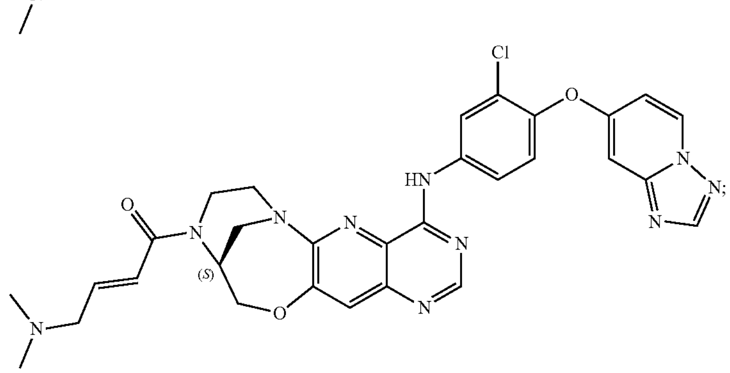

-continued
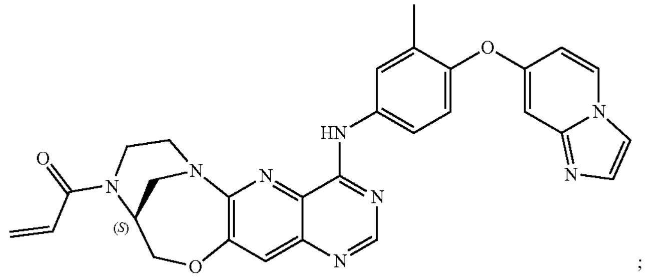
;
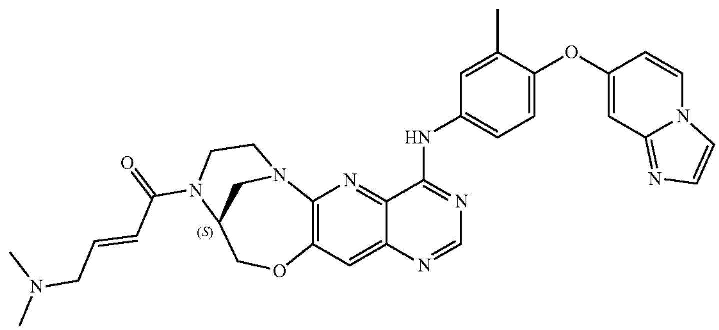
;
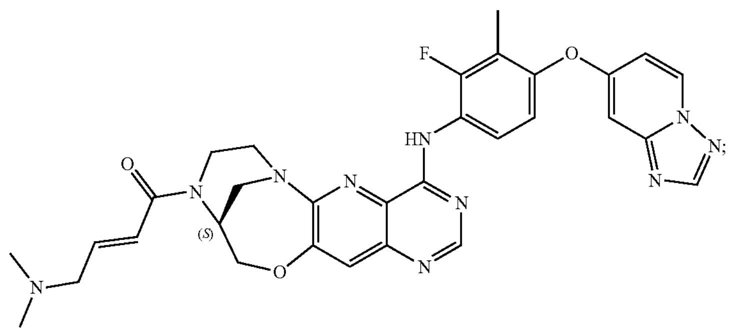
;
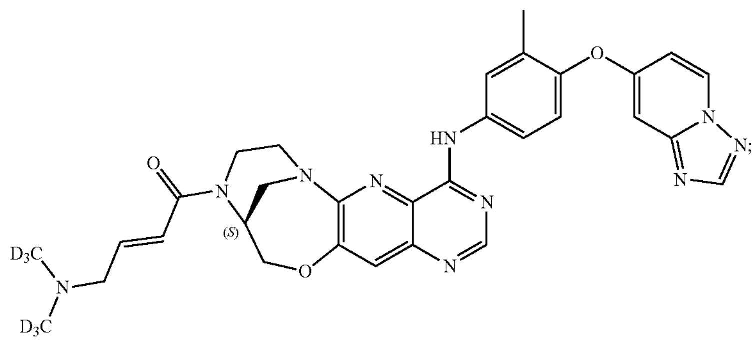
;
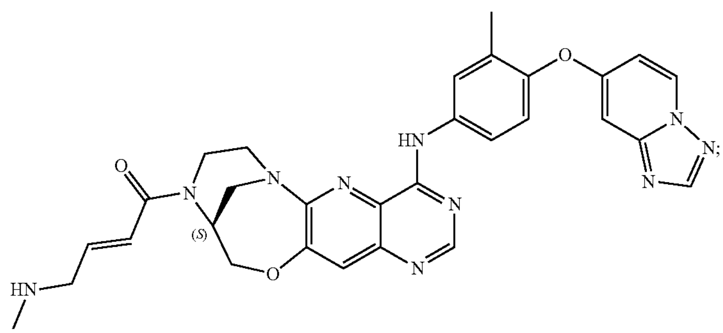
;

-continued
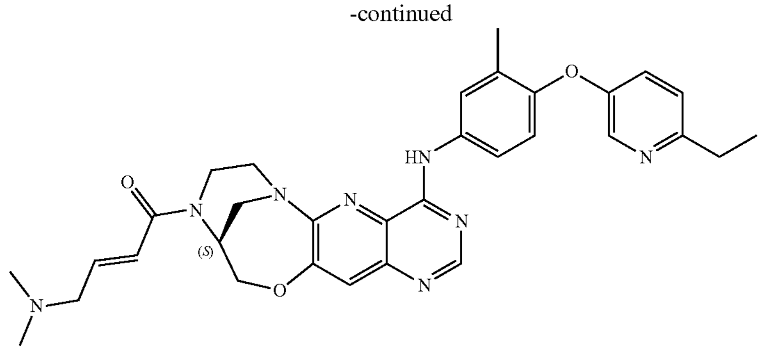
;
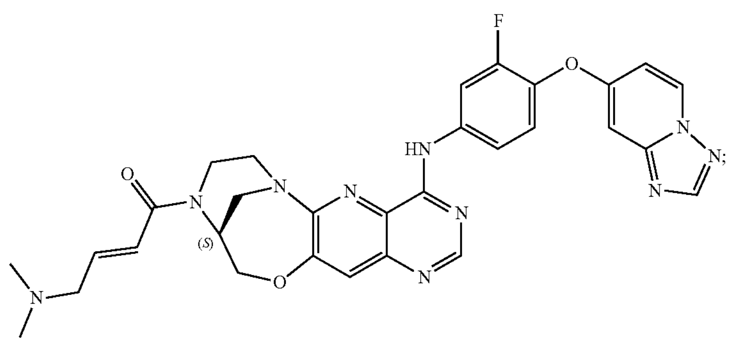
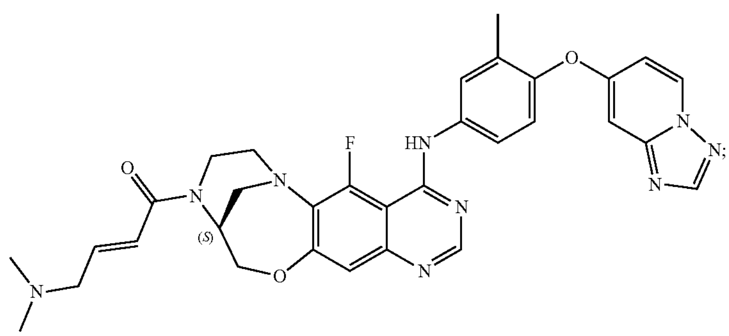
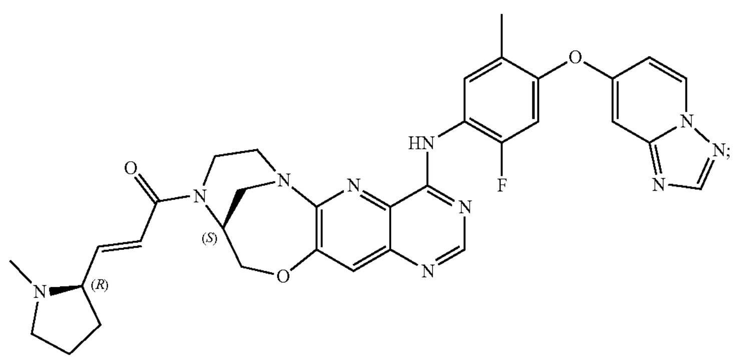
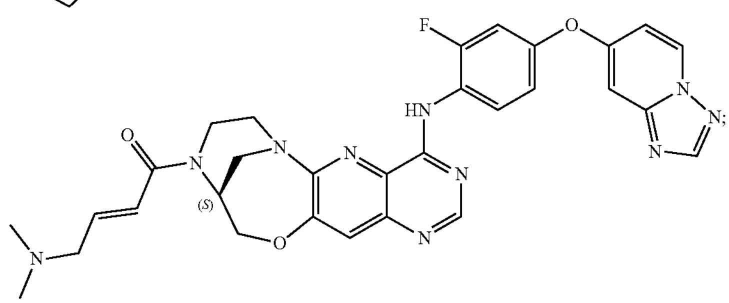

-continued
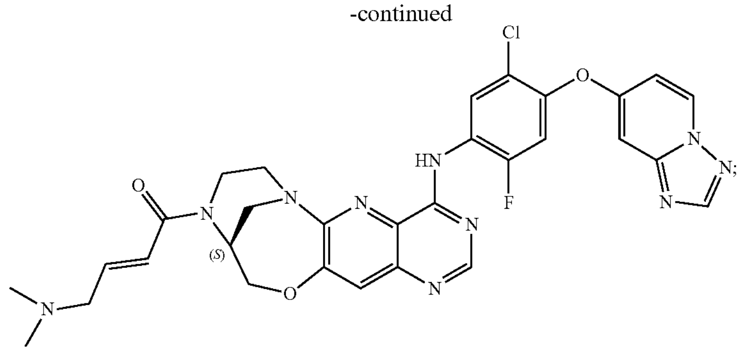
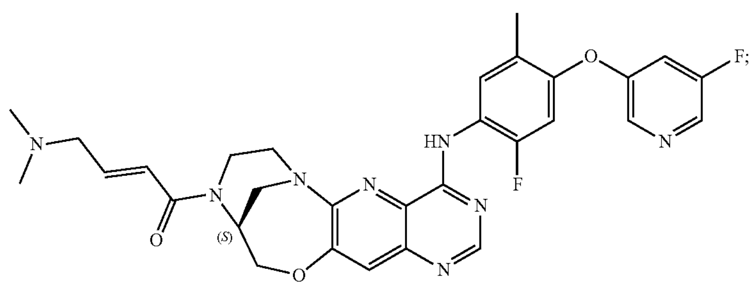
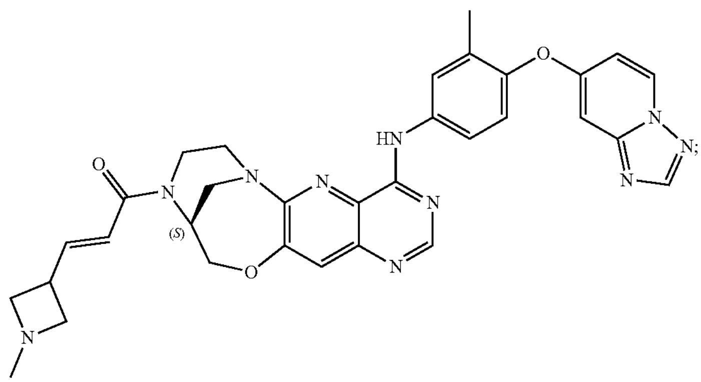
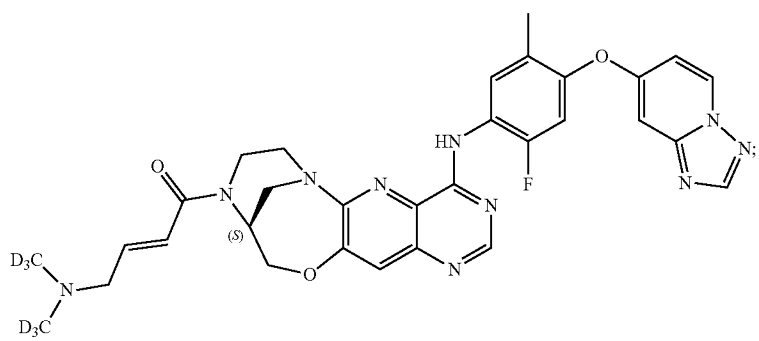
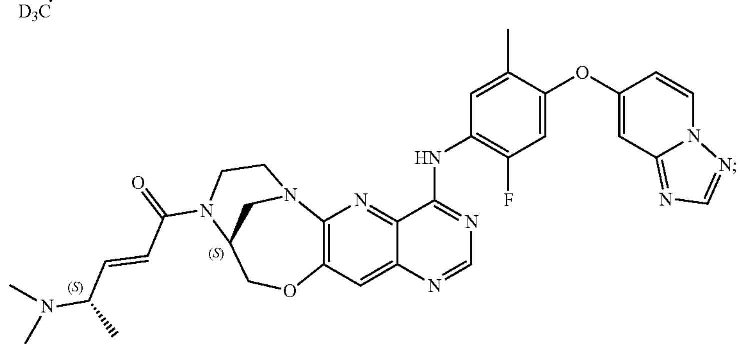

-continued
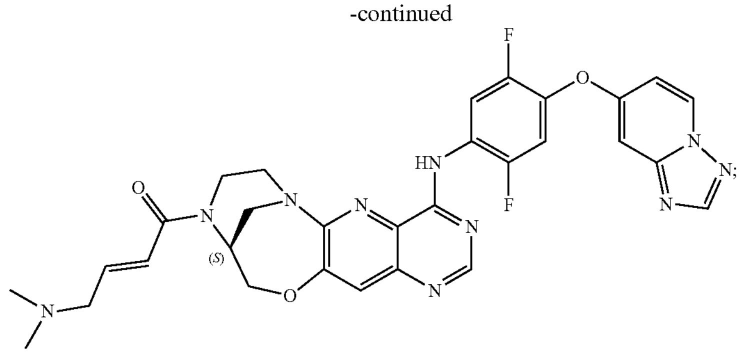
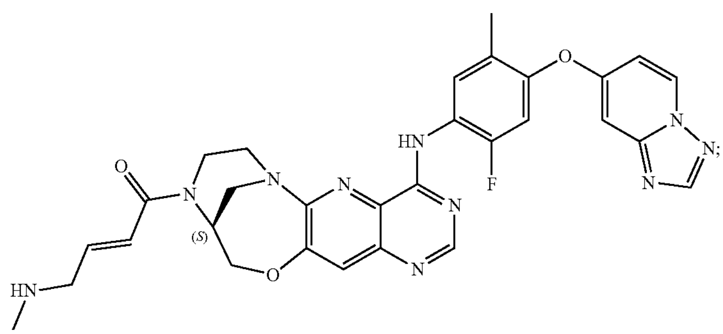
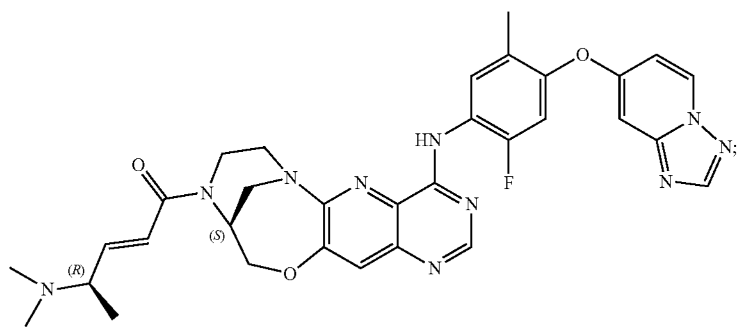
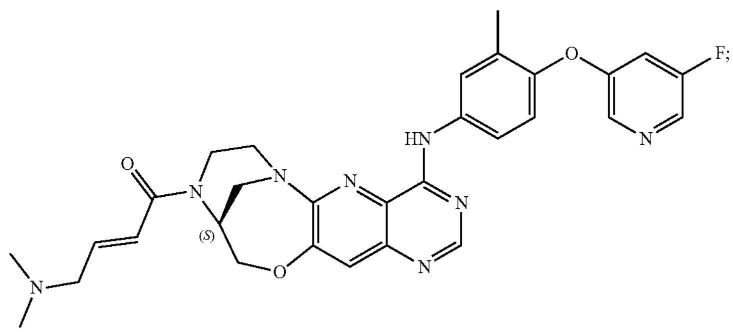
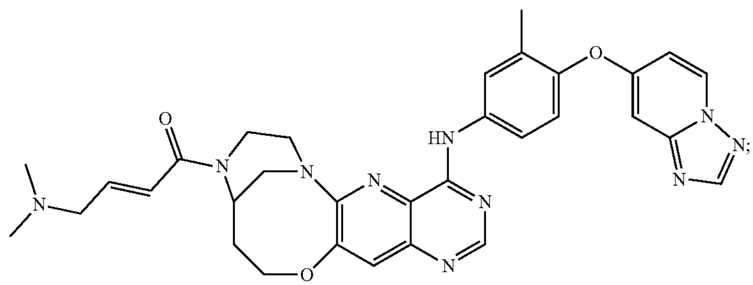

-continued
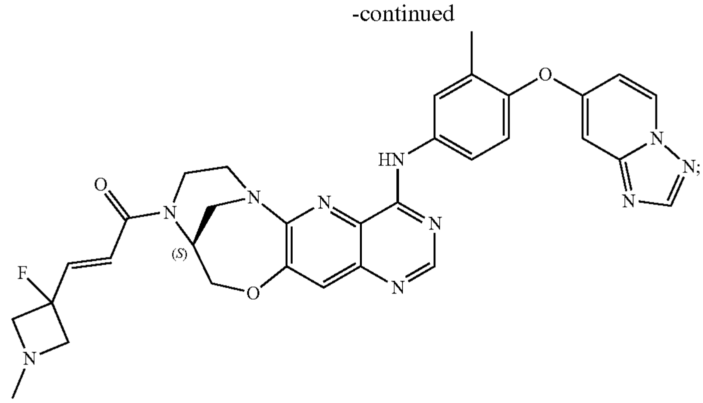
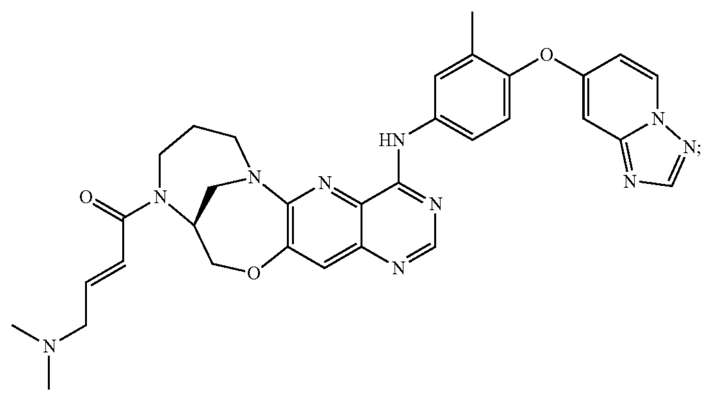
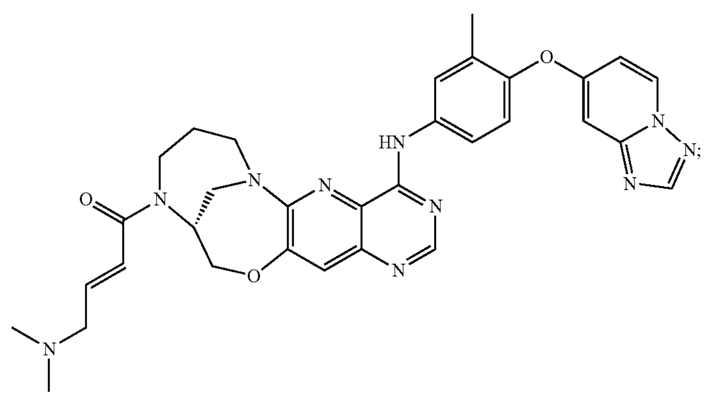
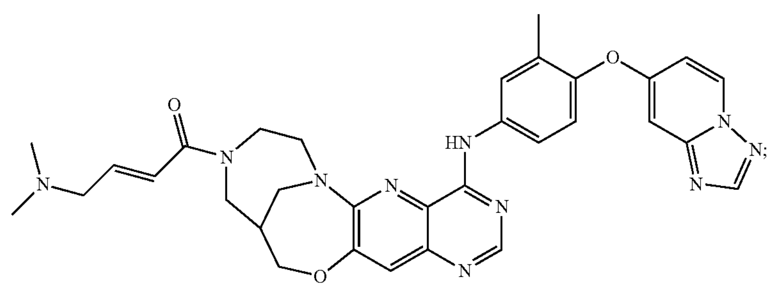

-continued

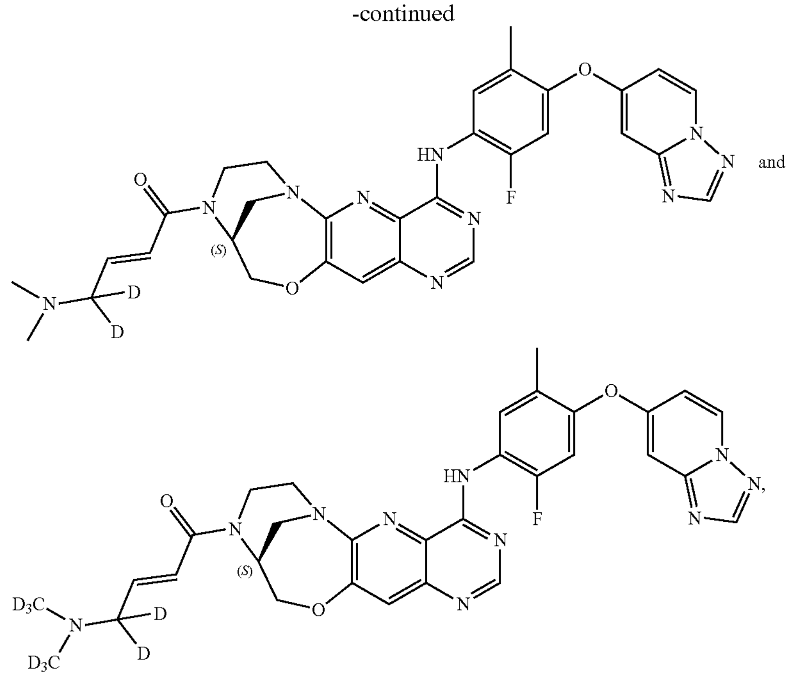

and or a pharmaceutically acceptable salt, solvate, hydrate, or co-crystal thereof, or a mixture of any of the foregoing.

Embodiment 88. A pharmaceutical composition comprising the compound of any one of embodiments 51 to 87, or a pharmaceutically acceptable salt, solvate, hydrate, or co-crystal thereof, or a mixture of any of the foregoing, and at least one pharmaceutically acceptable excipient.

Embodiment 89. A method of inhibiting kinase activity of a human receptor tyrosine kinase ErbB2 or a mutant form of human ErbB2 comprising contacting the ErbB2 or the mutant form with a therapeutically effective amount of the compound of any one of embodiments 51 to 87, or a pharmaceutically acceptable salt thereof, or a therapeutically effective amount of the pharmaceutical composition of embodiment 88.

Embodiment 90. The method of embodiment 89, wherein the mutant form of human ErbB2 comprises a mutation in Exon 20.

Embodiment 91. The method of embodiment 89 or embodiment 90, wherein the mutant form of human ErbB2 comprises one or more mutations that introduce amino acid deletions and/or insertions selected from the group consisting of: A775_A776insYVMA, A775_A776insAYVM, A775_A776insYVMS, A775_A776insVVMA, A775_A776insMMAY, A775_A776insYVMA-R678Q, G778_P780insGSP, G776delinsVC, P780 Y781insGSP, M774delinsWLV, A775 G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777 G778insQ, V777 G778insG, G778_S779insLPS, and G778_S779insAVG.

Embodiment 92. The method of embodiment 89, wherein the mutant form of human ErbB2 comprises a disease-associated point mutation in ErbB2.

Embodiment 93. The method of embodiment 89 or embodiment 92, wherein the mutant form of human ErbB2 comprises one or more point mutations in ErbB2 that introduce:

(a) an amino acid substitution selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232.

Embodiment 94. The method of embodiment 90, wherein the mutant form of human ErbB2 comprises amino terminally truncated carboxyl-terminal fragments of HER2.

Embodiment 95. A method of treating a patient having a cancer, comprising administering to the patient a therapeutically effective amount of the compound of any one of embodiments 51 to 87, or a pharmaceutically acceptable salt thereof, or a therapeutically effective amount of the pharmaceutical composition of embodiment 88.

Embodiment 96. The method of embodiment 95, wherein the cancer comprises cells or cell tissue having increased ErbB2 kinase activity as compared to a control.

Embodiment 97. The method of embodiment 95 or embodiment 96, wherein the cancer comprises cells or cell tissue having one or more mutations in Exon 20 of the ErbB2.

Embodiment 98. The method of any one of embodiments 95 to 97, wherein the cancer comprises cells or cell tissue having one or more mutations in Exon 20 of the ErbB2 that introduce amino acid deletions and/or insertions selected from the group consisting of A775_A776insYVMA, A775_A776insAYVM, A775_A776insYVMS, A775_A776insVVMA, A775_A776insMMAY, A775_A776insYVMA- R678Q, G778_P780insGSP, G776delinsVC, P780_Y781insGSP, M774delinsWLV, A775 G776insSVMA, A775_G776insI, G776delinsLC, G776delinsLV, G776delinsVV, G776insIC, G776delinsCVC, G776delinsAVGS, G776delinsAVGA, G776delinsAVGC G776_V777insLeu, G776_V777insVGS, G778_S779InsCPG; V777_G778insGSP, V777_G778insGC, V777_G778insCG, V777 G778insQ, V777_G778insG, G778 S779insLPS, and G778_S779insAVG.

Embodiment 99. The method of embodiment 95 or embodiment 96, wherein the cancer comprises cells or cell tissue having one or more disease-associated point mutations in ErbB2.

Embodiment 100. The method of any one of embodiments 95, 96 and 99, wherein the cancer comprises cells or cell tissue having one or more point mutations that introduce:

(a) an amino acid substitution selected from the group consisting of P122L, R217C, I263T, A293T, S305C, S310F/Y/P, H470Q, I655V, V659E/D, L674F, G660D, R678Q/C, L755R/S/P/Y/M, I767M, D769H/N/Y, V777L/M, V842I, R868W, H878Y, E930K/D, E1021Q, F1030C, V1128I, N1219S, G222C, A1057V, V842I, G776S/C/V/A, V773M, L869R,Y803F, H878Y, R896G, and E1195G; or (b) a frameshift at A1232.

Embodiment 101. The method of embodiment 95 or 96, wherein the cancer comprises cells or cell tissue having, expressing or over-expressing amino terminally truncated carboxyl-terminal fragments of HER2.

Embodiment 102. The method of any one of embodiments 95 to 101, wherein the cancer is lung, glioma, skin, head and neck, salivary gland, breast, esophageal, liver, stomach (gastric), uterine, cervical, biliary tract, pancreatic, colorectal, renal, bladder or prostate cancer.

Embodiment 103. The method of any one of embodiments 95 to 102, wherein the cancer is non-small cell lung cancer.

Embodiment 104. The method of any one of embodiments 95 to 103, wherein the patient has received at least one, at least two, or at least three prior therapies for the cancer.

Embodiment 105. The method of embodiment 104, wherein one or more of the prior therapies selected from the group consisting of lapatinib, neratinib, afatinib, pyrotinib, poziotinib, TAK-788, and tucatinib.

Embodiment 106. The method of any one of embodiments 95 to 105, wherein the method further comprises administering one or more additional anti-cancer agents.

Embodiment 107. The method of embodiment 106, wherein the method further comprises administering an anti-HER2 antibody or an anti-HER2 drug conjugate.

Embodiment 108. The method of embodiment 106 or 107, wherein the method further comprises administering KADCYLA® (ado-trastuzumab emtansine), ENHERTU® (fam-trastuzumab deruxtecan-nxki), or any biosimilar thereof.

VIII. General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

The intermediates described in the following preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994).

The compounds of the present invention, or salts thereof, may be prepared by a variety of procedures known in the art, some of which are illustrated in the Examples below. The specific synthetic steps for each of the routes described may be combined in different ways, to prepare compounds of the invention, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry which are analogous to the syntheses of known structurally-similar compounds and the procedures described in the Examples which follow including any novel procedures.

Compounds of formula (I'), (I), (I'-a-1), (I'-a-2), (I'-a-3), (I-a-1), (I-a-2), (I-a-3), (I'-b-1), (I'-b-2), (i-b-1), (i-b-2), (I'-c-1), (I-c-2), (I'-c-3), (I-c-4), (I-c-5), (I-c-6), (I-c-1), (I-c-2), (I-c-3), (I-c-4), (I-c-5), (I-c-6), (I'-d-1), (I'-d-2), (I'-d-3), (I'-d-4), (I'-d-5), (I'-d-6), (I'-d-7), (I-d-1), (I-d-2), (i-d-3), (I-d-4), (i-d-5), (I-d-6), (i-d-7), (I'-e-1), (I'-e-2), (I'-e-3), (I'-e-4), (I'-e-5), (I'-e-6), (I'-e-7), (I'-e-8), (I-e-1), (I-e-2), (I-e-3), (I-e-4), (I-e-5), (I-e-6), (I-e-7), (I'-f-1), (I'-f-2), (I'-f-3), (I'-f-4), (I'-f-5), (I'-f-6), (I-f-1), (I-f-2), (I-f-3), (I-f-4), (I-f-5), (I-f-6), (I'-g-1), (I'-g-2), (I'-g-3), (I'-g-4), (I'-g-5), (I'-g-6), (I'-g-7), (I'-g-8), (I-g-1), (I-g-2), (I-g-3), (I-g-4), (I-g-5), (I-g-6), (I-g-7), (I'-h-1), (I'-h-2), (I'-h-3), (I'-h-4), (I'-h-5), (I'-h-6), (I'-h-7), (I'-h-8), (I-h-1), (I-h-2), (I-h-3), (I-h-4), (I-h-5), (I-h-6), (I-h-7), (I'-i-1), (I'-i-2), (I'-i-3), (I'-i-4) can be prepared according to Scheme A, Scheme B, Scheme C, Scheme D, Scheme E, Scheme F, Scheme G, Scheme H, Scheme I, wherein the Ring A moiety, E, n, p, q, $R^1$, $R^2$, $R^3$, $R^4$, $R^5$, $R^6$, $R^7$, G, Ria, $R^{1b}$, V, $X^1$, $X^2$, Y, $R^y$, and Z are as defined for formula (I'), formula (I) or any applicable variations thereof as detailed herein.

Scheme A

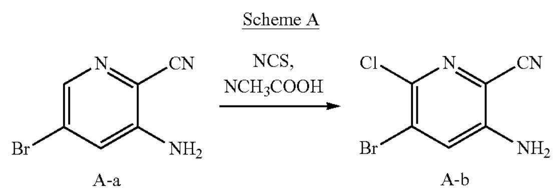 [SMILES: N#Cc1ncc(Br)cc1N ; N#Cc1nc(Cl)c(Br)cc1N]

A-a A-b

As shown in Scheme A, chlorination of compounds of general formula A-a, for example, with N-Chlorosuccinimide (NCS) and acetic acid, provides compounds of general formula A-b.

Scheme B

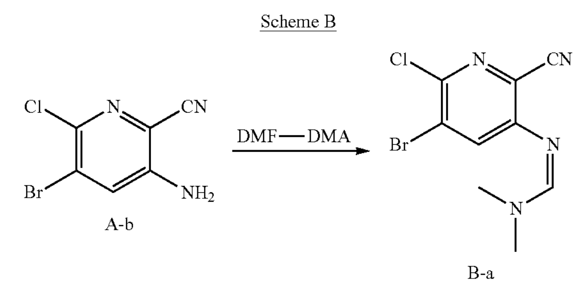

A-b B-a

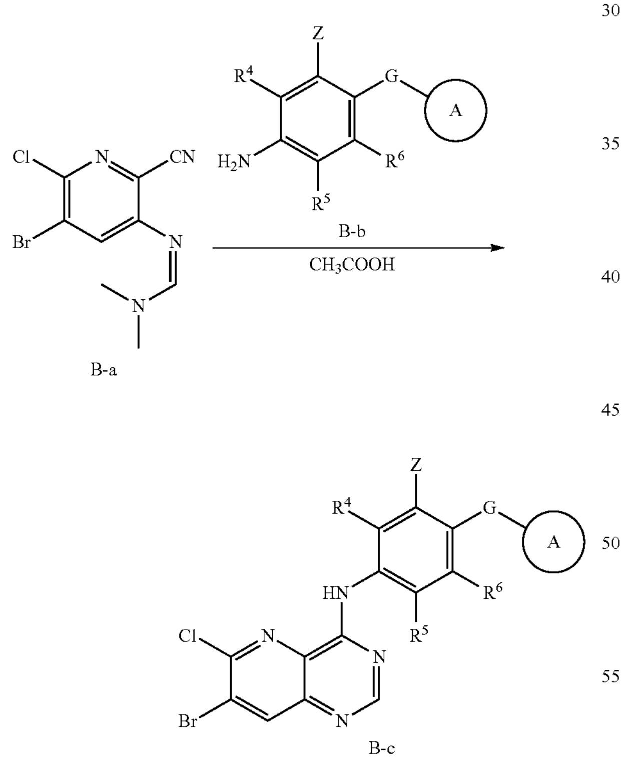

B-a B-b B-c

As shown in Scheme B, compounds of general formula A-b are reacted with N,N-dimethylformamide-dimethyl acetal (DMF-DMA) to give compounds of general formula B-a. Compounds of general formula B-a are further reacted with compounds of general formula B-b, for example, in the presence of acetic acid, to provide compounds of general formula B-C.

Scheme C

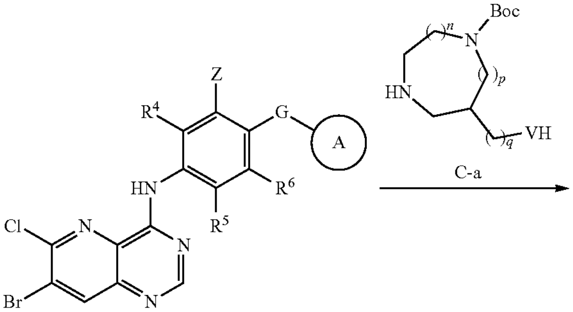

B-c C-a

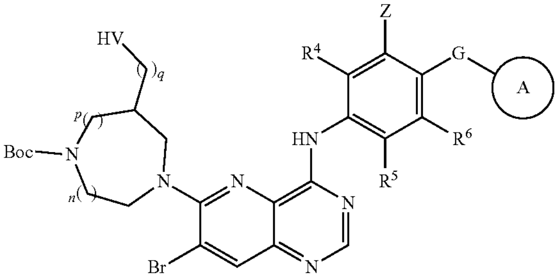

C-b

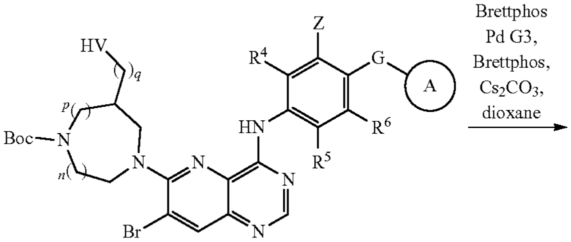

C-b

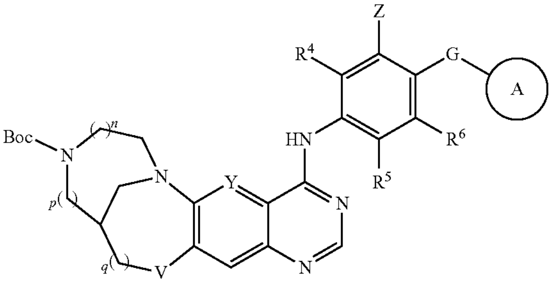

C-c

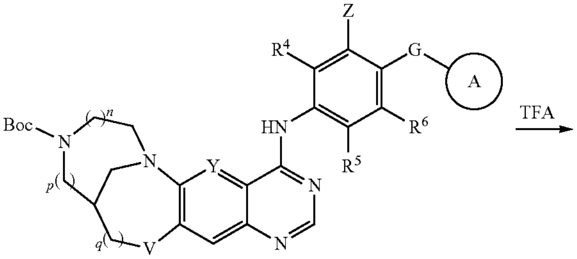

C-c

-continued

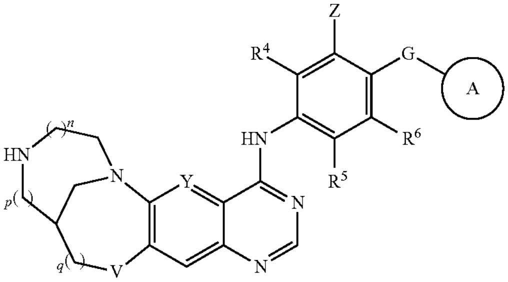

C-d

As shown in Scheme C, compounds of general formula B-c are reacted with compounds of general formula C-a to give compounds of general formula C-b. Compounds of general formula C-b are further cyclized, for example, in the presence of Brettphos Pd, Brettphos, $K_2CO_3$ and dioxane, to provide compounds of general formula C-c. Compounds of general formula C-c are further deprotected, for example, in the presence of trifluoroacetic acid (TFA), to provide compounds of general formula C-d.

Scheme D

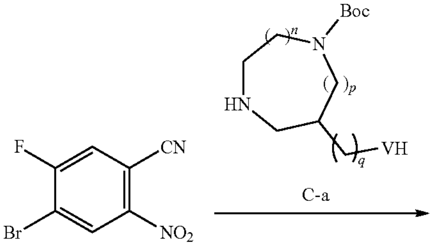

D-a

C-a

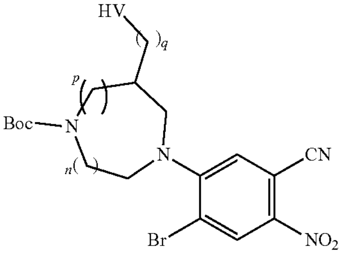

D-b

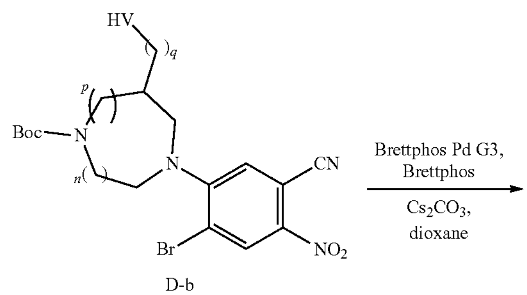

D-b

-continued

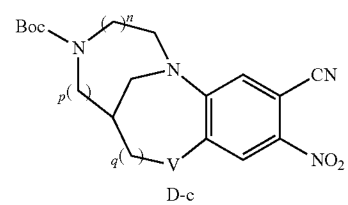

D-c

As shown in Scheme D, compounds of formula D-a are reacted with compounds of formula C-a to give compounds of formula D-b. Compounds of formula D-b are further cyclized, for example, in the presence of Brettphos Pd, Brettphos, $K_2CO_3$ and dioxane, to provide compounds of formula D-c.

Scheme E

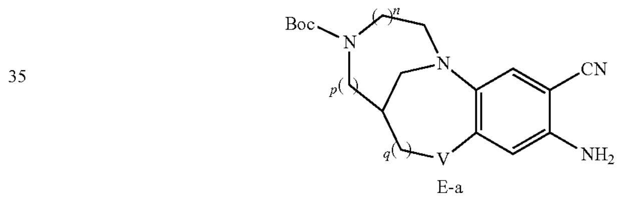

D-c

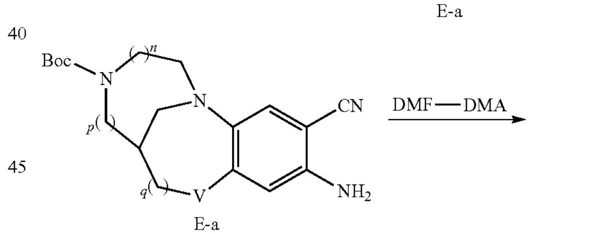

E-a

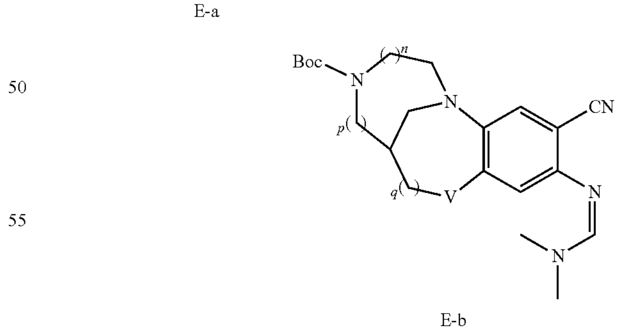

E-a

E-b

As shown in Scheme E, the nitrosyl group on the compounds of general formula D-c is reduced (for example, in the presence of Fe and acetic acid) to give compounds of general formula E-a. Compounds of general formula E-a are reacted with N,N-dimethylformamide-dimethyl acetal (DMF-DMA) to give compounds of general formula E-b.

Scheme F

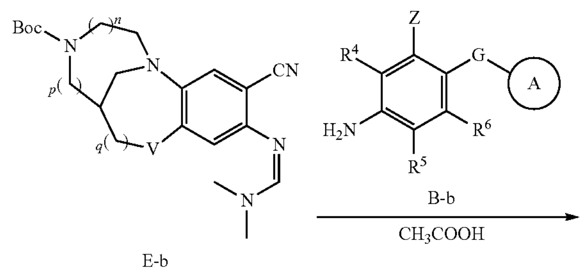

E-b

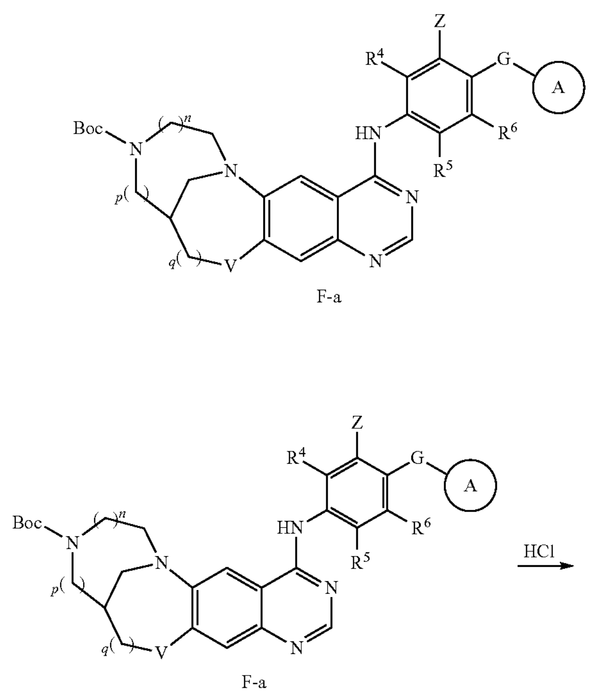

F-a

F-a

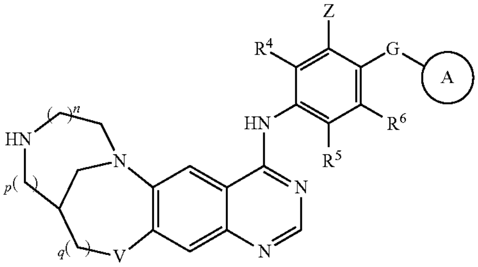

F-b

As shown in scheme F, compounds of general formula E-b are reacted with compounds of general formula B-b, for example, in the presence of acetic acid, to provide compounds of general formula F-a. Compounds of general formula F-a are further deprotected, for example, in the presence of HCl, to give compounds of general formula F-b.

Scheme G

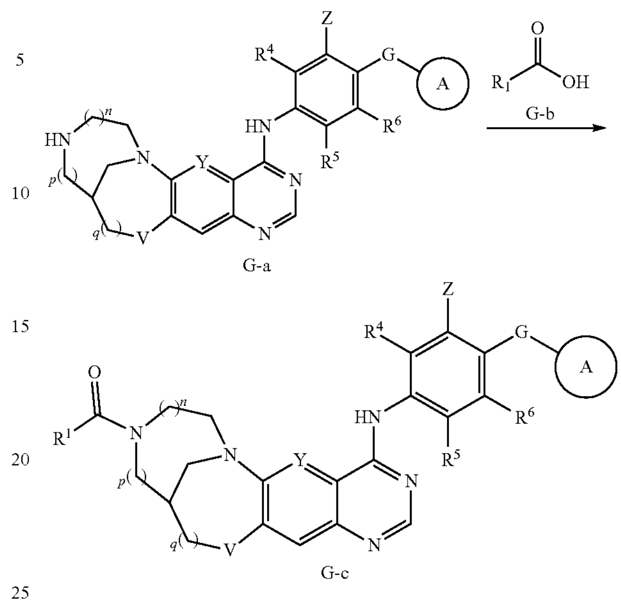

G-a

G-c

As shown in Scheme G, compounds of general formula G-a (corresponding to compounds of general formulae C-d and F-b) are reacted with compounds of general formula G-b to give compounds of general formula G-c. Optional substituents of the $R^1$ group of formula (I') as defined herein may be present in the compound of formula G-c. In some embodiments, the optional substituents of $R^1$ may be present on the intermediates of formula G-b prior to reaction with formula G-a to give the compound of formula G-c, or, may be added to $R^1$ of formula G-c after coupling of formula G-a and formula G-b.

Schemes H and I further detail the synthesis of general compounds of formula B-b.

Scheme H

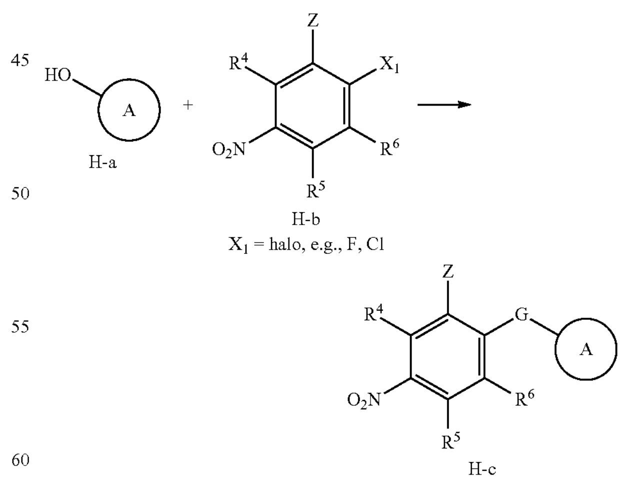

H-a

H-b $X_1$ = halo, e.g., F, Cl

H-c

As shown in Scheme H, nucleophilic substitution by hydroxylated Ring A-containing heterocycles of general formula H-a of nitrosylated benzenes of general formula H-b provides the coupled ether compounds of general formula H-c.

Scheme I

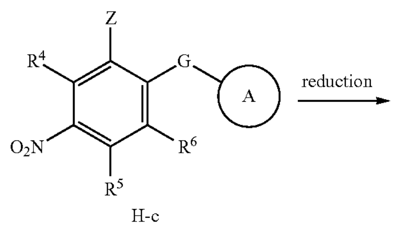

H-c

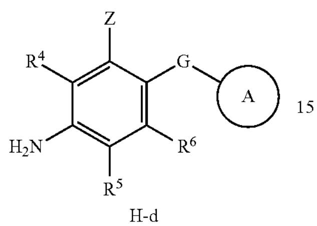

H-d

Compounds of formula H-d, which are compounds formula B-b, wherein G is —O—, may be prepared according to the general synthetic scheme shown in Scheme I. The nitrosyl group on the compounds of general formula H-c is reduced (for example, in the presence of $H_2$ and Pd/C) to give compounds of general formula H-d. The compounds of general formula H-d may be used as compounds of formula B-b and may be reacted with compounds of general formula B-a as shown in Scheme B above.

EXAMPLES

It is understood that the present disclosure has been made only by way of example, and that numerous changes in the combination and arrangement of parts can be resorted to by those skilled in the art without departing from the spirit and scope of present disclosure.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

Abbreviations used in the Examples include the following: ACN: acetonitrile; AcOH: acetic acid; 4AMS: 4-angstrom molecular sieves; BSA: bovine serum albumin; DCM: dichloromethane; DIEA: diisopropylethylamine; DMAC: dimethylacetamide; DMF: dimethylformamide; DMF-DMA: dimethylformamide-dimethyl acetal; DMSO: dimethyl sulfoxide; EDCI: 1-ethyl-3-(3-dimethylaminopropyl) carbodiimide; ESI: electrospray ionization; EtOAc: ethyl acetate; EtOH: ethanol or ethyl alcohol; $^1H$ NMR: proton nuclear magnetic resonance; HATU: 1-[Bis(dimethylamino) methylene]-1H-1,2,3-triazolo[4,5-b]pyridinium 3-oxide hexafluorophosphate (Hexafluorophosphate Azabenzotriazole Tetramethyl Uronium); LCMS: liquid chromatography—mass spectrometry; MeOH: methanol or methyl alcohol; n-BuLi: n-butyllithium; NCS: N-chlorosuccinimide; PBS: phosphate-buffered saline; PBST: PBS with Tween 20; Py: pyridine; TEA: triethylamine; TEMPO: (2,2,6,6-Tetramethylpiperidin-1-yl)oxyl; TFA: trifluoroacetic acid; and THF: tetrahydrofuran.

Example S1: Synthesis of 1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 1)

Step 1. Synthesis of 3-amino-5-bromo-6-chloropicolinonitrile

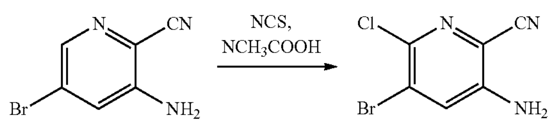 [SMILES: N#Cc1ncc(Br)cc1N ; N#Cc1nc(Cl)c(Br)cc1N]

To a solution of 3-amino-5-bromopyridine-2-carbonitrile (40.0 g, 202.0 mmol) in $CH_3COOH$ (2.0 L) was added NCS (29.7 g, 222.3 mmol) at room temperature. The resulting mixture was stirred at room temperature for 16 h. After the reaction was completed, the resulting mixture was diluted with $H_2O$ and filtered. The filter cake was purified by flash column chromatography with petroleum ether/ethyl acetate (1/1, v/v) to afford 3-amino-5-bromo-6-chloropicolinonitrile (25.0 g, 53%) as a light yellow solid. LCMS (ESI, m/z): $[M+H]^+$=231.9.

Step 2. Synthesis of (Z)—N'-(5-bromo-6-chloro-2-cyanopyridin-3-yl)-N,N-dimethylformimidamide

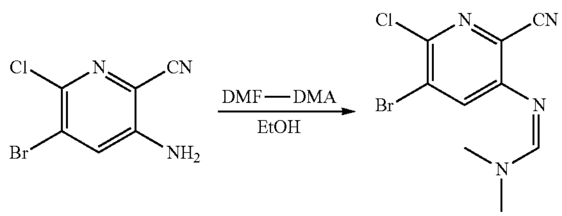

To a solution of 3-amino-5-bromo-6-chloropicolinonitrile (3.0 g, 12.90 mmol) in ethyl alcohol (200.0 mL) was added DMF-DMA (2.6 g, 21.90 mmol) at room temperature. The resulting mixture was stirred at 75° C. for 2 h. After the reaction was completed, the resulting mixture was concentrated under reduced pressure. The residue was diluted with water and filtered. The solid was washed with water and dried to afford (Z)—N'-(5-bromo-6-chloro-2-cyanopyridin-3-yl)-N,N-dimethylmethanimidamide (3.3 g, crude) as a yellow solid. LCMS (ESI, m/z): $[M+H]^+$=287.0.

Step 3: Synthesis of N-(4-([1,2,4]triazolo[1,5-a]pyridin-7-yloxy)-3-methylphenyl)-7-bromo-6-chloropyrido[3,2-d]pyrimidin-4-amine

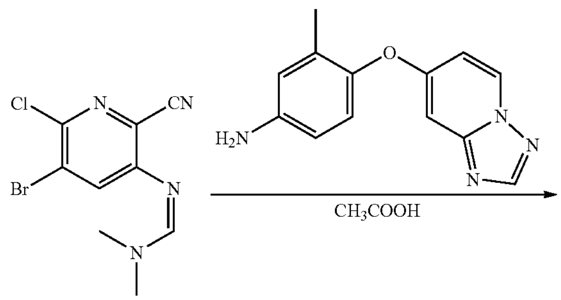

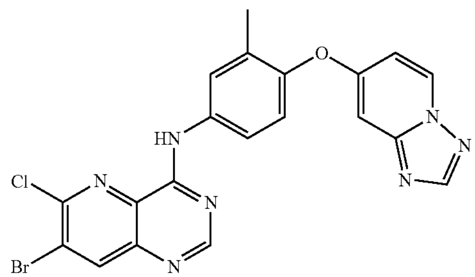

To a solution of (Z)—N'-(5-bromo-6-chloro-2-cyanopyridin-3-yl)-N,N-dimethylmethanimidamide (3.3 g, crude) in acetic acid (100.0 mL) was added 3-methyl-4-{[1,2,4]triazolo[1,5-a]pyridin-7-yloxy}aniline (2.7 g, 11.48 mmol) at room temperature. The resulting mixture was stirred at 85° C. for 2 h. After the reaction was completed, the resulting mixture was concentrated under reduced pressure. The resulting mixture was diluted with water and filtered. The solid was washed with water and dried to afford N-(4-([1,2,4]triazolo[1,5-a]pyridin-7-yloxy)-3-methylphenyl)-7-bromo-6-chloropyrido[3,2-d]pyrimidin-4-amine (5.0 g, crude) as a yellow solid. LCMS (ESI, m/z): $[M+H]^+$=482.0.

Step 4. Synthesis of tert-butyl (S)-4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)piperazine-1-carboxylate

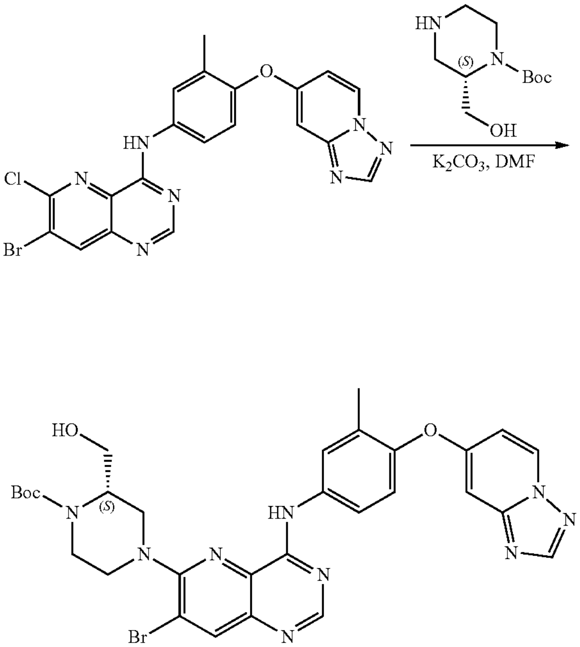

To a solution of N-(4-([1,2,4]triazolo[1,5-a]pyridin-7-yloxy)-3-methylphenyl)-7-bromo-6-chloropyrido[3,2-d]pyrimidin-4-amine (5.0 g, crude) in DMF (150.0 mL) was added (S)-tert-butyl 2-(hydroxymethyl)piperazine-1-carboxylate (3.4 g, 15.60 mmol) and $K_2CO_3$ (5.73 g, 41.40 mmol) at room temperature. The resulting mixture was stirred at 100° C. for 16 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash chromatography with $H_2O$/MeOH (1/7, v/v) to afford tert-butyl (S)-4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)piperazine-1-carboxylate (5.7 g, 83%) as a yellow solid. LCMS (ESI, m/z): $[M+H]^+$=662.2.

Step 5. Synthesis of tert-butyl (10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate

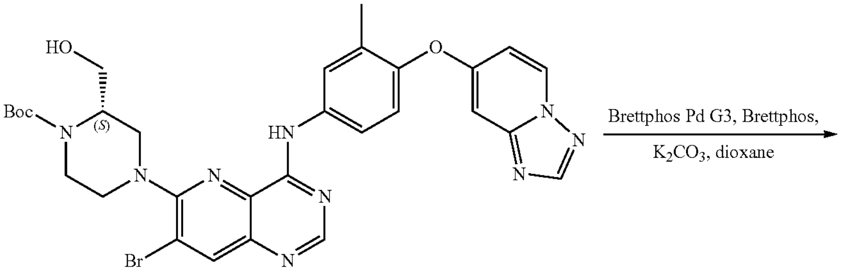

-continued

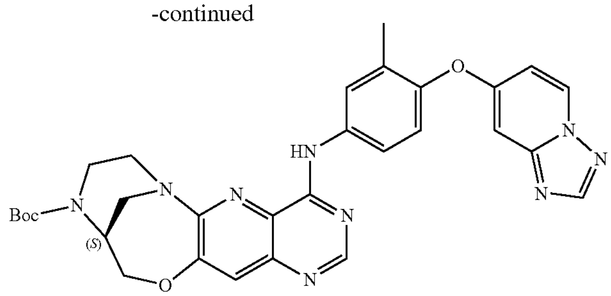

To a solution of tert-butyl (S)-4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)piperazine-1-carboxylate (4.1 g, 6.20 mmol) in dioxane (120.0 mL) was added $K_2CO_3$ (3.4 g, 24.80 mmol), BrettPhos (1.3 g, 2.46 mmol) and BrettPhos Pd G3 (1.1 g, 1.23 mmol) at room temperature under $N_2$. The resulting mixture was stirred at 100° C. for 16 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash chromatography with $H_2O$/MeOH (1/7, v/v) to afford tert-butyl (10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (1.7 g, 47%) as a brown oil. LCMS (ESI, m/z): $[M+H]^+$=582.2.

Step 6. Synthesis of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine

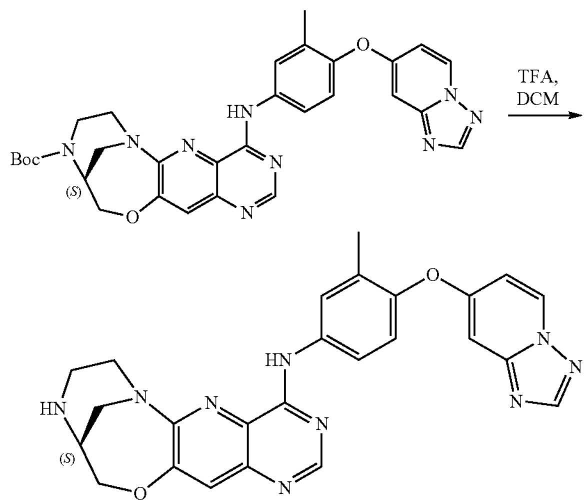

To a solution of tert-butyl (10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (1.7 g, 2.93 mmol) in DCM (20.0 mL) was added TFA (20.0 mL) at room temperature. The resulting mixture was stirred at room temperature for 4 h. After the reaction was completed, the resulting mixture was concentrated under reduced pressure. The residue was diluted with water. The pH value of the mixture was adjusted to 7 with aq.$NaHCO_3$. The mixture was extracted with EtOAc. The combined organic layer was washed with brine, dried over anhydrous sodium sulfate and filtered. The filtrate was concentrated under reduced pressure to afford (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (800.0 mg, crude) as a brown oil. LCMS (ESI, m/z): $[M+H]^+$=482.2.

Step 7. Synthesis of 1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 1)

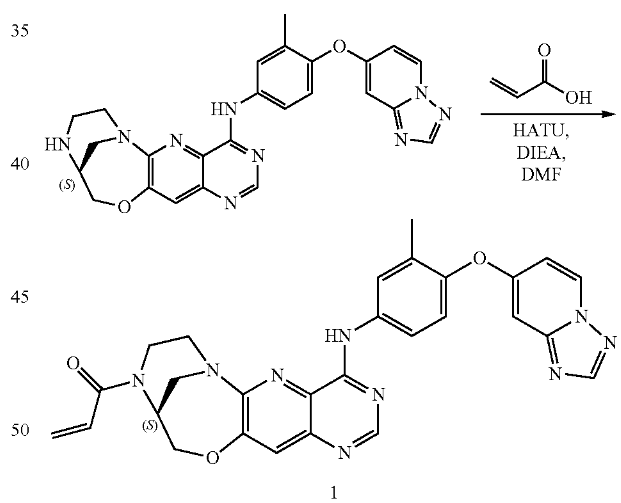

1

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (300.0 mg, crude) in DMF (10.0 mL) was added acrylic acid (89.6 mg, 1.24 mmol), DIEA (322.1 mg, 2.48 mmol) and HATU (564.4 mg, 1.45 mmol) at room temperature. The resulting mixture was stirred at room temperature for 2 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash chromatography with $H_2O$/

ACN (1/8, v/v) to afford 1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 1) (79.9 mg, 24%) as a white solid. LCMS (ESI, m/z): $[M+H]^+$ =536.3. $^1H$ NMR (400 MHz, DMSO-$d_6$): δ 9.57-9.52 (m, 1H), 8.94 (d, J=7.6 Hz, 1H), 8.48 (s, 1H), 8.40 (s, 1H), 8.02-8.00 (m, 2H), 7.52 (s, 1H), 7.22 (d, J=9.6 Hz, 1H), 7.04-7.02 (m, 1H), 6.87-6.79 (m, 2H), 6.18-6.13 (m, 1H), 5.75-5.72 (m, 1H), 5.13-4.64 (m, 3H), 4.29-4.08 (m, 3H), 3.87-3.42 (m, 1H), 3.39-3.32 (m, 1H), 3.30-3.24 (m, 1H), 2.18 (s, 3H).

Example S2: Synthesis of 1-((10R)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 2)

Step 1. Synthesis of (R)-tert-butyl 4-(4-(4-([1,2,4]triazolo[1,5-a]pyridin-7-yloxy)-3-methylphenylamino)-7-bromopyrido[3,2-d]pyrimidin-6-yl)-2-(hydroxymethyl)piperazine-1-carboxylate

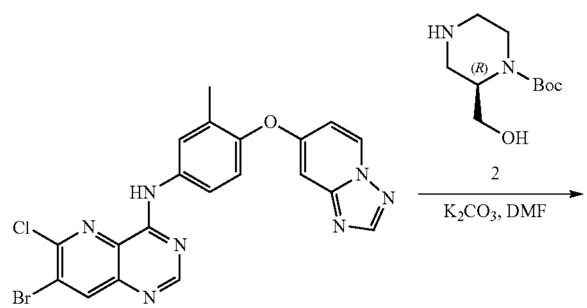

-continued

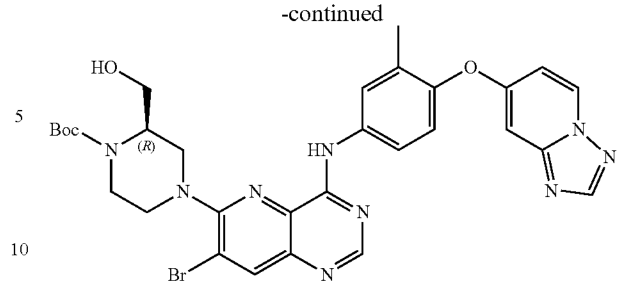

To a solution of N-(4-([1,2,4]triazolo[1,5-a]pyridin-7-yloxy)-3-methylphenyl)-7-bromo-6-chloropyrido[3,2-d]pyrimidin-4-amine (268.0 mg, 0.55 mmol) in DMF (10.0 mL) was added (R)-tert-butyl 2-(hydroxymethyl)piperazine-1-carboxylate (180.1 mg, 0.83 mmol) and $K_2CO_3$ (306.9 mg, 2.22 mmol) at room temperature. The resulting mixture was stirred at 100° C. for 16 h. After the reaction was completed, the resulting mixture was diluted with water and extracted with ethyl acetate. The combined organic layers were washed with brine, dried over anhydrous sodium sulfate and filtered. The filtrate was concentrated under reduced pressure to afford (R)-tert-butyl 4-(4-(4-([1,2,4]triazolo[1,5-a]pyridin-7-yloxy)-3-methylphenylamino)-7-bromopyrido[3,2-d]pyrimidin-6-yl)-2-(hydroxymethyl)piperazine-1-carboxylate (336.0 mg, crude) as a yellow solid. LCMS (ESI, m/z): $[M+H]^+$=662.2.

Step 2. Synthesis of tert-butyl (10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate

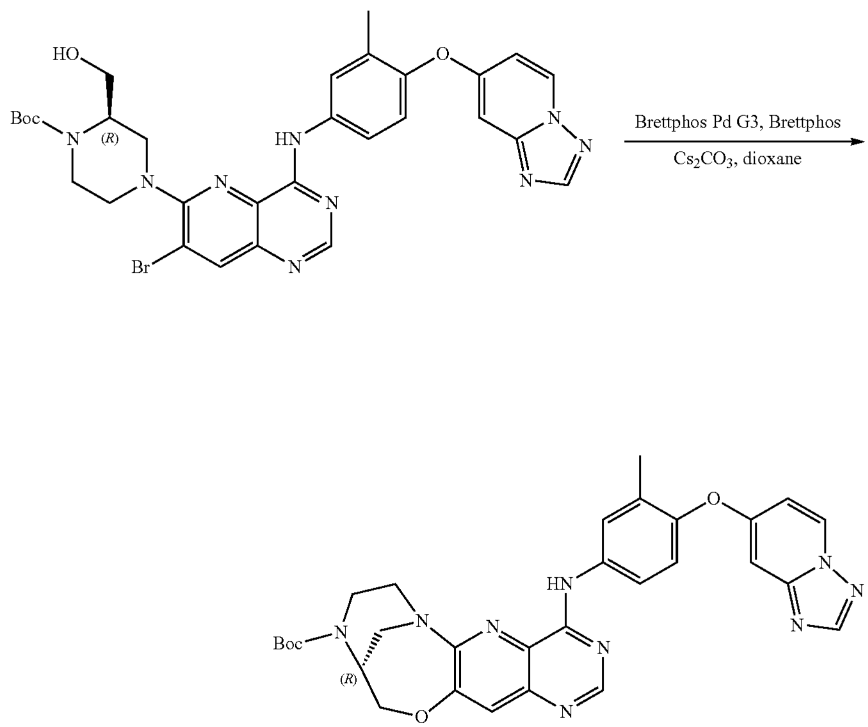

To a solution of (R)-tert-butyl 4-(4-(4-([1,2,4]triazolo[1,5-a]pyridin-7-yloxy)-3-methylphenylamino)-7-bromopyrido[3,2-d]pyrimidin-6-yl)-2-(hydroxymethyl)piperazine-1-carboxylate (316.0 mg, crude) in dioxane (5.0 mL) was added BrettPhos (51.2 mg, 0.10 mmol), $Cs_2CO_3$ (466.2 mg, 1.43 mmol) and BrettPhos Pd G3 (43.2 mg, 0.05 mmol) at room temperature under $N_2$. The resulting mixture was stirred at 100° C. for 4 h. After the reaction was completed, the resulting mixture was diluted with water and extracted with ethyl acetate. The combined organic layers were washed with brine, dried over anhydrous $Na_2SO_4$ and filtered. The filtrate was concentrated under reduced pressure. The residue was purified by reverse phase flash column chromatography with water/MeOH (1/7, v/v) to afford tert-butyl (10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (90.0 mg, 32%) as a yellow solid. LCMS (ESI, m/z): $[M+H]^+$=582.2.

Step 3: Synthesis of (10R)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine

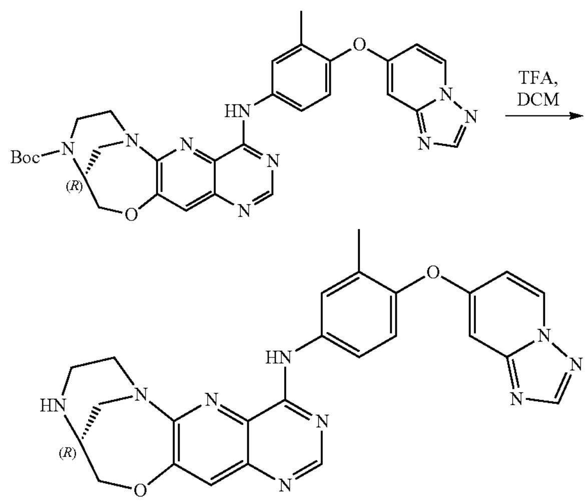

To a solution of tert-butyl (10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (80.0 mg, 0.03 mmol) in DCM (2.0 mL) was added TFA (2.0 mL) at room temperature. The resulting mixture was stirred at room temperature for 4 h. After the reaction was completed, the resulting mixture was concentrated under reduced pressure. The residue was diluted with water. The pH value of the mixture was adjusted to 8 with aqueous $NaHCO_3$. The mixture was extracted with ethyl acetate. The combined organic layer was washed with brine, dried over anhydrous sodium sulfate and filtered. The filtrate was concentrated under reduced pressure to afford (10R)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (50.0 mg, crude) as a yellow solid. LCMS (ESI, m/z): $[M+H]^+$=482.2.

Step 4. Synthesis of 1-((10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 2)

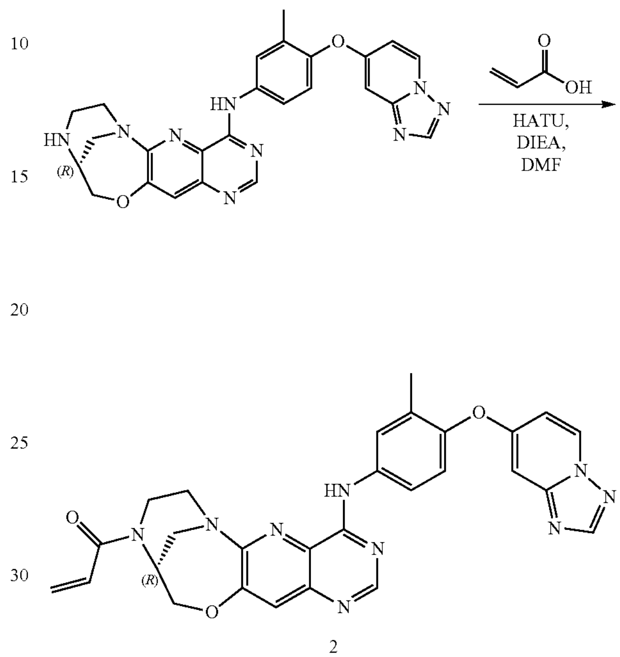

2

To a solution of (10R)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (50.0 mg, crude) in DMF (2.0 mL) was added DIEA (80.5 mg, 0.62 mmol), acrylic acid (9.0 mg, 0.13 mmol) and HATU (55.3 mg, 0.15 mmol) at room temperature. The resulting mixture was stirred at room temperature for 2 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by reverse phase flash chromatography with $MeOH/H_2O$ (7/1, v/v) and then purified by Prep-HPLC with the following conditions (Column: XBridge Prep Phenyl OBD Column, 19×150 mm, 5 μm; Mobile Phase A: Water (10 mmol/L $NH_4HCO_3$), Mobile Phase B: ACN; Flow rate: 60 mL/min; Gradient: 31% B to 31% B in 8 min; Wave Length: 254 nm) to afford 1-((10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 2) (6.6 mg, 12%) as a white solid. LCMS (ESI, m/z): $[M+H]^+$=536.3.

$^1H$ NMR (400 MHz, DMSO-$d_6$): δ 9.56-9.53 (m, 1H), 8.94 (d, J=7.2 Hz, 1H), 8.48 (s, 1H), 8.38 (s, 1H), 8.02-8.00 (m, 2H), 7.52 (s, 1H), 7.22 (d, J=9.2 Hz 1H), 7.04-7.02 (m, 1H), 6.87-6.79 (m, 2H), 6.18-6.13 (m, 1H), 5.75-5.72 (m, 1H), 5.15-4.71 (m, 3H), 4.29-4.23 (m, 1H), 4.20-4.11 (m, 1H), 3.98-3.60 (m, 1H), 3.42-3.32 (m, 1H), 3.29-3.25 (m, 1H), 2.22 (s, 3H).

Example S3: Synthesis of 1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)prop-2-en-1-one (Compound 3)

Step 1. Synthesis of tert-butyl (10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazoline-9-carboxylate

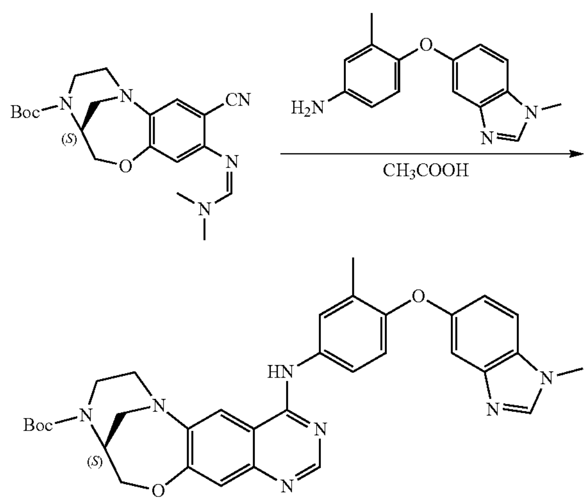

A mixture of tert-butyl (3S)-9-cyano-10-(((Z)-(dimethylamino)methylene)amino)-2,3,5,6-tetrahydro-4H-3,7-methanobenzo[b][1,4,7]oxadiazonine-4-carboxylate (1.0 g, 2.59 mmol) and 3-methyl-4-[(1-methyl-1,3-benzodiazol-5-yl)oxy]aniline (0.6 g, 2.59 mmol) in acetic acid (20.0 mL) was stirred at 85° C. for 2 h. After the reaction was completed, the resulting mixture was concentrated under reduced pressure. The residue was purified by flash column chromatography with $CH_2Cl_2$/MeOH (9/1, v/v) to afford tert-butyl (10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazoline-9-carboxylate (1.3 g, 84%) as a yellow solid. LCMS (ESI, m/z): $[M+H]^+$=594.1.

Step 2. Synthesis of (10S)—N-(3-methyl-4-((1-methyl-1H-benzo[d]imidazol-5-yl)oxy)phenyl)-8,9,10,11-tetrahydro-7H-6,10-methano[1,4,7]oxadiazonino[3,2-g]quinazolin-4-amine

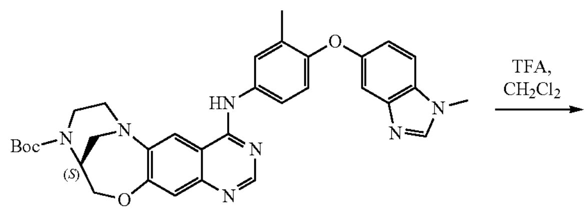

-continued

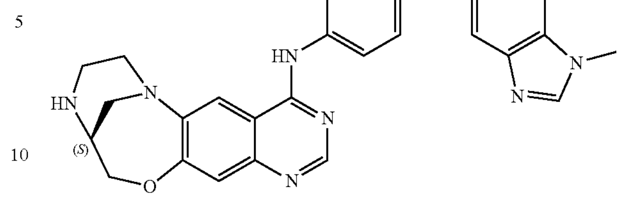

A mixture of tert-butyl tert-butyl (10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazoline-9-carboxylate (1.2 g, 2.02 mmol) in DCM (15.0 mL) and TFA (15.0 mL) was stirred at room temperature for 1 h. After the reaction was completed, the resulting mixture was neutralized to pH=7 with saturated $NaHCO_3$(aq). The resulting mixture was extracted with DCM. The combined organic layers were washed with brine, dried over anhydrous sodium sulfate and filtered. The filtrate was concentrated under reduced pressure. The residue was purified by reverse phase flash column chromatography with $CH_3CN/H_2O$ (60/40, v/v) to afford (10S)—N-(3-methyl-4-((1-methyl-1H-benzo[d]imidazol-5-yl)oxy)phenyl)-8,9,10,11-tetrahydro-7H-6,10-methano[1,4,7]oxadiazonino[3,2-g]quinazolin-4-amine (600.0 mg, 60%) as a yellow solid. LCMS (ESI, m/z): $[M+H]^+$=494.1.

Step 3: Synthesis of 1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)prop-2-en-1-one (Compound 3)

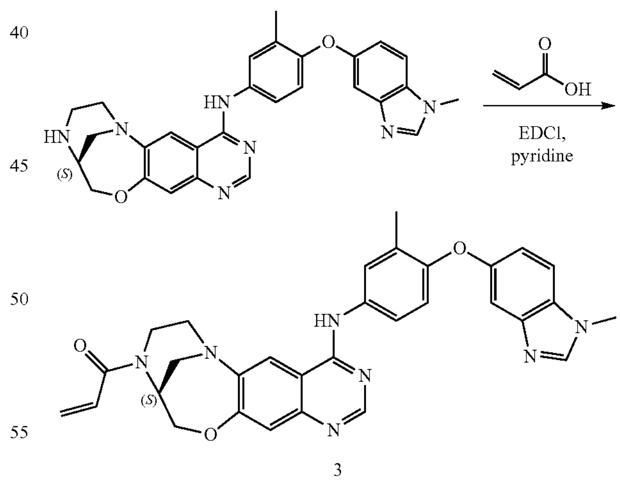

3

To a stirred mixture of (10S)—N-(3-methyl-4-((1-methyl-1H-benzo[d]imidazol-5-yl)oxy)phenyl)-8,9,10,11-tetrahydro-7H-6,10-methano[1,4,7]oxadiazonino[3,2-g]quinazolin-4-amine (100.0 mg, 0.20 mmol) and acrylic acid (14.6 mg, 0.20 mmol) in pyridine (3.0 mL) was added EDCI (77.6 mg, 0.40 mmol) at room temperature. The resulting mixture was stirred at room temperature for 1 h. After the reaction was completed, the mixture was evaporated in vacuo. The residue was purified by reverse phase flash column chromatography with $CH_3CN/H_2O$ (60/40, v/v) and then purified by Prep-HPLC with the following conditions Column: (XBridge Shield RP18 OBD Column, 19×250 mm, 10 μm; Mobile Phase A: Water (10 mmol/L $NH_4HCO_3$), Mobile Phase B: MeOH—HPLC; Flow rate: 25 mL/min; Gradient: 61% B to 71% B in 8 min; Wave Length: 254 nm) to afford 1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)prop-2-en-1-one (Compound 3) (17.6 mg, 15%) as a yellow solid. LCMS (ESI, m/z): $[M+H]^+$=548.2. $^1H$ NMR (400 MHz, DMSO-$d_6$): δ 9.50 (d, J=4.8 Hz, 1H), 8.41 (d, J=4.4 Hz, 1H), 8.28-8.24 (m, 1H), 8.17 (s, 1H), 7.74 (s, 1H), 7.64 (d, J=8.8 Hz, 1H), 7.56 (d, J=8.8 Hz, 1H), 7.21 (d, J=6.0 Hz, 1H), 7.09 (s, 1H), 7.01-6.98 (m, 1H), 6.88-6.77 (m, 2H), 6.18-6.13 (m, 1H), 5.74-5.71 (m, 1H), 4.93-4.61 (m, 1H), 4.58-4.41 (m, 1H), 4.19-4.16 (m, 1.5H), 3.93-3.80 (m, 4.5H), 3.69-3.60 (m, 1H), 3.49-3.40 (m, 1H), 3.29-3.25 (m, 2H), 2.24 (s, 3H).

Example S4: Synthesis of 1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)prop-2-en-1-one (Compound 4)

Step 1. Synthesis of tert-butyl (2S)-4-(2-bromo-5-cyano-4-nitrophenyl)-2-(hydroxymethyl)piperazine-1-carboxylate

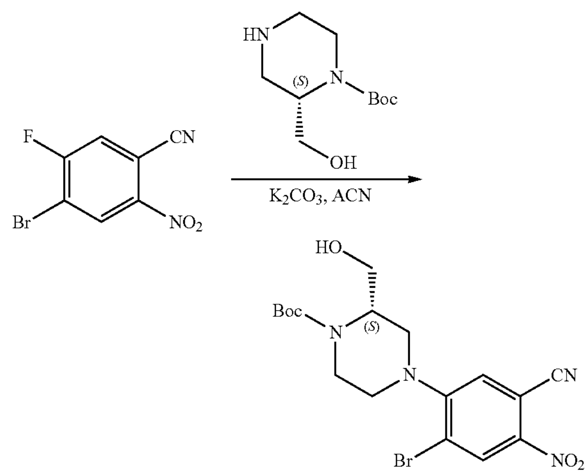

To a solution of 4-bromo-5-fluoro-2-nitrobenzonitrile (3.0 g, 12.24 mmol) in ACN (50.0 mL) was added tert-butyl (2S)-2-(hydroxymethyl)piperazine-1-carboxylate (2.9 g, 13.46 mmol) and $K_2CO_3$ (5.1 g, 36.72 mmol) at room temperature. The resulting mixture was stirred at 85° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with ethyl acetate/petroleum ether (90/10, v/v) to afford tert-butyl (2S)-4-(2-bromo-5-cyano-4-nitrophenyl)-2-(hydroxymethyl)piperazine-1-carboxylate (3.8 g, 99%) as a yellow solid. LCMS (ESI, m/z): $[M+H]^+$=441.1.

Step 2. Synthesis of tert-butyl (3S)-9-cyano-10-nitro-2,3,5,6-tetrahydro-4H-3,7-methanobenzo[b][1,4,7]oxadiazonine-4-carboxylate

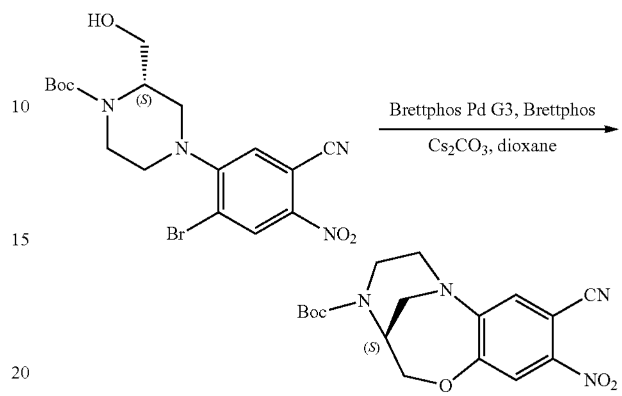

To a solution of tert-butyl (2S)-4-(2-bromo-5-cyano-4-nitrophenyl)-2-(hydroxymethyl)piperazine-1-carboxylate (1.0 g, 2.27 mmol) in dioxane (20.0 mL) was added $Cs_2CO_3$ (2.2 g, 6.80 mmol), BrettPhos (486.6 mg, 0.91 mmol) and Brettphos Pd G3 (410.9 mg, 0.45 mmol) at room temperature under $N_2$. The resulting mixture was stirred at 100° C. for 2 h. After the reaction was completed, the resulting mixture was filtered. The filtrate was concentrated under vacuum. The residue was purified by flash column chromatography with ethyl acetate/petroleum ether (50/50, v/v) to afford tert-butyl (3S)-9-cyano-10-nitro-2,3,5,6-tetrahydro-4H-3,7-methanobenzo[b][1,4,7]oxadiazonine-4-carboxylate (470.0 mg, 54%) as a yellow solid. LCMS (ESI, m/z): $[M+H]^+$=361.1.

Step 3: Synthesis of tert-butyl (3S)-10-amino-9-cyano-2,3,5,6-tetrahydro-4H-3,7-methanobenzo[b][1,4,7]oxadiazonine-4-carboxylate

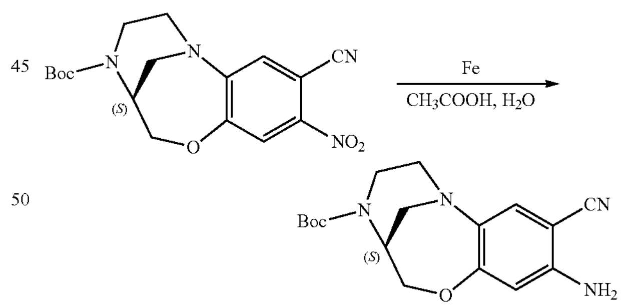

To a solution of tert-butyl (3S)-9-cyano-10-nitro-2,3,5,6-tetrahydro-4H-3,7-methanobenzo[b][1,4,7]oxadiazonine-4-carboxylate (2.0 g, 5.5 mmol) in $CH_3COOH$ (24.0 mL) was added Fe (1.6 g, 27.07 mmol) at room temperature. The resulting mixture was stirred at room temperature for 16 h. After the reaction was completed, the resulting mixture was filtered. The filtrate was concentrated under vacuum. The residue was purified by flash column chromatography with $CH_2Cl_2$/MeOH (90/10, v/v) to afford tert-butyl (3S)-10-amino-9-cyano-2,3,5,6-tetrahydro-4H-3,7-methanobenzo[b][1,4,7]oxadiazonine-4-carboxylate (1.0 g, 44%) as a yellow solid. LCMS (ESI, m/z): $[M+H]^+$=331.2.

Step 4. Synthesis of tert-butyl (3S)-9-cyano-10-(((Z)-(dimethylamino)methylene)amino)-2,3,5,6-tetrahydro-4H-3,7-methanobenzo[b][1,4,7]oxadiazonine-4-carboxylate

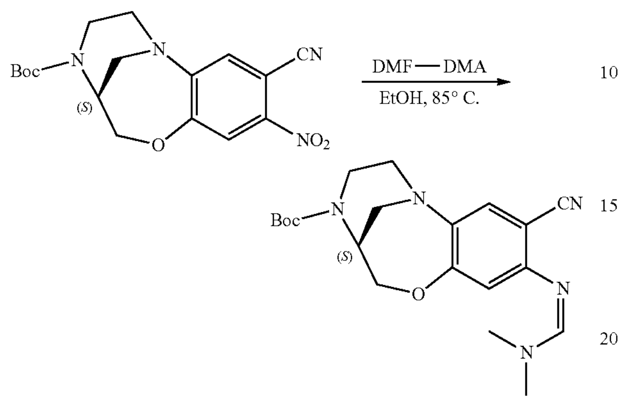

To a solution of tert-butyl (3S)-10-amino-9-cyano-2,3,5,6-tetrahydro-4H-3,7-methanobenzo[b][1,4,7]oxadiazonine-4-carboxylate (200.0 mg, 0.61 mmol) in EtOH (8.0 mL) was added DMF-DMA (66.4 mg, 0.91 mmol) at room temperature. The resulting mixture was stirred at 85° C. for 16 h. After the reaction was completed, the resulting mixture was concentrated under vacuum to afford tert-butyl (3S)-9-cyano-10-(((Z)-(dimethylamino)methylene)amino)-2,3,5,6-tetrahydro-4H-3,7-methanobenzo[b][1,4,7]oxadiazonine-4-carboxylate (200.0 mg, crude) as a yellow solid. LCMS (ESI, m/z): $[M+H]^+$=386.2.

Step 5. Synthesis of tert-butyl (10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazoline-9-carboxylate

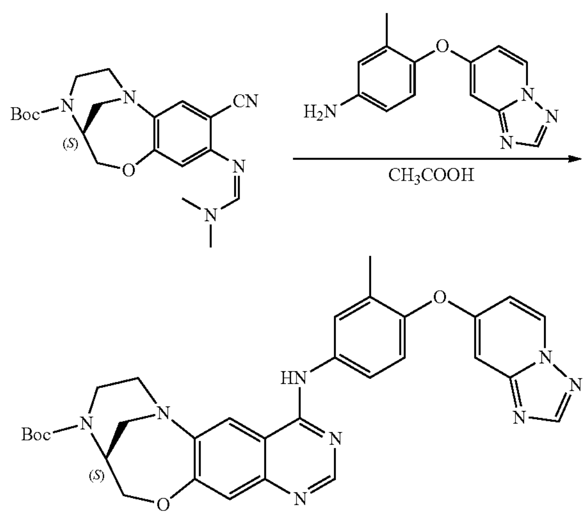

To a solution of tert-butyl (3S)-9-cyano-10-(((Z)-(dimethylamino)methylene)amino)-2,3,5,6-tetrahydro-4H-3,7-methanobenzo[b][1,4,7]oxadiazonine-4-carboxylate (500.0 mg, 1.30 mmol) in AcOH (8.0 mL) was added 3-methyl-4-{[1,2,4]triazolo[1,5-a]pyridin-7-yloxy}aniline (343.0 mg, 1.40 mmol) at room temperature. The resulting mixture was stirred at 85° C. for 16 h. After the reaction was completed, the resulting mixture was concentrated under vacuum. The residue was purified by flash column chromatography with ethyl acetate/petroleum ether (80/20, v/v) to afford tert-butyl (10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazoline-9-carboxylate (300.0 mg, 36%) as a yellow solid. LCMS (ESI, m/z): $[M+H]^+$=581.3.

Step 6. Synthesis of (10S)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine hydrochloride

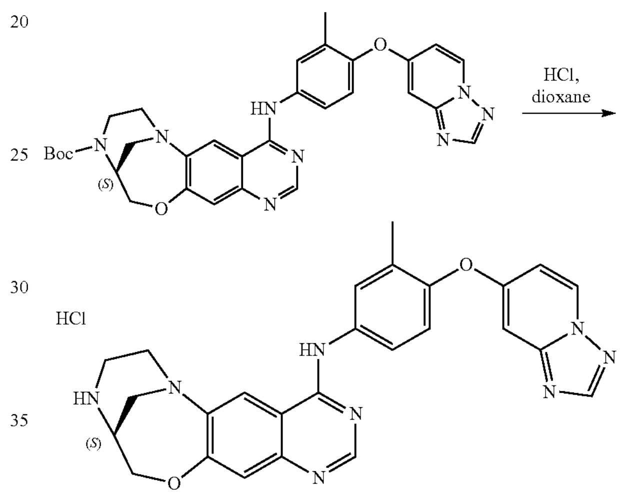

A solution of tert-butyl (10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazoline-9-carboxylate (100.0 mg, 0.22 mmol) in HCl/1,4-dioxane (4.0 mL, 4.0 mol/L) was stirred at room temperature for 1 h. After the reaction was completed, the resulting mixture was concentrated under vacuum to afford (10S)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine hydrochloride (80.0 mg, crude) as a yellow solid. LCMS (ESI, m/z): $[M+H]^+$=481.2.

Step 7. Synthesis of 1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)prop-2-en-1-one (Compound 4)

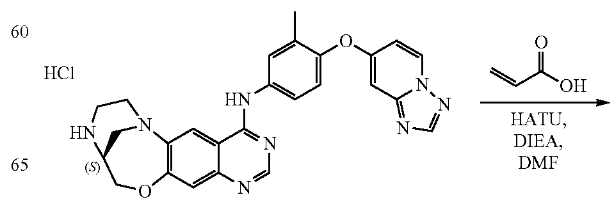

-continued

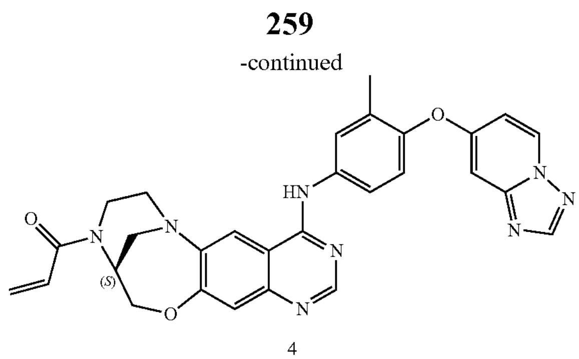

4

-continued

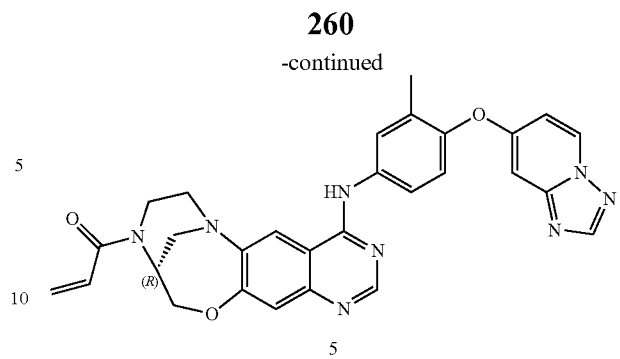

5

To a solution of (10S)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine hydrochloride (200.0 mg, crude) in DMF (10.0 mL) was added acrylic acid (29.0 mg, 0.54 mmol), DIEA (537.9 mg, 4.2 mmol) and HATU (253.1 mg, 0.67 mmol) at 0° C. under $N_2$. The resulting mixture was stirred at 0° C. for 1 h under $N_2$. After the reaction was completed, the resulting mixture was purified by reverse phase flash chromatography with $CH_3CN/H_2O$ (50/50, v/v) and then purified by Prep-HPLC with the following conditions: (Column: XBridge Prep Phenyl OBD Column, 19×250 mm, 5 μm; Mobile Phase A: Water (10 mmol/L $NH_4HCO_3$), Mobile Phase B: MeOH—HPLC; Flow rate: 25 mL/min; Gradient: 60% B to 75% B in 10 min; Wave Length: 254 nm) to afford 1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)prop-2-en-1-one (Compound 4) (20.2 mg, 9%) as a white solid. LCMS (ESI, m/z): $[M+H]^+$=535.3. $^1H$ NMR (400 MHz, DMSO-$d_6$): δ 9.59 (d, J=5.2 Hz, 1H), 8.94 (d, J=7.6 Hz, 1H), 8.47 (d, J=4.8 Hz, 1H), 8.39 (s, 1H), 8.31-8.27 (m, 1H), 7.87-7.85 (m, 2H), 7.24-7.20 (m, 2H), 7.05-7.02 (m, 1H), 6.85-6.80 (m, 2H), 6.19-6.14 (m, 1H), 6.75-5.72 (m, 1H), 4.99-4.63 (m, 1H), 4.62-4.47 (m, 1H), 4.21-4.18 (m, 1H), 3.91-3.81 (m, 2H), 3.68-3.57 (m, 1H), 3.52-3.44 (m, 1H), 3.32-3.25 (m, 2H), 2.20 (s, 3H).

Example S5: Synthesis of 1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)prop-2-en-1-one (Compound 5)

Step 1. Synthesis of 1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)prop-2-en-1-one (Compound 5)

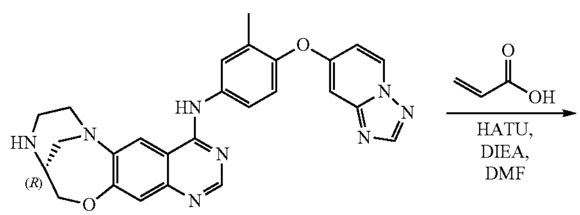

To a solution of (10R)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine (86.0 mg, 0.18 mmol) in DMF (3.0 mL) was added HATU (81.7 mg, 0.18 mmol), acrylic acid (12.9 mg, 0.18 mmol) and DIEA (115.65 mg, 1.80 mmol) at 0° C. under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with ACN/$H_2O$ (70/30, v/v) and then purified by Prep-HPLC with the following conditions: (Column: XBridge Prep Phenyl OBD Column, 19×250 mm, 5 μm; Mobile Phase A: Water (10 mmol/L $NH_4HCO_3$), Mobile Phase B: ACN; Flow rate: 25 mL/min; Gradient: 35% B to 45% B in 10 min; Wave Length: 254 nm) to afford 1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)prop-2-en-1-one (Compound 5) (6.0 mg, 6%) as a white solid. LCMS (ESI, m/z): $[M+H]^+$=535.3. $^1H$ NMR (400 MHz, DMSO-$d_6$): δ 9.59 (s, 1H), 8.95 (s, 1H), 8.47 (d, J=4.8 Hz, 1H), 8.38 (s, 1H), 8.31-8.27 (m, 1H), 7.87-7.85 (m, 2H), 7.25-7.20 (m, 2H), 7.05-7.02 (m, 1H), 6.88-6.78 (m, 2H), 6.19-6.14 (m, 1H), 5.75-5.72 (m, 1H), 4.95-4.68 (m, 1H), 4.62-4.47 (m, 1H), 4.21-4.18 (m, 1H), 3.93-3.81 (m, 2H), 3.71-3.62 (m, 2H), 3.55-3.50 (m, 1H), 3.27-3.25 (m, 1H), 2.20 (s, 3H).

Example S6: Synthesis of (E)-4-(dimethylamino)-1-((10S)-4-((3-methyl-4-((1-methyl-1H-benzo[d]imidazol-5-yl)oxy)phenyl)amino)-7,8,10,11-tetrahydro-9H-6,10-methanopyrimido[4,5':5,6]pyrido[3,2-b][1,4,7]oxadiazonin-9-yl)but-2-en-1-one (Compound 6)

Step 1. Synthesis of (E)-4-(dimethylamino)-1-((10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 6)

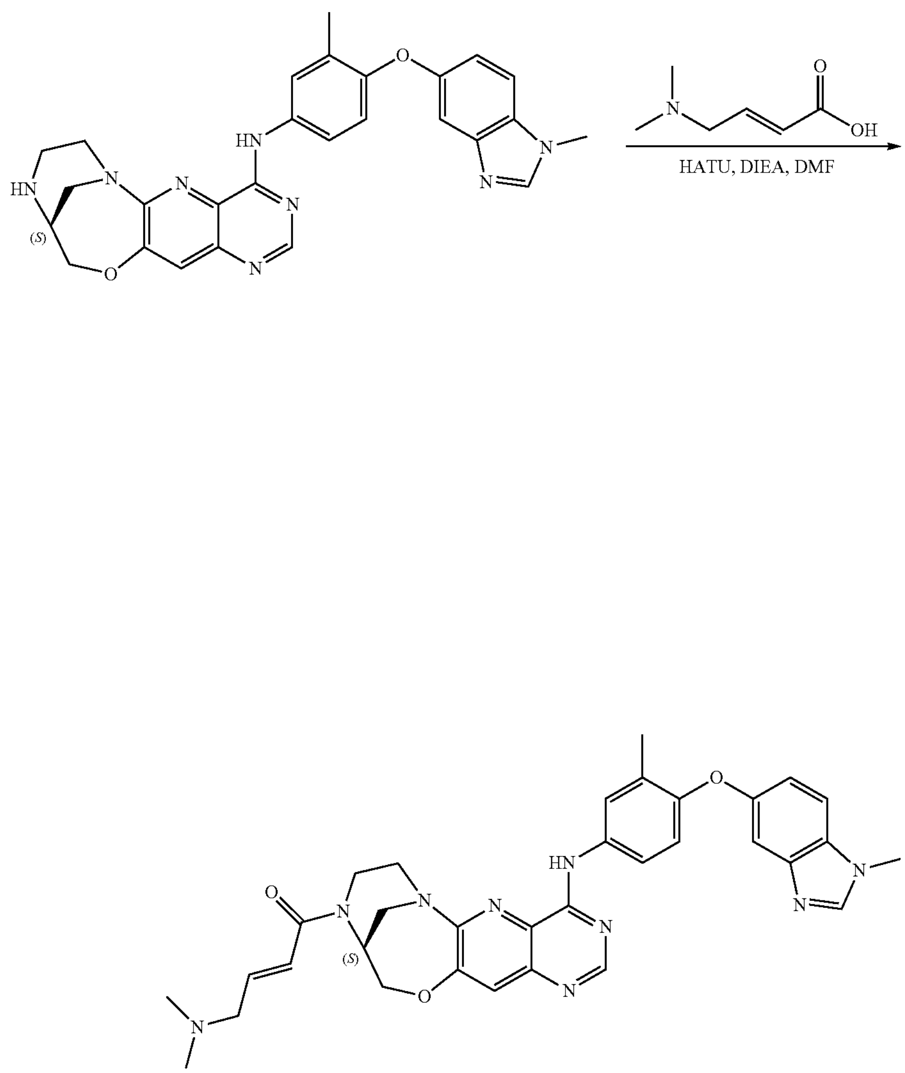

6

To a stirred mixture of (10S)—N-(3-methyl-4-((1-methyl-1H-benzo[d]imidazol-5-yl)oxy)phenyl)-8,9,10,11-tetrahydro-7H-6,10-methanopyrimido[4',5':5,6]pyrido[3,2-b][1,4,7]oxadiazonin-4-amine (170.0 mg, 0.34 mmol) and (2E)-4-(dimethylamino)but-2-enoic acid (88.8 mg, 0.69 mmol) in DMF (6.0 mL) were added DIEA (133.3 mg, 1.03 mmol) and HATU (261.4 mg, 0.69 mmol) at room temperature. The resulting mixture was stirred at room temperature for 1 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with acetonitrile/water (27/73, v/v) and then purified by Prep-HPLC with the following conditions: (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 40% B to 40% B in 8 min; Wave Length: 254 nm) to afford (E)-4-(dimethylamino)-1-((10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 6) (5.1 mg, 2%) as a yellow solid. LCMS (ESI, m/z): $[M+H]^+$=606.4. $^1H$ NMR (400 MHz, DMSO-$d_6$): δ 9.45-9.43 (m, 1H), 8.43 (s, 1H), 8.17 (s, 1H), 7.87 (d, J=2.4 Hz, 1H), 7.81-7.77 (m, 1H), 7.58-7.56 (m, 1H), 7.49 (s, 1H), 7.08 (d, J=2.4 Hz, 1H), 7.01-6.98 (m, 1H), 6.89 (d, J=8.8 Hz, 1H), 6.65-6.61 (m, 2H), 5.12-4.56 (m, 3H), 4.27-4.18 (m, 1H), 4.12-4.01 (m, 2H), 3.84 (s, 3H), 3.69-3.57 (m, 1H), 3.46-3.42 (m, 1H), 3.28-3.22 (m, 1H), 3.06 (s, 2H), 2.25 (s, 3H), 2.17 (d, J=7.2 Hz, 6H).

Example S7: Synthesis of (E)-4-(dimethylamino)-1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)but-2-en-1-one (Compound 7)

Step 1. Synthesis of (E)-4-(dimethylamino)-1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)but-2-en-1-one (Compound 7)

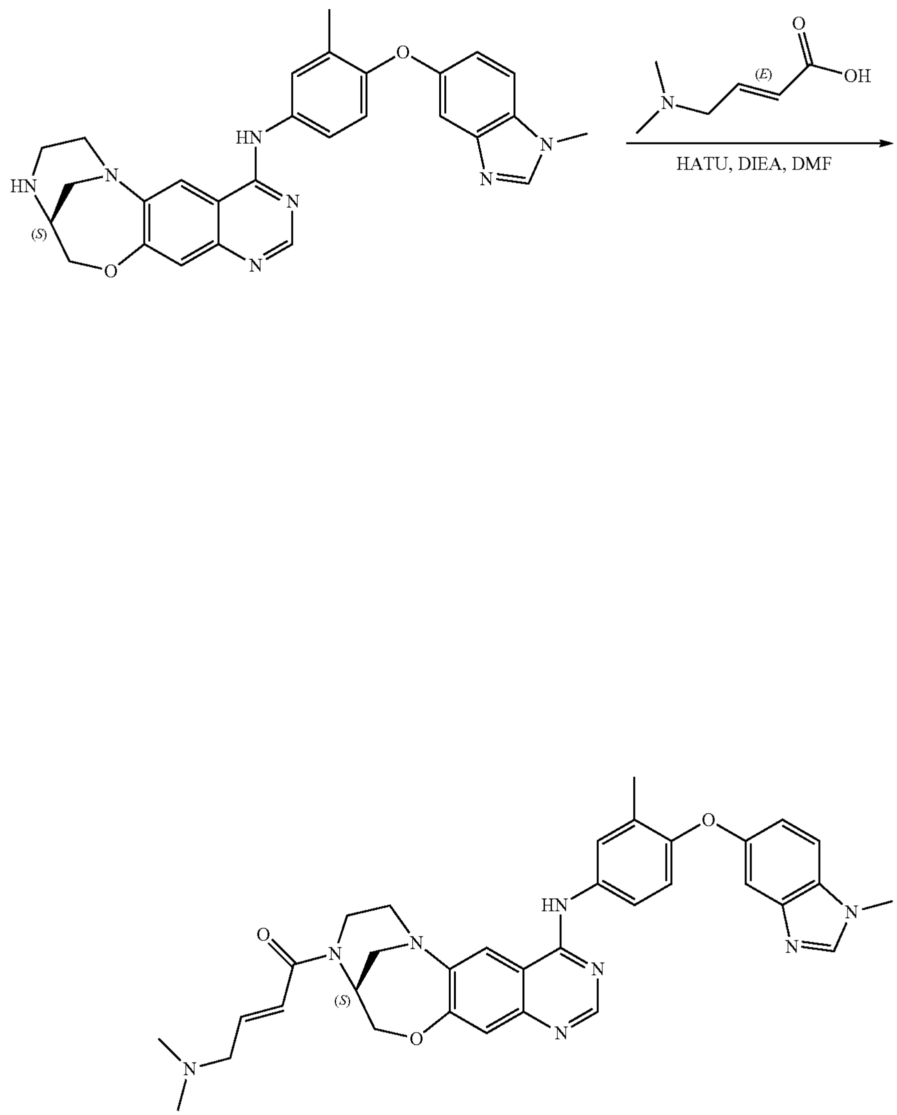

7

To a stirred mixture of (10S)—N-(3-methyl-4-((1-methyl-1H-benzo[d]imidazol-5-yl)oxy)phenyl)-8,9,10,11-tetrahydro-7H-6,10-methano[1,4,7]oxadiazonino[3,2-g]quinazolin-4-amine (200.0 mg, 0.40 mmol) and (2E)-4-(dimethylamino)but-2-enoic acid (52.3 mg, 0.40 mmol) in DMF (3.0 mL) were added DIEA (209.5 mg, 1.62 mmol) and HATU (308.2 mg, 0.81 mmol) at room temperature. The resulting mixture was stirred at room temperature for 1 h. After the reaction was completed, the mixture was purified by reverse phase flash column chromatography with $CH_3CN/H_2O$ (70/30, v/v) and then purified by Prep-HPLC with the following conditions Column: (XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 27% B to 37% B in 8 min; Wave Length: 254 nm) to afford (E)-4-(dimethylamino)-1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)but-2-en-1-one (Compound 7) (27.6 mg, 11%) as a white solid. LCMS (ESI, m/z): $[M+H]^+$=605.3. $^1H$ NMR (400 MHz, DMSO-$d_6$): δ 9.49 (s, 1H), 8.41 (d, J=3.6 Hz, 1H), 8.28-8.24 (m, 1H), 8.17 (s, 1H), 7.75 (s, 1H), 7.66-7.63 (m, 1H), 7.56 (d, J=8.4 Hz, 1H), 7.20 (d, J=4.4 Hz, 1H), 7.09 (d, J=2.4 Hz, 1H), 7.02-6.98 (m, 1H), 6.87 (d, J=8.8 Hz, 1H), 6.65-6.61 (m, 2H), 4.92-4.64 (m, 1H), 4.57-4.46 (m, 1H), 4.18-4.15 (m, 1H), 4.03-3.93 (m, 1H), 3.91-3.81 (m, 4H), 3.77-3.64 (m, 1H), 3.49-3.42 (m, 1H), 3.29-3.24 (m, 2H), 3.04 (d, J=5.6 Hz, 2H), 2.25 (s, 3H), 2.17-2.15 (m, 6H).

Example S8: Synthesis of (E)-1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)-4-(dimethylamino)but-2-en-1-one (Compound 8)

Step 1. Synthesis of (E)-1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)-4-(dimethylamino)but-2-en-1-one (Compound 8)

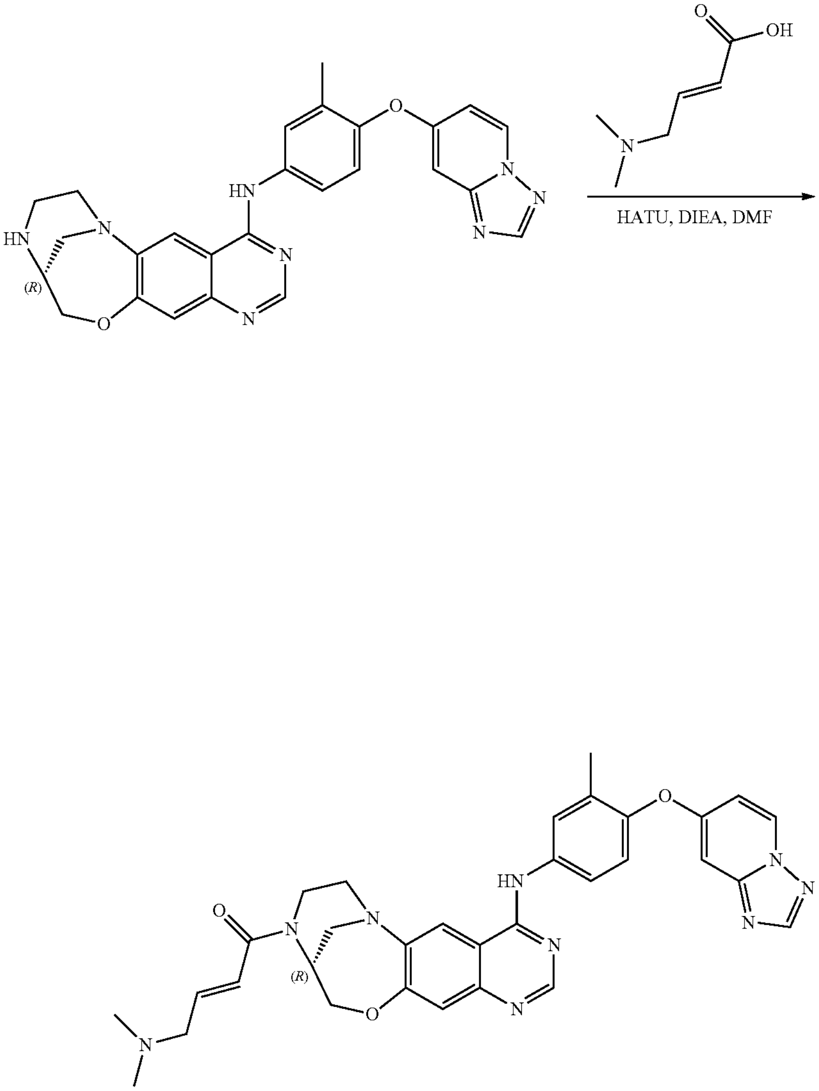

8

To a solution of (10R)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine (80.0 mg, 0.17 mmol) in DMF (5.0 mL) was added (2E)-4-(dimethylamino)but-2-enoic acid (25.8 mg, 0.20 mmol) and DIEA (215.2 mg, 1.67 mmol) and HATU (75.9 mg, 0.20 mmol) at 0° C. under $N_2$. The resulting mixture was stirred at 0° C. for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions: (Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 25% B to 45% B in 8 min; Wave Length: 254 nm) to afford (E)-1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)-4-(dimethylamino)but-2-en-1-one (Compound 8) (25.1 mg, 25%) as a white solid. LCMS (ESI, m/z): $[M+H]^+$=592.3. $^1H$ NMR (400 MHz, DMSO-$d_6$): δ 9.60 (s, 1H), 8.93 (d, J=7.2 Hz, 1H), 8.46 (s, 1H), 8.38 (s, 1H), 8.31-8.27 (m, 1H), 7.87-7.85 (m, 2H), 7.22-7.20 (m, 2H), 7.04-7.02 (m, 1H), 6.80 (s, 1H), 6.64-6.57 (m, 2H), 4.98-4.92 (m, 0.5H), 4.75-4.46 (m, 1.5H), 4.20-4.14 (m, 2H), 3.92-3.79 (m, 2H), 3.70-3.67 (m, 1H), 3.61-3.54 (m, 1H), 3.27-3.23 (m, 1H), 3.04 (s, 2H), 2.20-2.15 (m, 9H).

Example S9: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)-4-(dimethylamino)but-2-en-1-one (Compound 9)

Step 1. Synthesis of (E)-1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)-4-(dimethylamino)but-2-en-1-one (Compound 9)

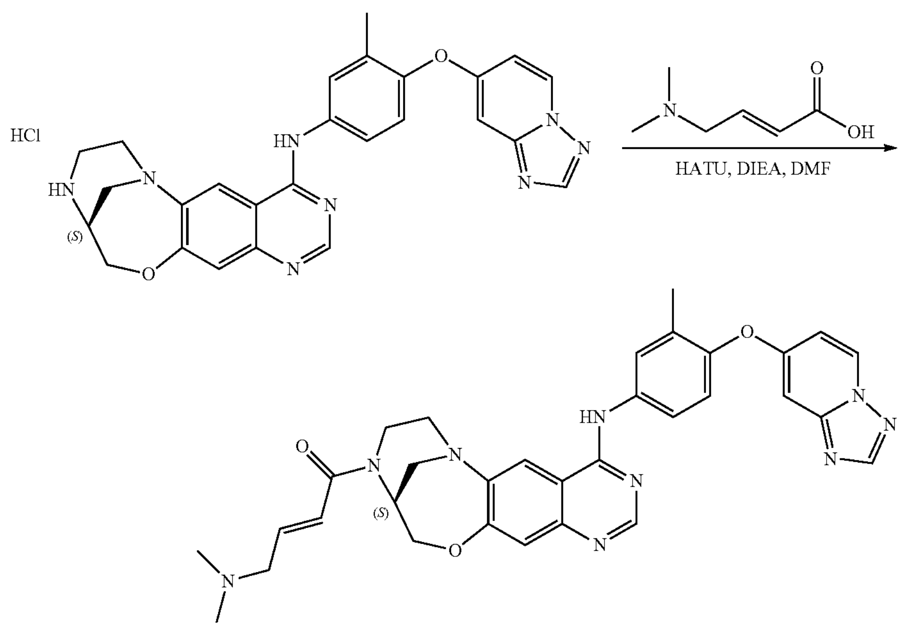

9

To a solution of (10S)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine hydrochloride (80.0 mg, crude) in DMF (5.0 mL) was added (2E)-4-(dimethylamino)but-2-enoic acid (25.8 mg, 0.20 mmol), DIEA (215.2 mg, 1.66 mmol) and HATU (75.9 mg, 0.20 mmol) at 0° C. under $N_2$. The resulting mixture was stirred at 0° C. for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by phase flash chromatography with ethyl acetate/methanol (90/10, v/v) and then purified by Prep-HPLC with the following conditions: (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 25% B to 35% B in 8 min; Wave Length: 254 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)-4-(dimethylamino)but-2-en-1-one (Compound 9) (34.8 mg, 35%) as a yellow solid. LCMS (ESI, m/z): $[M+H]^+$=592.4. $^1H$ NMR (400 MHz, DMSO-$d_6$): δ 9.60 (d, J=7.2 Hz, 1H), 8.94 (d, J=7.6 Hz, 1H), 8.46 (d, J=4.4 Hz, 1H), 8.39 (s, 1H), 8.31-8.27 (m, 1H), 7.87-7.85 (m, 2H), 7.23-7.20 (m, 2H), 7.05-7.02 (m, 1H), 6.80 (d, J=2.4 Hz, 1H), 6.65-6.62 (m, 2H), 4.94-4.65 (m, 1H), 4.61-4.45 (m, 1H), 4.20-4.17 (m, 1H), 3.92-3.79 (m, 2H), 3.70-3.60 (m, 1H), 3.54-3.43 (m, 1H), 3.29-3.23 (m, 2H), 3.07-3.03 (m, 2H), 2.20-2.15 (m, 9H).

Example S10: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 10)

Step 1. Synthesis of 3-amino-5-bromo-6-chloropicolinonitrile

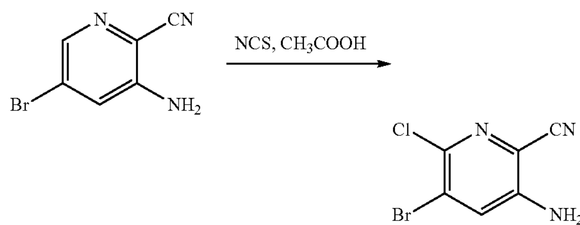

To a solution of 3-amino-5-bromopyridine-2-carbonitrile (40.0 g, 202.0 mmol) in $CH_3COOH$ (2.0 L) was added NCS (29.7 g, 222.3 mmol) at room temperature. The resulting mixture was stirred at room temperature for 72 h. After the reaction was completed, the resulting mixture was diluted with $H_2O$ and filtered. The solid was washed with water and dried to afford 3-amino-5-bromo-6-chloropicolinonitrile (25.0 g, crude) as a light yellow solid. LCMS (ESI, m/z): $[M+H]^+$=231.9.

Step 2. Synthesis of (Z)—N'-(5-bromo-6-chloro-2-cyanopyridin-3-yl)-N,N-dimethylformimidamide

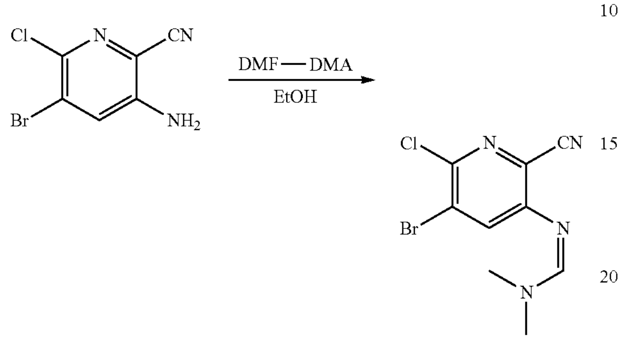

To a solution of 3-amino-5-bromo-6-chloropicolinonitrile (15.0 g, 64.52 mmol in EtOH (300.0 mL) was added DMF-DMA (9.4 g, 129.04 mmol) at room temperature. The resulting mixture was stirred at 75° C. for 2 h. After the reaction was completed, the resulting mixture was concentrated under reduced pressure to afford (Z)—N'-(5-bromo-6-chloro-2-cyanopyridin-3-yl)-N,N-dimethylmethanimidamide (18.0 g, crude) as a yellow solid. LCMS (ESI, m/z): $[M+H]^+$=287.0.

Step 3: Synthesis of N-(4-([1,2,4]triazolo[1,5-a]pyridin-7-yloxy)-3-methylphenyl)-7-bromo-6-chloropyrido[3,2-d]pyrimidin-4-amine

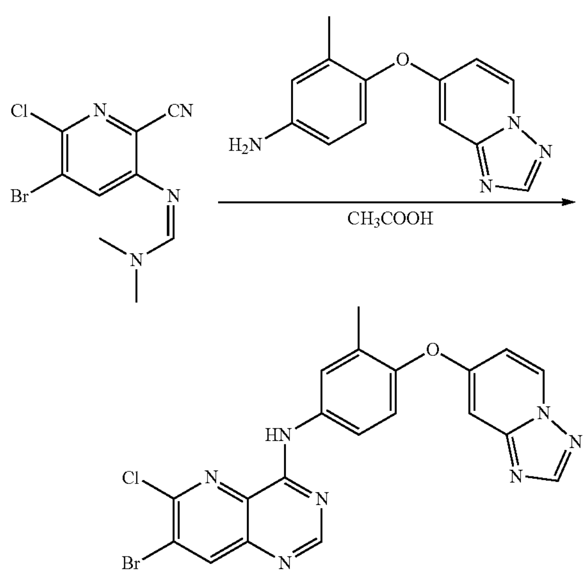

To a solution of (Z)—N'-(5-bromo-6-chloro-2-cyanopyridin-3-yl)-N,N-dimethylmethanimidamide (18.0 g, crude) in acetic acid (300.0 mL) was added 3-methyl-4-{[1,2,4]triazolo[1,5-a]pyridin-7-yloxy}aniline (15.0 g, 62.59 mmol) at room temperature. The resulting mixture was stirred at 85° C. for 2 h. After the reaction was completed, the resulting mixture was concentrated under reduced pressure. The residue was diluted with water and filtered. The precipitated solid was washed with water and dried to afford N-(4-([1,2,4]triazolo[1,5-a]pyridin-7-yloxy)-3-methylphenyl)-7-bromo-6-chloropyrido[3,2-d]pyrimidin-4-amine (30.0 g, crude) as a yellow solid. LCMS (ESI, m/z): $[M+H]^+$=482.0.

Step 4. Synthesis of tert-butyl (S)-4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)piperazine-1-carboxylate

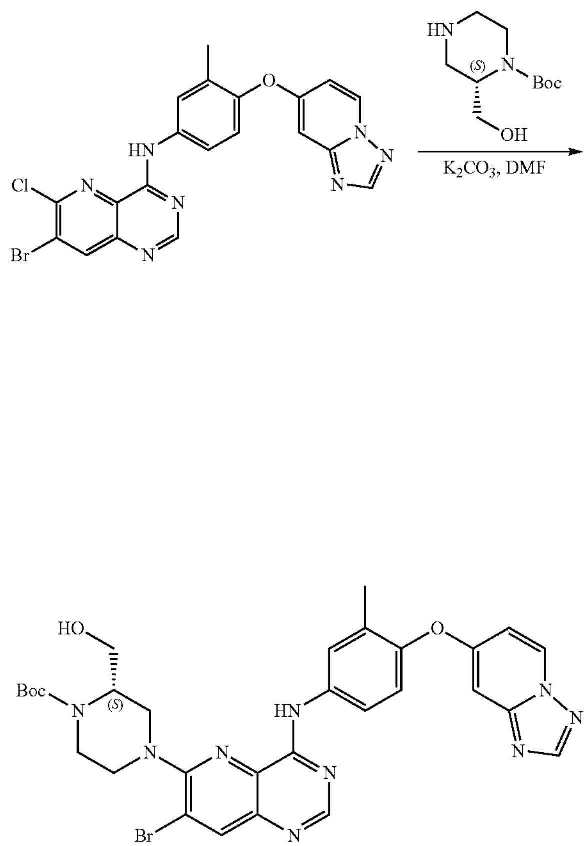

To a solution of N-(4-([1,2,4]triazolo[1,5-a]pyridin-7-yloxy)-3-methylphenyl)-7-bromo-6-chloropyrido[3,2-d]pyrimidin-4-amine (10.0 g, crude) in DMF (500.0 mL) were added tert-butyl (2S)-2-(hydroxymethyl)piperazine-1-carboxylate (6.7 g, 31.07 mmol) and $K_2CO_3$ (14.3 g, 103.58 mmol) at room temperature. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with $CH_2Cl_2$/$CH_3OH$ (10/1, v/v) to afford tert-butyl (S)-4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)piperazine-1-carboxylate (12.0 g, 87%) as a yellow solid. LCMS (ESI, m/z): $[M+H]^+$=662.2.

Step 5. Synthesis of tert-butyl (10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate

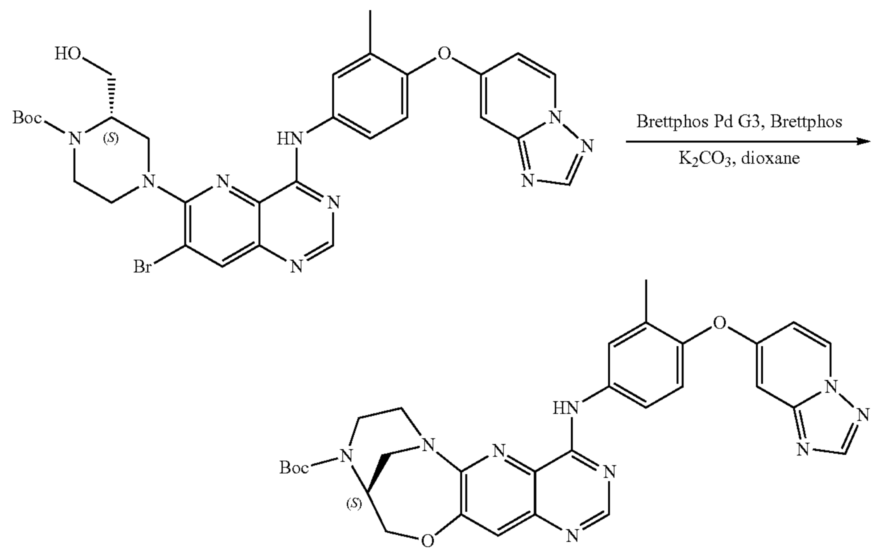

To a solution of tert-butyl (S)-4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)piperazine-1-carboxylate (4.1 g, 6.20 mmol) in dioxane (120.0 mL) was added $K_2CO_3$ (3.4 g, 24.80 mmol), BrettPhos (1.3 g, 2.46 mmol) and BrettPhos Pd G3 (1.1 g, 1.23 mmol) at room temperature under $N_2$. The resulting mixture was stirred at 100° C. for 16 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by flash column chromatography with $CH_2Cl_2$/MeOH (12/1, v/v) to afford tert-butyl (10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (1.7 g, 47%) as a brown oil. LCMS (ESI, m/z): $[M+H]^+$=582.2.

Step 6. Synthesis of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine

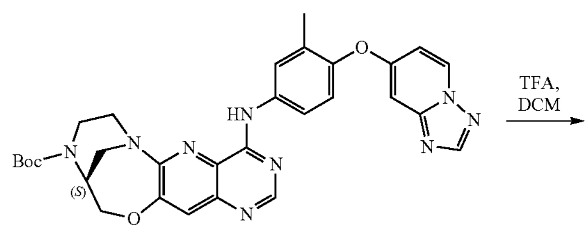

-continued

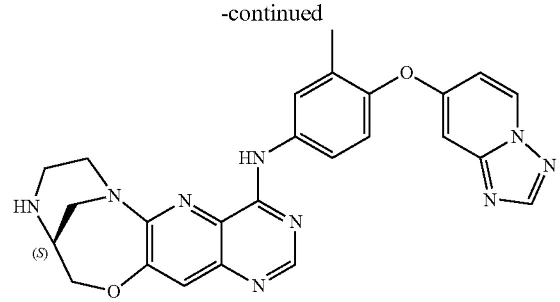

To a solution of tert-butyl (10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (1.7 g, 2.93 mmol) in DCM (20.0 mL) was added TFA (20.0 mL) at room temperature. The resulting mixture was stirred at room temperature for 4 h. After the reaction was completed, the resulting mixture was concentrated under reduced pressure. The residue was basified to pH=8 with saturated $NaHCO_3$(aq.). The resulting mixture was extracted with EtOAc. The combined organic layer was washed with brine, dried over anhydrous sodium sulfate and filtered. The filtrate was concentrated under reduced pressure to afford (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (800.0 mg, crude) as a brown oil. LCMS (ESI, m/z): $[M+H]^+$=482.2.

Step 7. Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 10)

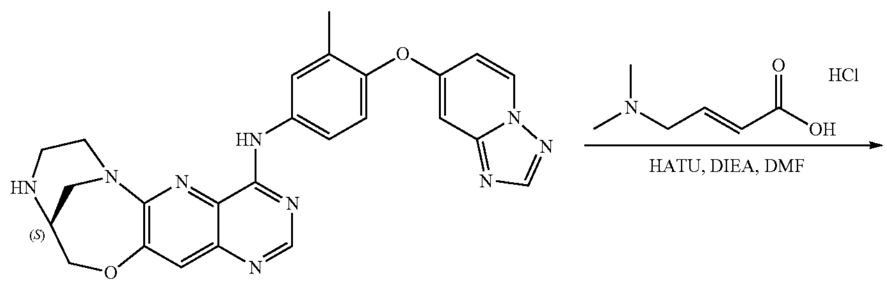

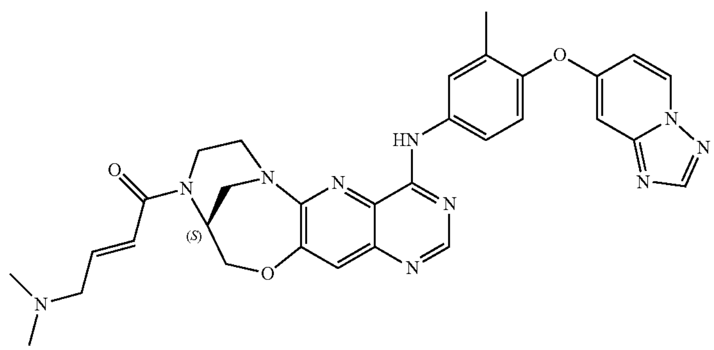

10

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (4.5 g, crude) in DMF (50.0 mL) was added (2E)-4-(dimethylamino)but-2-enoic acid hydrochloride (7.7 g, 46.8 mmol) and DIEA (14.4 g, 112.2 mmol). Then HATU (7.1 g, 18.70 mmol) was added to the mixture at 0° C. under $N_2$. The resulting mixture was stirred at room temperature for 1 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (40/60, v/v) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 10) (820.0 mg, 15%) as a light yellow solid. LCMS (ESI, m/z): $[M+H]^+$=593.5. $^1$H NMR (400 MHz, DMSO-$d_6$): δ 9.52-9.49 (m, 1H), 8.94 (d, J=7.6 Hz, 1H), 8.48 (s, 1H), 8.38 (s, 1H), 8.02-7.95 (m, 2H), 7.51 (s, 1H), 7.22 (d, J=8.8 Hz, 1H), 7.04-7.02 (m, 1H), 6.79 (d, J=2.8 Hz, 1H), 6.67-6.62 (m, 2H), 5.12-4.63 (m, 3H), 4.28-4.20 (m, 2H), 4.15-4.03 (m, 1H), 3.88-3.65 (m, 1H), 3.28-3.22 (m, 2H), 3.06-3.03 (m, 2H), 2.20-2.15 (m, 9H).

Example S11: Synthesis of 1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)but-2-yn-1-one (Compound 11)

Step 1. Synthesis of 1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)but-2-yn-1-one (Compound 11)

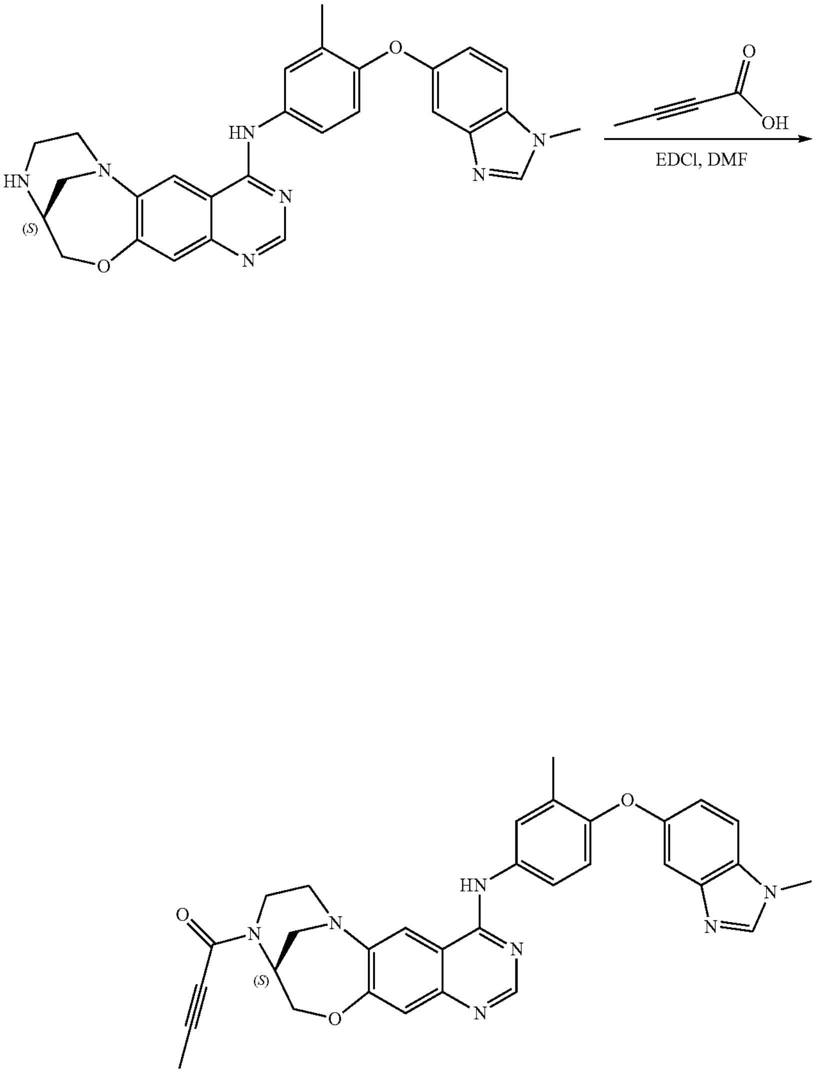

11

To a stirred mixture of (10S)—N-(3-methyl-4-((1-methyl-1H-benzo[d]imidazol-5-yl)oxy)phenyl)-8,9,10,11-tetrahydro-7H-6,10-methano[1,4,7]oxadiazonino[3,2-g]quinazolin-4-amine (150.0 mg, 0.30 mmol) and 2-butynoic acid (25.5 mg, 0.30 mmol) in DMF (2.0 mL) was added EDCI (116.5 mg, 0.61 mmol) at room temperature. The resulting mixture was stirred at room temperature for 1 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (70/30, v/v) and then purified by Prep-HPLC with the following conditions Column: (XSelect CSH Prep C18 OBD Column, 19×250 mm, 5 μm; Mobile Phase A: Water (10 mmol/L $NH_4HCO_3$), Mobile Phase B: MeOH—HPLC; Flow rate: 25 mL/min; Gradient: 68% B to 68% B in 10 min; Wave Length: 254 nm) to afford 1-((10S)-4-((3-methyl-4-((1-methyl-1H-benzo[d]imidazol-5-yl)oxy)phenyl)amino)-7,8,10,11-tetrahydro-9H-6,10-methano[1,4,7]oxadiazonino[3,2-g]quinazolin-9-yl)but-2-yn-1-one (Compound 11) (20.6 mg, 12%) as a yellow solid. LCMS (ESI, m/z): $[M+H]^+$=560.3. $^1H$ NMR (400 MHz, DMSO-$d_6$): δ 9.55-9.51 (m, 1H), 8.42 (d, J=4.8 Hz, 1H), 8.31-8.26 (m, 1H), 8.17 (s, 1H), 7.76-7.74 (m, 1H), 7.66-7.63 (m, 1H), 7.57 (d, J=8.8 Hz, 1H), 7.22 (d, J=6.0 Hz, 1H), 7.09 (d, J=2.0 Hz, 1H), 7.01-6.98 (m, 1H), 6.87 (d, J=8.8 Hz, 1H), 4.85-4.83 (m, 1H), 4.59-4.42 (m, 1H), 4.26-4.19 (m, 1H), 4.09-3.99 (m, 1H), 3.91-3.84 (m, 4H), 3.80-3.64 (m, 2H), 3.56-3.39 (m, 1H), 3.28-3.20 (m, 1H), 2.25 (s, 3H), 2.06 (d, J=8.4 Hz, 3H).

Example S12: Synthesis of 1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)but-2-yn-1-one (Compound 12)

Step 1. Synthesis of 1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)but-2-yn-1-one (Compound 12)

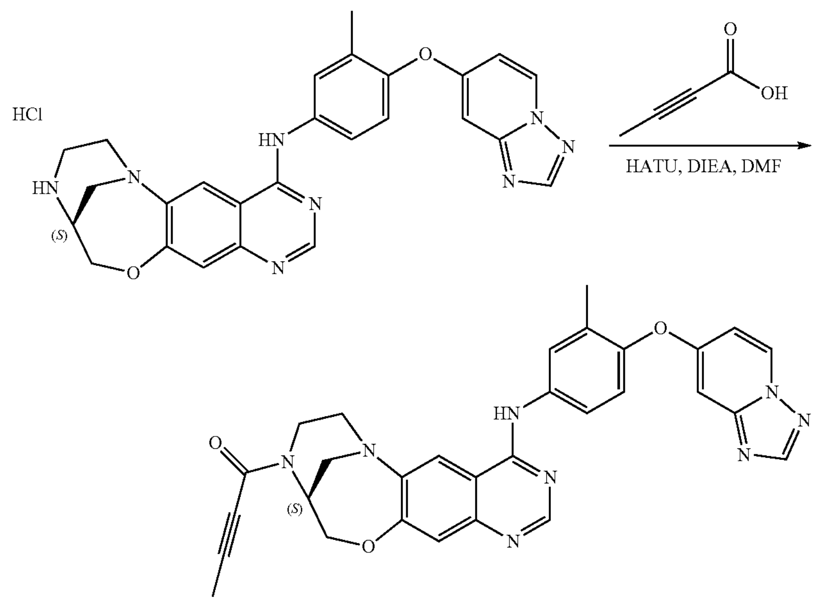

12

To a solution of (10S)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine hydrochloride (100.0 mg, crude) in DMF (2.0 mL) was added 2-butynoic acid (18.5 mg, 0.26 mmol), HATU (162.6 mg, 0.43 mmol) and DIEA (274.0 mg, 2.1 mmol) at 0° C. under $N_2$. The resulting mixture was stirred at room temperature for 3 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 27% B to 37% B in 8 min; Wave Length: 254 nm) to afford 1-((10S)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)but-2-yn-1-one (Compound 12) (23.4 mg, 40%) as a yellow solid. LCMS (ESI, m/z): $[M+H]^+$=547.3. $^1$H NMR (400 MHz, DMSO-$d_6$): δ 9.63-9.59 (m, 1H), 8.94 (d, J=7.6 Hz, 1H), 8.48 (s, 1H), 8.38-8.29 (m, 2H), 7.88-7.85 (m, 2H), 7.26-7.20 (m, 2H), 7.04-7.02 (m, 1H), 6.81 (d, J=2.4 Hz, 1H), 4.86-4.84 (m, 1H), 4.60-4.47 (m, 1H), 4.26-4.20 (m, 1H), 4.09-4.02 (m, 1H), 3.93-3.71 (m, 3H), 3.69-3.53 (m, 1H), 3.31-3.20 (m, 1H), 2.20 (s, 3H), 2.07 (s, 3H).

Example S13: Synthesis of 1-((10S)-4-((4-([1,2,4]triazolo[1,5-a]pyridin-7-ylmethyl)-3-methylphenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 13)

Step 1. Synthesis of Tert-butyl (S)-4-(4-((4-([1,2,4]triazolo[1,5-a]pyridin-7-ylmethyl)-3-methylphenyl)amino)-7-bromopyrido[3,2-d]pyrimidin-6-yl)-2-(hydroxymethyl)piperazine-1-carboxylate

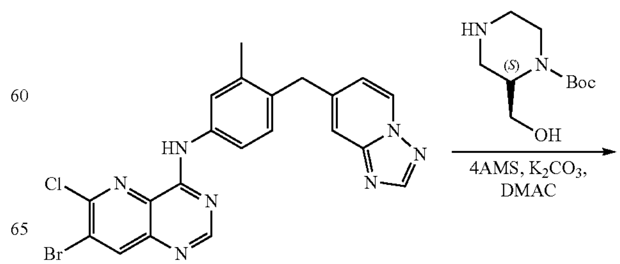

-continued

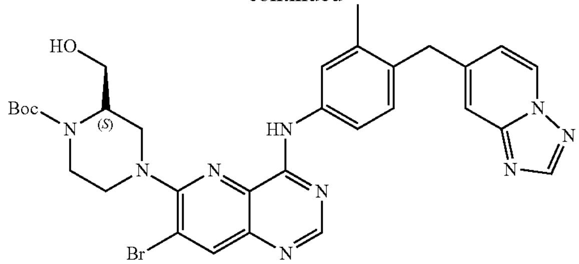

To a solution of N-(4-([1,2,4]triazolo[1,5-a]pyridin-7-ylmethyl)-3-methylphenyl)-7-bromo-6-chloropyrido[3,2-d]pyrimidin-4-amine (500.0 mg, 1.04 mmol) in DMAC (12.0 mL) was added tert-butyl (S)-2-(hydroxymethyl)piperazine-1-carboxylate (224.9 mg, 1.04 mmol), 4AMS (200.0 mg) and $K_2CO_3$ (431.2 mg, 3.12 mmol) at room temperature. The resulting mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (90/10, v/v) to afford tert-butyl (S)-4-(4-((4-([1,2,4]triazolo[1,5-a]pyridin-7-ylmethyl)-3-methylphenyl)amino)-7-bromopyrido[3,2-d]pyrimidin-6-yl)-2-(hydroxymethyl)piperazine-1-carboxylate (610.0 mg, 88%) as a yellow solid. LCMS (ESI, m/z): $[M+H]^+$=660.2.

Step 2. Synthesis of Tert-butyl (10S)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonine-9-carboxylate

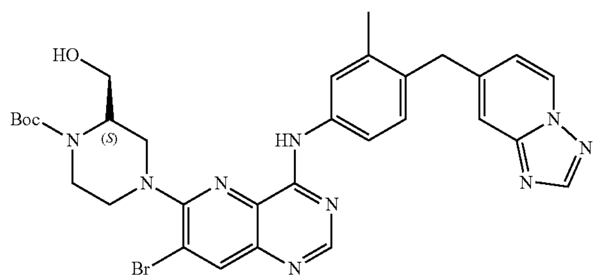

Brettphos, Brettphos Pd G3

$K_2CO_3$, dioxane

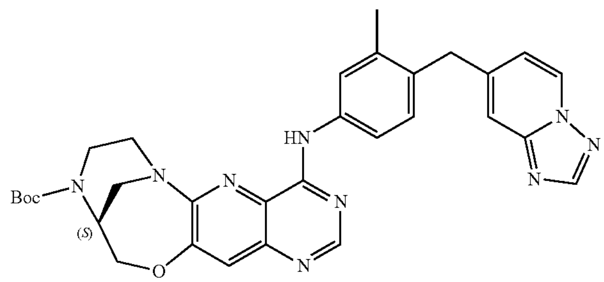

To a solution of tert-butyl (S)-4-(4-((4-([1,2,4]triazolo[1,5-a]pyridin-7-ylmethyl)-3-methylphenyl)amino)-7-bromopyrido[3,2-d]pyrimidin-6-yl)-2-(hydroxymethyl)piperazine-1-carboxylate (200.0 mg, 0.30 mmol) in 1,4-dioxane (10.0 mL) was added $K_2CO_3$ (167.4 mg, 1.21 mmol), BrettPhos Pd G3 (54.9 mg, 0.06 mmol) and BrettPhos (65.0 mg, 0.12 mmol) at room temperature under $N_2$. The resulting mixture was stirred at 100° C. for 16 h. After the reaction was completed, the resulting mixture was concentrated under reduced pressure. The residue was purified by flash column chromatography with ethyl acetate/MeOH (90/10, v/v) to afford tert-butyl (10S)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonine-9-carboxylate (100.0 mg, 57%) as a yellow solid. LCMS (ESI, m/z): $[M+H]^+$=580.0.

Step 3: Synthesis of (10S)—N-(4-([1,2,4]triazolo[1,5-a]pyridin-7-ylmethyl)-3-methylphenyl)-8,9,10,11-tetrahydro-7H-6,10-methanopyrimido[4',5':5,6]pyrido[3,2-b][1,4,7]oxadiazonin-4-amine hydrochloride

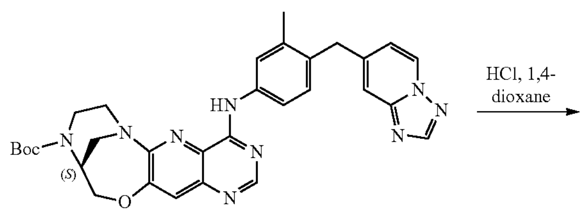

-continued

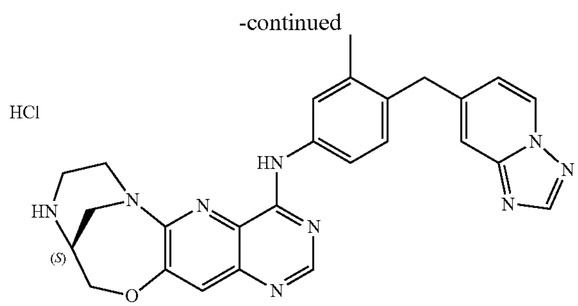

A solution of tert-butyl (10S)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonine-9-carboxylate (100.0 mg, 0.20 mmol) in HCl/1,4-dioxane (5.0 mL, 4.0 mol/L) was stirred at room temperature for 2 h. After the reaction was completed, the resulting mixture was concentrated under reduced pressure and afford (10S)—N-(4-([1,2,4]triazolo[1,5-a]pyridin-7-ylmethyl)-3-methylphenyl)-8,9,10,11-tetrahydro-7H-6,10-methanopyrimido[4',5':5,6]pyrido[3,2-b][1,4,7]oxadiazonin-4-amine hydrochloride (90.0 mg, crude) as a yellow solid. LCMS (ESI, m/z): $[M+H]^+$=480.0.

Step 4. Synthesis of 1-((10S)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 13)

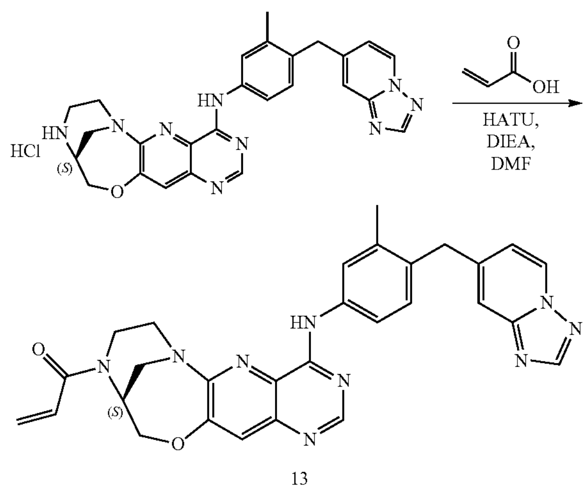

13

To a solution of (10S)—N-(4-([1,2,4]triazolo[1,5-a]pyridin-7-ylmethyl)-3-methylphenyl)-8,9,10,11-tetrahydro-7H-6,10-methanopyrimido[4',5':5,6]pyrido[3,2-b][1,4,7]oxadiazonin-4-amine hydrochloride (150.0 mg, crude) in DMF (5.0 mL) was added acrylic acid (22.5 mg, 0.31 mmol), DIEA (404.3 mg, 3.13 mmol) and HATU (237.9 mg, 0.63 mmol) at 0° C. under $N_2$. The resulting mixture was stirred at 0° C. for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (50/50, v/v) and then purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 27% B to 37% B in 8 min; Wave Length: 254 nm) to afford 1-((10S)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 13) (12.6 mg, 4%) as a yellow solid. LCMS (ESI, m/z): $[M+H]^+$= 534.3. $^1$H NMR (400 MHz, DMSO-$d_6$): δ 9.41-9.39 (m, 1H), 8.86-8.84 (m, 1H), 8.44 (s, 2H), 7.85-7.79 (m, 2H), 7.50-7.49 (m, 2H), 7.27-7.25 (m, 1H), 7.03-7.00 (m, 1H), 6.85-6.80 (m, 1H), 6.17-6.13 (m, 1H), 5.74-5.71 (m, 1H), 5.10-4.61 (m, 3H), 4.20-4.06 (m, 5H), 3.89-3.62 (m, 1H), 3.59-3.51 (m, 1H), 3.30-3.23 (m, 1H), 2.32 (s, 3H).

Example S14: Synthesis of 1-((10S)-4-((3-methyl-4-((1-methyl-1H-benzo[d]imidazol-5-yl)oxy)phenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 14)

Step 1. Synthesis of 7-bromo-6-chloro-N-{3-methyl-4-[(1-methyl-1,3-benzodiazol-5-yl)oxy]phenyl}pyrido[3,2-d]pyrimidin-4-amine

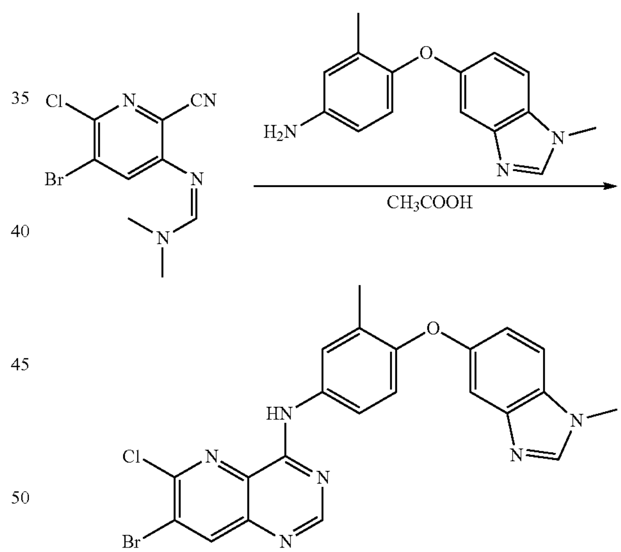

To a stirred mixture of (Z)—N'-(5-bromo-6-chloro-2-cyanopyridin-3-yl)-N,N-dimethylmethanimidamide (3.4 g, 11.82 mmol) in acetic acid (45.3 mL) was added 3-methyl-4-[(1-methyl-1,3-benzodiazol-5-yl)oxy]aniline (3.0 g, 11.82 mmol) at room temperature. The resulting mixture was stirred at 85° C. for 2 h. After the reaction was completed, the resulting mixture was concentrated under reduced pressure. The residue was purified by flash column chromatography with $CH_2Cl_2$/MeOH (6/1, v/v) to afford 7-bromo-6-chloro-N-{3-methyl-4-[(1-methyl-1,3-benzodiazol-5-yl)oxy]phenyl}pyrido[3,2-d]pyrimidin-4-amine (4.8 g, 81%) as an brown solid. LCMS (ESI, m/z): $[M+H]^+$=495.0.

Step 2. Synthesis of tert-butyl (2S)-4-[7-bromo-4-({3-methyl-4-[(1-methyl-1,3-benzodiazol-5-yl)oxy]phenyl}amino)pyrido[3,2-d]pyrimidin-6-yl]-2-(hydroxymethyl)piperazine-1-carboxylate

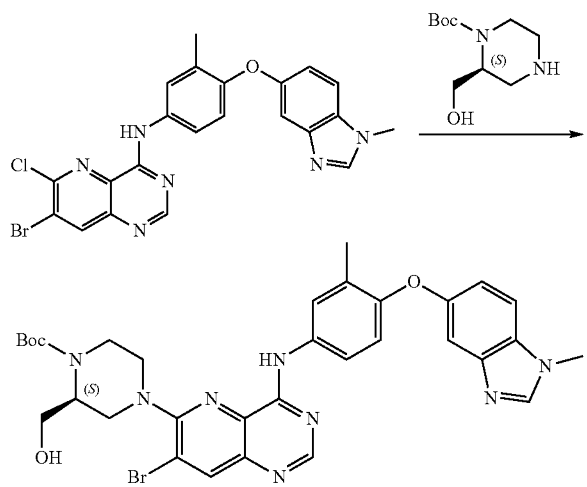

To a stirred mixture of 7-bromo-6-chloro-N-{3-methyl-4-[(1-methyl-1,3-benzodiazol-5-yl)oxy]phenyl}pyrido[3,2-d]pyrimidin-4-amine (4.2 g, 8.47 mmol) and tert-butyl (2S)-2-(hydroxymethyl)piperazine-1-carboxylate (14.7 g, 67.78 mmol) in ACN (40.0 mL) was added $K_2CO_3$ (5.9 g, 42.36 mmol) at room temperature. The resulting mixture was stirred at 100° C. for 16 h. After the reaction was completed, the resulting mixture was cooled to room temperature and filtered. The filtrate was concentrated under reduced pressure. The residue was purified by flash column chromatography with $CH_2Cl_2$/MeOH (6/1, v/v) to afford tert-butyl (2S)-4-[7-bromo-4-({3-methyl-4-[(1-methyl-1,3-benzodiazol-5-yl)oxy]phenyl}amino)pyrido[3,2-d]pyrimidin-6-yl]-2-(hydroxymethyl)piperazine-1-carboxylate (3.0 g, 52%) as a yellow solid. LCMS (ESI, m/z): $[M+H]^+$=675.2.

Step 3: Synthesis of tert-butyl (10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonine-9-carboxylate

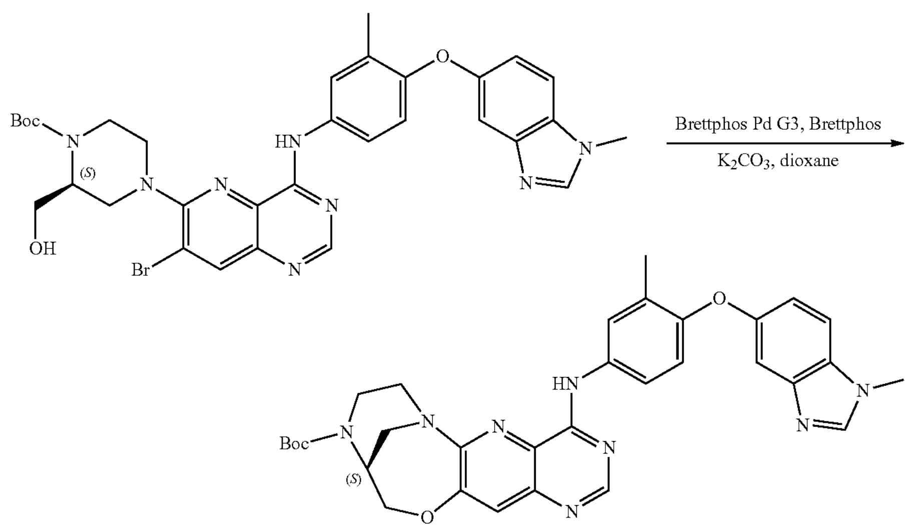

To a stirred mixture of tert-butyl (2S)-4-[7-bromo-4-({3-methyl-4-[(1-methyl-1,3-benzodiazol-5-yl)oxy]phenyl}amino)pyrido[3,2-d]pyrimidin-6-yl]-2-(hydroxymethyl)piperazine-1-carboxylate (3.5 g, 5.18 mmol) and $K_2CO_3$ (2.1 g, 15.54 mmol) in dioxane (40.0 mL) were added BrettPhos (1.1 g, 2.07 mmol) and BrettPhos Pd G3 (939.3 mg, 1.04 mmol) at room temperature under $N_2$. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (5/1, v/v) to afford tert-butyl (10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonine-9-carboxylate (1.3 g, 43%) as a brown solid. LCMS (ESI, m/z): $[M+H]^+$=595.2.

Step 4. Synthesis of (10S)—N-(3-methyl-4-((1-methyl-1H-benzo[d]imidazol-5-yl)oxy)phenyl)-8,9,10,11-tetrahydro-7H-6,10-methanopyrimido[4',5':5,6]pyrido[3,2-b][1,4,7]oxadiazonin-4-amine

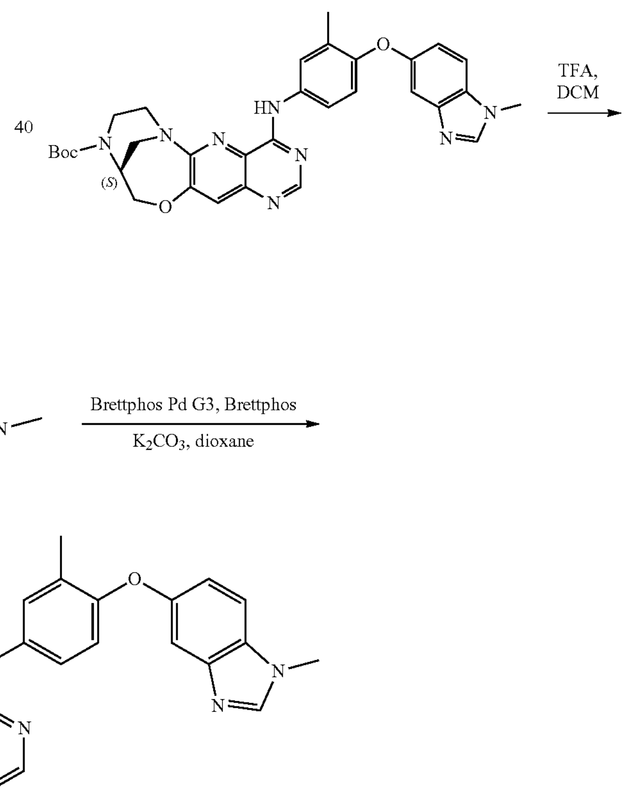

-continued

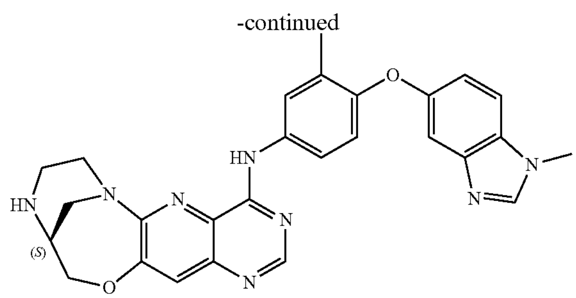

To a stirred solution of tert-butyl (10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonine-9-carboxylate (1.3 g, 2.27 mmol) in DCM (8.0 mL) was added TFA (4.0 mL) at room temperature. The resulting mixture was stirred at room temperature for 1 h. After the reaction was completed, the mixture was basified to pH=8 with saturated $NaHCO_3$(aq.). The resulting mixture was extracted with $CH_2Cl_2$. The combined organic layers were washed with brine, dried over anhydrous $Na_2SO_4$ and filtered. The filtrate was concentrated under reduced pressure. The residue was purified by reverse phase flash column chromatography with acetonitrile/water (43/57, v/v) to afford (10S)—N-(3-methyl-4-((1-methyl-1H-benzo[d]imidazol-5-yl)oxy)phenyl)-8,9,10,11-tetrahydro-7H-6,10-methanopyrimido[4',5':5,6]pyrido[3,2-b][1,4,7]oxadiazonin-4-amine (400.0 mg, 35%) as a yellow solid. LCMS (ESI, m/z): $[M+H]^+$=495.2.

Step 5. Synthesis of 1-((10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 14)

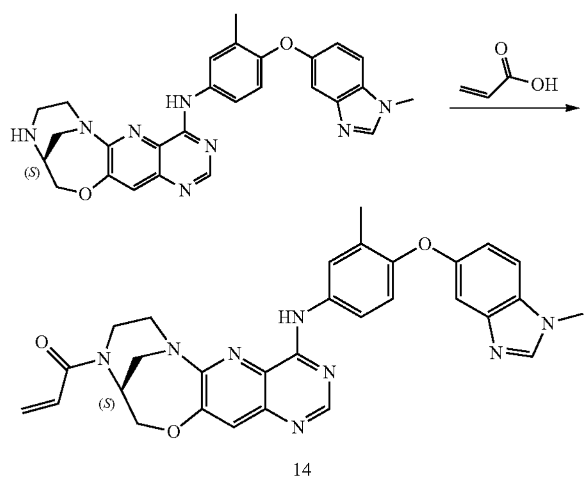

14

To a stirred mixture of (10S)—N-(3-methyl-4-((1-methyl-1H-benzo[d]imidazol-5-yl)oxy)phenyl)-8,9,10,11-tetrahydro-7H-6,10-methanopyrimido[4',5':5,6]pyrido[3,2-b][1,4,7]oxadiazonin-4-amine (180.0 mg, 0.36 mmol) and acrylic acid (52.5 mg, 0.73 mmol) in pyridine (6.0 mL) was added EDCI (139.5 mg, 0.73 mmol) at room temperature. The resulting mixture was stirred at room temperature for 1 h. After the reaction was completed, the mixture was concentrated under reduced pressure. The residue was purified by reverse phase flash column chromatography with acetonitrile/water (39/61, v/v) and then purified by Prep-HPLC with the following conditions: (Column: XSelect CSH Fluoro Phenyl, 30×150 mm, 5 μm; Mobile Phase A: ACN, Mobile Phase B: Water (0.1% FA); Flow rate: 60 mL/min; Gradient: 5% B to 25% B in 8 min, 25% B to 25% B in 12 min; Wave Length: 254/220 nm) to afford 1-((10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 14) (52.4 mg, 26%) as a yellow solid. LCMS (ESI, m/z): $[M+H]^+$=549.2. $^1H$ NMR (400 MHz, DMSO-$d_6$): δ 9.82-9.75 (m, 1H), 8.78 (d, J=6.4 Hz, 1H), 8.52 (s, 1H), 7.87 (s, 1H), 7.82-7.75 (m, 2H), 7.52 (s, 1H), 7.17-7.14 (m, 2H), 6.98 (d, J=8.4 Hz, 1H), 6.83-6.80 (m, 1H), 6.18-6.14 (m, 1H), 5.75-5.72 (m, 1H), 4.81-4.62 (m, 3H), 4.25-4.08 (m, 3H), 3.94 (s, 3H), 3.42-3.23 (m, 3H), 2.24 (s, 3H).

Example S15: Synthesis of (E)-1-((10R)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 15)

Step 1. Synthesis of tert-butyl (2R)-4-{7-bromo-4-[(3-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate

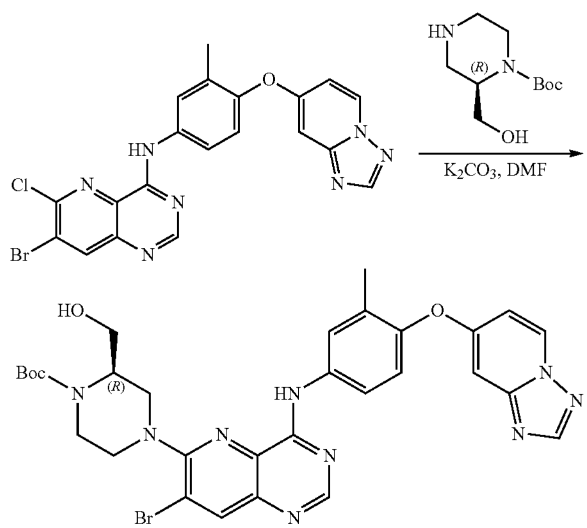

To a solution of 7-bromo-6-chloro-N-(3-methyl-4-{[1,2,4]triazolo[1,5-a]pyridin-7-yloxy}phenyl)pyrido[3,2-d]pyrimidin-4-amine (2.8 g, 5.80 mmol) in DMF (100.0 mL) was added tert-butyl (2R)-2-(hydroxymethyl)piperazine-1-carboxylate (1.9 g, 8.70 mmol) and $K_2CO_3$ (3.2 g, 23.20 mmol)

at room temperature. The resulting mixture was stirred at 100° C. for 16 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash column chromatography with $H_2O$/ACN (40/60, v/v) to afford tert-butyl (2R)-4-{7-bromo-4-[(3-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (2.0 g, 52%) as a brown solid. LCMS (ESI, m/z): $[M+H]^+$=662.2.

Step 2. Synthesis of tert-butyl (10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate

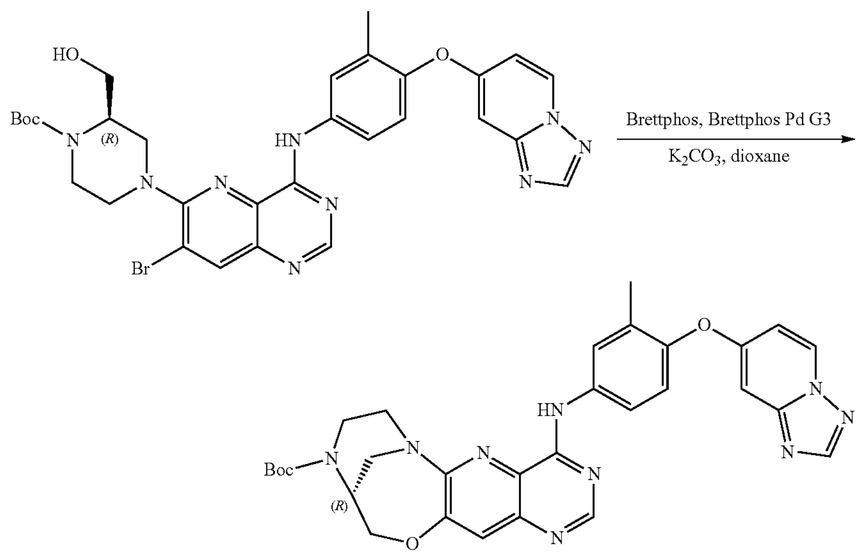

To a solution of tert-butyl (2R)-4-{7-bromo-4-[(3-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (1.2 g, 1.81 mmol) in dioxane (60.0 mL) was added BrettPhos (388.9 mg, 0.72 mmol), $K_2CO_3$ (751.0 mg, 5.43 mmol) and BrettPhos Pd G3 (328.4 mg, 0.36 mmol) at room temperature under $N_2$. The resulting mixture was stirred at 100° C. for 16 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash column chromatography with $H_2O$/MeOH (10/90, v/v) to afford tert-butyl (10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (190.0 mg, 18%) as a yellow solid. LCMS (ESI, m/z): $[M+H]^+$=582.2.

Step 3: Synthesis of (10R)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine

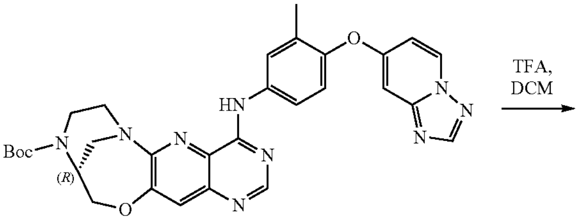

-continued

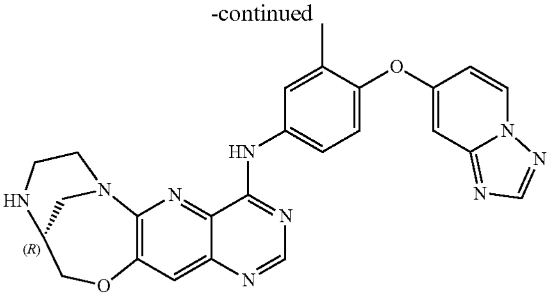

To a solution of tert-butyl (10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (190.0 mg, 0.33 mmol) in DCM (2.0 mL) was added TFA (2.0 mL) at room temperature. The resulting mixture was stirred at room temperature for 0.5 h. After the reaction was completed, the resulting mixture was concentrated under reduced pressure. The pH value of the mixture was adjusted to 7 with aq. $NaHCO_3$. The resulting mixture was extracted with EtOAc. The combined organic layer was washed with brine, dried over anhydrous sodium sulfate and filtered. The filtrate was concentrated under reduced pressure to afford (10R)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (100.0 mg, crude) as a yellow solid. LCMS (ESI, m/z): $[M+H]^+$=482.2.

Step 4. Synthesis of (E)-1-((10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 15)

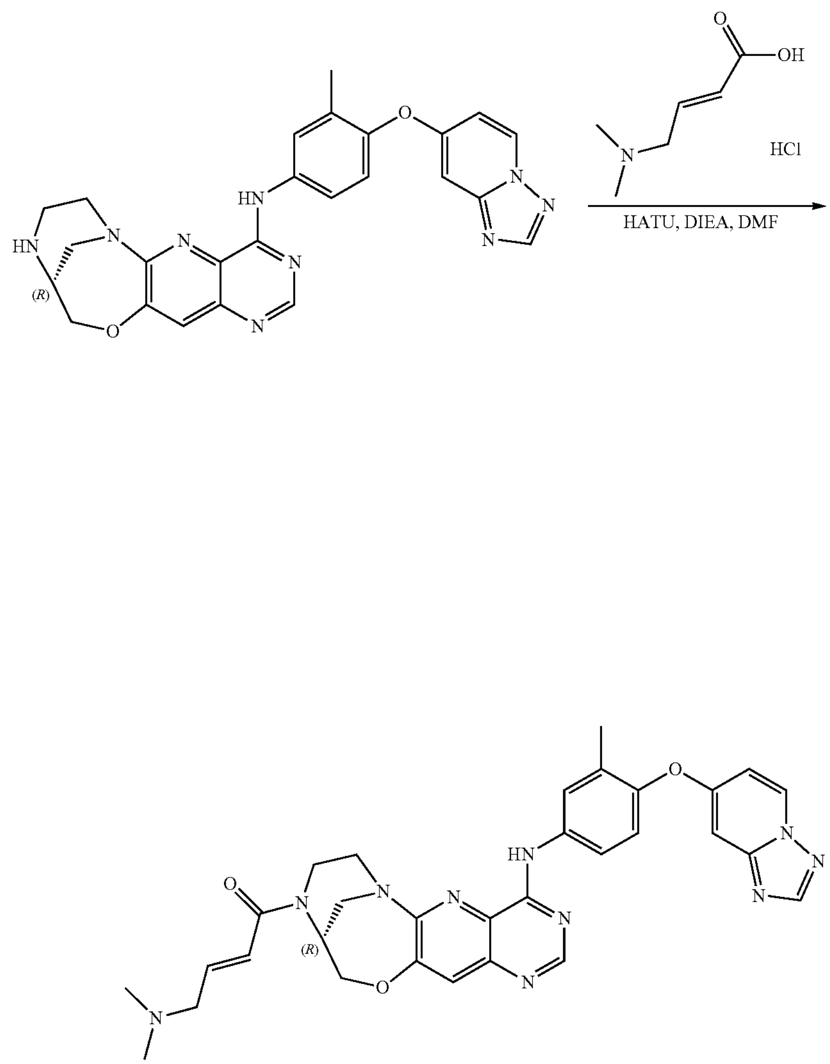

15

To a solution of (10R)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (70.0 mg, crude) in DMF (1.0 mL) was added DIEA (112.7 mg, 0.87 mmol), (E)-4-(dimethylamino)but-2-enoic acid hydrochloride (28.9 mg, 0.18 mmol) and HATU (82.9 mg, 0.22 mmol) at room temperature. The resulting mixture was stirred at room temperature for 1 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash column chromatography with $H_2O$/MeOH (50/50, v/v) and then purified by Prep-HPLC with the following conditions (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 34% B to 44% B in 8 min; Wave Length: 254 nm) to afford (E)-1-((10R)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 15) (10.7 mg, 12%) as a white solid. LCMS (ESI, m/z): $[M+H]^+$=593.3. $^1$H NMR (400 MHz, DMSO-$d_6$): δ 9.55-9.52 (m, 1H), 8.94 (d, J=7.2 Hz, 1H), 8.48 (s, 1H), 8.38 (s, 1H), 8.00 (s, 2H), 7.51 (s, 1H), 7.22 (d, J=9.2 Hz, 1H), 7.04-7.02 (m, 1H), 6.79 (d, J=2.8 Hz, 1H), 6.65-6.60 (m, 2H), 5.12-4.63 (m, 3H), 4.28-4.05 (m, 3H), 3.89-3.65 (m, 1H), 3.52-3.38 (m, 1H), 3.23-3.19 (m, 1H), 3.07-3.03 (m, 2H), 2.25-2.15 (m, 9H).

Example S16: Synthesis of 1-((10S)-4-((3-methyl-4-((1-methyl-1H-benzo[d]imidazol-5-yl)oxy)phenyl)amino)-7,8,10,11-tetrahydro-9H-6,10-methanopyrimido[4,5':5,6]pyrido[3,2-b][1,4,7]oxadiazonin-9-yl)but-2-yn-1-one (Compound 16)

Step 1. Synthesis of 1-((10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonin-9-yl)but-2-yn-1-one (Compound 16)

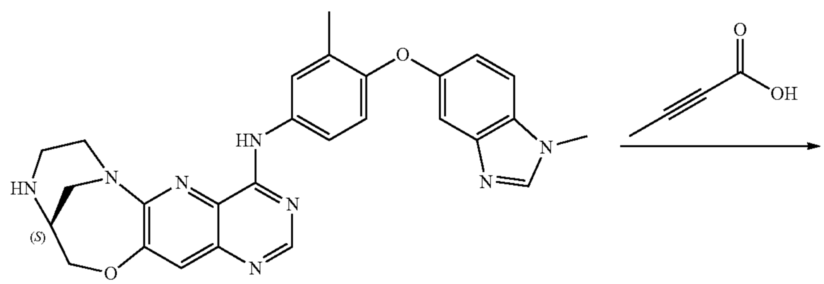

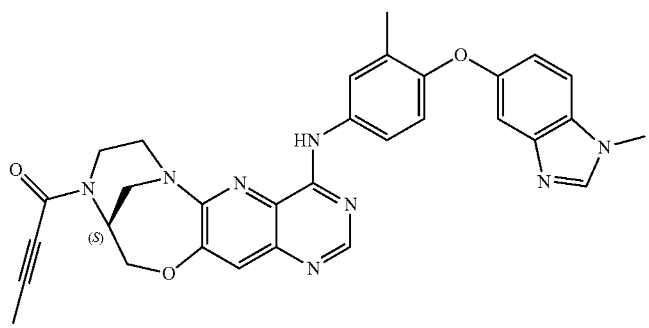

16

To a stirred mixture of (10S)—N-(3-methyl-4-((1-methyl-1H-benzo[d]imidazol-5-yl)oxy)phenyl)-8,9,10,11-tetrahydro-7H-6,10-methanopyrimido[4',5':5,6]pyrido[3,2-b][1,4,7]oxadiazonin-4-amine (170.0 mg, 0.34 mmol) and 2-butynoic acid (57.8 mg, 0.69 mmol) in pyridine (6.0 mL) was added EDCI (131.8 mg, 0.69 mmol) at room temperature. The resulting mixture was stirred at room temperature for 1 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (5/1, v/v) and then purified by Prep-HPLC with the following conditions: (Column: Xselect CSH OBD Column 30×150 mm, 5 um; Mobile Phase A:Water (10 mmol/L $NH_4HCO_3$), Mobile Phase B:ACN; Flow rate: 60 mL/min; Gradient: 33% B to 43% B in 9 min; 254/220 nm) to afford 1-((10S)-4-((3-methyl-4-((1-methyl-1H-benzo[d]imidazol-5-yl)oxy)phenyl)amino)-7,8,10,11-tetrahydro-9H-6,10-methanopyrimido[4',5':5,6]pyrido[3,2-b][1,4,7]oxadiazonin-9-yl)but-2-yn-1-one (Compound 16) (51.2 mg, 26%) as a yellow solid. LCMS (ESI, m/z): $[M+H]^+$=561.4. $^1$H NMR (400 MHz, DMSO-$d_6$): δ 9.43 (s, 1H), 8.43 (s, 1H), 8.17 (s, 1H), 7.87 (d, J=2.0 Hz, 1H), 7.82-7.78 (m, 1H), 7.56 (d, J=8.8 Hz, 1H), 7.49 (d, J=0.4 Hz, 1H), 7.08 (d, J=2.0 Hz, 1H), 7.01-6.98 (m, 1H), 6.90-6.87 (m, 1H), 5.04-5.02 (m, 1H), 4.77-4.65 (m, 2H), 4.26-4.07 (m, 3H), 3.84 (s, 3H), 3.81-3.65 (m, 1H), 3.45-3.38 (m, 1H), 3.25-3.12 (m, 1H), 2.25 (s, 3H), 2.07-2.04 (m, 3H).

Example S17. Synthesis of 1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)but-2-yn-1-one (Compound 17)

Step 1. Synthesis of 1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)but-2-yn-1-one (Compound 17)

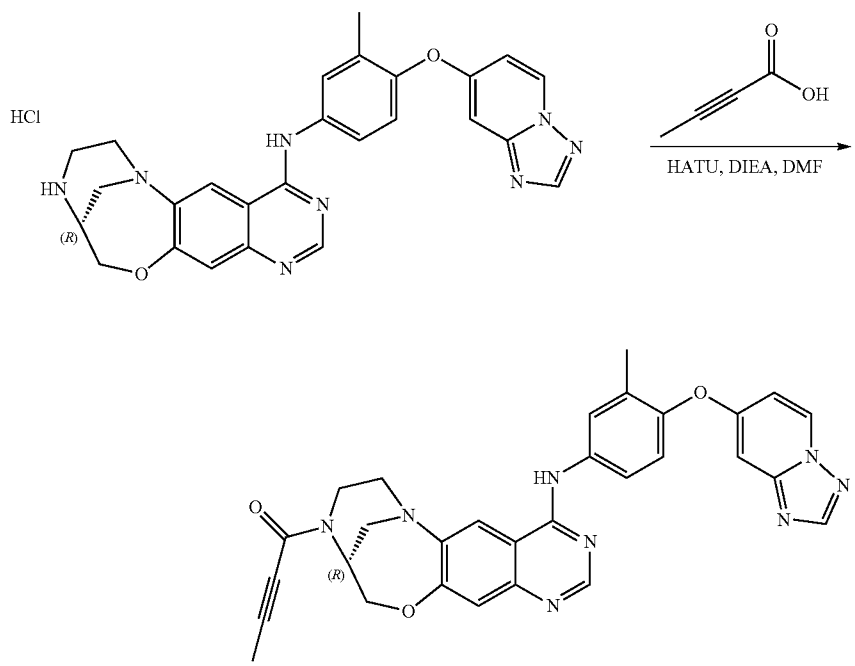

17

To a solution of (10R)—N-(4-([1,2,4]triazolo[1,5-a]pyridin-7-yloxy)-3-methylphenyl)-8,9,10,11-tetrahydro-7H-6,10-methano[1,4,7]oxadiazonino[3,2-g]quinazolin-4-amine hydrochloride (100.0 mg, crude) in DMF (2.0 mL) was added but-2-ynoic acid (19.2 mg, 0.26 mmol), HATU (162.6 mg, 0.43 mmol) and DIEA (274.0 mg, 2.1 mmol) at 0° C. under $N_2$. The resulting mixture was stirred at room temperature for 3 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash chromatography with $CH_3OH/H_2O$ (55/45, v/v) to afford 1-((10R)-4-((4-([1,2,4]triazolo[1,5-a]pyridin-7-yloxy)-3-methylphenyl)amino)-7,8,10,11-tetrahydro-9H-6,10-methano[1,4,7]oxadiazonino[3,2-g]quinazolin-9-yl)but-2-yn-1-one (Compound 17) (40.2 mg, 50%) as a yellow solid. LCMS (ESI, m/z): $[M+H]^+$ =547.4. $^1H$ NMR (400 MHz, DMSO-$d_6$): δ 9.64-9.60 (m, 1H), 8.93 (d, J=7.2 Hz, 1H), 8.47 (d, J=4.8 Hz, 1H), 8.38-8.30 (m, 2H), 7.88-7.85 (m, 2H), 7.25-7.20 (m, 2H), 7.04-7.02 (m, 1H), 6.81 (s, 1H), 4.86-4.84 (m, 1H), 4.60-4.42 (m, 1H), 4.26-4.21 (m, 1H), 4.09-4.02 (m, 1H), 3.93-3.90 (m, 0.5H), 3.77-3.63 (m, 2H), 3.60-3.44 (m, 1H), 3.28-3.20 (m, 1H), 2.20 (s, 3H), 2.07-2.05 (m, 3H).

Example S18: Synthesis of 1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)but-2-yn-1-one (Compound 18)

Step 1. Synthesis of 1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)but-2-yn-1-one (Compound 18)

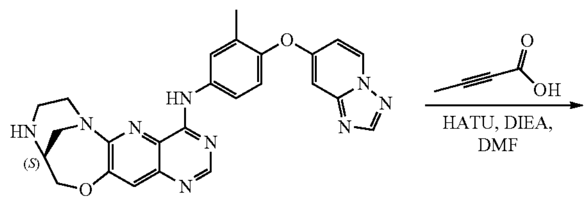

-continued

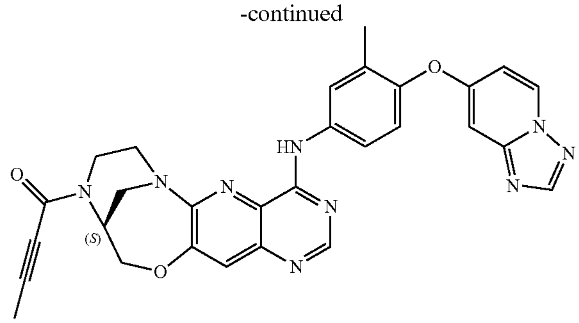

18

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (150.0 mg, crude) in DMF (5.0 mL) was added 2-butynoic acid (78.6 mg, 0.94 mmol), DIEA (161.0 mg, 1.25 mmol). and HATU (165.8 mg, 0.44 mmol) at 0° C. under $N_2$. The resulting mixture was stirred at 0° C. for 1 h. After the reaction was completed, the resulting mixture was diluted with water and extracted with EtOAc. The combined organic layer was washed with brine, dried over anhydrous sodium sulfate and filtered. The filtrate was concentrated under reduced pressure. The residue was purified by reverse phase flash column chromatography with $CH_3CN/H_2O$ (40/60, v/v) and then purified by Prep-HPLC with the following conditions (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 31% B to 41% B in 8 min; Wave Length: 254 nm) to afford 1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)but-2-yn-1-one (Compound 18) (53.7 mg, 30%) as a yellow solid. LCMS (ESI, m/z): $[M+H]^+$=548.4. $^1H$ NMR (400 MHz, DMSO-$d_6$): δ 9.54 (s, 1H), 8.94 (d, J=7.6 Hz, 1H), 8.48 (s, 1H), 8.38 (s, 1H), 8.02-8.00 (m, 2H), 7.52 (s, 1H), 7.22 (d, J=7.6 Hz, 1H), 7.03 (d, J=7.6 Hz, 1H), 6.79 (d, J=2.4 Hz, 1H), 5.05-4.97 (m, 1H), 4.81-4.63 (m, 2H), 4.27-4.07 (m, 3H), 3.75-3.42 (m, 2H), 3.26-3.21 (m, 1H), 2.20 (s, 3H), 2.07-2.05 (m, 3H).

Example S19: Synthesis of 1-((10R)-4-((4-([1,2,4]triazolo[1,5-a]pyridin-7-ylmethyl)-3-methylphenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 19)

Step 1. Synthesis of (Z)—N'-(5-bromo-6-chloro-2-cyanopyridin-3-yl)-N,N-dimethylformimidamide

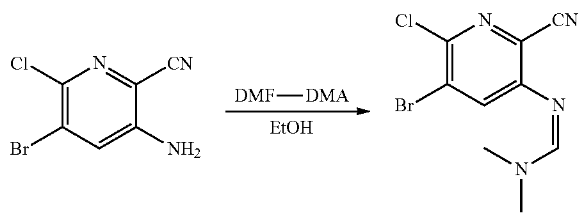

To a solution of 3-amino-5-bromo-6-chloropicolinonitrile (1.0 g, 4.30 mmol) in EtOH (20.0 mL) was added DMF-DMA (0.5 g, 4.73 mmol) at room temperature. The resulting mixture was stirred at 70° C. for 50 min. After the reaction was completed, the resulting mixture was concentrated under reduced pressure to afford (Z)—N'-(5-bromo-6-chloro-2-cyanopyridin-3-yl)-N,N-dimethylformimidamide (1.0 g, crude) as a yellow oil. LCMS (ESI, m/z): $[M+H]^+$=287.0.

Step 2. Synthesis of N-(4-([1,2,4]triazolo[1,5-a]pyridin-7-ylmethyl)-3-methylphenyl)-7-bromo-6-chloropyrido[3,2-d]pyrimidin-4-amine

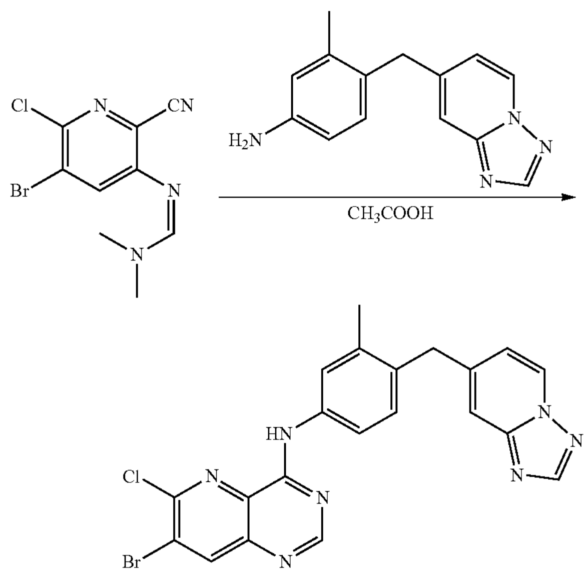

To a solution of (Z)—N'-(5-bromo-6-chloro-2-cyanopyridin-3-yl)-N,N-dimethylformimidamide (540.0 mg, 1.88 mmol) in $CH_3COOH$ (20.0 mL) was added 4-([1,2,4]triazolo[1,5-a]pyridin-7-ylmethyl)-3-methylaniline (671.3 mg, 2.82 mmol) at room temperature. The resulting mixture was stirred at 75° C. for 1 h. After the reaction was completed, the resulting mixture was concentrated under reduced pressure. The residue was purified by flash column with dichloromethane/methanol (83/17, v/v) to afford N-(4-([1,2,4]triazolo[1,5-a]pyridin-7-ylmethyl)-3-methylphenyl)-7-bromo-6-chloropyrido[3,2-d]pyrimidin-4-amine (920.0 mg, 98%) as a yellow solid. LCMS (ESI, m/z): $[M+H]^+$=480.0.

Step 3: Synthesis of tert-butyl (R)-4-(4-((4-([1,2,4]triazolo[1,5-a]pyridin-7-ylmethyl)-3-methylphenyl)amino)-7-bromopyrido[3,2-d]pyrimidin-6-yl)-2-(hydroxymethyl)piperazine-1-carboxylate

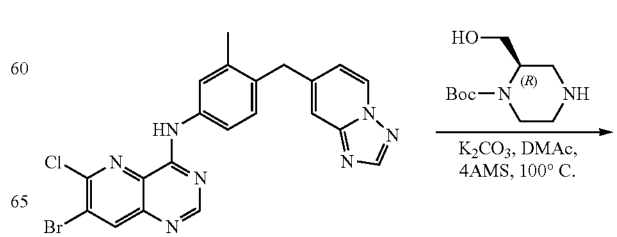

-continued

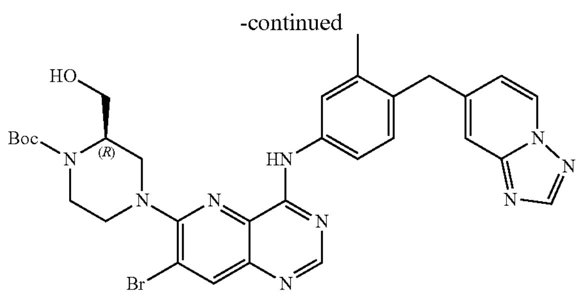

To a solution of N-(4-([1,2,4]triazolo[1,5-a]pyridin-7-ylmethyl)-3-methylphenyl)-7-bromo-6-chloropyrido[3,2-d]pyrimidin-4-amine (360.0 mg, 0.75 mmol) in DMAc (12.0 mL) was added tert-butyl (R)-2-(hydroxymethyl)piperazine-1-carboxylate (194.4 mg, 0.95 mmol), 4AMS (200.0 mg) and $K_2CO_3$ (310.5 mg, 2.25 mmol) at room temperature. The resulting mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (87/13, v/v) to afford tert-butyl (R)-4-(4-((4-([1,2,4]triazolo[1,5-a]pyridin-7-ylmethyl)-3-methylphenyl)amino)-7-bromopyrido[3,2-d]pyrimidin-6-yl)-2-(hydroxymethyl)piperazine-1-carboxylate (170.0 mg, 34%) as a yellow solid. LCMS (ESI, m/z): $[M+H]^+$=660.2.

Step 4. Synthesis of tert-butyl (10R)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonine-9-carboxylate

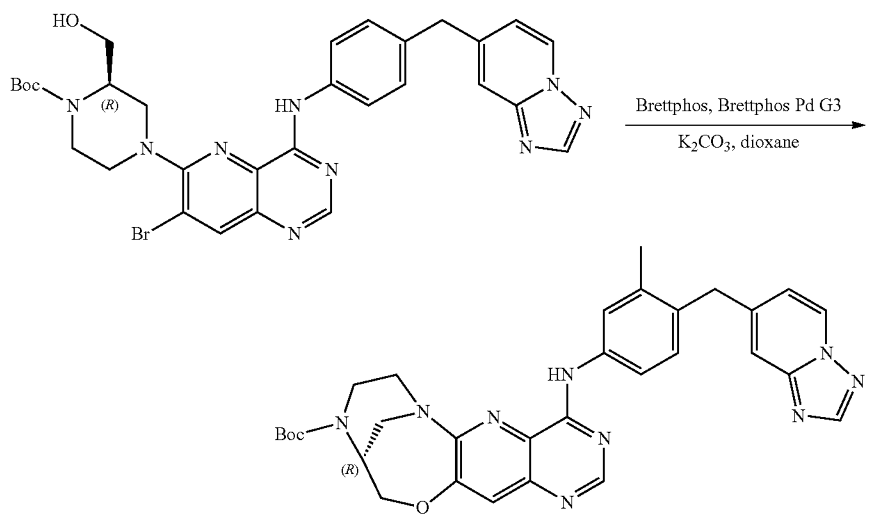

To a solution of tert-butyl (R)-4-(4-((4-([1,2,4]triazolo[1,5-a]pyridin-7-ylmethyl)-3-methylphenyl)amino)-7-bromopyrido[3,2-d]pyrimidin-6-yl)-2-(hydroxymethyl)piperazine-1-carboxylate (170.0 mg, 0.26 mmol) in 1,4-dioxane (6.0 mL) was added $K_2CO_3$ (142.3 mg, 1.03 mmol), BrettPhos Pd G3 (46.7 mg, 0.05 mmol) and BrettPhos (55.3 mg, 0.10 mmol) at room temperature under $N_2$. The resulting mixture was stirred at 100° C. for 16 h under $N_2$. After the reaction was completed, the resulting mixture was concentrated under reduced pressure. The residue was purified by flash column chromatography with ethyl acetate/MeOH (89/11, v/v) to afford tert-butyl (10R)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonine-9-carboxylate (136.0 mg, 91%) as a yellow solid. LCMS (ESI, m/z): $[M+H]^+$=580.0.

Step 5. Synthesis of (10R)—N-(4-([1,2,4]triazolo[1,5-a]pyridin-7-ylmethyl)-3-methylphenyl)-8,9,10,11-tetrahydro-7H-6,10-methanopyrimido[4',5':5,6]pyrido[3,2-b][1,4,7]oxadiazonin-4-amine hydrochloride

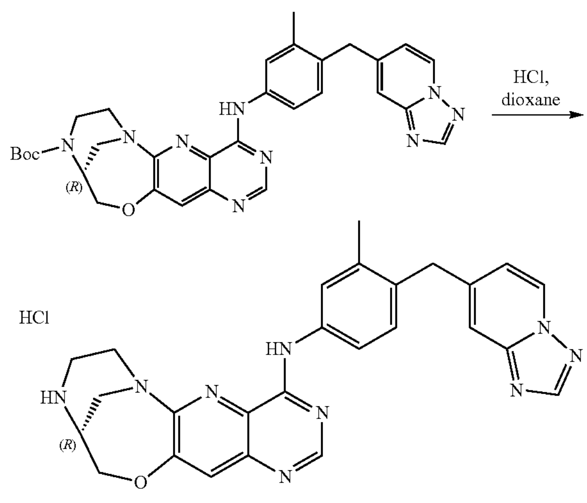

A solution of tert-butyl (10R)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonine-9-carboxylate (120.0 mg, 0.21 mmol) in HCl/1,4-dioxane (5.0 mL, 4.0 mol/L) was stirred at room temperature for 2 h. After the reaction was completed, the resulting mixture was concentrated under reduced pressure to afford (10R)—N-(4-([1,2,4]triazolo[1,5-a]pyridin-7-ylmethyl)-3-methylphenyl)-8,9,10,11-tetrahydro-7H-6,10-methanopyrimido[4',5':5,6]pyrido[3,2-b][1,4,7]oxadiazonin-4-amine hydrochloride (96.0 mg, crude) as a yellow solid. LCMS (ESI, m/z): $[M+H]^+$=480.0.

Step 6. Synthesis of 1-((10R)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 19)

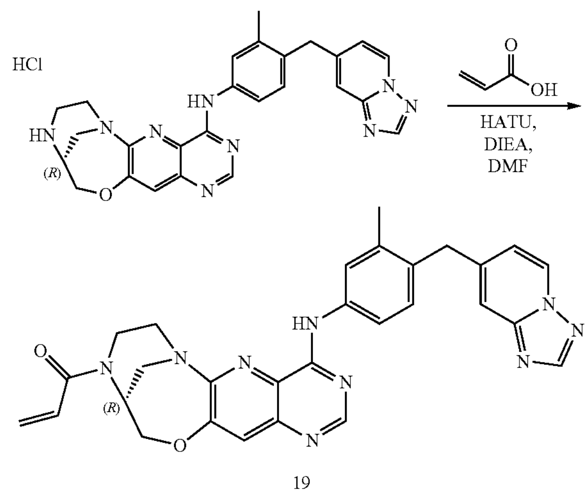

19

To a solution of (10R)—N-(4-([1,2,4]triazolo[1,5-a]pyridin-7-ylmethyl)-3-methylphenyl)-8,9,10,11-tetrahydro-7H-6,10-methanopyrimido[4',5':5,6]pyrido[3,2-b][1,4,7]oxadiazonin-4-amine hydrochloride (96.0 mg, crude) in DMF (5.0 mL) was added acrylic acid (17.3 mg, 0.24 mmol), DIEA (310.5 mg, 2.40 mmol) and HATU (152.2 mg, 0.40 mmol) at 0° C. under $N_2$. The resulting mixture was stirred at 0° C. for 1.5 h under $N_2$. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3OH/H_2O$ (80/20, v/v) and then purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 29% B to 66% B in 8 min; Wave Length: 254 nm) to afford 1-((10R)-4-((4-([1,2,4]triazolo[1,5-a]pyridin-7-ylmethyl)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 19) (8.6 mg, 8%) as a yellow solid. LCMS (ESI, m/z): $[M+H]^+$ =534.2. $^1$H NMR (400 MHz, DMSO-$d_6$): δ 9.40 (d, J=8.8 Hz, 1H), 8.85 (d, J=6.8 Hz, 1H), 8.43 (d, J=3.2 Hz, 2H), 7.90-7.80 (m, 2H), 7.50 (d, J=4.8 Hz, 2H), 7.26 (d, J=8.0 Hz, 1H), 7.02-7.00 (m, 1H), 6.91-6.80 (m, 1H), 6.15-6.10 (m, 1H), 5.74-5.71 (m, 1H), 5.12-4.64 (m, 3H), 4.27-4.05 (m, 5H), 3.91-3.60 (m, 1H), 2.26 (s, 3H).

Example S20: Synthesis of 1-((10S)-4-((3-methyl-4-((6-methylpyridin-3-yl)oxy)phenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 20)

Step 1. Synthesis of (10S)—N-(3-methyl-4-((6-methylpyridin-3-yl)oxy)phenyl)-8,9,10,11-tetrahydro-7H-6,10-methanopyrimido[4',5':5,6]pyrido[3,2-b][1,4,7]oxadiazonin-4-amine hydrochloride

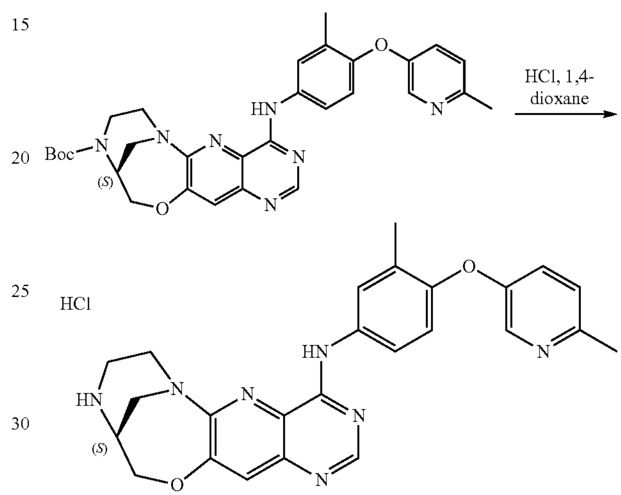

A solution of tert-butyl (10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonine-9-carboxylate (500.0 mg, 0.90 mmol) in HCl/1,4-dioxane (10.0 mL, 4.0 mol/L) was stirred at room temperature for 1 h. After the reaction was completed, the resulting mixture was concentrated under reduced pressure to afford (10S)—N-(3-methyl-4-((6-methylpyridin-3-yl)oxy)phenyl)-8,9,10,11-tetrahydro-7H-6,10-methanopyrimido[4',5':5,6]pyrido[3,2-b][1,4,7]oxadiazonin-4-amine hydrochloride (230.0 mg, crude) as a yellow solid. LCMS (ESI, m/z): $[M+H]^+$=456.2.

Step 2. Synthesis of 1-((10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 20)

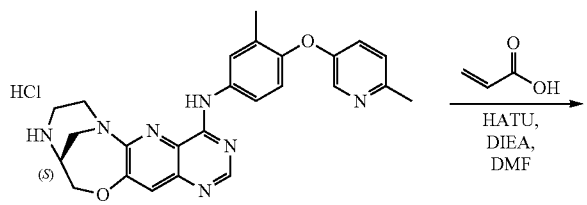

-continued

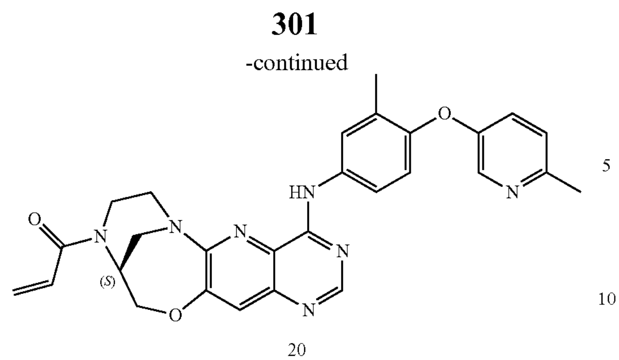

20

To a solution of (10S)—N-(3-methyl-4-((6-methylpyridin-3-yl)oxy)phenyl)-8,9,10,11-tetrahydro-7H-6,10-methanopyrimido[4',5':5,6]pyrido[3,2-b][1,4,7]oxadiazonin-4-amine hydrochloride (180.0 mg, crude) in DMF (5.0 mL) was added DIEA (510.7 mg, 3.95 mmol), acrylic acid (34.2 mg, 0.47 mmol) and HATU (300.5 mg, 0.79 mmol) at 0° C. under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (50/50, v/v) and then purified by Prep-HPLC with the following conditions: (Column: Xselect CSH C18 OBD Column 30×150 mm, 5 μm; Mobile Phase A: Water (0.1% FA), Mobile Phase B: ACN; Flow rate: 60 mL/min; Gradient: 10% B to 25% B in 12 min; Wave Length: 220 nm) to afford 1-((10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 20) (11.7 mg, 6%) as a yellow solid. LCMS (ESI, m/z): $[M+H]^+$=510.3. $^1H$ NMR (400 MHz, DMSO-$d_6$): δ 9.47-9.44 (m, 1H), 8.44 (s, 1H), 8.17 (d, J=2.4 Hz, 1H), 7.91-7.87 (m, 2H), 7.50 (s, 1H), 7.25-7.18 (m, 2H), 6.98 (d, J=8.4 Hz, 1H), 6.86-6.79 (m, 1H), 6.17-6.13 (m, 1H), 5.75-5.72 (m, 1H), 5.11-4.63 (m, 3H), 4.28-3.87 (m, 3H), 3.65-3.51 (m, 1H), 3.30-3.21 (m, 1H), 2.44 (s, 3H), 2.21 (s, 3H).

Example S21: Synthesis of (E)-4-(dimethylamino)-1-((10S)-4-((3-methyl-4-((6-methylpyridin-3-yl)oxy)phenyl)amino)-7,8,10,11-tetrahydro-9H-6,10-methanopyrimido[4,5':5,6]pyrido[3,2-b][1,4,7]oxadiazonin-9-yl)but-2-en-1-one (Compound 21)

Step 1. Synthesis of 7-bromo-6-chloro-N-(3-methyl-4-((6-methylpyridin-3-yl)oxy)phenyl)pyrido[3,2-d]pyrimidin-4-amine

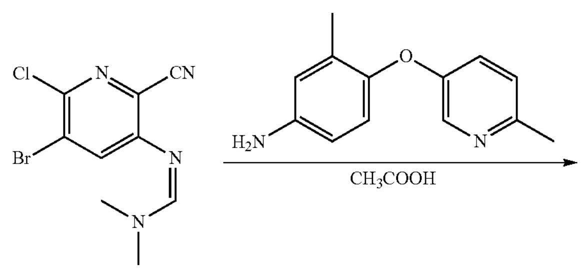

-continued

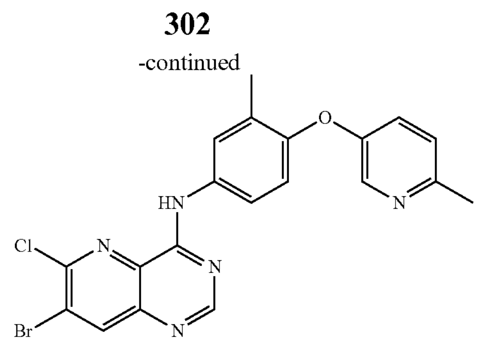

To a solution of (Z)—N'-(5-bromo-6-chloro-2-cyanopyridin-3-yl)-N,N-dimethylformimidamide (900.0 mg, 3.13 mmol) in $CH_3COOH$ (20.0 mL) was added 3-methyl-4-[(6-methylpyridin-3-yl)oxy]aniline (804.7 mg, 3.76 mmol) at room temperature. The resulting mixture was stirred at 75° C. for 1 h. After the reaction was completed, the resulting mixture was concentrated under reduced pressure. The residue was purified by flash column chromatography with $CH_2Cl_2$/MeOH (90/10, v/v) to afford 7-bromo-6-chloro-N-{3-methyl-4-[(6-methylpyridin-3-yl)oxy]phenyl}pyrido[3,2-d]pyrimidin-4-amine (1.3 g, 90%) as a yellow solid. LCMS (ESI, m/z): $[M+H]^+$=456.0.

Step 2. Synthesis of tert-butyl (S)-4-(7-bromo-4-((3-methyl-4-((6-methylpyridin-3-yl)oxy)phenyl)amino)pyrido[3,2-d]pyrimidin-6-yl)-2-(hydroxymethyl)piperazine-1-carboxylate

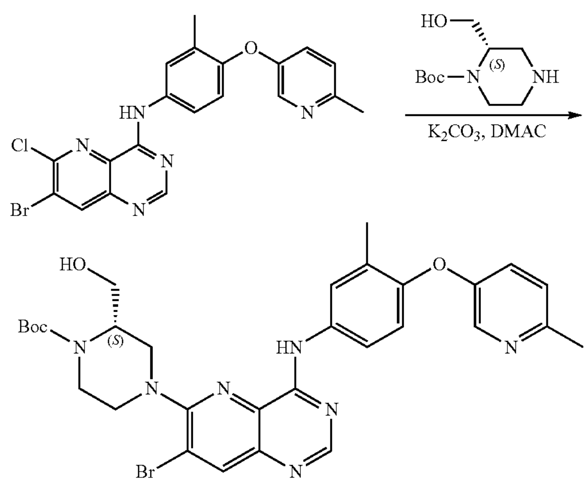

To a solution of 7-bromo-6-chloro-N-{3-methyl-4-[(6-methylpyridin-3-yl)oxy]phenyl}pyrido[3,2-d]pyrimidin-4-amine (650.0 mg, 1.42 mmol) in DMAC (15.0 mL) was added tert-butyl (2S)-2-(hydroxymethyl)piperazine-1-carboxylate (307.8 mg, 1.42 mmol) and $K_2CO_3$ (786.7 mg, 5.69 mmol) at room temperature. The resulting mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (92/8, v/v) to afford tert-butyl (2S)-4-[7-bromo-4-({3-methyl-4-[(6-methylpyridin-3-yl)oxy]phenyl}amino)pyrido[3,2-d]pyrimidin-6-yl]-2-(hydroxymethyl)piperazine-1-carboxylate (280.0 mg, 66.9%) as a yellow solid. LCMS (ESI, m/z): $[M+H]^+$=636.0.

Step 3: Synthesis of tert-butyl (10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonine-9-carboxylate

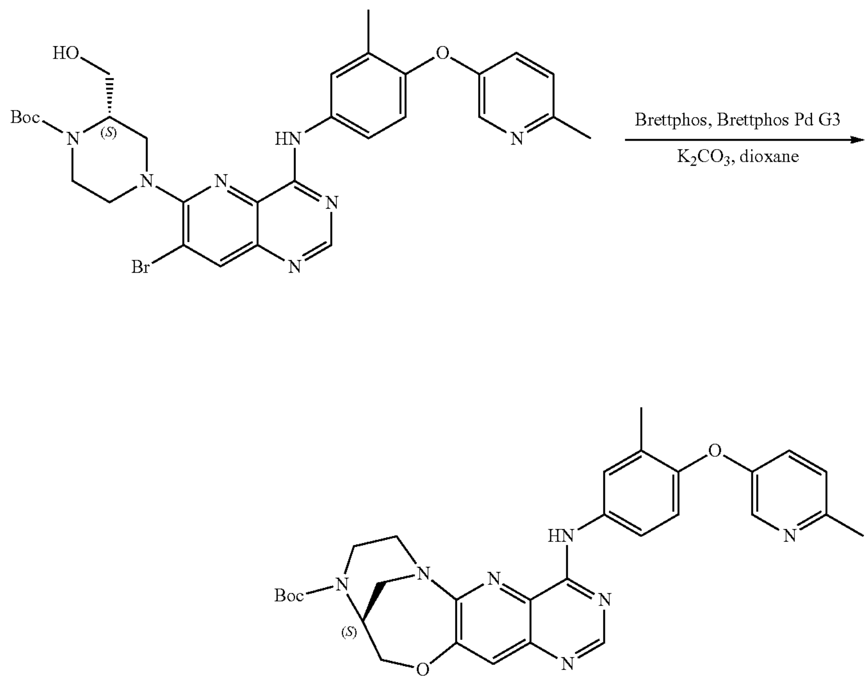

To a solution of tert-butyl (2S)-4-[7-bromo-4-({3-methyl-4-[(6-methylpyridin-3-yl)oxy]phenyl}amino)pyrido[3,2-d]pyrimidin-6-yl]-2-(hydroxymethyl)piperazine-1-carboxylate (300.0 mg, 0.47 mmol) in 1,4-dioxane (20.0 mL) was added BrettPhos (101.2 mg, 0.19 mmol), BrettPhos Pd G3 (50.6 mg, 0.09 mmol) and $K_2CO_3$ (130.3 mg, 0.94 mmol) at room temperature under $N_2$. The resulting mixture was stirred at 100° C. for 16 h. After the reaction was completed, the resulting mixture was concentrated under reduced pressure. The residue was purified by flash column chromatography with $CH_2Cl_2$/MeOH (95/5, v/v) to afford tert-butyl (10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonine-9-carboxylate (150.0 mg, 57%) as a yellow solid. LCMS (ESI, m/z): $[M+H]^+$=556.3.

Step 4. Synthesis of (10S)—N-(3-methyl-4-((6-methylpyridin-3-yl)oxy)phenyl)-8,9,10,11-tetrahydro-7H-6,10-methanopyrimido[4',5':5,6]pyrido[3,2-b][1,4,7]oxadiazonin-4-amine hydrochloride

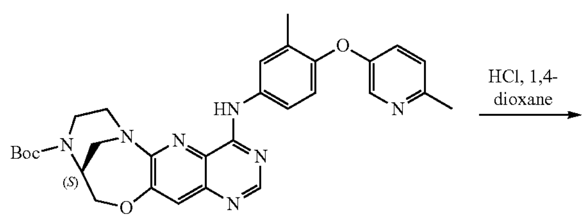

-continued

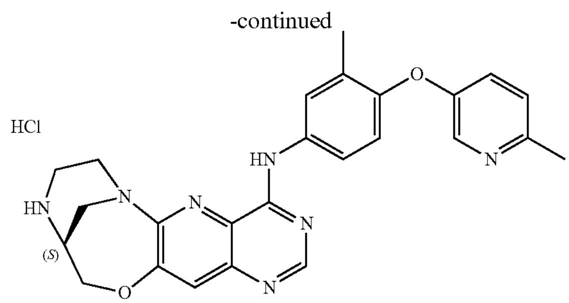

A solution of tert-butyl (10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonine-9-carboxylate (500.0 mg, 0.90 mmol) in HCl/1,4-dioxane (10.0 mL, 4 mol/L) was stirred at room temperature for 1 h. After the reaction was completed, the resulting mixture was concentrated under reduced pressure to afford (10S)—N-(3-methyl-4-((6-methylpyridin-3-yl)oxy)phenyl)-8,9,10,11-tetrahydro-7H-6,10-methanopyrimido[4',5':5,6]pyrido[3,2-b][1,4,7]oxadiazonin-4-amine hydrochloride (230.0 mg, crude) as a yellow solid. LCMS (ESI, m/z): $[M+H]^+$=456.2.

Step 5. Synthesis of (E)-4-(dimethylamino)-1-((10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 21)

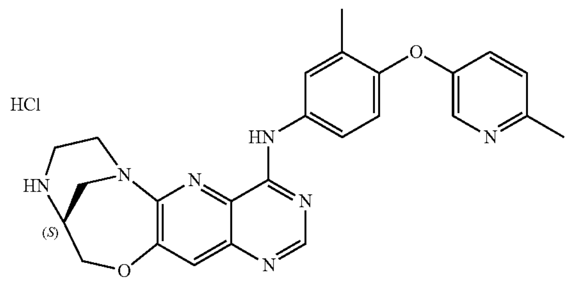

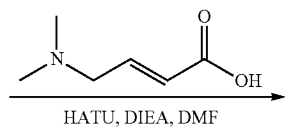

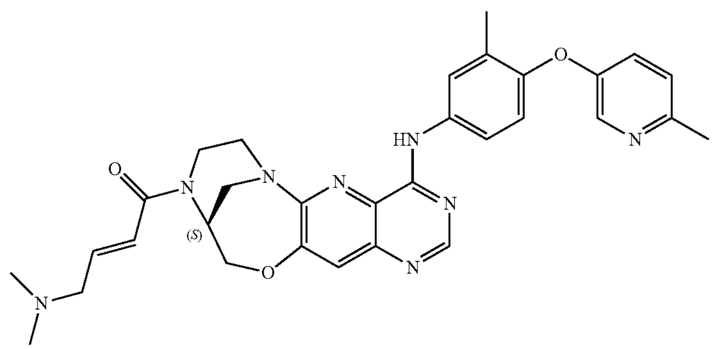

21

To a solution of (10S)—N-(3-methyl-4-((6-methylpyridin-3-yl)oxy)phenyl)-8,9,10,11-tetrahydro-7H-6,10-methanopyrimido[4',5':5,6]pyrido[3,2-b][1,4,7]oxadiazonin-4-amine hydrochloride (50.0 mg, crude) in DMF (10.0 mL) was added DIEA (141.9 mg, 1.10 mmol), (2E)-4-(dimethylamino)but-2-enoic acid (17.0 mg, 0.13 mmol) and HATU (83.5 mg, 0.22 mmol) at 0° C. under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (50/50, v/v) and then purified by Prep-HPLC with the following conditions: (Column: Xselect CSH C18 OBD Column 30×150 mm, 5 μm; Mobile Phase A: Water (0.1% FA), Mobile Phase B: ACN; Flow rate: 60 mL/min; Gradient: 7% B to 15% B in 12 min; Wave Length: 220 nm) to afford (E)-4-(dimethylamino)-1-((10S)-4-((3-methyl-4-((6-methylpyridin-3-yl)oxy)phenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 21) (14.3 mg, 23%) as a yellow solid. LCMS (ESI, m/z): $[M+H]^+$=567.3. $^1$H NMR (400 MHz, DMSO-$d_6$): δ 9.48-9.46 (m, 1H), 8.43 (s, 1H), 8.17 (s, 1H), 7.90-7.86 (m, 2H), 7.49 (s, 1H), 7.25-7.18 (m, 2H), 6.98 (d, J=8.8 Hz, 1H), 6.64 (s, 2H), 5.10-4.60 (m, 3H), 4.27-3.87 (m, 3H), 3.35-3.30 (m, 1H), 3.28-3.20 (m, 2H), 3.10-3.06 (m, 2H), 2.42 (s, 3H), 2.21-2.19 (m, 9H).

Example S22: Synthesis of 1-((10S)-4-((4-((6-ethylpyridin-3-yl)oxy)-3-methylphenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 22)

Step 1. Synthesis of (10S)—N-(4-((6-ethylpyridin-3-yl)oxy)-3-methylphenyl)-8,9,10,11-tetrahydro-7H-6,10-methanopyrimido [4',5':5,6]pyrido[3,2-b][1,4,7]oxadiazonin-4-amine hydrochloride

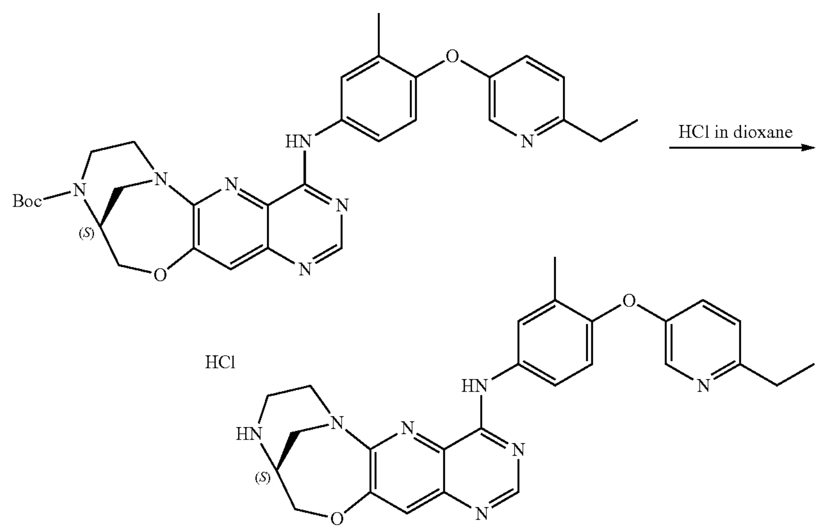

A solution of tert-butyl (10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate (250.0 mg, 0.44 mmol) in HCl/1,4-dioxane (5.0 mL, 4.0 mol/L) was stirred at room temperature for 1 h. After the reaction was completed, the mixture was concentrated under reduce pressure to afford (10S)—N-(4-((6-ethylpyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine hydrochloride (200.0 mg, crude) as yellow solid. LCMS (ESI, m/z): $[M+H]^+=470.2$.

Step 2. Synthesis of 1-((10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 22)

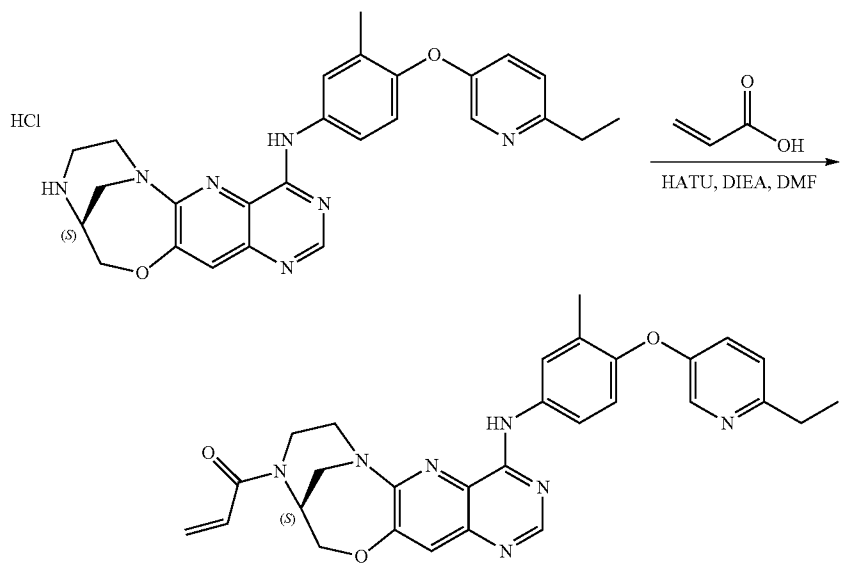

22

To a solution of (10S)—N-(4-((6-ethylpyridin-3-yl)oxy)-3-methylphenyl)-8,9,10,11-tetrahydro-7H-6,10-methanopyrimido [4',5':5,6]pyrido[3,2-b][1,4,7]oxadiazonin-4-amine hydrochloride (200.0 mg, crude) in DMF (5.0 mL) was added DIEA (165.2 mg, 1.28 mol), acrylic acid (36.8 mg, 0.51 mmol) and HATU (485.9 mg, 1.28 mmol) at 0° C. under $N_2$. The resulting mixture was stirred at room temperature for 30 min. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3OH/H_2O$ (80/20, v/v) and then purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 41% B to 46% B in 8 min; Wave Length: 254 nm) to afford 1-((10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 22) (12.5 mg, 6%) as a yellow solid. LCMS (ESI, m/z): $[M+H]^+$=524.4. $^1H$ NMR (400 MHz, DMSO-$d_6$): δ 9.48-9.46 (m, 1H), 8.44 (s, 1H), 8.21 (d, J=2.8 Hz, 1H), 7.92-7.87 (m, 2H), 7.50 (s, 1H), 7.27-7.20 (m, 2H), 6.99 (d, J=8.8 Hz, 1H), 6.85-6.77 (m, 1H), 6.18-6.13 (m, 1H), 5.75-5.72 (m, 1H), 5.12-4.61 (m, 3H), 4.28-4.19 (m, 1H), 4.15-4.03 (m, 1H), 3.91-3.59 (m, 1H), 3.32-3.28 (m, 2H), 2.76-2.70 (m, 2H), 2.22 (s, 3H), 1.24-1.20 (m, 3H).

Example S23: Synthesis of 1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-2-fluoroprop-2-en-1-one (Compound 23)

Step 1. Synthesis of 1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-2-fluoroprop-2-en-1-one (Compound 23)

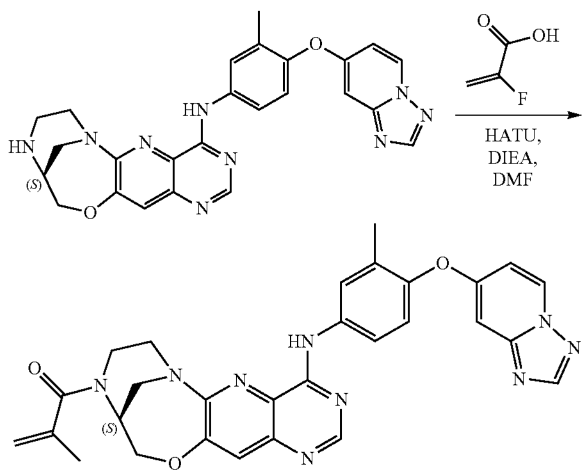

23

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (200.0 mg, 0.42 mmol) in DMF (2.0 mL) was added 2-fluoroacrylic acid (56.1 mg, 0.62 mmol), DIEA (214.7 mg, 1.66 mmol) and HATU (315.9 mg, 0.83 mmol) at room temperature. The resulting mixture was stirred at room temperature for 1 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions Column: (XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 31% B to 41% B in 8 min; Wave Length: 254 nm) to afford 1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-2-fluoroprop-2-en-1-one (Compound 23) (27.8 mg, 12%) as a yellow solid. LCMS (ESI, m/z): $[M+H]^+$=554.2. $^1H$ NMR (400 MHz, DMSO-$d_6$): δ 9.54 (s, 1H), 8.93 (d, J=7.6 Hz, 1H), 8.48 (s, 1H), 8.38 (s, 1H), 8.00 (s, 2H), 7.54 (s, 1H), 7.22 (d, J=9.2 Hz, 1H), 7.03 (d, J=6.8 Hz, 1H), 6.79 (s, 1H), 5.35-5.30 (m, 1H), 5.17-4.93 (m, 1H), 4.84-4.62 (m, 2H), 4.26-4.15 (m, 2H), 3.93-3.68 (m, 1H), 3.51-3.37 (m, 1H), 2.20 (s, 3H).

Example S24: Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 24)

Step 1. Synthesis of [1,2,4]triazolo[1,5-a]pyridin-7-ol

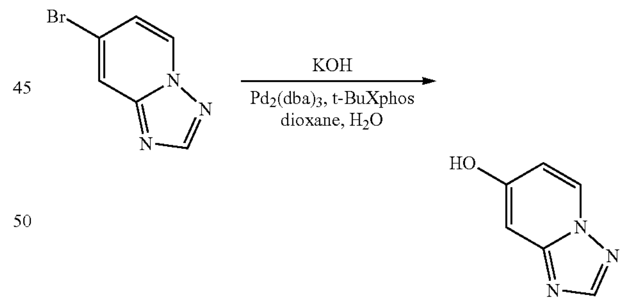

To a solution of 7-bromo-[1,2,4]triazolo[1,5-a]pyridine (501.0 mg, 2.53 mmol) in 1,4-dioxane (8.0 mL)/$H_2O$ (2.0 mL) was added KOH (625.7 mg, 11.15 mmol), $Pd_2(dba)_3$ (263.1 mg, 0.28 mmol) and t-BuXPhos (231.1 mg, 0.54 mmol) at room temperature. The resulting mixture was stirred at 100° C. for 4 h. After the reaction was completed, the resulting mixture was cooled to room temperature and diluted with water. The aqueous layer was adjusted to pH ~5 with 1N HCl and extracted with EtOAc. The combined organic layer was washed with brine, dried over anhydrous sodium sulfate and filtered. The filtrate was concentrated under reduced pressure. The residue was purified by flash column chromatography with $CH_2Cl_2$/MeOH (5/1, v/v) to afford [1,2,4]triazolo[1,5-a]pyridin-7-ol (140.0 mg, 40%) as a white solid. LCMS (ESI, m/z): $[M+H]^+$=136.0.

Step 2. Synthesis of 7-(5-fluoro-2-methyl-4-nitrophenoxy)-[1,2,4]triazolo[1,5-a]pyridine

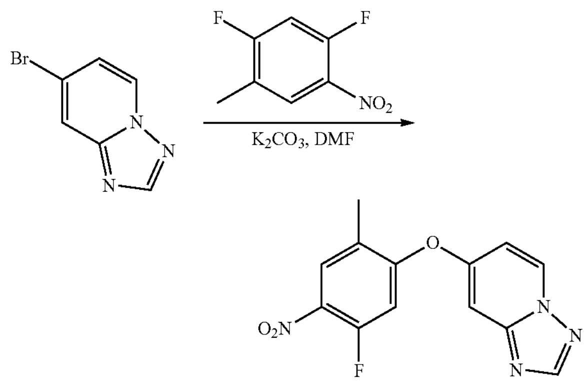

To a solution of [1,2,4]triazolo[1,5-a]pyridin-7-ol (1.3 g, 9.62 mmol) in DMF (30.0 mL) was added 1,5-difluoro-2-methyl-4-nitrobenzene (5.0 g, 28.86 mmol) and $K_2CO_3$ (8.0 g, 57.72 mmol) at room temperature. The resulting mixture was stirred at room temperature for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (2/1, v/v) to afford 7-(5-fluoro-2-methyl-4-nitrophenoxy)-[1,2,4]triazolo[1,5-a]pyridine (1.1 g, 39%) as a white solid. LCMS (ESI, m/z): $[M+H]^+$=289.1. $^1$H NMR (400 MHz, DMSO-$d_6$): δ 9.03 (d, J=7.5 Hz, 1H), 8.48 (s, 1H), 8.29-8.23 (m, 1H), 7.45-7.35 (m, 2H), 7.16-7.08 (m, 1H), 2.30 (s, 3H). MS (ESI, m/z): 289 $(M+H)^+$.

Step 3. Synthesis of 2-fluoro-5-methyl-4-[[1,2,4]triazolo[1,5-a]pyridin-7-yloxy]aniline

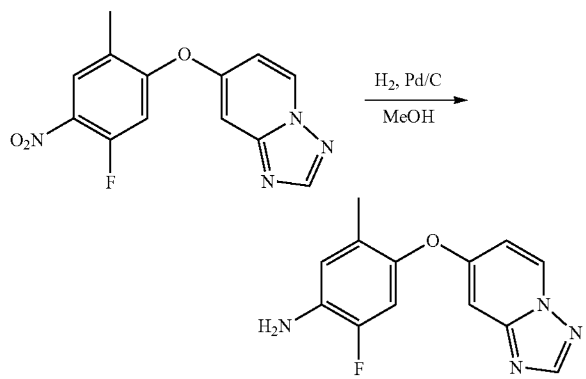

To a solution of 7-(5-fluoro-2-methyl-4-nitrophenoxy)-[1,2,4]triazolo[1,5-a]pyridine (500.0 mg, 1.73 mmol) in MeOH (10.0 mL) was added Pd/C (150.0 mg, dry) at room temperature. The resulting mixture was stirred at room temperature for 2 h under $H_2$. After the reaction was completed, the resulting mixture was filtered. The filtrate was concentrated under reduced pressure to afford 2-fluoro-5-methyl-4-[[1,2,4]triazolo[1,5-a]pyridin-7-yloxy]aniline (380.0 mg, crude) as a white solid. LCMS (ESI, m/z): $[M+H]^+$=259.1.

Step 4. Synthesis of 7-bromo-6-chloro-N-(2-fluoro-5-methyl-4-{[1,2,4]triazolo[1,5-a]pyridin-7-yloxy}phenyl)pyrido[3,2-d]pyrimidin-4-amine

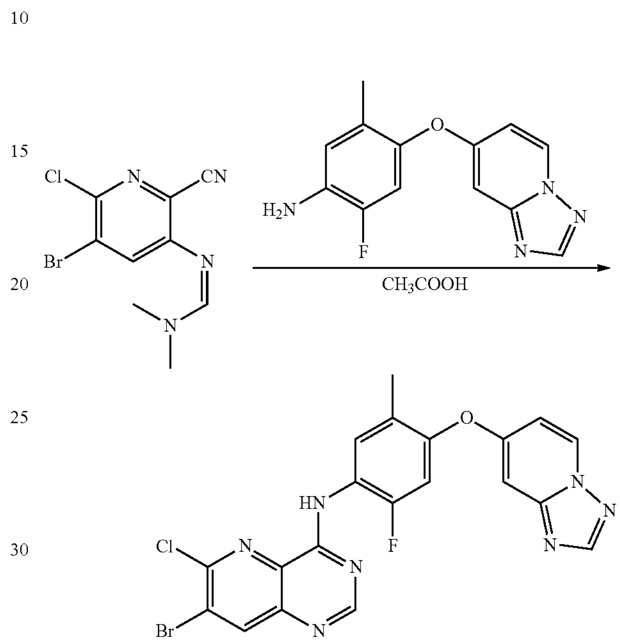

To a solution of (Z)—N'-(5-bromo-6-chloro-2-cyanopyridin-3-yl)-N,N-dimethylmethanimidamide (800.0 mg, 2.78 mmol) in $CH_3COOH$ (10.0 mL) was added 2-fluoro-5-methyl-4-{[1,2,4]triazolo[1,5-a]pyridin-7-yloxy}aniline (718.5 mg, 2.78 mmol) at room temperature. The resulting mixture was stirred at 90° C. for 16 h. After the reaction was completed, the resulting mixture was concentrated under vacuum. The residue was purified by flash column chromatography with $CH_2Cl_2$/MeOH (10/1, v/v) to afford 7-bromo-6-chloro-N-(2-fluoro-5-methyl-4-{[1,2,4]triazolo[1,5-a]pyridin-7-yloxy}phenyl)pyrido[3,2-d]pyrimidin-4-amine (1.0 g, 50%) as a yellow solid. LCMS (ESI, m/z): $[M+H]^+$=500.0.

Step 5. Synthesis of tert-butyl (2S)-4-{7-bromo-4-[(2-fluoro-5-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate

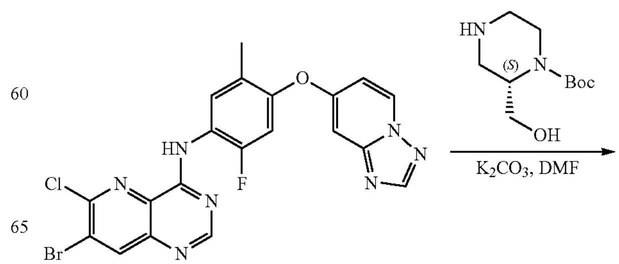

-continued

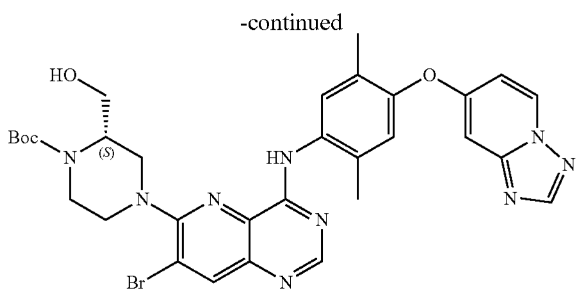

To a solution of 7-bromo-6-chloro-N-(2-fluoro-5-methyl-4-{[1,2,4]triazolo[1,5-a]pyridin-7-yloxy}phenyl)pyrido[3,2-d]pyrimidin-4-amine (1.0 g, 1.99 mmol) in DMF (10.0 mL) was added tert-butyl (2S)-2-(hydroxymethyl)piperazine-1-carboxylate (431.9 mg, 1.99 mmol) and $K_2CO_3$ (828.0 mg, 5.99 mmol) at room temperature. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (2S)-4-{7-bromo-4-[(2-fluoro-5-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (700.0 mg, 50%) as a yellow solid. LCMS (ESI, m/z): $[M+H]^+$=680.2.

Step 6: Synthesis of tert-butyl (10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonine-9-carboxylate

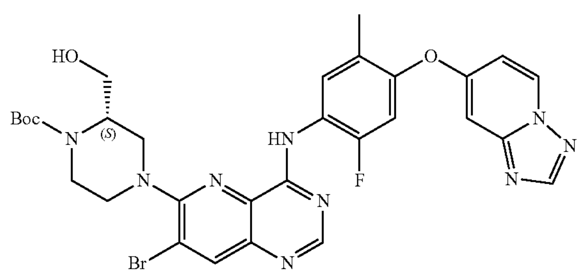

Brettphos Pd G3, Brettphos

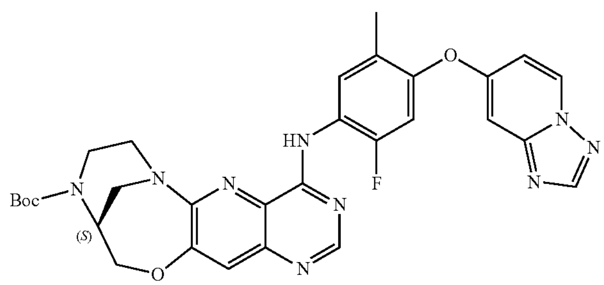

To a solution of tert-butyl (2S)-4-{7-bromo-4-[(2-fluoro-5-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (680.0 mg, 0.99 mmol) in dioxane (20.0 mL) was added $K_2CO_3$ (414.2 mg, 2.99 mmol), BrettPhos (107.2 mg, 0.20 mmol) and BrettPhos Pd G3 (90.5 mg, 0.10 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonine-9-carboxylate (400.0 mg, 66%) as a light yellow solid. LCMS (ESI, m/z): $[M+H]^+$=600.2.

Step 7. Synthesis of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine

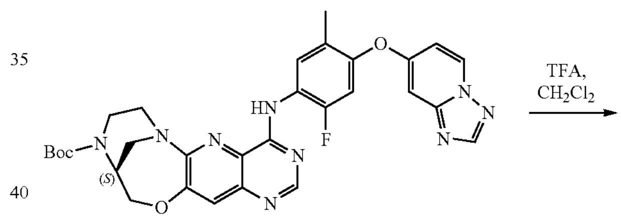

-continued

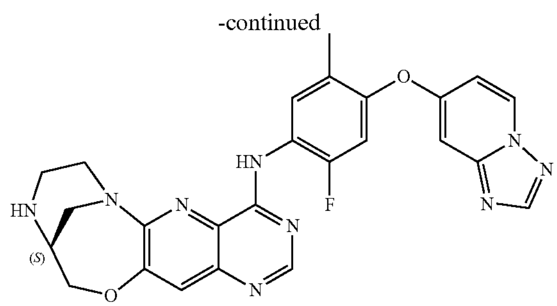

A solution of tert-butyl (10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonine-9-carboxylate (400.0 mg, 0.66 mmol) and TFA (4.0 mL) in $CH_2Cl_2$ (8.0 mL) was stirred at room temperature for 1 h. After the reaction was completed, the mixture was basified to pH=8 with saturated $NaHCO_3$ (aq.). The resulting mixture was extracted with $CH_2Cl_2$. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (300.0 mg, 90%) as a light yellow solid. LCMS (ESI, m/z): $[M+H]^+$=500.2.

Step 8. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 24)

To a solution of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (150.0 mg, 0.30 mmol) in DMF (4.0 mL) was added (2E)-4-(dimethylamino)but-2-enoic acid hydrochloride (38.7 mg, 0.30 mmol), DIEA (194.0 mg, 1.50 mmol) and HATU (228.3 mg, 0.60 mmol) at 0° C. under $N_2$. The resulting mixture was stirred at room temperature for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (50/50, v/v) and then purified by Prep-HPLC with the following conditions: (Column: XSelect CSH Prep C18 OBD Column, 19×250 mm, 5 μm; Mobile Phase A: Water (10 mmol/L $NH_4HCO_3$), Mobile Phase B: MeOH—HPLC; Flow rate: 25 mL/min; Gradient: 67% B to 67% B in 12 min; Wave Length: 254 nm) to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 24) (10.7 mg, 5%) as a light yellow solid. LCMS (ESI, m/z): $[M+H]^+$=611.4. $^1H$ NMR (400 MHz, DMSO-$d_6$): δ 9.39 (s, 1H), 8.97 (d, J=7.2 Hz, 1H), 8.42 (d, J=5.2 Hz, 2H), 8.01 (d, J=8.8 Hz, 1H), 7.53 (s, 1H), 7.32 (d, J=10.8 Hz, 1H), 7.07-7.05 (m, 1H), 6.92 (d, J=2.0 Hz, 1H), 6.69-6.57 (m, 2H), 5.11-4.79 (m, 1H), 4.78-4.55 (m, 2H), 4.28-4.04 (m, 3H), 3.90-3.67 (m, 1H), 3.48-3.34 (m, 1H), 3.31-3.20 (m, 1H), 3.05-2.99 (m, 2H), 2.20-2.15 (m, 9H).

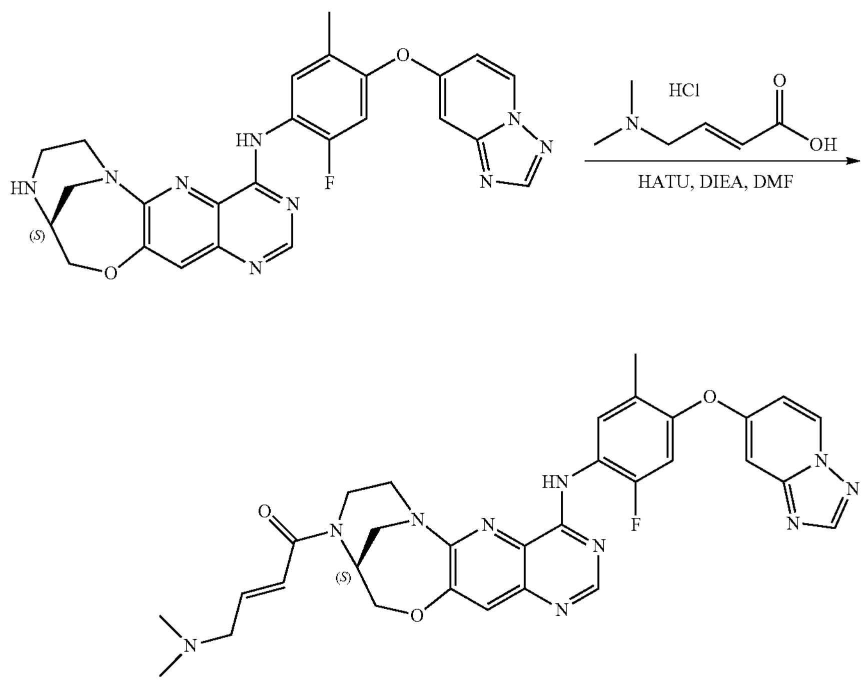

24

Example S25: Synthesis of (E)-4-(dimethylamino)-1-((10S)-4-((3-methyl-4-(pyridin-3-yloxy)phenyl)amino)-7,8,10,11-tetrahydro-9H-6,10-methanopyrimido[4,5':5,6]pyrido[3,2-b][1,4,7]oxadiazonin-9-yl)but-2-en-1-one (Compound 25)

Step 1. Synthesis of 7-bromo-6-chloro-N-[3-methyl-4-(pyridin-3-yloxy) phenyl]pyrido[3,2-d]pyrimidin-4-amine

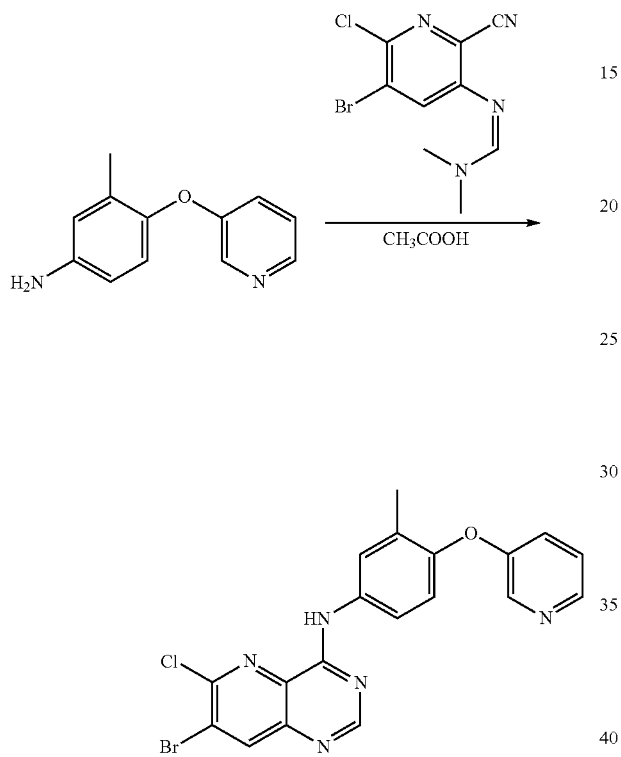

To a mixture of (Z)—N'-(5-bromo-6-chloro-2-cyanopyridin-3-yl)-N,N-dimethylmethanimidamide (1.0 g, 3.48 mmol) in acetic acid (15.0 mL) was added 3-methyl-4-(pyridin-3-yloxy)aniline (696.4 mg, 3.48 mmol) at room temperature. The resulting mixture was stirred at 80° C. for 2 h. After the reaction was completed, the resulting mixture was concentrated under reduced pressure. The residue was purified by flash column chromatography with petroleum ether/ethyl acetate (1/1, v/v) to afford 7-bromo-6-chloro-N-[3-methyl-4-(pyridin-3-yloxy)phenyl]pyrido[3,2-d]pyrimidin-4-amine (2.0 g, 90%) as a yellow solid. LCMS (ESI, m/z): $[M+H]^+$=442.1.

Step 2. Synthesis of tert-butyl (2S)-4-(7-bromo-4-{[3-methyl-4-(pyridin-3-yloxy)phenyl]amino}pyrido[3,2-d]pyrimidin-6-yl)-2-(hydroxymethyl)piperazine-1-carboxylate

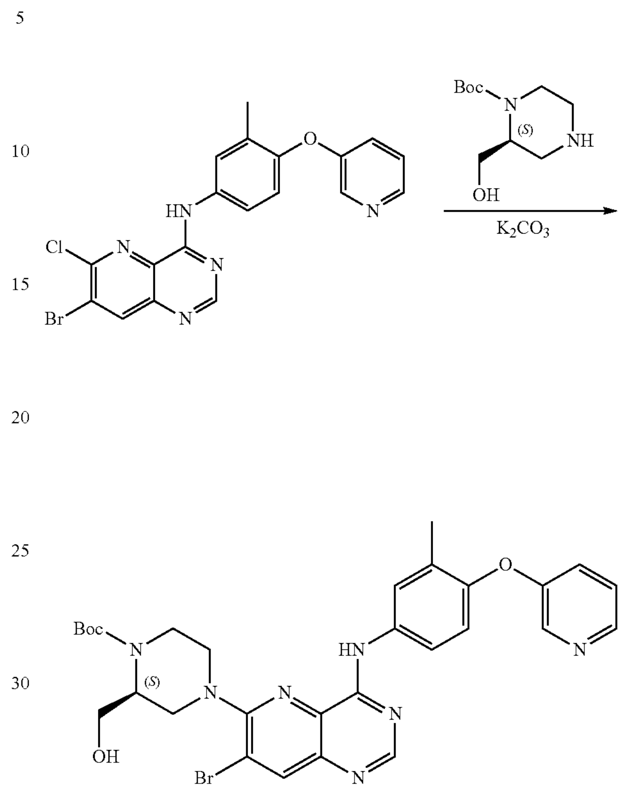

To a mixture of 7-bromo-6-chloro-N-[3-methyl-4-(pyridin-3-yloxy)phenyl]pyrido[3,2-d]pyrimidin-4-amine (2.0 g, 4.52 mmol) and tert-butyl (2S)-2-(hydroxymethyl)piperazine-1-carboxylate (1.5 g, 6.80 mmol) in ACN (50.0 mL) was added $K_2CO_3$ (3.8 g, 27.10 mmol) at room temperature. The resulting mixture was stirred at 80° C. for 16 h. After the reaction was completed, the mixture was filtered. The filtrate was concentrated under reduced pressure. The residue was purified by flash column chromatography with dichloromethane/methanol (10/1, v/v) to afford tert-butyl (2S)-4-(7-bromo-4-{[3-methyl-4-(pyridin-3-yloxy)phenyl]amino}pyrido[3,2-d]pyrimidin-6-yl)-2-(hydroxymethyl)piperazine-1-carboxylate (2.4 g, 85%) as a yellow solid. LCMS (ESI, m/z): $[M+H]^+$=622.5.

Step 3: Synthesis of tert-butyl (10S)-4-((3-methyl-4-(pyridin-3-yloxy)phenyl)amino)-7,8,10,11-tetrahydro-9H-6,10-methanopyrimido[4',5':5,6]pyrido[3,2-b][1,4,7]oxadiazonine-9-carboxylate

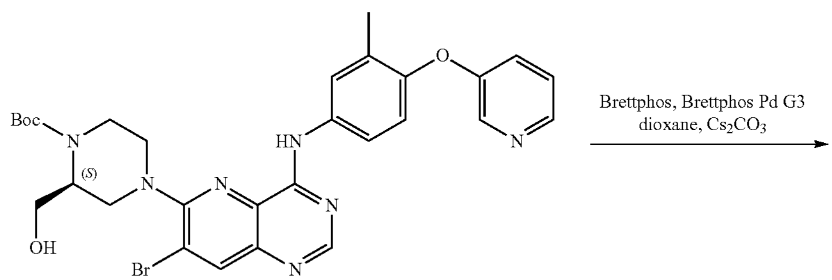

-continued

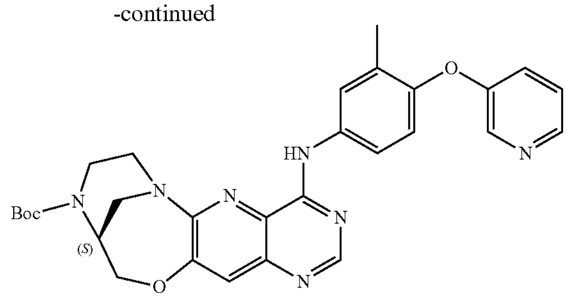

To a mixture of tert-butyl (S)-4-(7-bromo-4-((3-methyl-4-(pyridin-3-yloxy)phenyl)amino)pyrido[3,2-d]pyrimidin-6-yl)-2-(hydroxymethyl)piperazine-1-carboxylate (2.4 g, 3.86 mmol) in dioxane (50.0 mL) was added $Cs_2CO_3$ (3.8 g, 11.6 mmol), Brettphos (0.8 g, 1.5 mmol) and Brettphos Pd G3 (0.7 g, 0.8 mmol) at room temperature. The resulting mixture was stirred at 100° C. for 16 h under $N_2$. After the reaction was completed, the resulting mixture was diluted with EtOAc and filtered. The filtrate was washed with brine, dried over anhydrous sodium sulfate and filtered. The filtrate was concentrated under reduced pressure. The residue was purified by flash column chromatography with dichloromethane/methanol (10/1, v/v) to afford tert-butyl (10S)-4-((3-methyl-4-(pyridin-3-yloxy)phenyl)amino)-7,8,10,11-tetrahydro-9H-6,10-methanopyrimido[4',5':5,6]pyrido[3,2-b][1,4,7]oxadiazonine-9-carboxylate (1.7 g, 80%) as a yellow solid. LCMS (ESI, m/z): $[M+H]^+$=542.1.

Step 4. Synthesis of (10S)—N-(3-methyl-4-(pyridin-3-yloxy)phenyl)-8,9,10,11-tetrahydro-7H-6,10-methanopyrimido[4',5':5,6]pyrido[3,2-b][1,4,7]oxadiazonin-4-amine

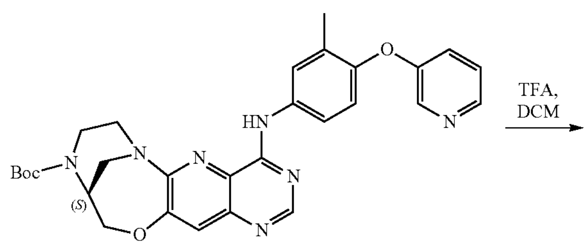

-continued

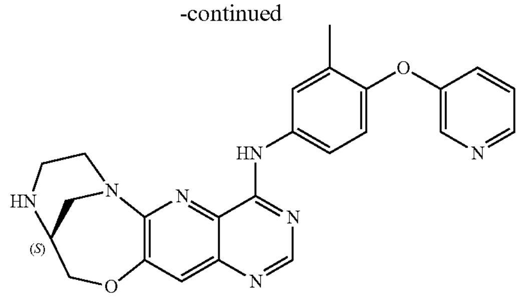

A mixture of tert-butyl (10S)-4-((3-methyl-4-(pyridin-3-yloxy)phenyl)amino)-7,8,10,11-tetrahydro-9H-6,10-methanopyrimido[4',5':5,6]pyrido[3,2-b][1,4,7]oxadiazonine-9-carboxylate (1.0 g, 1.90 mmol) in DCM (10.0 mL) and TFA (5.0 mL) was stirred at room temperature for 30 min. After the reaction was completed, the resulting mixture was neutralized to pH=8 with saturated $NaHCO_3$(aq). The resulting mixture was extracted with DCM. The combined organic layers were washed with brine, dried over anhydrous sodium sulfate and filtered. The filtrate was concentrated under reduced pressure. The residue was purified by flash column chromatography with dichloromethane/methanol (10/1, v/v) to afford (10S)—N-(3-methyl-4-(pyridin-3-yloxy)phenyl)-8,9,10,11-tetrahydro-7H-6,10-methanopyrimido[4',5':5,6]pyrido[3,2-b][1,4,7]oxadiazonin-4-amine (600.0 mg, 74%) as a yellow solid. LCMS (ESI, m/z): $[M+H]^+$=442.2.

Step 5. Synthesis of (E)-4-(dimethylamino)-1-((10S)-4-((3-methyl-4-(pyridin-3-yloxy)phenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 25)

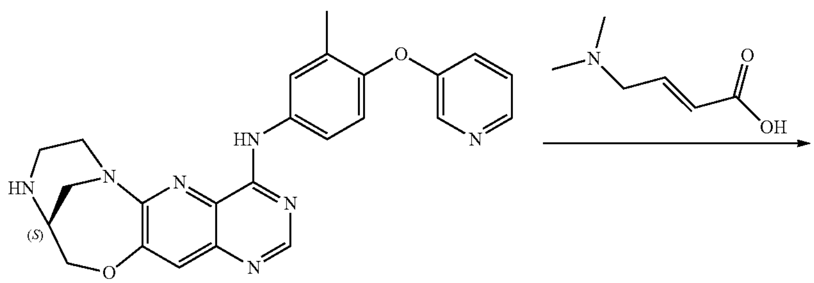

-continued

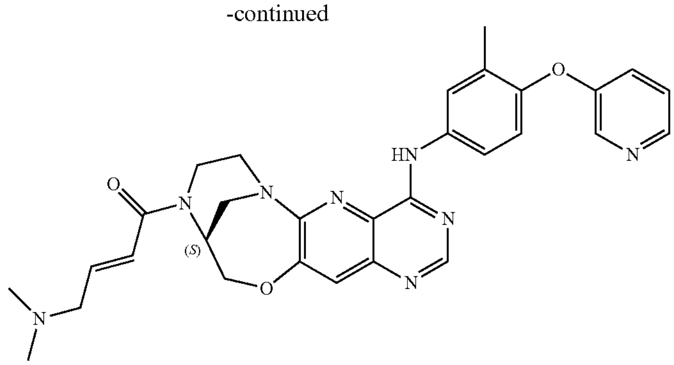

25

To a stirred mixture of (10S)—N-(3-methyl-4-(pyridin-3-yloxy)phenyl)-8,9,10,11-tetrahydro-7H-6,10-methanopyrimido[4',5':5,6]pyrido[3,2-b][1,4,7]oxadiazonin-4-amine (340.0 mg, 0.77 mmol) and (2E)-4-(dimethylamino)but-2-enoic acid (199.5 mg, 1.54 mmol) in pyridine (5.0 mL) was added EDCI (296.1 mg, 1.54 mmol) at room temperature. The resulting mixture was stirred at room temperature for 1 h. After the reaction was completed, the resulting mixture was concentrated under reduced pressure. The residue was purified by flash column chromatography with dichloromethane/methanol (10/1, v/v) and then purified by Prep-HPLC with the following conditions: (Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 34% B to 50% B in 8 min; Wave Length: 254 nm) to afford (E)-4-(dimethylamino)-1-((10S)-4-((3-methyl-4-(pyridin-3-yloxy)phenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 25) (41.0 mg, 9%) as a light yellow solid. LCMS (ESI, m/z): $[M+H]^+$=553.4. $^1H$ NMR (400 MHz, DMSO-$d_6$): δ 9.51-9.48 (m, 1H), 8.45 (s, 1H), 8.33-8.30 (m, 2H), 7.93-7.89 (m, 2H), 7.50 (s, 1H), 7.42-7.38 (m, 1H), 7.29-7.25 (m, 1H), 7.05 (d, J=8.0 Hz, 1H), 6.66-6.64 (m, 2H), 5.11-4.60 (m, 4H), 4.27-4.18 (m, 2H), 4.14-4.03 (m, 1H), 3.88-3.66 (m, 2H), 3.23-3.15 (m, 2H), 2.25-2.20 (m, 9H).

Example S26: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(azetidin-1-yl)but-2-en-1-one (Compound 26)

Step 1. Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one

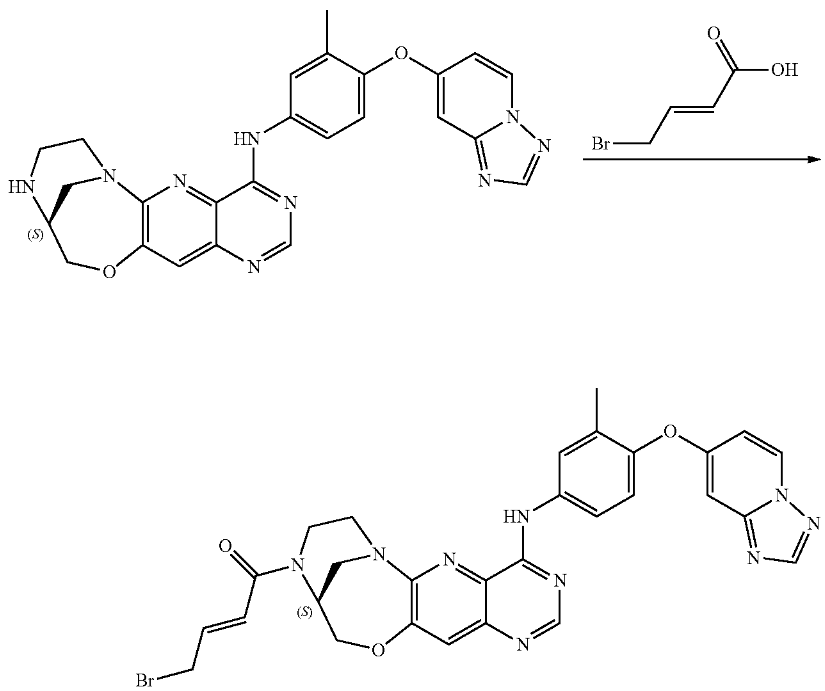

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (200.0 mg, 0.42 mmol) in THE (5.0 mL) was added 4-bromo-trans-crotonic acid (68.5 mg, 0.42 mmol) and EDCI (159.3 mg, 0.83 mmol) at room temperature. The resulting mixture was stirred at room temperature for 2 h. After the reaction was completed, the reaction mixture was diluted with water and extracted with ethyl acetate. The combined organic layers were washed with brine, dried over anhydrous $Na_2SO_4$ and filtered. The filtrate was concentrated under reduced pressure to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (200.0 mg, crude) as a yellow solid. LCMS (ESI, m/z): $[M+H]^+$=628.1.

Step 2. Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(azetidin-1-yl)but-2-en-1-one (Compound 26)

To a solution of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (200.0 mg, crude) in THE (5.0 mL) was added TEA (96.6 mg, 0.95 mmol) and azetidine (18.2 mg, 0.32 mmol) at room temperature. The resulting mixture was stirred at room temperature for 0.5 h. After the reaction was completed, the mixture was concentrated under reduced pressure. The residue was purified by flash column chromatography with $CH_2Cl_2$/MeOH (8/1, v/v) and then purified by Prep-HPLC with the following conditions: (Column: XSelect CSH Prep C18 OBD Column, 19×250 mm, m; Mobile Phase A: Water (10 mmol/L $NH_4HCO_3$), Mobile Phase B: MeOH—HPLC; Flow rate: 20 mL/min; Gradient: 71% B to 71% B in 11 min; Wave Length: 254 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(azetidin-1-yl)but-2-en-1-one (Compound 26) (4.8 mg, 2%) as a yellow solid. LCMS (ESI, m/z): $[M+H]^+$=605.4. $^1$H NMR (400 MHz, DMSO-$d_6$): δ 9.52 (s, 1H), 8.94 (d, J=7.2 Hz, 1H), 8.48 (s, 1H), 8.38 (s, 1H), 8.03-7.97 (m, 2H), 7.51 (s, 1H), 7.22 (d, J=9.2 Hz, 1H), 7.03 (d, J=7.6 Hz, 1H), 6.79 (d, J=1.6 Hz, 1H), 6.54-6.48 (m, 2H), 5.10-4.60 (m, 3H), 4.31-3.62 (m, 5H), 3.18-3.12 (m, 5H), 2.21 (s, 3H), 2.03-1.92 (m, 2H).

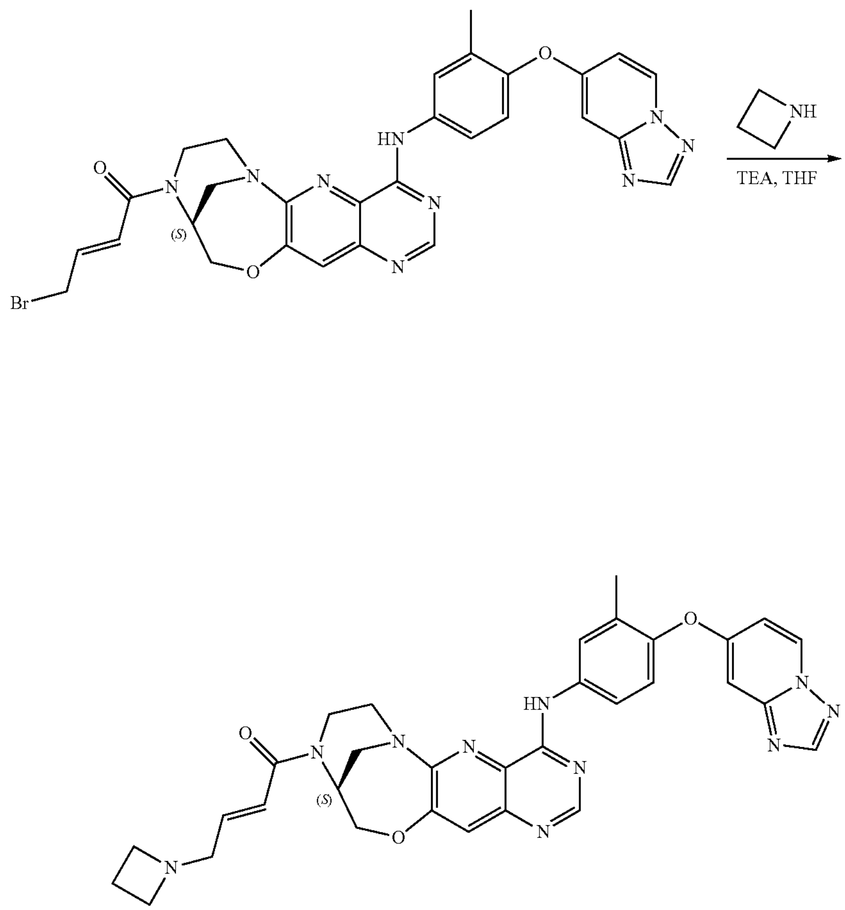

Example S27: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-((S)-1-methylpyrrolidin-2-yl)prop-2-en-1-one (Compound 28)

Step 1. Synthesis of (S)-pyrrolidine-2-carbaldehyde

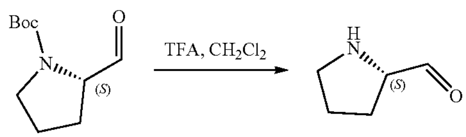

To a solution of tert-butyl (S)-2-formylpyrrolidine-1-carboxylate (10.0 g, 50.25 mmol) in $CH_2Cl_2$ (100.0 mL) was added TFA (30.0 mL) at room temperature. The resulting mixture was stirred at room temperature for 4 h. After the reaction was completed, the mixture was concentrated under reduced pressure. The pH value of the residue was adjusted to 8.0 with saturated $NaHCO_3$(aq.). The mixture was extracted with ethyl acetate. The combined organic layer was washed with brine, dried over anhydrous sodium sulfate and filtered. The filtrate was concentrated under reduced pressure to afford (S)-pyrrolidine-2-carbaldehyde (4.9 g, crude) as a brown oil. LCMS (ESI, m/z): $[M+H]^+$=100.1.

Step 2. Synthesis of (S)-1-methylpyrrolidine-2-carbaldehyde

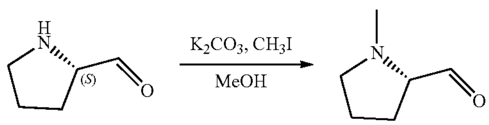

To a solution of (S)-pyrrolidine-2-carbaldehyde (1.0 g, crude) in MeOH (30.0 mL) was added $K_2CO_3$ (4.2 g, 30.30 mmol) and $CH_3I$ (2.15 g, 15.15 mmol) at room temperature. The resulting mixture was stirred at 40° C. for 16 h. After the reaction was completed, the resulting mixture was concentrated under reduced pressure. The residue was purified by flash column chromatography with petroleum ether/ethyl acetate (50/50, v/v) to afford (S)-1-methylpyrrolidine-2-carbaldehyde (300.0 mg, 26%) as a yellow oil. LCMS (ESI, m/z): $[M+H]^+$=114.1.

Step 3. Synthesis of ethyl (S,E)-3-(1-methylpyrrolidin-2-yl)acrylate

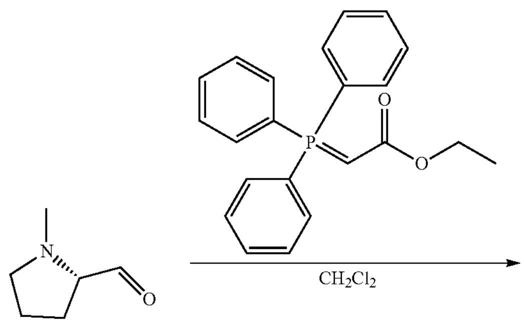

-continued

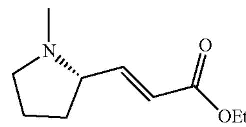

To a solution of (S)-1-methylpyrrolidine-2-carbaldehyde (300.0 mg, 1.64 mmol) in $CH_2Cl_2$ (10.0 mL) was added ethyl 2-(triphenyl-$\lambda^5$-phosphaneylidene)acetate (1.1 g, 3.18 mmol) at room temperature. The resulting mixture was stirred at room temperature for 16 h. After the reaction was completed, the mixture was concentrated under reduced pressure. The residue was purified by flash column chromatography with petroleum ether/ethyl acetate (70/30, v/v) to afford ethyl (S,E)-3-(1-methylpyrrolidin-2-yl)acrylate (200.0 mg, 41%) as a yellow oil. LCMS (ESI, m/z): $[M+H]^+$= 184.1.

Step 4. Synthesis of (S,E)-3-(1-methylpyrrolidin-2-yl)acrylic acid

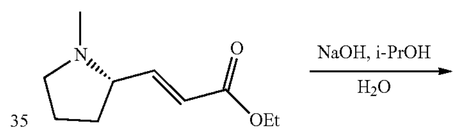

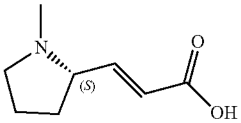

To a solution of ethyl (S,E)-3-(1-methylpyrrolidin-2-yl)acrylate (300.0 mg, 1.64 mmol) in i-PrOH (10.0 mL) and $H_2O$ (3.0 mL) was added NaOH (534.5 mg, 13.23 mmol) at room temperature. The resulting mixture was stirred at room temperature for 16 h. After the reaction was completed, the mixture was concentrated under reduced pressure. The pH value of the residue was adjusted to 5.0 with HCl (1.0 mol/L). The mixture was extracted with $CH_2Cl_2$. The combined organic layer was washed with brine, dried over anhydrous sodium sulfate and filtered. The filtrate was concentrated under vacuum to afford (S,E)-3-(1-methylpyrrolidin-2-yl)acrylic acid (150.0 mg, crude) as a white solid. LCMS (ESI, m/z): $[M+H]^+$=156.1.

Step 5. Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-((S)-1-methylpyrrolidin-2-yl)prop-2-en-1-one (Compound 28)

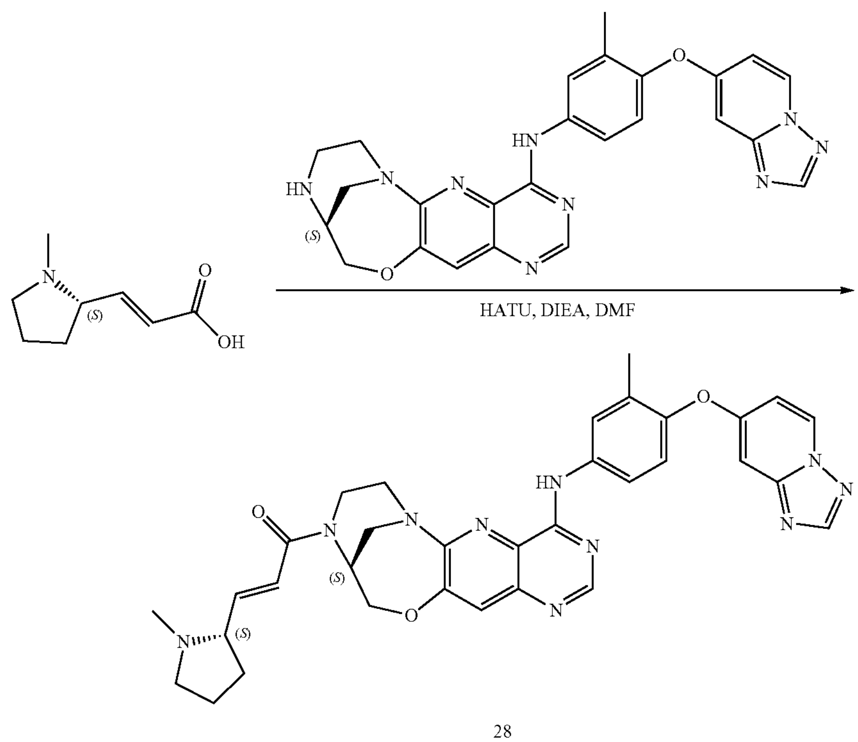

28

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (150.0 mg, 0.31 mmol) in DMF (5.0 mL) was added (S,E)-3-(1-methylpyrrolidin-2-yl)acrylic acid (580.0 mg, 3.10 mmol), DIEA (201.3 mg, 1.50 mmol) and HATU (1421.0 mg, 3.20 mmol) at 0° C. under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with ACN/$H_2O$ (60/40, v/v) and then purified by Prep-HPLC with the following conditions: (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 30% B to 40% B in 8 min; Wave Length: 254 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-((S)-1-methylpyrrolidin-2-yl)prop-2-en-1-one (Compound 28) (30.0 mg, 15%) as a light yellow solid. LCMS (ESI, m/z): $[M+H]^+$=619.3. $^1H$ NMR (400 MHz, DMSO-$d_6$): δ 9.53 (d, J=8.4 Hz, 1H), 8.94 (d, J=7.2 Hz, 1H), 8.48 (s, 1H), 8.38 (s, 1H), 8.03-7.97 (m, 2H), 7.51 (s, 1H), 7.22 (d, J=9.2 Hz, 1H), 7.04-7.02 (m, 1H), 6.79 (d, J=2.4 Hz, 1H), 6.60-6.51 (m, 2H), 5.17-4.60 (m, 3H), 4.28-4.03 (m, 3H), 3.88-3.64 (m, 1H), 3.01-2.97 (m, 1H), 2.81-2.75 (m, 1H), 2.21-2.18 (m, 7H), 2.08-1.96 (m, 1H), 1.79-1.72 (m, 2H), 1.59-1.51 (m, 1H).

Example S28: Synthesis of (4R,E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)pent-2-en-1-one (Compound 29)

Step 1. Synthesis of tert-butyl (R)-(1-hydroxypropan-2-yl)(methyl)carbamate

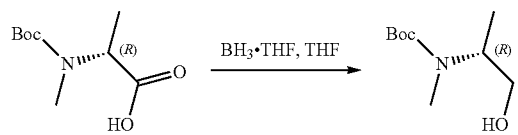

To a solution of N-(tert-butoxycarbonyl)-N-methyl-D-alanine (10.0 g, 96.97 mmol) in THE (100.0 mL) was added $BH_3$ in THE (145.5 mL, 1 mol/L) at 0° C. The resulting mixture was stirred at 0° C. for 1 h. After the reaction was completed, the reaction mixture was quenched with $H_2O$ at 0° C. Then 10% $Na_2CO_3$ (aq.) was added to the mixture at room temperature. The resulting mixture was stirred at room temperature for another 1 h. The mixture was extracted with ethyl acetate. The combined organic layers were washed with brine, dried over anhydrous sodium sulfate and filtered. The filtrate was concentrated under reduced pressure to afford tert-butyl (R)-(1-hydroxypropan-2-yl)(methyl)carbamate (13.0 g, crude) as a colorless oil. LCMS (ESI, m/z): $[M+H]^+$=190.1.

Step 2. Synthesis of tert-butyl (R)-methyl(1-oxopropan-2-yl)carbamate

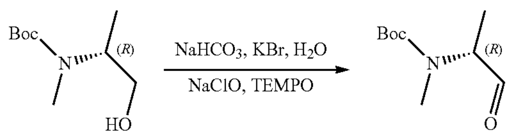

To a mixture of tert-butyl (R)-(1-hydroxypropan-2-yl)(methyl)carbamate (10.0 g, crude) in $CH_2Cl_2$ (200.0 mL) was added a mixture of $NaHCO_3$ (1.8 g, 21.66 mmol) and KBr (0.6 g, 5.28 mmol) in $H_2O$ (20.0 mL) at 0° C. under $N_2$. Then TEMPO (82.6 mg, 0.53 mmol) and NaClO (40.0 g, 537.37 mmol) were added to the mixture at 0° C. The mixture was stirred at 0° C. for 30 min. After the reaction was completed, the reaction mixture was quenched with 38% $NaHSO_3$ (aq.) at 0° C. The aqueous layer was extracted with EtOAc. The combined organic layers were washed with brine, dried over anhydrous $Na_2SO_4$ and filtered. The filtrate was concentrated under reduced pressure to afford tert-butyl (R)-methyl(1-oxopropan-2-yl)carbamate (6.0 g, crude) as a light yellow oil. LCMS (ESI, m/z): $[M+H]^+$=188.2.

Step 3. Synthesis of ethyl (R,E)-4-((tert-butoxycarbonyl)(methyl)amino)pent-2-enoate

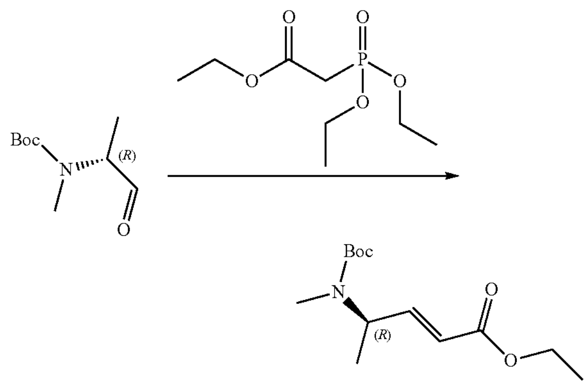

To a solution of ethyl 2-(diethoxyphosphoryl)acetate (25.1 g, 112.15 mmol) in THE (200.0 mL) was added t-BuOK (1.8 g, 16.02 mmol) at 0° C. under $N_2$. The mixture was stirred at 0° C. for 30 min. Then tert-butyl N-methyl-N-[(2R)-1-oxopropan-2-yl]carbamate (3.0 g, crude) was added to the mixture at 0° C. under $N_2$. The mixture was stirred at room temperature for 1 h. After the reaction was completed, the reaction mixture was diluted with $H_2O$ and extracted with EtOAc. The combined organic layers were washed with brine, dried over anhydrous $Na_2SO_4$ and filtered. The filtrate was concentrated under reduced pressure. The residue was purified by flash column chromatography with petroleum ether/ethyl acetate (5/1, v/v) to afford ethyl (R,E)-4-((tert-butoxycarbonyl)(methyl)amino)pent-2-enoate (2.0 g, 38%) as a yellow oil. LCMS (ESI, m/z): $[M+H]^+$=258.2.

Step 4. Synthesis of ethyl (R,E)-4-(methylamino)pent-2-enoate 2,2,2-trifluoroacetic acid salt

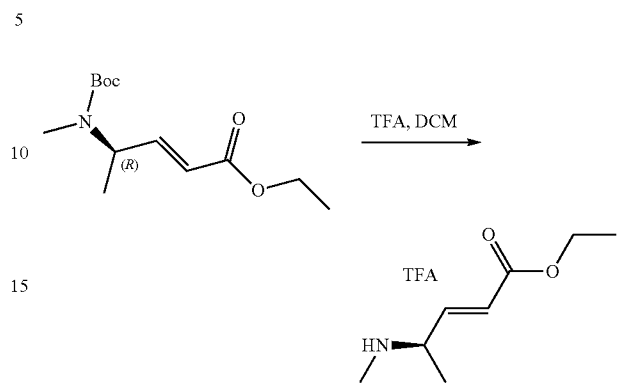

To a mixture of ethyl (R,E)-4-((tert-butoxycarbonyl)(methyl)amino)pent-2-enoate (2.5 g, 9.71 mmol) in DCM (12.0 mL) was added TFA (6.0 mL) at room temperature. The resulting mixture was stirred at room temperature for 30 min. After the reaction was completed, the resulting mixture was concentrated under reduced pressure to afford ethyl (R,E)-4-(methylamino)pent-2-enoate 2,2,2-trifluoroacetic acid salt (2.1 g, crude) as a yellow oil. LCMS (ESI, m/z): $[M+H]^+$=158.1.

Step 5. Synthesis of ethyl (R,E)-4-(dimethylamino)pent-2-enoate

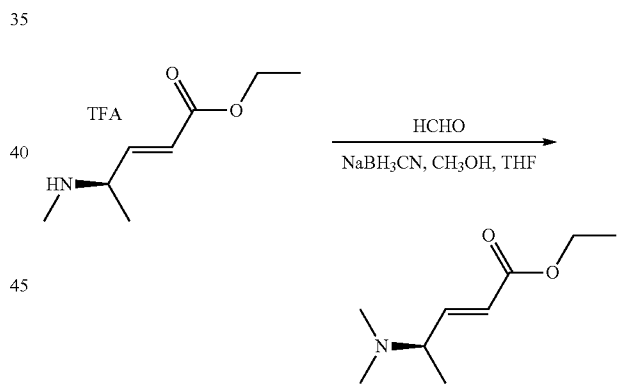

To a stirred mixture of ethyl (R,E)-4-(methylamino)pent-2-enoate 2,2,2-trifluoroacetic acid salt (2.5 g, crude) in THE (16.0 mL) and MeOH (3.0 mL) were added HCHO (3.5 g, 40% in $H_2O$) at room temperature. The resulting mixture was stirred at room temperature for 1.5 h. To the above mixture was added $NaBH_3CN$ (4.5 g, 71.55 mmol) at 0° C. The resulting mixture was stirred at room temperature for another 1 h. After the reaction was completed, the reaction mixture was quenched with water and extracted with ethyl acetate. The combined organic layers were washed with brine, dried over anhydrous sodium sulfate and filtered. The filtrate was concentrated under reduced pressure. The residue was purified by flash column chromatography with dichloromethane/methanol (5/1, v/v) to afford ethyl (R,E)-4-(dimethylamino)pent-2-enoate (850.0 mg, 31%) as a yellow oil. LCMS (ESI, m/z): $[M+H]^+$=172.1.

Step 6. Synthesis of (R,E)-4-(dimethylamino)pent-2-enoic acid

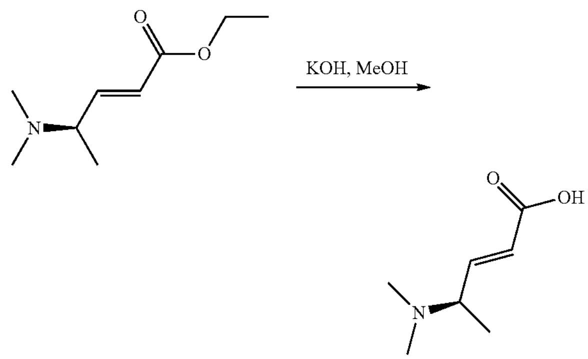

To a mixture of ethyl (2E,4R)-4-(dimethylamino)pent-2-enoate (850.0 mg, 4.96 mmol) in MeOH (10.0 mL) was added KOH (696.2 mg, 12.41 mmol) at room temperature. The resulting mixture was stirred at room temperature for 16 h. After the reaction was completed, the pH value of the mixture was adjusted to 3 with 2 M HCl (aq.). The mixture evaporated in vacuo. The residue was purified by reverse phase flash column chromatography with acetonitrile/$H_2O$ (10/90, v/v) to afford (2E,4R)-4-(dimethylamino)pent-2-enoic acid (1.0 g, crude) as a white solid. LCMS (ESI, m/z): $[M+H]^+$=144.1.

Step 7. Synthesis of (4R,E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)pent-2-en-1-one (Compound 29)

To a stirred mixture of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (250.0 mg, 0.51 mmol) and (2E,4R)-4-(dimethylamino)pent-2-enoic acid (1.1 g, crude) in pyridine (8.0 mL) was added EDCI (199.0 mg, 1.03 mmol) at room temperature. The resulting mixture was stirred at room temperature for 2 h. After the reaction was completed, the mixture was purified by reverse phase flash column chromatography with $CH_3CN/H_2O$ (70/30, v/v) and then purified by Prep-HPLC with the following conditions (Column: XBridge Shield RP18 OBD Column, 30×150 mm, 5 μm; Mobile Phase A: Water (10 mmol/L $NH_4HCO_3$), Mobile Phase B: ACN; Flow rate: 60 mL/min; Gradient: 35% B to 45% B in 8 min; Wave Length: 254 nm) to afford (4R,E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)pent-2-en-1-one (Compound 29) (95.0 mg, 30%) as a white solid. LCMS (ESI, m/z): $[M+H]^+$=607.3. $^1H$ NMR (400 MHz, DMSO-$d_6$): δ 9.54 (d, J=8.0 Hz, 1H), 8.94 (d, J=7.6 Hz, 1H), 8.47 (s, 1H), 8.38 (s, 1H), 8.03-7.97 (m, 2H), 7.51 (s, 1H), 7.22 (d, J=8.8 Hz, 1H), 7.04-7.01 (m, 1H), 6.78 (d, J=2.4 Hz, 1H), 6.69-6.50 (m, 2H), 5.11-4.61 (m, 3H), 4.29-4.19 (m, 1H), 4.15-4.04 (m, 1H), 3.90-3.62 (m, 1H), 3.47-3.37 (m, 1H), 3.28-3.22 (m, 1H), 3.13-3.04 (m, 1H), 2.20 (s, 3H), 2.16-2.12 (m, 6H), 1.15-1.08 (m, 3H).

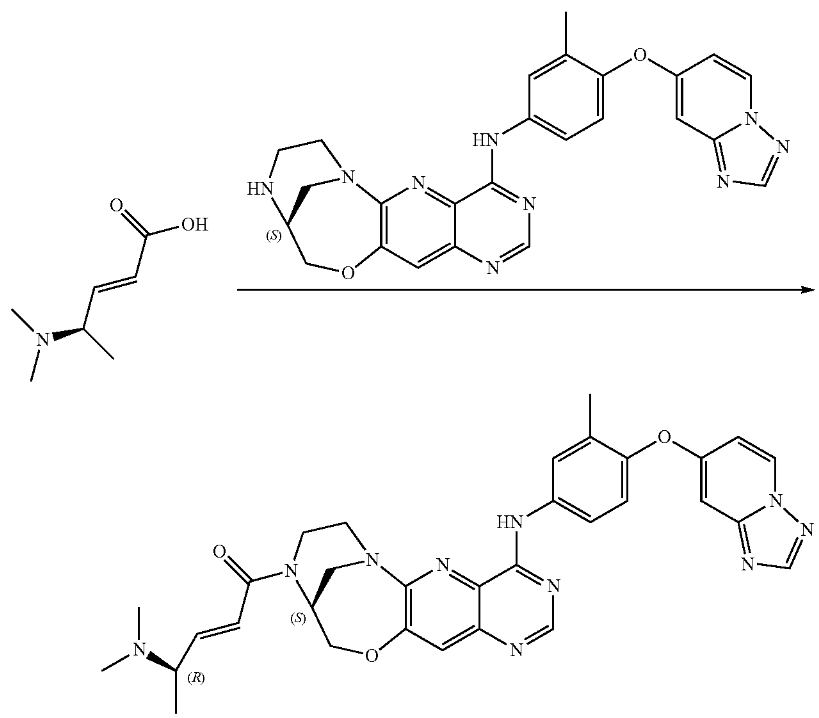

29

Example S29: Synthesis of (4S,E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)pent-2-en-1-one (Compound 30)

Step 1. Synthesis of tert-butyl (S)-(1-hydroxypropan-2-yl)(methyl)carbamate

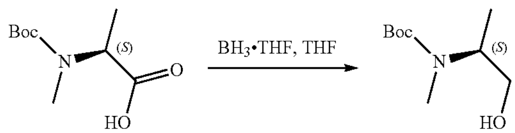

To a solution of N-(tert-butoxycarbonyl)-N-methyl-L-alanine (10.0 g, 96.97 mmol) in THE (100.0 mL) was added $BH_3$ in THE (145.5 mL, 1 mol/L) at 0° C. The resulting mixture was stirred at 0° C. for 1 h. After the reaction was completed, the reaction mixture was quenched with $H_2O$ at 0° C. Then 10% $Na_2CO_3$ (aq.) was added to the mixture at room temperature. The resulting mixture was stirred at room temperature for another 1 h. The mixture was extracted with ethyl acetate. The combined organic layers were washed with brine, dried over anhydrous $Na_2SO_4$ and filtered. The filtrate was concentrated under reduced pressure to afford tert-butyl (S)-(1-hydroxypropan-2-yl)(methyl)carbamate (13.0 g, crude) as a colorless oil. LCMS (ESI, m/z): $[M+H]^+$= 190.1.

Step 2. Synthesis of tert-butyl (S)-methyl(1-oxopropan-2-yl)carbamate

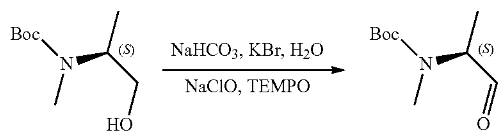

To a mixture of tert-butyl (S)-(1-hydroxypropan-2-yl)(methyl)carbamate (10.0 g, 52.84 mmol) in $CH_2Cl_2$ (200.0 mL) was added a mixture of $NaHCO_3$ (1.8 g, 21.66 mmol) and KBr (0.6 g, 5.28 mmol) in $H_2O$ (20.0 mL) at 0° C. under $N_2$. Then TEMPO (82.6 mg, 0.53 mmol) and NaClO (40.0 g, 537.37 mmol) were added to the mixture at 0° C. The mixture was stirred at 0° C. for 30 min. After the reaction was completed, the reaction mixture was quenched with 38% $NaHSO_3$ (aq.) at 0° C. The mixture was extracted with $CH_2Cl_2$. The combined organic layers were washed with 10% brine, dried over anhydrous $Na_2SO_4$ and filtered. The filtrate was concentrated under reduced pressure to afford tert-butyl (S)-methyl(1-oxopropan-2-yl)carbamate (6.0 g, crude) as a light yellow oil. LCMS (ESI, m/z): $[M+H]^+$= 188.2.

Step 3. Synthesis of ethyl (S,E)-4-((tert-butoxycarbonyl)(methyl)amino)pent-2-enoate

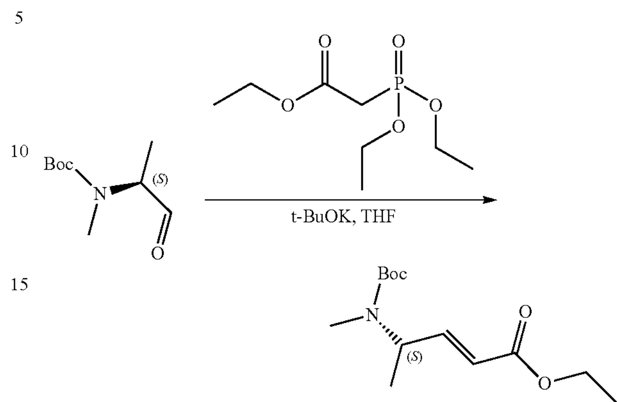

To a mixture of ethyl 2-(diethoxyphosphoryl)acetate (21.8 g, 97.20 mmol) in THE (200.0 mL) was added t-BuOK (1.6 g, 13.89 mmol) at 0° C. under $N_2$. The mixture was stirred at 0° C. for 30 min. Then tert-butyl (S)-methyl(1-oxopropan-2-yl)carbamate (2.6 g, 13.87 mmol) was added to the mixture at 0° C. under $N_2$. The mixture was stirred at room temperature for 1 h. After the reaction was completed, the reaction mixture was diluted with $H_2O$ and extracted with EtOAc. The combined organic layers were washed with brine, dried over anhydrous $Na_2SO_4$ and filtered. The filtrate was concentrated under reduced pressure. The residue was purified by flash column chromatography with petroleum ether/ethyl acetate (5/1, v/v) to afford ethyl (S,E)-4-((tert-butoxycarbonyl)(methyl)amino)pent-2-enoate (2.6 g, 72%) as a light yellow oil. LCMS (ESI, m/z): $[M+H]^+$=258.2.

Step 4. Synthesis of ethyl (S,E)-4-(methylamino)pent-2-enoate 2,2,2-trifluoroacetic acid salt

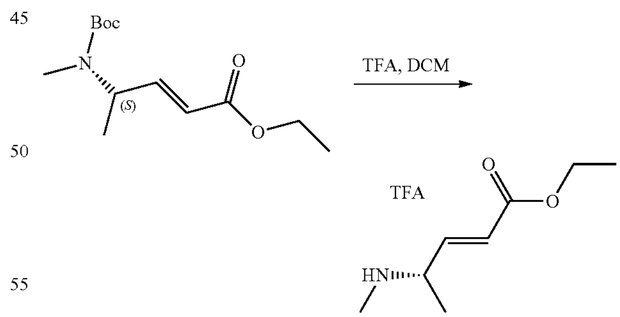

To a mixture of ethyl (S,E)-4-((tert-butoxycarbonyl)(methyl)amino)pent-2-enoate (2.5 g, 9.72 mmol) in DCM (40.0 mL) was added TFA (20.0 mL) at room temperature. The resulting mixture was stirred at room temperature for 30 min. After the reaction was completed, the resulting mixture was concentrated under reduced pressure to afford ethyl (S,E)-4-(methylamino)pent-2-enoate 2,2,2-trifluoroacetic acid salt (2.0 g, crude) as a light yellow oil. LCMS (ESI, m/z): $[M+H]^+$=158.1.

Step 5. Synthesis of ethyl (S,E)-4-(dimethylamino)pent-2-enoate

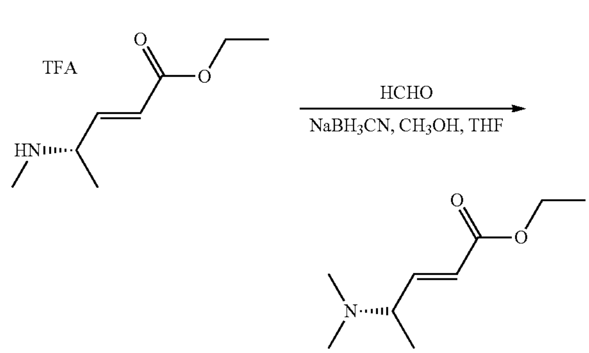

To a stirred mixture of ethyl (S,E)-4-(methylamino)pent-2-enoate 2,2,2-trifluoroacetic acid salt (1.8 g, crude) in THE (40.0 mL) and MeOH (20.0 mL) were added HCOH (2.8 g, 40% in $H_2O$) at room temperature. The resulting mixture was stirred at room temperature for 1.5 h. Then $NaBH_3CN$ (3.2 g, 51.52 mmol) was added to the mixture at 0° C. The resulting mixture was stirred at room temperature for 1 h. After the reaction was completed, the reaction mixture was quenched with water and extracted with ethyl acetate. The combined organic layers were washed with brine, dried over anhydrous sodium sulfate and filtered. The filtrate was concentrated under reduced pressure. The residue was purified by flash column chromatography with dichloromethane/methanol (5/1, v/v) to afford ethyl (S,E)-4-(dimethylamino)pent-2-enoate (340.0 mg, 17%) as a white solid. LCMS (ESI, m/z): $[M+H]^+$=172.1.

Step 6. Synthesis of (S,E)-4-(dimethylamino)pent-2-enoic acid

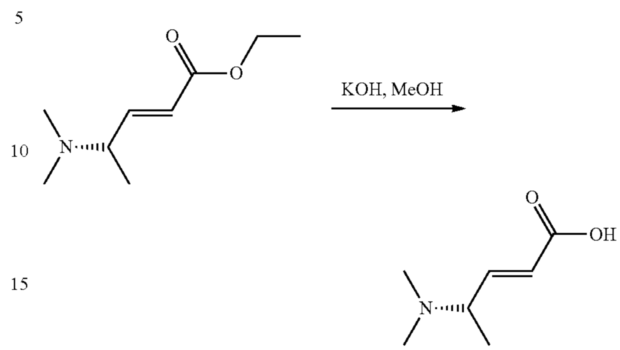

To a mixture of ethyl (S,E)-4-(dimethylamino)pent-2-enoate (330.0 mg, 1.93 mmol) in MeOH (5.0 mL) was added KOH (270.3 mg, 4.82 mmol) at room temperature. The resulting mixture was stirred at room temperature for 16 h. After the reaction was completed, t the pH value of the mixture was adjusted to 3 with 2 M HCl (aq.). The mixture was evaporated in vacuo. The residue was purified by reverse phase flash column chromatography with acetonitrile/$H_2O$ (10/90, v/v) to afford (S,E)-4-(dimethylamino)pent-2-enoic acid (270.0 mg, 97%) as a white solid. LCMS (ESI, m/z): $[M+H]^+$=144.1.

Step 7. Synthesis of (4S,E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)pent-2-en-1-one (Compound 30)

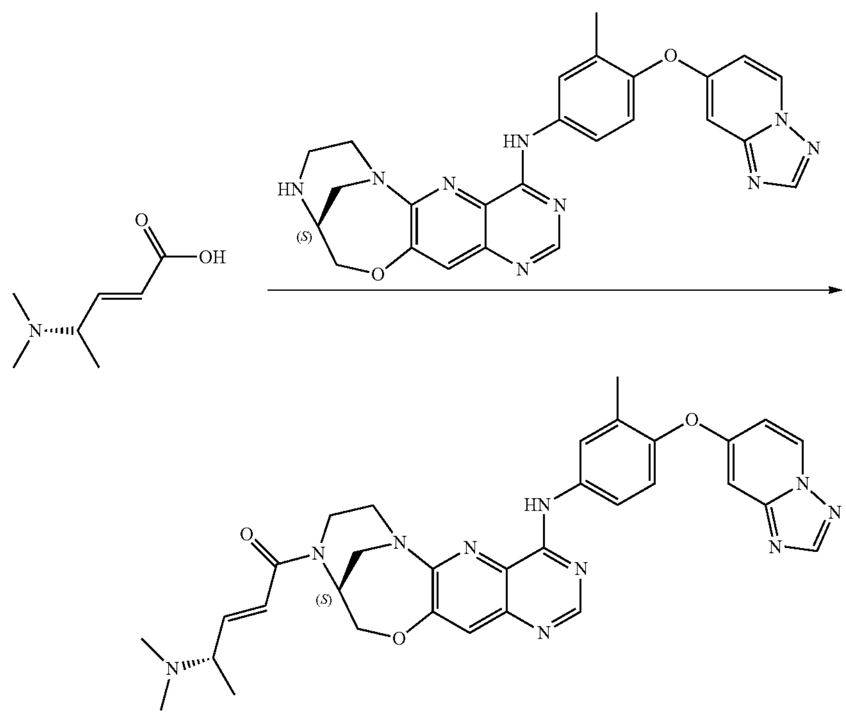

To a mixture of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (55.0 mg, 0.12 mmol) in pyridine (5.0 mL) were added (S,E)-4-(dimethylamino)pent-2-enoic acid (252.7 mg, 1.77 mmol) and EDCI (45.1 mg, 0.24 mmol) at room temperature. The resulting mixture was stirred at room temperature for 2 h. After the reaction was completed, the resulting mixture was concentrated under vacuum. The residue was purified by flash column chromatography with $CH_2Cl_2$/MeOH (10/1, v/v) and then purified by Prep-HPLC with the following conditions (Column: Xselect CSH C18 OBD Column 30×150 mm, 5 μm; Mobile Phase A: Water (0.1% FA), Mobile Phase B: ACN; Flow rate: 60 mL/min; Gradient: 5% B to 30% B in 10 min; Wave Length: 254 nm) to afford (4S,E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)pent-2-en-1-one (Compound 30) (6.3 mg, 8%) as a light yellow solid. LCMS (ESI, m/z): $[M+H]^+$=607.3. $^1$H NMR (400 MHz, DMSO-$d_6$): δ 9.54 (d, J=8.0 Hz, 1H), 8.94 (d, J=7.6 Hz, 1H), 8.47 (s, 1H), 8.38 (s, 1H), 8.02-8.00 (m, 2H), 7.51 (s, 1H), 7.22 (d, J=8.8 Hz, 1H), 7.05-7.02 (m, 1H), 6.78 (d, J=2.4 Hz, 1H), 6.67-6.50 (m, 2H), 5.11-4.59 (m, 3H), 4.28-4.03 (m, 3H), 3.91-3.86 (m, 1H), 3.68-3.61 (m, 1H), 3.29-3.22 (m, 1H), 3.12-3.06 (m, 1H), 2.20 (s, 3H), 2.15-2.13 (m, 6H), 1.14-1.07 (m, 3H).

Example S30: Synthesis of (E)-1-((10S)-4-((4-([1,2,4]triazolo[1,5-a]pyridin-7-yloxy)phenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 31)

Step 1. Synthesis of 7-bromo-6-chloro-N-(4-{[1,2,4]triazolo[1,5-a]pyridin-7-yloxy}phenyl)pyrido[3,2-d]pyrimidin-4-amine

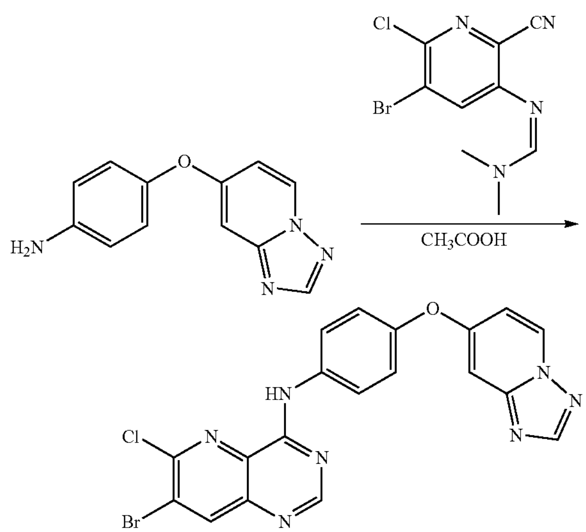

To a mixture of (Z)—N'-(5-bromo-6-chloro-2-cyanopyridin-3-yl)-N,N-dimethylmethanimidamide (900.0 mg, 3.13 mmol) in $CH_3COOH$ (25.0 mL) was added 4-{[1,2,4]triazolo[1,5-a]pyridin-7-yloxy}aniline (708.1 mg, 3.13 mmol) at room temperature. The resulting mixture was stirred at 85° C. for 3 h. After the reaction was completed, the resulting mixture was concentrated under reduced pressure. The residue was purified by flash column chromatography with $CH_2Cl_2$/MeOH (10/1, v/v) to afford 7-bromo-6-chloro-N-(4-{[1,2,4]triazolo[1,5-a]pyridin-7-yloxy}phenyl)pyrido[3,2-d]pyrimidin-4-amine (1.1 g, 75%) as a light yellow solid. LCMS (ESI, m/z): $[M+H]^+$=468.0.

Step 2. Synthesis of tert-butyl (2S)-4-{7-bromo-4-[(4-{[1,2,4]triazolo[1,5-a]pyridin-7-yloxy}phenyl)amino]pyrido[3,2-d]pyrimidin-6-yl}-2-(hydroxymethyl)piperazine-1-carboxylate

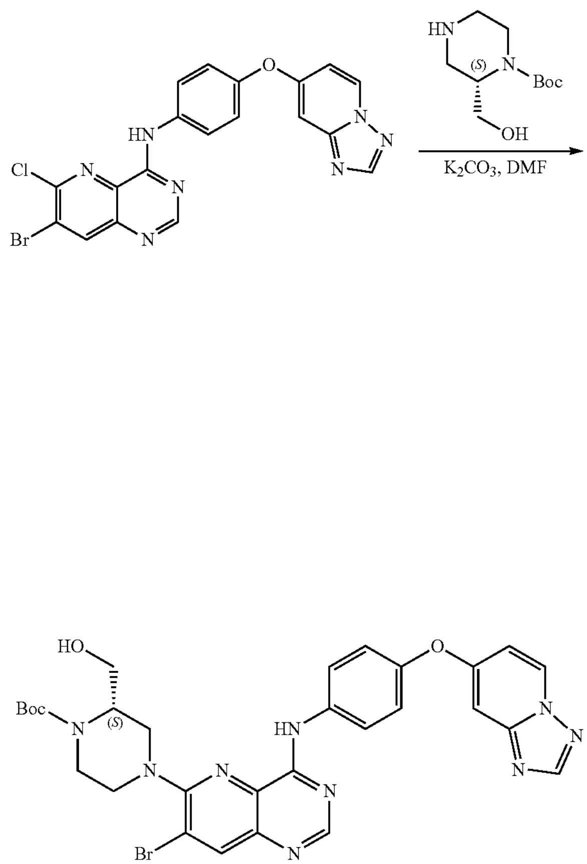

To a mixture of 7-bromo-6-chloro-N-(4-{[1,2,4]triazolo[1,5-a]pyridin-7-yloxy}phenyl)pyrido[3,2-d]pyrimidin-4-amine (1000.0 mg, 2.13 mmol) in DMF (30.0 mL) was added tert-butyl(2S)-2-(hydroxymethyl)piperazine-1-carboxylate (690.0 mg, 3.20 mmol) and $K_2CO_3$ (1180.0 mg, 8.54 mmol) at room temperature. The resulting mixture was stirred at 100° C. for 4 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (2S)-4-{7-bromo-4-[(4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (830.0 mg, 60%) as a yellow solid. LCMS (ESI, m/z): $[M+H]^+$=648.2.

Step 3. Synthesis of tert-butyl (10S)-4-((4-([1,2,4]triazolo[1,5-a]pyridin-7-yloxy)phenyl)amino)-7,8,10,11-tetrahydro-9H-6,10-methanopyrimido[4',5':5,6]pyrido[3,2-b][1,4,7]oxadiazonine-9-carboxylate

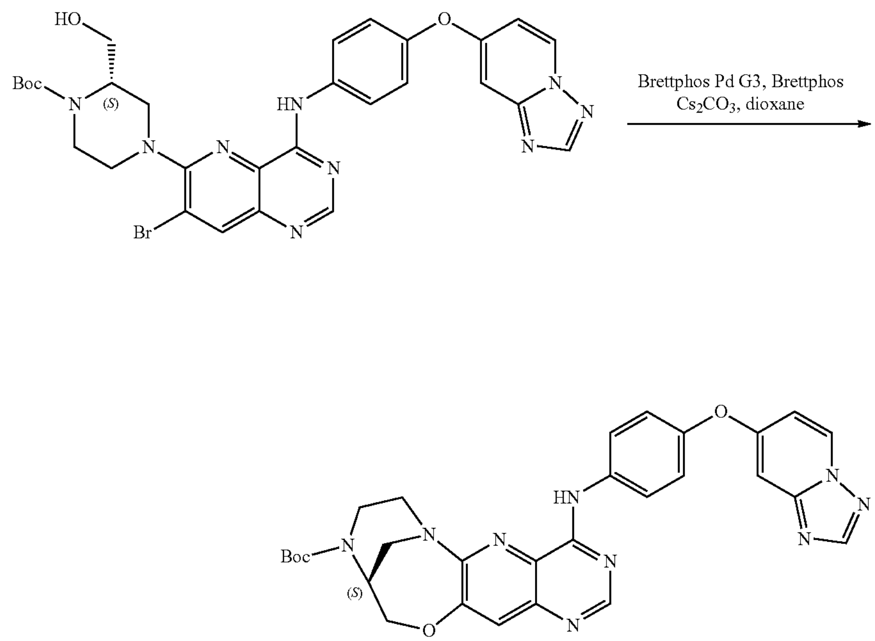

To a mixture of tert-butyl (2S)-4-{7-bromo-4-[(4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (770.0 mg, 1.19 mmol) in dioxane (20.0 mL) was added $Cs_2CO_3$ (1160.6 mg, 3.56 mmol), BrettPhos (254.9 mg, 0.48 mmol) and BrettPhos Pd G3 (215.3 mg, 0.24 mmol) at room temperature under $N_2$. The resulting mixture was stirred at 100° C. for 2 h. After the reaction was completed, the resulting mixture was diluted with water and extracted with ethyl acetate. The combined organic layers were washed with brine, dried over anhydrous sodium sulfate and filtered. The filtrate was evaporated in vacuo. The residue was purified by flash column chromatography with $CH_2Cl_2$/MeOH (10/1, v/v) to afford tert-butyl (10S)-4-((4-([1,2,4]triazolo[1,5-a]pyridin-7-yloxy)phenyl)amino)-7,8,10,11-tetrahydro-9H-6,10-methanopyrimido[4',5':5,6]pyrido[3,2-b][1,4,7]oxadiazonine-9-carboxylate (480.0 mg, 71%) as a yellow solid. LCMS (ESI, m/z): $[M+H]^+$=568.2.

Step 4. Synthesis of (10S)—N-(4-([1,2,4]triazolo[1,5-a]pyridin-7-yloxy)phenyl)-8,9,10,11-tetrahydro-7H-6,10-methanopyrimido[4',5':5,6]pyrido[3,2-b][1,4,7]oxadiazonin-4-amine

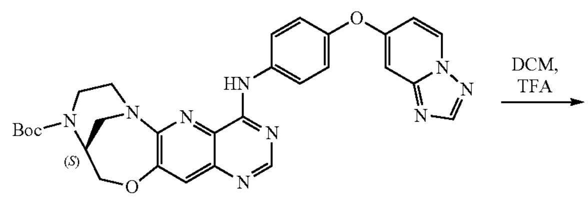

-continued

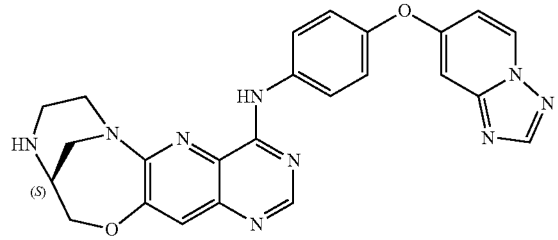

To a solution of tert-butyl (10S)-4-((4-([1,2,4]triazolo[1,5-a]pyridin-7-yloxy)phenyl)amino)-7,8,10,11-tetrahydro-9H-6,10-methanopyrimido[4',5':5,6]pyrido[3,2-b][1,4,7]oxadiazonine-9-carboxylate (480.0 mg, 0.85 mmol) in $CH_2Cl_2$ (3.0 mL) was added TFA (1.5 mL) at room temperature. The resulting mixture was stirred at room temperature for 1 h. After the reaction was completed, the resulting mixture was basified to pH=8 with saturated $NaHCO_3$(aq.) and then extracted with $CH_2Cl_2$. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford (10S)—N-(4-([1,2,4]triazolo[1,5-a]pyridin-7-yloxy)phenyl)-8,9,10,11-tetrahydro-7H-6,10-methanopyrimido[4',5':5,6]pyrido[3,2-b][1,4,7]oxadiazonin-4-amine (100.0 mg, 25%) as a yellow solid. LCMS (ESI, m/z): $[M+H]^+$=468.2.

Step 5. Synthesis of (E)-1-((10S)-4-((4-([1,2,4]triazolo[1,5-a]pyridin-7-yloxy)phenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 31)

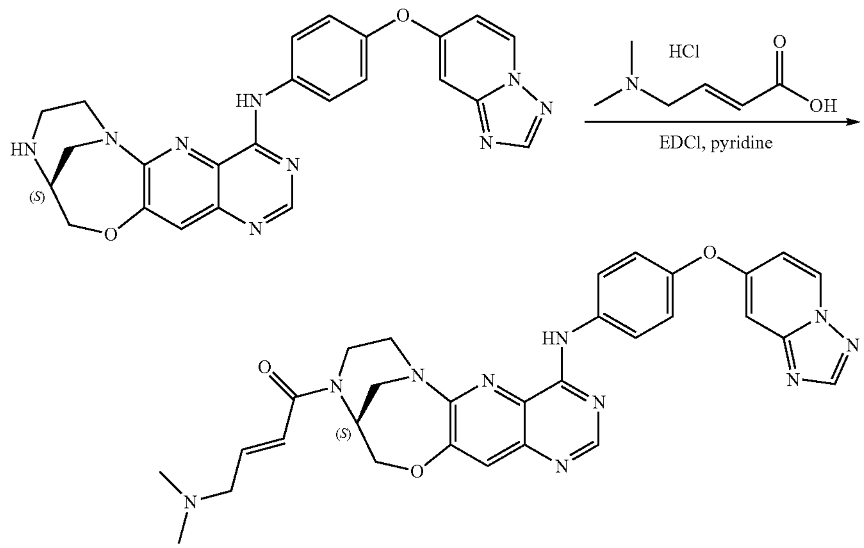

31

To a mixture of (10S)—N-(4-([1,2,4]triazolo[1,5-a]pyridin-7-yloxy)phenyl)-8,9,10,11-tetrahydro-7H-6,10-methanopyrimido[4',5':5,6]pyrido[3,2-b][1,4,7]oxadiazonin-4-amine (100.0 mg, 0.21 mmol) in pyridine (10.0 mL) was added (2E)-4-(dimethylamino)but-2-enoic acid hydrochloride (35.4 mg, 0.21 mmol) and EDCI (123.0 mg, 0.64 mmol) at room temperature. The mixture was stirred at room temperature for 2 h. After the reaction was completed, the resulting mixture was concentrated under reduced pressure. The residue was purified by flash column chromatography with $CH_2Cl_2$/MeOH (5/1, v/v) and then purified by Prep-HPLC with the following conditions: (Column: Aeris PEPTIDE 5 um XB-C18 Axia, 21.2 mm×250 mm, 5 μm; Mobile Phase A: Water(10 mmol/L $NH_4HCO_3$), Mobile Phase B: ACN; Flow rate: 60 mL/min; Gradient: 20% B to 30% B in 8 min; Wave Length: 254 nm; RT1(min): 7 min) to afford (E)-1-((10S)-4-((4-([1,2,4]triazolo[1,5-a]pyridin-7-yloxy)phenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 31) (9.7 mg, 7%) as a yellow solid. LCMS (ESI, m/z): $[M+H]^+$=579.4. $^1H$ NMR (400 MHz, DMSO-$d_6$): δ 9.63-9.61 (m, 1H), 8.95 (d, J=7.2 Hz, 1H), 8.46 (s, 1H), 8.40 (s, 1H), 8.11 (d, J=8.8 Hz, 2H), 7.51 (s, 1H), 7.29 (d, J=8.8 Hz, 2H), 7.04-7.00 (m, 2H), 6.67-6.63 (m, 2H), 5.11-4.59 (m, 3H), 4.28-4.19 (m, 1H), 4.16-4.01 (m, 1H), 3.89-3.65 (m, 1H), 3.28-3.16 (m, 2H), 3.03 (d, J=5.6 Hz, 2H), 2.16-2.14 (m, 6H).

Example S31: Synthesis of (E)-1-((10S)-4-((4-([1,2,4]triazolo[1,5-a]pyridin-7-yloxy)-3-chlorophenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 32)

Step 1. Synthesis of N-(4-([1,2,4]triazolo[1,5-a]pyridin-7-yloxy)-3-chlorophenyl)-7-bromo-6-chloropyrido[3,2-d]pyrimidin-4-amine

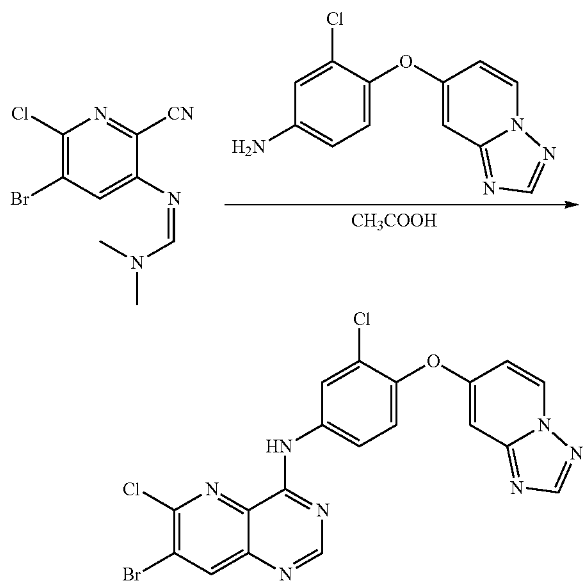

To a solution of (Z)—N'-(5-bromo-6-chloro-2-cyanopyridin-3-yl)-N,N-dimethylmethanimidamide (2.0 g, 6.95 mmol) in $CH_3COOH$ (20.0 mL) was added 4-([1,2,4]triazolo[1,5-a]pyridin-7-yloxy)-3-chloroaniline (2.7 g, 10.43 mmol) at room temperature. The resulting mixture was stirred at 85° C. for 4 h. After the reaction was completed, the resulting mixture was concentrated under vacuum. The residue was purified by flash column chromatography with $CH_2Cl_2$/MeOH (10/1, v/v) to afford N-(4-([1,2,4]triazolo[1,5-a]pyridin-7-yloxy)-3-chlorophenyl)-7-bromo-6-chloropyrido[3,2-d]pyrimidin-4-amine (2.1 g, 60%) as a yellow solid. LCMS (ESI, m/z): $[M+H]^+$=502.0.

Step 2. Synthesis of tert-butyl (S)-4-(4-((4-([1,2,4]triazolo[1,5-a]pyridin-7-yloxy)-3-chlorophenyl)amino)-7-bromopyrido[3,2-d]pyrimidin-6-yl)-2-(hydroxymethyl)piperazine-1-carboxylate

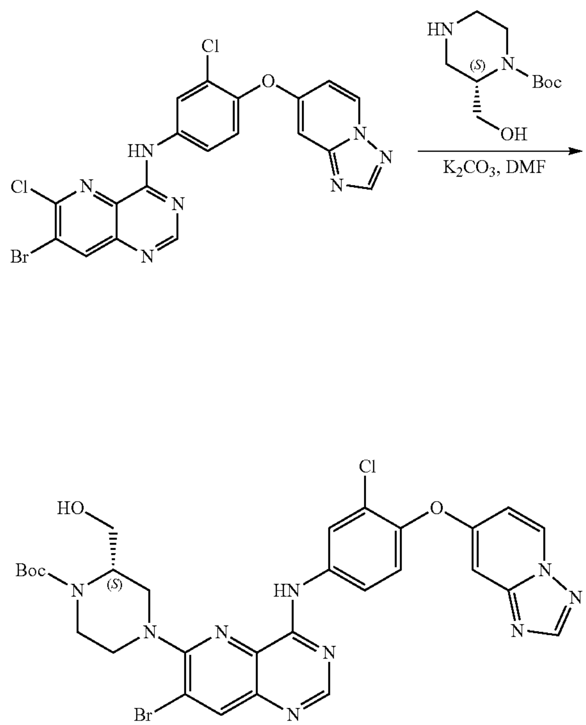

To a solution of N-(4-([1,2,4]triazolo[1,5-a]pyridin-7-yloxy)-3-chlorophenyl)-7-bromo-6-chloropyrido[3,2-d]pyrimidin-4-amine (1.0 g, 1.98 mmol) in DMF (10.0 mL) was added tert-butyl (S)-2-(hydroxymethyl)piperazine-1-carboxylate (64.4 mg, 0.29 mmol) and $K_2CO_3$ (824.0 mg, 5.96 mmol) at room temperature. The resulting mixture was stirred at 100° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (S)-4-(4-((4-([1,2,4]triazolo[1,5-a]pyridin-7-yloxy)-3-chlorophenyl)amino)-7-bromopyrido[3,2-d]pyrimidin-6-yl)-2-(hydroxymethyl)piperazine-1-carboxylate (1.0 g, 73%) as a yellow solid. LCMS (ESI, m/z): $[M+H]^+$=682.1.

Step 3. Synthesis of tert-butyl (10S)-4-((4-([1,2,4]triazolo[1,5-a]pyridin-7-yloxy)-3-chlorophenyl)amino)-7,8,10,11-tetrahydro-9H-6,10-methanopyrimido[4',5':5,6]pyrido[3,2-b][1,4,7]oxadiazonine-9-carboxylate

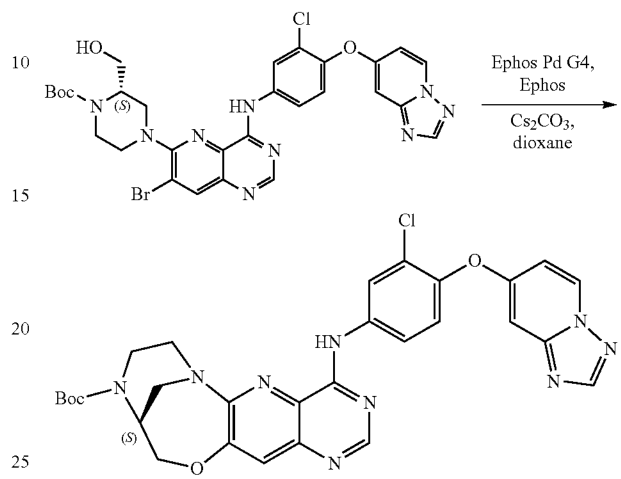

To a solution of tert-butyl (S)-4-(4-((4-([1,2,4]triazolo[1,5-a]pyridin-7-yloxy)-3-chlorophenyl)amino)-7-bromopyrido[3,2-d]pyrimidin-6-yl)-2-(hydroxymethyl)piperazine-1-carboxylate (800.0 mg, 1.17 mmol) in dioxane (10.0 mL) was added $Cs_2CO_3$ (1144.9 mg, 3.51 mmol), EPhos (26.3 mg, 0.11 mmol) and EPhos Pd G4 (135.5 mg, 0.23 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (10S)-4-((4-([1,2,4]triazolo[1,5-a]pyridin-7-yloxy)-3-chlorophenyl)amino)-7,8,10,11-tetrahydro-9H-6,10-methanopyrimido[4',5':5,6]pyrido[3,2-b][1,4,7]oxadiazonine-9-carboxylate (600.0 mg, 85%) as a light yellow solid. LCMS (ESI, m/z): $[M+H]^+$=602.2.

Step 4. Synthesis of (10S)—N-(4-([1,2,4]triazolo[1,5-a]pyridin-7-yloxy)-3-chlorophenyl)-8,9,10,11-tetrahydro-7H-6,10-methanopyrimido[4',5':5,6]pyrido[3,2-b][1,4,7]oxadiazonin-4-amine

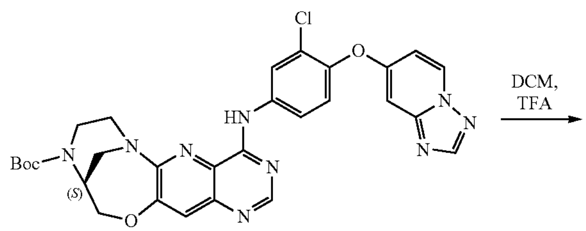

-continued

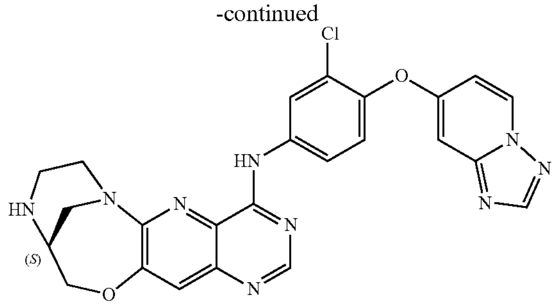

To a solution of tert-butyl (10S)-4-((4-([1,2,4]triazolo[1,5-a]pyridin-7-yloxy)-3-chlorophenyl)amino)-7,8,10,11-tetrahydro-9H-6,10-methanopyrimido[4',5':5,6]pyrido[3,2-b][1,4,7]oxadiazonine-9-carboxylate (480.0 mg, 0.79 mmol) in DCM (10.0 mL) was added TFA (2.0 mL) at room temperature. The mixture was stirred at room temperature for 1 h. After the reaction was completed, the reaction mixture was basified to pH=8 with saturated $NaHCO_3$(aq.). The resulting mixture was extracted with $CH_2Cl_2$. The combined organic layers were washed with brine and dried over anhydrous $Na_2SO_4$. After filtration, the filtrate was concentrated under reduced pressure to afford (10S)—N-(4-([1,2,4]triazolo[1,5-a]pyridin-7-yloxy)-3-chlorophenyl)-8,9,10,11-tetrahydro-7H-6,10-methanopyrimido[4',5':5,6]pyrido[3,2-b][1,4,7]oxadiazonin-4-amine (300.0 mg, crude) as a light yellow solid. LCMS (ESI, m/z): $[M+H]^+$=502.1.

Step 5. Synthesis of (E)-1-((10S)-4-((4-([1,2,4]triazolo[1,5-a]pyridin-7-yloxy)-3-chlorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 32)

To a solution of (2E)-4-(dimethylamino)but-2-enoic acid hydrochloride (64.4 mg, 0.30 mmol) in Pyridine (5.0 mL) was added (10S)—N-(4-([1,2,4]triazolo[1,5-a]pyridin-7-yloxy)-3-chlorophenyl)-8,9,10,11-tetrahydro-7H-6,10-methanopyrimido[4',5':5,6]pyrido[3,2-b][1,4,7]oxadiazonin-4-amine (150.0 mg, 0.29 mmol) and EDCI (114.5 mg, 0.59 mmol) at room temperature. The resulting mixture was stirred at room temperature for 1 h. After the reaction was completed, the resulting mixture was concentrated under vacuum. The residue was purified by Prep-HPLC with the following conditions (Column: Xselect CSH C18 OBD Column 30×150 mm, 5 μm; Mobile Phase A: Water (10 mmol/L $NH_4HCO_3$), Mobile Phase B: ACN; Flow rate: 60 mL/min; Gradient: 32% B to 38% B in 8 min; Wave Length: 254 nm) to afford (E)-1-((10S)-4-((4-([1,2,4]triazolo[1,5-a]pyridin-7-yloxy)-3-chlorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 32) (41.4 mg, 22%) as a white solid. LCMS (ESI, m/z): $[M+H]^+$=613.2. $^1H$ NMR (400 MHz, DMSO-$d_6$): δ 9.73 (d, J=8.0 Hz, 1H), 8.97 (d, J=7.6 Hz, 1H), 8.54 (s, 1H), 8.49 (d, J=2.4 Hz, 1H), 8.42 (s, 1H), 8.18-8.15 (m, 1H), 7.54 (s, 1H), 7.48 (d, J=9.2 Hz, 1H), 7.09-7.06 (m, 1H), 6.93 (d, J=2.4 Hz, 1H), 6.69-6.61 (m, 2H), 5.15-4.61 (m, 3H), 4.29-4.04 (m, 3H), 3.90-3.61 (m, 1H), 3.47-3.38 (m, 1H), 3.24-3.21 (m, 1H), 3.07-3.03 (m, 2H), 2.17-2.15 (m, 6H).

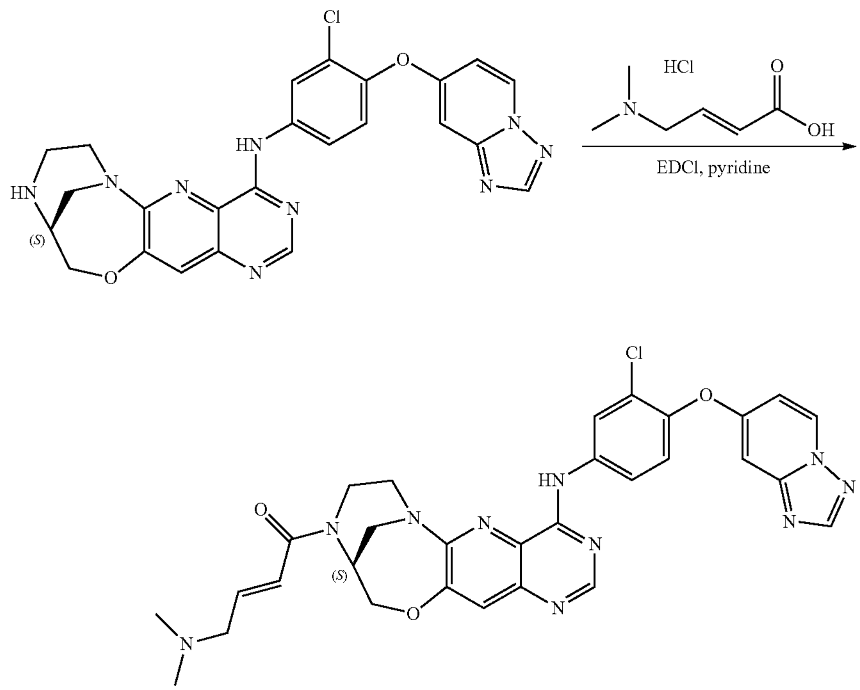

32

Example S32: Synthesis of 1-((10S)-4-((4-(imidazo[1,2-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)prop-2-en-1-one (Compound 33)

Step 1. Synthesis of 7-bromo-6-chloro-N-(4-{imidazo[1,2-a]pyridin-7-yloxy}-3-methylphenyl)pyrido[3,2-d]pyrimidin-4-amine

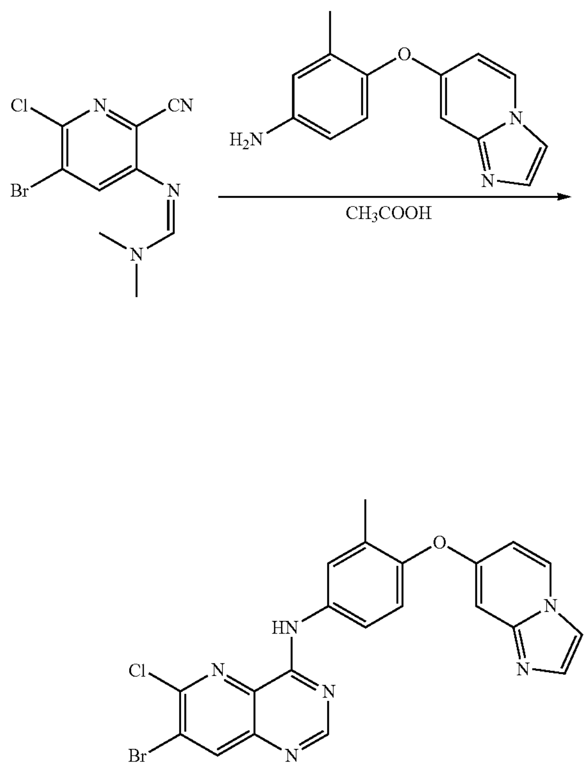

To a mixture of (Z)—N'-(5-bromo-6-chloro-2-cyanopyridin-3-yl)-N,N-dimethylmethanimidamide (721.0 mg, 2.51 mmol) in $CH_3COOH$ (10.0 mL) was added 4-{imidazo[1,2-a]pyridin-7-yloxy}-3-methylaniline (600 mg, 2.51 mmol) at room temperature. The resulting mixture was stirred at 85° C. for 2 h. After the reaction was completed, the resulting mixture was concentrated under reduced pressure. The residue was purified by flash column chromatography with $CH_2Cl_2$/MeOH (10/1, v/v) to afford 7-bromo-6-chloro-N-(4-{imidazo[1,2-a]pyridin-7-yloxy}-3-methylphenyl)pyrido[3,2-d]pyrimidin-4-amine (680.0 mg, 56%) as a light yellow solid. LCMS (ESI, m/z): $[M+H]^+$=481.0.

Step 2. Synthesis of Tert-butyl (2S)-4-{7-bromo-4-[(4-{imidazo[1,2-a]pyridin-7-yloxy}-3-methylphenyl)amino]pyrido[3,2-d]pyrimidin-6-yl}-2-(hydroxymethyl)piperazine-1-carboxylate

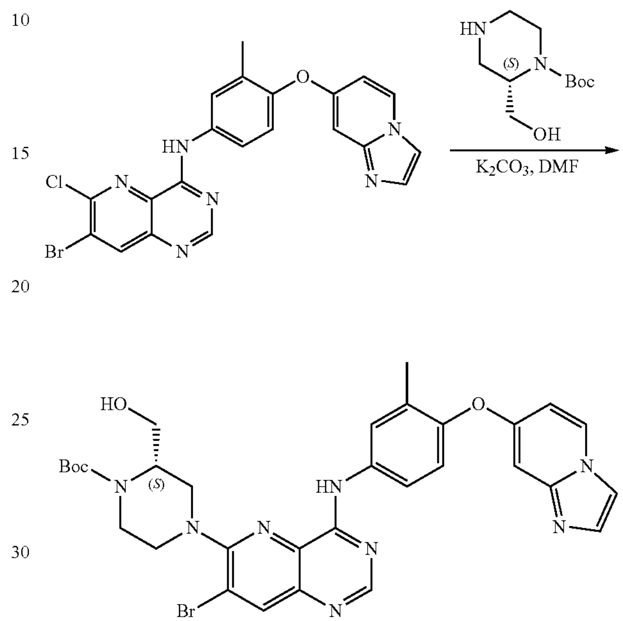

To a mixture of 7-bromo-6-chloro-N-(4-{imidazo[1,2-a]pyridin-7-yloxy}-3-methylphenyl)pyrido[3,2-d]pyrimidin-4-amine (680.0 mg, 1.41 mmol) and tert-butyl (2S)-2-(hydroxymethyl)piperazine-1-carboxylate (457.9 mg, 37.92 mmol) in DMF (10.0 mL) was added $K_2CO_3$ (780.3 mg, 5.65 mmol) at room temperature. The resulting mixture was stirred at 100° C. for 16 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (2S)-4-{7-bromo-4-[(4-{imidazo[1,2-a]pyridin-7-yloxy}-3-methylphenyl)amino]pyrido[3,2-d]pyrimidin-6-yl}-2-(hydroxymethyl)piperazine-1-carboxylate (660.0 mg, 71%) as a light yellow solid. LCMS (ESI, m/z): $[M+H]^+$=661.2.

Step 3. Synthesis of tert-butyl (10S)-4-((4-(imidazo[1,2-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate

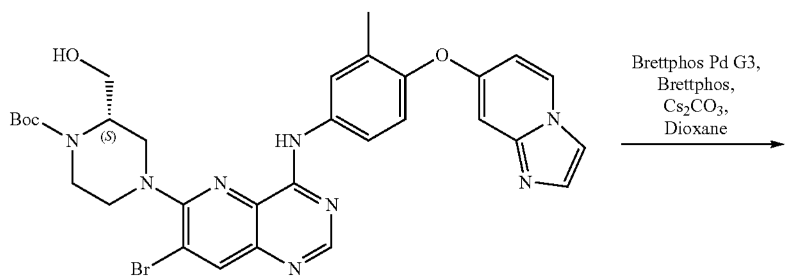

-continued

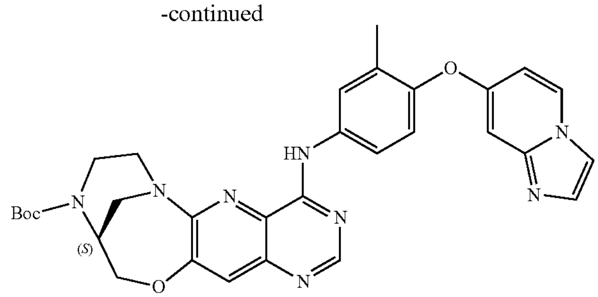

To a mixture of tert-butyl (2S)-4-{7-bromo-4-[(4-{imidazo[1,2-a]pyridin-7-yloxy}-3-methylphenyl)amino]pyrido[3,2-d]pyrimidin-6-yl}-2-(hydroxymethyl)piperazine-1-carboxylate (660.0 mg, 22.31 mmol) in dioxane (10.0 mL) was added BrettPhos Pd G3 (180.9 mg, 0.20 mmol), BrettPhos (214.2 mg, 0.40 mmol) and $Cs_2CO_3$ (975.2 mg, 2.99 mmol) at room temperature under $N_2$. The resulting mixture was stirred at 100° C. for 16 h under $N_2$. After the reaction was completed, the resulting mixture was diluted with water and extracted with ethyl acetate. The combined organic layers were washed with brine, dried over anhydrous sodium sulfate and filtered. The filtrate was evaporated in vacuo. The residue was purified by flash column chromatography with $CH_2Cl_2$/MeOH (10/1, v/v) to afford tert-butyl (10S)-4-((4-(imidazo[1,2-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (290.0 mg, 50%) as a yellow solid. LCMS (ESI, m/z): $[M+H]^+$=581.3.

Step 4. Synthesis of (10S)—N-(4-(imidazo[1,2-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine

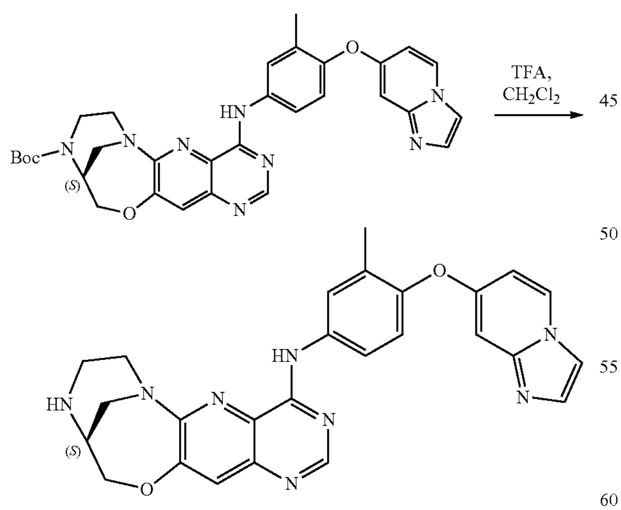

To a mixture of tert-butyl (10S)-4-((4-(imidazo[1,2-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonine-9-carboxylate (290.0 mg, 0.50 mmol) in $CH_2Cl_2$ (2.0 mL) was added TFA (1.0 mL) at room temperature. The resulting mixture was stirred at room temperature for 1 h. After the reaction was completed, the resulting mixture was basified to pH 8 with saturated $NaHCO_3$(aq.). The resulting mixture was extracted with $CH_2Cl_2$. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford (10S)—N-(4-(imidazo[1,2-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (120.0 mg, 50%) as a yellow solid. LCMS (ESI, m/z): $[M+H]^+$=481.2.

Step 5. Synthesis of 1-((10S)-4-((4-(imidazo[1,2-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 33)

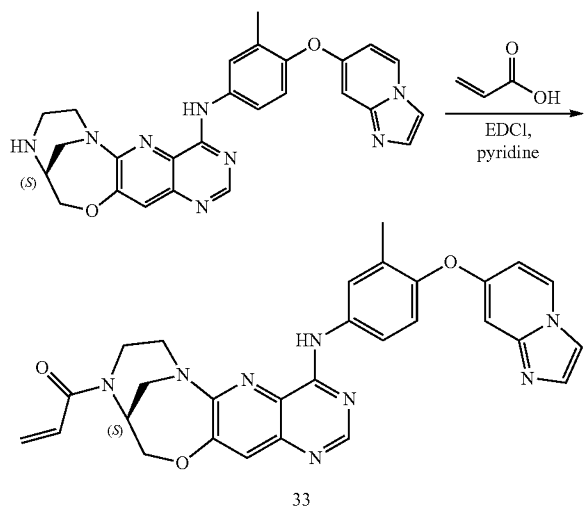

33

A mixture of (10S)—N-(4-(imidazo[1,2-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (100.0 mg, 0.21 mmol) and acrylic acid (15.0 mg, 0.21 mmol) in pyridine (10.0 mL) was stirred at room temperature for 15 min. Then EDCI (79.8 mg, 0.42 mmol) was added to the mixture at room temperature. The mixture was stirred at room temperature for 2 h. After the reaction was completed, the resulting mixture was concentrated under reduced pressure. The residue was purified by flash column chromatography with $CH_2Cl_2$/MeOH (10/1, v/v)

and then purified by Prep-HPLC with the following conditions: (Column: XBridge Prep OBD C18 Column, 19×250 mm, 5 μm; Mobile Phase A: Water (10 mmol/L $NH_4HCO_3$), Mobile Phase B: ACN; Flow rate: 25 mL/min; Gradient: 37% B to 37% B in 13 min; Wave Length: 254 nm) to afford 1-((10S)-4-((4-(imidazo[1,2-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)prop-2-en-1-one (Compound 33) (6.4 mg, 6%) as a yellow solid. LCMS (ESI, m/z): $[M+H]^+$=535.3. $^1H$ NMR (400 MHz, DMSO-$d_6$): δ 9.51 (d, J=10.8 Hz, 1H), 8.55 (d, J=6.8 Hz, 1H), 8.46 (s, 1H), 7.96 (s, 2H), 7.84 (s, 1H), 7.51 (s, 1H), 7.43 (s, 1H), 7.15 (d, J=9.2 Hz, 1H), 6.86-6.79 (m, 2H), 6.53 (s, 1H), 6.17-6.13 (m, 1H), 5.74-5.71 (m, 1H), 5.18-4.63 (m, 3H), 4.28-4.19 (m, 2H), 4.14-4.07 (m, 1H), 3.87-3.65 (m, 1H), 3.44-3.41 (m, 1H), 3.29-3.23 (m, 1H), 2.20 (s, 3H).

Example S33: Synthesis of (E)-4-(dimethylamino)-1-((10S)-4-((4-(imidazo[1,2-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)but-2-en-1-one (Compound 34)

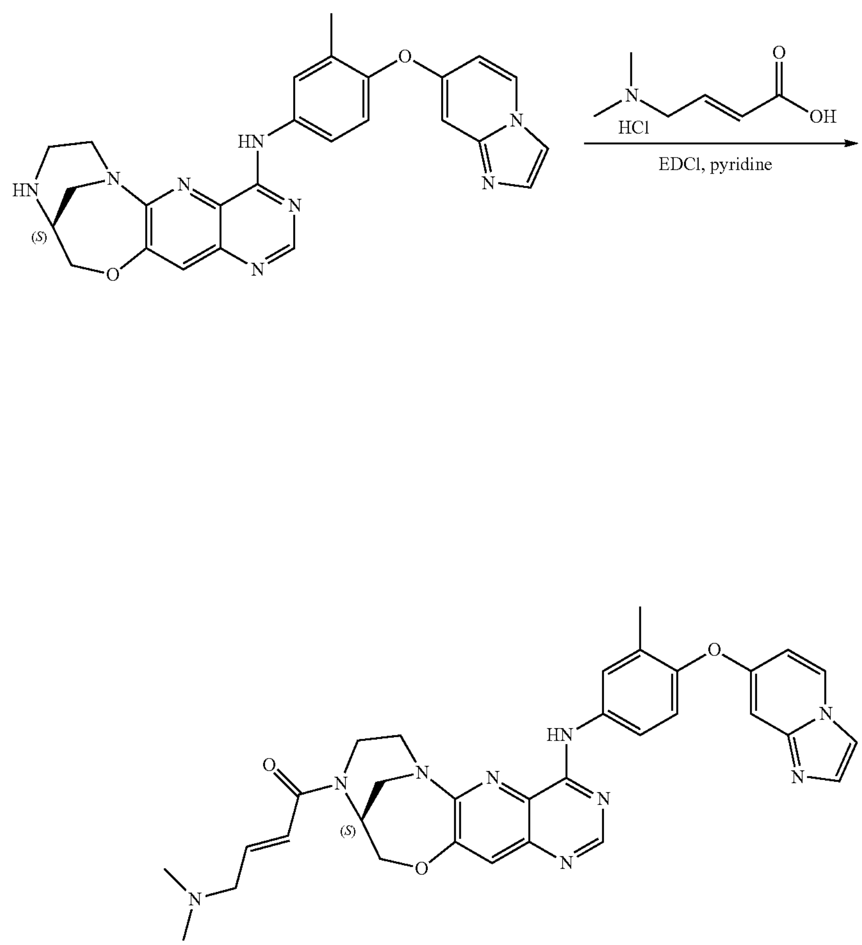

34

To a mixture of (10S)—N-(4-(imidazo[1,2-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (120.0 mg, 0.25 mmol) in pyridine (5.0 mL) was added (2E)-4-(dimethylamino)but-2-enoic acid hydrochloride (41.4 mg, 0.25 mmol) at room temperature. Then EDCI (95.7 mg, 0.50 mmol) was added to the mixture at room temperature. The mixture was stirred at room temperature for 2 h. After the reaction was completed, the resulting mixture was concentrated under reduced pressure. The residue was purified by flash column chromatography with $CH_2Cl_2$/MeOH (10/1, v/v) and then purified by Prep-HPLC with the following conditions: (Column: XBridge Shield RP18 OBD Column, 19×250 mm, 10 μm; Mobile Phase A: Water (10 mmol/L $NH_4HCO_3$), Mobile Phase B: MeOH—HPLC; Flow rate: 25 mL/min; Gradient: 66% B to 72% B in 8 min; Wave Length: 254 nm) to afford (E)-4-(dimethylamino)-1-((10S)-4-((4-(imidazo[1,2-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 34) (6.4 mg, 6%) as a yellow solid. LCMS (ESI, m/z): $[M+H]^+$=592.2. $^1H$ NMR (400 MHz, DMSO-$d_6$): δ 9.52-9.50 (m, 1H), 8.55 (d, J=7.2 Hz, 1H), 8.47 (s, 1H), 7.96-7.94 (m, 2H), 7.84 (s, 1H), 7.51 (s, 1H), 7.43 (d, J=1.2 Hz, 1H), 7.15 (d, J=8.8 Hz, 1H), 6.82-6.79 (m, 1H), 6.65-6.62 (m, 2H), 6.53 (d, J=2.4 Hz, 1H), 5.11-4.69 (m, 3H), 4.25-4.02 (m, 3H), 3.87-3.65 (m, 1H), 3.27-3.17 (m, 2H), 3.06-3.04 (m, 2H), 2.21 (s, 3H), 2.18-2.14 (m, 6H).

Example S34: Synthesis of (E)-1-((10S)-4-((4-([1,2,4]triazolo[1,5-a]pyridin-7-yloxy)-2-fluoro-3-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 35)

Step 1. Synthesis of N-(4-([1,2,4]triazolo[1,5-a]pyridin-7-yloxy)-2-fluoro-3-methylphenyl)-7-bromo-6-chloropyrido[3,2-d]pyrimidin-4-amine

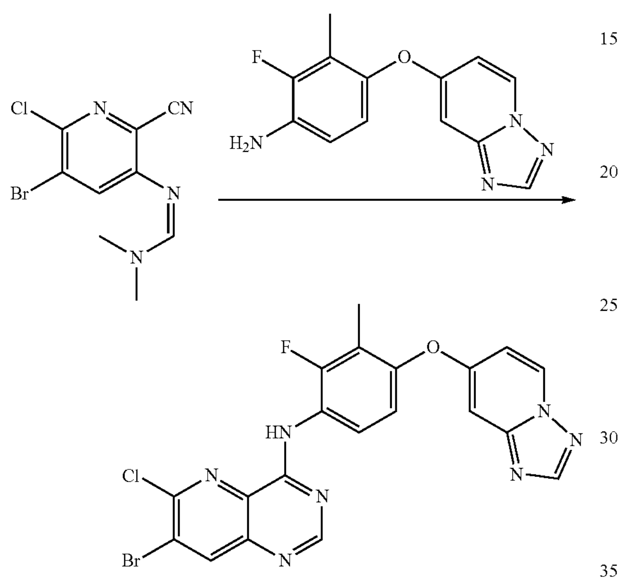

A mixture of (Z)—N'-(5-bromo-6-chloro-2-cyanopyridin-3-yl)-N,N-dimethylmethanimidamide (450.0 mg, 1.56 mmol) and 2-fluoro-3-methyl-4-{[1,2,4]triazolo[1,5-a]pyridin-7-yloxy}aniline (404.1 mg, 1.56 mmol) in acetic acid (10.0 mL) was stirred at 100° C. for 5 h. After the reaction was completed, the resulting mixture was concentrated under reduced pressure. The residue was purified by flash column chromatography with petroleum ether/ethyl acetate (1/1, v/v) to afford 7-bromo-6-chloro-N-(2-fluoro-3-methyl-4-{[1,2,4]triazolo[1,5-a]pyridin-7-yloxy}phenyl)pyrido[3,2-d]pyrimidin-4-amine (580.0 mg, 74%) as a yellow solid. LCMS (ESI, m/z): $[M+H]^+=500.1$.

Step 2. Synthesis of tert-butyl (2S)-4-{7-bromo-4-[(2-fluoro-3-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate

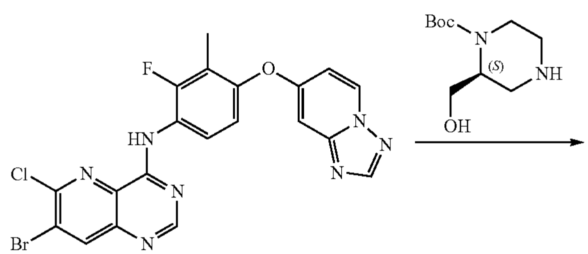

-continued

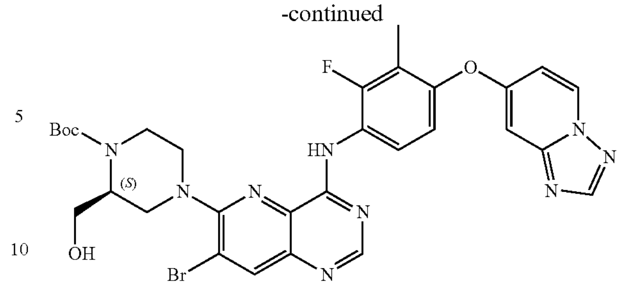

To a stirred mixture of 7-bromo-6-chloro-N-(2-fluoro-3-methyl-4-{[1,2,4]triazolo[1,5-a]pyridin-7-yloxy}phenyl)pyrido[3,2-d]pyrimidin-4-amine (560.0 mg, 1.12 mmol) and tert-butyl (2S)-2-(hydroxymethyl)piperazine-1-carboxylate (34.6 mg, 0.16 mmol) in ACN (10.0 mL) was added $K_2CO_3$ (772.8 mg, 5.59 mmol) at room temperature. The resulting mixture was stirred at 100° C. for 16 h. After the reaction was completed, the resulting mixture was filtered. The filtrate was concentrated under reduced pressure. The residue was purified by flash column chromatography with $CH_2Cl_2$/ethyl acetate (3/7, v/v) to afford tert-butyl (2S)-4-{7-bromo-4-[(2-fluoro-3-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (540.0 mg, 63%) as a yellow solid. LCMS (ESI, m/z): $[M+H]^+=680.1$.

Step 3. Synthesis of tert-butyl (10S)-4-((4-([1,2,4]triazolo[1,5-a]pyridin-7-yloxy)-2-fluoro-3-methylphenyl)amino)-7,8,10,11-tetrahydro-9H-6,10-methanopyrimido[4',5':5,6]pyrido[3,2-b][1,4,7]oxadiazonine-9-carboxylate

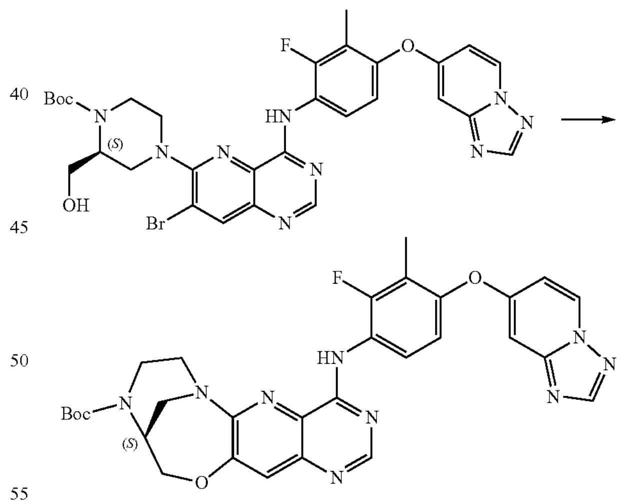

To a stirred mixture of tert-butyl (2S)-4-{7-bromo-4-[(2-fluoro-3-methyl-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (520.0 mg, 0.764 mmol) and BrettPhos Pd G3 (138.5 mg, 0.15 mmol) in 1,4-dioxane (12.0 mL) were added BrettPhos (164.1 mg, 0.31 mmol) and $K_2CO_3$ (316.8 mg, 2.29 mmol) at room temperature. The resulting mixture was stirred at 100° C. for 16 h under $N_2$. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/9, v/v) to afford tert-butyl (10S)-4-((4-([1,2,4]triazolo[1,5-a]pyridin-7-yloxy)-2-fluoro-3-methylphenyl)amino)-7,8,10,11-tetrahydro-9H-6,10-methanopyrimido[4',5':5,6]pyrido[3,2-b][1,4,7]oxadiazonine-9-carboxylate (230.0 mg, 50%) as a yellow solid. LCMS (ESI, m/z): $[M+H]^+=600.2$.

Step 4. Synthesis of (10S)—N-(4-([1,2,4]triazolo[1,5-a]pyridin-7-yloxy)-2-fluoro-3-methylphenyl)-8,9,10,11-tetrahydro-7H-6,10-methanopyrimido[4',5':5,6]pyrido[3,2-b][1,4,7]oxadiazonin-4-amine hydrochloride

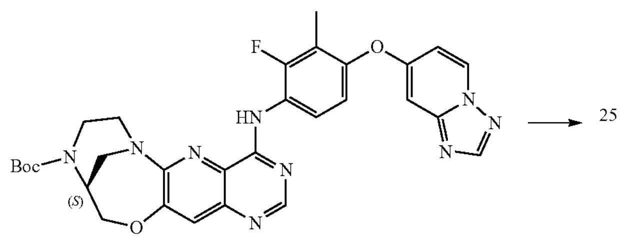

-continued

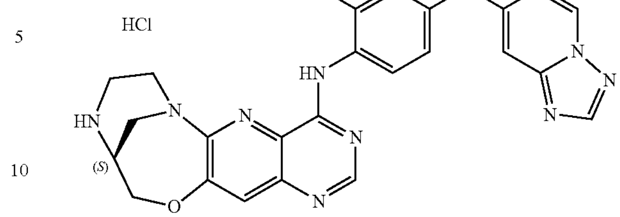

A mixture of tert-butyl (10S)-4-((4-([1,2,4]triazolo[1,5-a]pyridin-7-yloxy)-2-fluoro-3-methylphenyl)amino)-7,8,10,11-tetrahydro-9H-6,10-methanopyrimido[4',5':5,6]pyrido[3,2-b][1,4,7]oxadiazonine-9-carboxylate (210.0 mg, 0.03 mmol) in HCl/1,4-dioxane (5.0 mL, 4 mol/L) was stirred at room temperature for 1 h. After the reaction was completed, the resulting mixture was concentrated under reduced pressure to afford (10S)—N-(4-([1,2,4]triazolo[1,5-a]pyridin-7-yloxy)-2-fluoro-3-methylphenyl)-8,9,10,11-tetrahydro-7H-6,10-methanopyrimido[4',5':5,6]pyrido[3,2-b][1,4,7]oxadiazonin-4-amine hydrochloride (170.0 mg, crude) as a yellow solid. LCMS (ESI, m/z): $[M+H]^+=500.2$.

Step 5. Synthesis of (E)-1-((10S)-4-((4-([1,2,4]triazolo[1,5-a]pyridin-7-yloxy)-2-fluoro-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 35)

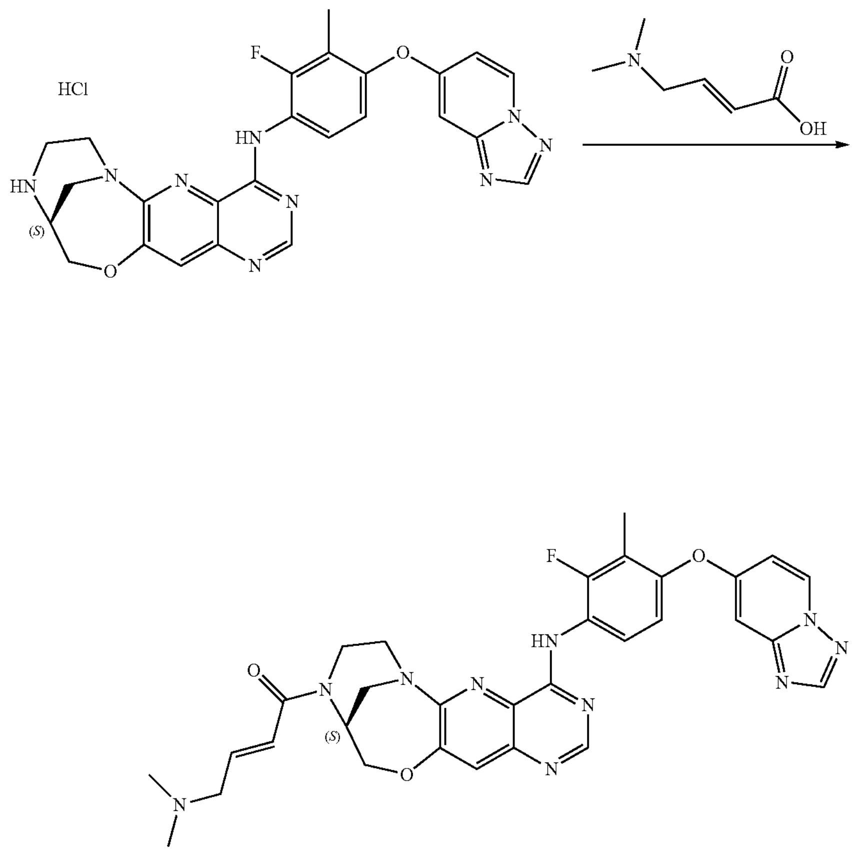

35

To a stirred mixture of (10S)—N-(4-([1,2,4]triazolo[1,5-a]pyridin-7-yloxy)-2-fluoro-3-methylphenyl)-8,9,10,11-tetrahydro-7H-6,10-methanopyrimido[4',5':5,6]pyrido[3,2-b][1,4,7]oxadiazonin-4-amine hydrochloride (150.0 mg, crude) and (2E)-4-(dimethylamino)but-2-enoic acid (38.8 mg, 0.30 mmol) in pyridine (10.0 mL) was added EDCI (115.1 mg, 0.60 mmol) at room temperature. The resulting mixture was stirred at room temperature for 1 h. After the reaction was completed, the resulting mixture was concentrated under reduced pressure. The residue was purified by flash column chromatography with $CH_2Cl_2$/MeOH (5/1, v/v) and then purified by Prep-HPLC with the following conditions (Column: XBridge Prep Phenyl OBD Column, 19×250 mm, 5 μm; Mobile Phase A: Water (10 mmol/L $NH_4HCO_3$), Mobile Phase B: MeOH—HPLC; Flow rate: 25 mL/min; Gradient: 68% B to 70% B in 12 min; Wave Length: 254 nm) to afford (E)-1-((10S)-4-((4-([1,2,4]triazolo[1,5-a]pyridin-7-yloxy)-2-fluoro-3-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 35) (31.8 mg, 16%) as a yellow solid. LCMS (ESI, m/z): $[M+H]^+$=611.3. $^1$H NMR (400 MHz, DMSO-$d_6$): δ 9.39 (s, 1H), 8.98 (d, J=7.6 Hz, 1H), 8.44-8.42 (m, 2H), 8.05-7.98 (m, 1H), 7.54 (s, 1H), 7.14 (d, J=8.8 Hz, 1H), 7.09-7.06 (m, 1H), 6.92 (d, J=2.0 Hz, 1H), 6.77-6.61 (m, 2H), 5.11-4.55 (m, 3H), 4.27-4.08 (m, 3H), 3.94-3.59 (m, 1H), 2.39-2.35 (m, 6H), 2.16 (s, 3H).

Example S35: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(bis(methyl-d3)amino)but-2-en-1-one formic acid (Compound 36)

To a solution of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (200.0 mg, crude) in THE (5.0 mL) was added TEA (96.6 mg, 0.95 mmol) and bis(methyl-d3)amine hydrochloride (27.8 mg, 0.32 mmol) at room temperature. The resulting mixture was stirred at room temperature for 0.5 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (7/1, v/v) and then purified by Prep-HPLC with the following conditions: (Column: XSelect CSH Fluoro Phenyl, 30×150 mm, 5 μm; Mobile Phase A: ACN, Mobile Phase B: Water (0.1% FA); Flow rate: 60 mL/min; Gradient: 3% B to 15% B in 10 min, 15% B to 15% B in 14 min; Wave Length: 254\220 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-d3)amino)but-2-en-1-one formic acid (Compound 36) (32.0 mg, 17%) as a yellow solid. LCMS (ESI, m/z): $[M+H]^+$=599.4. $^1$H NMR (400 MHz, DMSO-$d_6$): δ 9.53 (s, 1H), 8.94 (d, J=7.6 Hz, 1H), 8.48 (s, 1H), 8.38 (s, 1H), 8.14 (s, 1H), 8.00 (s, 2H), 7.52 (s, 1H), 7.22 (d, J=8.8 Hz, 1H), 7.04-7.02 (m, 1H), 6.78-6.74 (m, 2H), 6.67-6.61 (m, 1H), 5.12-4.62 (m, 3H), 4.25-4.21 (m, 1H), 4.17-4.05 (m, 1H), 3.85-3.79 (m, 1H), 3.67-3.61 (m, 1H), 3.48-3.33 (m, 4H), 2.20 (s, 3H).

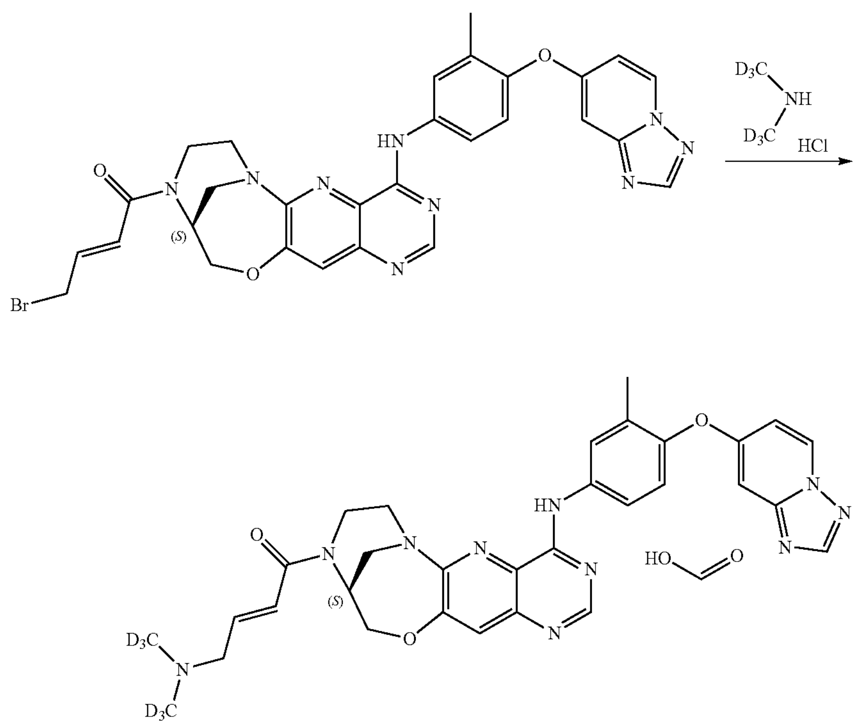

36

Example S36: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-4-(methylamino)but-2-en-1-one formate (Compound 37)

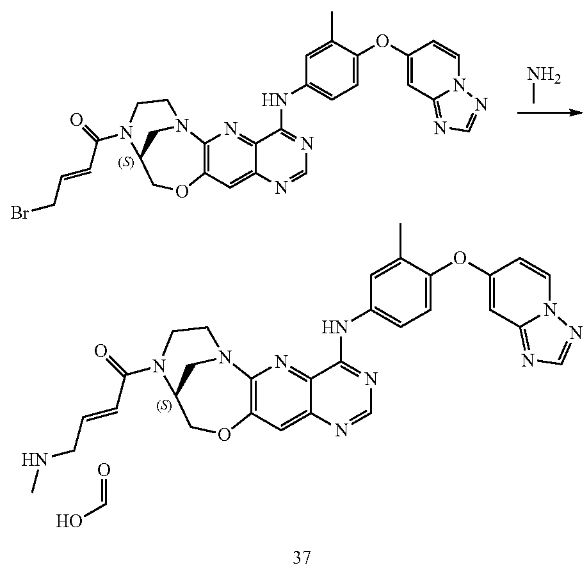

37

To a solution of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (200.0 mg, crude) in THE (3.0 mL) was added a solution of methylamine in THE (0.2 mL, 2 mol/L) and TEA (96.6 mg, 0.95 mmol) at room temperature. The resulting mixture was stirred at room temperature for 0.5 h. After the reaction was completed, the resulting mixture was concentrated under reduced pressure. The residue was purified by flash column chromatography with $CH_2Cl_2/CH_3OH$ (80/20, v/v) and then purified by Prep-HPLC with the following conditions: (Column: Xselect CSH C18 OBD Column 30×150 mm, 5 μm; Mobile Phase A: ACN, Mobile Phase B: Water (0.1% FA); Flow rate: 60 mL/min; Gradient: 3% B to 15% B in 10 min, 15% B to 15% B in 14 min; Wave Length: 254\220 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-4-(methylamino)but-2-en-1-one formate (Compound 37) (6.4 mg, 3%) as a yellow solid. LCMS (ESI, m/z): $[M+H]^+$=579.3. $^1H$ NMR (400 MHz, $CD_3OD$): δ 8.74 (s, 1H), 8.54 (s, 1H), 8.45 (s, 1H) 8.30 (s, 1H), 7.93-7.88 (m, 2H), 7.50 (s, 1H), 7.18 (d, J=8.4 Hz, 1H), 7.08 (d, J=5.2 Hz, 1H), 6.86-6.71 (m, 3H), 5.27-5.11 (m, 1H), 4.88-4.71 (m, 2H), 4.43-4.34 (m, 1H), 4.15-3.91 (m, 2H), 3.80-3.72 (m, 2H), 3.59-3.52 (m, 1H), 3.50-3.44 (m, 1H), 2.72-2.69 (m, 3H), 2.22 (s, 3H).

Example S37. Synthesis of (E)-4-(dimethylamino)-1-((10S)-4-((4-((6-ethylpyridin-3-yl)oxy)-3-methylphenyl)amino)-7,8,10,11-tetrahydro-9H-6,10-methanopyrimido[4,5':5,6]pyrido[3,2-b][1,4,7]oxadiazonin-9-yl)but-2-en-1-one formic acid (Compound 38)

Step 1. Synthesis of (Z)—N'-(5-bromo-6-chloro-2-cyanopyridin-3-yl)-N,N-dimethylformimidamide

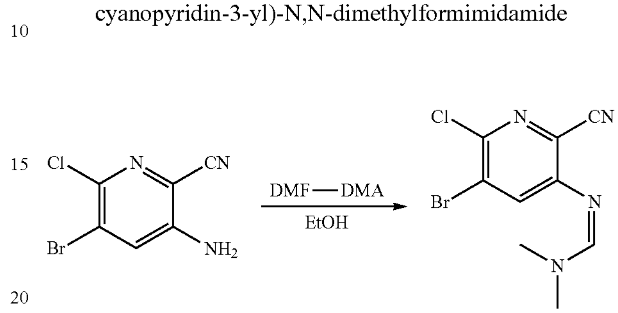

To a solution of 3-amino-5-bromo-6-chloropicolinonitrile (500.0 mg, 2.15 mmol) in EtOH (20.0 mL) was added DMF-DMA (0.5 mL) at room temperature. The resulting mixture was stirred at 80° C. for 2 h. After the reaction was completed, the resulting mixture was concentrated under reduced pressure to afford (Z)—N'-(5-bromo-6-chloro-2-cyanopyridin-3-yl)-N,N-dimethylformimidamide (1.0 g, crude) as a yellow solid. LCMS (ESI, m/z): $[M+H]^+$=287.0.

Step 2. Synthesis of 7-bromo-6-chloro-N-(4-((6-ethylpyridin-3-yl)oxy)-3-methylphenyl)pyrido[3,2-d]pyrimidin-4-amine

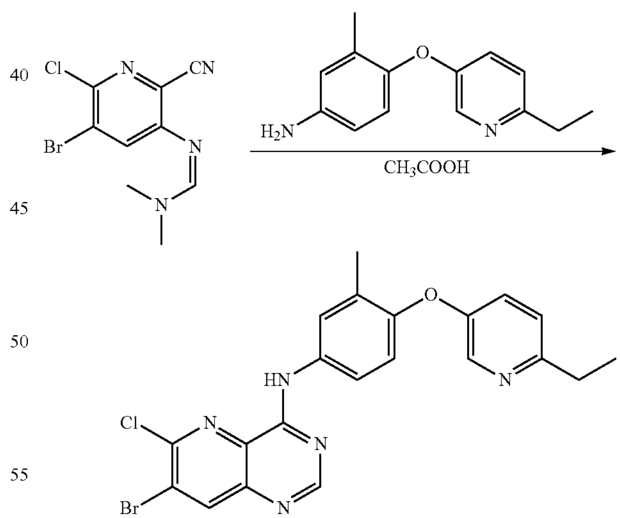

To a solution of (Z)—N'-(5-bromo-6-chloro-2-cyanopyridin-3-yl)-N,N-dimethylformimidamide (1.0 g, 3.47 mmol) in $CH_3COOH$ (20.0 mL) was added 4-((6-ethylpyridin-3-yl)oxy)-3-methylaniline (793.9 mg, 3.47 mmol) at room temperature. The resulting mixture was stirred at 85° C. for 2 h. After the reaction was completed, the resulting mixture was concentrated under reduced pressure. The residue was purified by flash column with dichloromethane/methanol (83/17, v/v) to afford 7-bromo-6-chloro-N-(4-((6-ethylpyridin-3-yl)oxy)-3-methylphenyl)pyrido[3,2-d]pyrimidin-4-amine (1.0 g, 98%) as a yellow solid. LCMS (ESI, m/z): $[M+H]^+$=470.1.

Step 3. Synthesis of Tert-butyl (S)-4-(7-bromo-4-((4-((6-ethylpyridin-3-yl)oxy)-3-methylphenyl)amino)pyrido[3,2-d]pyrimidin-6-yl)-2-(hydroxymethyl)piperazine-1-carboxylate

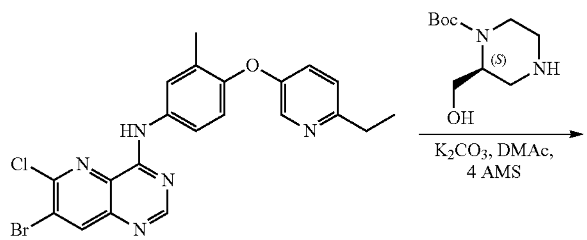

-continued

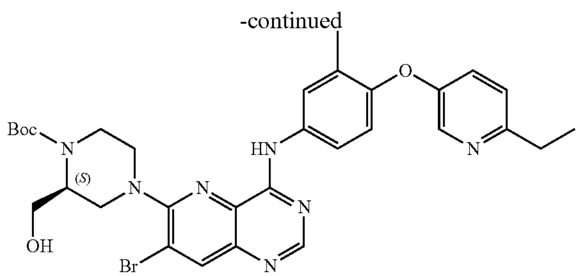

To a solution of 7-bromo-6-chloro-N-(4-((6-ethylpyridin-3-yl)oxy)-3-methylphenyl)pyrido[3,2-d]pyrimidin-4-amine (900.0 mg, 1.91 mmol) in DMAc (15.0 mL) was added tert-butyl (S)-2-(hydroxymethyl)piperazine-1-carboxylate (828.9 mg, 3.82 mmol), 4AMS (400.0 mg) and $K_2CO_3$ (791.9 mg, 5.73 mmol) at room temperature. The resulting mixture was stirred at 120° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (86/14, v/v) to afford tert-butyl (S)-4-(7-bromo-4-((4-((6-ethylpyridin-3-yl)oxy)-3-methylphenyl)amino)pyrido[3,2-d]pyrimidin-6-yl)-2-(hydroxymethyl)piperazine-1-carboxylate (900.0 mg, 68%) as a yellow solid. LCMS (ESI, m/z): $[M+H]^+$=650.2.

Step 4. Synthesis of tert-butyl (10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate

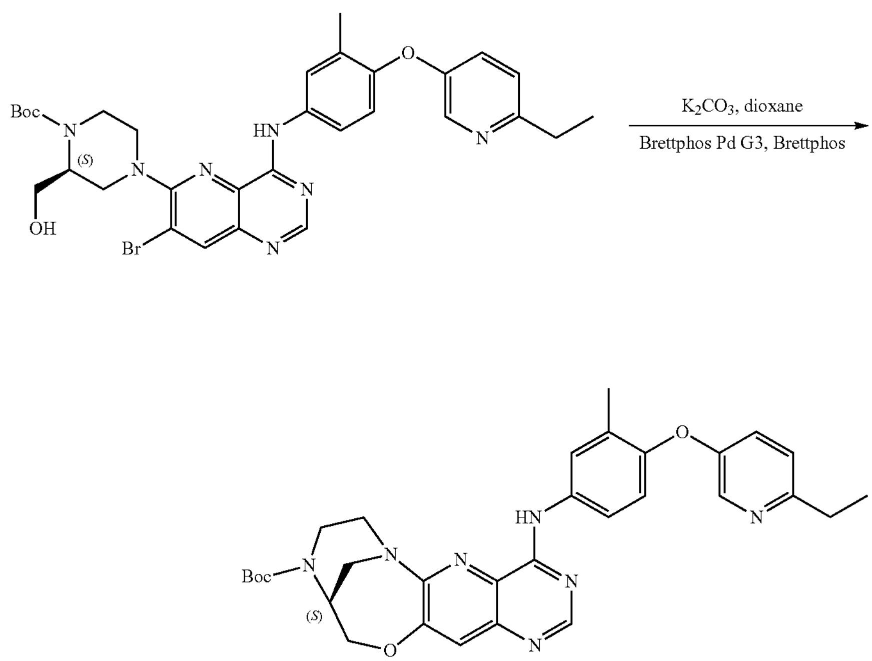

To a solution of tert-butyl (S)-4-(7-bromo-4-((4-((6-ethylpyridin-3-yl)oxy)-3-methylphenyl)amino)pyrido[3,2-d]pyrimidin-6-yl)-2-(hydroxymethyl)piperazine-1-carboxylate (800.0 mg, 1.23 mmol) in 1,4-dioxane (12.0 mL) was added $K_2CO_3$ (509.5 mg, 3.69 mmol), BrettPhos Pd G3 (108.7 mg, 0.12 mmol) and BrettPhos (128.6 mg, 0.24 mmol) at room temperature under $N_2$. The resulting mixture was stirred at 120° C. for 16 h under $N_2$. After the reaction was completed, the resulting mixture was filtered. The filtrate was concentrated under reduced pressure. The residue was purified by flash column chromatography with ethyl acetate/MeOH (89/11, v/v) to afford tert-butyl (10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate (400.0 mg, 35%) as a yellow solid. LCMS (ESI, m/z): $[M+H]^+$=570.3.

Step 5. Synthesis of (10S)—N-(4-((6-ethylpyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine hydrochloride

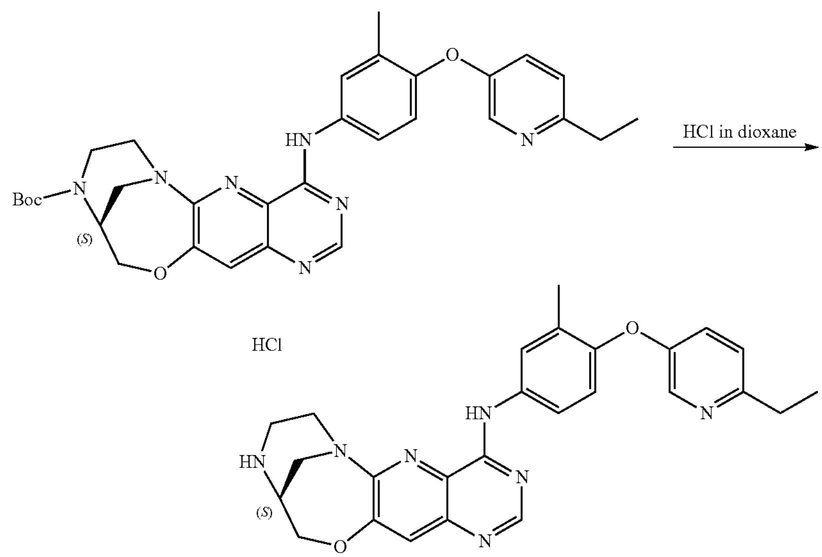

A solution of tert-butyl (10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate (220.0 mg, 0.38 mmol) in HCl/1,4-dioxane (10.0 mL, 4.0 mol/L) was stirred at room temperature for 2 h. After the reaction was completed, the resulting mixture was concentrated under reduced pressure and afford (10S)—N-(4-((6-ethylpyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine hydrochloride (220.0 mg, crude) as a yellow solid. LCMS (ESI, m/z): $[M+H]^+=470.2$.

Step 6. Synthesis of (E)-4-(dimethylamino)-1-((10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonin-9-yl)but-2-en-1-one formic acid (Compound 38)

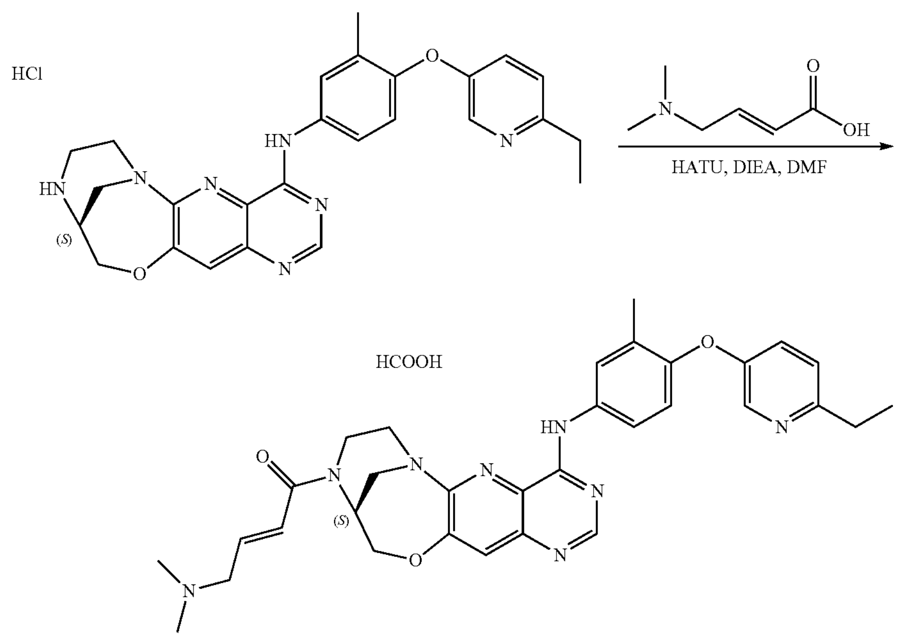

To a solution of (10S)—N-(4-((6-ethylpyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine hydrochloride (160.0 mg, crude) in DMF (5.0 mL) was added (E)-4-(dimethylamino)but-2-enoic acid (52.8 mg, 0.40 mmol), DIEA (264.2 mg, 2.04 mmol) and HATU (323.9 mg, 0.85 mmol) at 0° C. under $N_2$. The resulting mixture was stirred at 0° C. for 1.5 h under $N_2$. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3OH/H_2O$ (80/20, v/v) and then purified by Prep-HPLC with the following conditions: (Column: XBridge Shield RP18 OBD Column, 19×250 mm, 10 μm; Mobile Phase A: Water (0.05% FA), Mobile Phase B: ACN; Flow rate: 25 mL/min; Gradient: 18% B to 18% B in 8 min; Wave Length: 254 nm) to afford (E)-4-(dimethylamino)-1-((10S)-4-((4-((6-ethylpyridin-3-yl)oxy)-3-methylphenyl)amino)-7,8,10,11-tetrahydro-9H-6,10-methanopyrimido[4',5':5,6]pyrido[3,2-b][1,4,7]oxadiazonin-9-yl)but-2-en-1-one formic acid (Compound 38) (2.3 mg, 1%) as a yellow solid. LCMS (ESI, m/z): $[M+H]^+$=581.3. $^1$H NMR (400 MHz, DMSO-$d_6$): δ 9.45 (s, 1H), 8.44 (s, 1H), 8.28-8.11 (m, 2H), 7.90-7.77 (m, 2H), 7.50 (s, 1H), 7.27-7.20 (m, 2H), 6.99 (d, J=8.4 Hz, 1H), 6.69-6.51 (m, 2H), 5.17-5.08 (m, 1H), 4.89-4.58 (m, 3H), 4.23-4.08 (m, 3H), 3.12-3.04 (m, 3H), 2.77-2.72 (m, 3H), 2.22-2.16 (m, 9H), 1.24-1.20 (m, 3H).

Example S38: Synthesis of (E)-1-((10S)-4-((4-([1,2,4]triazolo[1,5-a]pyridin-7-yloxy)-3-fluorophenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 39)

Step 1. Synthesis of N-(4-([1,2,4]triazolo[1,5-a]pyridin-7-yloxy)-3-fluorophenyl)-7-bromo-6-chloropyrido[3,2-d]pyrimidin-4-amine

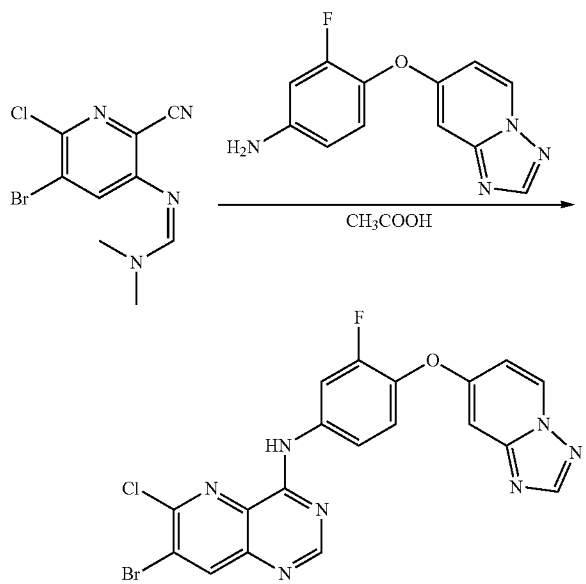

To a solution of (Z)—N'-(5-bromo-6-chloro-2-cyanopyridin-3-yl)-N,N-dimethylformimidamide (1.8 g, 6.26 mmol) in $CH_3COOH$ (40.0 mL) was added 4-([1,2,4]triazolo[1,5-a]pyridin-7-yloxy)-3-fluoroaniline (2.3 g, 9.41 mmol) at room temperature. The resulting mixture was stirred at 85° C. for 4 h. After the reaction was completed, the resulting mixture was concentrated under vacuum. The residue was purified by flash column chromatography with $CH_2Cl_2$/MeOH (10/1, v/v) to afford N-(4-([1,2,4]triazolo[1,5-a]pyridin-7-yloxy)-3-fluorophenyl)-7-bromo-6-chloropyrido[3,2-d]pyrimidin-4-amine (2.3 g, 75%) as a yellow solid. LCMS (ESI, m/z): $[M+H]^+$=486.0.

Step 2. Synthesis of tert-butyl (S)-4-(4-((4-([1,2,4]triazolo[1,5-a]pyridin-7-yloxy)-3-fluorophenyl)amino)-7-bromopyrido[3,2-d]pyrimidin-6-yl)-2-(hydroxymethyl)piperazine-1-carboxylate

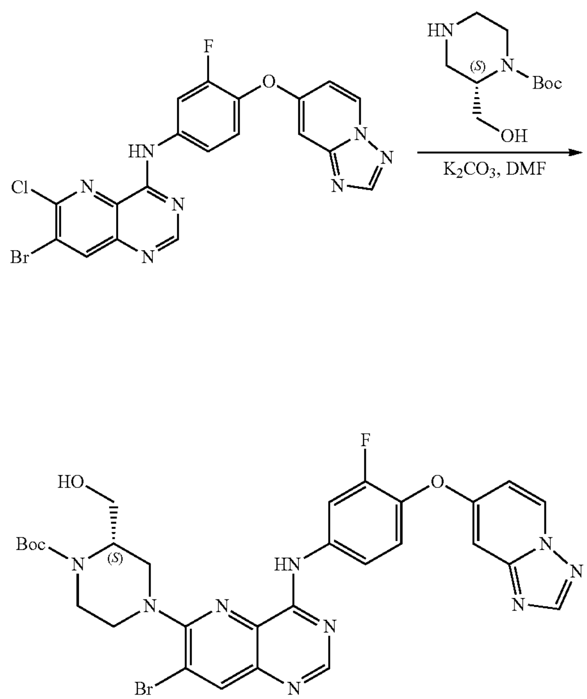

To a solution of N-(4-([1,2,4]triazolo[1,5-a]pyridin-7-yloxy)-3-fluorophenyl)-7-bromo-6-chloropyrido[3,2-d]pyrimidin-4-amine (500.0 mg, 1.02 mmol) in DMF (5.0 mL) was added tert-butyl (S)-2-(hydroxymethyl)piperazine-1-carboxylate (567.9 mg, 4.10 mmol) and $K_2CO_3$ (824.0 mg, 5.96 mmol) at room temperature. The resulting mixture was stirred at 100° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (S)-4-(4-((4-([1,2,4]triazolo[1,5-a]pyridin-7-yloxy)-3-fluorophenyl)amino)-7-bromopyrido[3,2-d]pyrimidin-6-yl)-2-(hydroxymethyl)piperazine-1-carboxylate (0.7 g, 73%) as a yellow solid. LCMS (ESI, m/z): $[M+H]^+$=666.2.

Step 3. Synthesis of tert-butyl (10S)-4-((4-([1,2,4]triazolo[1,5-a]pyridin-7-yloxy)-3-fluorophenyl)amino)-7,8,10,11-tetrahydro-9H-6,10-methanopyrimido[4',5':5,6]pyrido[3,2-b][1,4,7]oxadiazonine-9-carboxylate

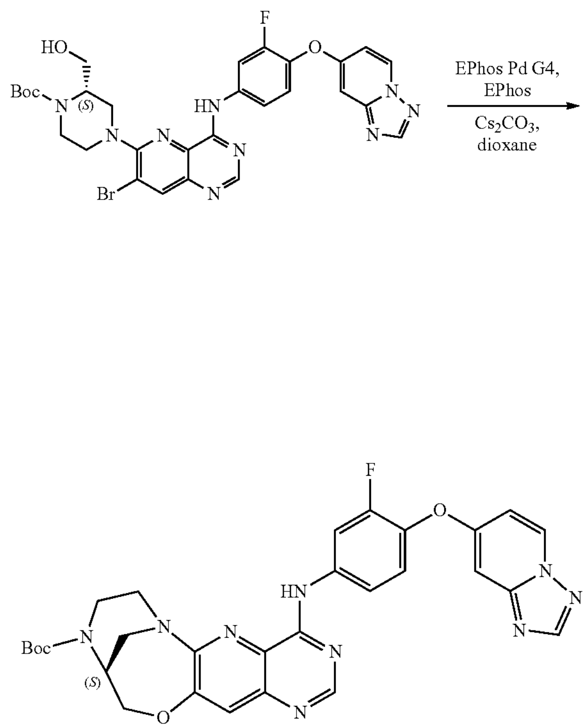

To a solution of tert-butyl (S)-4-(4-((4-([1,2,4]triazolo[1,5-a]pyridin-7-yloxy)-3-fluorophenyl)amino)-7-bromopyrido[3,2-d]pyrimidin-6-yl)-2-(hydroxymethyl)piperazine-1-carboxylate (800.0 mg, 1.20 mmol) in dioxane (300.0 mL) was added $Cs_2CO_3$ (1231.8 mg, 3.78 mmol), EPhos (134.8 mg, 0.25 mmol) and EPhos Pd G4 (115.7 mg, 0.12 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (10S)-4-((4-([1,2,4]triazolo[1,5-a]pyridin-7-yloxy)-3-fluorophenyl)amino)-7,8,10,11-tetrahydro-9H-6,10-methanopyrimido[4',5':5,6]pyrido[3,2-b][1,4,7]oxadiazonine-9-carboxylate (350.0 mg, 49%) as a light yellow solid. LCMS (ESI, m/z): $[M+H]^+$=586.2.

Step 4. Synthesis of (10S)—N-(4-([1,2,4]triazolo[1,5-a]pyridin-7-yloxy)-3-fluorophenyl)-8,9,10,11-tetrahydro-7H-6,10-methanopyrimido[4',5':5,6]pyrido[3,2-b][1,4,7]oxadiazonin-4-amine

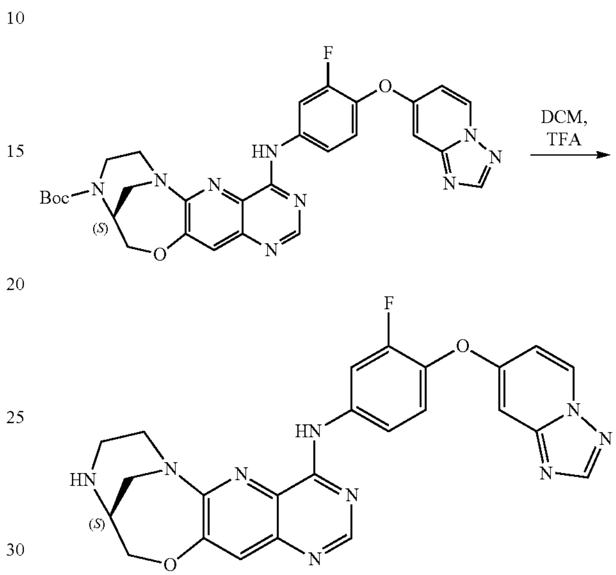

To a solution of tert-butyl (10S)-4-((4-([1,2,4]triazolo[1,5-a]pyridin-7-yloxy)-3-fluorophenyl)amino)-7,8,10,11-tetrahydro-9H-6,10-methanopyrimido[4',5':5,6]pyrido[3,2-b][1,4,7]oxadiazonine-9-carboxylate (320.0 mg, 0.54 mmol) in DCM (4.6 mL) was added TFA (1.8 mL) at room temperature. The mixture was stirred at room temperature for 1 h. After the reaction was completed, the mixture was basified to pH=8 with saturated $NaHCO_3$(aq.). The resulting mixture was extracted with $CH_2Cl_2$. The combined organic layers were washed with brine and dried over anhydrous $Na_2SO_4$. After filtration, the filtrate was concentrated under reduced pressure to afford (10S)—N-(4-([1,2,4]triazolo[1,5-a]pyridin-7-yloxy)-3-fluorophenyl)-8,9,10,11-tetrahydro-7H-6,10-methanopyrimido[4',5':5,6]pyrido[3,2-b][1,4,7]oxadiazonin-4-amine (180.0 mg, 72%) as a light yellow solid. LCMS (ESI, m/z): $[M+H]^+$=486.2.

Step 5. Synthesis of (E)-1-((10S)-4-((4-([1,2,4]triazolo[1,5-a]pyridin-7-yloxy)-3-fluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 39)

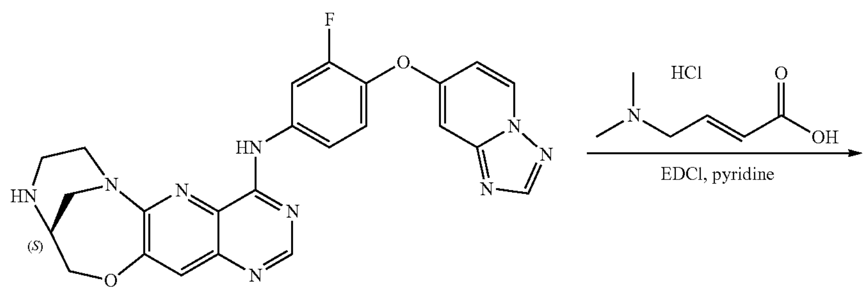

-continued

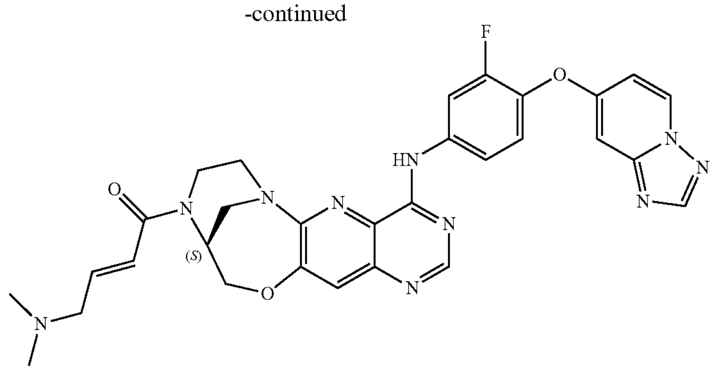

39

To a solution of (2E)-4-(dimethylamino)but-2-enoic acid hydrochloride (54.5 mg, 0.33 mmol) in pyridine (5.0 mL) was added (10S)—N-(4-([1,2,4]triazolo[1,5-a]pyridin-7-yloxy)-3-fluorophenyl)-8,9,10,11-tetrahydro-7H-6,10-methanopyrimido[4',5':5,6]pyrido[3,2-b][1,4,7]oxadiazonin-4-amine (160.0 mg, 0.33 mmol) and EDCI (126.3 mg, 0.66 mmol) at room temperature. The resulting mixture was stirred at room temperature for 1 h. After the reaction was completed, the resulting mixture was concentrated under vacuum. The residue was purified by Prep-HPLC with the following conditions (Column: Xselect CSH C18 OBD Column 30×150 mm, 5 μm; Mobile Phase A: Water (10 mmol/L $NH_4HCO_3$), Mobile Phase B: ACN; Flow rate: 60 mL/min; Gradient: 32% B to 38% B in 8 min; Wave Length: 254 nm) to afford (E)-1-((10S)-4-((4-([1,2,4]triazolo[1,5-a]pyridin-7-yloxy)-3-fluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 39) (24.4 mg, 12%) as a light white solid. LCMS (ESI, m/z): $[M+H]^+$=597.3. $^1H$ NMR (400 MHz, DMSO-$d_6$): δ 9.74-9.72 (m, 1H), 8.96 (d, J=7.6 Hz, 1H), 8.54 (s, 1H), 8.42 (s, 1H), 8.37-8.33 (m, 1H), 7.99-7.96 (m, 1H), 7.54 (s, 1H), 7.50-7.46 (m, 1H), 7.11-7.08 (m, 1H), 7.03 (d, J=2.4 Hz, 1H), 6.69-6.58 (m, 2H), 5.12-4.61 (m, 3H), 4.29-4.20 (m, 2H), 4.16-4.04 (m, 1H), 3.89-3.62 (m, 1H), 3.47-3.39 (m, 1H), 3.25-3.20 (m, 1H), 3.07-3.03 (m, 2H), 2.16 (d, J=6.0 Hz, 6H).

Example S39: Synthesis of (E)-1-((10S)-4-((4-([1,2,4]triazolo[1,5-a]pyridin-7-yloxy)-3-methylphenyl)amino)-5-fluoro-7,8,10,11-tetrahydro-9H-6,10-methano[1,4,7]oxadiazonino[3,2-g]quinazolin-9-yl)-4-(dimethylamino)but-2-en-1-one (Compound 40)

Step 1. Synthesis of tert-butyl (S)-4-(3-cyano-2-fluoro-4-nitrophenyl)-2-(hydroxymethyl)piperazine-1-carboxylate

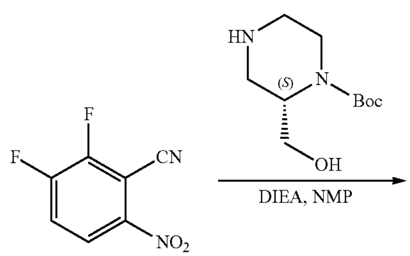

-continued

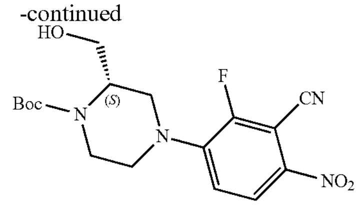

To a solution of 2,3-difluoro-6-nitrobenzonitrile (3.4 g, 18.52 mmol) in NMP (34.0 mL) was added tert-butyl (S)-2-(hydroxymethyl)piperazine-1-carboxylate (6.3 g, 40.75 mmol) and DIEA (14.4 g, 111.14 mmol) at room temperature. The mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with DCM/MeOH (88/12, v/v) to afford tert-butyl (S)-4-(3-cyano-2-fluoro-4-nitrophenyl)-2-(hydroxymethyl)piperazine-1-carboxylate (4.0 g, 81%) as a yellow solid. LCMS (ESI, m/z): $[M+H]^+$=381.1.

Step 2. Synthesis of tert-butyl (S)-4-(6-bromo-3-cyano-2-fluoro-4-nitrophenyl)-2-(hydroxymethyl)piperazine-1-carboxylate

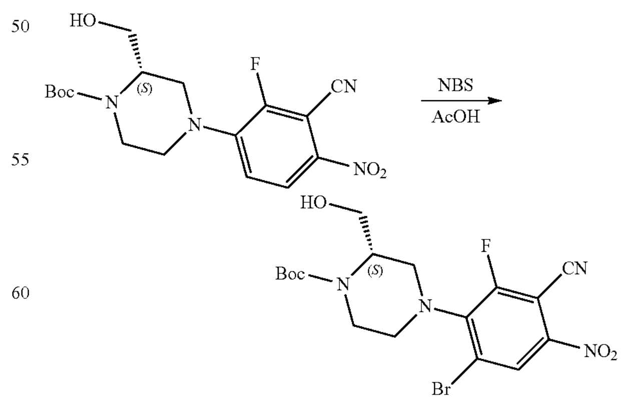

To a solution of tert-butyl (S)-4-(3-cyano-2-fluoro-4-nitrophenyl)-2-(hydroxymethyl)piperazine-1-carboxylate (4.0 g, 10.53 mmol) in $CH_3COOH$ (100.0 mL) was added NBS (19.5 g, 105.30 mmol) at room temperature. The mixture was stirred at room temperature for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure to afford tert-butyl (S)-4-(6-bromo-3-cyano-2-fluoro-4-nitrophenyl)-2-(hydroxymethyl)piperazine-1-carboxylate (4.0 g, crude) as a yellow solid. LCMS (ESI, m/z): $[M+H]^+$=459.1.

Step 3. Synthesis of tert-butyl (S)-4-(4-amino-6-bromo-3-cyano-2-fluorophenyl)-2-(hydroxymethyl)piperazine-1-carboxylate

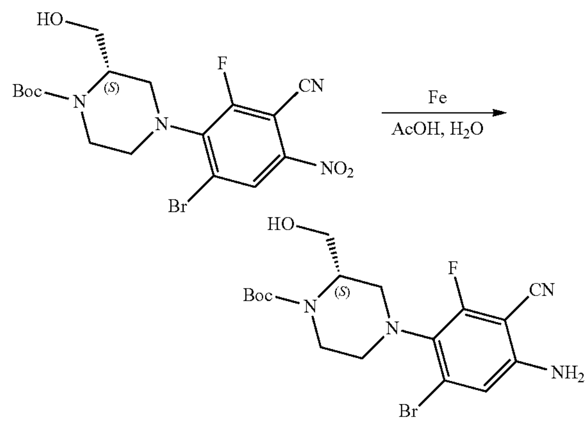

To a solution of tert-butyl (S)-4-(6-bromo-3-cyano-2-fluoro-4-nitrophenyl)-2-(hydroxymethyl)piperazine-1-carboxylate (4.0 g, crude) in $CH_3COOH/H_2O$ (40.0 mL/8.0 mL) was added Fe (2.4 g, 43.65 mmol) at room temperature. The mixture was stirred at room temperature for 2 h. After the reaction was completed, the mixture was filtered. The filtrate was concentrated under reduced pressure. The residue was purified by flash column chromatography with petroleum ether/ethyl acetate (22/78, v/v) to afford tert-butyl (S)-4-(4-amino-6-bromo-3-cyano-2-fluorophenyl)-2-(hydroxymethyl)piperazine-1-carboxylate (2.0 g, 53%) as a brown solid. LCMS (ESI, m/z): $[M+H]^+$=429.1.

Step 4. Synthesis of tert-butyl (3S)-10-amino-9-cyano-8-fluoro-2,3,5,6-tetrahydro-4H-3,7-methanobenzo[b][1,4,7]oxadiazonine-4-carboxylate

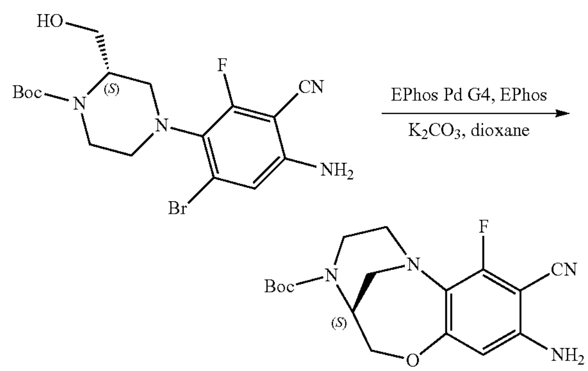

To a solution of tert-butyl (S)-4-(4-amino-6-bromo-3-cyano-2-fluorophenyl)-2-(hydroxymethyl)piperazine-1-carboxylate (800.0 mg, 1.86 mmol) in 1,4-dioxane (10.0 mL) was added $K_2CO_3$ (772.6 mg, 5.59 mmol), EPhos Pd G4 (171.2 mg, 0.19 mmol) and EPhos (199.3 mg, 0.37 mmol) at room temperature under $N_2$. The mixture was stirred at 85° C. for 2 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (15/85, v/v) to afford tert-butyl (3S)-10-amino-9-cyano-8-fluoro-2,3,5,6-tetrahydro-4H-3,7-methanobenzo[b][1,4,7]oxadiazonine-4-carboxylate (400.0 mg, 61%) as a yellow solid. LCMS (ESI, m/z): $[M+H]^+$=349.2.

Step 5. Synthesis of Tert-butyl (3S)-9-cyano-10-(((E)-(dimethylamino)methylene)amino)-8-fluoro-2,3,5,6-tetrahydro-4H-3,7-methanobenzo[b][1,4,7]oxadiazonine-4-carboxylate

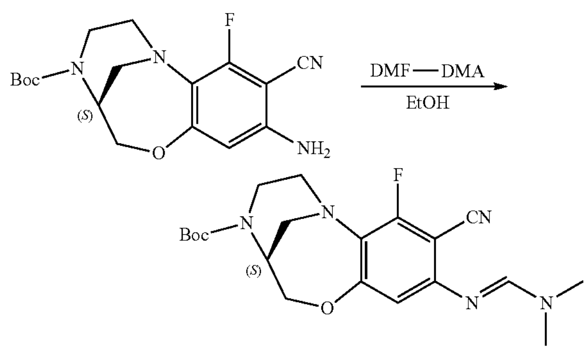

To a solution of tert-butyl (3S)-10-amino-9-cyano-8-fluoro-2,3,5,6-tetrahydro-4H-3,7-methanobenzo[b][1,4,7]oxadiazonine-4-carboxylate (230.0 mg, 0.66 mmol) in EtOH (3.0 mL) was added DMF-DMA (235.6 mg, 1.98 mmol) at room temperature. The mixture was stirred at 85° C. for 2 h. After the reaction was completed, the mixture was concentrated under reduced pressure to afford tert-butyl (3S)-9-cyano-10-(((E)-(dimethylamino)methylene)amino)-8-fluoro-2,3,5,6-tetrahydro-4H-3,7-methanobenzo[b][1,4,7]oxadiazonine-4-carboxylate (250.0 mg, crude) as a brown solid. LCMS (ESI, m/z): $[M+H]^+$=404.2.

Step 6. Synthesis of tert-butyl (10S)-4-((4-([1,2,4]triazolo[1,5-a]pyridin-7-yloxy)-3-methylphenyl)amino)-5-fluoro-7,8,10,11-tetrahydro-9H-6,10-methano[1,4,7]oxadiazonino[3,2-g]quinazoline-9-carboxylate

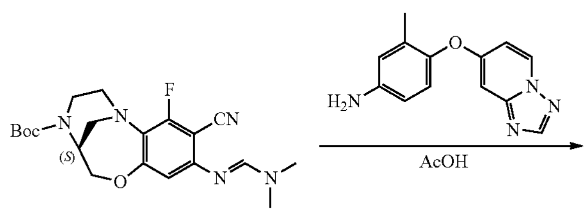

-continued

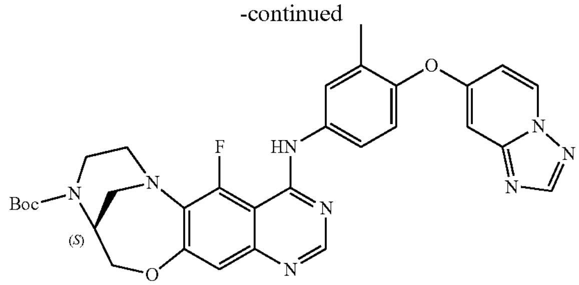

To a solution of tert-butyl (3S)-9-cyano-10-(((E)-(dimethylamino)methylene)amino)-8-fluoro-2,3,5,6-tetrahydro-4H-3,7-methanobenzo[b][1,4,7]oxadiazonine-4-carboxylate (230.0 mg, crude) in $CH_3COOH$ (4.0 mL) was added 4-([1,2,4]triazolo[1,5-a]pyridin-7-yloxy)-3-methylaniline (137.0 mg, 0.57 mmol) at room temperature. The mixture was stirred at 85° C. for 2 h. After the reaction was completed, the mixture was concentrated under reduced pressure. The residue was purified by reverse phase flash column chromatography with $MeOH/H_2O$ (66/34, v/v) to afford tert-butyl (10S)-4-((4-([1,2,4]triazolo[1,5-a]pyridin-7-yloxy)-3-methylphenyl)amino)-5-fluoro-7,8,10,11-tetrahydro-9H-6,10-methano[1,4,7]oxadiazonino[3,2-g]quinazoline-9-carboxylate (150.0 mg, 43%) as a brown solid. LCMS (ESI, m/z): $[M+H]^+$=599.2.

Step 7. Synthesis of (10S)—N-(4-([1,2,4]triazolo[1,5-a]pyridin-7-yloxy)-3-methylphenyl)-5-fluoro-8,9,10,11-tetrahydro-7H-6,10-methano[1,4,7]oxadiazonino[3,2-g]quinazolin-4-amine

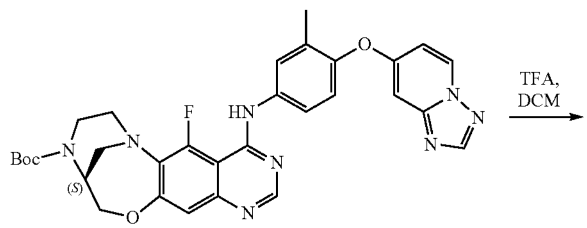

-continued

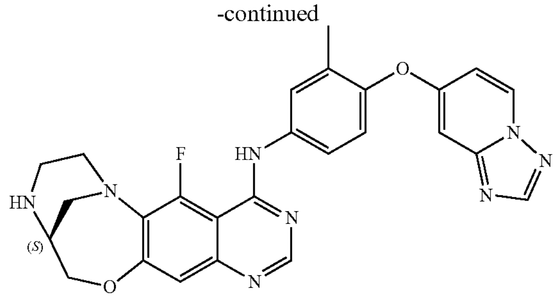

To a solution of tert-butyl (10S)-4-((4-([1,2,4]triazolo[1,5-a]pyridin-7-yloxy)-3-methylphenyl)amino)-5-fluoro-7,8,10,11-tetrahydro-9H-6,10-methano[1,4,7]oxadiazonino[3,2-g]quinazoline-9-carboxylate (140.0 mg, 0.23 mmol) in DCM (2.0 mL) was added TFA (2.0 mL) at room temperature. The resulting mixture was stirred at room temperature for 0.5 h. After the reaction was completed, the mixture was concentrated under reduced pressure. The residue was adjusted pH to 8.0 with aq. $NaHCO_3$ and then extracted with ethyl acetate. The combined organic layer was washed with brine, dried over anhydrous sodium sulfate and filtered. The filtrate was concentrated under reduced pressure to afford (10S)—N-(4-([1,2,4]triazolo[1,5-a]pyridin-7-yloxy)-3-methylphenyl)-5-fluoro-8,9,10,11-tetrahydro-7H-6,10-methano[1,4,7]oxadiazonino[3,2-g]quinazolin-4-amine (180.0 mg, crude) as yellow solid. LCMS (ESI, m/z): $[M+H]^+$=499.2.

Step 8. Synthesis of Step 7. Synthesis of (10S)—N-(4-([1,2,4]triazolo[1,5-a]pyridin-7-yloxy)-3-methylphenyl)-5-fluoro-8,9,10,11-tetrahydro-7H-6,10-methano[1,4,7]oxadiazonino[3,2-g]quinazolin-4-amine (Compound 40)

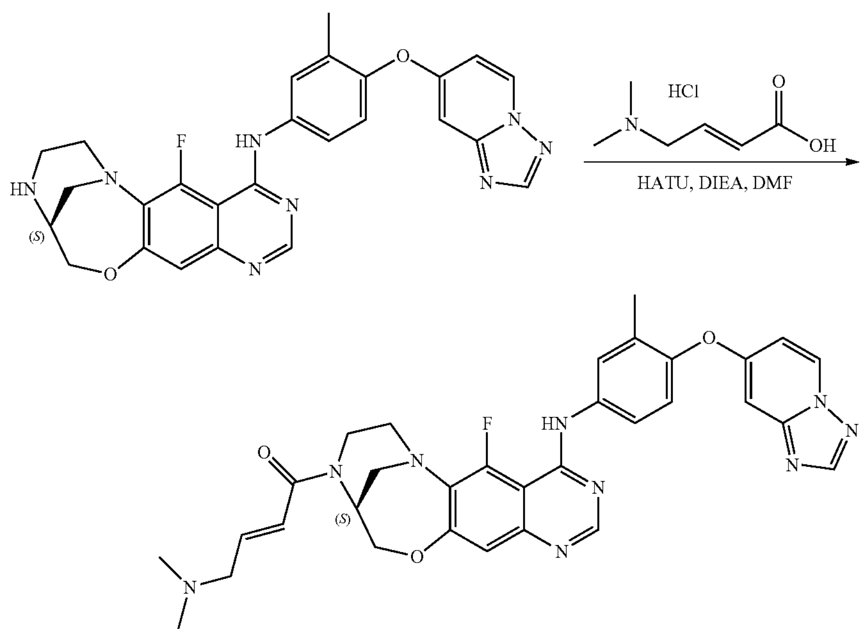

40

To a solution of (10S)—N-(4-([1,2,4]triazolo[1,5-a]pyridin-7-yloxy)-3-methylphenyl)-5-fluoro-8,9,10,11-tetrahydro-7H-6,10-methano[1,4,7]oxadiazonino[3,2-g]quinazolin-4-amine (170.0 mg, crude) in DMF (4.0 mL) was added (E)-4-(dimethylamino)but-2-enoic acid hydrochloride (113.0 mg, 0.68 mmol), DIEA (264.5 mg, 2.05 mmol) and HATU (285.3 mg, 0.75 mmol) at 0° C. The mixture was stirred at room temperature for 2 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions: (Column: XBridge Prep Phenyl OBD Column, 19×250 mm, 5 μm; Mobile Phase A: Water(10 mmol/L $NH_4HCO_3$), Mobile Phase B: ACN; Flow rate: 60 mL/min; Gradient: 30% B to 50% B in 10 min; Wave Length: 254 nm) to afford (E)-1-((10S)-4-((4-([1,2,4]triazolo[1,5-a]pyridin-7-yloxy)-3-methylphenyl)amino)-5-fluoro-7,8,10,11-tetrahydro-9H-6,10-methano[1,4,7]oxadiazonino[3,2-g]quinazolin-9-yl)-4-(dimethylamino)but-2-en-1-one (Compound 40) (30.8 mg, 14%) as a white solid. LCMS (ESI, m/z): $[M+H]^+$=610.2. $^1$H NMR (400 MHz, DMSO-$d_6$): δ 9.18-9.08 (m, 1H), 8.94 (d, J=7.6 Hz, 1H), 8.46 (d, J=2.0 Hz, 1H), 8.38 (s, 1H), 7.77-7.74 (m, 2H), 7.21 (d, J=8.4 Hz, 1H), 7.14 (s, 1H), 7.05-7.02 (m, 1H), 6.80 (d, J=2.4 Hz, 1H), 6.68-6.59 (m, 2H), 4.98-4.90 (m, 1H), 4.68-4.47 (m, 1H), 4.32-4.27 (m, 1H), 4.21-4.17 (m, 0.5H), 3.86-3.72 (m, 1.5H), 3.65-3.52 (m, 1H), 3.45-3.33 (m, 2H), 3.30-3.28 (m, 1H), 3.04 (d, J=5.2 Hz, 2H), 2.19-2.15 (m, 9H)

Example S40: Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-3-((R)-1-methylpyrrolidin-2-yl)prop-2-en-1-one (Compound 41)

To a solution of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (160.0 mg, 0.32 mmol) in DMF (15.0 mL) was added (R,E)-3-(1-methylpyrrolidin-2-yl)acrylic acid (54.7 mg, 0.35 mmol), DIEA (248.4 mg, 1.92 mmol) and HATU (146.2 mg, 0.38 mmol) at room temperature under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with ACN/$H_2O$ (50/50, v/v) and then purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 35% B to 45% B in 8 min; Wave Length: 254 nm) to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-3-((R)-1-methylpyrrolidin-2-yl)prop-2-en-1-one (Compound 41) (23.5 mg, 11%) as a light yellow solid. LCMS (ESI, m/z): $[M+H]^+$=637.3. $^1$H NMR (400 MHz, DMSO-$d_6$): δ 9.37 (s, 1H), 8.97 (d, J=7.6 Hz, 1H), 8.42 (d, J=5.2 Hz, 2H), 8.01 (d, J=8.8 Hz, 1H), 7.53 (s, 1H), 7.32 (d, J=10.8 Hz, 1H), 7.07-7.05 (m, 1H), 6.93-6.91 (m, 1H), 6.59-6.48 (m, 2H), 5.17-4.82 (m, 1H), 4.73-4.52 (m, 2H), 4.25-4.06 (m, 3H), 3.83-3.74 (m, 1H), 3.44-3.32 (m, 1H), 3.30-3.26 (m, 1H), 3.04-2.97 (m, 1H), 2.76-2.72 (m, 1H), 2.20-2.13 (m, 7H), 1.99-1.90 (m, 1H), 1.77-1.68 (m, 2H), 1.56-1.46 (m, 1H).

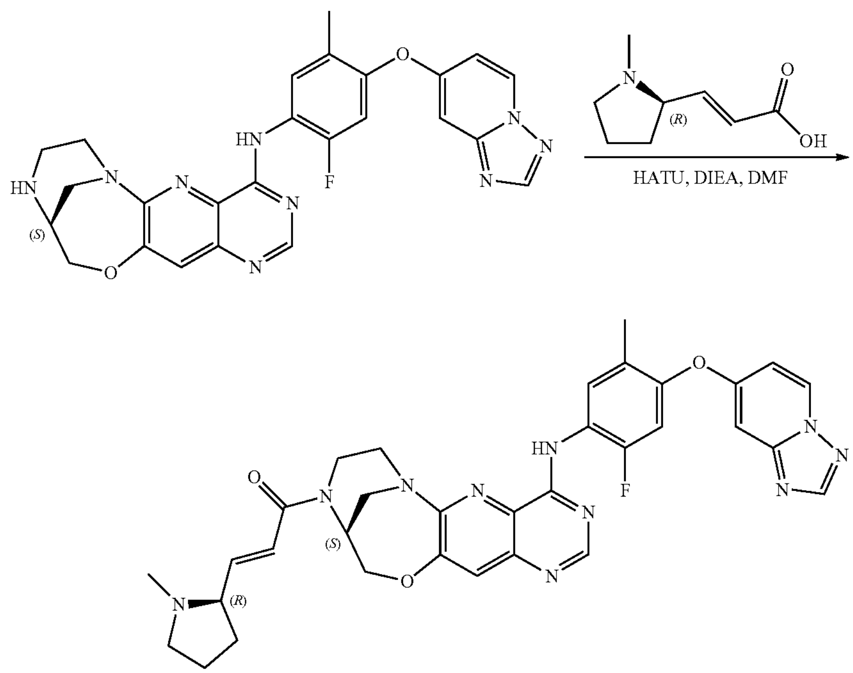

41

Example S41: Synthesis of (E)-1-((10S)-4-((4-([1,2,4]triazolo[1,5-a]pyridin-7-yloxy)-2-fluorophenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 42)

Step 1. Synthesis of 7-(3-fluoro-4-nitrophenoxy)-[1,2,4]triazolo[1,5-a]pyridine

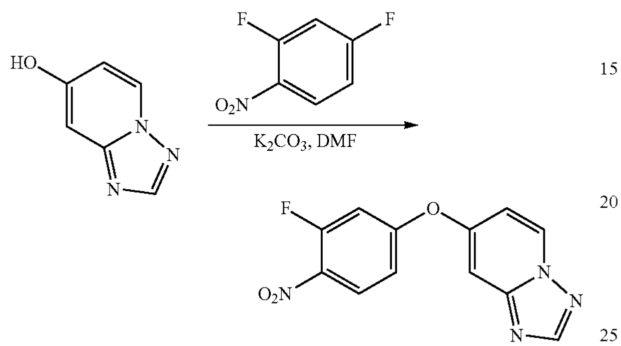

To a solution of [1,2,4]triazolo[1,5-a]pyridin-7-ol (2.0 g, 14.80 mmol) in DMF (20.0 mL) was added $K_2CO_3$ (920.5 mg, 6.66 mmol) and 2,4-difluoro-1-nitrobenzene (4.7 g, 29.60 mmol) at room temperature. The resulting mixture was stirred at 60° C. for 4 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash chromatography with acetonitrile/water (30/70, v/v) to afford 7-(3-fluoro-4-nitrophenoxy)-[1,2,4]triazolo[1,5-a]pyridine (1.1 g, 27%) as a white solid. LCMS (ESI, m/z): $[M+H]^+$=275.1.

Step 2. Synthesis of 2-fluoro-4-{[1,2,4]triazolo[1,5-a]pyridin-7-yloxy}aniline

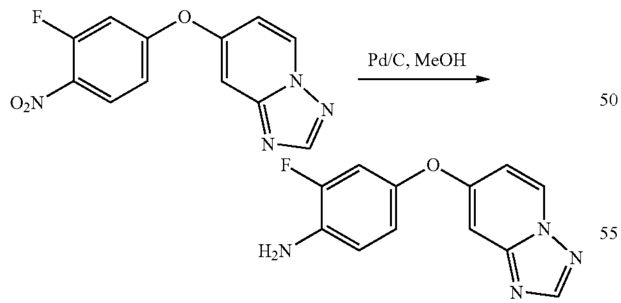

To a solution of 7-(3-fluoro-4-nitrophenoxy)-[1,2,4]triazolo[1,5-a]pyridine (1.0 g, 3.65 mmol) in MeOH (20.0 mL) was added Pd/C (350.0 mg, 10%) at room temperature under $N_2$. The resulting mixture was stirred at room temperature for 16 h under $H_2$. After the reaction was completed, the resulting mixture was filtered. The filtrate was concentrated under reduced pressure. The residue was purified by flash chromatography with $CH_2Cl_2$/MeOH (92/8, v/v) to afford 2-fluoro-4-{[1,2,4]triazolo[1,5-a]pyridin-7-yloxy}aniline (700.0 mg, 79%) as a white solid. LCMS (ESI, m/z): $[M+H]^+$=245.0.

Step 3. Synthesis of N-(4-([1,2,4]triazolo[1,5-a]pyridin-7-yloxy)-2-fluorophenyl)-7-bromo-6-chloropyrido[3,2-d]pyrimidin-4-amine

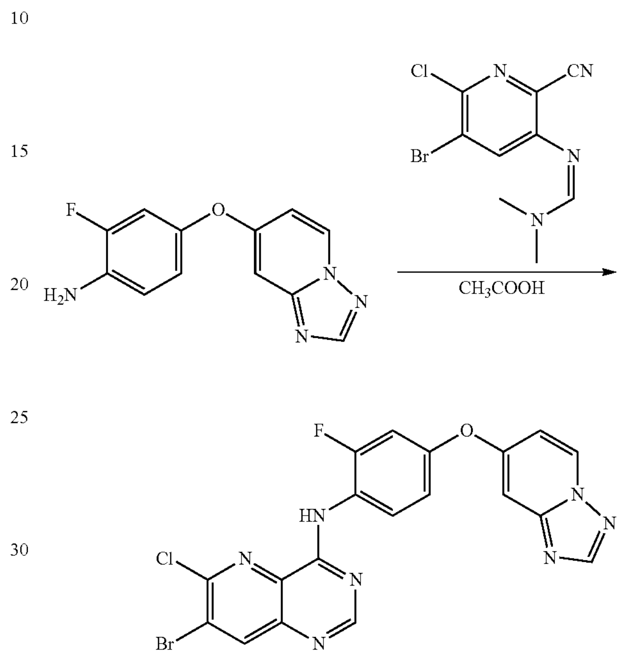

To a solution of (Z)—N'-(5-bromo-6-chloro-2-cyanopyridin-3-yl)-N,N-dimethylmethanimidamide (600.0 mg, 2.08 mmol) in acetic acid (10.0 mL) was added 2-fluoro-4-{[1,2,4]triazolo[1,5-a]pyridin-7-yloxy}aniline (509.6 mg, 2.08 mmol) at room temperature. The resulting mixture was stirred at 85° C. for 2 h. After the reaction was completed, the resulting mixture was concentrated under reduced pressure. The residue was purified by flash chromatography with $CH_2Cl_2$/MeOH (80/20, v/v) to afford 7-bromo-6-chloro-N-(2-fluoro-4-{[1,2,4]triazolo[1,5-a]pyridin-7-yloxy}phenyl)pyrido[3,2-d]pyrimidin-4-amine (500.0 mg, 49%) as a yellow solid. LCMS (ESI, m/z): $[M+H]^+$=486.0.

Step 4. Synthesis of tert-butyl (S)-4-(4-((4-([1,2,4]triazolo[1,5-a]pyridin-7-yloxy)-2-fluorophenyl)amino)-7-bromopyrido[3,2-d]pyrimidin-6-yl)-2-(hydroxymethyl)piperazine-1-carboxylate

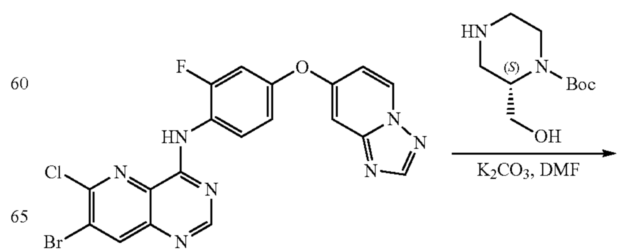

-continued

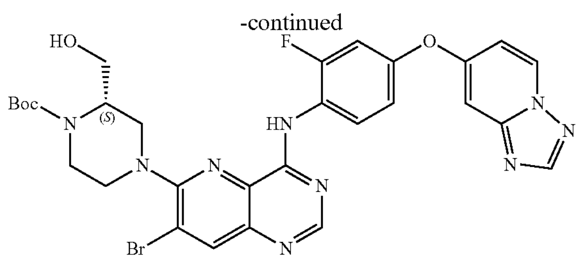

To a solution of 7-bromo-6-chloro-N-(2-fluoro-4-{[1,2,4]triazolo[1,5-a]pyridin-7-yloxy}phenyl)pyrido[3,2-d]pyrimidin-4-amine (200.0 mg, 0.41 mmol) in DMF (10.0 mL) was added $K_2CO_3$ (170.4 mg, 1.23 mmol) and tert-butyl (S)-2-(hydroxymethyl)piperazine-1-carboxylate (133.2 mg, 0.62 mmol) at room temperature. The resulting mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash chromatography with $CH_2Cl_2$/MeOH (85/15, v/v) to afford tert-butyl (2S)-4-{7-bromo-4-[(2-fluoro-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (180.0 mg, 65%) as a white solid. LCMS (ESI, m/z): $[M+H]^+$=666.0.

Step 5. Synthesis of tert-butyl (10S)-4-((4-([1,2,4]triazolo[1,5-a]pyridin-7-yloxy)-2-fluorophenyl)amino)-7,8,10,11-tetrahydro-9H-6,10-methanopyrimido[4',5':5,6]pyrido[3,2-b][1,4,7]oxadiazonine-9-carboxylate

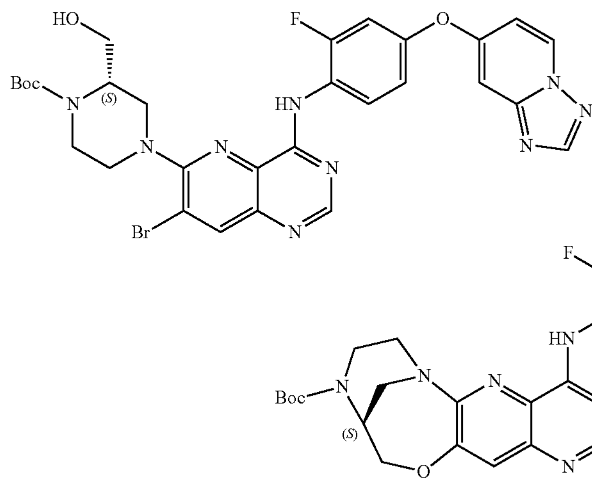

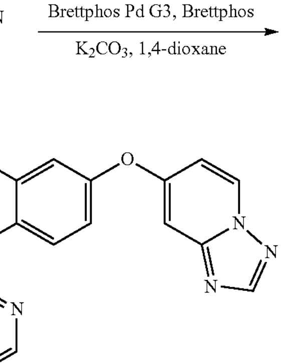

To a solution of tert-butyl (2S)-4-{7-bromo-4-[(2-fluoro-4-{[1,2,4]triazolo[1,5-a]pyridin-7-yloxy}phenyl)amino]pyrido[3,2-d]pyrimidin-6-yl}-2-(hydroxymethyl)piperazine-1-carboxylate (200.0 mg, 0.30 mmol) in 1,4-dioxane (8.0 mL) was added BrettPhos (64.4 mg, 0.12 mmol), BrettPhos Pd G3 (54.4 mg, 0.06 mmol) and $K_2CO_3$ (124.4 mg, 0.90 mmol) at room temperature under $N_2$. The resulting mixture was stirred at 100° C. for 16 h under $N_2$. After the reaction was completed, the resulting mixture was filtered. The filtrate was concentrated under reduced pressure. The residue was purified by flash chromatography with $CH_2Cl_2$/MeOH (92/8, v/v) to afford tert-butyl (10S)-4-((4-([1,2,4]triazolo[1,5-a]pyridin-7-yloxy)-2-fluorophenyl)amino)-7,8,10,11-tetrahydro-9H-6,10-methanopyrimido[4',5':5,6]pyrido[3,2-b][1,4,7]oxadiazonine-9-carboxylate (100.0 mg, 56%) as a white solid. LCMS (ESI, m/z): $[M+H]^+$=586.0.

Step 6. Synthesis of (10S)—N-(4-([1,2,4]triazolo[1,5-a]pyridin-7-yloxy)-2-fluorophenyl)-8,9,10,11-tetrahydro-7H-6,10-methanopyrimido[4',5':5,6]pyrido[3,2-b][1,4,7]oxadiazonin-4-amine hydrochloride

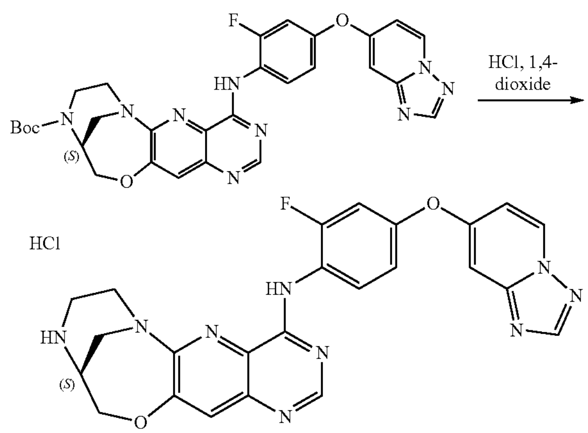

A solution of tert-butyl (10S)-4-((4-([1,2,4]triazolo[1,5-a]pyridin-7-yloxy)-2-fluorophenyl)amino)-7,8,10,11-tetrahydro-9H-6,10-methanopyrimido[4',5':5,6]pyrido[3,2-b][1,4,7]oxadiazonine-9-carboxylate (100.0 mg, 0.17 mmol) in HCl/1,4-dioxane (6.0 mL, 4.0 mol/L) was stirred at room temperature for 1 h. After the reaction was completed, the resulting mixture was concentrated under reduced pressure to afford (10S)—N-(4-([1,2,4]triazolo[1,5-a]pyridin-7-yloxy)-2-fluorophenyl)-8,9,10,11-tetrahydro-7H-6,10-methanopyrimido[4',5':5,6]pyrido[3,2-b][1,4,7]oxadiazonin-4-amine hydrochloride (60.0 mg, crude) as a yellow solid. LCMS (ESI, m/z): $[M+H]^+$=486.0.

Step 7. Synthesis of (E)-1-((10S)-4-((4-([1,2,4]triazolo[1,5-a]pyridin-7-yloxy)-2-fluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 42)

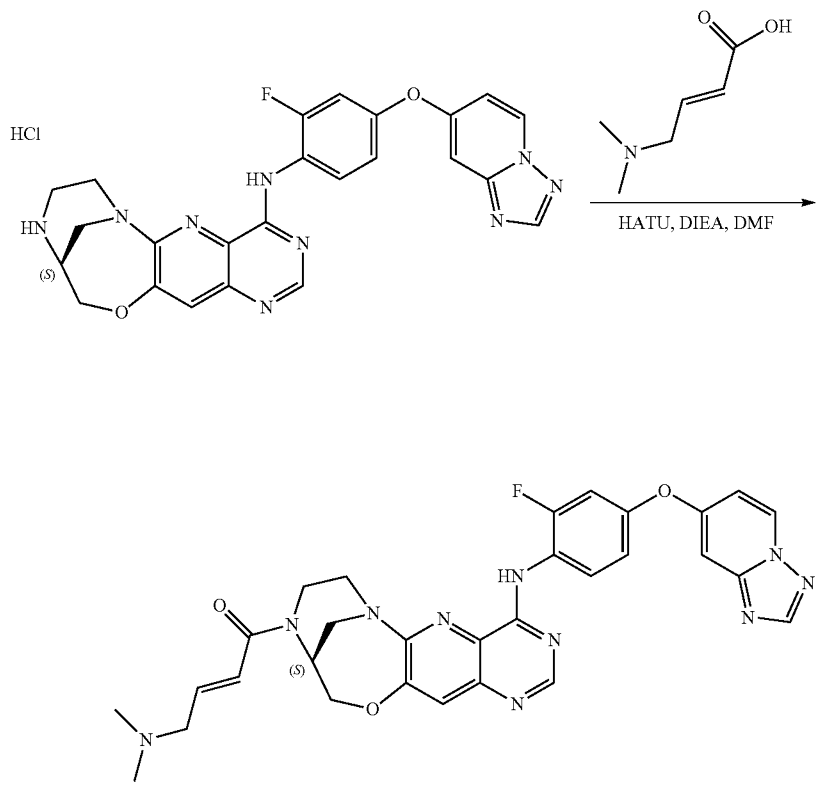

42

To a solution of (10S)—N-(4-([1,2,4]triazolo[1,5-a]pyridin-7-yloxy)-2-fluorophenyl)-8,9,10,11-tetrahydro-7H-6,10-methanopyrimido[4',5':5,6]pyrido[3,2-b][1,4,7]oxadiazonin-4-amine hydrochloride (60.0 mg, crude) in DMF (5.0 mL) was added DIEA (159.7 mg, 1.24 mmol), (2E)-4-(dimethylamino)but-2-enoic acid (23.9 mg, 0.18 mmol) and HATU (140.9 mg, 0.37 mmol) at room temperature. The resulting mixture was stirred at room temperature for 3 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash chromatography with $CH_3CN/H_2O$ (80/20, v/v) and then purified by Prep-HPLC with the following conditions: (Column: XSelect CSH Prep C18 OBD Column, 19×250 mm, 5 μm; Mobile Phase A: Water (0.1% FA), Mobile Phase B: MeOH-HPLC; Flow rate: 25 mL/min; Gradient: 68% B to 68% B in 11 min; Wave Length: 254 nm) to afford (E)-1-((10S)-4-((4-([1,2,4]triazolo[1,5-a]pyridin-7-yloxy)-2-fluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 42) (18.3 mg, 24%) as a yellow solid. LCMS (ESI, m/z): $[M+H]^+$=597.2. $^1$H NMR (400 MHz, DMSO-$d_6$): δ 9.42 (s, 1H), 8.99 (d, J=7.6 Hz, 1H), 8.44-8.41 (m, 2H), 8.08-8.04 (m, 1H), 7.52 (s, 1H), 7.39 (d, J=10.8 Hz, 1H), 7.19-7.14 (m, 2H), 7.08-7.06 (m, 1H), 6.68-6.57 (m, 2H), 5.11-4.79 (m, 1H), 4.73-4.55 (m, 2H), 4.28-4.09 (m, 3H), 3.90-3.64 (m, 1H), 3.47-3.44 (m, 1H), 3.33-3.23 (m, 1H), 3.04-2.98 (m, 2H), 2.32-2.30 (m, 6H).

Example S42: Synthesis of (E)-1-((10S)-4-((4-([1,2,4]triazolo[1,5-a]pyridin-7-yloxy)-5-chloro-2-fluorophenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 43)

Step 1. Synthesis of N-(4-([1,2,4]triazolo[1,5-a]pyridin-7-yloxy)-5-chloro-2-fluorophenyl)-7-bromo-6-chloropyrido[3,2-d]pyrimidin-4-amine

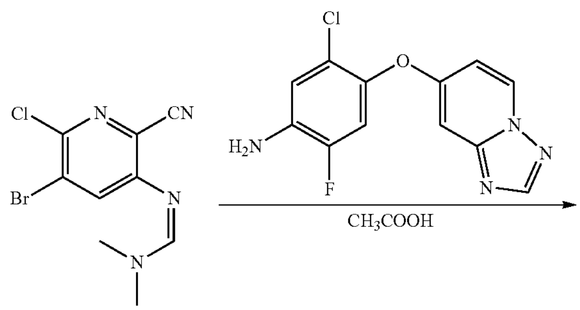

-continued

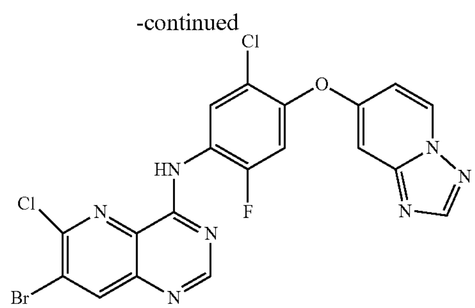

To a solution of (Z)—N'-(5-bromo-6-chloro-2-cyanopyridin-3-yl)-N,N-dimethylformimidamide (1.5 g, 1.74 mmol) in $CH_3COOH$ (30.0 mL) was added 4-([1,2,4]triazolo[1,5-a]pyridin-7-yloxy)-5-chloro-2-fluoroaniline (1.4 g, 1.74 mmol) at room temperature. The resulting mixture was stirred at 80° C. for 16 h. After the reaction was completed, the mixture was concentrated under reduced pressure. The residue was purified by flash chromatography with dichloromethane/methanol (95/5, v/v) to afford N-(4-([1,2,4]triazolo[1,5-a]pyridin-7-yloxy)-5-chloro-2-fluorophenyl)-7-bromo-6-chloropyrido[3,2-d]pyrimidin-4-amine (0.6 g, 22%) as a yellow solid. LCMS (ESI, m/z): $[M+H]^+$=520.1.

Step 2. Synthesis of tert-butyl (S)-4-(4-((4-([1,2,4]triazolo[1,5-a]pyridin-7-yloxy)-5-chloro-2-fluorophenyl)amino)-7-bromopyrido[3,2-d]pyrimidin-6-yl)-2-(hydroxymethyl)piperazine-1-carboxylate

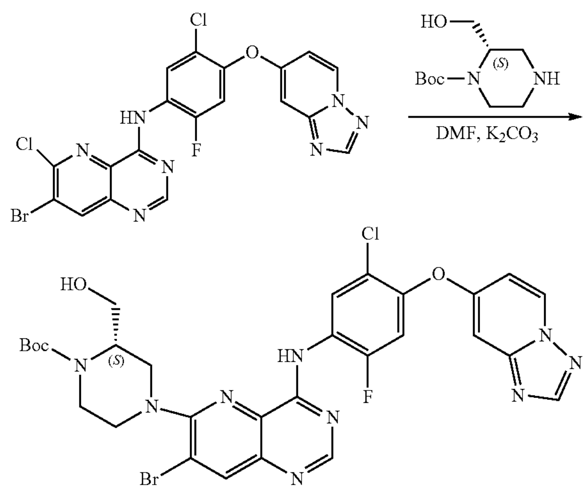

To a solution of N-(4-([1,2,4]triazolo[1,5-a]pyridin-7-yloxy)-5-chloro-2-fluorophenyl)-7-bromo-6-chloropyrido[3,2-d]pyrimidin-4-amine (500.0 mg, 0.96 mmol) in DMF (10.0 mL) was added tert-butyl (S)-2-(hydroxymethyl)piperazine-1-carboxylate (420.3 mg, 1.92 mmol) and $K_2CO_3$ (423.3 mg, 2.87 mmol) at room temperature. The resulting mixture was stirred at 80° C. for 16 h. After the reaction was completed, the mixture was cooled to room temperature and diluted with $H_2O$. The mixture was extracted with ethyl acetate. The combined organic layer was washed with brine, dried over anhydrous sodium sulfate and filtered. The filtrate was concentrated under reduced pressure. The residue was purified by flash chromatography with dichloromethane/methanol (90/10, v/v) to afford tert-butyl (S)-4-(4-((4-([1,2,4]triazolo[1,5-a]pyridin-7-yloxy)-5-chloro-2-fluorophenyl)amino)-7-bromopyrido[3,2-d]pyrimidin-6-yl)-2-(hydroxymethyl)piperazine-1-carboxylate (302.1 mg, 44%) as a yellow solid. LCMS (ESI, m/z): $[M+H]^+$=700.1.

Step 3. Synthesis of tert-butyl (10S)-4-((4-([1,2,4]triazolo[1,5-a]pyridin-7-yloxy)-5-chloro-2-fluorophenyl)amino)-7,8,10,11-tetrahydro-9H-6,10-methanopyrimido[4',5':5,6]pyrido[3,2-b][1,4,7]oxadiazonine-9-carboxylate

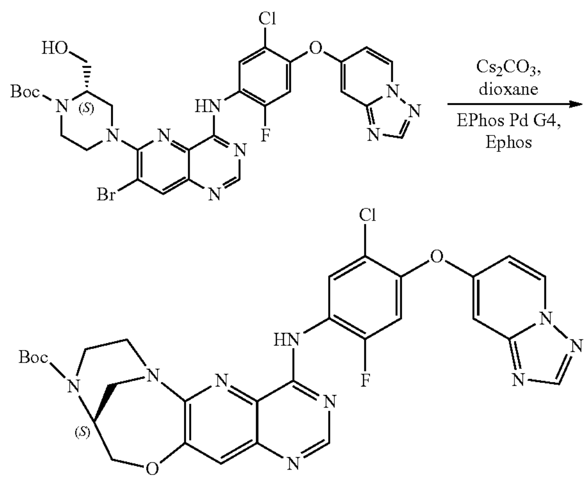

To a solution of tert-butyl (S)-4-(4-((4-([1,2,4]triazolo[1,5-a]pyridin-7-yloxy)-5-chloro-2-fluorophenyl)amino)-7-bromopyrido[3,2-d]pyrimidin-6-yl)-2-(hydroxymethyl)piperazine-1-carboxylate (300.0 mg, 0.43 mmol) in 1,4-dioxane (10.0 mL) was added $Cs_2CO_3$ (420.3 mg, 1.28 mmol), EPhos Pd G4 (157.2 mg, 0.17 mmol) and EPhos (45.7 mg, 0.09 mmol) at room temperature under $N_2$. The resulting mixture was stirred at 80° C. for 16 h. After the reaction was completed, the mixture was cooled to room temperature and filtered. The filtrate was concentrated under reduced pressure. The residue was purified by flash chromatography with dichloromethane/methanol (90/10, v/v) to afford tert-butyl (10S)-4-((4-([1,2,4]triazolo[1,5-a]pyridin-7-yloxy)-5-chloro-2-fluorophenyl)amino)-7,8,10,11-tetrahydro-9H-6,10-methanopyrimido[4',5':5,6]pyrido[3,2-b][1,4,7]oxadiazonine-9-carboxylate (235.0 mg, 89%) as a yellow solid. LCMS (ESI, m/z): $[M+H]^+$=620.2.

Step 4. Synthesis of (10S)—N-(4-([1,2,4]triazolo[1,5-a]pyridin-7-yloxy)-5-chloro-2-fluorophenyl)-8,9,10,11-tetrahydro-7H-6,10-methanopyrimido[4',5':5,6]pyrido[3,2-b][1,4,7]oxadiazonin-4-amine

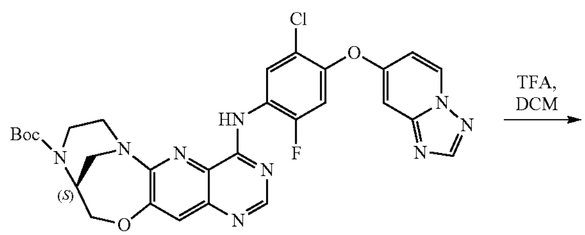

-continued

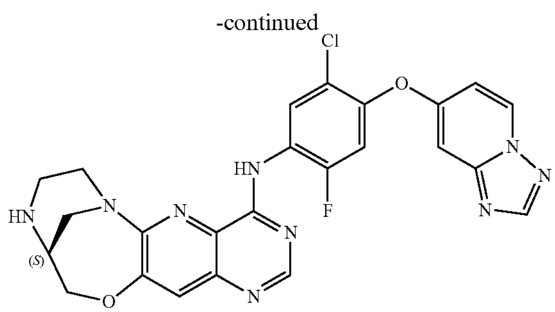

To a solution of tert-butyl (10S)-4-((4-([1,2,4]triazolo[1,5-a]pyridin-7-yloxy)-5-chloro-2-fluorophenyl)amino)-7,8,10,11-tetrahydro-9H-6,10-methanopyrimido[4',5':5,6]pyrido[3,2-b][1,4,7]oxadiazonine-9-carboxylate (200.0 mg, 0.32 mmol) in DCM (5.0 mL) was added TFA (2.0 mL) at room temperature. The mixture was stirred at room temperature for 1 h. After the reaction was completed, the pH value of the mixture was adjusted to 8.0 with saturated $NaHCO_3$(aq.). The mixture was extracted with $CH_2Cl_2$. The combined organic layers were washed with brine, dried over anhydrous sodium sulfate and filtered. The filtrate was concentrated under vacuum to afford (10S)—N-(4-([1,2,4]triazolo[1,5-a]pyridin-7-yloxy)-5-chloro-2-fluorophenyl)-8,9,10,11-tetrahydro-7H-6,10-methanopyrimido[4',5':5,6]pyrido[3,2-b][1,4,7]oxadiazonin-4-amine (130.1 mg, crude) as a yellow solid. LCMS (ESI, m/z): $[M+H]^+$=520.1.

Step 5. Synthesis of (E)-1-((10S)-4-((4-([1,2,4]triazolo[1,5-a]pyridin-7-yloxy)-5-chloro-2-fluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 43)

To a solution of (10S)—N-(4-([1,2,4]triazolo[1,5-a]pyridin-7-yloxy)-5-chloro-2-fluorophenyl)-8,9,10,11-tetrahydro-7H-6,10-methanopyrimido[4',5':5,6]pyrido[3,2-b][1,4,7]oxadiazonin-4-amine (130.0 mg, crude) in DMF (5.0 mL) was added (E)-4-(dimethylamino)but-2-enoic acid (38.7 mg, 0.30 mmol), DIEA (484.5 mg, 3.75 mmol) and HATU (114.0 mg, 0.30 mmol) at 0° C. under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with ACN/$H_2O$ (50/50, v/v) and then purified by Prep-HPLC with the following conditions: (Column: Xselect CSH C18 OBD Column 30×150 mm, 5 μm; Mobile Phase A: ACN, Mobile Phase B: Water (0.1% FA); Flow rate: 60 mL/min; Gradient: 13% B to 23% B in 10 min; Wave Length: 254 nm) to afford (E)-1-((10S)-4-((4-([1,2,4]triazolo[1,5-a]pyridin-7-yloxy)-5-chloro-2-fluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 43) (9.1 mg, 5%) as a light yellow solid. LCMS (ESI, m/z): $[M+H]^+$=631.4. $^1$H NMR (400 MHz, DMSO-$d_6$): δ 9.43 (s, 1H), 9.00 (d, J=7.6 Hz, 1H), 8.50 (s, 1H), 8.47-8.45 (m, 2H), 7.67-7.65 (m, 1H), 7.56 (s, 1H), 7.13-7.10 (m, 2H), 6.69-6.57 (m, 2H), 5.14-5.08 (m, 0.5H), 4.82-4.53 (m, 3H), 4.28-4.05 (m, 3H), 3.90-3.87 (m, 1H), 3.69-3.63 (m, 1H), 3.03-2.99 (m, 2H), 2.17-2.15 (m, 6H).

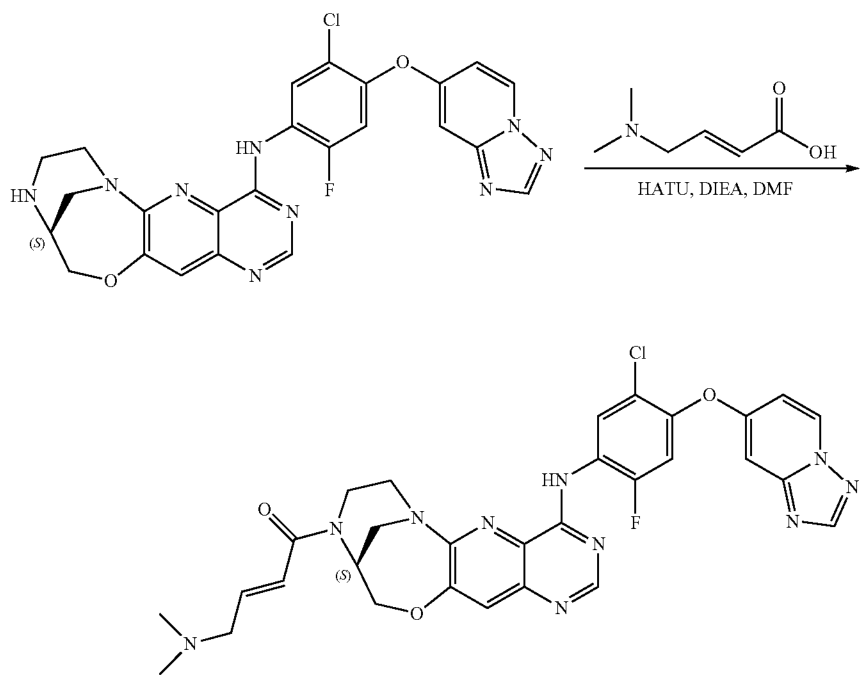

43

Example S43: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-3-((R)-1-methylpyrrolidin-2-yl)prop-2-en-1-one (Compound 27)

Step 1. Synthesis of (R)-pyrrolidine-2-carbaldehyde

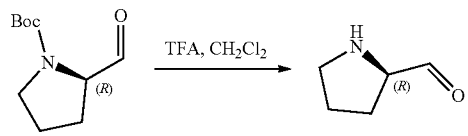

To a solution of tert-butyl (R)-2-formylpyrrolidine-1-carboxylate (10.0 g, 50.25 mmol) in $CH_2Cl_2$ (100.0 mL) was added TFA (20.0 mL) at room temperature. The resulting mixture was stirred at room temperature for 4 h. After the reaction was completed, the mixture was concentrated under reduced pressure. The pH value of the residue was adjusted to 8.0 with saturated $NaHCO_3$(aq.). The mixture was extracted with $CH_2Cl_2$. The combined organic layer was washed with brine, dried over anhydrous sodium sulfate and filtered. The filtrate was concentrated under reduced pressure to afford (R)-pyrrolidine-2-carbaldehyde (4.9 g, crude) as a brown oil. LCMS (ESI, m/z): $[M+H]^+$=100.1.

Step 2. Synthesis of (R)-1-methylpyrrolidine-2-carbaldehyde

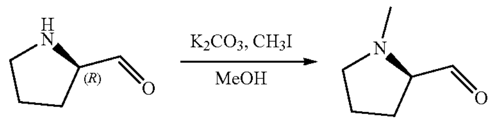

To a solution of (R)-pyrrolidine-2-carbaldehyde (1.0 g, crude) in MeOH (30.0 mL) was added $K_2CO_3$ (4.2 g, 30.30 mmol) and $CH_3I$ (2.1 g, 15.15 mmol) at room temperature. The resulting mixture was stirred at 40° C. for 16 h. After the reaction was completed, the resulting mixture was cooled to room temperature and filtered. The filtrate was concentrated under reduced pressure. The residue was purified by flash column chromatography with petroleum ether/ethyl acetate (50/50, v/v) to afford (R)-1-methylpyrrolidine-2-carbaldehyde (300.0 mg, 26%) as a yellow oil. LCMS (ESI, m/z): $[M+H]^+$=114.1.

Step 3. Synthesis of ethyl (R,E)-3-(1-methylpyrrolidin-2-yl)acrylate

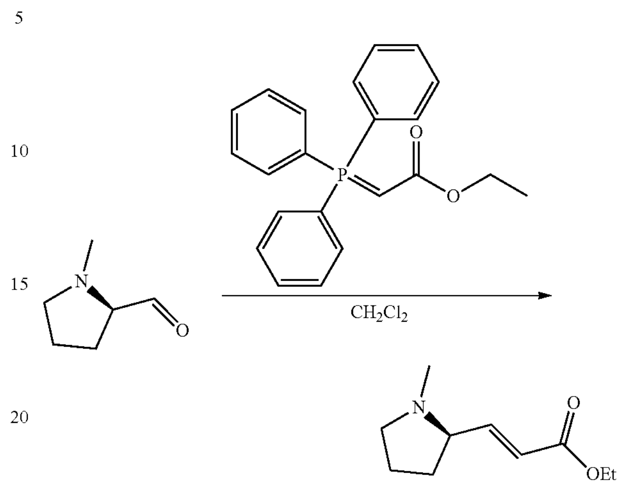

To a solution of (R)-1-methylpyrrolidine-2-carbaldehyde (300.0 mg, 1.64 mmol) in $CH_2Cl_2$ (10.0 mL) was added ethyl 2-(triphenyl-15-phosphaneylidene)acetate (1.1 g, 3.18 mmol) at room temperature. The resulting mixture was stirred at room temperature for 16 h. After the reaction was completed, the mixture was concentrated under reduced pressure. The residue was purified by flash column chromatography with petroleum ether/ethyl acetate (70/30, v/v) to afford ethyl (R,E)-3-(1-methylpyrrolidin-2-yl)acrylate (200.0 mg, 41%) as a yellow oil. LCMS (ESI, m/z): $[M+H]^+$=184.1.

Step 4. Synthesis of (R,E)-3-(1-methylpyrrolidin-2-yl)acrylic acid

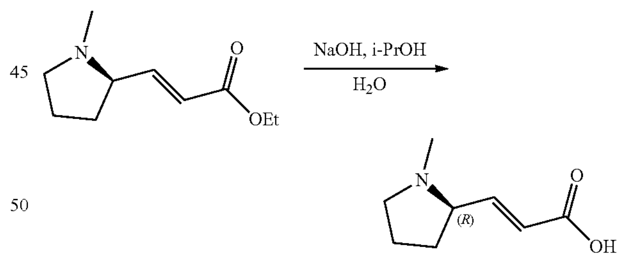

To a solution of ethyl (R,E)-3-(1-methylpyrrolidin-2-yl)acrylate (300.0 mg, 1.64 mmol) in i-PrOH (10.0 mL) and $H_2O$ (3.0 mL) was added NaOH (534.5 mg, 13.23 mmol) at room temperature. The resulting mixture was stirred at room temperature for 16 h. After the reaction was completed, the mixture was concentrated under reduced pressure. The pH value of the residue was adjusted to 5.0 with HCl (1.0 mol/L). The mixture was extracted with $CH_2Cl_2$. The combined organic layer was washed with brine, dried over anhydrous sodium sulfate and filtered. The filtrate was concentrated under vacuum to afford (R,E)-3-(1-methylpyrrolidin-2-yl)acrylic acid (150.0 mg, crude) as a white solid. LCMS (ESI, m/z): $[M+H]^+$=156.1.

Step 5. Synthesis of (E)-1-((10S)-4-((4-([1,2,4]tri-azolo[1,5-a]pyridin-7-yloxy)-3-methylphenyl) amino)-7,8,10,11-tetrahydro-9H-6,10-methanopy-rimido[4',5':5,6]pyrido[3,2-b][1,4,7]oxadiazonin-9-yl)-3-((R)-1-methylpyrrolidin-2-yl)prop-2-en-1-one (Compound 27)

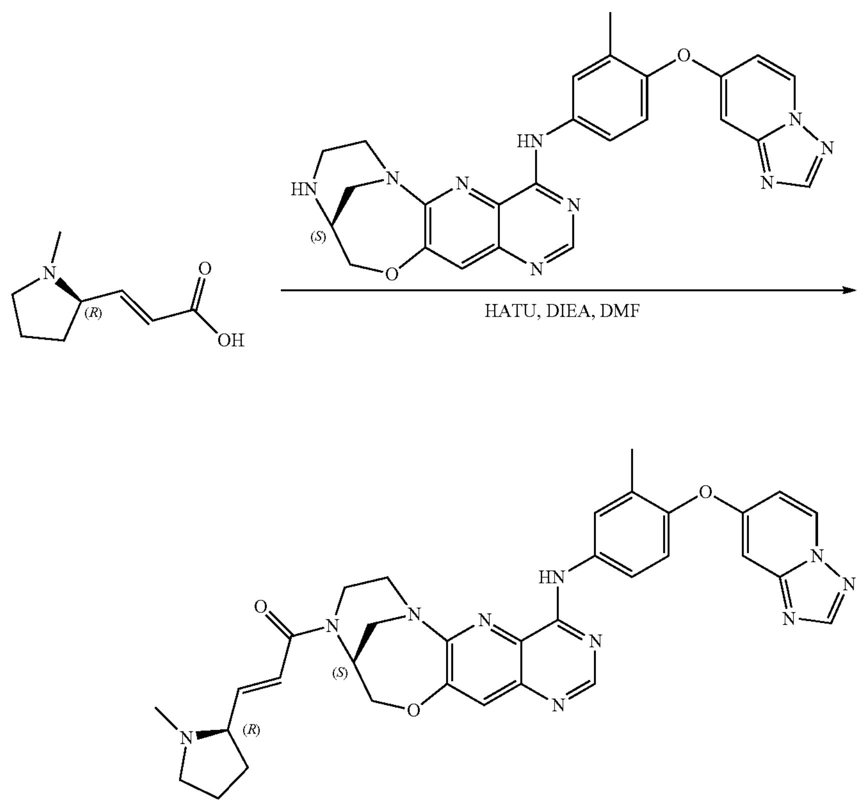

27

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (372.3 mg, 0.77 mmol) in DMF (5.0 mL) was added (R,E)-3-(1-methylpyrrolidin-2-yl)acrylic acid (600.0 mg, crude), DIEA (832.8 mg, 6.44 mmol) and HATU (367.5 mg, 0.97 mmol) at 0° C. under $N_2$. The resulting mixture was stirred at room temperature for 1.5 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with ACN/$H_2O$ (60/40, v/v) and then purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 28% B to 38% B in 8 min; Wave Length: 254 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-((R)-1-methylpyrrolidin-2-yl)prop-2-en-1-one (Compound 27) (61.8 mg, 15%) as a white solid. LCMS (ESI, m/z): $[M+H]^+$=619.5. $^1H$ NMR (400 MHz, DMSO-$d_6$): δ 9.54-9.52 (m, 1H), 8.94 (d, J=7.6 Hz, 1H), 8.47 (s, 1H), 8.38 (s, 1H), 8.02-7.98 (m, 2H), 7.51 (s, 1H), 7.22 (d, J=9.2 Hz, 1H), 7.04-7.02 (m, 1H), 6.79 (d, J=2.4 Hz, 1H), 6.59-6.48 (m, 2H), 5.12-4.67 (m, 3H), 4.25-4.08 (m, 3H), 3.89-3.63 (m, 1H), 3.42-3.38 (m, 1H), 3.26-3.23 (m, 1H), 3.02-3.00 (m, 1H), 2.76-2.73 (m, 1H), 2.20-2.15 (m, 6H), 1.98-1.94 (m, 1H), 1.79-1.71 (m, 2H), 1.56-1.49 (m, 1H).

Example S44: Synthesis of (E)-4-(dimethylamino)-1-((10S)-4-((2-fluoro-4-((5-fluoropyridin-3-yl)oxy)-5-methylphenyl)amino)-7,8,10,11-tetrahydro-9H-6,10-methanopyrimido[4,5':5,6]pyrido[3,2-b][1,4,7]oxadiazonin-9-yl)but-2-en-1-one (Compound 44)

Step 1. Synthesis of tert-butyl (S)-4-(7-bromo-4-((2-fluoro-4-((5-fluoropyridin-3-yl)oxy)-5-methylphenyl)amino)pyrido[3,2-d]pyrimidin-6-yl)-2-(hydroxymethyl)piperazine-1-carboxylate

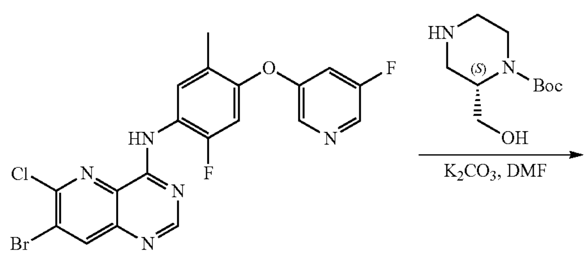

-continued

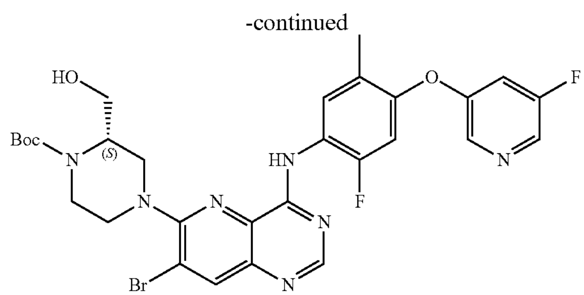

To a solution of 7-bromo-6-chloro-N-(2-fluoro-4-((5-fluoropyridin-3-yl)oxy)-5-methylphenyl)pyrido[3,2-d]pyrimidin-4-amine (2.5 g, 5.22 mmol) in DMF (70.0 mL) was added tert-butyl (S)-2-(hydroxymethyl)piperazine-1-carboxylate (1.1 g, 5.22 mmol) and $K_2CO_3$ (2.8 g, 20.89 mmol) at room temperature. The resulting mixture was stirred at 100° C. for 4 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (S)-4-(7-bromo-4-((2-fluoro-4-((5-fluoropyridin-3-yl)oxy)-5-methylphenyl)amino)pyrido[3,2-d]pyrimidin-6-yl)-2-(hydroxymethyl)piperazine-1-carboxylate (1.8 g, 52%) as a yellow solid. LCMS (ESI, m/z): $[M+H]^+$=658.2.

Step 2. Synthesis of tert-butyl (10S)-4-((2-fluoro-4-((5-fluoropyridin-3-yl)oxy)-5-methylphenyl)amino)-7,8,10,11-tetrahydro-9H-6,10-methanopyrimido[4',5':5,6]pyrido[3,2-b][1,4,7]oxadiazonine-9-carboxylate

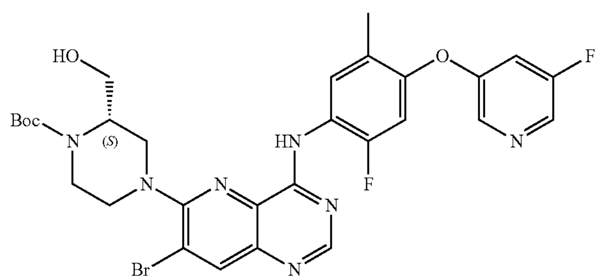

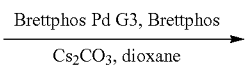

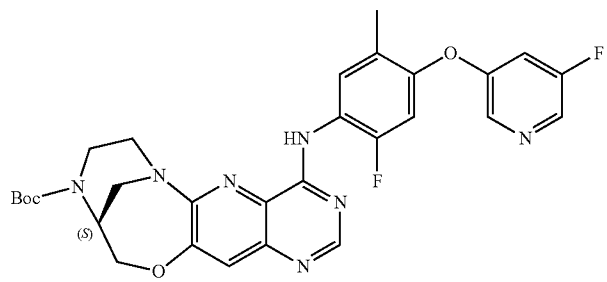

To a solution of tert-butyl (2S)-4-[7-bromo-4-({2-fluoro-4-[(5-fluoropyridin-3-yl)oxy]-5-methylphenyl}amino)pyrido[3,2-d]pyrimidin-6-yl]-2-(hydroxymethyl)piperazine-1-carboxylate (1.6 g, 2.43 mmol) in dioxane (30.0 mL) was added $Cs_2CO_3$ (1.5 g, 4.86 mmol), BrettPhos (0.3 g, 0.48 mmol) and BrettPhos Pd G3 (0.2 g, 0.24 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford tert-butyl (10S)-4-((2-fluoro-4-((5-fluoropyridin-3-yl)oxy)-5-methylphenyl)amino)-7,8,10,11-tetrahydro-9H-6,10-methanopyrimido[4',5':5,6]pyrido[3,2-b][1,4,7]oxadiazonine-9-carboxylate (850.0 mg, 60%) as a yellow solid. LCMS (ESI, m/z): $[M+H]^+$=578.2.

Step 3. Synthesis of (10S)—N-(2-fluoro-4-((5-fluoropyridin-3-yl)oxy)-5-methylphenyl)-8,9,10,11-tetrahydro-7H-6,10-methanopyrimido[4',5':5,6]pyrido[3,2-b][1,4,7]oxadiazonin-4-amine

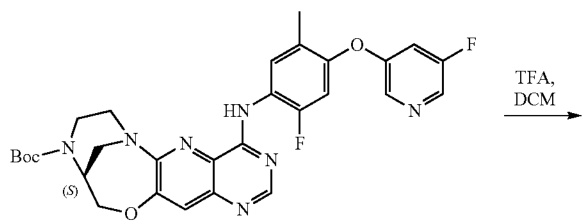

-continued

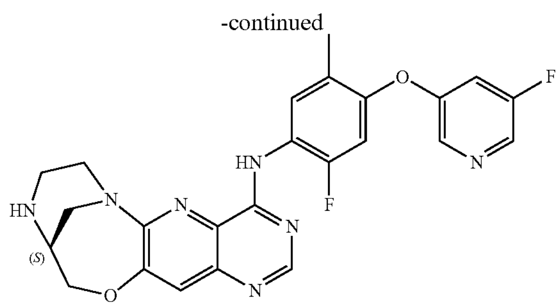

To a solution of tert-butyl (10S)-4-((2-fluoro-4-((5-fluoropyridin-3-yl)oxy)-5-methylphenyl)amino)-7,8,10,11-tetrahydro-9H-6,10-methanopyrimido[4',5':5,6]pyrido[3,2-b][1,4,7]oxadiazonine-9-carboxylate (800.0 mg, 1.38 mmol) in DCM (15.0 mL) was added TFA (5.0 mL) at room temperature. The mixture was stirred at room temperature for 1 h. After the reaction was completed, the mixture was basified to pH=8 with saturated $NaHCO_3$(aq.). The resulting mixture was extracted with DCM. The combined organic layers were washed with brine and dried over anhydrous $Na_2SO_4$. After filtration, the filtrate was concentrated under reduced pressure to afford (10S)—N-(2-fluoro-4-((5-fluoropyridin-3-yl)oxy)-5-methylphenyl)-8,9,10,11-tetrahydro-7H-6,10-methanopyrimido[4',5':5,6]pyrido[3,2-b][1,4,7]oxadiazonin-4-amine (380.0 mg, crude) as a yellow solid. LCMS (ESI, m/z): $[M+H]^+$=478.2.

Step 4. Synthesis of (E)-4-(dimethylamino)-1-((10S)-4-((2-fluoro-4-((5-fluoropyridin-3-yl)oxy)-5-methylphenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 44)

To a solution of (10S)—N-(2-fluoro-4-((5-fluoropyridin-3-yl)oxy)-5-methylphenyl)-8,9,10,11-tetrahydro-7H-6,10-methanopyrimido[4',5':5,6]pyrido[3,2-b][1,4,7]oxadiazonin-4-amine (150.0 mg, crude) in Pyridine (10.0 mL) was added (2E)-4-(dimethylamino)but-2-enoic acid hydrochloride (40.5 mg, 0.31 mmol) and EDCI (120.4 mg, 0.62 mmol) at room temperature. The resulting mixture was stirred at room temperature for 1 h. After the reaction was completed, the resulting mixture was concentrated under vacuum. The residue was purified by Achiral-SFC with the following conditions (Column: GreenSep Naphthyl, 3×25 cm, 5 μm; Mobile Phase A: $CO_2$, Mobile Phase B: MeOH(0.1% 2M $NH_3$-MeOH); Flow rate: 75 mL/min; Gradient: isocratic 39% B; Column Temperature(° C.): 35; Wave Length: 254 nm) to afford (E)-4-(dimethylamino)-1-((10S)-4-((2-fluoro-4-((5-fluoropyridin-3-yl)oxy)-5-methylphenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 44) (39.9 mg, 21%) as a light white solid. LCMS (ESI, m/z): $[M+H]^+$=589.2. $^1H$ NMR (400 MHz, DMSO-$d_6$): δ 9.37 (s, 1H), 8.41 (s, 2H), 8.26 (s, 1H), 7.96 (d, J=8.8 Hz, 1H), 7.52 (s, 1H), 7.44-7.40 (m, 1H), 7.19 (d, J=10.8 Hz, 1H), 6.67-6.57 (m, 2H), 5.12-4.77 (m, 1H), 4.72-4.54 (m, 2H), 4.27-4.04 (m, 3H), 3.88-3.62 (m, 1H), 3.51-3.38 (m, 1H), 3.27-3.22 (m, 1H), 3.03 (d, J=6.0 Hz, 2H), 2.21 (s, 3H). 2.16-2.14 (m, 6H).

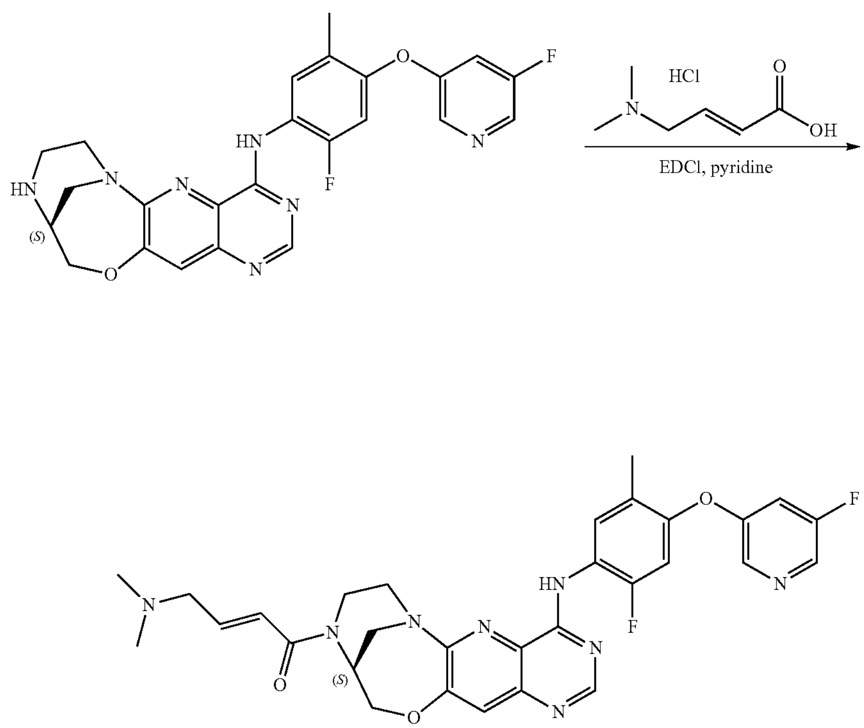

44

Example S45: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-3-(1-methylazetidin-3-yl)prop-2-en-1-one (Compound 45)

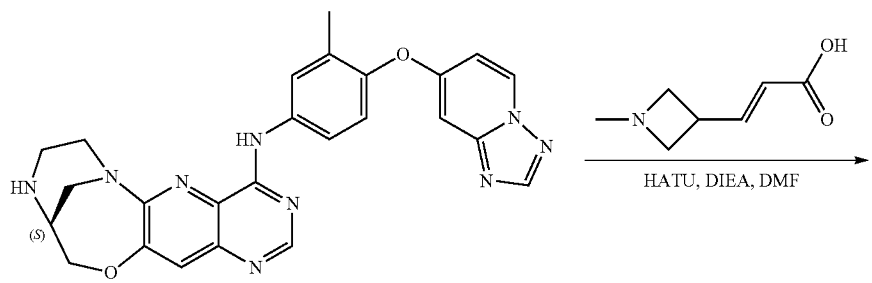

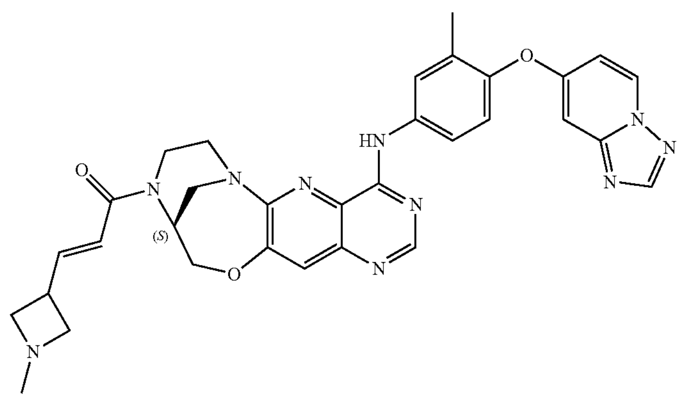

45

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (100.0 mg, 0.20 mmol) in DMF (10.0 mL) was added (E)-3-(1-methylazetidin-3-yl)acrylic acid (58.6 mg, 0.41 mmol), DIEA (268.4 mg, 2.08 mmol) and HATU (197.4 mg, 0.52 mmol) at 0° C. under $N_2$. The mixture was stirred at 0° C. for 1 h. After the reaction was completed, the resulting mixture was diluted with $H_2O$ and extracted with EtOAc. The combined organic layer was washed with brine, dried over anhydrous sodium sulfate and filtered. The filtrate was concentrated under reduced pressure. The residue was purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 21% B to 30% B in 8 min; Wave Length: 254 nm) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-(1-methylazetidin-3-yl)prop-2-en-1-one (Compound 45) (17.3 mg, 13%) as a white solid. LCMS (ESI, m/z): $[M+H]^+$= 605.3. $^1H$ NMR (400 MHz, DMSO-$d_6$): δ 9.55-9.52 (m, 1H), 8.94 (d, J=7.6 Hz, 1H), 8.47 (s, 1H), 8.38 (s, 1H), 8.03-7.97 (m, 2H), 7.51 (s, 1H), 7.22 (d, J=9.2 Hz, 1H), 7.04-7.02 (m, 1H), 6.89-6.83 (m, 1H), 6.79 (d, J=2.4 Hz, 1H), 6.51-6.46 (m, 1H), 5.12-4.62 (m, 3H), 4.29-4.01 (m, 3H), 3.90-3.59 (m, 1H), 3.41-3.39 (m, 3H), 3.29-3.16 (m, 2H), 2.94-2.90 (m, 2H), 2.20-2.18 (m, 6H).

Example S46: Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-d3)amino)but-2-en-1-one (Compound 46)

Step 1. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one

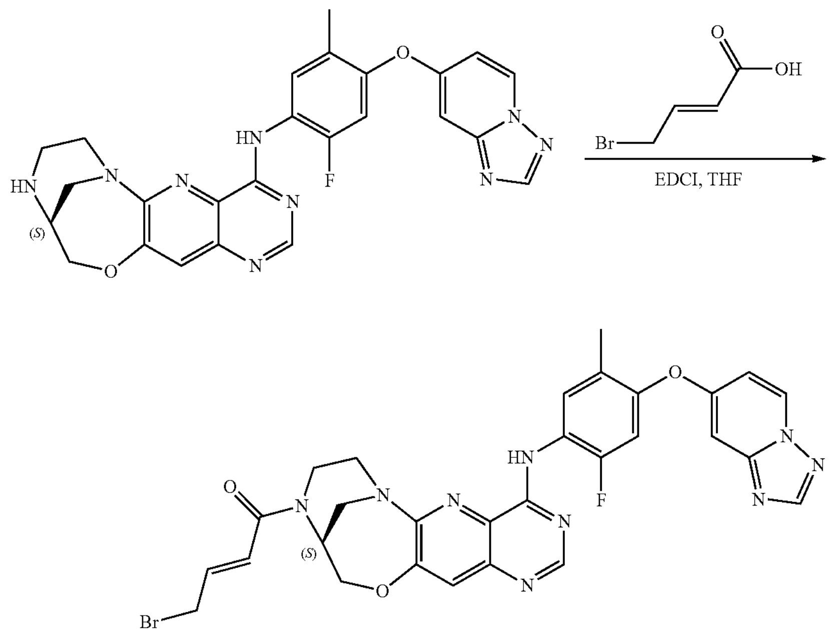

To a solution of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (150.0 mg, 0.30 mmol) in THE (4.0 mL) was added (E)-4-bromobut-2-enoic acid (54.5 mg, 0.33 mmol) and EDCI (115.1 mg, 0.60 mmol) at room temperature. The resulting mixture was stirred at room temperature for 1 h. After the reaction was completed, the resulting mixture was diluted with water and extracted with ethyl acetate. The combined organic layers were washed with brine, dried over anhydrous sodium sulfate and filtered. The filtrate was concentrated under reduced pressure to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (150.0 mg, crude) as a yellow solid. LCMS (ESI, m/z): $[M+H]^+$=646.1.

Step 2. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-d3)amino)but-2-en-1-one (Compound 46)

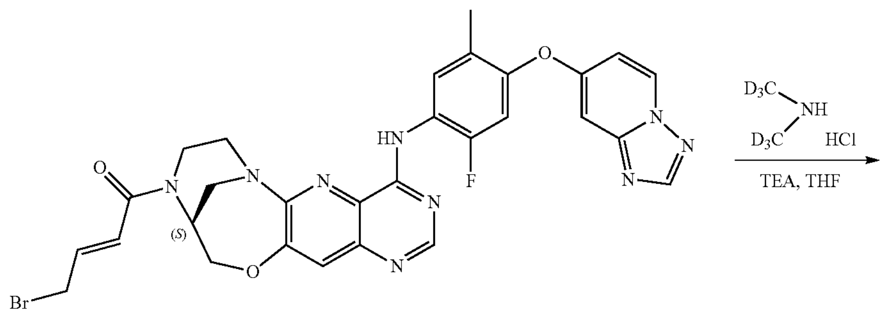

-continued

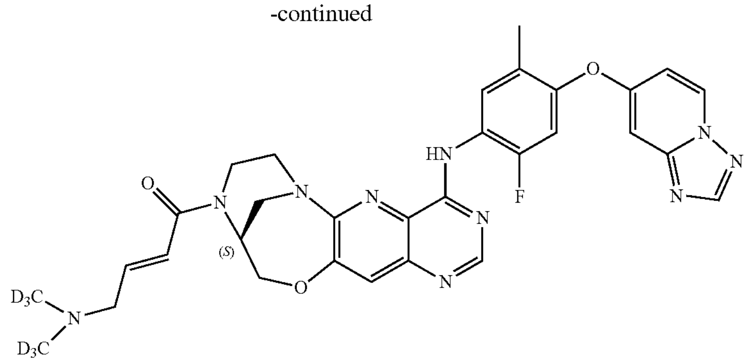

46

To a solution of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (130.0 mg, crude) in THE (5.0 mL) was added dimethyl-D6-amine hydrochloride (17.5 mg, 0.20 mmol) and TEA (40.7 mg, 0.40 mmol) at room temperature. The resulting mixture was stirred at room temperature for 0.5 h. After the reaction was completed, the resulting mixture was concentrated under reduced pressure. The residue was purified by flash column chromatography with $CH_2Cl_2$/MeOH (5/1, v/v) and then purified by Prep-HPLC with the following conditions (Column: XBridge Shield RP18 OBD Column, 30×150 mm, 5 μm; Mobile Phase A: Water 10 mmol/L $NH_4HCO_3$), Mobile Phase B: ACN; Flow rate: 60 mL/min; Gradient: 27% B to 42% B in 8 min, Wave Length: 254 nm) to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-d3)amino)but-2-en-1-one (Compound 46) (14.4 mg, 11%) as a yellow solid. LCMS (ESI, m/z): $[M+H]^+$=617.3. $^1H$ NMR (400 MHz, DMSO-$d_6$): δ 9.39 (s, 1H), 8.97 (d, J=7.6 Hz, 1H), 8.43-8.41 (m, 2H), 8.01 (d, J=8.8 Hz, 1H), 7.53 (s, 1H), 7.32 (d, J=11.2 Hz, 1H), 7.07-7.05 (m, 1H), 6.92 (d, J=2.4 Hz, 1H), 6.65-6.60 (m, 2H), 5.18-4.79 (m, 1H), 4.77-4.49 (m, 2H), 4.25-4.19 (m, 2H), 4.15-4.01 (m, 1H), 3.92-3.61 (m, 1H), 3.40-3.36 (m, 1H), 3.32-3.28 (m, 1H), 3.03 (d, J=6.4 Hz, 2H), 2.20 (s, 3H).

Example S47: Synthesis of (4S,E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)pent-2-en-1-one (Compound 47)

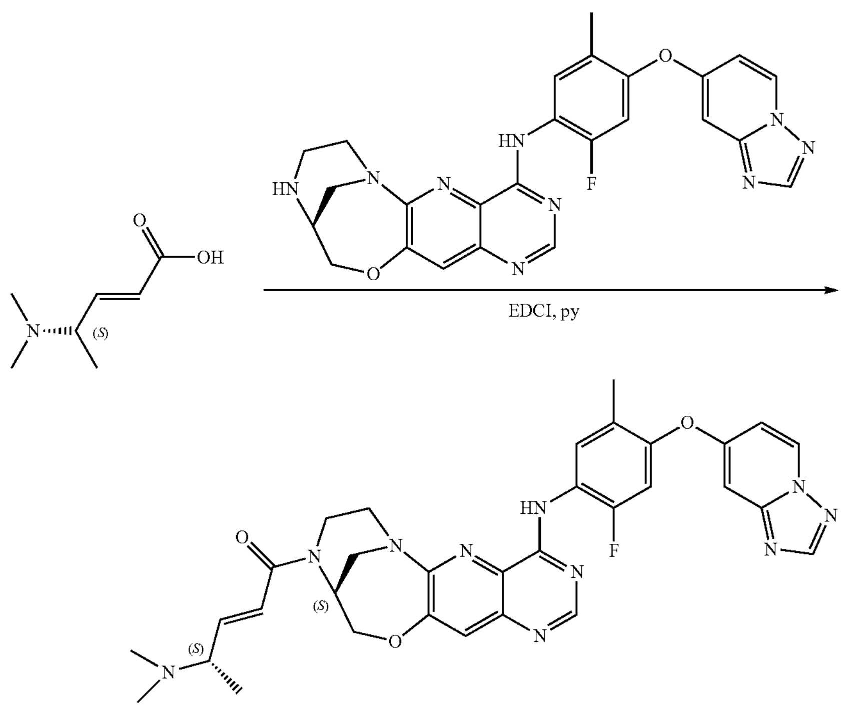

47

To a solution of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (52.5 mg, 0.11 mmol) in pyridine (3.0 mL) was added (S,E)-4-(dimethylamino)pent-2-enoic acid (150.5 mg, 1.05 mmol) and EDCI (40.3 mg, 0.21 mmol) at room temperature. The resulting mixture was stirred at room temperature for 2 h. After the reaction was completed, the resulting mixture was diluted with water and extracted with ethyl acetate. The combined organic layers were washed with brine, dried over anhydrous sodium sulfate and filtered. The filtrate was concentrated under reduced pressure. The residue was purified by Prep-HPLC with the following conditions (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 31% B to 41% B in 11 min; Wave Length: 254 nm) to afford (4S,E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)pent-2-en-1-one (Compound 47) (3.0 mg, 4%) as a yellow solid. LCMS (ESI, m/z): $[M+H]^+$=625.3. $^1H$ NMR (400 MHz, DMSO-$d_6$): δ 9.39 (s, 1H), 8.97 (d, J=7.2 Hz, 1H), 8.43-8.41 (m, 2H), 8.00 (d, J=8.8 Hz, 1H), 7.52 (s, 1H), 7.32 (d, J=11.2 Hz, 1H), 7.07-7.05 (m, 1H), 6.92 (d, J=2.0 Hz, 1H), 6.66-6.60 (m, 1H), 6.56-6.49 (m, 1H), 5.11-4.81 (m, 1H), 4.74-4.58 (m, 2H), 4.27-4.13 (m, 2H), 3.92-3.61 (m, 1H), 3.51-3.39 (m, 1H), 3.34-3.24 (m, 1H), 3.11-3.06 (m, 1H), 2.19 (s, 3H), 2.14 (s, 6H), 1.13-1.06 (m, 3H).

Example S48: Synthesis of (E)-1-((10S)-4-((4-([1,2,4]triazolo[1,5-a]pyridin-7-yloxy)-2,5-difluorophenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one (Compound 48)

Step 1. Synthesis of 7-(2,5-difluoro-4-nitrophenoxy)-[1,2,4]triazolo[1,5-a]pyridine

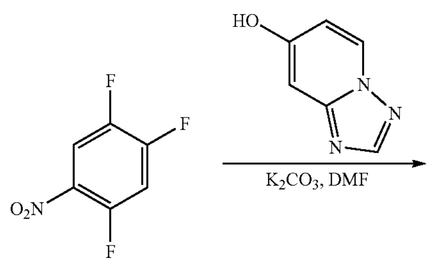

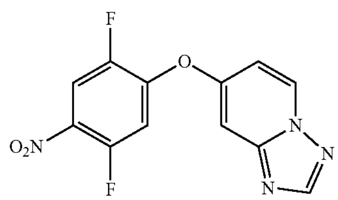

To a solution of 1,2,4-trifluoro-5-nitrobenzene (5.0 g, 28.2 mmol) in DMF (60 mL) was added [1,2,4]triazolo[1,5-a]pyridin-7-ol (3.8 g, 28.2 mmol) and $K_2CO_3$ (11.7 g, 84.8 mmol) at 0° C. The mixture was stirred at room temperature for 16 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash chromatography with ethyl acetate/petroleum ether (30/70, v/v) to afford 7-(2,5-difluoro-4-nitrophenoxy)-[1,2,4]triazolo[1,5-a]pyridine (6.6 g, 81%) as a yellow solid. LCMS (ESI, m/z): $[M+H]^+$=293.0.

Step 2. Synthesis of 4-([1,2,4]triazolo[1,5-a]pyridin-7-yloxy)-2,5-difluoroaniline

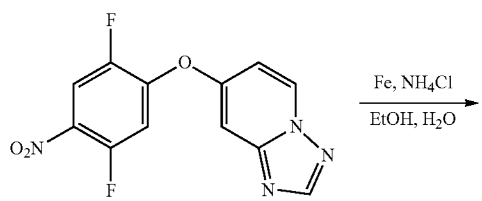

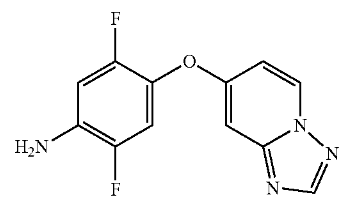

To a solution of 7-(2,5-difluoro-4-nitrophenoxy)-[1,2,4]triazolo[1,5-a]pyridine (6.6 g, 22.5 mmol) in EtOH (30.0 ml) and water (30.0 ml) was added Fe (3.8 g, 67.5 mmol) and $NH_4C_1$ (1.2 g, 22.5 mmol) at room temperature. The mixture was stirred at 80° C. for 2 h. After the reaction was completed, the mixture was filtered. The filtrate was concentrated under vacuum. The residue was purified by flash chromatography with $CH_2Cl_2$/MeOH (95/5, v/v) to afford 4-([1,2,4]triazolo[1,5-a]pyridin-7-yloxy)-2,5-difluoroaniline (4.6 g, 78%) as a yellow solid. LCMS (ESI, m/z): $[M+H]^+$=263.0.

Step 3. Synthesis of N-(4-([1,2,4]triazolo[1,5-a]pyridin-7-yloxy)-2,5-difluorophenyl)-7-bromo-6-chloropyrido[3,2-d]pyrimidin-4-amine

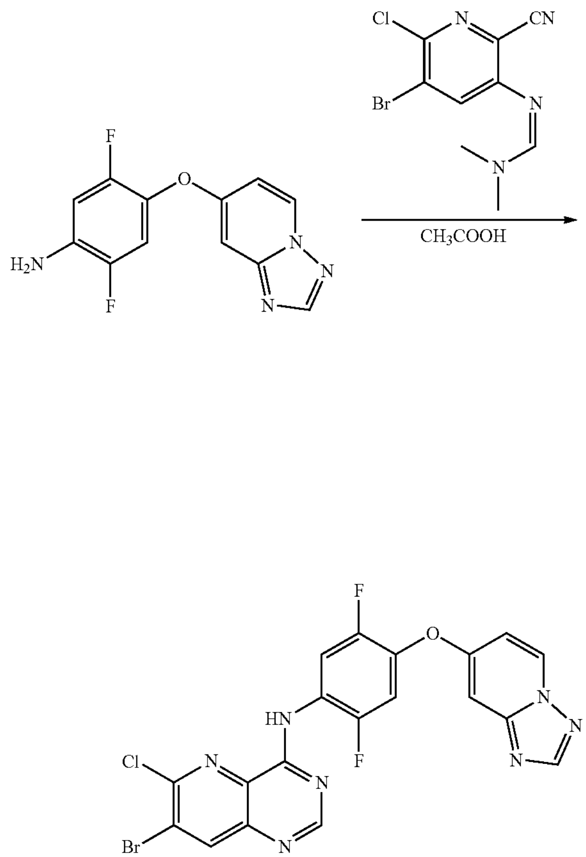

To a solution of 4-([1,2,4]triazolo[1,5-a]pyridin-7-yloxy)-2,5-difluoroaniline (4.6 g, 17.5 mmol) in $CH_3COOH$ (50 mL) was added (Z)—N'-(5-bromo-6-chloro-2-cyanopyridin-3-yl)-N,N-dimethylformimidamide (5.0 g, 17.5 mmol) at room temperature. The mixture was stirred at 85° C. for 4 h. After the reaction was completed, the mixture was concentrated under vacuum. The residue was purified by flash chromatography with $CH_2Cl_2$/MeOH (80/20, v/v) to afford N-(4-([1,2,4]triazolo[1,5-a]pyridin-7-yloxy)-2,5-difluorophenyl)-7-bromo-6-chloropyrido[3,2-d]pyrimidin-4-amine (5.7 g, 65%) as a yellow solid. LCMS (ESI, m/z): $[M+H]^+$=504.0.

Step 4. Synthesis of tert-butyl (S)-4-(4-((4-([1,2,4]triazolo[1,5-a]pyridin-7-yloxy)-2,5-difluorophenyl)amino)-7-bromopyrido[3,2-d]pyrimidin-6-yl)-2-(hydroxymethyl)piperazine-1-carboxylate

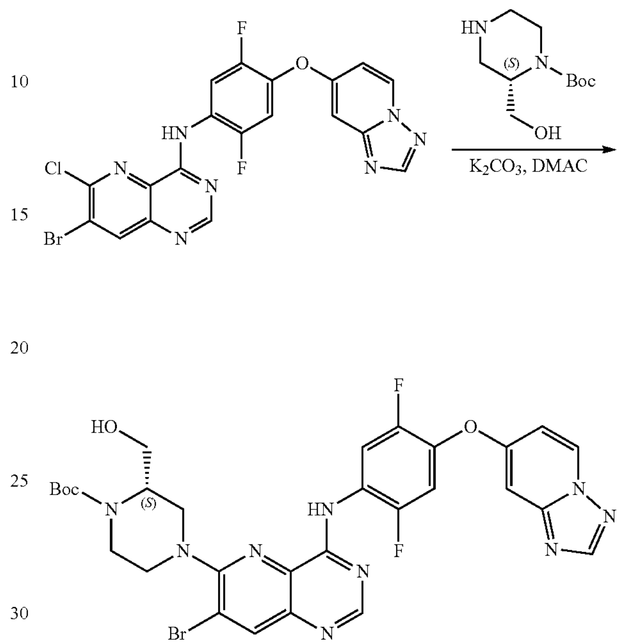

To a solution of N-(4-([1,2,4]triazolo[1,5-a]pyridin-7-yloxy)-2,5-difluorophenyl)-7-bromo-6-chloropyrido[3,2-d]pyrimidin-4-amine (1.5 g, 2.98 mmol) in DMAC (30.0 mL) was added tert-butyl (S)-2-(hydroxymethyl)piperazine-1-carboxylate (1.6 g, 7.45 mmol) and $K_2CO_3$ (1.2 g, 8.94 mmol) at room temperature. The mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by reverse phase flash chromatography with $CH_3OH/H_2O$ (75/25, v/v) to afford tert-butyl (S)-4-(4-((4-([1,2,4]triazolo[1,5-a]pyridin-7-yloxy)-2,5-difluorophenyl)amino)-7-bromopyrido[3,2-d]pyrimidin-6-yl)-2-(hydroxymethyl)piperazine-1-carboxylate (200.0 mg, 14%) as a yellow solid. LCMS (ESI, m/z): $[M+H]^+$=604.2.

Step 5. Synthesis of tert-butyl (10S)-4-((4-([1,2,4]triazolo[1,5-a]pyridin-7-yloxy)-2,5-difluorophenyl)amino)-7,8,10,11-tetrahydro-9H-6,10-methanopyrimido[4',5':5,6]pyrido[3,2-b][1,4,7]oxadiazonine-9-carboxylate

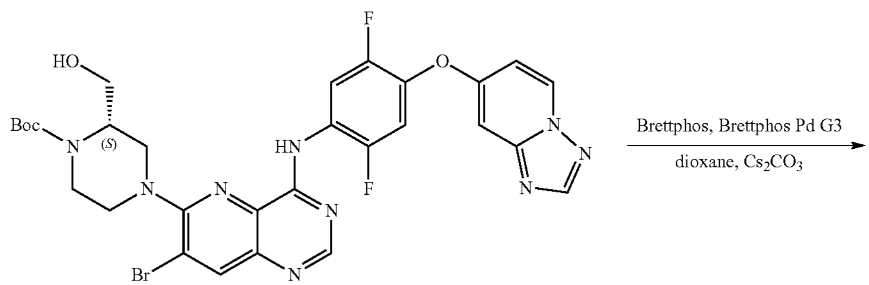

-continued

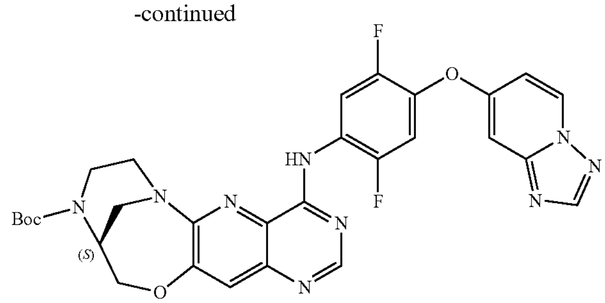

To a solution of tert-butyl (S)-4-(4-((4-([1,2,4]triazolo[1,5-a]pyridin-7-yloxy)-2,5-difluorophenyl)amino)-7-bromopyrido[3,2-d]pyrimidin-6-yl)-2-(hydroxymethyl)piperazine-1-carboxylate (200.0 mg, 0.29 mmol) in dioxane (8.0 mL) was added Brettphos (27.3 mg, 0.06 mmol), Brettphos Pd G3 (26.5 mg, 0.03 mmol) and $Cs_2CO_3$ (285.4 mg, 0.87 mmol) at room temperature under $N_2$. The mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under vacuum. The residue was purified by flash chromatography with $CH_3OH/CH_2Cl_2$ (94/6, v/v) to afford tert-butyl (10S)-4-((4-([1,2,4]triazolo[1,5-a]pyridin-7-yloxy)-2,5-difluorophenyl)amino)-7,8,10,11-tetrahydro-9H-6,10-methanopyrimido[4',5':5,6]pyrido[3,2-b][1,4,7]oxadiazonine-9-carboxylate (100.0 mg, 57%) as a yellow solid. LCMS (ESI, m/z): $[M+H]^+$=604.2.

Step 6. Synthesis of (10S)—N-(4-([1,2,4]triazolo[1,5-a]pyridin-7-yloxy)-2,5-difluorophenyl)-8,9,10,11-tetrahydro-7H-6,10-methanopyrimido[4',5':5,6]pyrido[3,2-b][1,4,7]oxadiazonin-4-amine hydrochloride

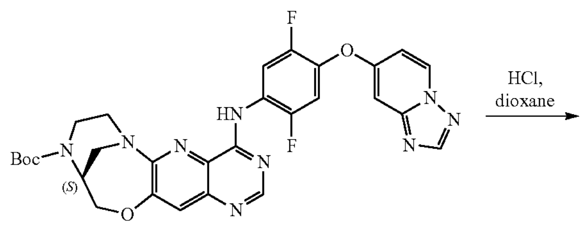

-continued

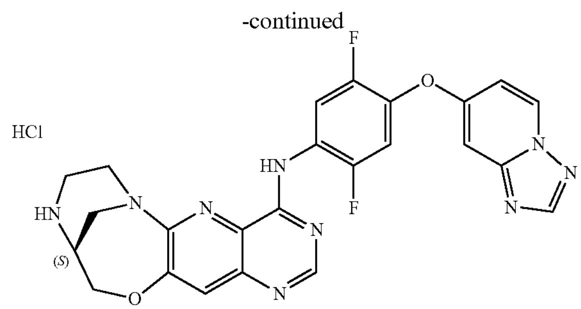

A solution of tert-butyl (10S)-4-((4-([1,2,4]triazolo[1,5-a]pyridin-7-yloxy)-2,5-difluorophenyl) amino)-7,8,10,11-tetrahydro-9H-6,10-methanopyrimido[4',5':5,6]pyrido[3,2-b][1,4,7] oxadiazonine-9-carboxylate (200.0 mg, 0.33 mmol) in HCl/1,4-dioxane (5.0 mL, 4.0 mol/L) was stirred at room temperature for 1 h. After the reaction was completed, the mixture was concentrated under reduce pressure to afford (10S)—N-(4-([1,2,4]triazolo[1,5-a]pyridin-7-yloxy)-2,5-difluorophenyl)-8,9,10,11-tetrahydro-7H-6,10-methanopyrimido[4',5':5,6]pyrido[3,2-b][1,4,7]oxadiazonin-4-amine hydrochloride (166.0 mg, crude) as yellow solid. LCMS (ESI, m/z): $[M+H]^+$=504.2.

Step 7. Synthesis of (E)-1-((10S)-4-((4-([1,2,4]triazolo[1,5-a]pyridin-7-yloxy)-2,5-difluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 48)

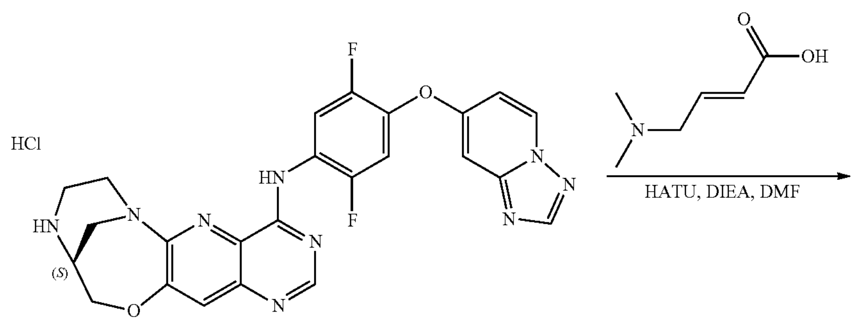

-continued

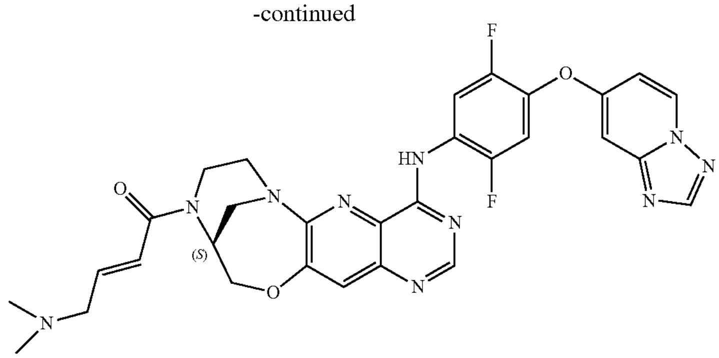

48

To a solution of (10S)—N-(4-([1,2,4]triazolo[1,5-a]pyridin-7-yloxy)-2,5-difluorophenyl)-8,9,10,11-tetrahydro-7H-6,10-methanopyrimido[4',5':5,6]pyrido[3,2-b][1,4,7]oxadiazonin-4-amine hydrochloride (166.0 mg, crude) in DMF (4.0 mL) was added DIEA (127.7 mg, 0.99 mmol), (E)-4-(dimethylamino)but-2-enoic acid (85.1 mg, 0.66 mmol) and HATU (376.2 mg, 0.99 mmol) at 0° C. under $N_2$. The resulting mixture was stirred at room temperature for 30 min. After the reaction was completed, the resulting mixture was purified by reverse phase flash chromatography with $CH_3OH/H_2O$ (81/19, v/v) and then purified by Prep-HPLC with the following conditions: (Column: XBridge Prep Phenyl OBD Column, 19×250 mm, 5 μm; Mobile Phase A: Water (10 mmol/L $NH_4HCO_3$), Mobile Phase B: ACN; Flow rate: 25 mL/min; Gradient: 30% B to 45% B in 10 min; Wave Length: 254 nm) to afford (E)-1-((10S)-4-((4-([1,2,4]triazolo[1,5-a]pyridin-7-yloxy)-2,5-difluorophenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one (Compound 48) (18.0 mg, 9%) as a white solid. LCMS (ESI, m/z): $[M+H]^+$=615.3. $^1H$ NMR (400 MHz, DMSO-$d_6$): δ 9.38 (s, 1H), 8.99 (d, J=7.6 Hz, 1H), 8.50 (s, 1H), 8.44 (s, 1H), 8.39-8.34 (m, 1H), 7.68-7.63 (m, 1H), 7.56 (s, 1H), 7.18 (s, 1H), 7.14-7.12 (m, 1H), 6.67-6.57 (m, 2H), 5.12-4.70 (m, 1H), 4.68-4.51 (m, 2H), 4.29-4.04 (m, 2H), 3.90-3.67 (m, 1H), 3.50-3.41 (m, 1H), 3.04 (s, 2H), 2.18-2.15 (m, 6H).

Example S49: Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4,5':5,6]pyrido[3,2-b][1,4,7]oxadiazonin-9-yl)-4-(methylamino)but-2-en-1-one (Compound 49)

Step 1. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one

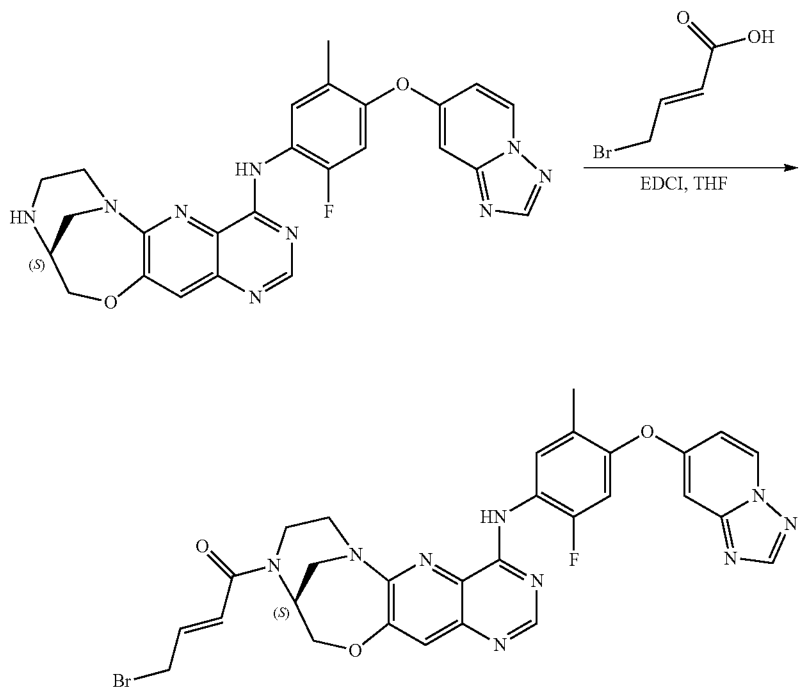

To a solution of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (180.0 mg, 0.36 mmol) in THE (3.0 mL) was added (E)-4-bromobut-2-enoic acid (59.4 mg, 0.36 mmol) at room temperature. The resulting mixture was stirred at room temperature for 1 h. After the reaction was completed, the resulting mixture was filtered. The filtrate was concentrated under reduced pressure to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-bromobut-2-en-1-one (180.0 mg, crude) a light yellow solid. LCMS (ESI, m/z): $[M+H]^+$=646.1.

Step 2. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(methylamino)but-2-en-1-one (Compound 49)

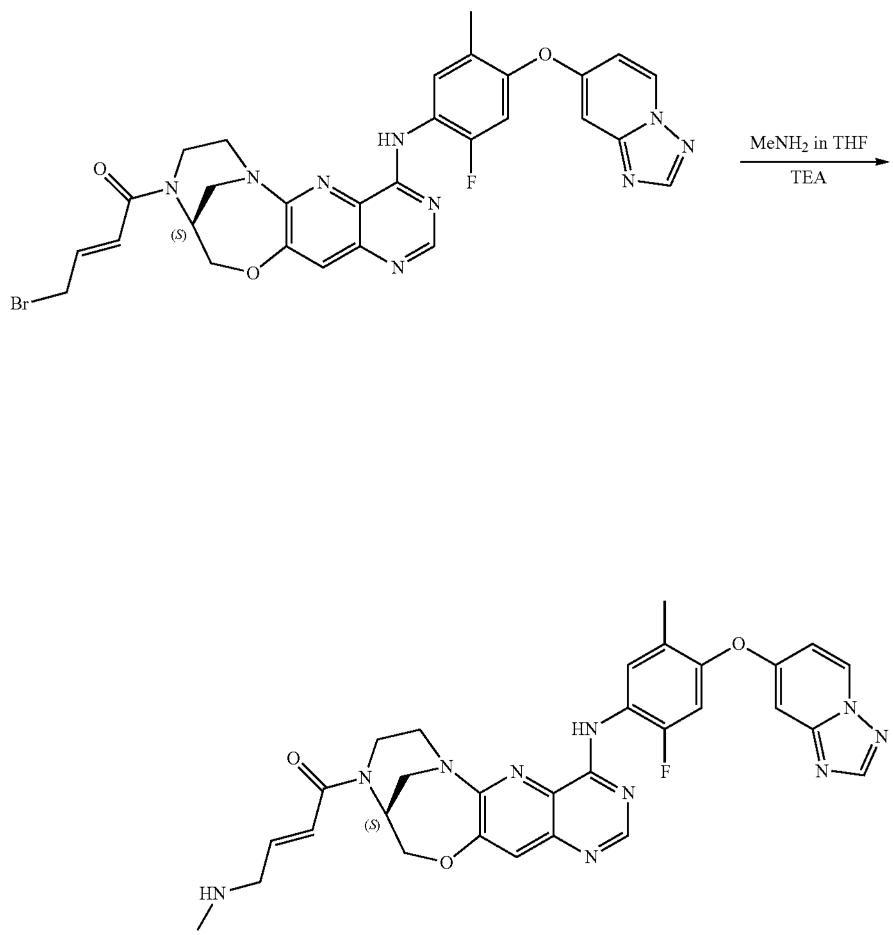

49

To a solution of (2E)-4-bromo-1-[(14S)-5-[(2-fluoro-5-methyl-4-{[1,2,4]triazolo[1,5-a]pyridin-7-yloxy}phenyl)amino]-12-oxa-1,3,6,8,15-pentaazatetracyclo[12.3.1.0^{2,11}0.0^{4,9}]octadeca-2 (11),3,5,7,9-pentaen-15-yl]but-2-en-1-one (150.0 mg, crude) in THE (3.0 mL) was added a solution of $MeNH_2$ in THE (0.26 mL, 1.0 mol/L) and TEA (70.4 mg, 0.69 mmol) at room temperature. The resulting mixture was stirred at room temperature for 30 min. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by Prep-HPLC with the following conditions: (Column: Xselect CSH C18 OBD Column 30×150 mm, 5 μm; Mobile Phase A: ACN, Mobile Phase B: Water (0.1% FA); Flow rate: 60 mL/min; Gradient: 9% B to 16% B in 10 min; Wave Length: 254/220 nm) to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(methylamino)but-2-en-1-on (Compound 49) (14.9 mg, 8%) as a white solid. LCMS (ESI, m/z): $[M+H]^+$=597.2. $^1H$ NMR (400 MHz, DMSO-$d_6$): δ 9.39 (s, 1H), 8.97 (d, J=7.6 Hz, 1H), 8.43-8.41 (m, 2H), 8.02 (d, J=8.4 Hz, 1H), 7.53 (s, 1H), 7.32 (d, J=10.8 Hz, 1H), 7.07-7.05 (m, 1H), 6.92 (d, J=2.4 Hz, 1H), 6.71-6.56 (m, 2H), 5.14-4.78 (m, 1H), 4.73-4.55 (m, 2H), 4.28-4.04 (m, 3H), 3.80-3.35 (m, 6H), 2.33-2.30 (m, 3H), 2.20 (s, 3H).

Example S50: Synthesis of (4R,E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)pent-2-en-1-one (Compound 50)

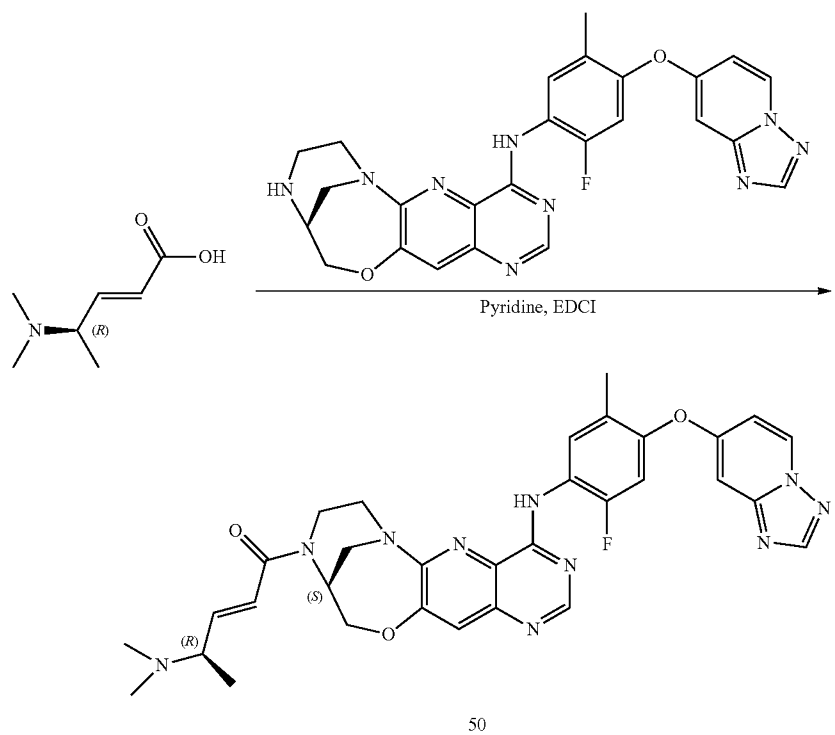

50

To a solution of (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (120.0 mg, 0.24 mmol) in pyridine (5.0 mL) was added (R,E)-4-(dimethylamino)pent-2-enoic acid (688.0 mg, 4.80 mmol) and EDCI (92.1 mg, 0.48 mmol) at room temperature. The resulting mixture was stirred at room temperature for 2 h. After the reaction was completed, the mixture was concentrated under reduced pressure. The residue was purified by flash column chromatography with DCM/MeOH (92/8, v/v) and then purified by Prep-HPLC with the following conditions: (Column: XBridge Shield RP18 OBD Column, 30×150 mm, 5 μm; Mobile Phase A: Water(10 mmol/L $NH_4HCO_3$), Mobile Phase B: ACN; Flow rate: 60 mL/min; Gradient: 30% B to 45% B in 8 min; Wave Length: 254 nm) to afford (4R,E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)pent-2-en-1-one (Compound 50) (5.2 mg, 3%) as a white solid. LCMS (ESI, m/z): $[M+H]^+$=625.3. $^1H$ NMR (400 MHz, DMSO-$d_6$): δ 9.39 (s, 1H), 8.97 (d, J=7.6 Hz, 1H), 8.43-8.41 (m, 2H), 8.02 (d, J=8.8 Hz, 1H), 7.52 (s, 1H), 7.33-7.31 (m, 1H), 7.07-7.05 (m, 1H), 6.93 (s, 1H), 6.66-6.60 (m, 1H), 6.58-6.49 (m, 1H), 5.11-4.81 (m, 1H), 4.73-4.55 (m, 2H), 4.28-4.10 (m, 2H), 3.92-3.64 (m, 1H), 3.51-3.40 (m, 1H), 3.32-3.23 (m, 1H), 3.09 (d, J=6.4 Hz, 1H), 2.20-2.03 (m, 9H), 1.11-1.07 (m, 3H).

Example S51: Synthesis of (E)-4-(dimethylamino)-1-((10S)-4-((4-((5-fluoropyridin-3-yl)oxy)-3-methylphenyl)amino)-7,8,10,11-tetrahydro-9H-6,10-methanopyrimido[4,5':5,6]pyrido[3,2-b][1,4,7]oxadiazonin-9-yl)but-2-en-1-one (Compound 51)

Step 1. Synthesis of 3-fluoro-5-(2-methyl-4-nitrophenoxy)pyridine

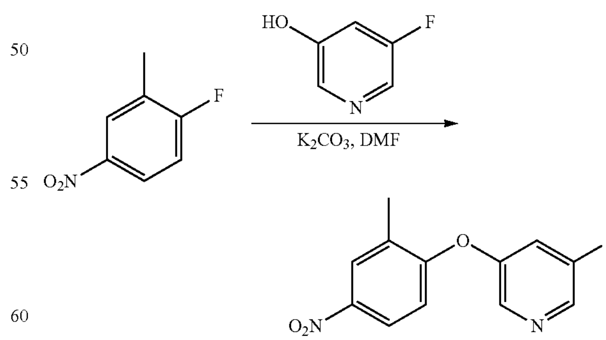

To a solution of 5-fluoropyridin-3-ol (6.8 g, 44.21 mmol) in DMF (50.0 mL) was added 1-fluoro-2-methyl-4-nitrobenzene (5.0 g, 44.21 mmol) and $K_2CO_3$ (18.3 g, 132.63 mmol) at room temperature. The resulting mixture was stirred at 50° C. for 12 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure to afford 3-fluoro-5-(2-methyl-4-nitrophenoxy)pyridine (10.0 g, crude) as a light yellow solid. LCMS (ESI, m/z): $[M+H]^+$=249.1.

Step 2. Synthesis of 4-((5-fluoropyridin-3-yl)oxy)-3-methylaniline

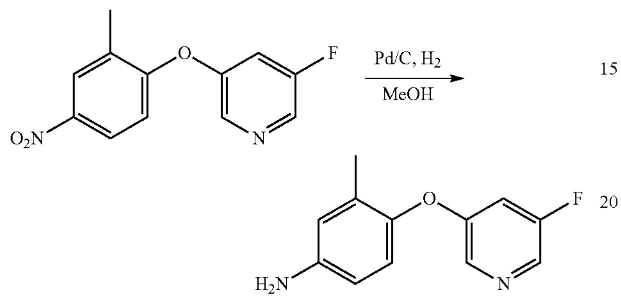

To a solution of 3-fluoro-5-(2-methyl-4-nitrophenoxy) pyridine (9.0 g, 36.25 mmol) in MeOH (90.0 mL) was added Pd/C (2.7 g, 10% wet) at room temperature under $N_2$. The resulting mixture was stirred at room temperature for 2 h under $H_2$. After the reaction was completed, the resulting mixture was filtered. The filtrate was concentrated under reduced pressure. The residue was purified by flash column chromatography with $CH_2Cl_2$/MeOH (10/1, v/v) to afford 4-[(5-fluoropyridin-3-yl)oxy]-3-methylaniline (7.0 g, 88%) as a yellow oil. LCMS (ESI, m/z): $[M+H]^+$=219.1.

Step 3. Synthesis of 7-bromo-6-chloro-N-(4-((5-fluoropyridin-3-yl)oxy)-3-methylphenyl)pyrido[3,2-d]pyrimidin-4-amine

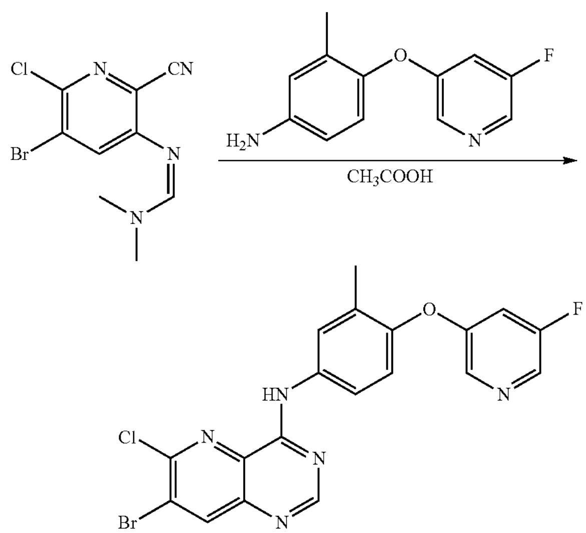

To a solution of (Z)—N'-(5-bromo-6-chloro-2-cyanopyridin-3-yl)-N,N-dimethylformimidamide (1.9 g, 6.60 mmol) in acetic acid (20.0 mL) was added 4-((5-fluoropyridin-3-yl)oxy)-3-methylaniline (1.4 g, 6.60 mmol) at room temperature. The resulting mixture was stirred at 85° C. for 2 h. After the reaction was completed, the resulting mixture was concentrated under reduced pressure. The residue was purified by flash column chromatography with $CH_2Cl_2$/MeOH (10/1, v/v) to afford 7-bromo-6-chloro-N-(4-((5-fluoropyridin-3-yl)oxy)-3-methylphenyl)pyrido[3,2-d]pyrimidin-4-amine (3.0 g, 98%) as a yellow solid. LCMS (ESI, m/z): $[M+H]^+$=460.0.

Step 4. Synthesis of tert-butyl (S)-4-(7-bromo-4-((4-((5-fluoropyridin-3-yl)oxy)-3-methylphenyl)amino)pyrido[3,2-d]pyrimidin-6-yl)-2-(hydroxymethyl)piperazine-1-carboxylate

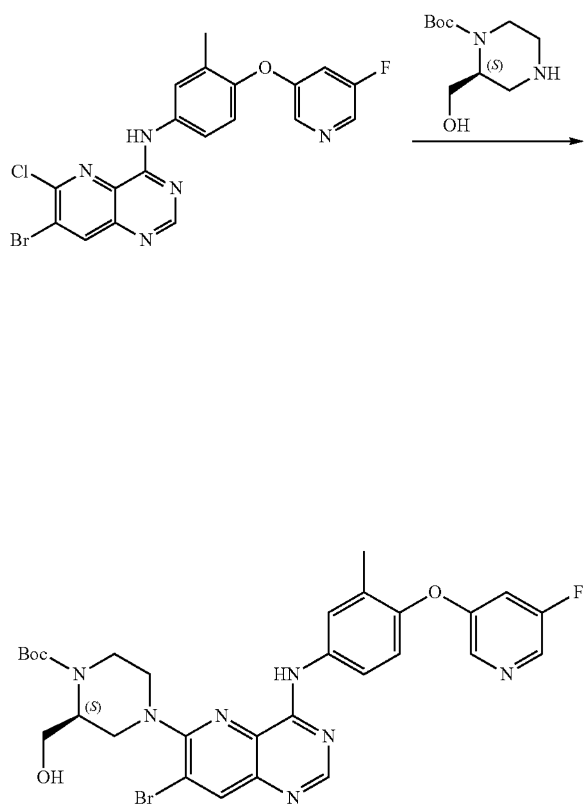

To a solution of 7-bromo-6-chloro-N-(4-((5-fluoropyridin-3-yl)oxy)-3-methylphenyl)pyrido[3,2-d]pyrimidin-4-amine (1.2 g, 2.60 mmol) in NMP (15.0 mL) was added tert-butyl (S)-2-(hydroxymethyl)piperazine-1-carboxylate (0.8 g, 3.90 mmol) and DIEA (0.6 g, 5.21 mmol) at room temperature. The resulting mixture was stirred at 80° C. for 12 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (10/1) to afford tert-butyl (S)-4-(7-bromo-4-((4-((5-fluoropyridin-3-yl)oxy)-3-methylphenyl)amino)pyrido[3,2-d]pyrimidin-6-yl)-2-(hydroxymethyl)piperazine-1-carboxylate (1.3 g, 81%) as a yellow solid. LCMS (ESI, m/z): $[M+H]^+$=640.2.

Step 5. Synthesis of tert-butyl (10S)-4-((4-((5-fluoropyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate

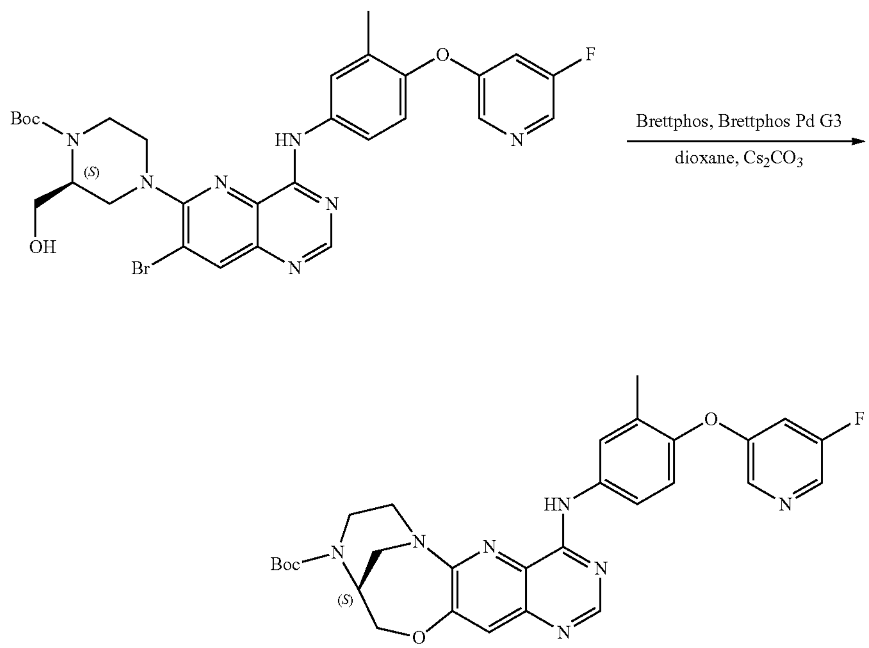

To a solution of tert-butyl (S)-4-(7-bromo-4-((4-((5-fluoropyridin-3-yl)oxy)-3-methylphenyl)amino)pyrido[3,2-d]pyrimidin-6-yl)-2-(hydroxymethyl)piperazine-1-carboxylate (1.2 g, 1.91 mmol) in dioxane (12.0 mL) was added $Cs_2CO_3$ (1.8 g, 5.74 mmol), BrettPhos (0.4 g, 0.76 mmol) and BrettPhos Pd G3 (0.3 g, 0.38 mmol) at room temperature under $N_2$. The resulting mixture was stirred at 100° C. for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with with $CH_2Cl_2$/MeOH (10/1, v/v) to afford tert-butyl (10S)-4-((4-((5-fluoropyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate (470.0 mg, 45%) as a brown yellow solid. LCMS (ESI, m/z): $[M+H]^+$=560.2.

Step 6. Synthesis of (10S)—N-(4-((5-fluoropyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine

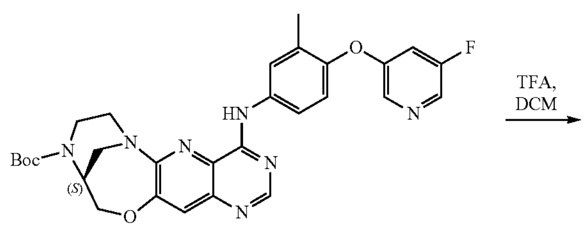

-continued

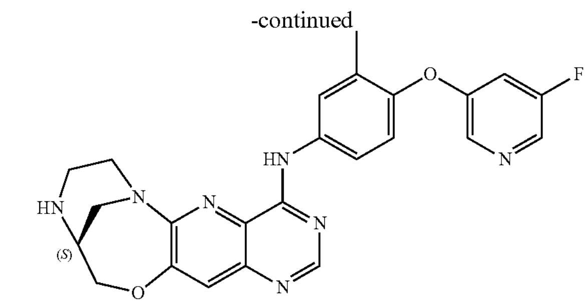

To a solution of tert-butyl (10S)-4-((4-((5-fluoropyridin-3-yl)oxy)-3-methylphenyl)amino)-7,8,10,11-tetrahydro-9H-6,10-methanopyrimido[4',5':5,6]pyrido[3,2-b][1,4,7]oxadiazonine-9-carboxylate (460.0 mg, 0.82 mmol) in DCM (5.0 mL) was added TFA (2.5 mL) at room temperature. The resulting mixture was stirred at room temperature for 30 min. After the reaction was completed, the resulting mixture was neutralized to pH=8 with saturated $NaHCO_3$(aq). The resulting mixture was extracted with $CH_2Cl_2$. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford (10S)—N-(4-((5-fluoropyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine (350.0 mg, 92%) as a yellow solid. LCMS (ESI, m/z): $[M+H]^+$=460.2.

Step 7. Synthesis of (E)-4-(dimethylamino)-1-((10S)-4-((4-((5-fluoropyridin-3-yl)oxy)-3-methylphenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 51)

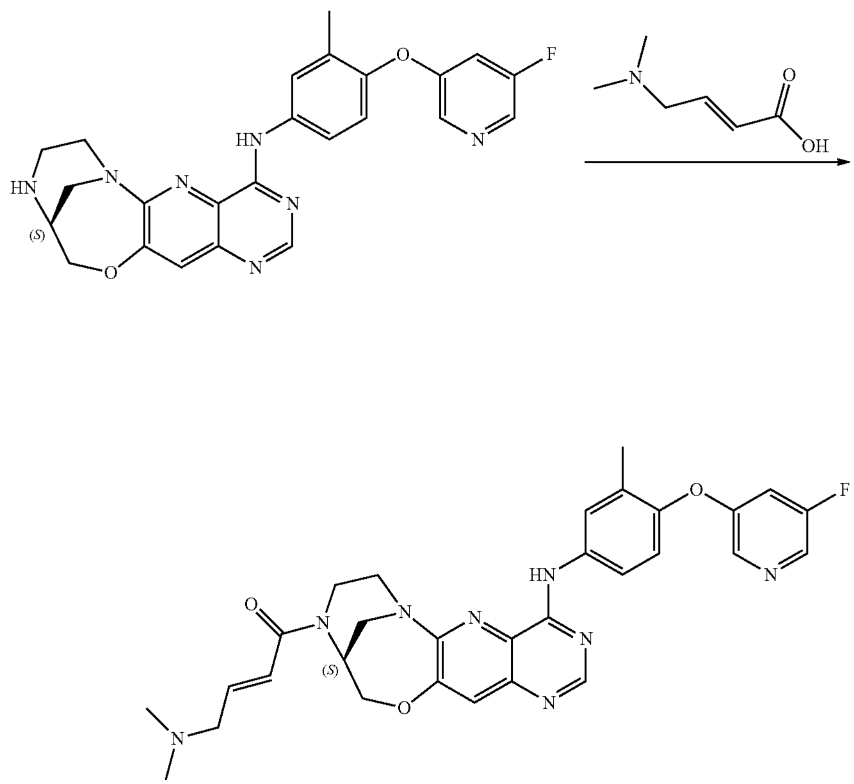

51

To a solution of (10S)—N-(4-((5-fluoropyridin-3-yl)oxy)-3-methylphenyl)-8,9,10,11-tetrahydro-7H-6,10-methanopyrimido[4',5':5,6]pyrido[3,2-b][1,4,7]oxadiazonin-4-amine (200.0 mg, 0.43 mmol) in pyridine (4.0 mL) was added (E)-4-(dimethylamino)but-2-enoic acid (112.4 mg, 0.87 mmol) and EDCI (155.3 mg, 0.81 mmol) at room temperature. The resulting mixture was stirred at room temperature for 2 h. After the reaction was completed, the resulting mixture was concentrated under reduced pressure. The residue was purified by flash column chromatography with $CH_2Cl_2$/MeOH (10/1, v/v) and then purified by Prep-HPLC with the following conditions: (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 38% B to 58% B in 10 min; Wave Length: 254 nm) to afford (E)-4-(dimethylamino)-1-((10S)-4-((4-((5-fluoropyridin-3-yl)oxy)-3-methylphenyl)amino)-7,8,10,11-tetrahydro-9H-6,10-methanopyrimido[4',5':5,6]pyrido[3,2-b][1,4,7]oxadiazonin-9-yl)but-2-en-1-one (Compound 51) (80.0 mg, 31%) as a yellow solid. LCMS (ESI, m/z): $[M+H]^+$=571.2. $^1$H NMR (400 MHz, DMSO-$d_6$): δ 9.52-9.50 (m, 1H), 8.46 (s, 1H), 8.34 (d, J=2.4 Hz, 1H), 8.20 (s, 1H), 7.96-7.93 (m, 2H), 7.51 (s, 1H), 7.30-7.26 (m, 1H), 7.13 (d, J=9.2 Hz, 1H), 6.65-6.61 (m, 2H), 5.12-4.60 (m, 3H), 4.28-4.02 (m, 3H), 3.88-3.62 (m, 1H), 3.46-3.36 (m, 1H), 3.29-3.22 (m, 1H), 3.03 (d, J=5.6 Hz, 2H), 2.21 (s, 3H), 2.16-2.12 (m, 6H).

Example S52: Synthesis of (E)-1-(4-((4-([1,2,4]triazolo[1,5-a]pyridin-7-yloxy)-3-methylphenyl)amino)-7,8,11,12-tetrahydro-6,10-methanopyrimido[4,5':5,6]pyrido[3,2-b][1,4,7]oxadiazecin-9 (10H)-yl)-4-(dimethylamino)but-2-en-1-one (Compound 52)

Step 1. Synthesis of tert-butyl 4-(4-((4-([1,2,4]triazolo[1,5-a]pyridin-7-yloxy)-3-methylphenyl)amino)-7-bromopyrido[3,2-d]pyrimidin-6-yl)-2-(2-hydroxyethyl)piperazine-1-carboxylate

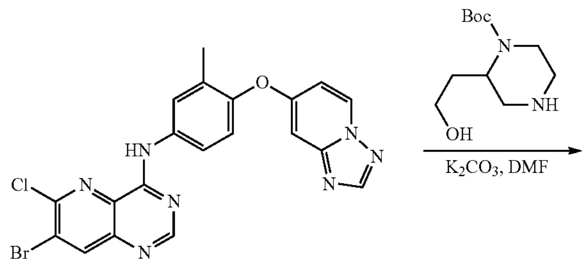

-continued

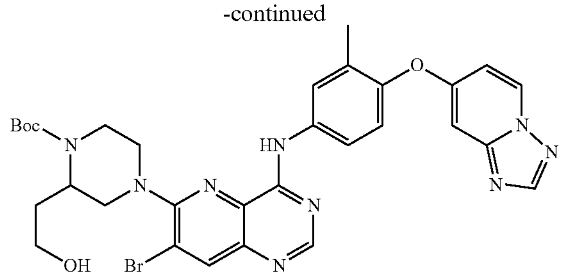

To a solution of N-(4-([1,2,4]triazolo[1,5-a]pyridin-7-yloxy)-3-methylphenyl)-7-bromo-6-chloropyrido[3,2-d]pyrimidin-4-amine (1.0 g, 2.07 mmol) in DMF (30.0 mL) was added tert-butyl 2-(2-hydroxyethyl)piperazine-1-carboxylate (1.4 g, 6.22 mmol) and $K_2CO_3$ (0.9 g, 6.22 mmol) at room temperature. The resulting mixture was stirred at 100° C. for 2 h. After the reaction was completed, the resulting mixture was diluted with water and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (90/10, v/v) to afford tert-butyl 4-(4-((4-([1,2,4]triazolo[1,5-a]pyridin-7-yloxy)-3-methylphenyl)amino)-7-bromopyrido[3,2-d]pyrimidin-6-yl)-2-(2-hydroxyethyl)piperazine-1-carboxylate (1.1 g, 78%) as a yellow solid. LCMS: (ESI, m/z): $[M+H]^+$=676.2.

Step 2. Synthesis of tert-butyl 4-((4-([1,2,4]triazolo[1,5-a]pyridin-7-yloxy)-3-methylphenyl)amino)-7,8,11,12-tetrahydro-6,10-methanopyrimido[4',5':5,6]pyrido[3,2-b][1,4,7]oxadiazecine-9 (10H)-carboxylate

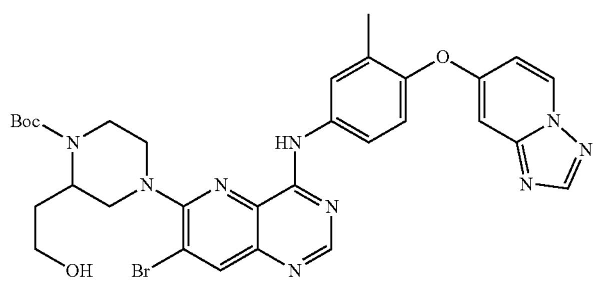

Brettphos, Brettphos Pd $G_3$
$K_2CO_3$, dioxane

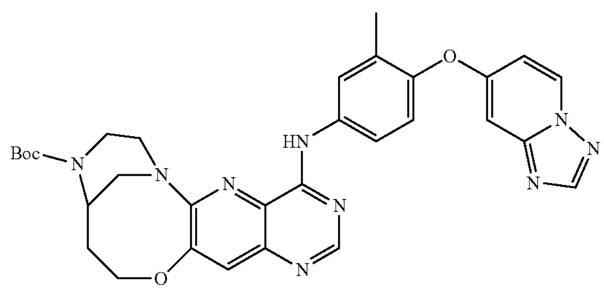

To a solution of tert-butyl 4-(4-((4-([1,2,4]triazolo[1,5-a]pyridin-7-yloxy)-3-methylphenyl)amino)-7-bromopyrido[3,2-d]pyrimidin-6-yl)-2-(2-hydroxyethyl)piperazine-1-carboxylate (1.1 g, 1.63 mmol) in dioxane (30.0 mL) was added $K_2CO_3$ (0.7 g, 4.88 mmol), BrettPhos (0.2 g, 0.33 mmol) and BrettPhos Pd G3 (0.2 g, 0.16 mmol) at room temperature under $N_2$. The resulting mixture was stirred at 100° C. for 2 h under $N_2$. After the reaction was completed, the resulting mixture was diluted with water and extracted with ethyl acetate. The combined organic layer was washed with brine, dried over anhydrous sodium sulfate and filtered. The filtrate was concentrated under reduced pressure. The residue was purified by flash column chromatography with $CH_2Cl_2$/MeOH (95/5, v/v) to afford tert-butyl 4-((4-([1,2,4]triazolo[1,5-a]pyridin-7-yloxy)-3-methylphenyl)amino)-7,8,11,12-tetrahydro-6,10-methanopyrimido[4',5':5,6]pyrido[3,2-b][1,4,7]oxadiazecine-9 (10H)-carboxylate (100.0 mg, 10%) as a yellow solid. LCMS (ESI, m/z): $[M+H]^+$=596.3.

Step 3. Synthesis of N-(4-([1,2,4]triazolo[1,5-a]pyridin-7-yloxy)-3-methylphenyl)-7,8,9,10,11,12-hexahydro-6,10-methanopyrimido[4',5':5,6]pyrido[3,2-b][1,4,7]oxadiazecin-4-amine

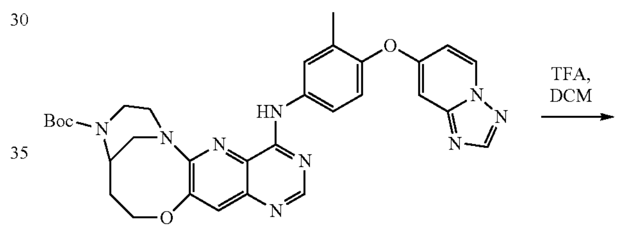

-continued

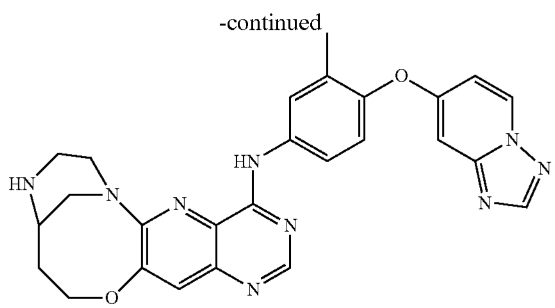

To a solution of tert-butyl 4-((4-([1,2,4]triazolo[1,5-a]pyridin-7-yloxy)-3-methylphenyl)amino)-7,8,11,12-tetrahydro-6,10-methanopyrimido[4',5':5,6]pyrido[3,2-b][1,4,7]oxadiazecine-9 (10H)-carboxylate (90.0 mg, 0.15 mmol) in DCM (3.0 mL) was added TFA (3.0 mL) at room temperature. The resulting mixture was stirred at room temperature for 0.5 h. After the reaction was completed, the resulting mixture was concentrated under reduced pressure. The pH value of the residue was adjusted to 7 with $NaHCO_3$(aq.). The mixture was extracted with $CH_2Cl_2$. The combined organic layer was washed with brine, dried over anhydrous sodium sulfate and filtered. The filtrate was evaporated in vacuo to afford N-(4-([1,2,4]triazolo[1,5-a]pyridin-7-yloxy)-3-methylphenyl)-7,8,9,10,11,12-hexahydro-6,10-methanopyrimido[4',5':5,6]pyrido[3,2-b][1,4,7]oxadiazecin-4-amine (50.0 mg, crude) as a yellow solid. LCMS (ESI, m/z): $[M+H]^+$=496.2.

Step 4. Synthesis of (E)-1-(4-((4-([1,2,4]triazolo[1,5-a]pyridin-7-yloxy)-3-methylphenyl)amino)-7,8,11,12-tetrahydro-6,10-methanopyrimido[4',5':5,6]pyrido[3,2-b][1,4,7]oxadiazecin-9 (10H)-yl)-4-(dimethylamino)but-2-en-1-one (Compound 52)

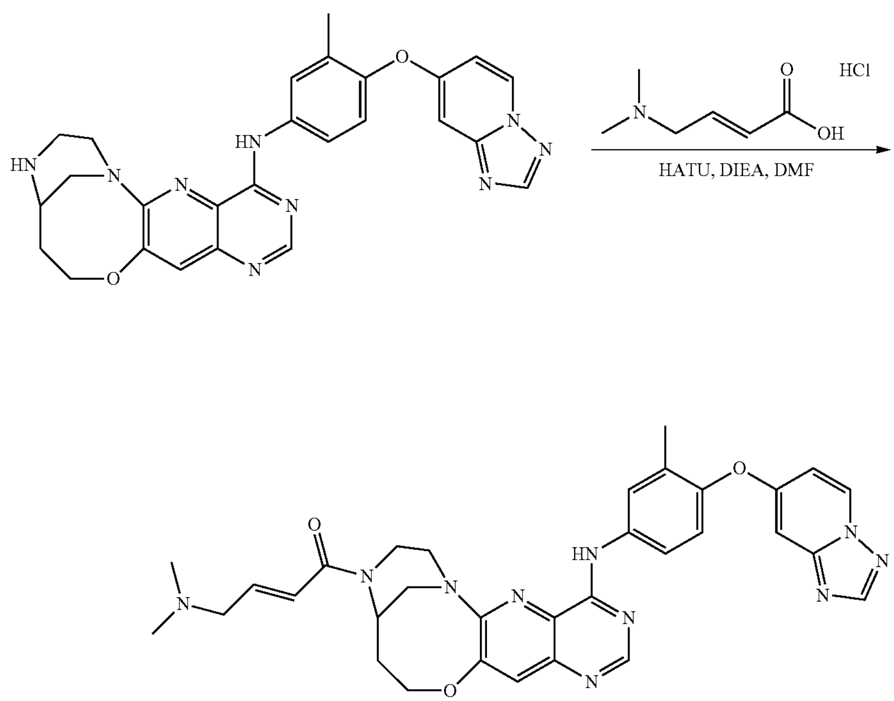

52

To a solution of (2E)-4-(dimethylamino)but-2-enoic acid hydrochloride (26.7 mg, 0.16 mmol) in DMF (1.0 mL) was added DIEA (62.6 mg, 0.47 mmol), N-(4-([1,2,4]triazolo[1,5-a]pyridin-7-yloxy)-3-methylphenyl)-7,8,9,10,11,12-hexahydro-6,10-methanopyrimido[4',5':5,6]pyrido[3,2-b][1,4,7]oxadiazecin-4-amine (40.0 mg, 0.08 mmol) and HATU (67.5 mg, 0.18 mmol) at 0° C. under $N_2$. The resulting mixture was stirred at room temperature for 1 h. After the reaction was completed, the resulting mixture was diluted with water and extracted with EtOAc. The combined organic layer was washed with brine, dried over anhydrous sodium sulfate and filtered. The filtrate was evaporated in vacuo. The residue was purified by Prep-HPLC with the following conditions (Column: YMC-Actus Triart C18 ExRS, 30×150 mm, 5 μm; Mobile Phase A: Water (10 mmol/L $NH_4HCO_3$), Mobile Phase B: ACN; Flow rate: 60 mL/min; Gradient: 30% B to 38% B in 10 min; Wave Length: 254 nm) to afford (E)-1-(4-((4-([1,2,4]triazolo[1,5-a]pyridin-7-yloxy)-3-methylphenyl)amino)-7,8,11,12-tetrahydro-6,10-methanopyrimido[4',5':5,6]pyrido[3,2-b][1,4,7]oxadiazecin-9 (10H)-yl)-4-(dimethylamino)but-2-en-1-one (Compound 52) (1.5 mg, 3%) as a white solid. LCMS (ESI, m/z): $[M+H]^+$=607.3. $^1$H NMR (400 MHz, DMSO-$d_6$): δ 9.42 (d, J=8.4 Hz, 1H), 8.94 (d, J=7.2 Hz, 1H), 8.43-8.38 (m, 2H), 8.01-7.97 (m, 2H), 7.62 (d, J=3.2 Hz, 1H), 7.22 (d, J=8.4 Hz, 1H), 7.05-7.02 (m, 1H), 6.79 (d, J=2.4 Hz, 1H), 6.66 (s, 1H), 6.60-6.57 (m, 1H), 5.43-5.40 (m, 1H), 4.95-4.89 (m, 2H), 4.58-4.48 (m, 2H), 4.29-4.25 (m, 1H), 4.15-4.12 (m, 1H), 3.90-3.80 (m, 1H), 3.06-3.01 (m, 2H), 2.21 (s, 3H), 2.16-2.14 (m, 6H), 1.78-1.71 (m, 1H).

Example S53: Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4,5':5,6]pyrido[3,2-b][1,4,7]oxadiazonin-9-yl)-3-(3-fluoro-1-methylazetidin-3-yl)prop-2-en-1-one (Compound 53)

Step 1. Synthesis of tert-butyl 3-fluoro-3-formylazetidine-1-carboxylate

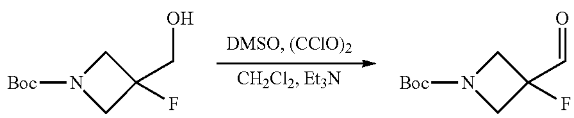

To a solution of DMSO (2.3 g, 29.23 mmol) in $CH_2Cl_2$ (40.0 mL) was added oxalyl chloride (3.7 g, 29.23 mmol) at −78° C. under $N_2$. The resulting mixture was stirred at −78° C. for 10 min. Then a solution of tert-butyl 3-fluoro-3-(hydroxymethyl)azetidine-1-carboxylate (2.0 g, 9.74 mmol) in $CH_2Cl_2$ (8.0 mL) was added dropwise to the mixture at −78° C. The mixture was stirred at −78° C. for 30 min. Then TEA (8.9 g, 87.70 mmol) was added to the mixture at −78° C. under $N_2$. The mixture was stirred at −78° C. for additional 2 h. After the reaction was completed, the mixture was diluted with water and extracted with $CH_2Cl_2$. The combined organic layer was washed with brine, dried over anhydrous sodium sulfate and filtered. The filtrate was concentrated under reduced pressure. The residue was purified by flash column chromatography with petroleum ether/ethyl acetate (45/55, v/v) to afford tert-butyl 3-fluoro-3-formylazetidine-1-carboxylate (915.0 mg, 45%) as a yellow solid. LCMS (ESI, m/z): $[M+H]^+$=204.1.

Step 2. Synthesis of tert-butyl (E)-3-(3-ethoxy-3-oxoprop-1-en-1-yl)-3-fluoroazetidine-1-carboxylate

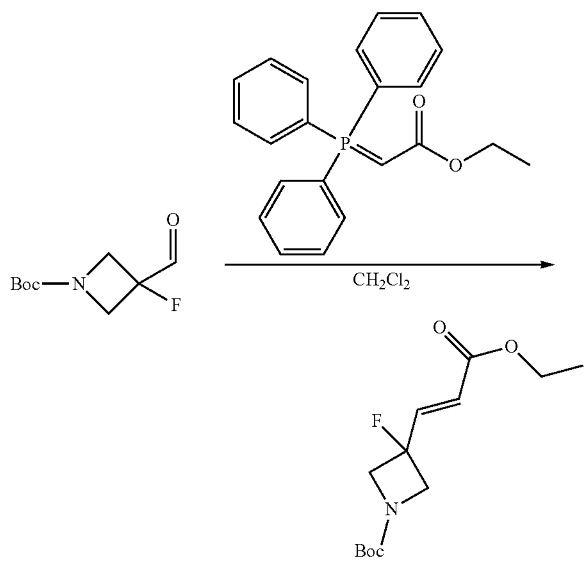

To a solution of tert-butyl 3-fluoro-3-formylazetidine-1-carboxylate (1.0 g, 4.92 mmol) in $CH_2Cl_2$ (15.0 mL) was added ethyl 2-(triphenyl-lambda5-phosphanylidene)acetate (1.9 g, 5.41 mmol) at room temperature. The resulting mixture was stirred at 35° C. for 2 h. After the reaction was completed, the resulting mixture was concentrated under reduced pressure. The residue was purified by flash column chromatography with petroleum ether/ethyl acetate (25/75, v/v) to afford tert-butyl (E)-3-(3-ethoxy-3-oxoprop-1-en-1-yl)-3-fluoroazetidine-1-carboxylate (300.0 mg, 22%) as a yellow solid. LCMS (ESI, m/z): $[M+H]^+$=274.1.

Step 3. Synthesis of ethyl (2E)-3-(3-fluoroazetidin-3-yl)prop-2-enoate

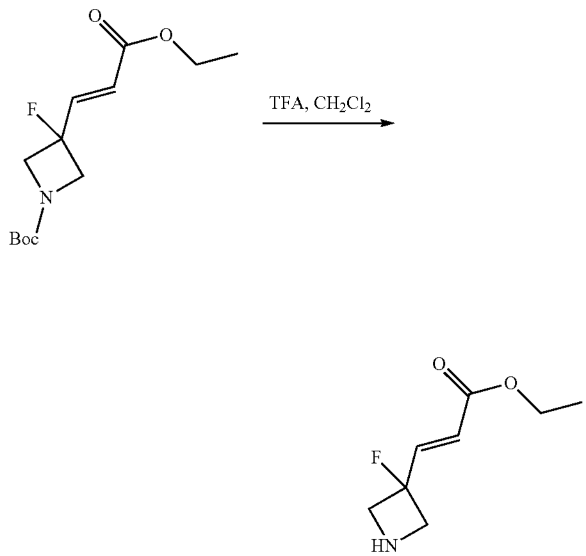

To a solution of tert-butyl 3-[(1E)-3-ethoxy-3-oxoprop-1-en-1-yl]-3-fluoroazetidine-1-carboxylate (200.0 mg, 0.73 mmol) in $CH_2Cl_2$ (4.0 mL) was added TFA (2.0 mL) at room temperature. The resulting mixture was stirred at room temperature for 2 h. After the reaction was completed, the resulting mixture was concentrated under reduced pressure. The pH value of the residue was adjusted to 8.0 with sat. $NaHCO_3$. The mixture was extracted with $CH_2Cl_2$. The combined organic layer was washed with brine, dried over anhydrous sodium sulfate and filtered. The filtrate was concentrated under vacuum to afford ethyl (2E)-3-(3-fluoroazetidin-3-yl)prop-2-enoate (100.0 mg, crude) as a yellow oil. LCMS (ESI, m/z): $[M+H]^+$=174.1.

Step 4. Synthesis of ethyl (E)-3-(3-fluoro-1-methylazetidin-3-yl)acrylate

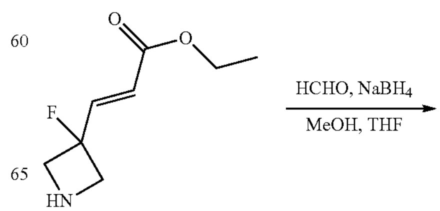

-continued

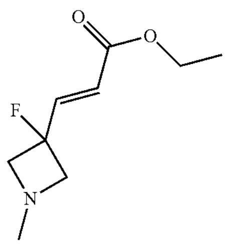

To a solution ethyl (2E)-3-(3-fluoroazetidin-3-yl)prop-2-enoate (900.0 mg, crude) in THE (15.0 mL) and MeOH (3.0 mL) was added formaldehyde (468.1 mg, 15.59 mmol) at room temperature. The resulting mixture was stirred at room temperature for 1 h. Then $NaBH_4$ (982.9 mg, 25.98 mmol) was added to the mixture at 0° C. under $N_2$. The resulting mixture was stirred at room temperature for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under vacuum. The residue was purified by flash column chromatography with petroleum ether/ethyl acetate (60/40, v/v) to afford ethyl (E)-3-(3-fluoro-1-methylazetidin-3-yl) acrylate (400.0 mg, 41%) as a yellow solid. LCMS (ESI, m/z): $[M+H]^+$=188.1.

Step 5. Synthesis of (2E)-3-(3-fluoro-1-methylazetidin-3-yl)prop-2-enoic acid

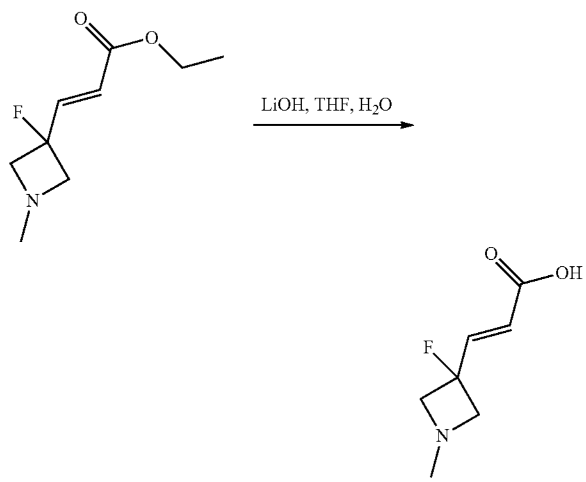

To a solution of ethyl (2E)-3-(3-fluoro-1-methylazetidin-3-yl)prop-2-enoate (500.0 mg, 2.67 mmol) in THF (8.0 mL) and $H_2O$ (5.0 mL) was added LiOH (544.7 mg, 16.02 mmol) at room temperature. The resulting mixture was stirred at room temperature for 16 h. After the reaction was completed, the pH value of the mixture was adjusted to 5.0 with HCl (1.0 mol/L). The mixture was extracted with $CH_2Cl_2$. The combined organic layer was washed with brine, dried over anhydrous sodium sulfate and filtered. The filtrate was concentrated under vacuum. The residue was purified by reverse phase flash column chromatography with ACN/$H_2O$ (10/90, v/v) to afford (2E)-3-(3-fluoro-1-methylazetidin-3-yl)prop-2-enoic acid (100.0 mg, 23%) as a white solid. LCMS (ESI, m/z): $[M+H]^+$=160.1.

Step 6. Synthesis of (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-(3-fluoro-1-methylazetidin-3-yl)prop-2-en-1-one (Compound 53)

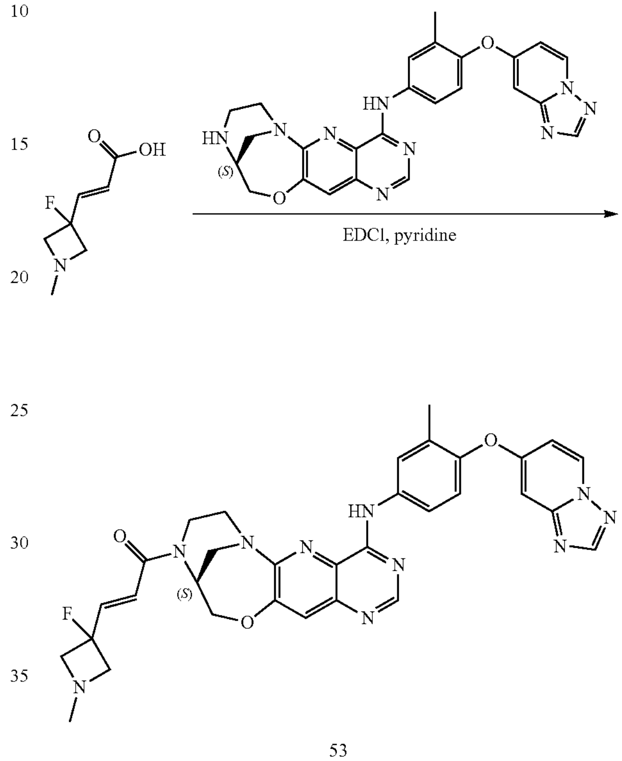

53

To a solution of (10S)—N-(4-([1,2,4]triazolo[1,5-a]pyridin-7-yloxy)-3-methylphenyl)-8,9,10,11-tetrahydro-7H-6,10-methanopyrimido[4',5':5,6]pyrido[3,2-b][1,4,7]oxadiazonin-4-amine (50.0 mg, 0.10 mmol) in Pyridine (3.0 mL) was added (2E)-3-(3-fluoro-1-methylazetidin-3-yl)prop-2-enoic acid (49.5 mg, 0.31 mmol) and EDCI (99.5 mg, 0.50 mmol) at room temperature. The resulting mixture was stirred at room temperature for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with ACN/$H_2O$ (60/40, v/v) to afford (E)-1-((10S)-4-((4-([1,2,4]triazolo[1,5-a]pyridin-7-yloxy)-3-methylphenyl)amino)-7,8,10,11-tetrahydro-9H-6,10-methanopyrimido[4',5':5,6]pyrido[3,2-b][1,4,7]oxadiazonin-9-yl)-3-(3-fluoro-1-methylazetidin-3-yl)prop-2-en-1-one (Compound 53) (3.1 mg, 5%) as a white solid. LCMS (ESI, m/z): $[M+H]^+$=623.3. 1H NMR (400 MHz, DMSO-$d_6$): δ 10.18 (s, 1H), 8.96 (d, J=7.6 Hz, 1H), 8.44-8.35 (m, 3H), 7.64-7.61 (m, 1H), 7.45 (d, J=9.2 Hz, 1H), 7.36-7.33 (m, 1H), 7.07-7.04 (m, 1H), 6.92-6.83 (m, 2H), 6.55-6.46 (m, 1H), 5.04-4.79 (m, 2H), 4.45-4.42 (m, 1H), 4.15-4.02 (m, 2H), 3.82-3.64 (m, 2H), 3.39-3.34 (m, 2H), 3.20-3.18 (m, 2H), 2.94-2.90 (m, 2H), 2.20-2.18 (m, 6H).

Example S54: Synthesis of (E)-1-(4-((4-([1,2,4]triazolo[1,5-a]pyridin-7-yloxy)-3-methylphenyl)amino)-8,9,11,12-tetrahydro-6,11-methanopyrimido[4,5':5,6]pyrido[3,2-b][1,4,8]oxadiazecin-10 (7H)-yl)-4-(dimethylamino)but-2-en-1-one (Compound 54)

Step 1. Synthesis of 1-(tert-butyl) 2-methyl 4-(4-((4-([1,2,4]triazolo[1,5-a]pyridin-7-yloxy)-3-methylphenyl)amino)-7-bromopyrido[3,2-d]pyrimidin-6-yl)-1,4-diazepane-1,2-dicarboxylate

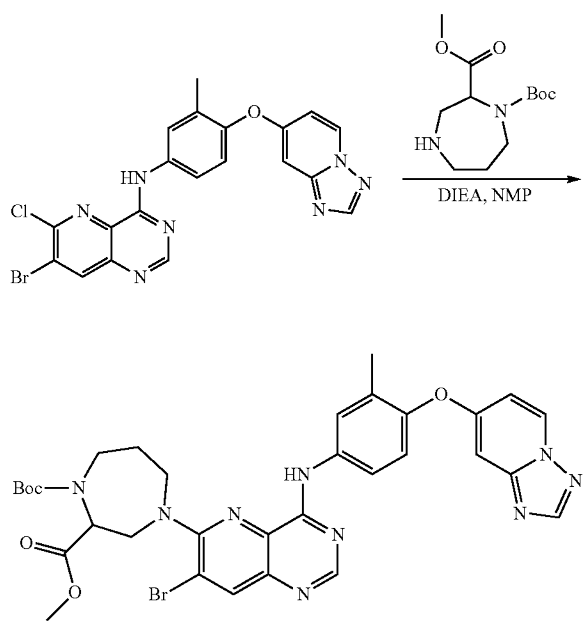

To a solution of N-(4-([1,2,4]triazolo[1,5-a]pyridin-7-yloxy)-3-methylphenyl)-7-bromo-6-chloropyrido[3,2-d]pyrimidin-4-amine (1.0 g, 2.08 mmol) in NMP (10.0 mL) was added 1-(tert-butyl)-2-methyl-1,4-diazepane-1,2-dicarboxylate (1.1 g, 4.16 mmol) and DIEA (0.8 g, 6.24 mmol) at room temperature. The mixture was stirred at 100° C. for 16 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/99, v/v) to afford 1-(tert-butyl)-2-methyl-4-(4-((4-([1,2,4]triazolo[1,5-a]pyridin-7-yloxy)-3-methylphenyl)amino)-7-bromopyrido[3,2-d]pyrimidin-6-yl)-1,4-diazepane-1,2-dicarboxylate (0.8 g, 54%) as a yellow solid. LCMS (ESI, m/z): $[M+H]^+$=704.2.

Step 2. Synthesis of tert-butyl 4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)-1,4-diazepane-1-carboxylate

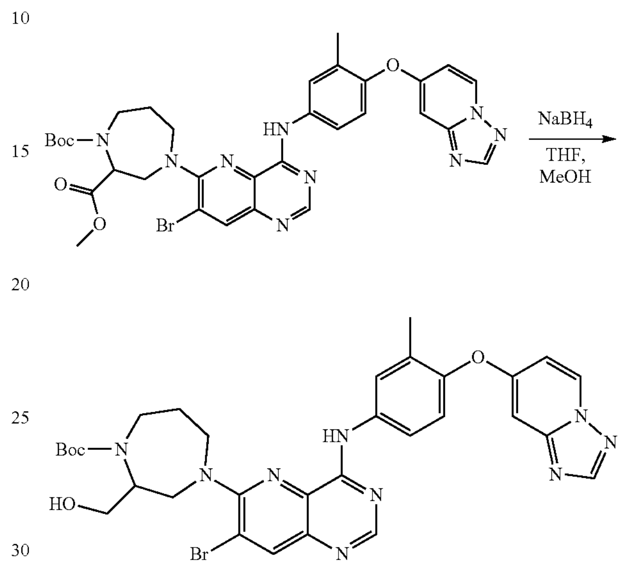

To a solution of 1-(tert-butyl)-2-methyl-4-(4-((4-([1,2,4]triazolo[1,5-a]pyridin-7-yloxy)-3-methylphenyl)amino)-7-bromopyrido[3,2-d]pyrimidin-6-yl)-1,4-diazepane-1,2-dicarboxylate (800.0 mg, 1.14 mmol) in THF/MeOH (5.0 mL/5.0 mL) was added $NaBH_4$ (215.9 mg, 5.68 mmol) at room temperature. The mixture was stirred at room temperature for 30 min. After the reaction was completed, the reaction mixture was quenched with water and then extracted with ethyl acetate. The combined organic layer was washed with brine, dried over anhydrous sodium sulfate and filtered. The filtrate was concentrated under reduced pressure. The residue was purified by flash column chromatography with DCM/MeOH (96/4, v/v) to afford tert-butyl 4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)-1,4-diazepane-1-carboxylate (450.0 mg, 58%) as a yellow solid. LCMS (ESI, m/z): $[M+H]^+$=676.2.

Step 3. Synthesis of tert-butyl 4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecine-10 (7H)-carboxylate

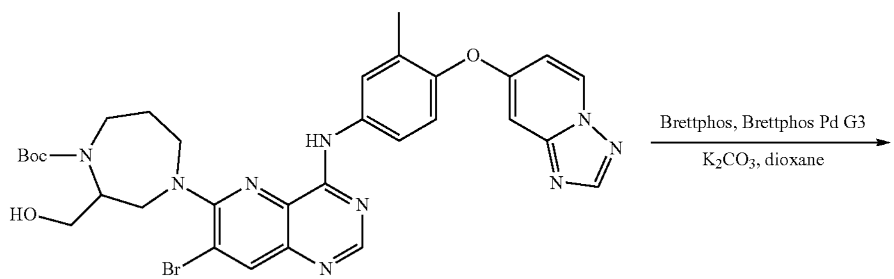

-continued

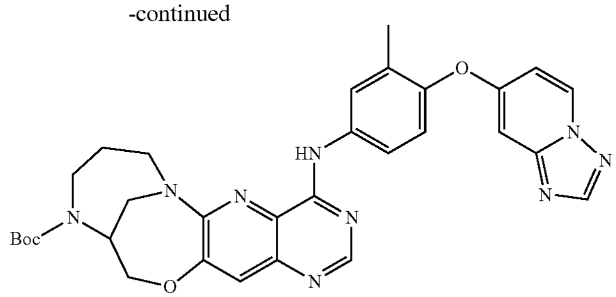

To a solution of tert-butyl 4-(4-((4-([1,2,4]triazolo[1,5-a]pyridin-7-yloxy)-3-methylphenyl)amino)-7-bromopyrido[3,2-d]pyrimidin-6-yl)-2-(hydroxymethyl)-1,4-diazepane-1-carboxylate (370.0 mg, 0.56 mmol) in dioxane (5.0 mL) was added $K_2CO_3$ (226.8 mg, 1.67 mmol), Brettphos (58.6 mg, 0.11 mmol) and Brettphos Pd G3 (49.6 mg, 0.06 mmol) at room temperature under $N_2$. The resulting mixture was stirred at 100° C. for 2 h under $N_2$. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with DCM/MeOH (92/8, v/v) to afford tert-butyl 4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecine-10 (7H)-carboxylate (240.0 mg, 73%) as a yellow solid. LCMS (ESI, m/z): $[M+H]^+$=596.3.

Step 4. Synthesis of N-(4-([1,2,4]triazolo[1,5-a]pyridin-7-yloxy)-3-methylphenyl)-7,8,9,10,11,12-hexahydro-6,11-methanopyrimido[4',5':5,6]pyrido[3,2-b][1,4,8]oxadiazecin-4-amine

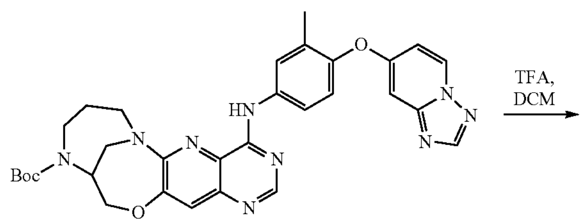

-continued

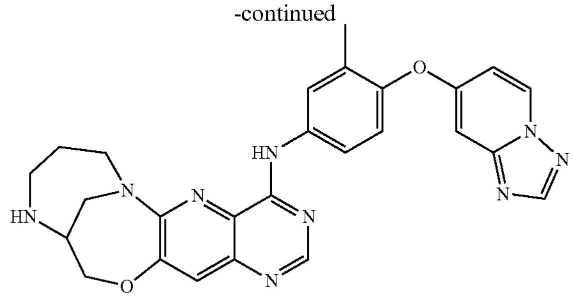

To a solution of tert-butyl 4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecine-10 (7H)-carboxylate (220.0 mg, 0.37 mmol) in DCM (2.0 mL) was added TFA (2.0 mL) at room temperature. The resulting mixture was stirred at room temperature for 30 min. After the reaction was completed, the resulting mixture was concentrated under reduced pressure. The pH value of the residue was adjusted to 7 with $NaHCO_3$(aq.). The mixture was extracted with $CH_2Cl_2$. The combined organic layer was washed with brine, dried over anhydrous sodium sulfate and filtered. The filtrate was concentrated under reduced pressure to afford N-(4-([1,2,4]triazolo[1,5-a]pyridin-7-yloxy)-3-methylphenyl)-7,8,9,10,11,12-hexahydro-6,11-methanopyrimido[4',5':5,6]pyrido[3,2-b][1,4,8]oxadiazecin-4-amine (220.0 mg, crude) as a yellow solid. LCMS (ESI, m/z): $[M+H]^+$=496.2.

Step 5. Synthesis of (E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one

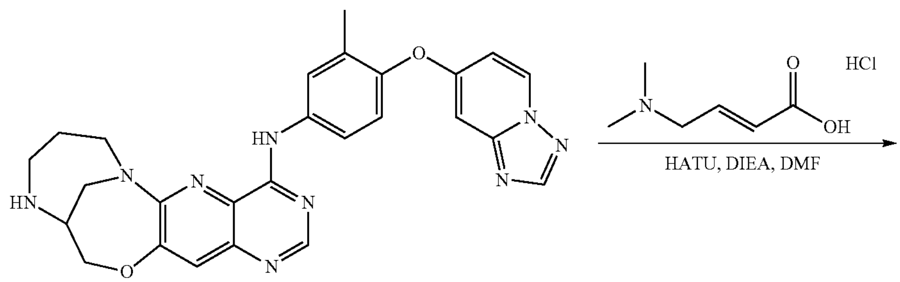

-continued

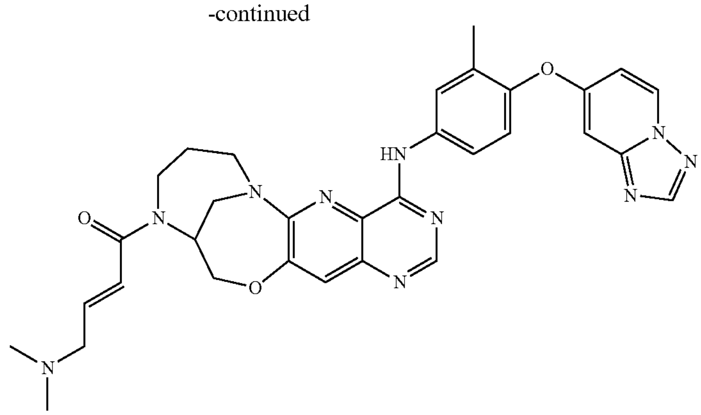

54

To a solution of N-(4-([1,2,4]triazolo[1,5-a]pyridin-7-yloxy)-3-methylphenyl)-7,8,9,10,11,12-hexahydro-6,11-methanopyrimido[4',5':5,6]pyrido[3,2-b][1,4,8]oxadiazecin-4-amine (220.0 mg, 0.44 mmol) in DMF (5.0 mL) was added (E)-4-(dimethylamino)but-2-enoic acid hydrochloride (88.2 mg, 0.53 mmol), DIEA (459.0 mg, 3.55 mmol) and HATU (337.6 mg, 0.89 mmol) at 0° C. under $N_2$. The mixture was stirred at room temperature for 1 h. After the reaction was completed, the mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with DCM/MeOH (9/1, v/v) and then purified by Prep-HPLC with the following conditions: (Column: XBridge Prep OBD C18 Column, 30×150 mm, 5 μm; Mobile Phase A: Water (10 mmol/L $NH_4HCO_3$), Mobile Phase B: ACN; Flow rate: 60 mL/min; Gradient: 33% B to 41% B; Wave Length: 220/254 nm) to afford (E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one (Compound 54) (60.6 mg, 22%) as a yellow solid. LCMS (ESI, m/z): $[M+H]^+$=607.3. 1H NMR (400 MHz, $CD_3OD$): δ 8.75 (d, J=8.0 Hz, 1H), 8.40 (d, J=4.4 Hz, 1H), 8.30 (s, 1H), 7.90-7.86 (m, 2H), 7.34 (d, J=4.8 Hz, 1H), 7.19 (d, J=8.4 Hz, 1H), 7.10-7.07 (m, 1H), 7.04-7.01 (m, 1H), 6.80 (d, J=2.4 Hz, 1H), 6.76-6.65 (m, 1H), 5.20-5.11 (m, 1H), 4.77-4.45 (m, 4H), 4.02-3.96 (m, 3H), 3.71-3.66 (m, 2H), 3.42-3.32 (m, 1H), 2.95-2.92 (m, 6H), 2.40-2.30 (m, 1H), 2.26 (s, 3H), 2.23-2.03 (m, 1H).

Example S55: Separation of (E)-1-((11S)-4-((4-([1,2,4]triazolo[1,5-a]pyridin-7-yloxy)-3-methylphenyl)amino)-8,9,11,12-tetrahydro-6,11-methanopyrimido[4,5':5,6]pyrido[3,2-b][1,4,8]oxadiazecin-10 (7H)-yl)-4-(dimethylamino)but-2-en-1-one and (E)-1-((11R)-4-((4-([1,2,4]triazolo[1,5-a]pyridin-7-yloxy)-3-methylphenyl)amino)-8,9,11,12-tetrahydro-6,11-methanopyrimido[4,5':5,6]pyrido[3,2-b][1,4,8]oxadiazecin-10 (7H)-yl)-4-(dimethylamino)but-2-en-1-one (Compound 55 and Compound 56)

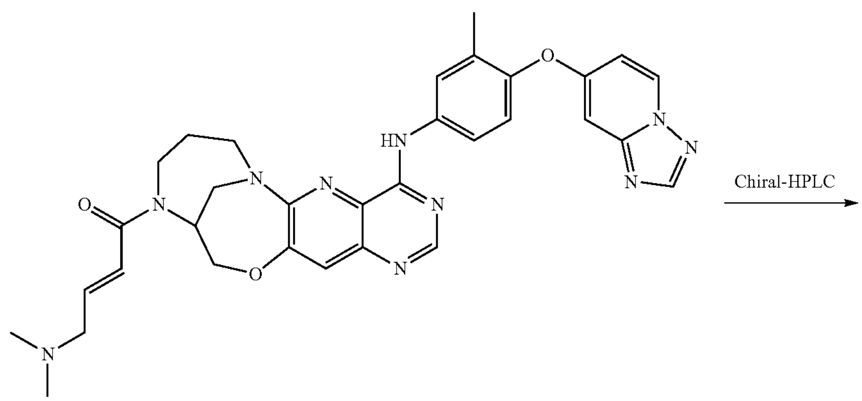

-continued

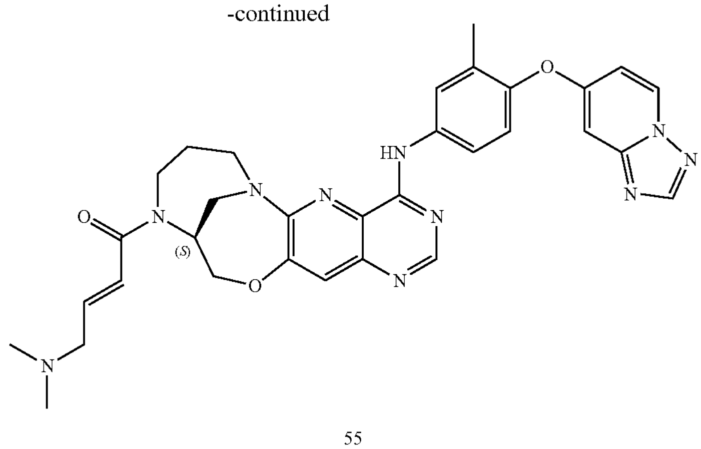

55

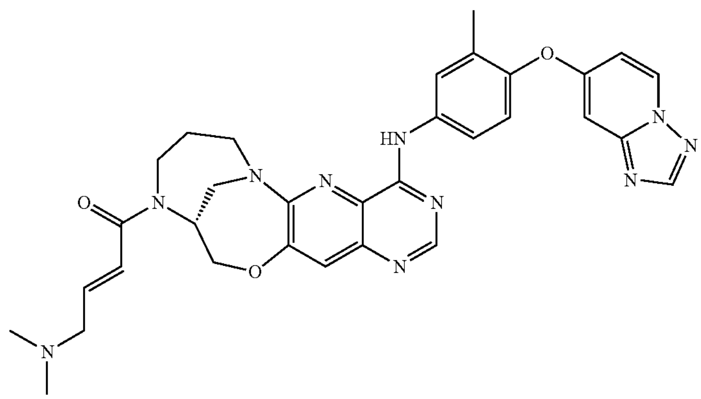

56

The product of (E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one (57.0 mg, 0.09 mmol) was separated by Prep-Chiral-HPLC with the following conditions (Column: CHIRALPAK ID, 2×25 cm, 5 μm; Mobile Phase A: Hex(0.5% 2M $NH_3$-MeOH)—HPLC, Mobile Phase B: EtOH:DCM=1:1—HPLC; Flow rate: 20 mL/min; Gradient: 70% B to 70% B in 20 min; Wave Length: 254/220 nm; RT1(min): 9.95; RT2(min): 13.35) to afford (E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one Enantiomer 1 (retention time: 9.95 min, 15.7 mg, 55%) as a white solid and (E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one Enantiomer 2 (retention time 13.35 min, 16.9 mg, 59%) as a white solid. The absolute stereochemistry of Enantiomers 1 and 2 was not assigned. The two enantiomeric structures that could be obtained from chiral separation of the enantiomeric mixture as described above are shown as Compounds 55 and 56 in Table 1.

(E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one Enantiomer 1: RT1(min): 9.95; LCMS (ESI, m/z): $[M+H]^+$=607.4. 1H NMR (400 MHz, DMSO-$d_6$): δ 9.23 (s, 1H), 8.93 (d, J=7.6 Hz, 1H), 8.40-8.37 (m, 2H), 7.99-7.95 (m, 2H), 7.35 (s, 1H), 7.21 (d, J=8.8 Hz, 1H), 7.04-7.02 (m, 1H), 6.78 (d, J=2.8 Hz, 1H), 6.72-6.57 (m, 2H), 5.12-5.05 (m, 0.5H), 4.82-4.75 (m, 1H), 4.59-4.38 (m, 2H), 4.31-4.13 (m, 2H), 4.01-3.91 (m, 1.5H), 3.63-3.58 (m, 2H), 3.26-3.19 (m, 1H), 3.07 (d, J=4.4 Hz, 2H), 2.20-2.17 (m, 10H), 2.04-1.99 (m, 1H).

(E)-1-(4-((4-([1,2,4]triazolo[1,5-a]pyridin-7-yloxy)-3-methylphenyl)amino)-8,9,11,12-tetrahydro-6,11-methanopyrimido[4',5':5,6]pyrido[3,2-b][1,4,8]oxadiazecin-10 (7H)-yl)-4-(dimethylamino)but-2-en-1-one Enantiomer 2: RT2 (min): 13.35; LCMS (ESI, m/z): $[M+H]^+$=607.4. 1H NMR (400 MHz, DMSO-$d_6$): δ 9.23 (s, 1H), 8.94 (d, J=7.6 Hz, 1H), 8.40-8.37 (m, 2H), 8.00-7.96 (m, 2H), 7.35 (s, 1H), 7.21 (d, J=8.8 Hz, 1H), 7.04-7.02 (m, 1H), 6.78 (d, J=2.4 Hz, 1H), 6.72-6.57 (m, 2H), 5.12-5.05 (m, 0.5H), 4.82-4.75 (m, 1H), 4.60-4.38 (m, 2H), 4.35-4.23 (m, 1H), 4.13-3.89 (m, 2H), 3.63-3.58 (m, 1.5H), 3.26-3.19 (m, 1H), 3.09 (d, J=4.8 Hz, 2H), 2.21-2.19 (m, 10H), 2.04-1.99 (m, 1H).

Example S56: Synthesis of (E)-1-(4-((4-([1,2,4]triazolo[1,5-a]pyridin-7-yloxy)-3-methylphenyl)amino)-7,8,11,12-tetrahydro-6,11-methanopyrimido[4,5':5,6]pyrido[3,2-b][1,4,7]oxadiazecin-9 (10H)-yl)-4-(dimethylamino)but-2-en-1-one (Compound 57)

Step 1. Synthesis of tert-butyl (2-((2-nitrophenyl)sulfonamido)ethyl)carbamate

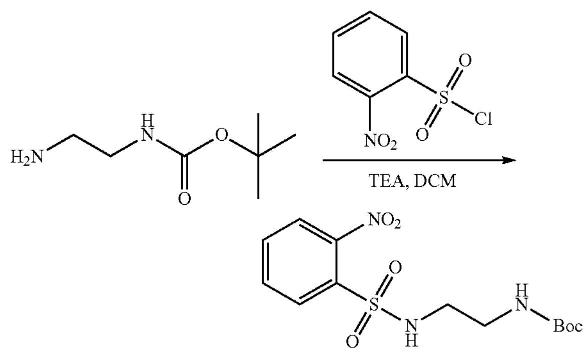

To a solution of tert-butyl (2-aminoethyl)carbamate (20.0 g, 124.83 mmol) in DCM (500.0 mL) was added 2-nitrobenzenesulfonyl chloride (15.2 g, 68.66 mmol) and TEA (37.9 g, 374.49 mmol) at room temperature. The resulting mixture was stirred at 30° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (2/3, v/v) to afford tert-butyl (2-((2-nitrophenyl)sulfonamido)ethyl)carbamate (40.0 g, 88%) as a colorless oil. LCMS (ESI, m/z): $[M+H]^+$=346.1.

Step 2. Synthesis of tert-butyl 6-methylene-4-((2-nitrophenyl)sulfonyl)-1,4-diazepane-1-carboxylate

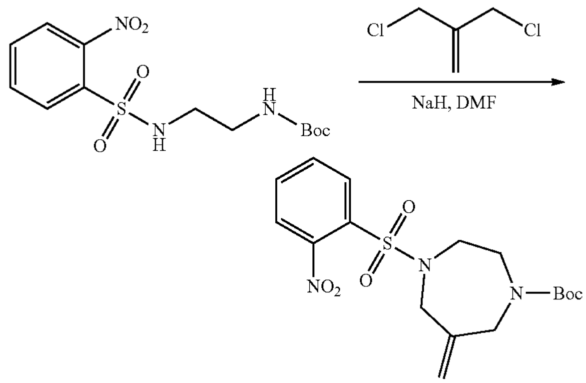

To a solution of tert-butyl (2-((2-nitrophenyl)sulfonamido)ethyl)carbamate (5.0 g, 14.48 mmol) in DMF (120.0 mL) was added NaH (1.7 g, 60%) at 0° C. under $N_2$. The resulting mixture stirred at 0° C. for 1 h under $N_2$. Then 3-chloro-2-(chloromethyl)prop-1-ene (1.8 g, 14.48 mmol) was added to the mixture at 0° C. The resulting mixture was stirred at 60° C. for additional 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by flash column chromatography with petroleum ether/ethyl acetate (1/1, v/v) to afford tert-butyl 6-methylene-4-((2-nitrophenyl)sulfonyl)-1,4-diazepane-1-carboxylate (5.0 g, 82%) as a yellow oil. LCMS (ESI, m/z): $[M+H]^+$=398.1.

Step 3. Synthesis of tert-butyl 6-(hydroxymethyl)-4-((2-nitrophenyl)sulfonyl)-1,4-diazepane-1-carboxylate

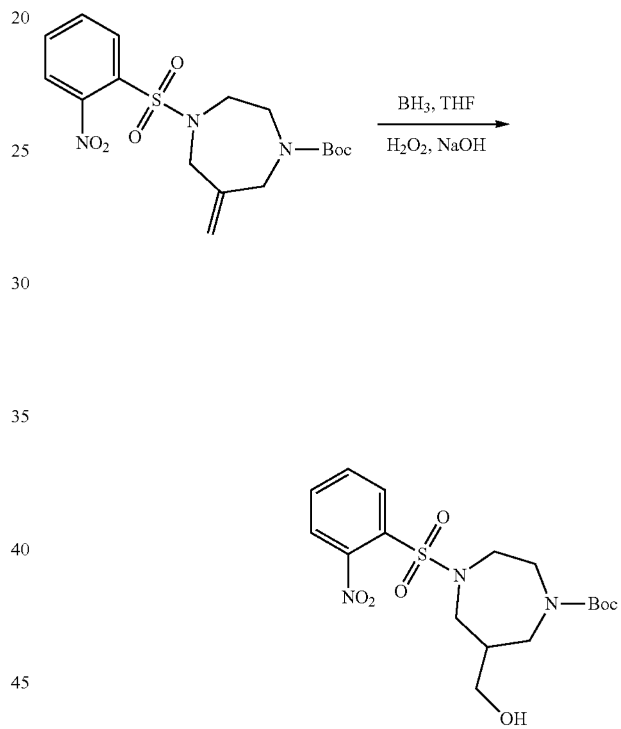

To a solution of tert-butyl 6-methylene-4-((2-nitrophenyl)sulfonyl)-1,4-diazepane-1-carboxylate (900.0 mg, 2.26 mmol) in THE (2.0 mL) was added dropwise $BH_3$-THF (2.5 mL, 1.0 mol/L) at 0° C. under $N_2$. The resulting mixture was stirred at room temperature for 1 h. After the reaction was completed, the pH value of the mixture was adjusted to 9 with NaOH (aq.). Then $H_2O_2$ (0.9 mL, 30%) was added to the mixture at 0° C. The resulting mixture was stirred at 100° C. for additional 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (1/2, v/v) to afford tert-butyl 6-(hydroxymethyl)-4-((2-nitrophenyl)sulfonyl)-1,4-diazepane-1-carboxylate (35.0 mg, 4%) as a light brown oil. LCMS (ESI, m/z): $[M+H]^+$=416.1.

Step 4. Synthesis of (1-((2-nitrophenyl)sulfonyl)-1,4-diazepan-6-yl)methanol

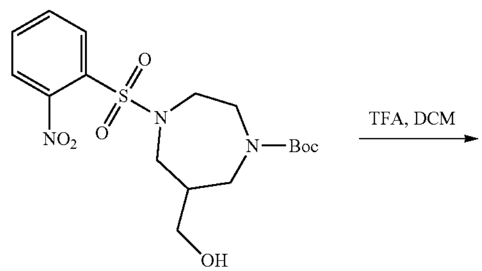

-continued

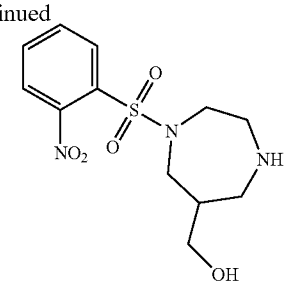

To a solution of tert-butyl 6-(hydroxymethyl)-4-((2-nitrophenyl)sulfonyl)-1,4-diazepane-1-carboxylate (550.0 mg, 1.32 mmol) in DCM (2.0 mL) was added TFA (2.0 mL) at room temperature. The resulting mixture was stirred at room temperature for 1 h. After the reaction was completed, the resulting mixture was diluted with water. The pH value of the mixture was adjusted to 7 with $NaHCO_3$(aq.) The mixture was extracted with $CH_2Cl_2$. The combined organic layer was washed with brine, dried over anhydrous sodium sulfate and filtered. The filtrate was concentrated under reduced pressure. The residue was purified by flash column chromatography with $CH_2Cl_2$/MeOH (10/1, v/v) to afford (1-((2-nitrophenyl)sulfonyl)-1,4-diazepan-6-yl)methanol (130.0 mg, 30%) as a yellow oil. LCMS (ESI, m/z): $[M+H]^+$= 316.1.

Step 5. Synthesis of (1-(4-((4-([1,2,4]triazolo[1,5-a]pyridin-7-yloxy)-3-methylphenyl)amino)-7-bromopyrido[3,2-d]pyrimidin-6-yl)-4-((2-nitrophenyl)sulfonyl)-1,4-diazepan-6-yl)methanol

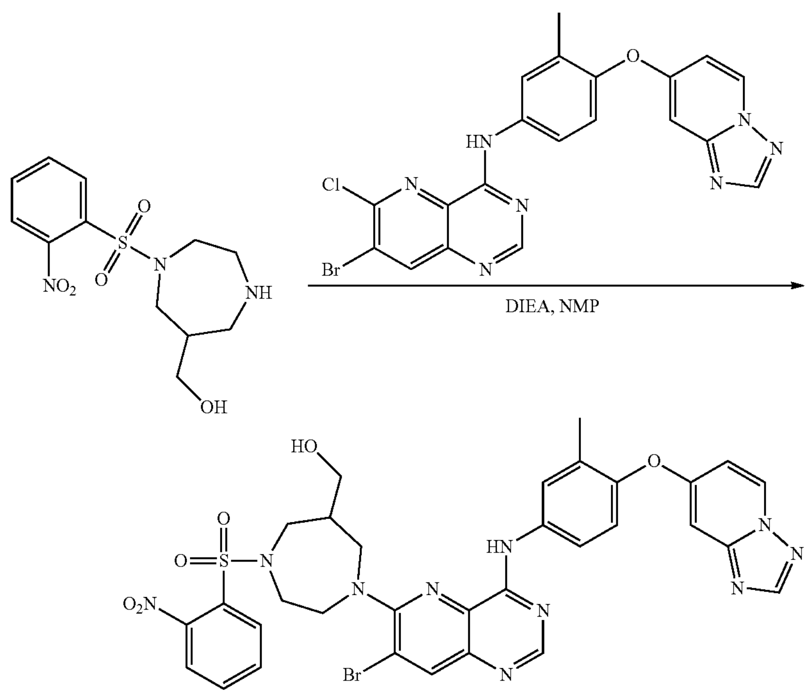

To a solution of (1-((2-nitrophenyl)sulfonyl)-1,4-diazepan-6-yl)methanol (100.0 mg, 0.32 mmol) in NMP (3.0 mL) was added N-(4-([1,2,4]triazolo[1,5-a]pyridin-7-yloxy)-3-methylphenyl)-7-bromo-6-chloropyrido[3,2-d]pyrimidin-4-amine (306.2 mg, 0.63 mmol) and DIEA (123.0 mg, 0.95 mmol) at room temperature. The resulting mixture was stirred at 100° C. for 16 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (5/1, v/v) to afford (1-(4-((4-([1,2,4]triazolo[1,5-a]pyridin-7-yloxy)-3-methylphenyl)amino)-7-bromopyrido[3,2-d]pyrimidin-6-yl)-4-((2-nitrophenyl)sulfonyl)-1,4-diazepan-6-yl)methanol (120.0 mg, 47%) as a yellow solid. LCMS (ESI, m/z): $[M+H]^+$=761.1.

Step 6. Synthesis of N-(4-([1,2,4]triazolo[1,5-a]pyridin-7-yloxy)-3-methylphenyl)-9-((2-nitrophenyl)sulfonyl)-7,8,9,10,11,12-hexahydro-6,11-methano-pyrimido[4',5':5,6]pyrido[3,2-b][1,4,7]oxadiazecin-4-amine

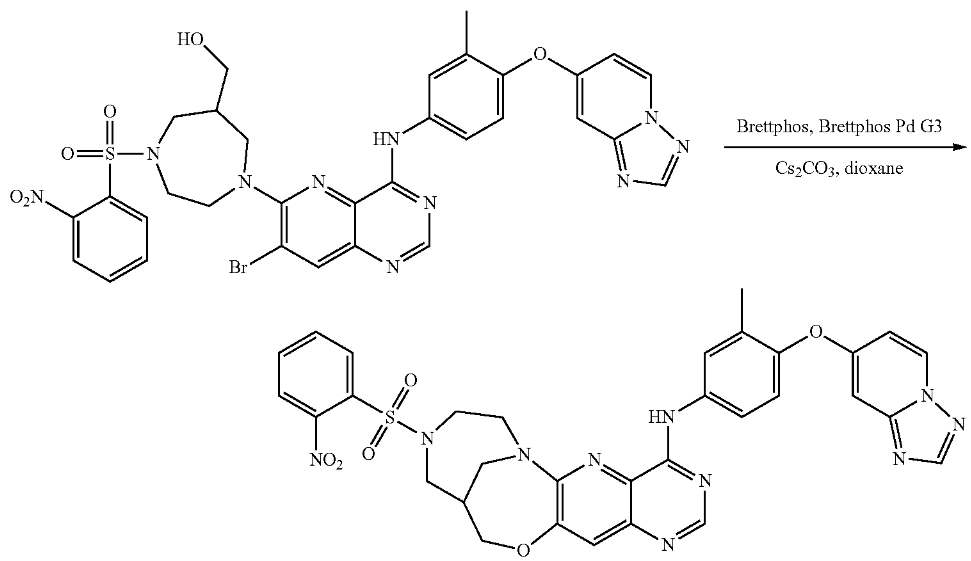

To a solution of (1-(4-((4-([1,2,4]triazolo[1,5-a]pyridin-7-yloxy)-3-methylphenyl)amino)-7-bromopyrido[3,2-d]pyrimidin-6-yl)-4-((2-nitrophenyl)sulfonyl)-1,4-diazepan-6-yl)methanol (120.0 mg, 0.16 mmol) in dioxane (2.0 mL) was added BrettPhos (17.0 mg, 0.03 mmol), $Cs_2CO_3$ (154.0 mg, 0.47 mmol) and BrettPhos Pd G3 (14.3 mg, 0.02 mmol) at room temperature under $N_2$. The resulting mixture was stirred at 100° C. for 4 h under $N_2$. After the reaction was completed, the resulting mixture was concentrated under reduced pressure. The residue was purified by reverse phase flash column chromatography with $CH_3CN/H_2O$ (2/1, v/v) to afford N-(4-([1,2,4]triazolo[1,5-a]pyridin-7-yloxy)-3-methylphenyl)-9-((2-nitrophenyl)sulfonyl)-7,8,9,10,11,12-hexahydro-6,11-methanopyrimido[4',5':5,6]pyrido[3,2-b][1,4,7]oxadiazecin-4-amine (50.0 mg, 44%) as a yellow solid. LCMS (ESI, m/z): $[M+H]^+$=681.2.

Step 7. Synthesis of N-(4-([1,2,4]triazolo[1,5-a]pyridin-7-yloxy)-3-methylphenyl)-7,8,9,10,11,12-hexahydro-6,11-methanopyrimido[4',5':5,6]pyrido[3,2-b][1,4,7]oxadiazecin-4-amine

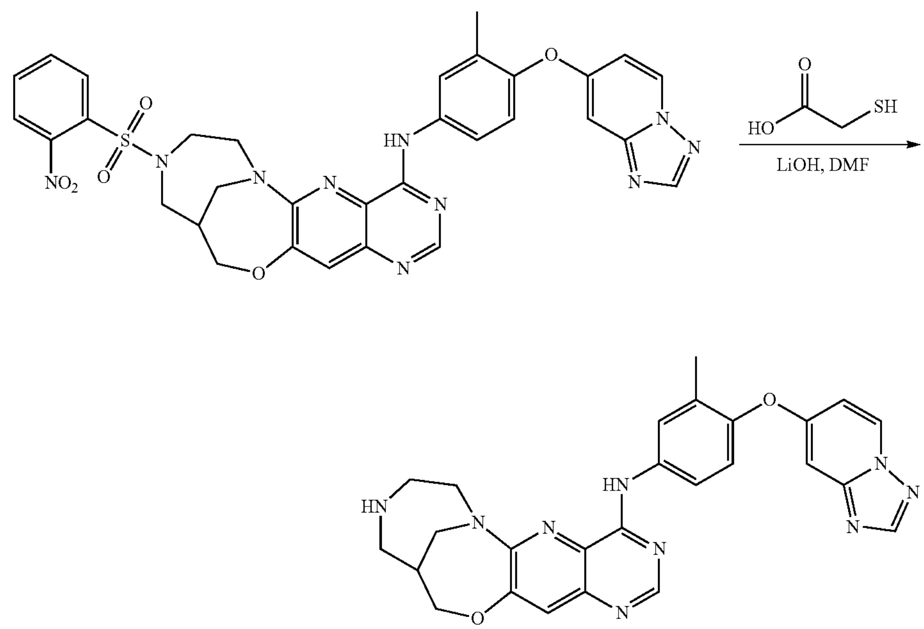

To a solution of N-(4-([1,2,4]triazolo[1,5-a]pyridin-7-yloxy)-3-methylphenyl)-9-((2-nitrophenyl)sulfonyl)-7,8,9,10,11,12-hexahydro-6,11-methanopyrimido[4',5':5,6]pyrido[3,2-b][1,4,7]oxadiazecin-4-amine (100.0 mg, 0.15 mmol) in DMF (3.0 mL) was added 2-mercaptoacetic acid (27.1 mg, 0.29 mmol) and LiOH (14.1 mg, 0.59 mmol) at room temperature. The resulting mixture was stirred at room temperature for 2 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure to afford N-(4-([1,2,4]triazolo[1,5-a]pyridin-7-yloxy)-3-methylphenyl)-7,8,9,10,11,12-hexahydro-6,11-methanopyrimido[4',5':5,6]pyrido[3,2-b][1,4,7]oxadiazecin-4-amine (50.0 mg, crude) as a yellow solid. LCMS (ESI, m/z): $[M+H]^+$=496.2.

Step 8. Synthesis of (E)-1-(4-((4-([1,2,4]triazolo[1,5-a]pyridin-7-yloxy)-3-methylphenyl)amino)-7,8,11,12-tetrahydro-6,11-methanopyrimido[4',5':5,6]pyrido[3,2-b][1,4,7]oxadiazecin-9 (10H)-yl)-4-(dimethylamino)but-2-en-1-one

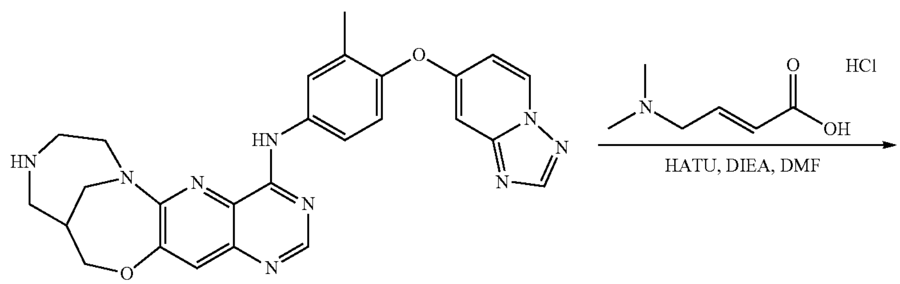

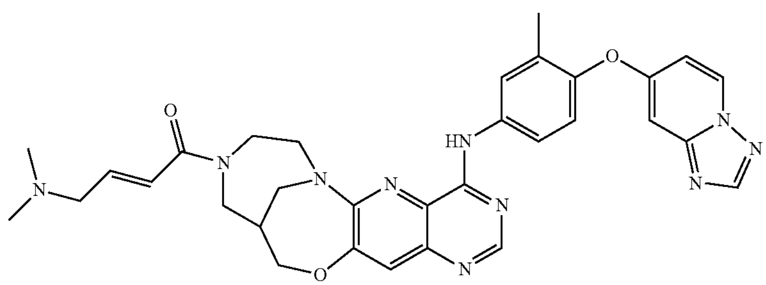

57

To a solution of N-(4-([1,2,4]triazolo[1,5-a]pyridin-7-yloxy)-3-methylphenyl)-7,8,9,10,11,12-hexahydro-6,11-methanopyrimido[4',5':5,6]pyrido[3,2-b][1,4,7]oxadiazecin-4-amine (50.0 mg, crude) in DMF (2.0 mL) was added (E)-4-(dimethylamino)but-2-enoic acid hydrochloride (33.4 mg, 0.20 mmol), DIEA (78.3 mg, 0.61 mmol) and HATU (84.4 mg, 0.22 mmol) at room temperature. The resulting mixture was stirred at room temperature for 1 h. After the reaction was completed, the resulting mixture was diluted with $H_2O$ and extracted with ethyl acetate. The combined organic layer was washed with brine, dried over anhydrous sodium sulfate and filtered. The filtrate was concentrated under reduced pressure. The residue was purified by reverse phase flash column chromatography with $CH_3CN/H_2O$ (1/1, v/v) and then purified by Prep-HPLC with the following conditions (Column: Xselect CSH C18 OBD Column 30×150 mm, 5 μm; Mobile Phase A: ACN, Mobile Phase B: Water (0.1% FA); Flow rate: 60 mL/min; Gradient: 3% B to 20% B in 10 min, 20% B to 20% B in 12 min; Wave Length: 254 nm) to afford (E)-1-(4-((4-([1,2,4]triazolo[1,5-a]pyridin-7-yloxy)-3-methylphenyl)amino)-7,8,11,12-tetrahydro-6,11-methanopyrimido[4',5':5,6]pyrido[3,2-b][1,4,7]oxadiazecin-9 (10H)-yl)-4-(dimethylamino)but-2-en-1-one (4.7 mg, 8%) as a light yellow solid. LCMS (ESI, m/z): $[M+H]^+$=607.2. 1H NMR (400 MHz, DMSO-$d_6$): δ 9.22-9.07 (m, 1H), 8.94 (d, J=7.6 Hz, 1H), 8.38 (s, 2H), 7.97-7.93 (m, 2H), 7.28 (d, J=2.4 Hz, 1H), 7.24-7.19 (m, 1H), 7.04-7.02 (m, 1H), 6.79-6.76 (m, 1H), 6.65-6.50 (m, 2H), 4.69-4.45 (m, 2H), 4.39-4.09 (m, 3H), 3.92-3.69 (m, 3H), 3.47-3.36 (m, 2H), 3.00-2.91 (m, 2H), 2.62-2.51 (m, 1H), 2.20 (s, 3H), 2.10 (s. 3H), 1.96 (s, 3H).

Example S57. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4,5':5,6]pyrido[3,2-b][1,4,7]oxadiazonin-9-yl)-4-(dimethylamino)but-2-en-1-one-4,4-$d_2$ (Compound 58)

Step 1. Synthesis of 2-(benzyloxy)ethan-1,1-$d_2$-1-ol

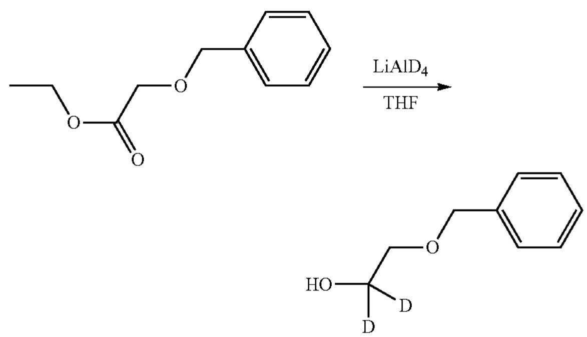

To a stirred solution of $LiAlD_4$ (3.7 g, 88.61 mmol) in THE (200.0 mL) was dropwise added a solution of ethyl 2-(benzyloxy)acetate (20.0 g, 102.97 mmol) in THE (20 mL) at 0° C. under $N_2$. The resulting mixture was stirred at room temperature for 1 h. After the reaction was completed, the reaction mixture was quenched by the addition of NaOH (12.0 M, 15%) and water (4.0 mL) at 0° C. The resulting mixture was filtered. The filtrate was concentrated under reduced pressure. The residue was purified by flash column chromatography with petroleum ether/ethyl acetate (7/3, v/v) to afford 2-(benzyloxy)ethan-1,1-$d_2$-1-ol (13.8 g, 86%) as a colorless oil.

Step 2. Synthesis of 2-(benzyloxy)acetaldehyde-1-d

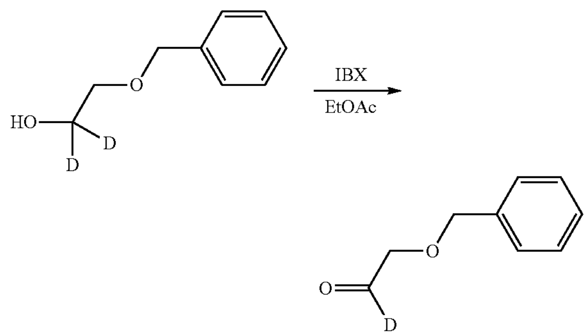

To a solution of 2-(benzyloxy)ethan-1,1-$d_2$-1-ol (13.8 g, 89.49 mmol) in ethyl acetate (200.0 mL) was added IBX (75.2 g, 268.47 mmol) at room temperature. The resulting mixture was stirred at 80° C. for 16 h. After the reaction was completed, the resulting mixture was cooled to room temperature and then filtered. The filtrate was concentrated under reduced pressure. The residue was purified by flash column chromatography with petroleum ether/ethyl acetate (8/2, v/v) to afford 2-(benzyloxy)acetaldehyde-1-d (10.1 g, 74%) as a colorless oil.

Step 3. Synthesis of 2-(benzyloxy)-N-methylethan-1,1-$d_2$-1-amine

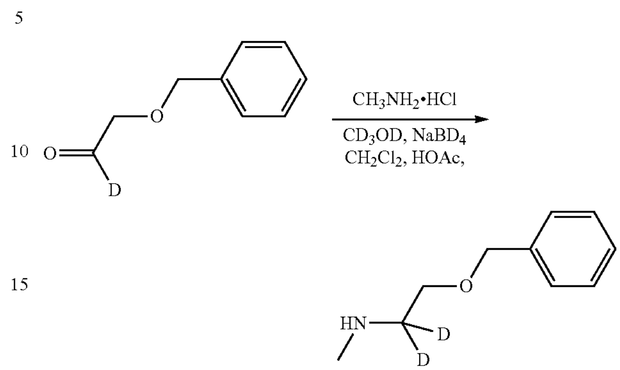

To a solution of 2-(benzyloxy)acetaldehyde-1-d (10.1 g, 66.74 mmol) in $CH_2Cl_2$ (120.0 mL)/$CD_3OD$ (24.0 mL) was added methanamine hydrochloride (6.8 g, 100.12 mmol) and $CH_3COOH$ (0.8 mL) at room temperature. The resulting mixture was stirred at room temperature for 1 h. Then $NaBD_4$ (3.4 g, 80.03 mmol) was added to the mixture at 0° C. under $N_2$. The resulting mixture was stirred at room temperature for additional 16 h. After the reaction was completed, the resulting mixture was used in the next step directly without further purification. LCMS (ESI, m/z): $[M+H]^+$=168.1.

Step 4. Synthesis of tert-butyl (2-(benzyloxy)ethyl-1,1-$d_2$)(methyl)carbamate

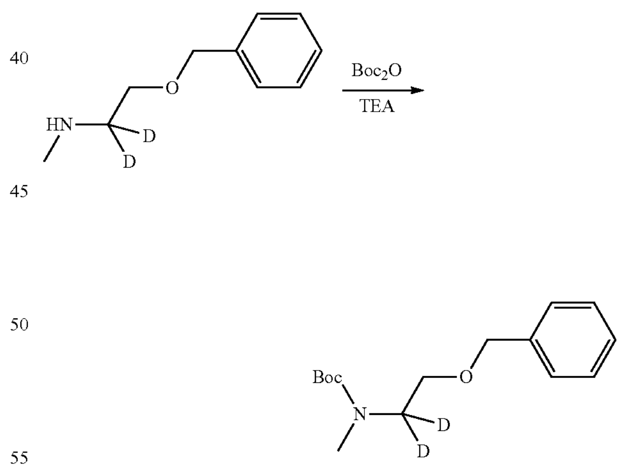

TEA (21.0 g, 207.92 mmol) and di-tert-butyl dicarbonate (33.6 g, 154.11 mmol) were added to the resulting mixture (2-(benzyloxy)-N-methylethan-1,1-$d_2$-1-amine at room temperature. The resulting mixture was stirred at room temperature for 16 h. After the reaction was completed, the mixture was concentrated under reduced pressure. The residue was purified by flash column chromatography with petroleum ether/ethyl acetate (10/1, v/v) to afford tert-butyl (2-(benzyloxy)ethyl-1,1-$d_2$)(methyl)carbamate (8.2 g, 46%) as a colorless oil. LCMS (ESI, m/z): $[M+H]^+$=268.2.

Step 5. Synthesis of tert-butyl (2-hydroxyethyl-1,1-$d_2$)(methyl)carbamate

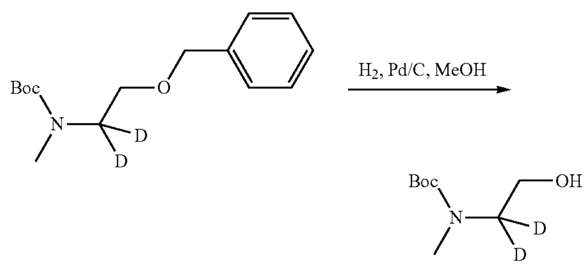

To a solution of tert-butyl (2-(benzyloxy)ethyl-1,1-$d_2$)(methyl)carbamate (8.2 g, 30.67 mmol) in MeOH (100.0 mL) was Pd/C (2.5 g, 10%) at room temperature under $N_2$. The resulting mixture was stirred at room temperature for 16 h under $H_2$. After the reaction was completed, the resulting mixture was filtered. The filtrate was concentrated under reduced pressure to afford tert-butyl (2-hydroxyethyl-1,1-$d_2$)(methyl)carbamate (5.0 g, crude) as a colorless oil. LCMS (ESI, m/z): $[M+H]^+$=178.1.

Step 6. Synthesis of tert-butyl methyl(2-oxoethyl-1,1-$d_2$)carbamate

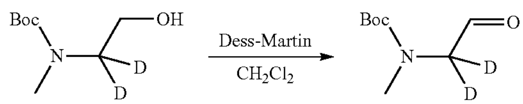

To a solution of tert-butyl (2-hydroxyethyl-1,1-$d_2$)(methyl)carbamate (2.0 g, crude) in $CH_2Cl_2$ (50.0 mL) were added Dess-Martin (4.8 g, 11.28 mmol) at room temperature. The resulting mixture was stirred at room temperature for 2 h. After the reaction was completed, the resulting mixture was filtered. The filtrate was concentrated under reduced pressure. The residue was purified by flash column chromatography with petroleum ether/ethyl acetate (8/2, v/v) to afford tert-butyl methyl(2-oxoethyl-1,1-$d_2$)carbamate (800.0 mg, 40%) as a colorless oil. LCMS (ESI, m/z): $[M+H]^+$=176.1.

Step 7. Synthesis of ethyl (E)-4-((tert-butoxycarbonyl)(methyl)amino)but-2-enoate-4,4-$d_2$

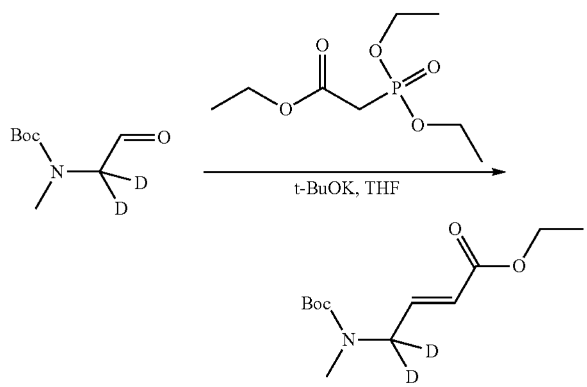

To a solution of triethyl phosphonoacetate (7.2 g, 31.96 mmol) in THE (5.0 mL) was added t-BuOK (512.3 mg, 4.57 mmol) at 0° C. under $N_2$. The resulting mixture was stirred at 0° C. for 30 min under $N_2$. Then a solution of tert-butyl methyl(2-oxoethyl-1,1-$d_2$)carbamate (800.0 mg, 4.57 mmol) in THE (5.0 mL) was added to the mixture at 0° C. under $N_2$. The resulting mixture was stirred at room temperature for additional 2 h. After the reaction was completed, the mixture was diluted with $H_2O$ and extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford ethyl (E)-4-((tert-butoxycarbonyl)(methyl)amino)but-2-enoate-4,4-$d_2$ (600.0 mg, 53%) as a colorless oil. LCMS (ESI, m/z): $[M+H]^+$=246.2.

Step 8. Synthesis of (E)-4-((tert-butoxycarbonyl)(methyl)amino)but-2-enoic-4,4-$d_2$ acid

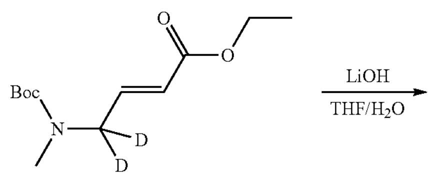

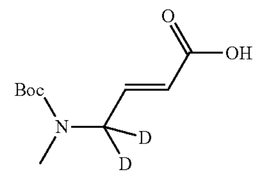

To a solution of ethyl (E)-4-((tert-butoxycarbonyl)(methyl)amino)but-2-enoate-4,4-$d_2$ (200.0 mg, 0.82 mmol) in THE (1.0 mL)/$H_2O$ (1.0 mL) was added LiOH (39.1 mg, 1.63 mmol) at room temperature. The resulting mixture was stirred at room temperature for 2 h. After the reaction was completed, the pH of the mixture was adjusted to 2 with HCl(aq.). The resulting mixture was extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford (E)-4-((tert-butoxycarbonyl)(methyl)amino)but-2-enoic-4,4-$d_2$ acid (80.0 mg, 45%) as a colorless oil. LCMS (ESI, m/z): $[M+H]^+$=218.1.

Step 9. Synthesis of tert-butyl ((E)-4-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-oxobut-2-en-1-yl-1,1-$d_2$)(methyl)carbamate

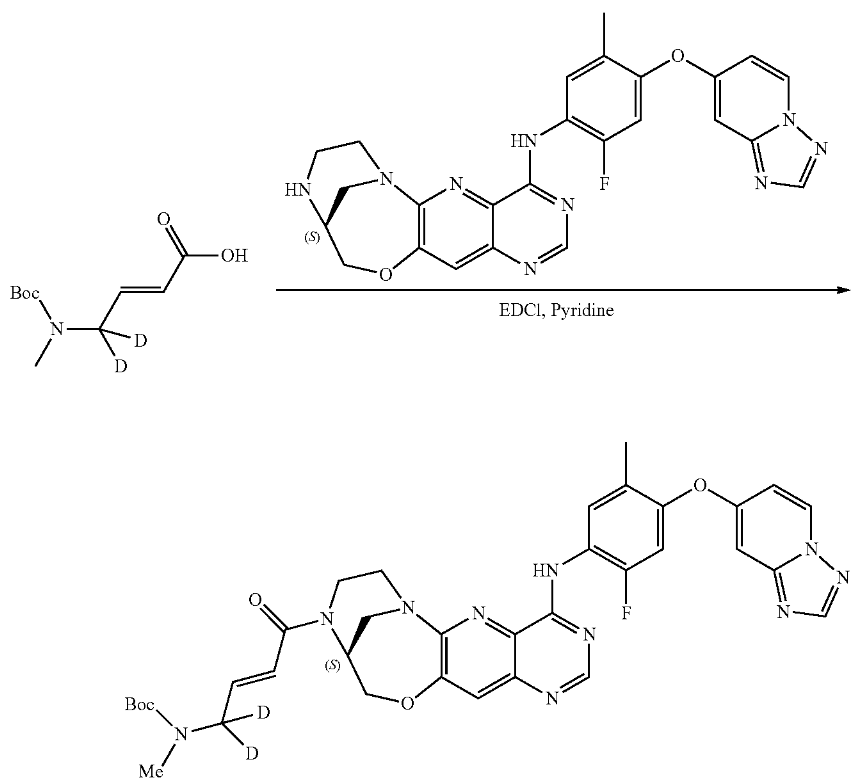

To a solution of (E)-4-((tert-butoxycarbonyl)(methyl)amino)but-2-enoic-4,4-$d_2$ acid (60.0 mg, 0.28 mmol) in pyridine (5.0 mL) was added (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (134.0 mg, 0.28 mmol) at 0° C. under $N_2$. Then EDCI (105.9 mg, 0.55 mmol) was added to the mixture at room temperature. The mixture was stirred at room temperature for 2 h. After the reaction was completed, the resulting mixture was concentrated under reduced pressure. The residue was purified by flash column chromatography with $CH_2Cl_2$/MeOH (10/1, v/v) to afford tert-butyl ((E)-4-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-oxobut-2-en-1-yl-1,1-$d_2$)(methyl)carbamate (120.0 mg, 62%) as a yellow solid. LCMS (ESI, m/z): $[M+H]^+$=699.3.

Step 10. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(methylamino)but-2-en-1-one-4,4-$d_2$

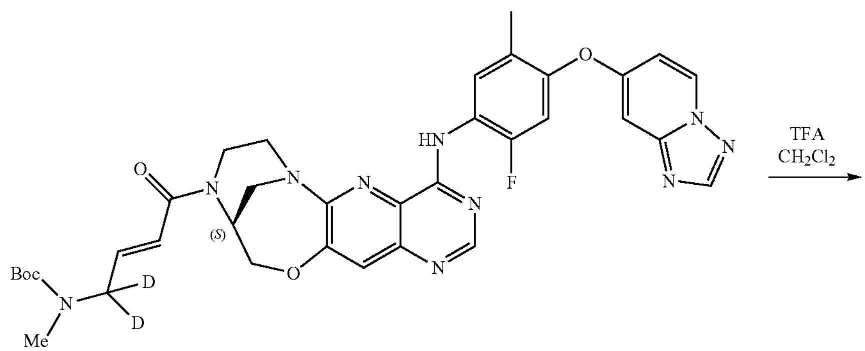

-continued

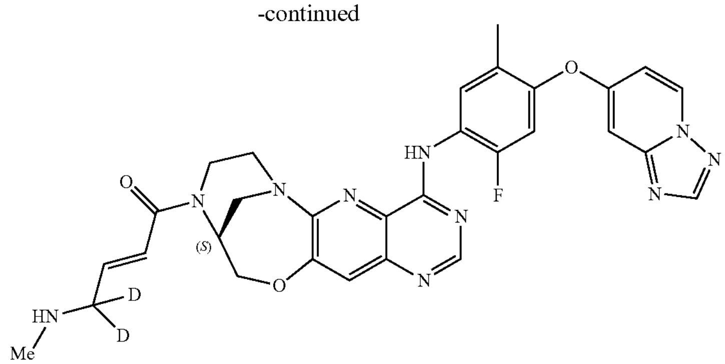

To a solution of tert-butyl ((E)-4-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-oxobut-2-en-1-yl-1,1-$d_2$)(methyl)carbamate (110.0 mg, 0.16 mmol) in $CH_2Cl_2$ (10.0 mL) was added TFA (5.0 mL) at room temperature. The resulting mixture was stirred at room temperature for 1 h. After the reaction was completed, the pH of the mixture was adjusted to 8 with saturated $NaHCO_3$(aq.). The resulting mixture was extracted with $CH_2Cl_2$. The combined organic layers were washed with brine, dried over anhydrous sodium sulfate and filtered. The filtrate was concentrated under reduced pressure to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(methylamino)but-2-en-1-one-4,4-$d_2$ (90.0 mg, crude) as a yellow solid. LCMS (ESI, m/z): $[M+H]^+$=599.3.

Step 11. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one-4,4-$d_2$ (Compound 58)

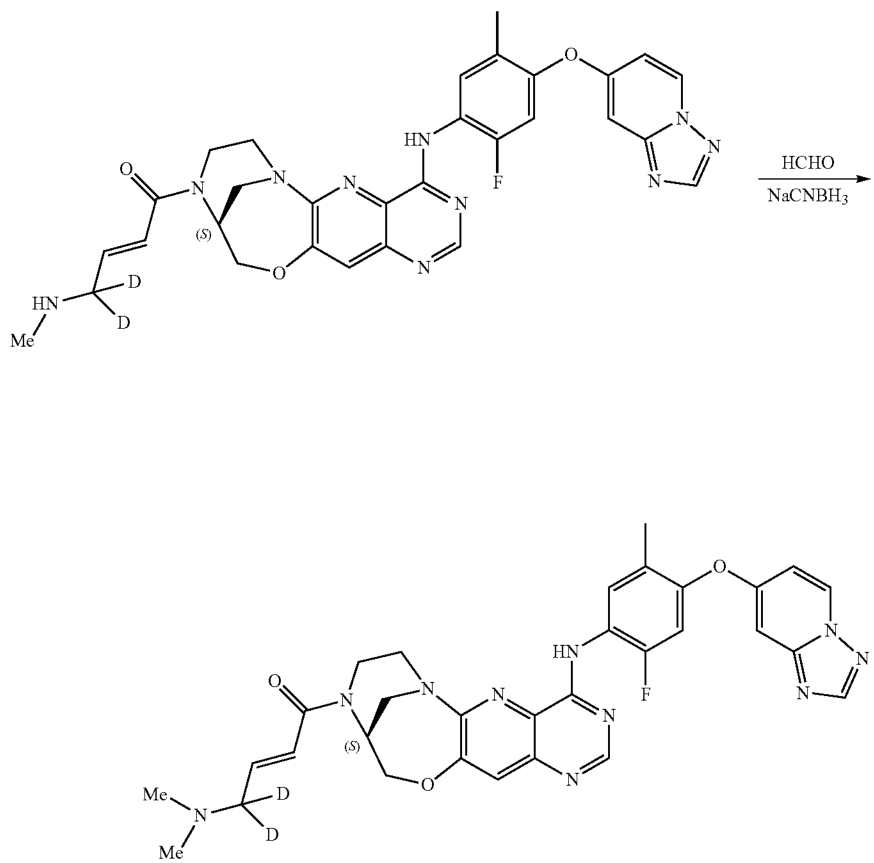

58

To a solution of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(methylamino)but-2-en-1-one-4,4-$d_2$ (80.0 mg, crude) in THE (8.0 mL)/MeOH (1.6 mL) was added HCHO (28.1 mg, 37%) at room temperature. The mixture was stirred at room temperature for 1 h. Then $NaBH_3CN$ (37.8 mg, 0.60 mmol) was added to the mixture at 0° C. under $N_2$. The mixture was stirred at room temperature for additional 2 h. After the reaction was completed, the resulting mixture was concentrated under reduced pressure. The residue was purified by flash column chromatography with $CH_2Cl_2$/MeOH (10/1, v/v) and then purified by Prep-HPLC with the following conditions: (Column: XSelect CSH Prep C18 OBD Column, 19×250 mm, 5 μm; Mobile Phase A: Water (10 mmol/L $NH_4HCO_3$), Mobile Phase B: MeOH—Preparative; Flow rate: 20 mL/min; Gradient: 67% B to 72% B in 10 min; Wave Length: 254 nm) to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(dimethylamino)but-2-en-1-one-4,4-$d_2$ (Compound 58) (14.1 mg, 17%) as a light yellow solid. LCMS (ESI, m/z): $[M+H]^+$=613.2. $^1H$ NMR (400 MHz, DMSO-$d_6$): δ 9.40 (s, 1H), 8.97 (d, J=7.6 Hz, 1H), 8.42-8.41 (m, 2H), 8.00 (d, J=8.8 Hz, 1H), 7.52 (s, 1H), 7.32 (d, J=10.8 Hz, 1H), 7.07-7.04 (m, 1H), 6.92 (d, J=2.4 Hz, 1H), 6.66-6.56 (m, 2H), 5.11-4.70 (m, 1H), 4.69-4.58 (m, 2H), 4.27-4.10 (m, 3H), 3.89-3.63 (m, 1H), 3.47-3.38 (m, 1H), 3.27-3.22 (m, 1H), 2.19 (s, 3H), 2.16-2.14 (m, 6H).

Example S58: Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-$d_3$)amino)but-2-en-1-one-4,4-$d_2$ (Compound 59)

Step 1. Synthesis of 2-(benzyloxy)-N-(methyl-$d_3$)ethan-1,1-$d_2$-1-amine

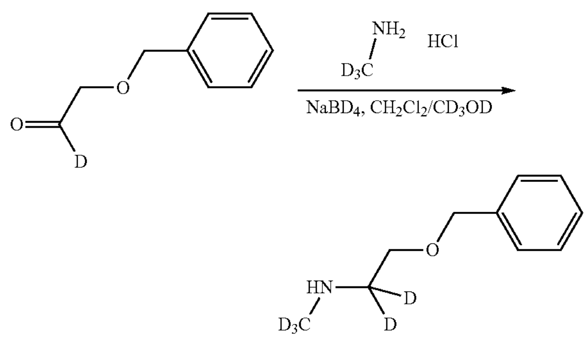

To a solution of 2-(benzyloxy)acetaldehyde-1-d (7.8 g, 51.59 mmol) in $CH_2Cl_2$ (105.0 mL)/$CD_3OD$ (21.0 mL) was added methyl-$d_3$-amine hydrochloride (5.5 g, 77.39 mmol) and $CH_3COOH$ (0.7 mL) at room temperature. The resulting mixture was stirred at room temperature for 1 h. Then $NaBD_4$ (2.6 g, 61.91 mmol) was added to the mixture at 0° C. under $N_2$. The resulting mixture was stirred at room temperature for 16 h. After the reaction was completed, the mixture was concentrated under reduced pressure to afford 2-(benzyloxy)-N-(methyl-$d_3$)ethan-1,1-$d_2$-1-amine (8.7 g, crude) as a colorless oil. LCMS (ESI, m/z): $[M+H]^+$=171.1.

Step 2. Synthesis of tert-butyl (2-(benzyloxy)ethyl-1,1-$d_2$)(methyl-$d_3$)carbamate

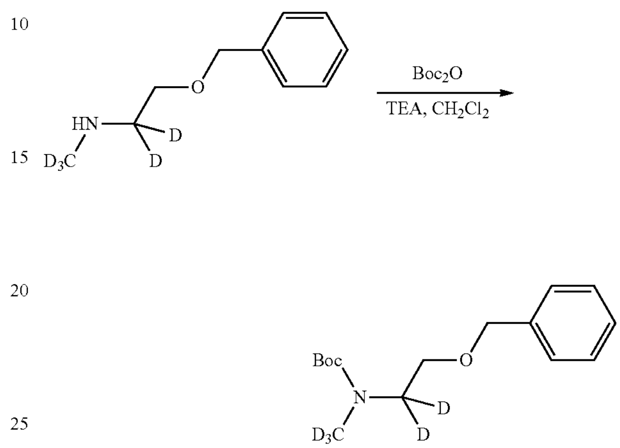

To a solution of 2-(benzyloxy)-N-(methyl-$d_3$)ethan-1,1-$d_2$-1-amine (8.7 g, crude) in $CH_2Cl_2$ (100.0 mL) was added TEA (16.2 g, 159.93 mmol) and di-tert-butyl dicarbonate (25.9 g, 118.54 mmol) at room temperature. The resulting mixture was stirred at room temperature for 16 h. After the reaction was completed, the mixture was concentrated under reduced pressure. The residue was purified by flash column chromatography with petroleum ether/ethyl acetate (10/1, v/v) to afford tert-butyl (2-(benzyloxy)ethyl-1,1-$d_2$)(methyl-$d_3$)carbamate (7.8 g, 56%) as a colorless oil. LCMS (ESI, m/z): $[M+H]^+$=271.2.

Step 3. Synthesis of tert-butyl (2-hydroxyethyl-1,1-$d_2$)(methyl-$d_3$)carbamate

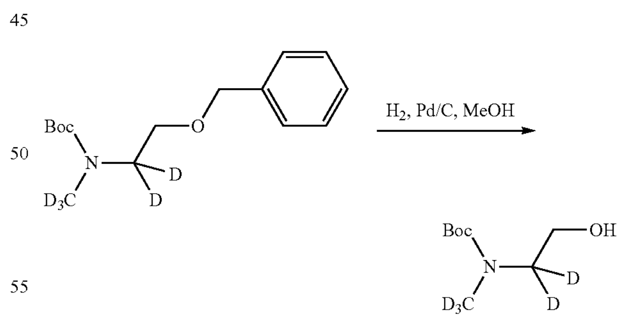

To a solution of tert-butyl (2-(benzyloxy)ethyl-1,1-$d_2$)(methyl-$d_3$)carbamate (3.0 g, 11.10 mmol) in MeOH (30.0 mL) was Pd/C (0.9 g, 10%) at room temperature under $N_2$. The resulting mixture was stirred at room temperature for 16 h under $H_2$. After the reaction was completed, the resulting mixture was filtered. The filtrate was concentrated under reduced pressure to afford tert-butyl (2-hydroxyethyl-1,1-$d_2$)(methyl-$d_3$)carbamate (1.9 g, 95%) as a colorless oil. LCMS (ESI, m/z): $[M+H]^+$=181.2.

Step 4. Synthesis of tert-butyl (methyl-$d_3$)(2-oxoethyl-1,1-$d_2$)carbamate

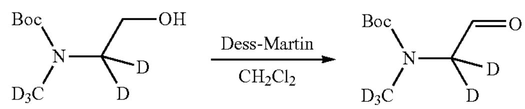

To a solution of tert-butyl (2-hydroxyethyl-1,1-$d_2$)(methyl-$d_3$)carbamate (1.9 g, crude) in $CH_2Cl_2$ (50.0 mL) were added Dess-Martin (4.5 g, 10.54 mmol) at room temperature. The resulting mixture was stirred at room temperature for 2 h. After the reaction was completed, the resulting mixture was filtered. The filtrate was concentrated under reduced pressure. The residue was purified by flash column chromatography with petroleum ether/ethyl acetate (8/2, v/v) to afford tert-butyl (methyl-$d_3$)(2-oxoethyl-1,1-$d_2$)carbamate (1.0 g, 53%) as a colorless oil. LCMS (ESI, m/z): $[M+H]^+$=179.1.

Step 5. Synthesis of ethyl (E)-4-((tert-butoxycarbonyl)(methyl-$d_3$)amino)but-2-enoate-4,4-$d_2$

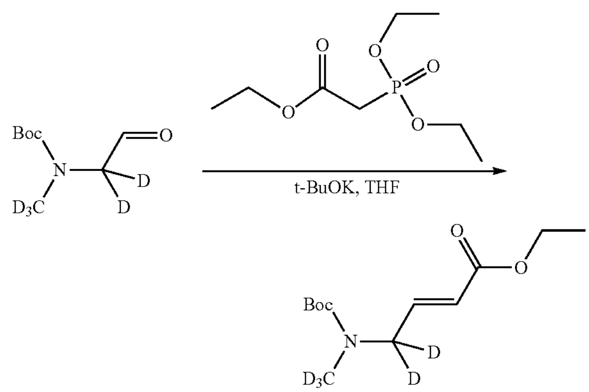

To a solution of triethyl phosphonoacetate (8.8 g, 39.27 mmol) in THE (5.0 mL) was added t-BuOK (630.0 mg, 5.61 mmol) at 0° C. under $N_2$. The resulting mixture was stirred at 0° C. for 30 min under $N_2$. Then a solution of tert-butyl (methyl-$d_3$)(2-oxoethyl-1,1-$d_2$)carbamate (1.0 g, 5.61 mmol) in THE (5.0 mL) was added to the mixture at 0° C. under $N_2$. The resulting mixture was stirred at room temperature for additional 2 h. After the reaction was completed, the resulting mixture was diluted with $H_2O$ and extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford ethyl (E)-4-((tert-butoxycarbonyl)(methyl-$d_3$)amino)but-2-enoate-4,4-$d_2$ (850.0 mg, 61%) as a colorless oil. LCMS (ESI, m/z): $[M+H]^+$=249.2.

Step 6. Synthesis of (E)-4-((tert-butoxycarbonyl)(methyl-$d_3$)amino)but-2-enoic-4,4-$d_2$ acid

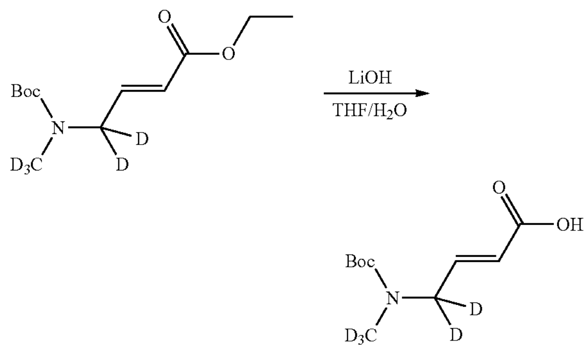

To a solution of ethyl (E)-4-((tert-butoxycarbonyl)(methyl-$d_3$)amino)but-2-enoate-4,4-$d_2$ (850.0 mg, 3.42 mmol) in THE (5.0 mL)/$H_2O$ (5.0 mL) was added LiOH (164.0 mg, 6.85 mmol) at room temperature. The resulting mixture was stirred at room temperature for 2 h. After the reaction was completed, the pH of the mixture was adjusted to 2 with HCl(aq.). The resulting mixture was extracted with ethyl acetate. The combined organic layers were washed with brine, dried over anhydrous sodium sulfate and filtered. The filtrate was concentrated under reduced pressure. The residue was purified by flash column chromatography with $CH_2Cl_2$/MeOH (10/1, v/v) to afford (E)-4-((tert-butoxycarbonyl)(methyl-$d_3$)amino)but-2-enoic-4,4-$d_2$ acid (450.0 mg, 59%) as a colorless oil. LCMS (ESI, m/z): $[M+H]^+$=221.1.

Step 7. Synthesis of tert-butyl ((E)-4-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-oxobut-2-en-1-yl-1,1-$d_2$)(methyl-$d_3$)carbamate

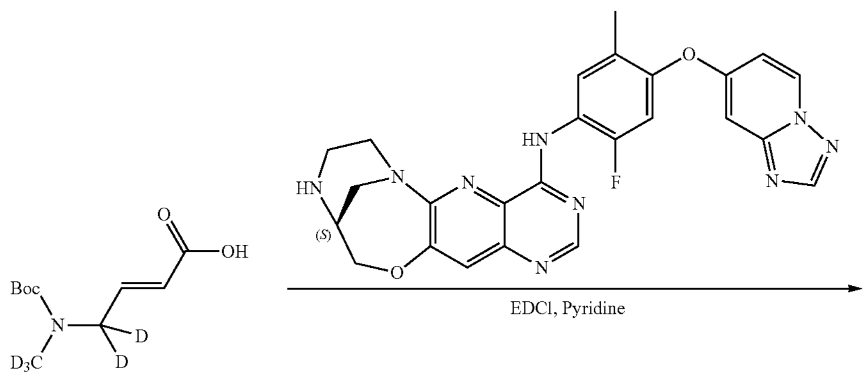

-continued

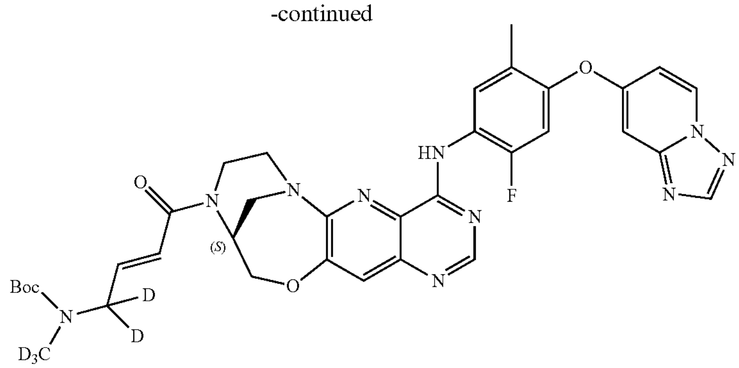

To a solution of (E)-4-((tert-butoxycarbonyl)(methyl-$d_3$)amino)but-2-enoic-4,4-$d_2$ acid (140.0 mg, 0.64 mmol) in pyridine (5.0 mL) was added (10S)—N-(4-([1,2,4]triazolo[1,5-a]pyridin-7-yloxy)-2-fluoro-5-methylphenyl)-8,9,10,11-tetrahydro-7H-6,10-methanopyrimido[4',5':5,6]pyrido[3,2-b][1,4,7]oxadiazonin-4-amine (317.5 mg, 0.64 mmol) at 0° C. under $N_2$. Then EDCI (243.7 mg, 1.27 mmol) was added to the mixture at room temperature. The mixture was stirred at room temperature for 2 h. After the reaction was completed, the resulting mixture was concentrated under reduced pressure. The residue was purified by flash column chromatography with $CH_2Cl_2$/MeOH (10/1, v/v) to afford tert-butyl ((E)-4-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-oxobut-2-en-1-yl-1,1-$d_2$)(methyl-$d_3$)carbamate (350.0 mg, 78%) as a yellow solid. LCMS (ESI, m/z): $[M+H]^+$=702.3.

Step 8. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-((methyl-$d_3$)amino)but-2-en-1-one-4,4-$d_2$

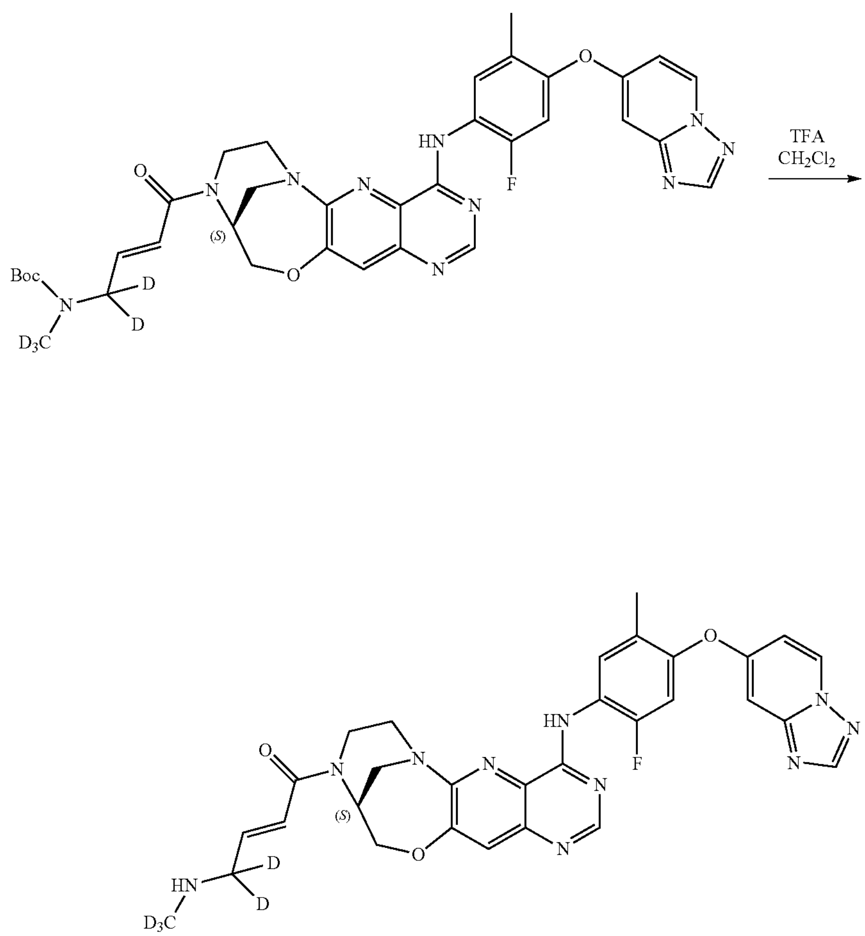

To a solution of tert-butyl ((E)-4-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-oxobut-2-en-1-yl-1,1-$d_2$)(methyl-$d_3$)carbamate (350.0 mg, 0.50 mmol) in $CH_2Cl_2$ (5.0 mL) was added TFA (2.5 mL) at room temperature. The resulting mixture was stirred at room temperature for 1 h. After the reaction was completed, the pH of the mixture was adjusted to 8 with saturated $NaHCO_3$ (aq.). The resulting mixture was extracted with $CH_2Cl_2$. The combined organic layers were washed with brine, dried over anhydrous sodium sulfate and filtered. The filtrate was concentrated under reduced pressure to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-((methyl-$d_3$)amino)but-2-en-1-one-4,4-$d_2$ (270.0 mg, crude) as a yellow solid. LCMS (ESI, m/z): $[M+H]^+$=602.3.

Step 9. Synthesis of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-$d_3$)amino)but-2-en-1-one-4,4-$d_2$ (Compound 59)

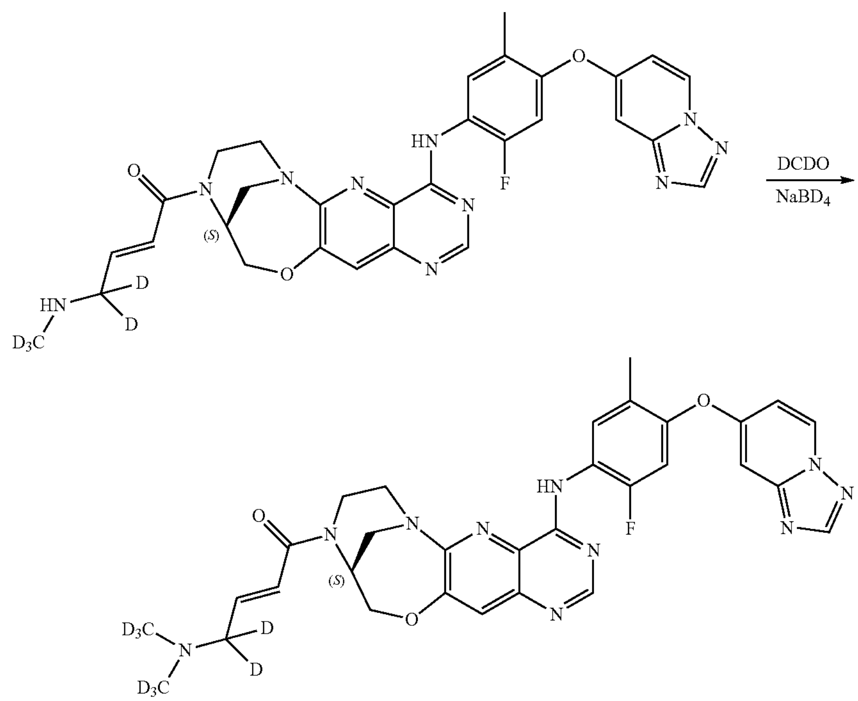

59

To a solution of (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-((methyl-$d_3$)amino)but-2-en-1-one-4,4-$d_2$ (270.0 mg, crude) in THE (5.0 mL)/$CD_3OD$ (1.0 mL) was added DCDO (100.6 mg, 20%) at room temperature. The mixture was stirred at room temperature for 1 h. Then $NaBD_4$ (84.5 mg, 2.02 mmol) was added to the mixture at 0° C. under $N_2$. The mixture was stirred at room temperature for additional 2 h. After the reaction was completed, the resulting mixture was concentrated under reduced pressure. The residue was purified by flash column chromatography with $CH_2Cl_2$/MeOH (10/1, v/v) and then purified by Prep-HPLC with the following conditions: (Column: XBridge Prep OBD C18 Column, 30×150 mm, 5 m; Mobile Phase A: Water (10 mmol/L $NH_4HCO_3$), Mobile Phase B: ACN; Flow rate: 60 mL/min; Gradient: 23% B to 33% B in 10 min; Wave Length: 220/254 nm) to afford (E)-1-((10S)-4-((4-([1,2,4]triazolo[1,5-a]pyridin-7-yloxy)-2-fluoro-5-methylphenyl)amino)-7,8,10,11-tetrahydro-9H-6,10-methanopyrimido[4',5':5,6]pyrido[3,2-b][1,4,7]oxadiazonin-9-yl)-4-(bis(methyl-$d_3$)amino)but-2-en-1-one-4,4-$d_2$ (Compound 59) (10.7 mg, 3%) as a white solid. LCMS (ESI, m/z): $[M+H]^+$=619.3. $^1$H NMR (400 MHz, DMSO-$d_6$): δ 9.39 (s, 1H), 8.97 (d, J=7.6 Hz, 1H), 8.43-8.41 (m, 2H), 8.01 (d, J=8.8 Hz, 1H), 7.53 (s, 1H), 7.32 (d, J=10.8 Hz, 1H), 7.07-7.05 (m, 1H), 6.92 (d, J=2.4 Hz, 1H), 6.67-6.57 (m, 2H), 5.11-4.78 (m, 1H), 4.76-4.55 (m, 2H), 4.28-4.04 (m, 3H), 3.89-3.67 (m, 1H), 3.47-3.39 (m, 1H), 3.28-3.22 (m, 1H), 2.20 (s, 3H).

BIOLOGICAL EXAMPLES

Example B1. Cell Viability Assays

Cells were treated with compounds, and cell viability was measured as a metric of kinase inhibition.

BT-474, A431, MDA-MB-175VII, NCI-H1781, MCF7, and Ba/F3 cell lines were tested. The Ba/F3 cell line is IL-3-dependent mouse cell line derived from the C3H mouse strain. Ba/F3 cell lines were engineered to express human ERBB2 or EGFR kinases, rendering the cells IL-3 independent. The lines were generated via retroviral transduction utilizing a Moloney murine leukemia virus (MMLV) promoter, and constructs are stably integrated into the cell genome. The sequences of the ERBB2 and EGFR genes used were NCBI Reference Sequences NM_004448.3 and NM_005228.3, respectively.

BT-474, A431, MDA-MB-175VII, NCI-H1781 and MCF7 cells were grown in the appropriate growth medium as described in Table B2 below, and harvested at 50-80% confluence. BT-474, A431, MDA-MB-175VII, NCI-H1781 and MCF7 cells were counted and seeded at 2,000 or 1,500 cells per well in 384-well tissue culture plates (see Table B2). Similarly, Ba/F3 cell lines engineered to express EGFR, ERBB2, or ERBB2 mutants were grown, harvested, counted and seeded at 3000 cells per well in 96-well plates. A subset of wells contained media only (low control, "LC").

Table B1 provides the growth media and number of cells seeded per well for the each cell line.

TABLE B1

| Cell Line | Growth Medium | Number of cells seeded per well |
|---|---|---|
| BT-474 | Dulbecco's Modified Eagle Medium (DMEM) + 10% fetal bovine serum (FBS) | 2000 |
| A431 | DMEM + 10% FBS | 1500 |
| MDA-MB-175VII | RPMI + 10% FBS | 2000 |
| NCI-H1781 | RPMI + 10% FBS | 1500 |
| MCF7 | EMEM + 10% FBS + 100 ng/ml human insulin | 2000 |
| Ba/F3 | RPMI + 10% FBS | 3000 |

Compounds were dissolved in DMSO and serially diluted. Serially-diluted compound or a DMSO only control (high control, "HC") was added to the plated cells in each well. Compounds were tested at concentrations of about 10 μM to 0.51 nM, using three-fold dilutions. The final proportion of DMSO never exceeded 0.1%.

Plates were placed in a 37° C., 5% $CO_2$ incubator for 72 hours. Plates were then removed from the incubator and equilibrated for 15 minutes at room temperature. 40 μl of CellTiter Glo reagent (Promega) was added to measure the relative level of metabolically active cells by quantifying intracellular ATP concentrations. Plates were incubated for 30 minutes at room temperature, and luminescence was measured. Percent viability was normalized to a vehicle control only using the following formula: % viability=100×($Lum_{Sample}$−$Lum_{LC}$)/($Lum_{HC}$−$Lum_{LC}$). $IC_{50}$ values were calculated using XLFit software or Prism (GraphPad Software), as shown in Table B2, below. Graphical curves were fitted using a nonlinear regression model with a sigmoidal dose response.

TABLE B2

| Compound | Ba/F3 ERBB2 YVMA, $IC_{50}$, nM |
|---|---|
| Tucatinib | 105 |
| Neratinib | 3.5 |
| 1 | 7.77 |
| 2 | 116 |
| 3 | 18 |
| 4 | 8.63 |
| 5 | 304 |
| 6 | 15.8 |
| 7 | 78.7 |
| 8 | >500 |
| 9 | 85.9 |
| 10 | 7.02 |
| 11 | 37.7 |
| 12 | 44 |
| 13 | 8.92 |
| 14 | 21.6 |
| 15 | 82.3 |
| 16 | 14 |

TABLE B2-continued

| Compound | Ba/F3 ERBB2 YVMA, $IC_{50}$, nM |
|---|---|
| 17 | >500 |
| 18 | 21.6 |
| 19 | >500 |
| 20 | 5.28 |
| 21 | 5.23 |
| 22 | 56.1 |
| 23 | 222 |
| 24 | 6.4 |
| 25 | 2.02 |
| 26 | 24.9 |
| 27 | 10.6 |
| 28 | 6.84 |
| 29 | 19.6 |
| 30 | 10.5 |
| 31 | 19.9 |
| 32 | 4.54 |
| 33 | 12 |
| 34 | 7.18 |
| 35 | 1.29 |
| 36 | 6.19 |
| 37 | 52.3 |
| 38 | 11.8 |
| 39 | 5.54 |
| 40 | 29.4 |
| 41 | 8.67 |
| 42 | 10.3 |
| 43 | 4.65 |
| 44 | 9.18 |
| 45 | 46.7 |
| 46 | 7.04 |
| 47 | 13 |
| 48 | 4.85 |
| 49 | 37.6 |
| 50 | 62.6 |
| 51 | 3.37 |
| 52 | 109 |
| 53 | 117 |
| 54 | 8.66 |
| Example S55, Enantiomer 1 | 5.88 |
| Example S55, Enantiomer 2 | >500 |
| 57 | 173 |
| 58 | 7.79 |
| 59 | 6.5 |

Example B2. Detection of Phosphorylated ERBB2 (pERBB2) and Phosphorylated EGFR (pEGFR)

BT-474 cells were seeded into a 96-well at 2.0*$10^4$cells/100 μl/well.

Compounds were dissolved and serially diluted in DMSO. The compounds were then were added, mixed, and incubated for four hours at 37° C., 5% $CO_2$. Compounds were added using four-fold dilutions at final concentrations ranging from 10 μM to 0.01 nM.

Following the four hour incubation with compounds, cell lysates were prepared. Plates were centrifuged for 5 min at 3000 RPM, and supernatant was removed from each well. Cells were washed 3 times by resuspension in 150 μl PBS, followed by centrifugation and removal of the supernatant, as above. 100 μl of cell lysis buffer (Boston BioProducts, cat #BP-115D) supplied with 1×complete ULTRA cocktail inhibitor (Thermo Scientific™, cat #78443) was then added to the washed cells. Cells were incubated with lysis buffer for 1 hour at 4° C., and then stored at −80° C.

Enzyme-linked immunosorbent assays (ELISA) were performed to measure phosphorylated ERBB2 levels. A capture antibody able to detect phosphorylated and non-phosphorylated ERBB2 (R&D Systems, cat #841425) was added to ELISA plates and incubated at 4° C. overnight. The next day, plates were washed with PBS+0.05% Tween20 (PBST). 150 μl of 5% BSA blocking solution was added for 1 hour at room temperature, with shaking. Plates were washed with PBST. Cell lysates were thawed and 100 μl of lysate was added to the ELISA plate. The plates were incubated for 2 hours at room temperature, with shaking. ELISA plates were then washed with PBST and 100 μl of an HRP-labeled detection antibody that binds phosphorylated tyrosine (R&D Systems, cat #841913) was added to each well. Plates were incubated for 1 hour at room temperature, with shaking. Plates were then washed with PBST, and 100 μl TMB substrate solution (R&D Systems, cat #DY999) was added. Plate were incubated in the dark for 20 minutes at room temperature. 50 μl of Stop solution (R&D Systems, cat #DY994) (50 μl) was added to each well and mixed.

Optical density at 450 nm was read on an EnSpire plate reader (Perkin Elmer). The remaining kinase activity by calculated using the following formula: % Relative activity=100×($A450_{sample}$−$A450_{LC}$)/($A450_{HC}$−$A450_{LC}$). The low and high control values ("LC" and "HC") were generated from lysate from wells without cells or with cells treated with 0.1% DMSO, respectively. $IC_{50}$ values were calculated using XLFit software using a nonlinear regression model with a sigmoidal dose response, as shown in Table B3 below.

TABLE B3

| Compound | pERBB2 $IC_{50}$ (nM) |
|---|---|
| Tucatinib | 12.0 |
| Neratinib | 13.2 |
| 1 | 9.77 |
| 2 | 422 |
| 3 | 28.3 |
| 4 | 7.36 |
| 5 | 1200 |
| 6 | 34.2 |
| 7 | 41.3 |
| 8 | 547 |
| 9 | 18.9 |
| 10 | 5.2 |
| 11 | 103 |
| 12 | 42.8 |
| 13 | 15.8 |
| 14 | 43.8 |
| 15 | 343 |
| 16 | 242 |
| 17 | 1050 |
| 18 | 62.8 |
| 19 | 1930 |
| 20 | 21.1 |
| 21 | 25 |
| 22 | 70 |
| 23 | 209 |
| 24 | 8.38 |
| 25 | 5.54 |
| 26 | 41.1 |
| 27 | 14.4 |
| 28 | 10.8 |
| 29 | 16.8 |
| 30 | 10.6 |
| 31 | 18.5 |
| 32 | 8.41 |
| 33 | 16.8 |
| 34 | 17.7 |
| 35 | 5.48 |
| 36 | 9.92 |
| 37 | 28 |
| 38 | 126 |
| 39 | 8.92 |
| 40 | 18.5 |
| 41 | 24.5 |
| 42 | 10.8 |

TABLE B3-continued

| Compound | pERBB2 $IC_{50}$ (nM) |
|---|---|
| 43 | 8.69 |
| 44 | 36 |
| 45 | 27.3 |
| 46 | 6.84 |
| 47 | 29.2 |
| 48 | 10.8 |
| 49 | 31.5 |
| 50 | 72.4 |
| 51 | 8.84 |
| 52 | 635 |
| 53 | 51.1 |
| 54 | 29.2 |
| Example S55, Enantiomer 1 | 17.4 |
| Example S55, Enantiomer 2 | 304 |
| 57 | 32.8 |
| 58 | 5.5 |
| 59 | 9 |

Enzyme-linked immunosorbent assays (ELISA) were performed to measure phosphorylated EGFR levels using A431 cells (10% FBS). A431 (1.0*$10^4$cells/40 μl/well) cells were seeded in 384 well. Compounds were dissolved in DMSO, serially diluted in DMSO and then were added, mixed, and incubated for 4 hours at 37° C., 500 $CO_2$. Following the 4-hours incubation, cells were stimulated for 10 minutes with EGF (Invitrogen, cat #PHG0311) at a final concentration of 30 ng/mL in the incubator. The media was aspirated and cells were lysed in 10 μL lysis buffer with protease and phosphatase inhibitors (PerkinElmer, cat #ALSU-PEGFR-A50K). The plates were placed on a shaker for 5 minutes and then incubated for 30 min at 4° C. for complete lysis. The lysate was transferred to an Optiplate (Perkin Elmer, cat #6007290).

Acceptor mix (PerkinElmer, cat #ALSU-PEGFR-A50K) was prepared just before use and 5 μL was dispensed to all the wells, followed by a 1.5-2 h incubation at room temperature in dark. The donor mix (PerkinElmer, cat #ALSU-PEGFR-A50K) was prepared under low light conditions prior to use and 5 μl of donor mix was added to all the wells under subdued lighting or green filters. The plates were placed on a shaker for 5 min, sealed, and incubated overnight at room temperature in dark. Plates were read on the Envision (PerkinElmer) using standard AlphaLISA settings.

The percentage of inhibition on EGFR phosphorylation was calculated following equation: % Inhibition=100×(LumHC−LumSample)/(LumHC−LumLC). The low and high controls (LC/HC) are generated from lysate from wells with cells treated with DMSO or 10 mM Staurosporine (BioAustralis, cat #BIA-S1086), respectively. IC50 values were calculated by fitting the Curve using XLfit (v5.3.1.3), equation 201: Y=Bottom+(Top−Bottom)/(1+10^((LogIC50−X)*HillSlope)). The $IC_{50}$ values are shown in Table B4 below.

TABLE B4

| Compound | pEGFR $IC_{50}$ (nM) |
|---|---|
| 1 | 450 |
| 2 | >10.0E+03 |
| 3 | 1470 |
| 4 | 1860 |
| 5 | >10.0E+03 |
| 6 | 2190 |
| 7 | >10.0E+03 |
| 8 | >10.0E+03 |

TABLE B4-continued

| Compound | pEGFR $IC_{50}$ (nM) |
|---|---|
| 9 | >10.0E+03 |
| 10 | 3040 |
| 11 | >10.0E+03 |
| 12 | 7060 |
| 13 | 1580 |
| 14 | 532 |
| 15 | >10.0E+03 |
| 16 | >10.0E+03 |
| 17 | >10.0E+03 |
| 18 | 4430 |
| 19 | >10.0E+03 |
| 20 | 192 |
| 21 | 621 |
| 22 | 684 |
| 23 | >10.0E+03 |
| 24 | 2160 |
| 25 | 338 |
| 26 | >10.0E+03 |
| 27 | 5260 |
| 28 | 8770 |
| 29 | >10.0E+03 |
| 30 | >10.0E+03 |
| 31 | >10.0E+03 |
| 32 | 920 |
| 33 | 164 |
| 34 | 465 |
| 35 | 309 |
| 36 | 1620 |
| 37 | 3620 |
| 38 | 3080 |
| 39 | 6170 |
| 40 | >10.0E+03 |
| 41 | 7300 |
| 42 | 1940 |
| 43 | 1400 |
| 44 | 337 |
| 45 | >10.0E+03 |
| 46 | 2470 |
| 47 | >10.0E+03 |
| 48 | 3300 |
| 49 | 2650 |
| 50 | >10.0E+03 |
| 51 | 177 |
| 52 | >10.0E+03 |
| 53 | 3390 |
| 54 | >10.0E+03 |
| Example S55, Enantiomer 1 | >10.0E+03 |
| Example S55, Enantiomer 2 | >10.0E+03 |
| 57 | >10.0E+03 |
| 58 | 869 |
| 59 | 1380 |

What is claimed is:

1. A method of treating a patient having a cancer, wherein the cancer comprises cells or cell tissue having (i) one or more disease-associated point mutation in ErbB2 or (ii) increased ErbB2 kinase activity as compared to a control, or both (i) and (ii), the method comprising administering to the patient a therapeutically effective amount of the compound of formula (I')

(I')

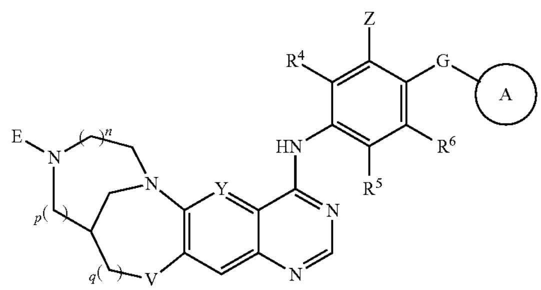

or a pharmaceutically acceptable salt thereof, wherein Ring A is

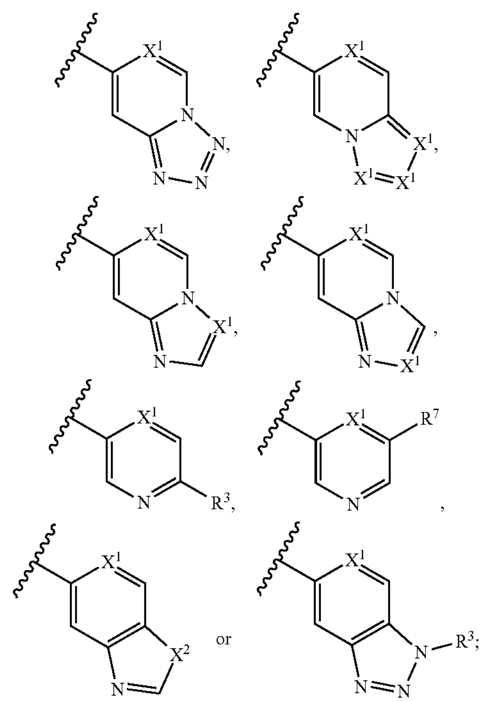

E is —C(═O)—$R^1$;

G is —O—, —C(═O)—, —S—, —S(O)—, —$S(O)_2$—, or —$CH_2$—;

V is O, S, or N—$R^2$;

each $X^1$ is independently N or CH;

$X^2$ is O, S, or N—$R^3$;

is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen;

$R^6$ is —H or halogen;

$R^7$ is —H, halogen, $C_1$-$C_6$ alkyl, —$CD_3$ or $C_1$-$C_6$ cycloalkyl;

n is 1 or 2;

p is 0 or 1; and q is 1 or 2.

2. The method of claim 1, wherein the cancer is lung, glioma, skin, head and neck, salivary gland, breast, esophageal, liver, stomach-(gastric), uterine, cervical, biliary tract, pancreatic, colorectal, renal, bladder or prostate cancer.

3. The method of claim 2, wherein the cancer is non-small cell lung cancer.

4. The method of claim 1, wherein the compound or a pharmaceutically acceptable salt thereof is a compound of formula (I)

(I)

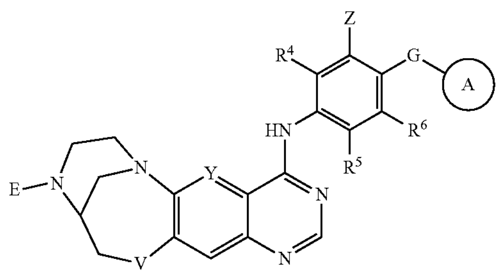

or a pharmaceutically acceptable salt thereof, wherein:

Ring A is

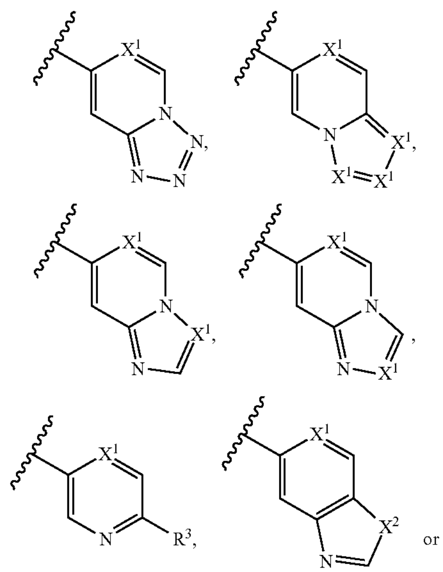

-continued

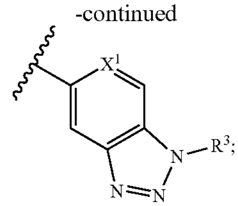

E is —C(═O)—$R^1$;

G is —O—, —C(═O)—, —S—, —S(O)—, —$S(O)_2$—, or —$CH_2$—;

V is O, S, or N—$R^2$;

each $X^1$ $X^2$ is independently N or CH;

is O, S, or N—$R^3$;

Y is N or C—$R^y$, wherein $R^y$ is —H or —F;

Z is —H, halogen, —C≡CH, —$OCH_3$, or $C_1$-$C_2$ alkyl;

$R^1$ is $C_2$-$C_4$ alkenyl or $C_2$-$C_4$ alkynyl, each of which is independently optionally substituted by 1-4 substituents selected from the group consisting of halogen, $C_1$-$C_3$ alkyl, a 3- to 7-membered carbon-linked N-heterocycloalkyl, or —$NR^{1a}R^{1b}$, wherein each $R^{1a}$ and $R^{1b}$ are independently —H, $C_1$-$C_3$ alkyl, or —$CD_3$, or wherein each pair of geminal $R^{1a}$ and $R^{1b}$ may be taken together with the nitrogen atom to which they are attached to form a 3- to 6-membered N-heterocyclyl, and wherein each heterocyclic nitrogen atom, if present, is independently optionally substituted with $C_1$-$C_3$ alkyl;

$R^2$ is $C_1$-$C_6$ alkyl or $C_1$-$C_6$ cycloalkyl, each of which is independently optionally substituted by 1-4 fluorines;

$R^3$ is —H, $C_1$-$C_6$ alkyl, —$CD_3$ or $C_1$-$C_6$ cycloalkyl;

$R^4$ is —H or halogen;

$R^5$ is —H or halogen; and $R^6$ is —H or halogen.

5. The method of claim 1, wherein:

ring A is

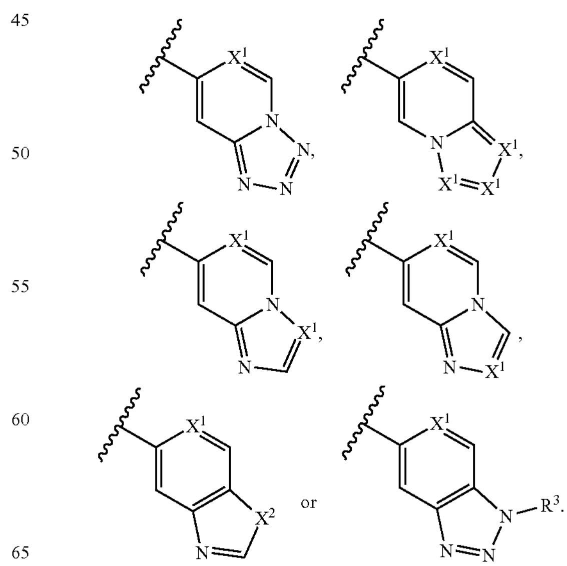

6. The method of claim 1, wherein:
ring A is
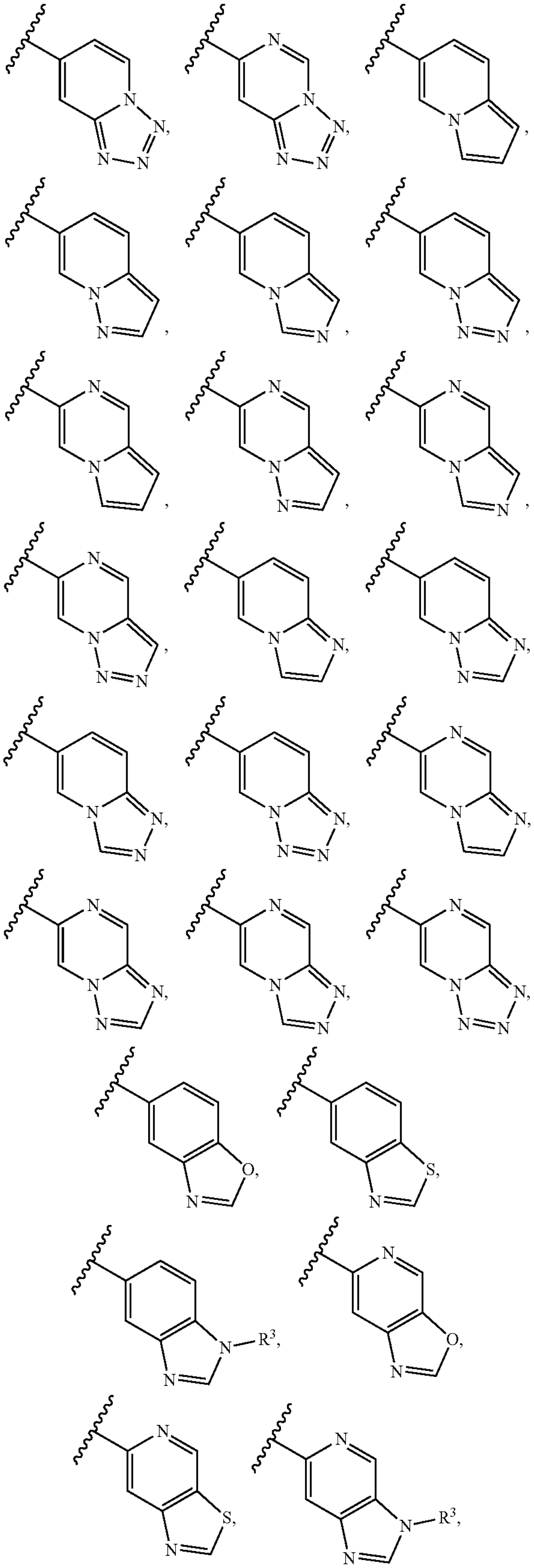
-continued
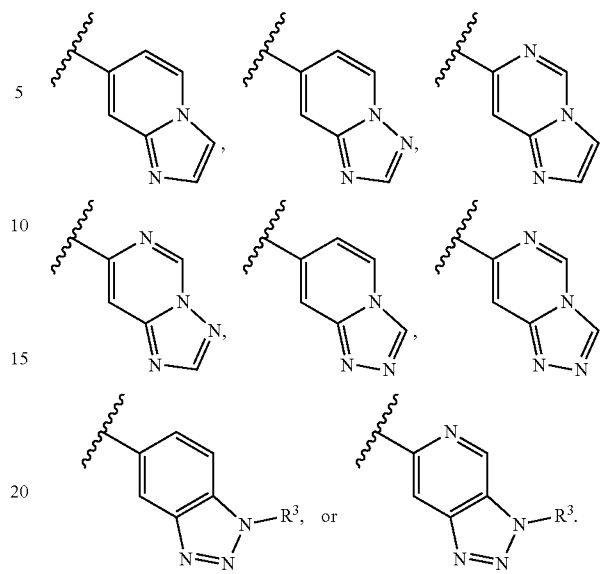
7. The method of claim 1, wherein:
ring A is
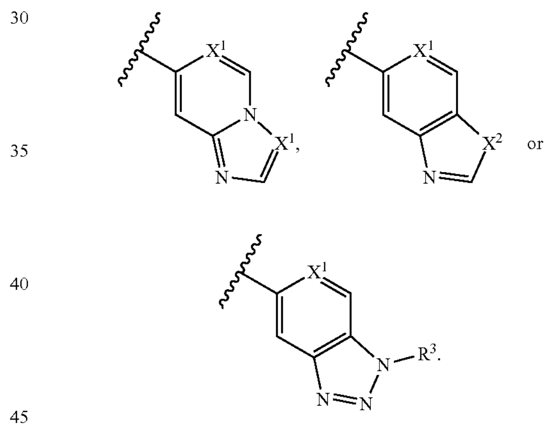
8. The method of claim 1, wherein:
ring A is
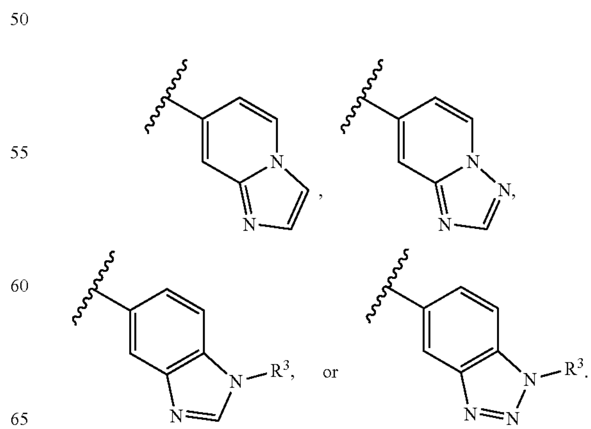

9. The method of claim 1, wherein:

ring A is

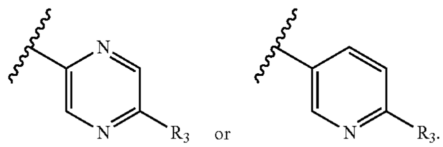

10. The method of claim 1, wherein $R^3$ is —$CH_3$.

11. The method of claim 1, wherein Z is —H, —F, —Cl, —C≡CH, —$OCH_3$, or —$CH_3$.

12. The method of claim 1, wherein Z is —$CH_3$.

13. The method of claim 1, wherein $R^1$ is $C_2$-$C_4$ alkenyl, optionally substituted by —$NR^{1a}R^{1b}$.

14. The method of claim 1, wherein $R^1$ is —CH═$CH_2$.

15. The method of claim 1, wherein $R^1$ is —CH═CH—$CH_2$—$N(CH_3)_2$ or —CH═CH—$CH(CH_3)$—$N(CH_3)_2$.

16. The method of claim 1, wherein $R^1$ is $C_2$-$C_4$ alkynyl, optionally substituted by —$NR^{1a}R^{1b}$.

17. The method of claim 1, wherein $R^1$ is —C≡C—$CH_3$.

18. The method of claim 1, wherein Y is N.

19. The method of claim 1, wherein Y is C—$R^y$.

20. The method of claim 1, wherein Y is C—$R^y$, and $R^y$ is —H.

21. The method of claim 1, wherein V is O.

22. The method of claim 1, wherein G is —O—.

23. The method of claim 1, wherein G is —$CH_2$—.

24. The method of claim 1, wherein $R^4$ is —H.

25. The method of claim 1, wherein $R^5$ is —H.

26. The method of claim 1, wherein $R^5$ is halogen.

27. The method of claim 1, wherein $R^6$ is —H.

28. The method of claim 1, wherein the compound or a pharmaceutically acceptable salt thereof is a compound selected from the group consisting of:

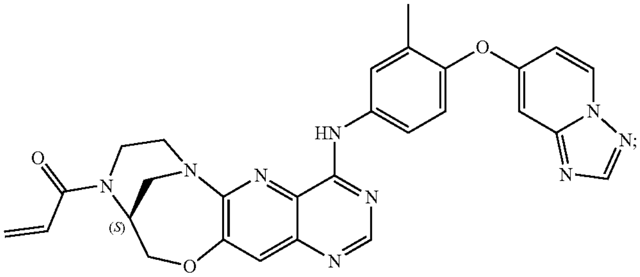

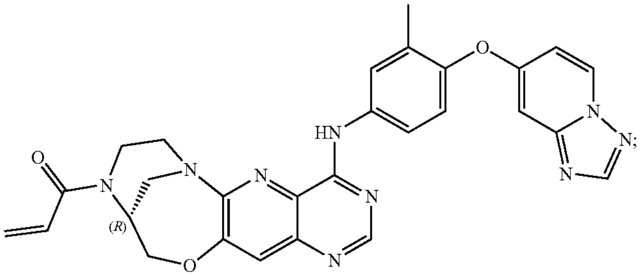

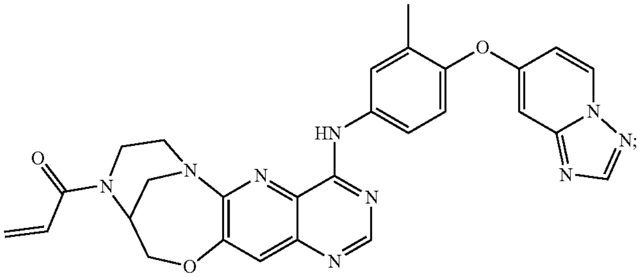

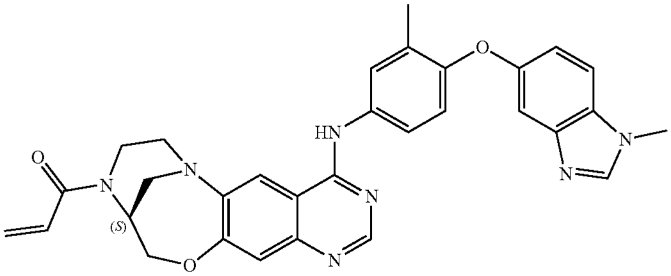

;

-continued
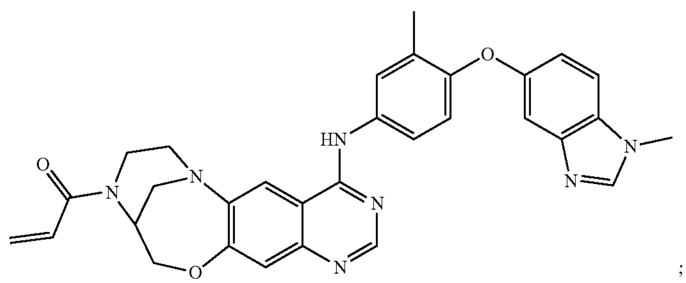
;
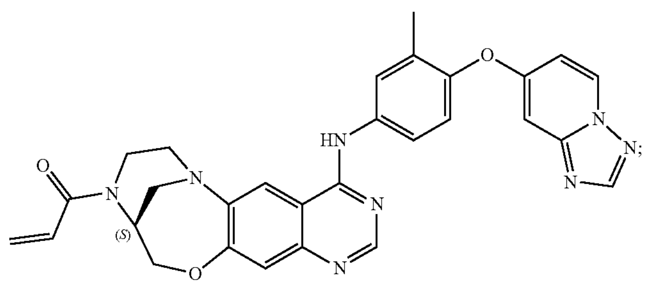
;
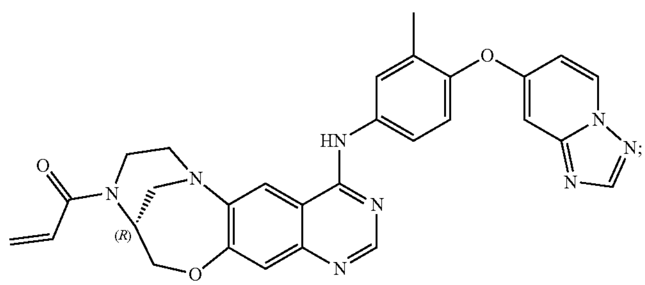
;
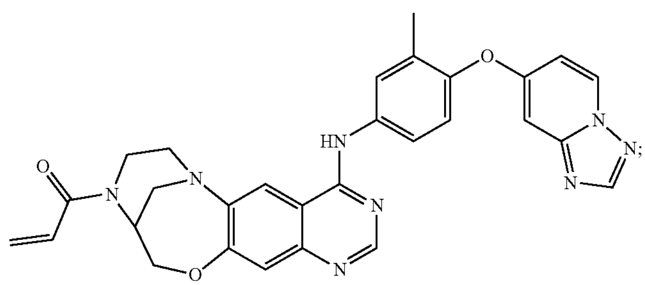
;
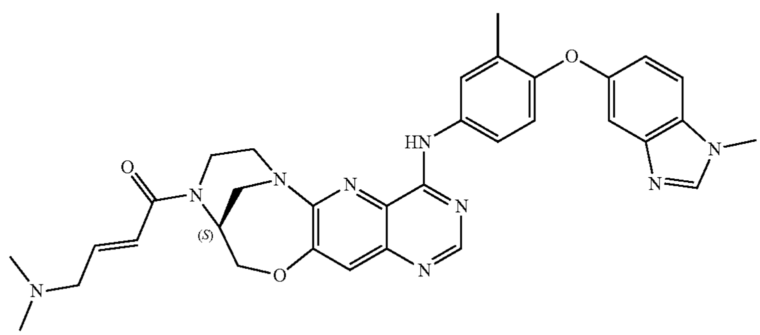
;

-continued
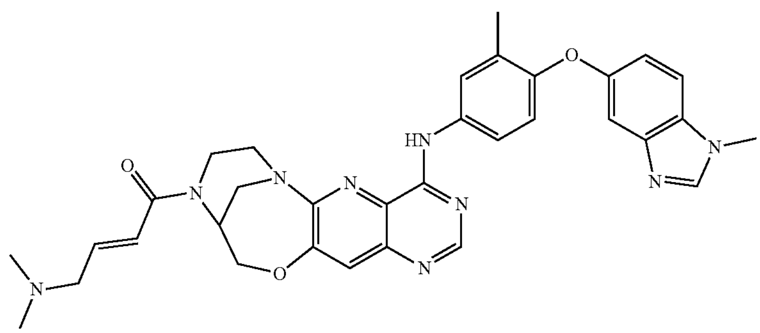
;
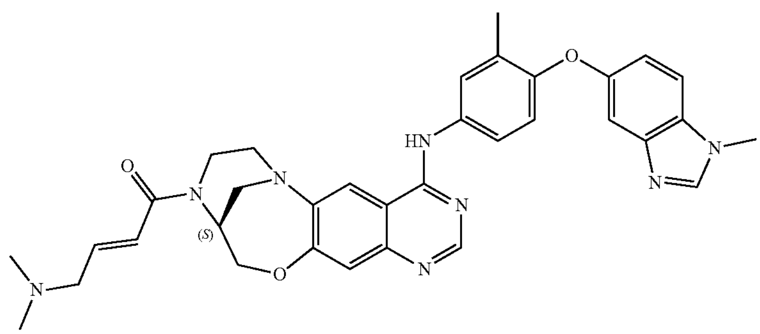
;
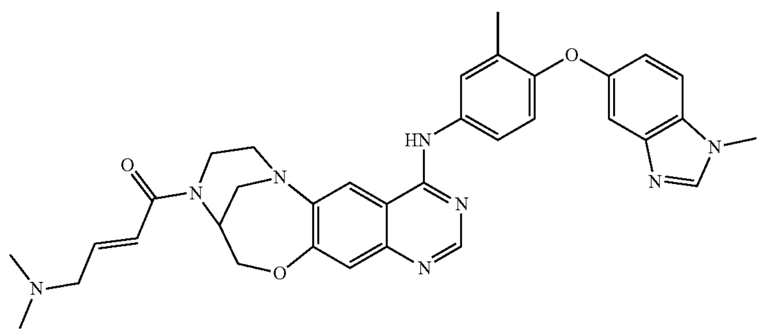
;
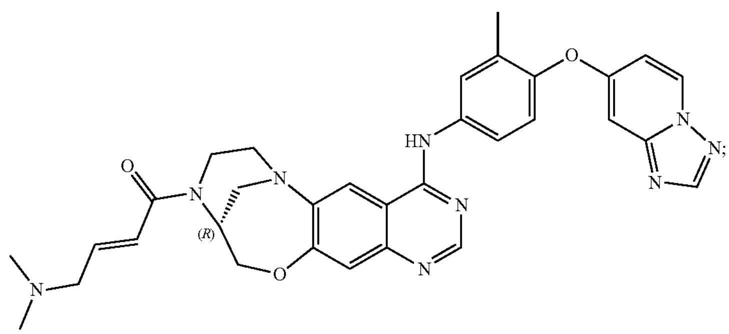
;
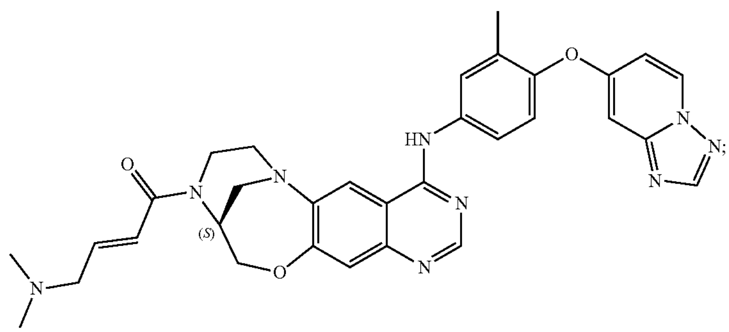
;

-continued
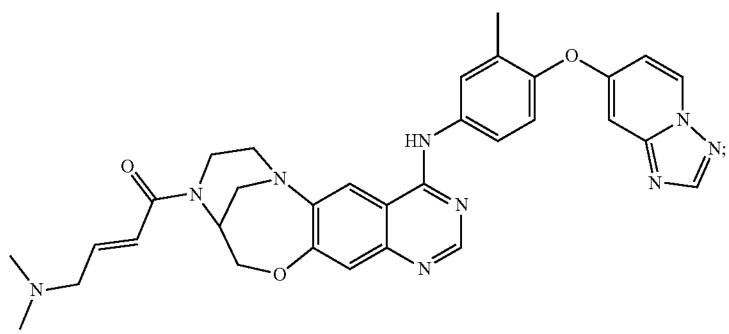
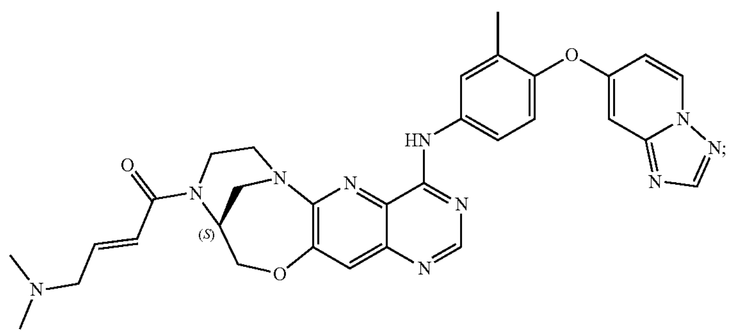
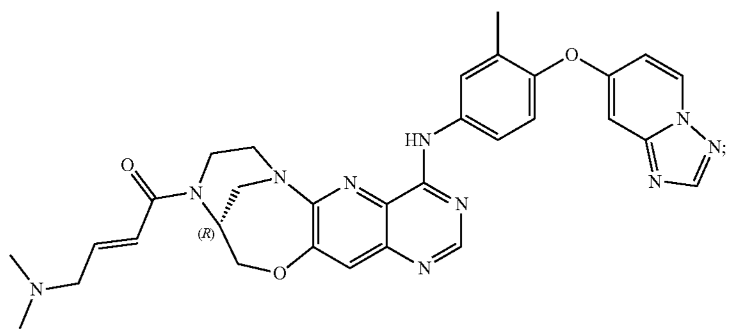
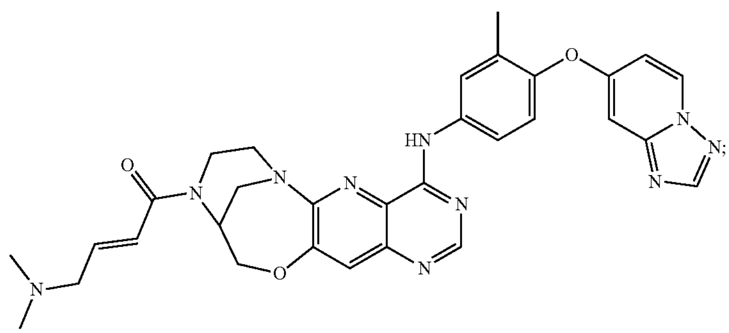
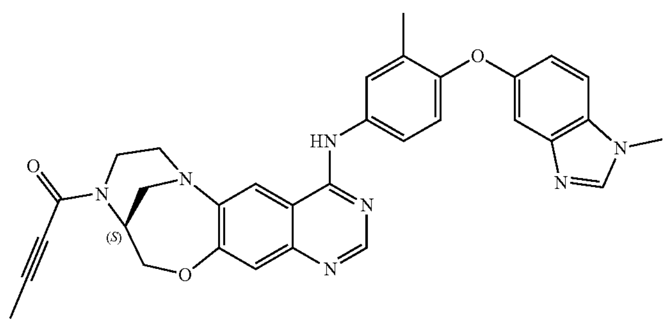
;

-continued
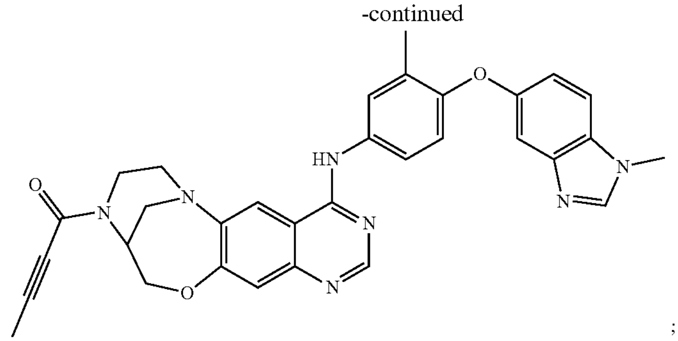
;
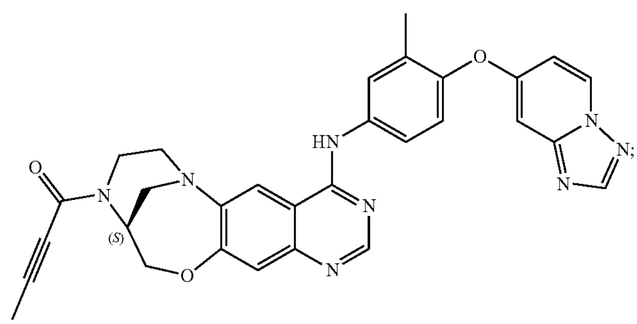
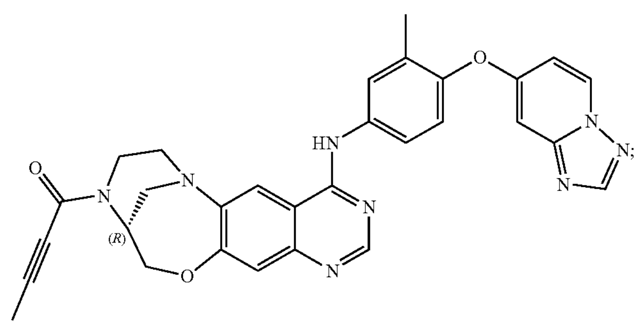
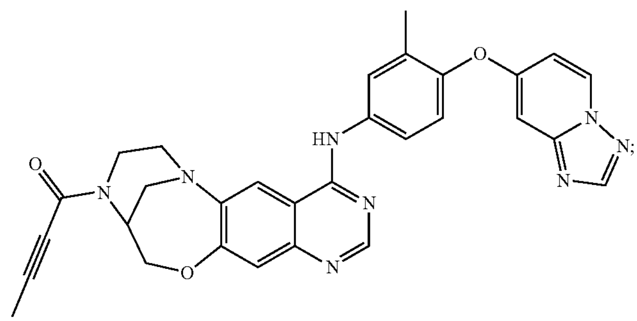
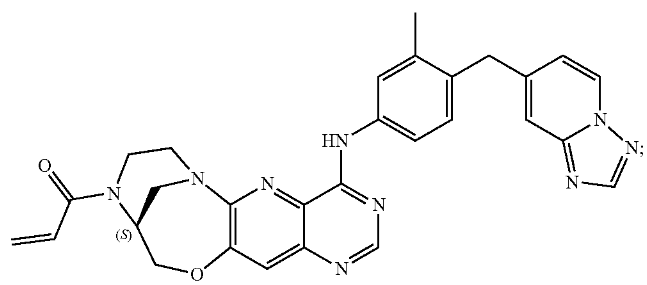

-continued
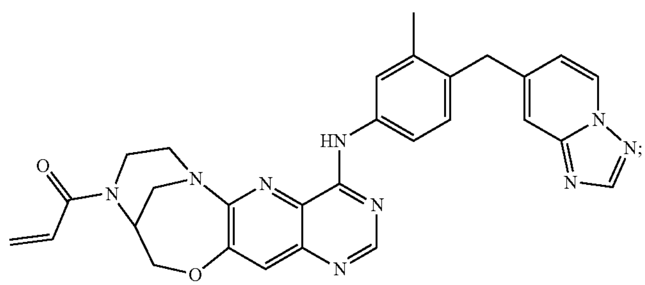
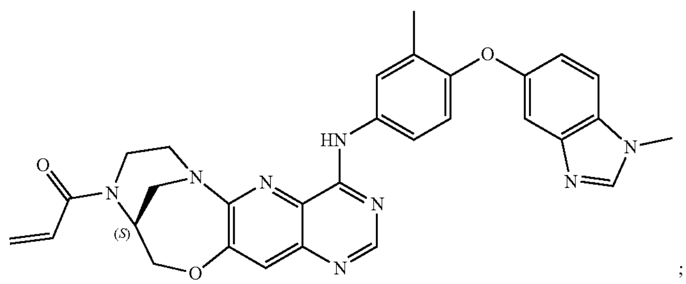
;
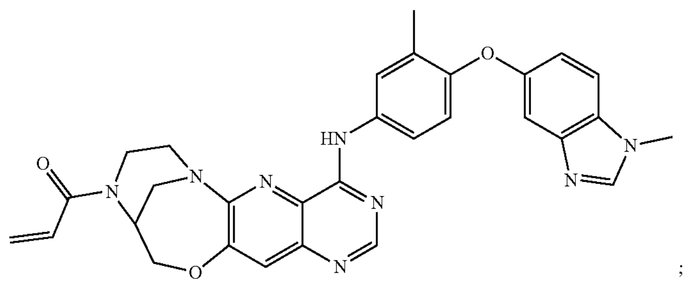
;
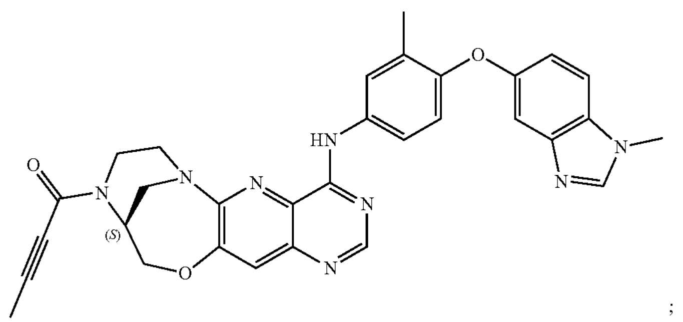
;
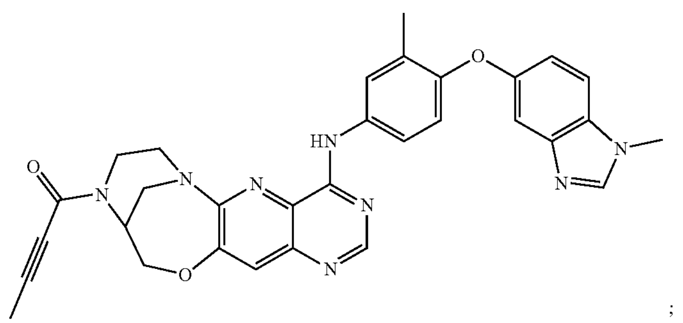
;

-continued
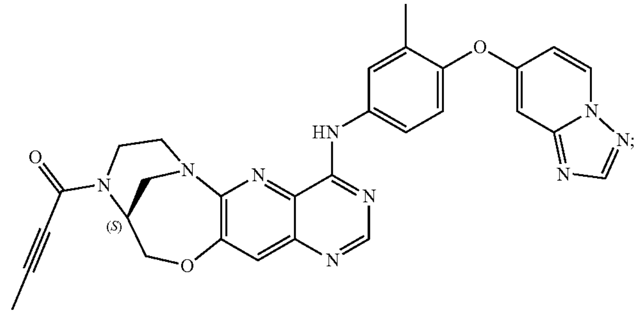
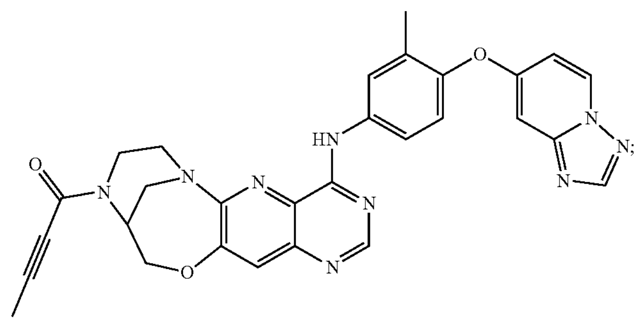
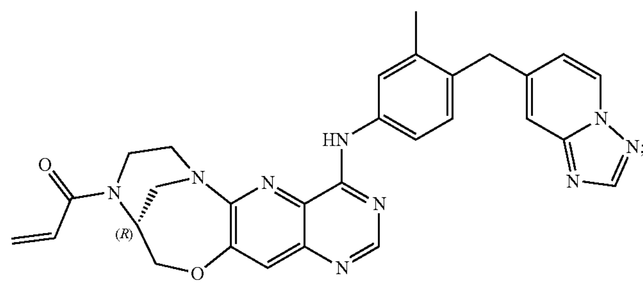
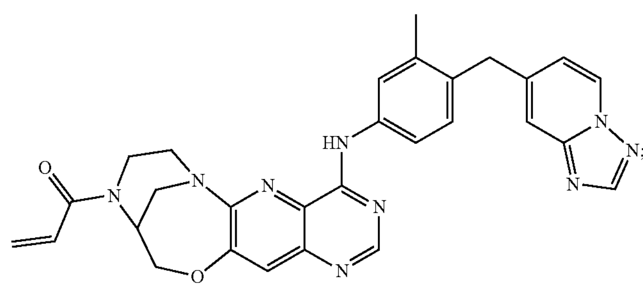
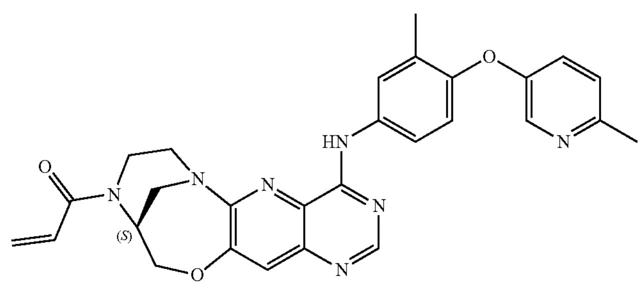
;

-continued
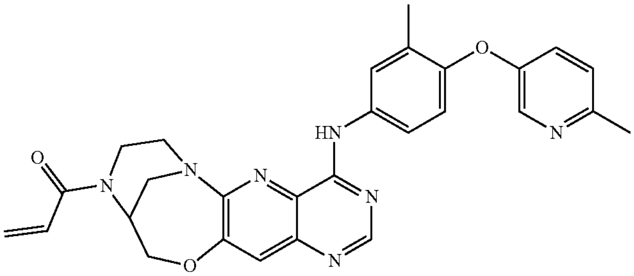
;
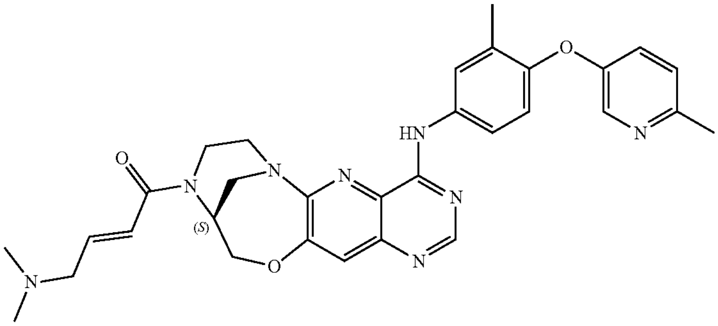
;
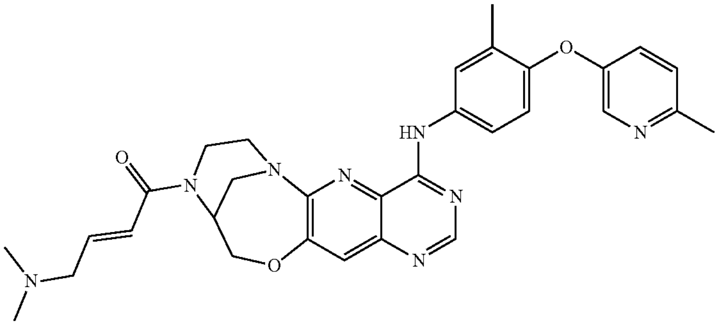
;
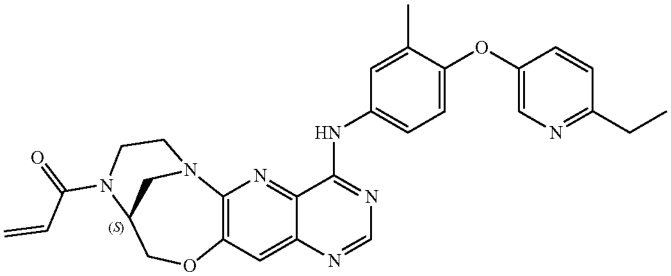
;
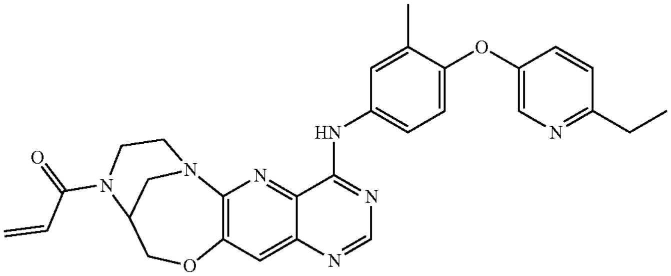
;

-continued
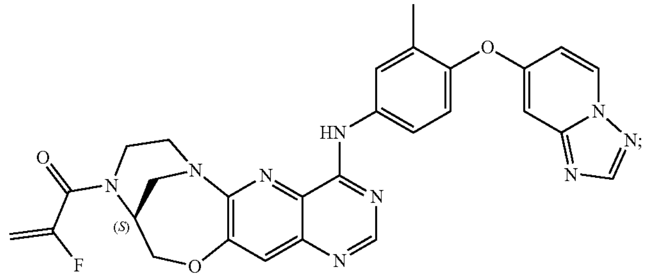
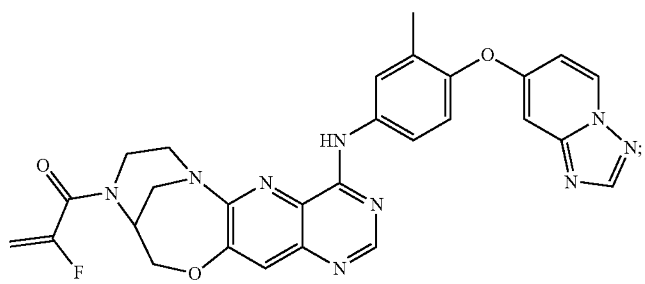
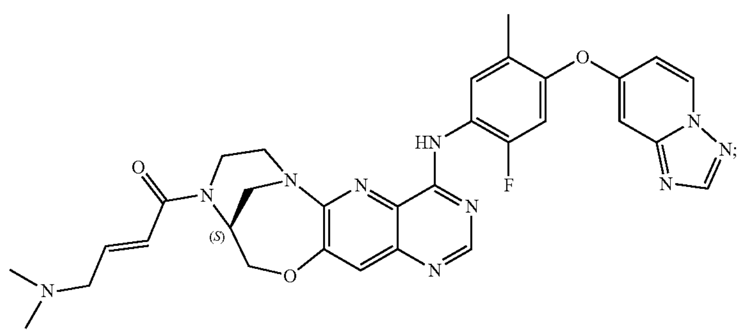
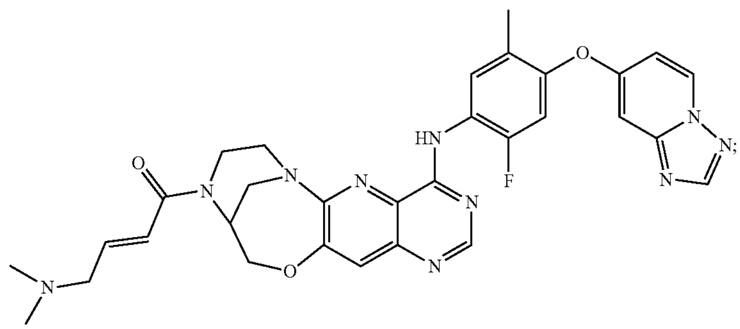
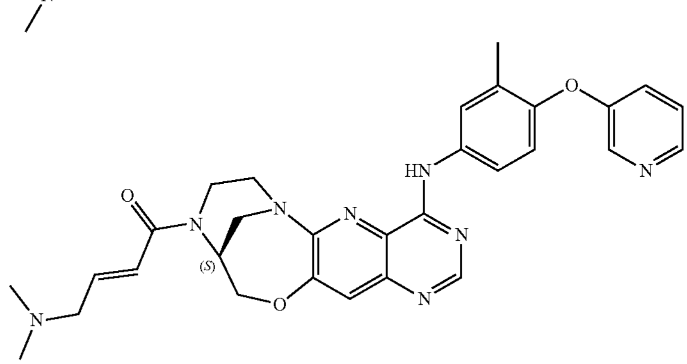

-continued
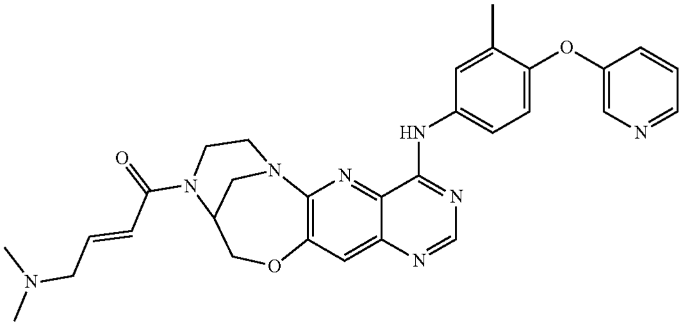
;
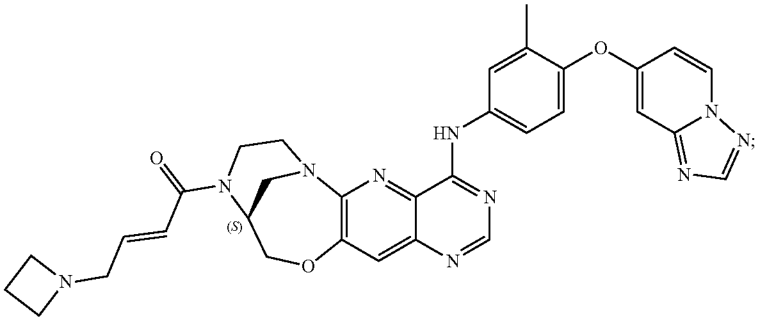
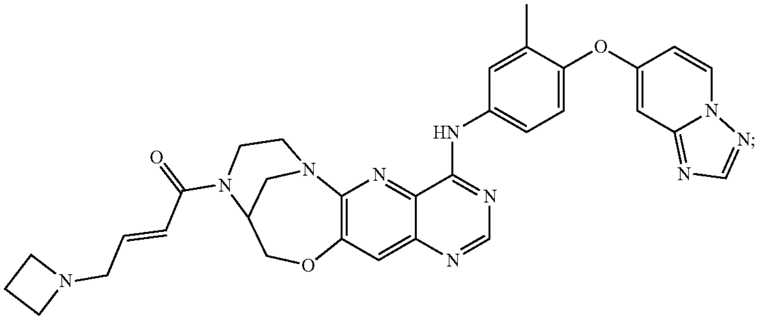
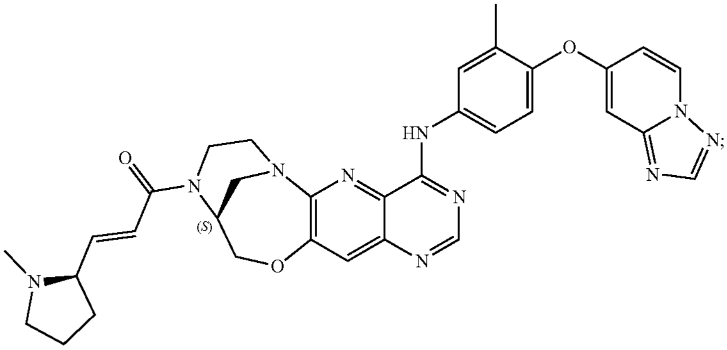
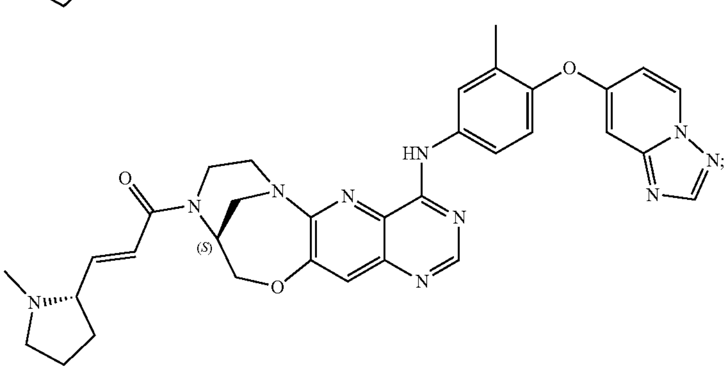

-continued
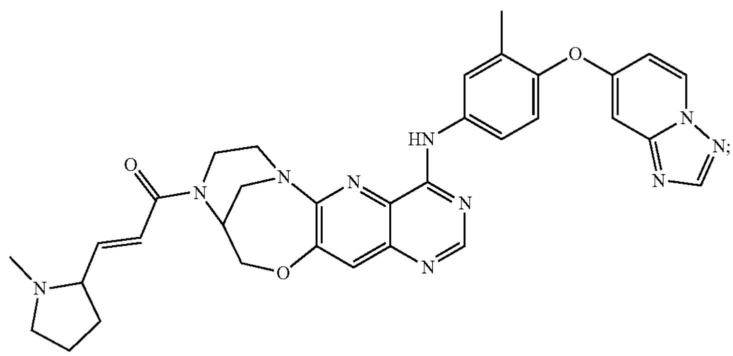
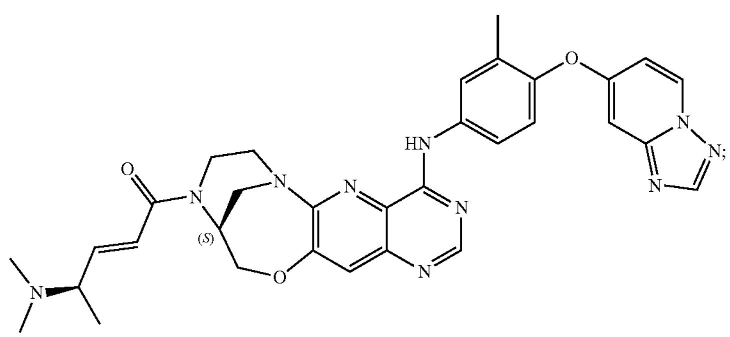
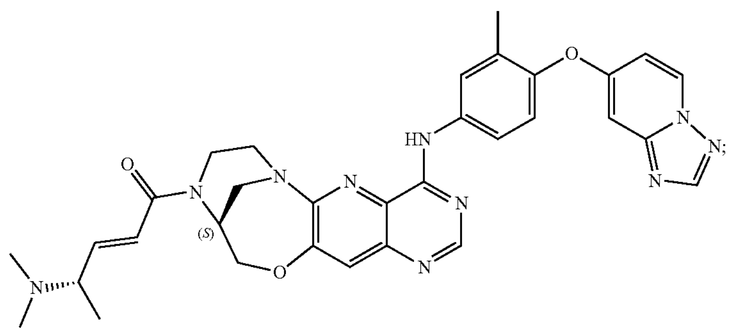
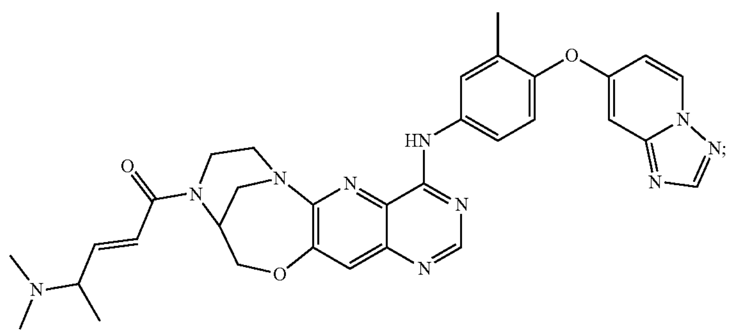
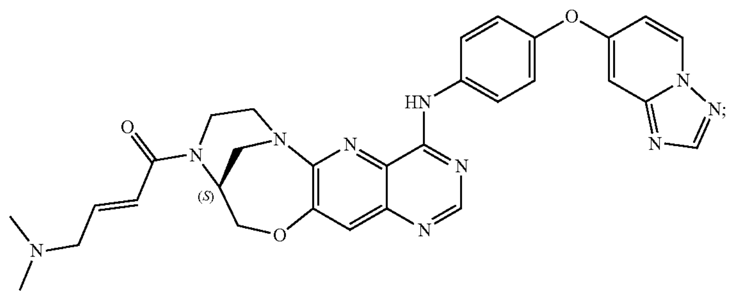

-continued
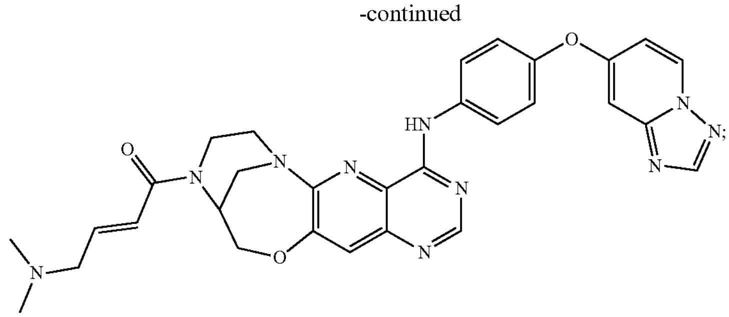
;
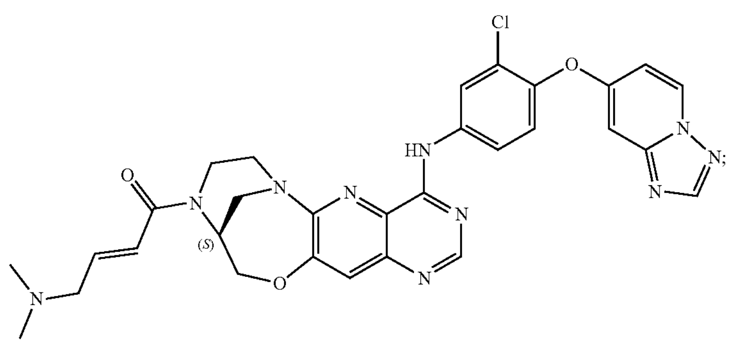
;
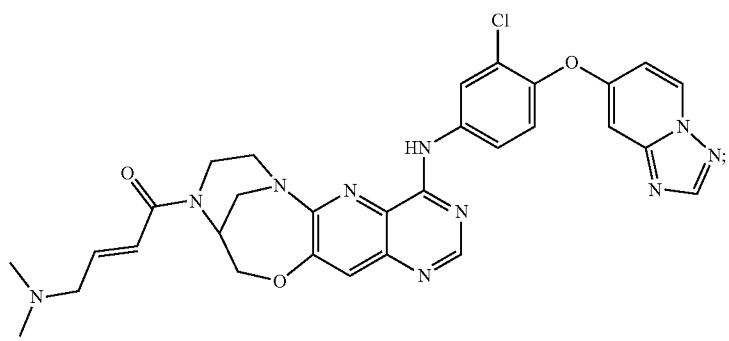
;
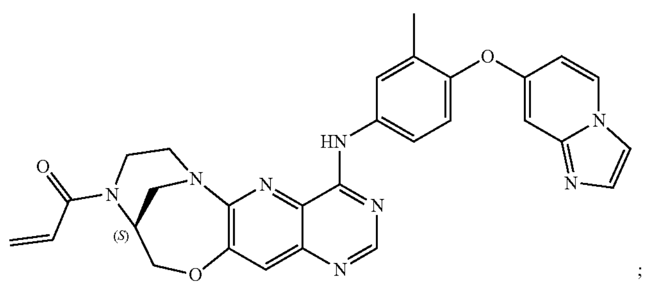
;
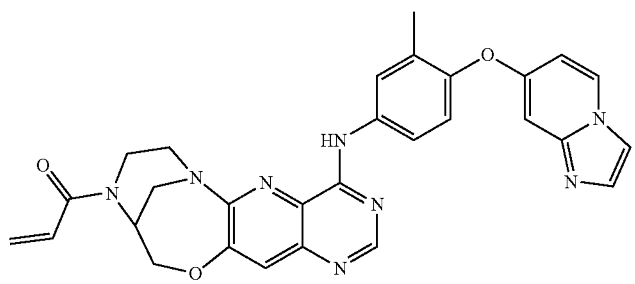
;

-continued
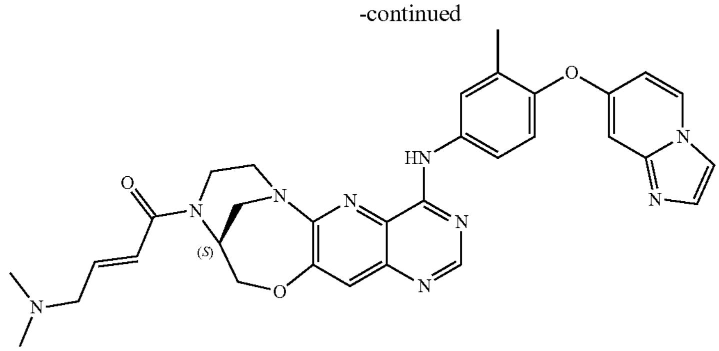
;
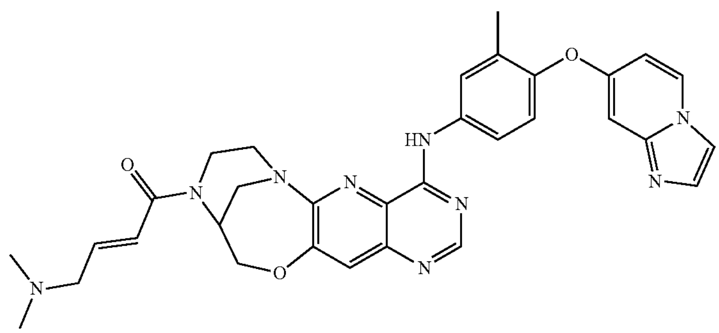
;
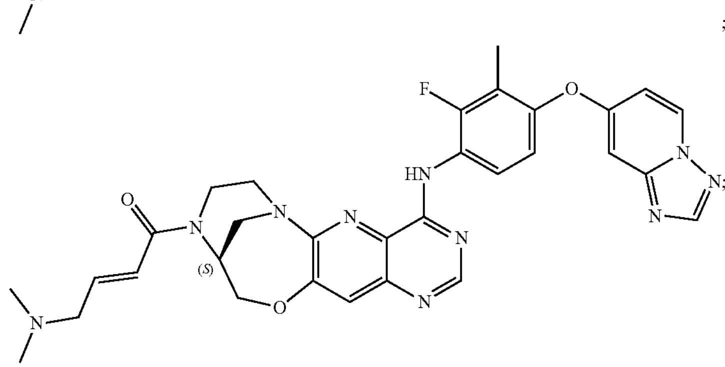
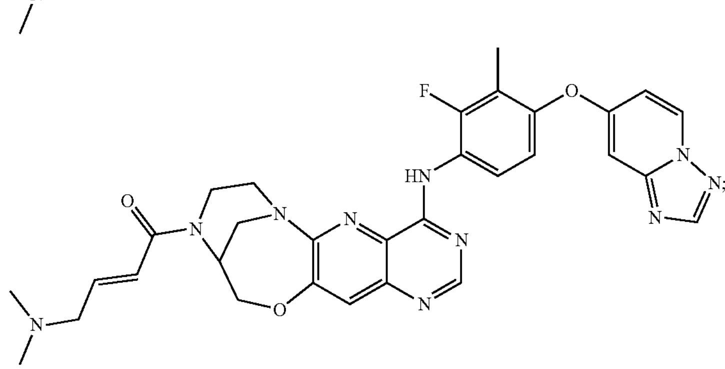
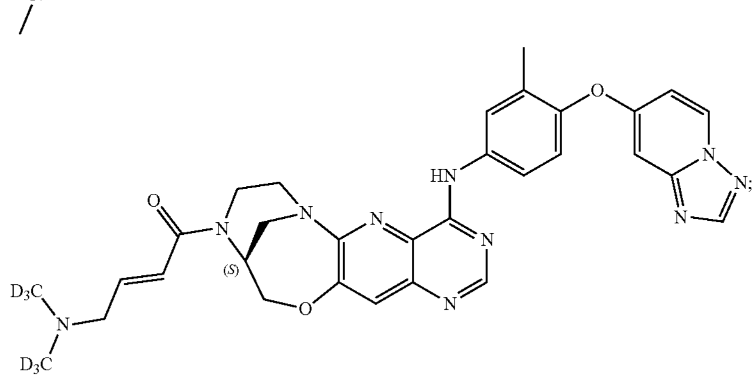

-continued
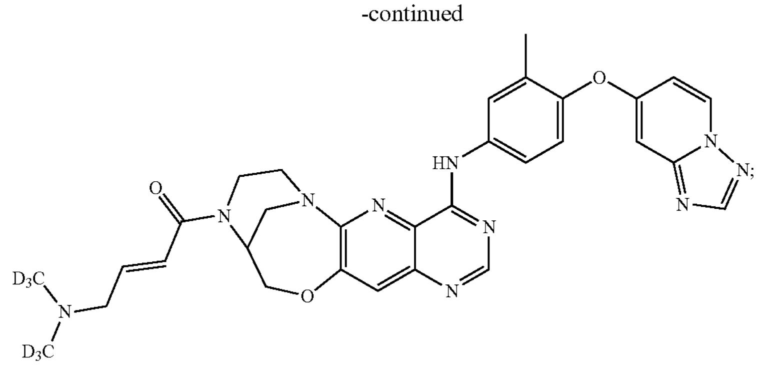
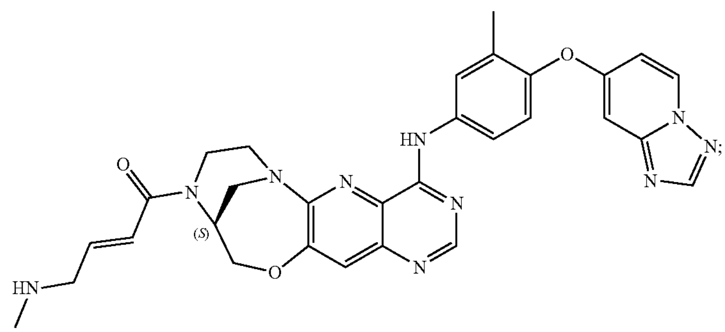
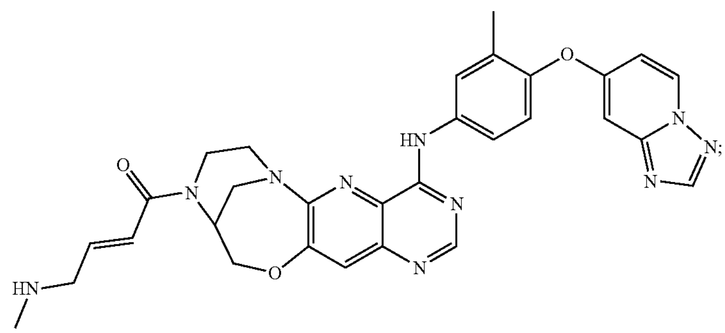
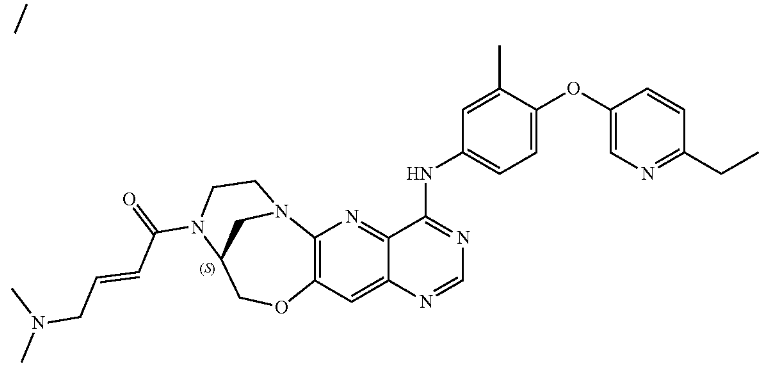
;
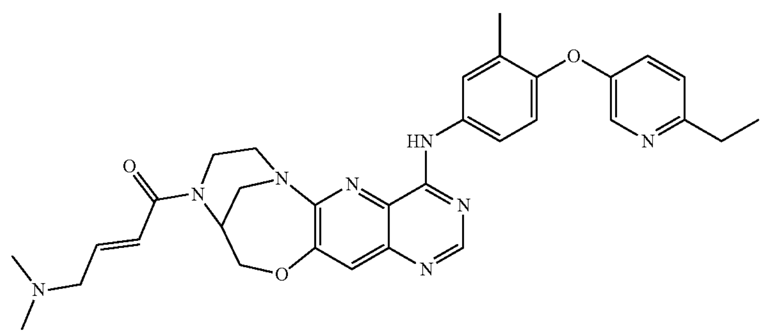
;

-continued
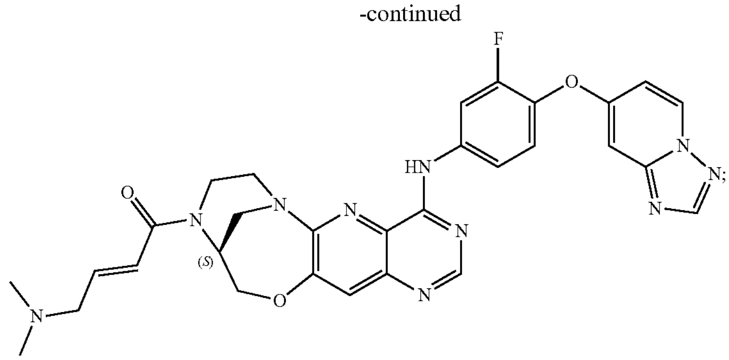
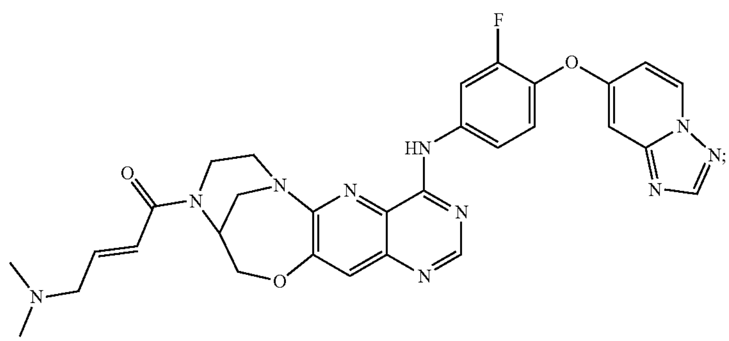
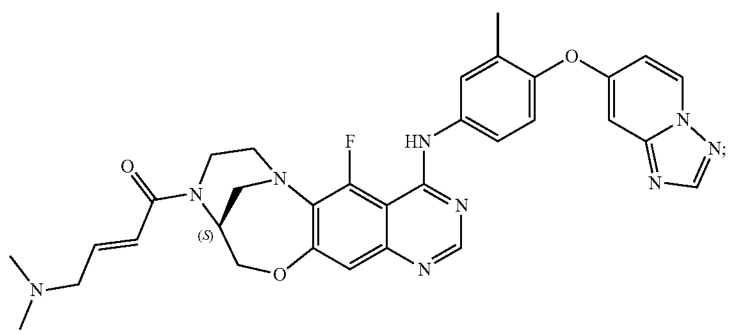
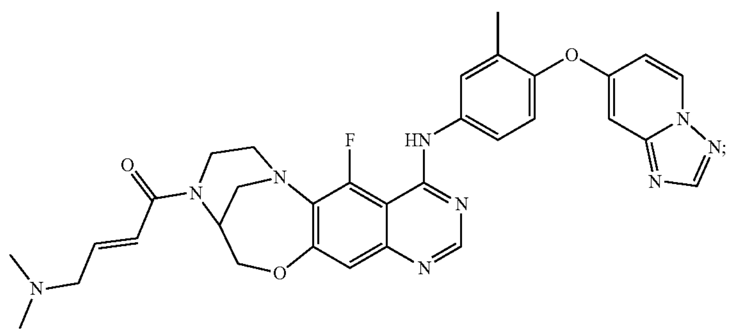
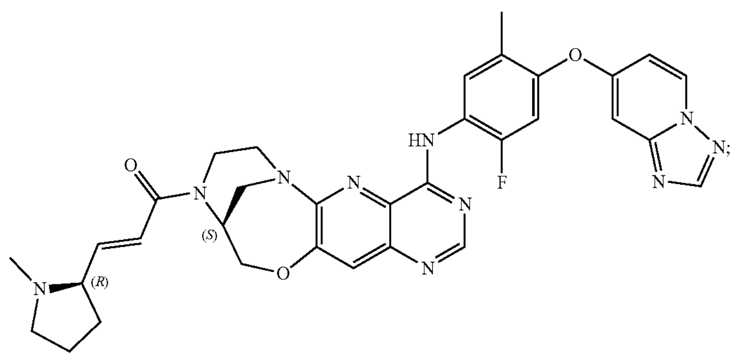

-continued
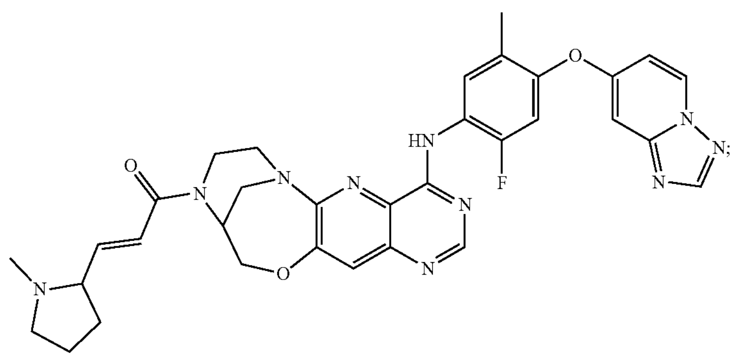
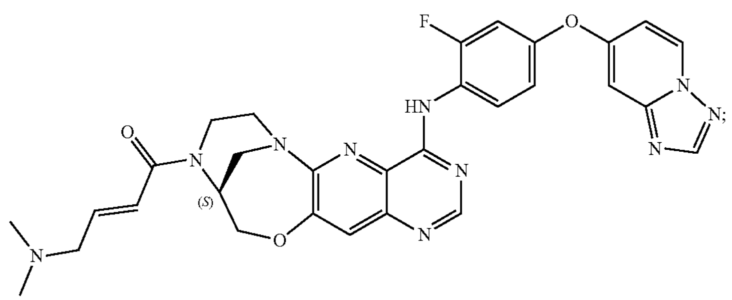
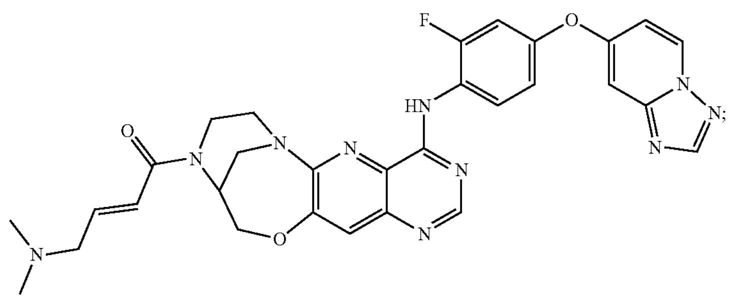
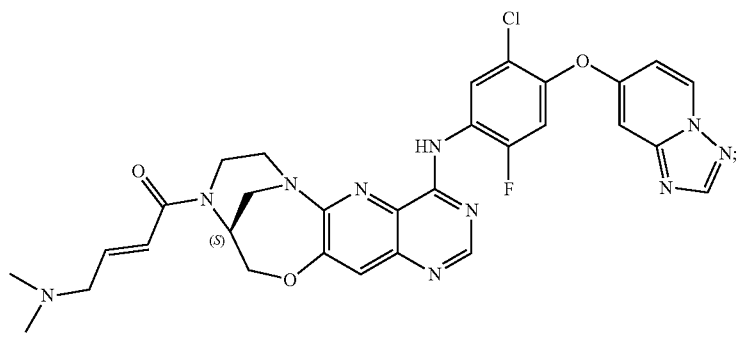
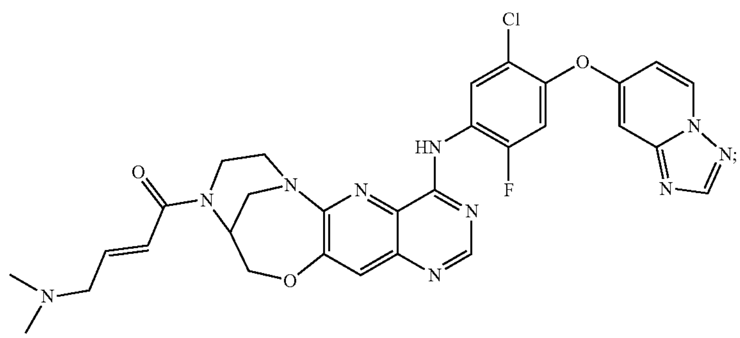

-continued
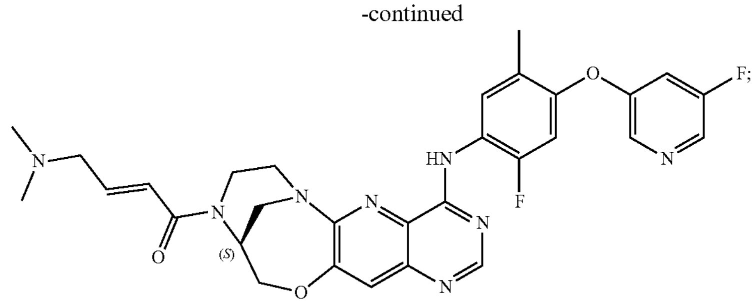
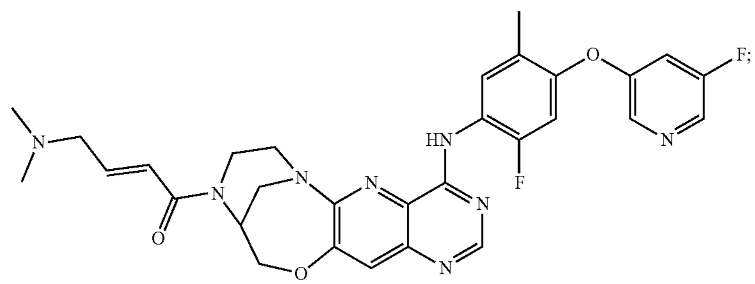
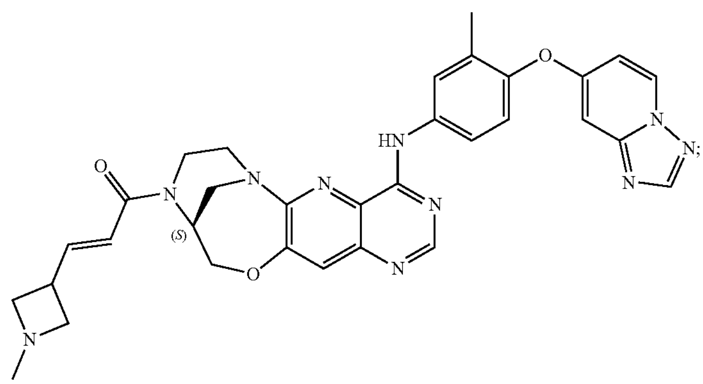
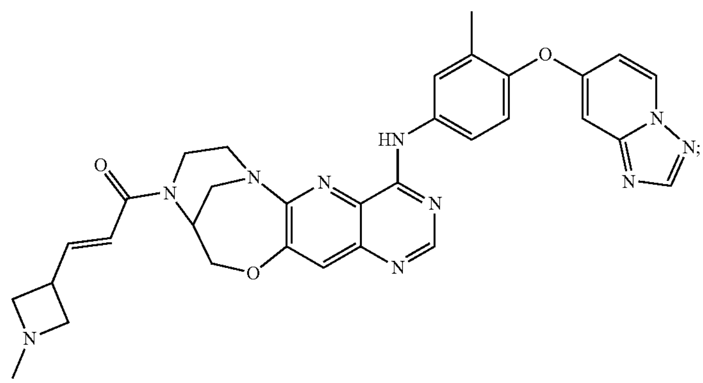
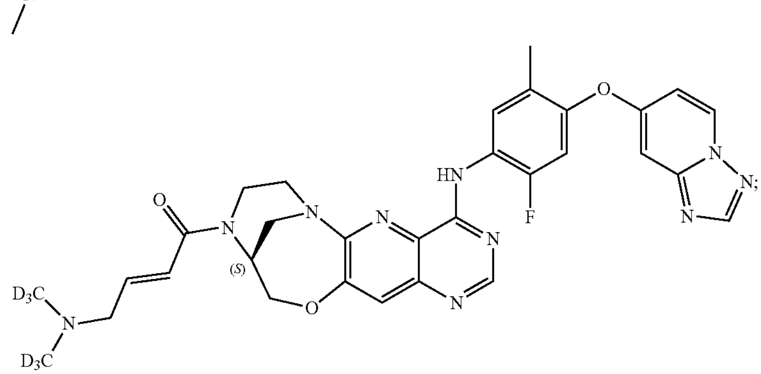

-continued
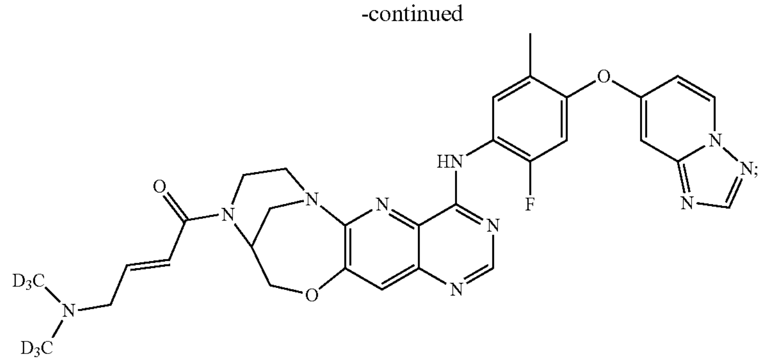
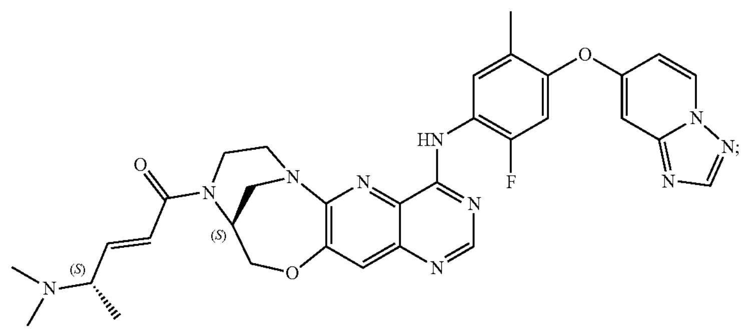
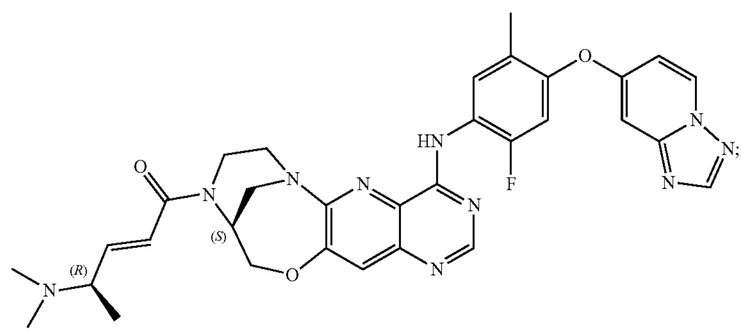
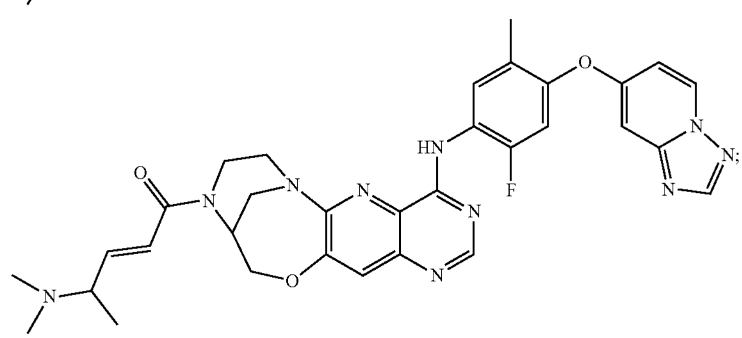
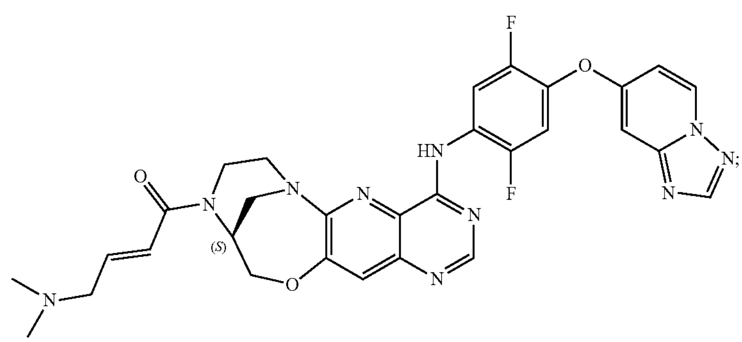

-continued
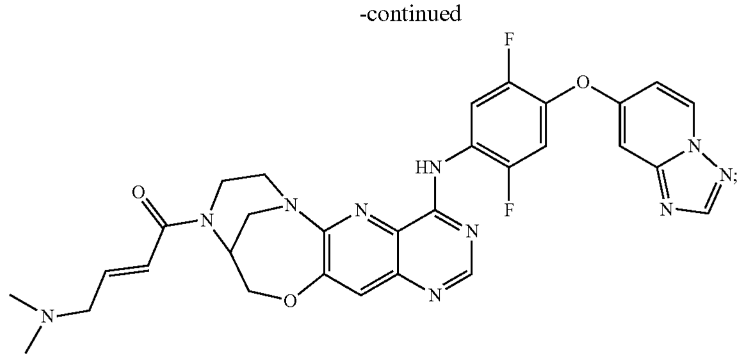
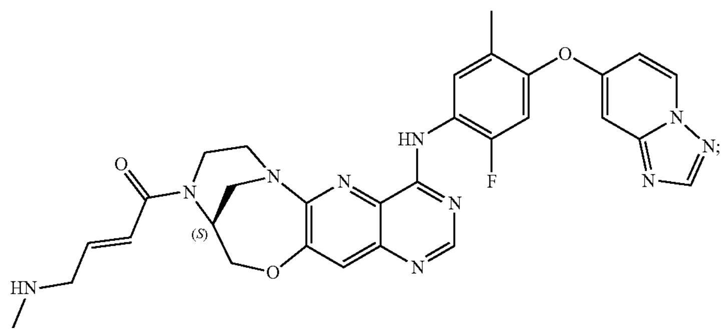
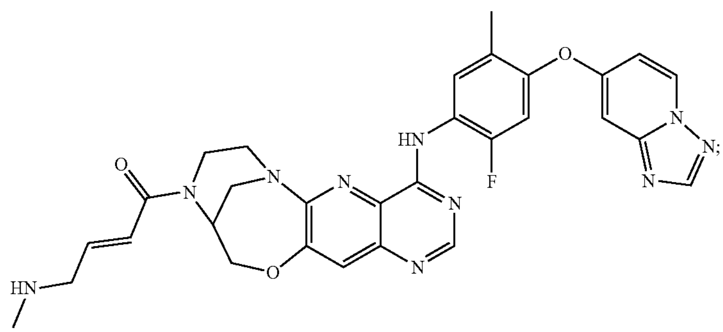
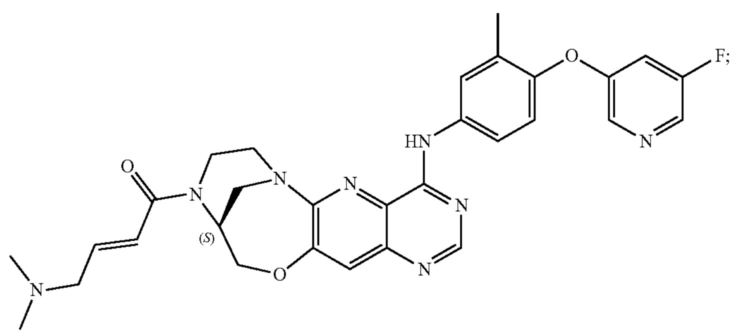
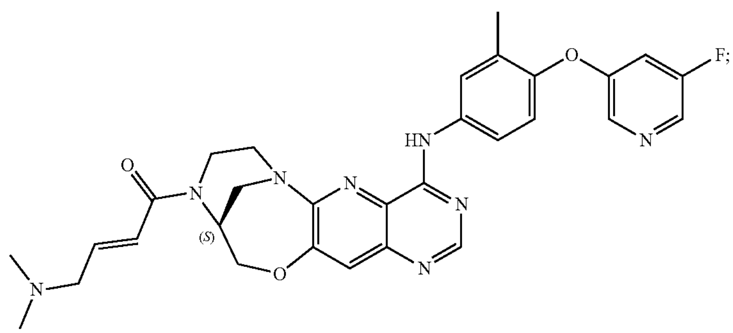

-continued
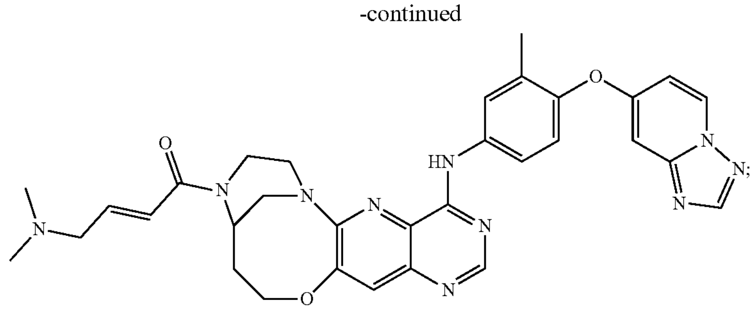
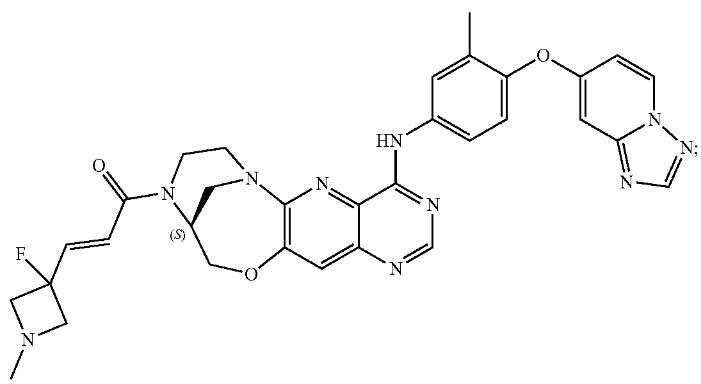
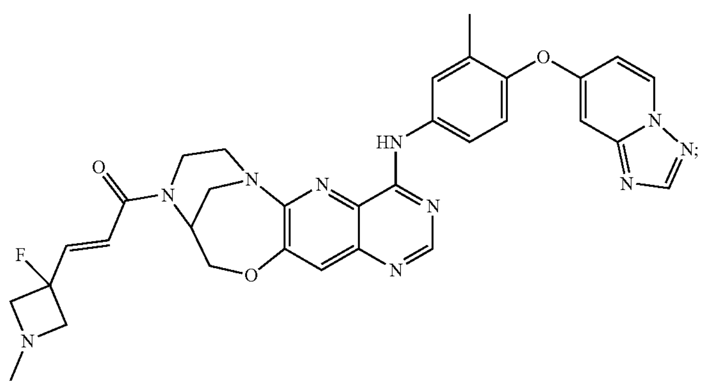
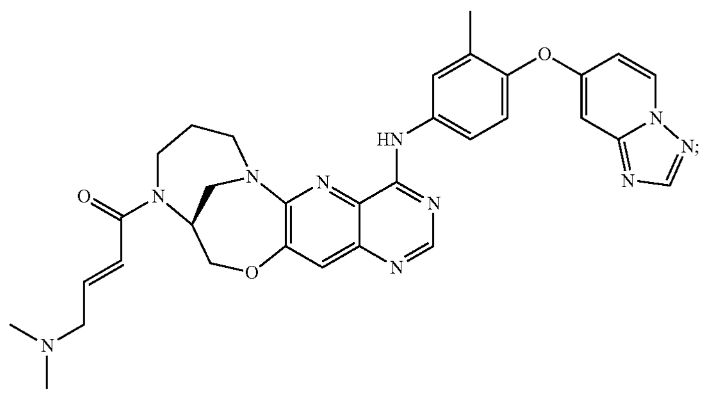

-continued
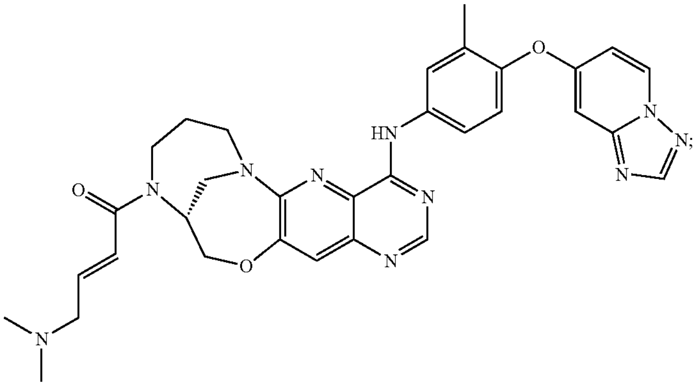
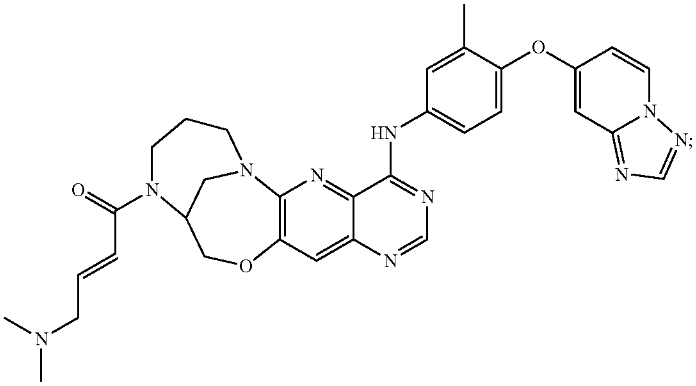
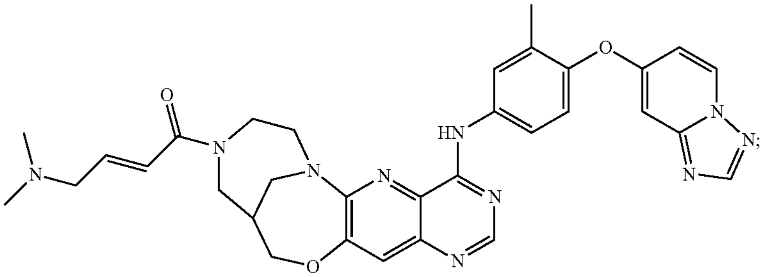
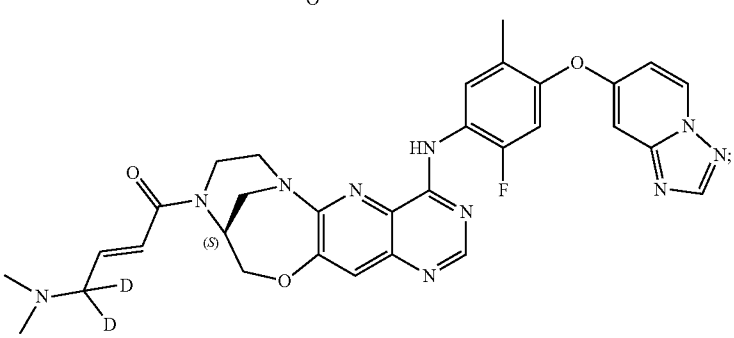
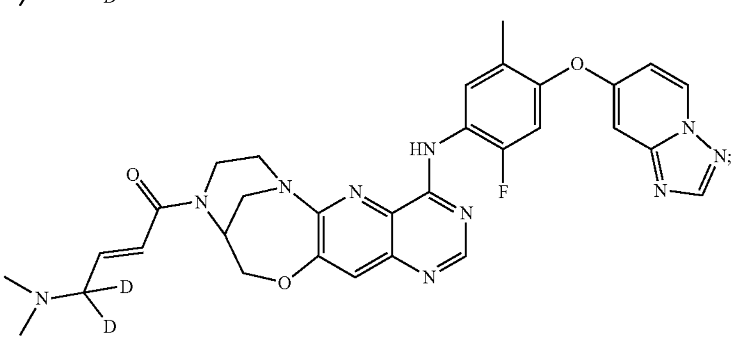

-continued

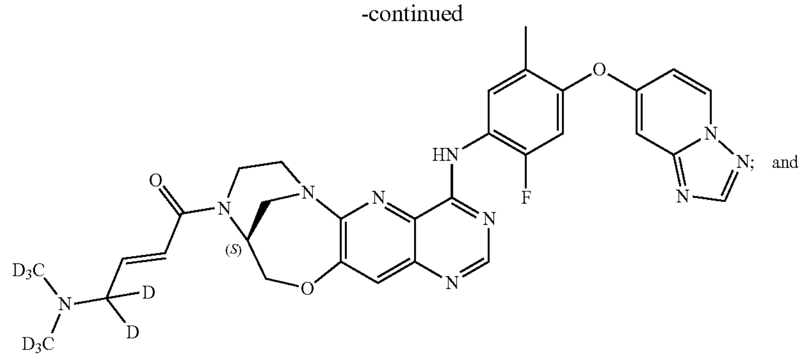

and

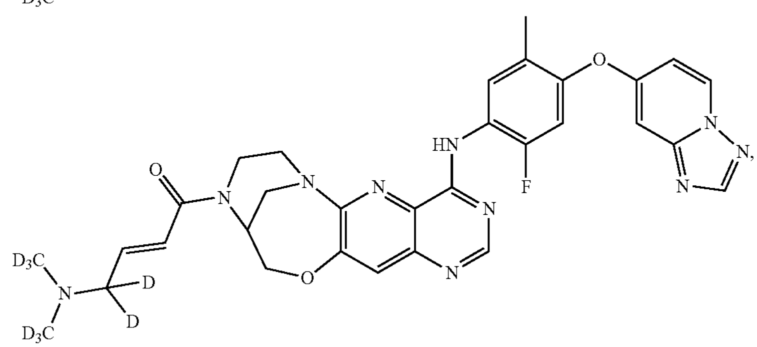

or a pharmaceutically acceptable salt thereof.

29. The method of claim 1, wherein the compound or a pharmaceutically acceptable salt thereof is

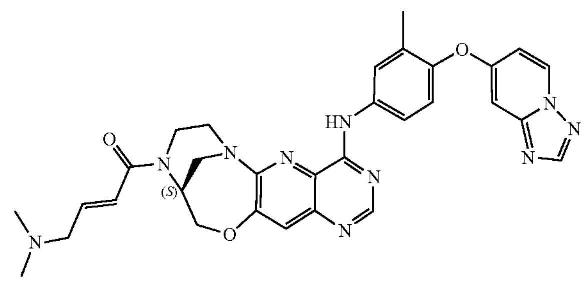

or a pharmaceutically acceptable salt thereof.

30. The method of claim 29, wherein the pharmaceutically acceptable salt of the compound is a salt of hydrochloric acid, hydrobromic acid, sulfuric acid, acetic acid, malonic acid, benzoic acid, succinic acid, benzenesulfonic acid, p-tolylsulfonic acid, glucuronic acid or a salt of an amino acid.

31. The method of claim 1, wherein the compound or a pharmaceutically acceptable salt thereof is

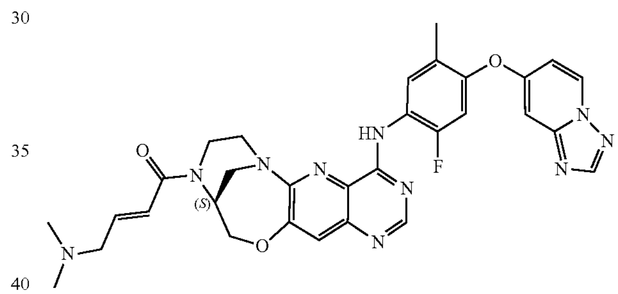

or a pharmaceutically acceptable salt thereof.

32. The method of claim 31, wherein the pharmaceutically acceptable salt of the compound is a salt of hydrochloric acid, hydrobromic acid, sulfuric acid, acetic acid, malonic acid, benzoic acid, succinic acid, benzenesulfonic acid, p-tolylsulfonic acid, glucuronic acid or a salt of an amino acid.

33. The method of claim 1, wherein the compound or a pharmaceutically acceptable salt thereof is

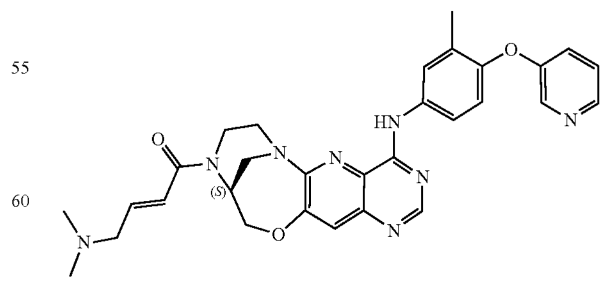

or a pharmaceutically acceptable salt thereof.

34. The method of claim 33, wherein the pharmaceutically acceptable salt of the compound is a salt of hydrochloric acid, hydrobromic acid, sulfuric acid, acetic acid, malonic acid, benzoic acid, succinic acid, benzenesulfonic acid, p-tolylsulfonic acid, glucuronic acid or a salt of an amino acid.

35. The method of claim 1, wherein the compound or a pharmaceutically acceptable salt thereof is a compound selected from the group consisting of:

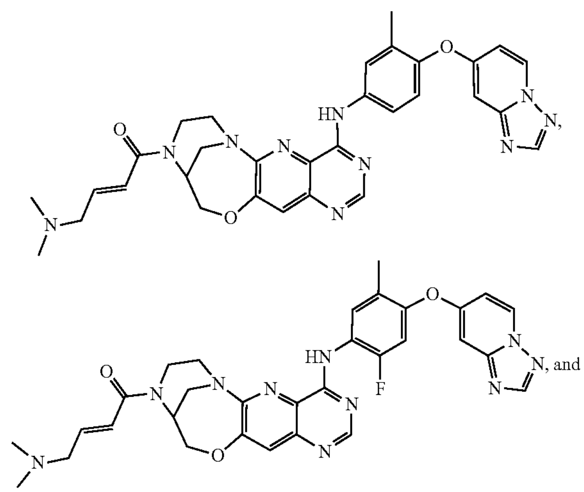

, and

-continued

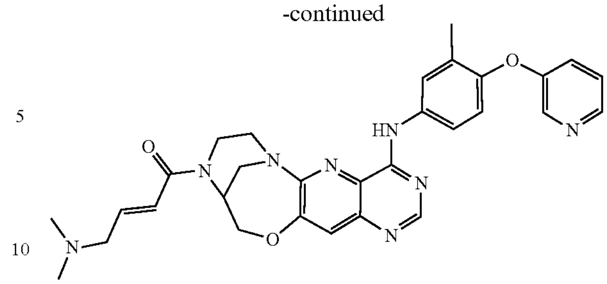

, or a pharmaceutically acceptable salt thereof.

36. The method of claim 35, wherein the pharmaceutically acceptable salt of the compound is a salt of hydrochloric acid, hydrobromic acid, sulfuric acid, acetic acid, malonic acid, benzoic acid, succinic acid, benzenesulfonic acid, p-tolylsulfonic acid, glucuronic acid or a salt of an amino acid.

* * * * *